US012448373B2

(12) United States Patent
Fan et al.

(10) Patent No.: US 12,448,373 B2
(45) Date of Patent: Oct. 21, 2025

(54) AZETIDINYL-ACETAMIDES AS CXCR7 INHIBITORS

(71) Applicant: CHEMOCENTRYX, INC., San Carlos, CA (US)

(72) Inventors: Pingchen Fan, Hayward, CA (US); Christopher W. Lange, Hayward, CA (US); Rebecca M. Lui, Mountain View, CA (US); Darren J. McMurtrie, Vancouver (CA); Ryan J. Scamp, Fremont, CA (US); Ju Yang, Palo Alto, CA (US); Yibin Zeng, Foster City, CA (US); Penglie Zhang, Foster City, CA (US)

(73) Assignee: AMGEN INC., Thousand Oaks, CA (US)

( * ) Notice: Subject to any disclaimer, the term of this patent is extended or adjusted under 35 U.S.C. 154(b) by 834 days.

(21) Appl. No.: 17/722,491

(22) Filed: Apr. 18, 2022

(65) Prior Publication Data

US 2022/0348568 A1 Nov. 3, 2022

Related U.S. Application Data

(60) Provisional application No. 63/176,451, filed on Apr. 19, 2021.

(51) Int. Cl.

| | |
|---|---|
| ***C07D 413/14*** | (2006.01) |
| ***C07D 413/12*** | (2006.01) |
| ***C07D 417/12*** | (2006.01) |
| ***C07D 417/14*** | (2006.01) |
| ***G01N 33/68*** | (2006.01) |

(52) U.S. Cl.

CPC ......... *C07D 413/14* (2013.01); *C07D 413/12* (2013.01); *C07D 417/12* (2013.01); *C07D 417/14* (2013.01); *G01N 33/6863* (2013.01); *G01N 2333/7158* (2013.01); *G01N 2458/00* (2013.01)

(58) Field of Classification Search

CPC .. C07D 417/14; C07D 417/12; C07D 413/12; C07D 413/14

See application file for complete search history.

(56) References Cited

U.S. PATENT DOCUMENTS

| | | | |
|---|---|---|---|
| 7,678,891 | B2 | 3/2010 | Howard et al. |
| 7,871,619 | B2 | 1/2011 | Burns et al. |
| 2005/0214287 | A1 | 9/2005 | Burns et al. |
| 2011/0015174 | A1 | 1/2011 | Pauls et al. |
| 2015/0307452 | A1 | 10/2015 | Frei et al. |

FOREIGN PATENT DOCUMENTS

WO 2005/000333 A1 1/2005

OTHER PUBLICATIONS

International Search Report and Written Opinion dated Jun. 29, 2022 corresponding to PCT/US2022/025167 filed Apr. 18, 2022; 10 pages.

Balabanian, Karl et al., "The Chemokine SDF-1/CXCL 12 Binds to and Signals through the Orphan Receptor RDC1 in T Lymphocytes," *Journal of Biological Chemistry* (Oct. 21, 2005) 280(42):35760-35766.

Bertolini et al., "CXCR4 Neutralization, a Novel Therapeutic Approach for Non-Hodgkin's Lymphoma," *Cancer Research* (Jun. 1, 2002) 62:3106-3112.

D'Huys, Thomas et al., "CXCR7/ACKR3-targeting ligands interfere with X7 HIV-1 and HIV-2 entry and replication in human host cells," *Heliyon* 4 (2018; accepted Feb. 22, 2018) Article e00557; 23 pages.

Hattori, Koichi et al., "Plasma elevation of stromal cell-derived factor-1 induces mobilization of mature and immature hematopoietic progenitor and stem cells," *Blood* (Jun. 1, 2001) 97(11):3354-3360.

Heeson, Michael et al., "Cloning and chromosomal mapping of an orphan chemokine receptor: mouse RDC1," *Immunogenetics* (1998; revised Oct. 6, 1997); 47:364-370.

Kolonin, Mikhail G et al., "Reversal of obesity by targeted ablation of adipose tissue," *Nature Medicine* (Jun. 1, 2004) 10(6):625-632.

Levine, Richard J et al., "Circulating Angiogenic Factors and the Risk of Preeclampsia," *N Engl J Med* (Feb. 12, 2004) 350:672-683.

Libert, Frederick et al., "Selective Amplification and Cloning of Four New Members of the G Protein-coupled Receptor Family," *Science* (May 5, 1989); 244(4904):569-572.

Libert, F. et al., "Complete nucleotide sequence of a putative G protein coupled receptor: RDC1," *Nucleic Acids Research* (1990; submitted Dec. 1, 1989) 18(7): 1917; EMBL accession No. X14048.

Liu, Hongbao et al., "The Role of SDF-1-CXCR4/CXCR7 Axis in the Therapeutic Effects of Hypoxia-Preconditioned Mesenchymal Stem Cells for Renal Ischemia/Reperfusion Injury," *Plos One* (Apr. 12, 2012) 7(4): e34608; 13 pages.

(Continued)

*Primary Examiner* — James W Rogers
(74) *Attorney, Agent, or Firm* — Robert Bernstein

(57) ABSTRACT

Compounds having formula I, (I)

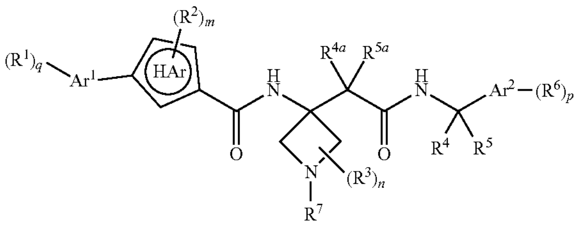

or pharmaceutically acceptable salts, hydrates or N-oxides thereof are provided and are useful for binding to CXCR7, and treating diseases that are dependent, at least in part, on CXCR7 activity. Accordingly, the present invention provides in further aspects, compositions containing one or more of the above-noted compounds in admixture with a pharmaceutically acceptable excipient.

30 Claims, No Drawings

(56) References Cited

OTHER PUBLICATIONS

Luo, Yong et al., "Enzalutamide and CXCR7 inhibitor combination treatment suppresses cell growth and angiogenic signaling in castration-resistant prostate cancer models," *Int. J. Cancer* (Mar. 25, 2018) 142(10):2163-2174.

March, Keith L et al., "Cellular Plasticity in the Cardiovascular System," *Am J Physiol Heart Circ Physiol* (Aug. 2004) 287:H458-H463.

Maynard, Sharon E. et al., "Excess placental soluble fms-like tyrosine kinase 1 (sFlt1) may contribute to endothelial dysfunction, hypertension, and proteinuria in preeclampsia," *J Clin Invest.* (Mar. 2003) 111(5):649-658.

Mazzinghi, Benedetta et al., "Essential but differential role for CXCR4 and CXCR7 in the therapeutic homing of human renal progenitor cells," *J Exp Med* (Feb. 18, 2008) 205(2):479-490.

Melo, Rita de Cassia Carvalho et al., "CXCR7 participates in CXCL12-mediated migration and homing of leukemic and normal hematopoietic cells," *Stem Cell Research & Therapy* (Feb. 12, 2018) 9:34; 5 pages.

Meyrath, Max et al., "The atypical chemokine receptor ACKR3/CXCR7 is a broad-spectrum scavenger for opioid peptides," *Nature Communications* (Jun. 19, 2020) 11(3033); 16 pages.

Muller, Anja et al., "Involvement of Chemokine Receptors in Breast Cancer Metastasis," *Nature* (Mar. 1, 2001) 410:50-56.

Ngamsri, Krisitan-Christos et al., "Inhibition of CXCR4 and CXCR7 is Protective in Acute Peritoneal Inflammation," *Frontiers in Immunology* (Mar. 10, 2020) vol. 11, Article 407; 19 pages.

Petruzziello-Pellegrini, Tania N et al., "The CXCR4/CXCR7/SDF-1 pathway contributes to the pathogenesis of Shiga toxin-associated hemolytic uremic syndrome in humans and mice," *J Clin Invest.* (Feb. 2012) 122(2):759-776.

PUBCHEM-SID-370284414, Modify Date: May 25, 2018 (May 25, 2018), p. 2, figure, this is a purchasable chemical; accessed Jun. 20, 22; 5 pages.

Rehman, Jalees et al., "Secretion of Angiogenic and Antiapoptotic Factors by Human Adipose Stromal Cells," *Circulation* (Mar. 16, 2004) 109:1292-1298.

Romoli, Simone et al., "CXCL12 blockade preferentially regenerates lost podocytes in cortical nephrons by targeting an intrinsic podocyte-progenitor feedback mechanism," *Kidney International* (Oct. 29, 2018) 94:1111-1126.

Shi, Yi et al., "The Role of the CXCL 12/CXCR4/CXCR7 Chemokine Axis in Cancer," *Frontiers in Pharmacology* (Dec. 8, 2020) vol. 11, Article 574667; 14 pages.

Shimizu, Nobuaki et al., "A Putative G Protein-Coupled Receptor, RDC!, Is a Novel Coreceptor for Human and Simian Immunodeficiency Viruses," *Journal of Virology* (Jan. 2002) 74(2):619-626.

Sreedharan, Sunil P. et al., Cloning and expression of the human vasoactive intestinal peptide receptor, *Proc. Natl. Acad. Sci. USA* (Jun. 1991) 88:4986-4990.

Williams, Jessica et al., "Astrocyte-T cell crosstalk regulates region-specific neuroinflammation," *Glia.* (2020; accepted Jan. 5, 2020) 68:1361-1374.

Zhang, Sheng et al., "Activation of CXCR7 alleviates cardiac insufficiency after myocardial infarction by promoting angiogenesis and reducing apoptosis," *Biomedicine & Pharmacotherapy* (2020; accepted Apr. 13, 2020) 127; Article110168; 9 pages.

AZETIDINYL-ACETAMIDES AS CXCR7 INHIBITORS

CROSS-REFERENCES TO RELATED APPLICATIONS

This application claims the benefit of priority under 35 U.S.C. § 119(e) to U.S. Provisional Application Ser. No. 63/176,451 filed Apr. 19, 2021, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention is directed to novel compounds and pharmaceutical compositions that inhibit the binding of the SDF-1 chemokine (also known as the CXCL12 chemokine) or I-TAC (also known as CXCL11) to the chemokine receptor CXCR7 (also known as ACKR3). These compounds are useful in preventing tumor cell proliferation, tumor formation, tumor vascularization, metastasis, inflammatory diseases including, but not limited to arthritis, renal inflammatory disorders and multiple sclerosis, conditions of improper vasculatization including, but not limited to wound healing, treatment of HIV infectivity, and treatment of stem cell differentiation and mobilization disorders, acute renal failure, hemolytic uremic syndrome, ischemia/reperfusion injury, opioid addiction and neuropathic pain (see also, co-pending U.S. Ser. Nos. 10/912,638, 11/407,729 and 11/050,345).

Chemokines are a superfamily of small, cytokine-like proteins that induce cytoskeletal rearrangement, firm adhesion of leukocytes to endothelial cells, leukocyte degranulation and directional migration and may also effect cell activation and proliferation. Chemokines act in a coordinated fashion with cell surface proteins to direct the specific homing of various subsets of cells to specific anatomical sites.

Early research efforts by a number of groups have indicated a role for the chemokine receptor CXCR4 in metastasis and tumor growth. Muller, et al., "Involvement of Chemokine Receptors in Breast Cancer Metastasis," Nature, 410:50-56 (2001) demonstrated that breast tumor cells use chemokine-mediated mechanisms, such as those regulating leukocyte trafficking, during the process of metastasis. Tumor cells express a distinct, non-random pattern of functionally active chemokine receptors. Signaling through CXCR4 mediates actin polymerization and pseudopodia formation in breast cancer cells, and induces chemotactic and invasive responses. Additionally, the organs representing the main sites of breast cancer metastasis (such as lymph nodes, bone marrow, and lungs) are the most abundant sources of ligand for the CXCR4 receptor.

Using immunodeficient mice, Muller and colleagues succeeded in reducing the metastasis of injected human breast cancer cells by treating mice with an antibody known to bind CXCR4. Their finding suggests that breast cancer metastasis could be reduced by treating a patient with a CXCR4 antagonist.

Bertolini, et al., "CXCR4 Neutralization, a Novel Therapeutic Approach for Non-Hodgkin's Lymphoma," Cancer Research, 62:3106-3112 (2002) demonstrated a reduction of tumor volume as well as prolonged survival of immunodeficient mice injected with human lymphoma cells treated with anti-CXCR4 antibodies. They interpreted their finding to mean that tumor volume could be reduced by treating a patient with a CXCR4 antagonist.

Later studies suggested that another chemokine receptor, CXCR7, may also be a target in the treatment of cancer. CXCR7 is preferentially expressed in transformed cells over normal cells, with detectable expression in a number of human cancers. In vitro studies indicate that proliferation of CXCR7 expressing cells can be inhibited by an antagonist of CXCR7. In vivo studies in mice indicate that CXCR7 antagonists can inhibit tumor formation and tumor growth (Reviewed in Morian, D. et al., Front Immunol (2020) 11:952-971.

Certain CXCR7 antagonists can prevent the growth and spread of cancer, and expression patterns indicate a limited tissue distribution for the CXCR7 receptor which correlates to tumorigenesis (Luo, Y. et al., *Int. J. Cancer*, (2018) 142:2163-2174).

Moreover, CXCR7 can serve as a co-receptor for certain genetically divergent human immunodeficiency virus (HIV) and simian immunodeficiency virus (SIV), in particular for the HIV-2-ROD, an X4-tropic isolate (Shimizu, N. et al., *J. Virol*., (2000) 74: 619-626; Balabanian, K., et al., *J. Biol. Chem*., (2005) 280:35760-35766; D'huys, T., et al., *Heliyon*, (2018) 4:e00557).

Still further, SDF-1, has been described to have a role in the mobilization of hematopoietic progenitor cells and stem cells, and in particular of those cells bearing the CXCR4 receptor, from specific hematopoietic tissues including bone marrow has been described (Hattori, K., et al., *Blood*, (2000) 97:3354-3360; WO 2005/000333, the disclosure of which are incorporated herein by reference). More recent studies suggest that CXCR7 may also play a part in stem cell mobilization processes Melo, R D et al., *Stem Cell Res Ther*, (2018) 9:34-38.

In addition to the original discoveries of roles for CXCR7 in cancer and stem cell mobilization, modulation of this receptor has shown promise in preventing HIV infectivity, Shiga toxin-associated hemolytic uremic syndrome, ischemia/reperfusion injury in cardiac tissue and in transplanted kidney and reduction of muscular sclerosis pathology. The recent discovery that CXCR7 binds to opioids suggests that modulation of this receptor may modulate pain and potently treat opioid addiction In view of the above, it is apparent that compounds that are able to bind specifically to CXCR7 receptors can be useful for treating diseases and other biological conditions that may benefit from such interactions. The present invention provides such compounds along with pharmaceutical compositions and related methods for treatment.

BRIEF SUMMARY OF THE INVENTION

The present invention provides, in one aspect, compounds having formula I, (I)

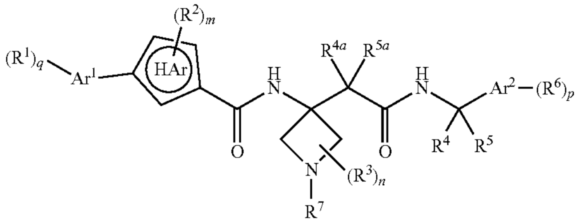

or pharmaceutically acceptable salts, hydrates or N-oxides thereof. The various groups (e.g., $R^1$, $R^2$, $R^3$, $R^4$, $R^{4a}$, $R^5$, $R^{5a}$, $R^6$, $R^7$, $Ar^1$, $Ar^2$, HAr and the subscripts m, n, p and q) are described in the Detailed Description of the Invention.

The compounds provided herein are useful for binding to CXCR7, and treating diseases that are dependent, at least in part, on CXCR7 activity. Accordingly, the present invention provides in further aspects, compositions containing one or more of the above-noted compounds in admixture with a pharmaceutically acceptable excipient.

In still another aspect, the present invention provides methods for treating various diseases, discussed further herein, comprising administering to a subject in need to such treatment a therapeutically effective amount of a compound of the above formula for a period of time sufficient to treat the disease.

In yet another aspect, the present invention provides methods of diagnosing disease in an individual. In these methods, the compounds provided herein are administered in labeled form to a subject, followed by diagnostic imaging to determine the presence or absence of CXCR7. In a related aspect, a method of diagnosing disease is carried out by contacting a tissue or blood sample with a labeled compound as provided herein and determining the presence, absence, or amount of CXCR7 in the sample.

In some embodiments, an amount of a chemotherapeutic agent or radiation is administered to the subject prior to, subsequent to or in combination with the compounds of the present invention. In some embodiments, the amount is sub-therapeutic when the chemotherapeutic agent or radiation is administered alone.

BRIEF DESCRIPTION OF THE DRAWINGS

Not Applicable

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "cycloalkyl" refers to a saturated or partially unsaturated hydrocarbon ring having the indicated number of ring atoms (e.g., $C_{3-6}$ cycloalkyl). Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, and $C_{3-10}$. Partially unsaturated cycloalkyl groups have one or more double or triple bonds in the ring, but cycloalkyl groups are not aromatic. Saturated monocyclic cycloalkyl rings include, for example, cyclopropyl, cyclobutyl, cyclopentyl, cyclohexyl, and cyclooctyl.

The term "cycloalkyloxy" refers to a cycloalkyl group having an oxygen atom that connects the cycloalkyl group to the point of attachment: cycloalkyl-O—. The cycloalkyl group is as defined herein.

The terms "bridged cyclyl" or "bridged cycloalkyl" refer to a cycloalkyl ring (having 4 to 8 ring vertices) in which two non-adjacent ring atoms are linked by a $(CRR')_n$ group where n is 1 to 3 and each R is independently H or methyl (also may be referred to herein as "bridging" group). Bridged cycloalkyl groups do not have any heteroatoms as ring vertices. Additionally, $C_{5-8}$ refers to a bridged cycloalkyl group having 5-8 ring members. Examples include, but are not limited to, bicyclo[1.1.1]pentane, bicyclo[2.2.2]octane, bicyclo[2.2.1]heptane, and the like.

The terms "spirocyclyl" or "spirocycloalkyl" refer to a saturated or partially unsaturated bicyclic ring having 6 to 12 ring atoms, where the two rings are connected via a single carbon atom (also called the spiroatom). Partially unsaturated spirocycloalkyl groups have one or more double or triple bonds in the ring, but spirocycloalkyl groups are not aromatic. Representative examples include, but are not limited to, spiro[3.3]heptane, spiro[4.4]nonane, spiro[3.4]octane, and the like.

The term "heterocycloalkyl" refers to a saturated or partially unsatured monocyclic ring having the indicated number of ring vertices (e.g., a 3- to 7-membered ring) and having from one to five heteroatoms selected from N, O, and S as ring vertices. Partially unsaturated heterocycloalkyl groups have one or more double or triple bonds in the ring, but heterocycloalkyl group are not aromatic. Heterocycloalkyl groups can include any number of ring atoms, such as, 3 to 6, 4 to 6, 5 to 6, 3 to 7, 4 to 7, or 5 to 7 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Non-limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "bicyclic heterocycloalkyl" or "bicyclic heterocyclyl" refers to a saturated or partially unsaturated fused bicyclic ring having the indicated number of ring vertices (e.g., a 6- to 12-membered ring) and having from one to five heteroatoms selected from N, O, and S as ring vertices. Partially unsaturated bicyclic heterocycloalkyl groups have one or more double or triple bonds in the ring, but bicyclic heterocycloalkyl groups are not aromatic. Bicyclic heterocycloalkyl groups can include any number of ring atoms, such as, 6 to 8, 6 to 9, 6 to 10, 6 to 11, or 6 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Non-limiting examples of bicyclic heterocycloalkyl groups include decahydro-1,5-naphthyridine, octahydropyrrolo[1,2-a]pyrazine, and the like.

The terms “bridged heterocyclyl” or “bridged heterocycloalkyl” refers to a heterocycloalkyl ring (having 5 to 7 ring vertices) in which two non-adjacent ring atoms are linked by a $(CRR')_n$ group where n is 1 to 3 and each R is independently H or methyl (also may be referred to herein as “bridging” group). Bridged heterocyclyl groups have one to five heteroatoms selected from N, O, and S as ring vertices. The heteroatom ring vertices can be in both the heterocycloalkyl ring portion as well as the bridging group. When in the bridging group, the heteroatom replaces a CRR' group. Examples include, but are not limited to, 2-azabicyclo[2.2.2]octane, quinuclidine, 7-oxabicyclo[2.2.1]heptane, and the like.

The terms “spiroheterocyclyl” or “spiroheterocycloalkyl” refer to a saturated or partially unsaturated bicyclic ring having 6 to 12 ring atoms, where the two rings are connected via a single carbon atom (also called the spiroatom). Spiroheterocyclyl groups have from one to five heteroatoms selected from N, O, and S as ring vertices, and the nitrogen atom(s) are optionally quaternized. Partially unsaturated spiroheterocycloalkyl groups have one or more double or triple bonds in the ring, but spiroheterocycloalkyl groups are not aromatic. Representative examples include, but are not limited to, 2,6-diazaspiro[3.3]heptane, 2,6-diazaspiro[3.4]octane, 2-azaspiro[3.4]octane, 2-azaspiro[3.5]-nonane, 2,7-diazaspiro[4.4]nonane, and the like.

The term “alkylene” by itself or as part of another substituent means a divalent radical derived from an alkane, as exemplified by $—CH_2CH_2CH_2CH_2—$. Typically, an alkyl (or alkylene) group will have from 1 to 24 carbon atoms, with those groups having 10 or fewer carbon atoms being preferred in the present invention. A “lower alkyl” or “lower alkylene” is a shorter chain alkyl or alkylene group, generally having four or fewer carbon atoms. Similarly, “alkenylene” and “alkynylene” refer to the unsaturated forms of “alkylene” having double or triple bonds, respectively.

As used herein, a wavy line, “ 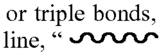 ”, that intersects a single, double or triple bond in any chemical structure depicted herein, represent the point attachment of the single, double, or triple bond to the remainder of the molecule.

The terms “alkoxy,” “alkylamino” and “alkylthio” (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as $—NR^aR^b$ is meant to include piperidinyl, pyrrolidinyl, morpholinyl, azetidinyl and the like.

The terms “halo” or “halogen,” by themselves or as part of another substituent, mean, unless otherwise stated, a fluorine, chlorine, bromine, or iodine atom. Additionally, terms such as “haloalkyl,” are meant to include monohaloalkyl and polyhaloalkyl. For example, the term “$C_{1-4}$ haloalkyl” is meant to include trifluoromethyl, 2,2,2-trifluoroethyl, 4-chlorobutyl, 3-bromopropyl, and the like.

The term “hydroxyalkyl” is meant to refer to an alkyl group as defined above, having one or two hydroxyl groups as substituents. For example, the term “$C_{1-6}$ hydroxyalkyl” is mean to include 2-hydroxyethyl and 2,4-dihydroxybutyl.

The term “aryl” means, unless otherwise stated, a polyunsaturated, typically aromatic, hydrocarbon group which can be a single ring or multiple rings (up to three rings) which are fused together or linked covalently. The term “heteroaryl” refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term “arylalkyl” is meant to include those radicals in which an aryl group is attached to an alkyl group (e.g., benzyl, phenethyl, and the like). Similarly, the term “heteroaryl-alkyl” is meant to include those radicals in which a heteroaryl group is attached to an alkyl group (e.g., pyridylmethyl, thiazolylethyl, and the like).

The above terms (e.g., “alkyl,” “aryl” and “heteroaryl”), in some embodiments, will include both substituted and unsubstituted forms of the indicated radical. Preferred substituents for each type of radical are provided below.

Substituents for the alkyl radicals (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', $—CO_2R'$, —CONR'R", —OC(O)NR'R", —NR"C(O)R', —NR'C(O)NR"R'", $—NR"C(O)_2R'$, $—NHC(NH_2)═NH$, $—NR'C(NH_2)═NH$, $—NHC(NH_2)═NR'$, —S(O)R', $—S(O)_2R'$, $—S(O)_2NR'R"$, $—NR'S(O)_2R"$, —CN and $—NO_2$ in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, unsubstituted $C_{1-8}$alkyl, $C_{1-8}$ alkoxy or $C_{1-8}$thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, $—NO_2$, $—CO_2R'$, —CONR'R", —C(O)R', —OC(O)NR'R", —NR"C(O)R', $—NR"C(O)_2R'$, —NR'C(O)NR"R'", $—NHC(NH_2)═NH$, $—NR'C(NH_2)═NH$, $—NHC(NH_2)═NR'$, —S(O)R', $—S(O)_2R'$, $—S(O)_2NR'R"$, $—NR'S(O)_2R"$, $—N_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$haloalkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula —T-C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula —A-$(CH_2)_r$—B—, wherein A and B are independently —$CH_2$—, —O—, —NH—, —S—, —S(O)—, —$S(O)_2$—, —$S(O)_2NR'$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —$S(O)_2$—, or —$S(O)_2NR'$—. The substituent R' in —NR'— and —$S(O)_2NR'$— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. In some embodiments, the compounds of the invention are present in an enantiomerically enriched form, wherein the amount of enantiomeric excess for a particular enantiomer is calculated by known methods. The preparation of enantiomerically enriched forms is also well known in the art and can be accomplished using, for example, chiral resolution via chromatography or via chiral salt formation. Additionally, different conformers are contemplated by the present invention, as well as distinct rotamers. Conformers are conformational isomers that can differ by rotations about one or more σ bonds. Rotamers are conformers that differ by rotation about only a single σ bond. Still further, the compounds of the present invention may also contain unnatural proportions of atomic isotopes at one or more of the atoms that constitute such compounds. Accordingly, in some embodiments, the compounds of the invention are present in isotopically enriched form. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

"CXCR7" also referred to as "RDC1" or "CCXCKR2" refers to a seven-transmembrane domain presumed G-protein coupled receptor (GPCR). The CXCR7 dog ortholog was originally identified in 1991. See, Libert et al. *Science* 244:569-572 (1989). The dog sequence is described in Libert et al., *Nuc. Acids Res.* 18(7):1917 (1990). The mouse sequence is described in, e.g., Heesen et al., *Immunogenetics* 47:364-370 (1998). The human sequence is described in, e.g., Sreedharan et al., *Proc. Natl. Acad. Sci. USA* 88:4986-4990 (1991), which mistakenly described the protein as a receptor of vasoactive intestinal peptide.

II. General

Compounds of the present invention can inhibit the binding of ligands to the CXCR7 receptor and are useful in the treatment of various diseases, including cancer, particularly solid tumor cancers and lymphomas. More recently, the inhibition of ligand binding to CXCR7 was noted to reduce the severity of rheumatoid arthritis in an animal model.

Those of skill in the art will understand that agents that modulate CCX-CKR2 activity (CXCR7 activity) can be combined in treatment regimens with other anti-angiogenesis agents and/or with chemotherapeutic agents or radiation and/or other anti-arthritis agents. In some cases, the amount of chemotherapeutic agent or radiation is an amount which would be sub-therapeutic if provided without combination with an anti-angiogenic agent. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

III. Embodiments of the Invention

A. Compounds

The present invention provides, in one aspect, compounds having formula I, (I)

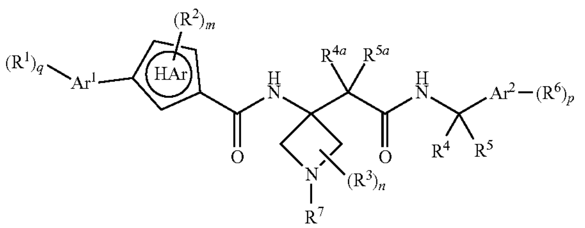

or a pharmaceutically acceptable salt, hydrate, N-oxide, isotopically enriched or enantiomerically enriched version or a rotamer thereof, wherein HAr is a five-membered heteroaryl ring;

$Ar^1$ is selected from the group consisting of phenyl, pyridyl, pyrimidinyl, and pyrazinyl;

$Ar^2$ is aryl or heteroaryl, each of which is independently monocyclic or fused-bicyclic;

the subscript m is 0, 1 or 2;

the subscript n is 0, 1, 2 or 3;

the subscript p is 0, 1, 2 or 3;

the subscript q is 0, 1, 2, 3 or 4;

each $R^1$ is a member independently selected from the group consisting of halogen, CN, $C_{1-4}$ alkyl, $C_{1-4}$ haloalkyl, —$NR^aR^b$, —$OR^a$, —$CO_2R^a$, and —C(O)$NR^aR^b$;

each $R^2$ is a member independently selected from the group consisting of halogen, CN, $C_{1-4}$ alkyl, $C_{1-4}$ haloalkyl, —$NR^aR^b$, —$OR^a$, —$CO_2R^a$, and —C(O)$NR^aR^b$;

each $R^3$ is a member selected from the group consisting of $C_{1-4}$ alkyl, $C_{1-4}$ haloalkyl, $C_{1-4}$ hydroxyalkyl, —$CO_2R^a$, —X—$CO_2R^a$, —C(O)$NR^aR^b$ and —X—C(O)$NR^aR^b$;

each of $R^{4a}$ and $R^{5a}$, is a member independently selected from the group consisting of H, $C_{1-6}$ alkyl, $C_{1-6}$ haloalkyl, $C_{1-6}$ hydroxyalkyl, —$CO_2R^a$, —X—$CO_2R^a$, —X—$NR^aR^b$, —C(O)$NR^aR^b$ and —X—C(O)$NR^aR^b$;

each of $R^4$ and $R^5$, is a member independently selected from the group consisting of H, $C_{1-6}$ alkyl, $C_{1-6}$ haloalkyl, $C_{1-6}$ hydroxyalkyl, —$CO_2R^a$, —X—$CO_2R^a$, —X—$NR^aR^b$, —C(O)$NR^aR^b$ and —X—C(O)$NR^aR^b$; or $R^4$ and $R^5$ are combined to form a three- to five-membered ring having 0 or 1 heteroatom ring vertex selected from O, S or N, wherein said three to five-membered ring is unsubstituted or substituted with 1-4 substituents independently selected from the group consisting of halogen, CN, $C_{1-4}$ alkyl, $C_{1-4}$ haloalkyl, $C_{1-4}$ alkoxy, and $C_{1-4}$ haloalkoxy;

each $R^6$ is a member independently selected from the group consisting of halogen, CN, —X—CN, $C_{1-4}$ alkyl, $C_{1-4}$ haloalkyl, $C_{3-6}$ cycloalkyl, $C_{1-4}$ hydroxyalkyl, —OR', —$CO_2R^a$, —X—$CO_2R^a$, —$NR^aR^b$, —X—$NR^aR^b$, —C(O)$NR^aR^b$, and —X—C(O)$NR^aR^b$, $R^7$ is a member selected from the group consisting of $C_{1-8}$ alkyl, $C_{3-8}$ hydroxyalkyl, $C_{1-4}$ alkoxy-$C_{24}$ alkyl, —C(O)NH—$C_{1-8}$ alkyl, —C(O)—$C_{1-8}$ alkyl, —$S(O)_2$—$C_{1-8}$ alkyl, $C_{3-8}$ cycloalkyl, —X—$C_{3-8}$ cycloalkyl, $C_{6-9}$ spirocycloalkyl, —X—$C_{6-9}$ spirocycloalkyl, 4- to 7-membered heterocycloalkyl, —X-4- to 7-membered heterocycloalkyl, 7- to 11-membered spiroheterocycloalkyl, and —X-7- to 11-membered spiroheterocycloalkyl, wherein each $R^7$ is substituted with zero to four substituents independently selected from the group consisting of hydroxy, methyl, ethyl, hydroxymethyl, fluoro, chloro, methoxy, ethoxy and cyclopropyl;

each $R^a$ and $R^b$ is independently selected from the group consisting of H, $C_{1-4}$ alkyl, $C_{1-4}$ haloalkyl, $C_{3-6}$ cycloalkyl, and $C_{3-6}$ cycloalkyl-$C_{14}$ alkyl; and each X is a $C_{1-4}$ alkylene linking group wherein any of the methylene portions of X are unsubstituted or substituted with one or two methyl groups.

In one group of embodiments, compounds having formula I are provided wherein HAr is selected from the group consisting of isoxazole, isothiazole, imidazole, pyrazole, thiazole, 1,2,4-oxadiazole, 1,3,4-oxadiazole, 1,2,4-thiadiazole, 1,3,4-thiadiazole, 1,2,3-triazole, and 1,2,4-triazole. In another group of embodiments, HAr is selected from isoxazole and thiadiazole.

In one group of embodiments, compounds having formula I are provided wherein $Ar^1$ is phenyl.

In one group of embodiments, compounds having formula I are provided, as well as additional embodiments above, wherein the subscript q is 1, 2, or 3; and each $R^1$ is a member independently selected from the group consisting of halogen, CN, $C_{1-4}$ alkyl and $C_{1-4}$ haloalkyl.

In another group of embodiments, compounds having formula I are provided, as well as additional embodiments above, wherein $Ar^2$ is selected from the group consisting of pyridyl, pyrimidinyl, pyrazinyl, phenyl, indolyl, thiazolyl, pyrazolyl, indazolyl and pyrrolopyridinyl. In still other embodiments, $Ar^2$ is selected from pyrimidinyl, pyridyl and phenyl.

In another group of embodiments, compounds having formula I are provided, as well as additional embodiments above, wherein $Ar^2$ is selected from the group consisting of 2-pyridyl, 4-pyridyl, 2-pyrimidinyl, 4-pyrimidinyl, 2-thiazolyl, 4-pyrazolyl, phenyl and indolyl; and each $R^6$ is independently selected from the group consisting of halogen, CN, $C_{1-4}$ alkyl, $C_{1-4}$ haloalkyl, $C_{3-6}$ cycloalkyl and $C_{1-4}$ alkoxy.

In another group of embodiments, compounds having formula I are provided, as well as additional embodiments above, wherein $—Ar^2—(R^6)_p$ is selected from the group consisting of

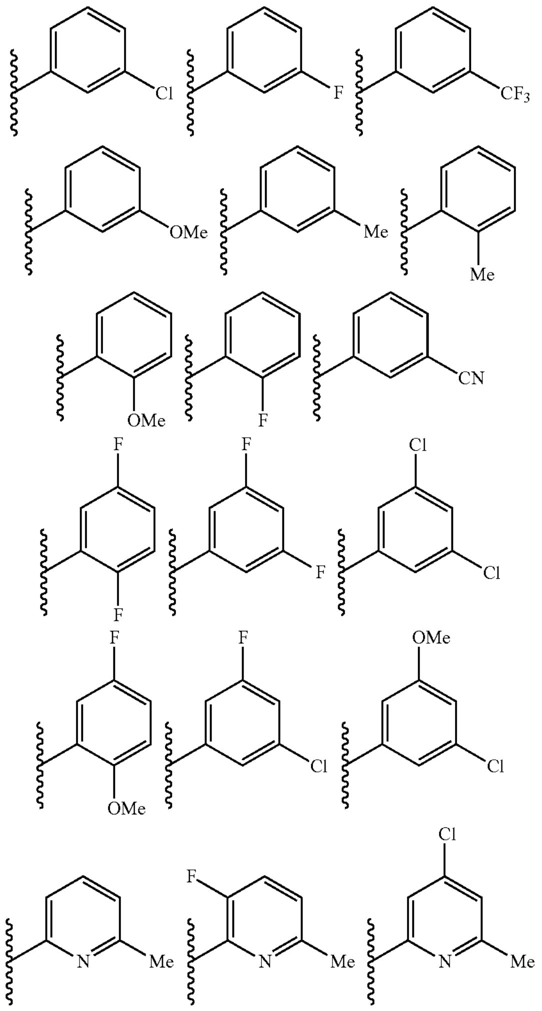

-continued

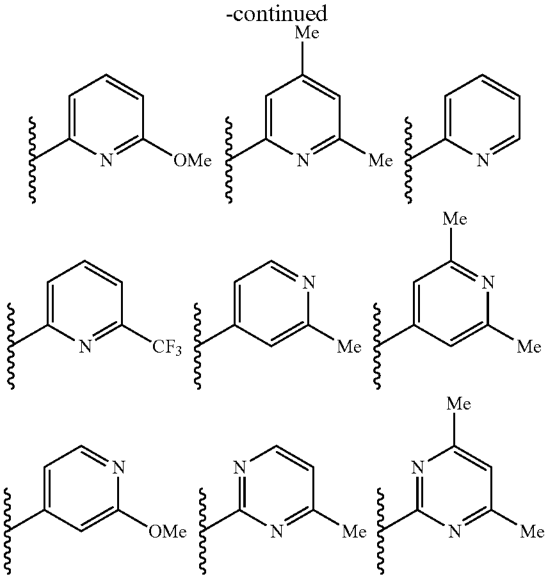

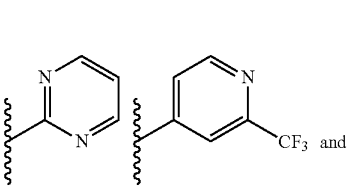

and

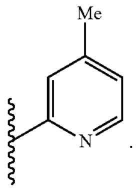

.

In another group of embodiments, compounds having formula I are provided, as well as additional embodiments above, wherein $R^7$ is selected from the group consisting of

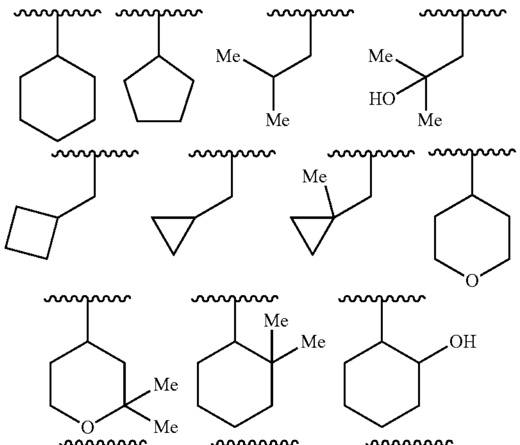

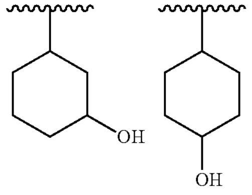

and

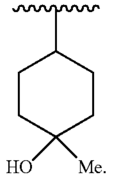

In another group of embodiments, compounds having formula I are provided, as well as additional embodiments above, wherein the subscript m is 0.

In another group of embodiments, compounds having formula I are provided, as well as additional embodiments above, wherein the subscript n is 0.

In another group of embodiments, compounds having formula I are provided, as well as additional embodiments above, wherein the subscript p is 0, 1 or 2.

In another group of embodiments, compounds having formula I are provided, as well as additional embodiments above, wherein the subscript q is 1 or 2.

In another group of embodiments, compounds having formula I are provided, as shown in with formula (Ia):

(Ia)

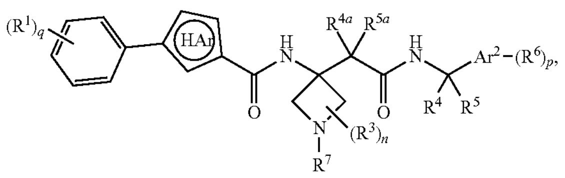

or a pharmaceutically acceptable salt thereof, where the variables have the meanings provided for formula I, or any of the embodiments noted above. In some selected embodiments, HAr is isoxazole or thiadiazole.

In another group of embodiments, compounds having formula I are provided, as shown in with formula (Ia1):

(Ia1)

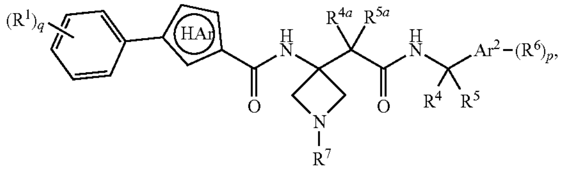

or a pharmaceutically acceptable salt thereof, where the variables have the meanings provided for formula I, or any of the embodiments noted above. In some selected embodiments, HAr is isoxazole or thiadiazole.

In another group of embodiments, compounds having formula I are provided, as shown in with formula (Ia2):

(Ia2)

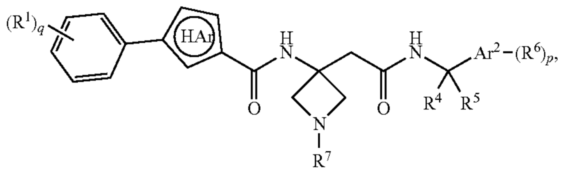

or a pharmaceutically acceptable salt thereof, where the variables have the meanings provided for formula I, or any of the embodiments noted above. In some selected embodiments, HAr is isoxazole or thiadiazole.

In another group of embodiments, compounds having formula I are provided, as shown in with formula (Ib), (Ic), or (Id):

(Ib)

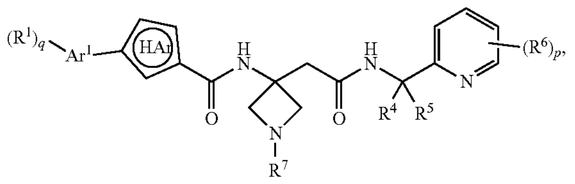

(Ic)

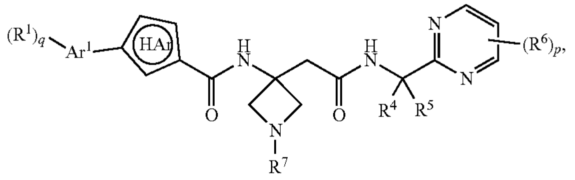

(Id)

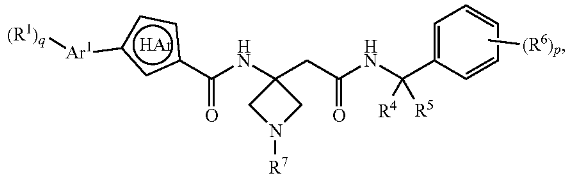

or a pharmaceutically acceptable salt thereof, where the variables have the meanings provided for formula I, or any of the embodiments noted above. In some selected embodiments, HAr is isoxazole or thiadiazole.

In another group of embodiments, compounds having formula I are provided, as shown in with formula (Ib1), (Ic1), or (Id1):

(Ib1)

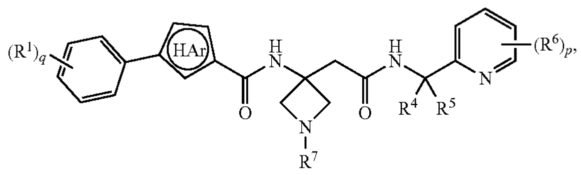

(Ic1)

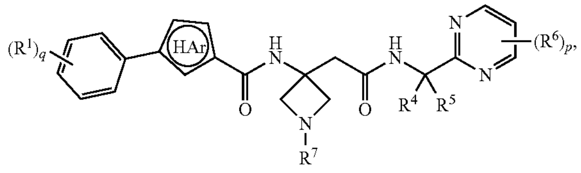

(Id1)

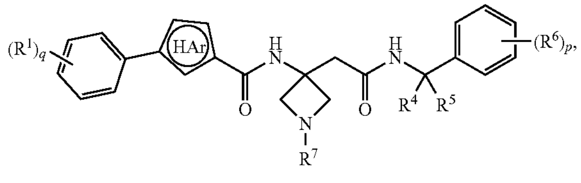

or a pharmaceutically acceptable salt thereof, where the variables have the meanings provided for formula I, or any of the embodiments noted above. In some selected embodiments, HAr is isoxazole or thiadiazole.

In another group of embodiments, compounds having formula I are provided, as well as additional formulae and embodiments above, wherein $R^7$ is a member selected from the group consisting of $C_{1-8}$ alkyl, $C_{3-8}$ hydroxyalkyl, $C_{1-4}$ alkoxy-$C_{24}$ alkyl, $C_{3-8}$ cycloalkyl, $C_{6-9}$ spirocycloalkyl, 4- to 7-membered heterocycloalkyl, and 7- to 11-membered spiroheterocycloalkyl, wherein each $R^7$ is substituted with zero to four substituents independently selected from the group consisting of hydroxy, methyl, ethyl, hydroxymethyl, fluoro, chloro, methoxy, ethoxy and cyclopropyl.

In another group of embodiments, compounds having formula I are provided, as well as additional formulae and embodiments above, wherein $R^7$ is a member selected from the group consisting of —X—$C_{3-8}$ cycloalkyl, —X—$C_{6-9}$ spirocycloalkyl, —X-4- to 7-membered heterocycloalkyl, and —X-7- to 11-membered spiroheterocycloalkyl, wherein each $R^7$ is substituted with zero to four substituents independently selected from the group consisting of hydroxy, methyl, ethyl, hydroxymethyl, fluoro, chloro, methoxy, ethoxy and cyclopropyl.

In another group of embodiments, compounds having formula I are provided, as well as additional formulae and embodiments above, wherein $R^7$ is a member selected from the group consisting of cyclohexyl, cyclopentyl, piperidinyl, tetrahydropyranyl, and tetrahydrofuranyl, each of which is substituted with zero to two substituents independently selected from the group consisting of hydroxy, methyl, ethyl, hydroxymethyl, fluoro, chloro, methoxy, and ethoxy.

In one selected group of embodiments, the compound is selected from those provided in the Examples below, or in Table 1.

In other selected embodiments, the noted compounds may be present in a pharmaceutically acceptable salt or hydrate form.

Still further, for those compounds shown above without stereochemistry, the present invention is also directed to chiral forms of each of the compounds, as well as enantiomerically enriched forms of the noted compounds. Enantiomerically enriched forms can be prepared using chiral chromatography according to well known methods practiced in the art or, for example, by chiral resolution with a chiral salt form. In some embodiments, the enantiomeric excess for an enantiomerically enriched form is at least 10%, 20%, 30%, 40%, 50%, 60% or more. In still other embodiments, an enantiomerically enriched form is provided that is at least 70%, 80%, 90%, 95%, or more.

Preparation of Compounds

Compounds of the invention can be prepared following methodology as described in the Examples section of this document. In addition, the syntheses of certain intermediate compounds that are useful in the preparation of compounds of the invention are also described.

B. Compositions

In addition to the compounds provided above, compositions for modulating CXCR7 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

C. Methods of Use

While not wishing to be bound by any particular theory, the compounds and compositions of the present invention are considered to provide a therapeutic effect by inhibiting the binding of SDF-1 and/or I-TAC to the CXCR7 receptor. Therefore, the compounds and compositions of the present invention can be used in the treatment or prevention of diseases or disorders in a mammal in which the inhibition of binding of SDF-1 and/or I-TAC to the CXCR7 receptor would provide a therapeutic effect.

In one embodiment, a preferred method of inhibiting the binding of the chemokines SDF-1 and/or I-TAC to a CXCR7 receptor includes contacting one or more of the previously mentioned compounds with a cell that expresses the CXCR7 receptor for a time sufficient to inhibit the binding of these chemokines to the CXCR7 receptor.

In some embodiments, the compounds and compositions of the invention are administered to a subject having cancer. In some cases, CXCR7 modulators are administered to treat cancer, e.g., carcinomas, gliomas, mesotheliomas, melanomas, lymphomas, leukemias (including acute lymphocytic leukemias), adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, renal cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease, multiple sclerosis and demyelinating diseases; hypertensive disorders such as pulmonary arterial hypertension; kidney dysfunction; renal dysfunction; rheumatoid arthritis; allograft rejection; atherosclerosis (and elevated cholesterol levels); asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma.

The present invention also encompasses decreasing angiogenesis in any subject in need thereof by administering the compounds and compositions of the invention. For example, decreasing CXCR7 activity by contacting CXCR7 with a compound of the invention, thereby decreasing angiogenesis, is useful to inhibit formation, growth and/or metastasis of tumors, especially solid tumors. Description of embodiments relating to modulated CXCR7 and angiogenesis are described in, e.g., U.S. patent application Ser. No. 11/050,345.

Other disorders involving unwanted or problematic angiogenesis include rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; disease of excessive or abnormal stimulation of endothelial cells, including intestinal adhesions, Crohn's disease, skin diseases such as psoriasis, eczema, and scleroderma, diabetes, diabetic retinopathy, retinopathy of prematurity, age-related macular degeneration, atherosclerosis, scleroderma, wound granulation and hypertrophic scars, i.e., keloids, and diseases that have angiogenesis as a pathologic consequence such as cat scratch disease and ulcers (*Helicobacter pylori*), can also be treated with antibodies of the invention. Angiogenic inhibitors can be used to prevent or inhibit adhesions, especially intra-peritoneal or pelvic adhesions such as those resulting after open or laproscopic surgery, and burn contractions. Other conditions which should be beneficially treated using the angiogenesis inhibitors include prevention of scarring following transplantation, cirrhosis of the liver, pulmonary fibrosis following acute respiratory distress syndrome or other pulmonary fibrosis of the newborn, implantation of temporary prosthetics, and adhesions after surgery between the brain and the dura. Endometriosis, polyposis, cardiac hypertrophyy, as well as obesity, may also be treated by inhibition of angiogenesis. These disorders may involve increases in size or growth of other types of normal tissue, such as uterine fibroids, prostatic hypertrophy, and amyloidosis. Compounds and compositions of the present invention may be used prophylactically or therapeutically for any of the disorders or diseases described herein.

Decreasing CXCR7 activity with the compounds and compositions of the present invention can also be used in the prevention of neovascularization to effectively treat a host of disorders. Thus, for example, the decreasing angiogenesis can be used as part of a treatment for disorders of blood vessels (e.g., hemangiomas and capillary proliferation within atherosclerotic plaques), muscle diseases (e.g., myocardial angiogenesis, myocardial infarction or angiogenesis within smooth muscles), joints (e.g., arthritis, hemophiliac joints, etc.), and other disorders associated with angiogenesis. Promotion of angiogenesis can also aid in accelerating various physiological processes and treatment of diseases requiring increased vascularization such as the healing of wounds, fractures, and burns, inflammatory diseases, ischeric heart, and peripheral vascular diseases. The compounds of the present invention can also provide benefit in conditions in which normal blood flow is restricted, such as pulmonary hypertension.

The compounds and compositions of the present invention may also be used to enhance wound healing. Without intending to limit the invention to a particular mechanism of action, it may be that antagonism of CXCR7 allows for endogenous ligands to instead bind to lower affinity receptors, thereby triggering enhanced wound healing. For example, SDF-1 binds to both CXCR7 and CXCR4, but binds to CXCR4 with a lower affinity. Similarly, I-TAC binds to CXCR3 with a lower affinity than I-TAC binds to CXCR7. By preventing binding of these ligands to CXCR7, CXCR7 antagonists may allow the ligands to bind to the other receptors, thereby enhancing wound healing. Thus, the antagonism of CXCR7 to enhance wound healing may be mediated by a different mechanism than enhancing wound healing by stimulating CXCR7 activity with an agonist.

Aside from treating disorders and symptoms associated with neovascularization, the inhibition of angiogenesis can be used to modulate or prevent the occurrence of normal physiological conditions associated with neovascularization. Thus, for example the compounds and compositions can be used as a birth control. In accordance with the present invention, decreasing CXCR7 activity within the ovaries or endometrium can attenuate neovascularization associated with ovulation, implantation of an embryo, placenta formation, etc.

Inhibitors of angiogenesis have yet other therapeutic uses. For example, the compounds and compositions of the present invention may be used for the following:

(a) Adipose tissue ablation and treatment of obesity. See, e.g., Kolonin et al., *Nature Medicine* 10(6):625-632 (2004);

(b) Treatment of preclampsia. See, e.g., Levine et al., *N. Engl. J. Med.* 350(7): 672-683 (2004); Maynard, et al., *J. Clin. Invest.* 111(5): 649-658 (2003);

(c) Treatment of cardiovascular disease. See, e.g., March, et al., *Am. J. Physiol. Heart Circ. Physiol.* 287:H458-H463 (2004); Rehman et al., *Circulation* 109: 1292-1298 (2004);

(d) Treatment/prevention of ischemia/reperfusion injury by inhibition of hypoxic precondition of mesenchymal stem cells, and rescue of ischemic tissue, including but not limited to myocardium and transplanted renal tissue and. See e.g., Liu, H., et al., *PLoS One* (2012) 7:e34608 and Zhang, S. et al, *Biomed Pharmacother* (2020) 127:110168;

(e) Treatment of Shiga toxin-associated hemolytic uremic syndrome See e.g., Petruzziello-Pellegrini, T. N. et al., *J Clin Invest* (2012) 122:759-776;

(f) Treatment of pain, anxiety, stress, opioid addiction and other CNS conditions See e.g. Meyrath M. et al., *Nat Commun* (2020) 19:3033 and Zhu, Y. et al.;

(g) Treatment/prevention of acute renal failure by blocking the detrimental migration of renal projenitor cells withing glomuleri See e.g. Mazzinghi, B, et al., *J Exp Med* (2008) 205:479-490 and Romaol, S. et al., *Kidney Int* (2018) 94:1111-1126;

(h) Treatment of neuroinflammatory disorders, including but not limited to multiple sclerosis (MS) See e.g. Williams, J. L. et al., *Glia* (2020) 68:1361-1374.

Methods of Treating Cancer

More specifically, the present invention also provides a method of treating cancer. A preferred method of treating cancer, includes administering a therapeutically effective amount of one or more of the previously mentioned compounds (or salts thereof) to a cancer patient for a time sufficient to treat the cancer.

For treatment, the compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In some embodiments, CXCR7 modulators of the present invention can be administered in combination with other appropriate therapeutic agents, including, e.g., chemotherapeutic agents, radiation, etc. It is understood that such administration may be prior to, subsequent to or in unison with the second therapeutic agent, such that the therapeutic effects of the second agent are enhanced when compared to administration of the second agent in the absence of the CXCR7 modulator. Selection of the appropriate agents for use in combination therapy may be made by one of ordinary skill in the art, according to conventional pharmaceutical principles. The combination of therapeutic agents may act synergistically to effect the treatment or prevention of the various disorders such as, e.g., cancer, wounds, kidney dysfunction, brain dysfunction or neuronal dysfunction. Using this approach, one may be able to achieve therapeutic efficacy with lower dosages of each agent, thus reducing the potential for adverse side effects.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

In the treatment or prevention of conditions which require chemokine receptor modulation an appropriate dosage level will generally be about 0.001 to 100 mg per kg patient body weight per day which can be administered in single or multiple doses.

Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat cancer and diseases or conditions associated with CXCR7 signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of cancer or inflammation with the present compounds. Accordingly, combination methods and compositions are also a component of the present invention to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Method of Inducing Progenitor/Stem Cell Mobilization

Still further, the compounds and compositions of the present invention can be useful for mobilizing progenitor/stem cells and thus for treating or ameliorating disorders or conditions for which progenitor/stem cell mobilization is efficacious or desirable, optionally using the compounds of the present invention according to the procedures and protocols as described in WO05/000333, incorporated herein by reference in its entirety for all purposes. Conditions that may be ameliorated or otherwise benefited include, for example, hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound he Still further, the compounds and compositions of the present invention can be useful for mobilizing progenitor/stem cells and thus for treating or ameliorating disorders or conditions for which progenitor/stem cell mobilization is efficacious or desirable, optionally using the compounds of the present invention according to the procedures and protocols as described in WO05/000333, incorporated herein by reference in its entirety for all purposes. Conditions that may be ameliorated or otherwise benefited include, for example, hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound healing and treatment of bacterial infections. Optionally, following administration of the compounds of the invention, and following progenitor/stem cell mobilization, blood comprising the mobilized cells is collected and optionally, the mobilized cells are purified and optionally expanded, and where desired, reintroduced into the same person or into a second person (e.g., a matched donor).

A number of different types of cells can be mobilized as desired. In some embodiments, hematopoietic progenitor cells (HSCs) are mobilized following administration of the compounds or compositions of the invention, and optionally harvested and purified from other blood components. Optionally, HSC mobilization is induced by administration of at least one compound of the invention in conjunction with one or more of granulocyte-colony stimulating factor (G-CSF) or AMD3100 (1,1'-[1,4-Phenylenebis(methylene)] bis [1,4,8,11-tetraazacyclotetradecane] octohydrobromide dihydrate) or salts, racemates, or isomers thereof.

In some embodiments, endothelial progenitor cells (EPCs) are mobilized following administration of the compounds or compositions of the invention, and optionally harvest and purified from other blood components. Optionally, EPC mobilization is induced by administration of at least one compound of the invention in conjunction with one or more of vascular endothelial growth factor (VEGF), a VEGF agonist (including but not limited to a VEGF agonist antibody) or AMD3100 or salts, racemates, or isomers thereof.

In some embodiments, mesenchymal stem cells (MSCs) or stromal progenitor cells (SPCs) are mobilized following administration of the compounds or compositions of the invention, and optionally harvest and purified from other blood components. Optionally, such mobilization is induced by administration of at least one compound of the invention in conjunction with one or more of G-CSF, VEGF, a VEGF agonist (including but not limited to a VEGF agonist antibody), AMD3100, or salts, racemates, or isomers thereof.

For immobilizing progenitor or stem cells, an appropriate dosage level will generally be about 0.001 to 100 mg per kg patient body weight per day which can be administered in single or multiple doses. The compounds may be administered as a single dose, a dose over time, as in i.v., or transdermal administration, or in multiple doses. The compounds of the invention can also be used in ex vivo treatment protocols to prepare cell cultures which are then used to replenish the blood cells of the subject. Ex vivo treatment can be conducted on autologous cells harvested from the peripheral blood or bone marrow or from allografts from matched donors.

The present compounds can be combined with other compounds and compositions that induce activation, proliferation or mobilization of progenitor/stem cells. In addition to those described above, these include but are not limited to Fms-related tyrosine kinase 3 ligand (Flt3 ligand), interleukin 3 (IL-3), interleukin 7 (IL-7), interleukin 20 (IL-20), Steel factor (SF) and granulocyte macrophage colony-stimulating factor (GM-CSF) and may provide therapeutic utilities that may require or benefit from treatment either before, after or simultaneously with mobilization of progenitor/stem cells. Accordingly, combination methods and compositions are also a component of the present invention to prevent and treat the condition or disease of interest. Additionally, the compounds of the present invention can provide benefit in conditions in which disregulation of stem cell mobilization may play a role, such as heart disease and pulmonary hypertension.

Method of Diagnosing Diseases and Disorders Associated with CXCR7

Still further, the compounds and compositions of the present invention are useful for the diagnosis of diseases and disorders associated with CXCR7. In particular, the compounds of the present invention can be prepared in a labeled form (e.g., radiolabeled) and used for the diagnosis of, for example, cancer. Labeled compounds of the present invention that bind to CXCR7 (e.g., antagonists or agonists) can be used to determine levels of CXCR7 in a mammalian subject. In some embodiments, the CXCR7 modulators are administered to a subject having cancer. In some cases, labeled compounds are administered to detect developing cancers, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma (see, CANCER:PRINCIPLES AND PRACTICE (DeVita, V. T. et al. eds 1997) for additional cancers); as well as brain and neuronal dysfunction, such as Alzheimer's disease and multiple sclerosis; kidney dysfunction; rheumatoid arthritis; cardiac allograft rejection; atherosclerosis (and elevated cholesterol levels); asthma; glomerulonephritis; contact dermatitis; inflammatory bowel disease; colitis; psoriasis; reperfusion injury; as well as other disorders and diseases described herein. In some embodiments, the subject does not have Kaposi's sarcoma, multicentric Castleman's disease or AIDS-associated primary effusion lymphoma. Since CXCR7 is often expressed in cancer cells but not non-cancer cells, it is typically desirable to administer antagonists of CXCR7 to subjects at risk of having cancer.

A variety of imaging and detection methods can be used for the detection of cancers. In some embodiments, direct methods are available to evaluate CXCR7 biodistribution in the body such as magnetic resonance imaging ("MRI"), positron emission tomography ("PET"), and single photon emission computed tomography ("SPECT"). Each of these methods can detect the distribution of a suitably labeled compound (generally as bound to CXCR7) within the body if that compound contains an atom with the appropriate nuclear properties. MRI detects paramagnetic nuclei; PET and SPECT detect the emission of particles from the decay of radionuclei.

For methods involving PET, it is necessary to incorporate an appropriate positron-emitting radionuclide. There are relatively few positron-emitting isotopes that are suitable for labeling a therapeutic agent. The carbon isotope, $^{11}C$, has been used for PET, but has a short half-life of 20.5 minutes. Accordingly, the facilities for synthesis and use are typically near to a cyclotron where the precursor $^{11}C$ starting material is generated. Another useful isotope, $^{18}F$, has a half-life of 110 minutes. This allows sufficient time for incorporation into a radiolabeled tracer, for purification and for administration into a human or animal subject. Other isotopes have even shorter half-lives. $^{13}N$ has a half-life of 10 minutes and $^{15}O$ has an even shorter half-life of 2 minutes. The emissions of both are more energetic, however, than those of $^{11}C$ and PET studies have been carried out with these isotopes (see, Clinical Positron Emission Tomography, Mosby Year Book, 1992, K. F. Hubner, et al., Chapter 2).

SPECT imaging employs isotope tracers that are γ-emitters. While the range of useful isotopes is greater than for PET, imaging with SPECT provides lower three-dimensional resolution. However, in some instances, SPECT is used to obtain clinically significant information about compound binding, localization and clearance rates. One useful isotope for SPECT imaging is $^{123}I$, a γ-emitter with a 13.3 hour half life. Compounds labeled with $^{123}I$ can be shipped up to about 1000 miles from the manufacturing site, or the isotope itself can be transported for on-site synthesis. Eighty-five percent of the isotope's emissions are 159 KeV photons, which are readily measured by SPECT instrumentation currently in use. Other halogen isotopes can serve for PET or SPECT imaging, or for conventional tracer labeling. These include $^{75}Br$, $^{76}Br$, $^{77}Br$ and $^{82}Br$ as having usable half-lives and emission characteristics.

In view of the above, the present invention provides methods for imaging a tumor, organ, or tissue, said method comprising:

(a) administering to a subject in need of such imaging, a radiolabeled or detectable form of a compound of Formula I; and (b) detecting said compound to determine where said compound is concentrated in said subject.

Additionally, the present invention provides methods for detecting elevated levels of CXCR7 in a sample, said method comprising:

(a) contacting a sample suspected of having elevated levels of CXCR7 with a radiolabeled or detectable form of a compound of Formula I;

(b) determining a level of compound that is bound to CXCR7 present in said sample to determine the level of CXCR7 present in said sample; and (c) comparing the level determined in step (b) with a control sample to determine if elevated levels of CXCR7 are present in said sample.

As with the treatment methods described herein, administration of the labeled compounds can be by any of the routes normally used for introducing a compound into ultimate contact with the tissue to be evaluated and is well known to those of skill in the art. Although more than one route can be used to administer a particular composition, a particular route can often provide a more immediate and more effective diagnosis than another route.

Combination Therapies

Inhibitors of CXCR7 can be supplied alone or in conjunction with one or more other drugs. Possible combination partners can include, e.g., additional anti-angiogenic factors and/or chemotherapeutic agents (e.g., cytotoxic agents) or radiation, a cancer vaccine, an immunomodulatory agent, an anti-vascular agent, a signal transduction inhibitor, an anti-proliferative agent, or an apoptosis inducer.

IV. Examples

The following examples are offered to illustrate, but not to limit the claimed invention.

Reagents and solvents used below can be obtained from commercial sources such as Aldrich Chemical Co. (Milwaukee, Wisconsin, USA). $^1H$-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the invention: rt, room temperature; HPLC, high pressure liquid chromatography; TFA, trifluoroacetic acid; LC-MSD, liquid chromatograph/mass selective detector; LC-MS, liquid chromatograph/mass spectrometer; $Pd_2dba_3$, tris(dibenzylideneacetone) dipalladium; THF, tetrahydrofuran; DMF, dimethylformamide or N,N-dimethylformamide; DCM, dichloromethane; DMSO, dimethyl sulfoxide; TLC, thin-layer chromatography; KHMDS, potassium hexamethyldisilazane; ES, electrospray; sat., saturated.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: 5-(2,4-difluorophenyl)-N-(1-(4-hydroxy-4-methylcyclohexyl)-3-(2-oxo-2-((2-(pyridin-2-yl)propan-2-yl)amino)ethyl)azetidin-3-yl)isoxazole-3-carboxamide

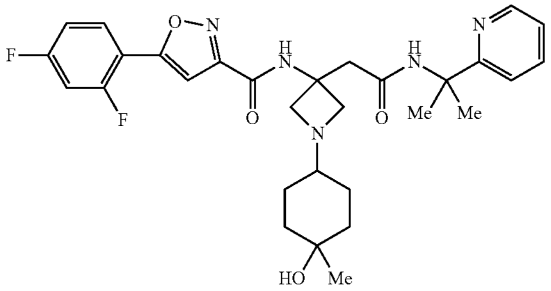 [SMILES: CC1(O)CCC(N2CC(CC(=O)NC(C)(C)c3ccccn3)(NC(=O)c3cc(-c4ccc(F)cc4F)on3)C2)CC1]

Step a: A mixture of tert-butyl 3-oxoazetidine-1-carboxylate (15 g, 88 mmol), ethyl hydrogen malonate (17 g, 130 mmol), and ammonium formate (20 g, 260 mmol) in 120 mL EtOH was stirred at 85° C. for 3 h. The volatiles were removed in vacuo and the residue was diluted with $Et_2O$ and washed with saturated $NaHCO_3$ (aq). The organic layer was dried over $MgSO_4$, filtered, and then concentrated in vacuo. The crude material was purified by silica gel column chromatography to give tert-butyl 3-amino-3-(2-ethoxy-2-oxoethyl)azetidine-1-carboxylate. MS: (ES) m/z calculated for $C_{12}H_{23}N_2O_4$ $[M+H]^+$ 259.2, found 259.3.

Step b: To a solution of tert-butyl 3-amino-3-(2-ethoxy-2-oxoethyl)azetidine-1-carboxylate (1.8 g, 7.1 mmol), 5-(2,4-difluorophenyl)isoxazole-3-carboxylic acid (1.6 g, 7.1 mmol), and DIPEA (1.3 mL, 7.5 mmol) in 40 mL DCM was added HATU (2.8 g, 7.4 mmol). The mixture was stirred at room temperature for 2 h. The reaction was quenched with saturated $NH_4Cl$ (aq) and the phases were separated. The aqueous phase was extracted with DCM and the combined organic layers were dried over $MgSO_4$, filtered and concentrated in vacuo. The crude material was purified by silica gel column chromatography to give tert-butyl 3-(5-(2,4-difluorophenyl)isoxazole-3-carboxamido)-3-(2-ethoxy-2-oxoethyl)azetidine-1-carboxylate. MS: (ES) m/z calculated for $C_{22}H_{26}F_2N_3O_6$ $[M+H]^+$ 466.2, found 466.2.

Step c: A mixture of tert-butyl 3-(5-(2,4-difluorophenyl)isoxazole-3-carboxamido)-3-(2-ethoxy-2-oxoethyl)azetidine-1-carboxylate (1.2 g, 3.3 mmol) in 4:1 DCM/TFA (20 mL) was stirred for 1 h. The contents were concentrated in vacuo to give ethyl 2-(3-(5-(2,4-difluorophenyl)isoxazole-3-carboxamido)azetidin-3-yl)acetate. MS: (ES) m/z calculated for $C_{17}H_{18}F_2N_3O_4$ $[M+H]^+$ 366.1, found 366.1.

Step d: To a mixture of ethyl 2-(3-(5-(2,4-difluorophenyl)isoxazole-3-carboxamido)azetidin-3-yl)acetate (800 mg, 2.0 mmol), triethylamine (0.55 mL, 4.0 mmol), and 4-hydroxy-4-methylcyclohexan-1-one (510 mg, 4.0 mmol) in 4:1 DCM/MeOH (20 mL) was added $NaBH(OAc)_3$ (840 mg, 4.0 mmol). The contents were stirred at room temperature for 1 h. The reaction was quenched with saturated $NaHCO_3$ (aq) and extracted with DCM. The combined organic layers were dried over $MgSO_4$, filtered, and concentrated in vacuo. The crude material was purified by silica gel column chromatography to give ethyl 2-(3-(5-(2,4-difluorophenyl)isoxazole-3-carboxamido)-1-(4-hydroxy-4-methylcyclohexyl)azetidin-3-yl)acetate (mixture of cis/trans isomers). MS: (ES) m/z calculated for $C_{24}H_{30}F_2N_3O_5$ $[M+H]^+$ 478.2, found 478.5.

Step e: To a solution of ethyl 2-(3-(5-(2,4-difluorophenyl)isoxazole-3-carboxamido)-1-(4-hydroxy-4-methylcyclohexyl)azetidin-3-yl)acetate (600 mg, 1.2 mmol) in 1:1 THF/$H_2O$ (20 mL) was added NaOH (300 mg, 7.5 mmol). The mixture was stirred at room temperature overnight. The reaction was quenched with 1N HCl (10 mL) and MeCN. The contents were concentrated in vacuo. The residue was triturated with acetone and filtered through Celite. The filtrate was concentrated to yield 2-(3-(5-(2,4-difluorophenyl)isoxazole-3-carboxamido)-1-(4-hydroxy-4-methylcyclohexyl)azetidin-3-yl)acetic acid (mixture of cis/trans isomers). MS: (ES) m/z calculated for $C_{22}H_{26}F_2N_3O_5$ $[M+H]^+$ 450.2, found 450.2.

Step f: To a mixture of 2-(3-(5-(2,4-difluorophenyl)isoxazole-3-carboxamido)-1-(4-hydroxy-4-methylcyclohexyl)azetidin-3-yl)acetic acid (100 mg, 0.21 mmol) in DCM (2 mL) was added 2-(pyridin-2-yl)propan-2-amine dihydrochloride (43 mg, 0.21 mmol), DIPEA (0.14 mL, 0.82 mmol), and HATU (82 mg, 0.22 mmol). The mixture was stirred for 1 h then concentrated in vacuo. The residue was purified by preparative HPLC to give the two separated isomers of 5-(2,4-difluorophenyl)-N-(1-(4-hydroxy-4-methylcyclohexyl)-3-(2-oxo-2-((2-(pyridin-2-yl)propan-2-yl)amino)ethyl)azetidin-3-yl)isoxazole-3-carboxamide.

Isomer 1: $^1H$ NMR (400 MHz, DMSO-$d_6$) δ 8.59-8.49 (m, 1H), 8.22-8.12 (m, 1H), 8.06 (d, J=8.1 Hz, 1H), 7.83-7.77 (m, 1H), 7.67-7.58 (m, 1H), 7.25 (dd, J=20.8, 9.8 Hz, 2H), 7.15-7.07 (m, 1H), 4.58-4.27 (m, 4H), 3.20-3.11 (m, 3H), 1.83-1.73 (m, 2H), 1.56-1.44 (m, 9H), 1.37-1.15 (m, 4H), 1.21 (s, 3H). MS: (ES) m/z calculated for $C_{30}H_{36}F_2N_5O_4$ $[M+H]^+$ 568.3, found 568.3.

Isomer 2: $^1H$ NMR (400 MHz, $CD_3OD$) δ 8.54-8.48 (m, 1H), 8.06 (m, 2H), 7.71 (d, J=8.0 Hz, 1H), 7.56-7.50 (m, 1H), 7.32-7.17 (m, 2H), 7.11 (dd, J=10.4, 3.5 Hz, 1H), 4.52 (d, J=11.8 Hz, 1H), 4.49-4.46 (m, 2H), 4.37 (d, J=11.7 Hz, 1H), 3.16-3.10 (m, 3H), 1.80-1.66 (m, 4H), 1.66 (s, 6H), 1.62-1.52 (m, 2H), 1.46-1.39 (m, 2H), 1.20 (s, 3H). MS: (ES) m/z calculated for $C_{30}H_{36}F_2N_5O_4$ $[M+H]^+$ 568.3, found 568.4.

Example 2: 5-(2,4-difluorophenyl)-N-(1-(4-hydroxy-4-methylcyclohexyl)-3-(2-oxo-2-((2-phenylpropan-2-yl)amino)ethyl)azetidin-3-yl)isoxazole-3-carboxamide

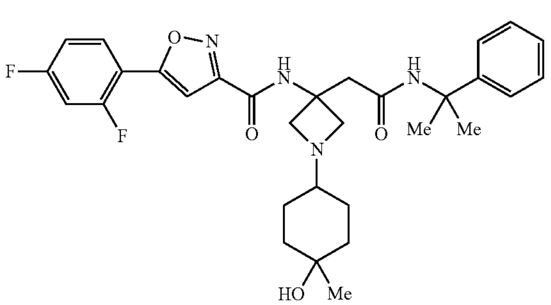 [SMILES: CC1(O)CCC(N2CC(CC(=O)NC(C)(C)c3ccccc3)(NC(=O)c3cc(-c4ccc(F)cc4F)on3)C2)CC1]

To a solution 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DMF (2 mL) was added 2-phenylpropan-2-amine (31 mg, 0.20 mmol), HATU (77 mg, 0.20 mmol) and DIPEA (0.070 mL, 0.40 mmol). The reaction mixture stirred at room temperature for 1 h and then quenched with 3 drops of $H_2O$. The crude material was purified by preparative HPLC to give the two separated isomers of 5-(2,4-difluorophenyl)-N-(1-(4-hydroxy-4-methylcyclohexyl)-3-(2-oxo-2 ((2-phenylpropan-2-yl)amino) ethyl)azetidin-3-yl)isoxazole-3-carboxamide.

Isomer 1: $^1$H NMR (400 MHz, DMSO-$d_6$) δ 9.61-9.48 (m, 1H), 8.41-8.36 (s, 1H), 8.19-8.07 (m, 1H), 7.67-7.58 (m, 1H), 7.42-7.32 (m, 1H), 7.31-7.18 (m, 3H), 7.16-7.02 (m, 3H), 4.49-4.27 (m, 4H), 3.31-3.16 (m, 1H), 3.14-3.04 (m, 2H), 1.88-1.73 (m, 2H), 1.61-1.46 (m, 8H), 1.38-1.15 (m, 4H), 1.12-1.02 (m, 3H). MS: (ES) m/z calculated for $C_{31}H_{37}F_2N_4O_4$ $[M+H]^+$ 567.3, found 567.3.

Isomer 2: $^1$H NMR (400 MHz, DMSO-$d_6$) δ 9.50 (s, 1H), 8.36-8.32 (m, 1H), 8.17-8.07 (m, 1H), 7.68-7.59 (m, 1H), 7.41-7.34 (m, 1H), 7.31-7.17 (m, 3H), 7.14-7.02 (m, 3H), 4.46-4.26 (m, 4H), 3.19-3.01 (m, 3H), 1.73-1.37 (m, 12H), 1.30-1.16 (m, 2H), 1.10 (s, 3H). MS: (ES) m/z calculated for $C_{31}H_{37}F_2N_4O_4$ $[M+H]^+$ 567.3, found 567.3.

Example 3: 5-(2,4-difluorophenyl)-N-3-(2-((2-(3-fluorophenyl)propan-2-yl)amino)-2-oxoethyl)-(1-(4-hydroxy-4-methylcyclohexyl)azetidin-3-yl)isoxazole-3-carboxamide

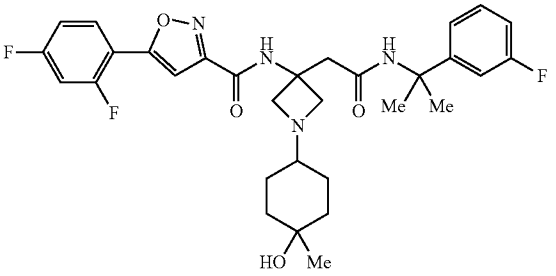 [SMILES: CC1(O)CCC(N2CC(CC(=O)NC(C)(C)c3cccc(F)c3)(NC(=O)c3cc(-c4ccc(F)cc4F)on3)C2)CC1]

To a solution of 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DMF (2 mL) was added 2-(3-fluororophenyl)propan-2-amine (32 mg, 0.20 mmol), HATU (77 mg, 0.20 mmol) and DIPEA (0.070 mL, 0.40 mmol). The reaction mixture was stirred at room temperature for 1 h and then quenched with 3 drops of $H_2O$. The crude material was purified by preparative HPLC to give the two separated isomers of 5-(2,4-difluorophenyl)-N-3-(2-((2-(3-fluorophenyl)propan-2-yl)amino)-2-oxoethyl)-(1-(4-hydroxy-4-methylcyclohexyl)azetidin-3-yl) isoxazole-3-carboxamide.

Isomer 1: $^1$H NMR (400 MHz, DMSO-$d_6$) δ 9.61-9.48 (m, 1H), 8.41-8.36 (s, 1H), 8.16-8.02 (m, 1H), 7.65-7.56 (m, 1H), 7.39-7.30 (m, 1H), 7.27-7.09 (m, 2H), 7.08-7.01 (m, 1H), 7.01-6.93 (m, 1H), 6.92-6.82 (m, 1H), 4.50-4.25 (m, 4H), 3.22 (s, 1H), 3.18-3.08 (m, 2H), 1.78 (d, J=8.5 Hz, 2H), 1.58-1.42 (m, 8H), 1.38-1.15 (m, 4H), 1.11-1.01 (m, 3H). MS: (ES) m/z calculated for $C_{31}H_{36}F_3N_4O_4$ $[M+H]^+$ 585.3, found 585.5.

Isomer 2: $^1$H NMR (400 MHz, DMSO-$d_6$) δ 9.50 (s, 1H), 8.40-8.35 (m, 1H), 8.14-8.04 (m, 1H), 7.67-7.55 (m, 1H), 7.35 (dd, J=8.8, 8.8 Hz, 1H), 7.28-7.08 (m, 2H), 7.08-7.01 (m, 1H), 7.00-6.82 (m, 2H), 4.48-4.19 (m, 4H), 3.10-3.01 (m, 3H), 1.72-1.52 (m, 4H), 1.48 (d, J=2.4 Hz, 8H), 1.28-1.13 (m, 2H), 1.08 (d, J=2.5 Hz, 3H). MS: (ES) m/z calculated for $C_{31}H_{36}F_3N_4O_4$ $[M+H]^+$ 585.3, found 585.5.

Example 4: N-(3-(2-((2-(3-chlorophenyl)propan-2-yl)amino)-2-oxoethyl)-1-(4-hydroxy-4-methylcyclohexyl)azetidin-3-yl)-5-(2,4-difluorophenyl)isoxazole-3-carboxamide

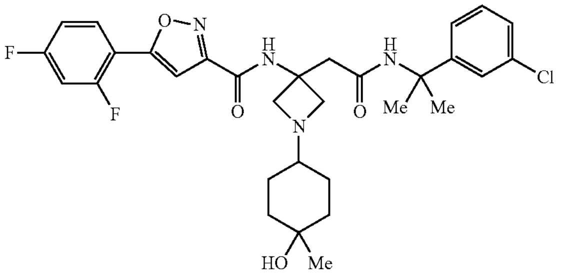 [SMILES: CC1(O)CCC(N2CC(CC(=O)NC(C)(C)c3cccc(Cl)c3)(NC(=O)c3cc(-c4ccc(F)cc4F)on3)C2)CC1]

Step a: To a solution of 3-chlorobenzonitrile (1.00 g, 7.30 mmol) in ether (100 mL) was added dropwise a solution of 3.0 M methylmagnesium bromide (7.30 mL, 21.9 mmol) followed by titanium(IV) isopropoxide (2.16 mL, 7.30 mmol). The mixture was refluxed overnight under $N_2$ then cooled to 0° C. and quenched with water followed by 10% NaOH (aq). The contents were filtered through a plug of Celite and washed with DCM. The organic layer of the filtrate was collected, dried over $Na_2SO_4$, concentrated in vacuo and purified by silica gel column chromatography to give 2-(3-chlorophenyl)propan-2-amine. MS: (ES) m/z calculated for $C_9H_{13}ClN$ $[M+H]^+$ 170.1, found 170.2.

Step b: To a solution of 2-(3-(5-(2,4-difluorophenyl) isoxazole-3-carboxamido)-1-(4-hydroxy-4-methylcyclohexyl)azetidin-3-yl)acetic acid (50 mg, 0.10 mmol) in DMF (2 mL) was added 2-(3-chlorophenyl)propan-2-amine (34 mg, 0.20 mmol), HATU (77 mg, 0.20 mmol) and DIPEA (0.070 mL, 0.40 mmol). The reaction mixture was stirred at room temperature for 1 h and then quenched with 3 drops of $H_2O$. The mixture purified by preparative HPLC to give the two separated isomers of N-(3-(2-((2-(3-chlorophenyl)propan-2-yl)amino)-2-oxoethyl)-1-(4-hydroxy-4-methylcyclohexyl)azetidin-3-yl)-5-(2,4-difluorophenyl)isoxazole-3-carboxamide.

Isomer 1: $^1$H NMR (400 MHz, $CD_3OD$) δ 8.58 (s, 1H), 8.47 (s, 1H), 8.12-7.96 (m, 1H), 7.38-7.05 (m, 7H), 4.58-4.35 (m, 4H), 3.30-3.09 (m, 3H), 2.03-1.91 (m, 2H), 1.74-1.64 (m, 2H), 1.63-1.55 (m, 6H), 1.55-1.45 (m, 2H), 1.44-1.25 (m, 2H), 1.20 (s, 3H). MS: (ES) m/z calculated for $C_{31}H_{36}ClF_2N_4O_4$ $[M+H]^+$ 601.2, found 601.3.

Isomer 2: $^1$H NMR (400 MHz, $CD_3OD$) δ 8.49 (s, 1H), 8.47 (s, 1H), 8.10-8.02 (m, 1H), 7.32-7.07 (m, 7H), 4.56-4.33 (m, 4H), 3.30-3.07 (m, 3H), 1.86-1.70 (m, 4H), 1.65-1.49 (m, 8H), 1.48-1.35 (m, 2H), 1.20 (s, 3H). MS: (ES) m/z calculated for $C_{31}H_{36}ClF_2N_4O_4$ $[M+H]^+$ 601.2, found 601.3.

Example 5: 5-(2,4-difluorophenyl)-N-3-(2-((2-(2,5-difluorophenyl)propan-2-yl)amino)-2-oxoethyl)-(1-(4-hydroxy-4-methylcyclohexyl)-azetidin-3-yl) isoxazole-3-carboxamide

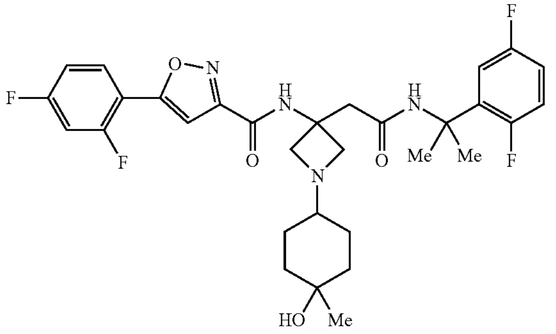 [SMILES: CC1(O)CCC(N2CC(CC(=O)NC(C)(C)c3cc(F)ccc3F)(NC(=O)c3cc(-c4ccc(F)cc4F)on3)C2)CC1]

Step a: To a solution of 2,5-difluorobenzonitrile (1.00 g, 7.19 mmol) in ether (100 mL) was added dropwise a solution of 3.0 M methylmagnesium bromide (7.30 mL, 21.9 mmol) followed by titanium(IV) isopropoxide (2.16 mL, 7.30 mmol). The resulting mixture was refluxed overnight under $N_2$, then cooled to 0° C. and quenched with water followed by 10% NaOH (aq). The contents were filtered through a plug of Celite and washed with DCM. The organic layer of the filtrate was collected, dried over $Na_2SO_4$, concentrated in vacuo and purified by silica gel column chromatography to give 2-(2,5-difluorophenyl)propan-2-amine. MS: (ES) m/z calculated for $C_9H_{12}F_2N$ $[M+H]^+$ 172.1, found 172.2.

Step b: To a solution of 2-(3-(5-(2,4-difluorophenyl) isoxazole-3-carboxamido)-1-(4-hydroxy-4-methylcyclohexyl)azetidin-3-yl)acetic acid (50 mg, 0.10 mmol) in DMF (2 mL) was added 2-(2,5-difluorophenyl)propan-2-amine (35 mg, 0.20 mmol), HATU (77 mg, 0.20 mmol) and DIPEA (0.070 mL, 0.40 mmol). The reaction mixture was stirred at room temperature for 1 h and then quenched with 3 drops of $H_2O$. The mixture purified by preparative HPLC to give the two separated isomers of 5-(2,4-difluorophenyl)-N-(3-(2-((2-(2,5-difluorophenyl)propan-2-yl)amino)-2-oxoethyl)-1-(4-hydroxy-4-methylcyclohexyl)azetidin-3-yl)isoxazole-3-carboxamide.

Isomer 1: $^1H$ NMR (400 MHz, $CD_3OD$) δ 8.65 (s, 1H), 8.55 (s, 1H), 8.14-8.02 (m, 1H), 7.32-7.18 (m, 2H), 7.15-7.02 (m, 2H), 6.98-6.74 (m, 2H), 4.57-4.33 (m, 4H), 3.30-3.07 (m, 3H), 1.97 (s, 2H), 1.75-1.56 (m, 8H), 1.55-1.30 (m, 4H), 1.21 (s, 3H). MS: (ES) m/z calculated for $C_{31}H_{35}F_4N_4O_4$ $[M+H]^+$ 603.3, found 603.5.

Isomer 2: $^1H$ NMR (400 MHz, $CD_3OD$) δ 8.57 (s, 1H), 8.55 (s, 1H), 8.13-8.03 (m, 1H), 7.33-7.18 (m, 2H), 7.14-7.02 (m, 2H), 6.96-6.87 (m, 1H), 6.86-6.75 (m, 1H), 4.55-4.30 (m, 4H), 3.15-3.08 (m, 3H), 1.85-1.71 (m, 4H), 1.66-1.51 (m, 8H), 1.47-1.35 (m, 2H), 1.20 (s, 3H). MS: (ES) m/z calculated for $C_{31}H_{35}F_4N_4O_4$ $[M+H]^+$ 603.3, found 603.5.

Example 6: 5-(2,4-difluorophenyl)-N-(3-(2-((2-(3,5-difluorophenyl)propan-2-yl)amino)-2-oxoethyl)-1-(4-hydroxy-4-methylcyclohexyl)azetidin-3-yl)isoxazole-3-carboxamide

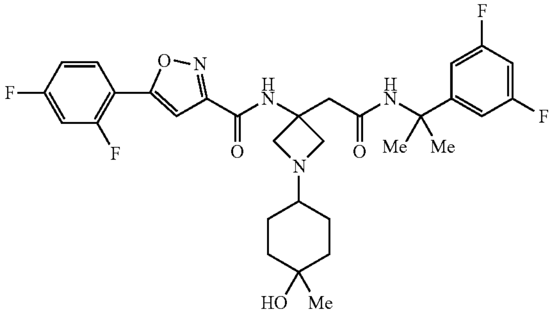 [SMILES: CC1(O)CCC(N2CC(CC(=O)NC(C)(C)c3cc(F)cc(F)c3)(NC(=O)c3cc(-c4ccc(F)cc4F)on3)C2)CC1]

Step a: To a solution of 3,5-difluorobenzonitrile (1.00 g, 7.19 mmol) in ether (100 mL) was added dropwise a solution of 3.0 M methylmagnesium bromide (7.30 mL, 21.9 mmol) followed by titanium(IV) isopropoxide (2.16 mL, 7.30 mmol). The resulting mixture was refluxed overnight under $N_2$, then cooled to 0° C. and quenched with water followed by 10% NaOH (aq). The mixture was filtered through a plug of Celite and washed with DCM. The organic layer of the filtrate was collected, dried over $Na_2SO_4$, concentrated in vacuo and purified by silica gel column chromatography to give 2-(3,5-difluorophenyl)propan-2-amine. MS: (ES) m/z calculated for $C_9H_{12}F_2N$ $[M+H]^+$ 172.1, found 172.2.

Step b: To a solution of 2-(3-(5-(2,4-difluorophenyl) isoxazole-3-carboxamido)-1-(4-hydroxy-4-methylcyclohexyl)azetidin-3-yl)acetic acid (50 mg, 0.10 mmol) in DMF (2 mL) was added 2-(3,5-difluorophenyl)propan-2-amine (35 mg, 0.20 mmol), HATU (77 mg, 0.20 mmol) and DIPEA (0.070 mL, 0.40 mmol). The reaction mixture was stirred at room temperature for 1 h and then quenched with 3 drops of $H_2O$. The crude material was purified by reverse phase HPLC to give the two separated isomers of 5-(2,4-difluorophenyl)-N-(3-(2-((2-(3,5-difluorophenyl)propan-2-yl) amino)-2-oxoethyl)-1-(4-hydroxy-4-methylcyclohexyl)azetidin-3-yl)isoxazole-3-carboxamide.

Isomer 1: $^1H$ NMR (400 MHz, $CD_3OD$) δ 8.58 (s, 1H), 8.49 (s, 1H), 8.11-8.01 (m, 1H), 7.32-7.18 (m, 2H), 7.13-7.06 (m, 1H), 6.95-6.84 (m, 2H), 6.76-6.65 (m, 1H), 4.58-4.35 (m, 4H), 3.30-3.09 (m, 3H), 2.05-1.92 (m, 2H), 1.75-1.65 (m, 2H), 1.64-1.46 (m, 8H), 1.45-1.31 (m, 2H), 1.21 (s, 3H). MS: (ES) m/z calculated for $C_{31}H_{35}F_4N_4O_4$ $[M+H]^+$ 603.3, found 603.5.

Isomer 2: $^1H$ NMR (400 MHz, $CD_3OD$) δ 8.51 (s, 1H), 8.48 (s, 1H), 8.11-8.01 (m, 1H), 7.31-7.18 (m, 2H), 7.10 (dd, J=10.1, 3.5 Hz, 1H), 6.92-6.83 (m, 2H), 6.74-6.66 (m, 1H), 4.55-4.34 (m, 4H), 3.30-3.11 (m, 3H), 1.86-1.70 (m, 4H), 1.66-1.50 (m, 8H), 1.48-1.34 (m, 2H), 1.20 (s, 3H). MS: (ES) m/z calculated for $C_{31}H_{35}F_4N_4O_4$ $[M+H]^+$ 603.3, found 603.5.

Example 7: N-(3-(2-((2-(3-cyanophenyl)propan-2-yl)amino)-2-oxoethyl)-1-(4-hydroxy-4-methylcyclohexyl)azetidin-3-yl)-5-(2,4-difluorophenyl)isoxazole-3-carboxamide

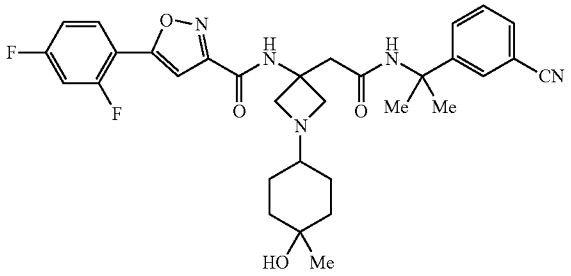 [SMILES: CC1(O)CCC(N2CC(CC(=O)NC(C)(C)c3cccc(C#N)c3)(NC(=O)c3cc(-c4ccc(F)cc4F)on3)C2)CC1]

Step a: To a solution of tert-butyl (2-(3-bromophenyl) propan-2-yl)carbamate (1.00 g, 3.18 mmol) in 40 mL of dioxane was added $Zn(CN)_2$ (0.747 g, 6.36 mmol). The contents were sparged with $N_2$ for 10 min before Pd(dppf) $Cl_2$ (0.233 g, 0.318 mmol) was added and the resulting mixture was heated for 4 h under $N_2$. The reaction was cooled to room temperature and quenched with saturated $NH_4Cl$ (aq) then extracted with DCM. The organic layer was collected, dried over $MgSO_4$, concentrated in vacuo and purified by silica gel column chromatography to give tert-butyl (2-(3-cyanophenyl)propan-2-yl)carbamate. MS: (ES) m/z calculated for $C_{15}H_{21}N_2O_2$ $[M+H]^+$ 261.2, found 261.2.

Step b: To a solution of tert-butyl (2-(3-cyanophenyl) propan-2-yl)carbamate (0.50 g, 1.9 mmol) in 8 mL of DCM was added trifluoroacetic acid. The reaction mixture was stirred overnight at room temperature then quenched with saturated $NaHCO_3$ (aq). The contents were extracted with DCM and the organic layer was collected, dried over $MgSO_4$, and concentrated in vacuo to give 3-(2-aminopropan-2-yl)benzonitrile. MS: (ES) m/z calculated for $C_{10}H_{13}N_2$ $[M+H]^+$ 161.1, found 161.2.

Step c: To a mixture of 2-(3-(5-(2,4-difluorophenyl)isoxazole-3-carboxamido)-1-(4-hydroxy-4-methylcyclohexyl) azetidin-3-yl)acetic acid (50 mg, 0.10 mmol) in DMF (2 mL) was added 3-(2-aminopropan-2-yl)benzonitrile (32 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The mixture purified by preparative HPLC to give the two separated isomers of N-(3-(2-((2-(3-cyanophenyl)propan-2-yl)amino)-2-oxoethyl)-1-(4-hydroxy-4-methylcyclohexyl) azetidin-3-yl)-5-(2,4-difluorophenyl)isoxazole-3-carboxamide.

Isomer 1: $^1H$ NMR (400 MHz, $CD_3OD$) δ 8.61 (s, 1H), 8.52 (s, 1H), 8.12-8.02 (m, 1H), 7.71-7.59 (m, 2H), 7.56-7.49 (m, 1H), 7.46-7.35 (m, 1H), 7.30-7.17 (m, 2H), 7.14-7.07 (m, 1H), 4.61-4.32 (m, 4H), 3.30-3.09 (m, 2H), 2.05-1.91 (m, 2H), 1.77-1.45 (m, 8H), 1.45-1.27 (m, 1H), 1.20 (s, 3H). MS: (ES) m/z calculated for $C_{32}H_{36}F_2N_5O_4$ $[M+H]^+$ 592.3, found 592.3.

Isomer 2: $^1H$ NMR (400 MHz, $CD_3OD$) δ 8.55 (s, 1H), 8.52 (s, 1H), 8.11-8.03 (m, 1H), 7.68-7.59 (m, 2H), 7.55-7.49 (m, 1H), 7.45-7.35 (m, 1H), 7.31-7.17 (m, 2H), 7.13-7.07 (m, 1H), 4.56-4.33 (m, 4H), 3.30-3.11 (m, 3H), 1.86-1.70 (m, 4H), 1.66-1.50 (m, 8H), 1.48-1.33 (m, 2H), 1.20 (s, 3H). MS: (ES) m/z calculated for $C_{32}H_{36}F_2N_5O_4$ $[M+H]^+$ 592.3, found 592.3.

Example 8: 5-(2,4-difluorophenyl)-N-(1-(4-hydroxy-4-methylcyclohexyl)-3-(2-((2-(3-methoxyphenyl)propan-2-yl)amino)-2-oxoethyl)azetidin-3-yl) isoxazole-3-carboxamide

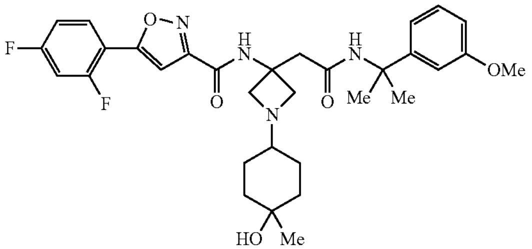 [SMILES: COc1cccc(C(C)(C)NC(=O)CC2(NC(=O)c3cc(-c4ccc(F)cc4F)on3)CN(C3CCC(C)(O)CC3)C2)c1]

Step a: To a solution of 3-methoxybenzonitrile (5.0 g, 29.8 mmol) in ether (120 mL) was added dropwise a solution of 3.0 M methylmagnesium bromide (29.8 mL, 89.5 mmol) followed by titanium(IV) isopropoxide (8.82 mL, 29.8 mmol). The mixture was refluxed overnight under $N_2$ then cooled to 0° C., quenched with water followed by 10% NaOH (aq). The contents were filtered through a plug of Celite and washed with DCM. The organic layer of the filtrate was collected, dried over $Na_2SO_4$, concentrated in vacuo and purified by silica gel column chromatography to give 2-(3-methoxyphenyl)propan-2-amine. MS: (ES) m/z calculated for $C_{10}H_{16}NO$ $[M+H]^+$ 166.1, found 166.0.

Step b: To a solution of 2-(3-(5-(2,4-difluorophenyl) isoxazole-3-carboxamido)-1-(4-hydroxy-4-methylcyclohexyl)azetidin-3-yl)acetic acid (50 mg, 0.10 mmol) in DMF (2 mL) was added 2-(3-methoxyphenyl)propan-2-amine (40 mg, 0.24 mmol), HATU (100 mg, 0.26 mmol) and DIPEA (0.57 mL, 0.82 mmol). The reaction mixture was stirred at room temperature for 1 h and then quenched with 3 drops of $H_2O$. The crude material was purified by preparative HPLC to give the two separated isomers of 5-(2,4-difluorophenyl)-N-(1-(4-hydroxy-4-methylcyclohexyl)-3-(2-((2-(3-methoxyphenyl)propan-2-yl)amino)-2-oxoethyl)azetidin-3-yl)isoxazole-3-carboxamide.

Isomer 1: $^1H$ NMR (400 MHz, $CD_3OD$) δ 8.50 (s, 1H), 8.41 (s, 1H), 8.10-8.02 (m, 1H), 7.30-7.18 (m, 2H), 7.14-7.06 (m, 1H), 6.92-6.72 (m, 1H), 6.69 (d, J=8.0 Hz, 1H), 4.57-4.35 (m, 4H), 3.70-3.64 (m, 3H), 3.18-3.08 (m, 2H), 1.95 (bs, 2H), 1.73-1.30 (m, 13H), 1.20 (s, 3H). MS: (ES) m/z calculated for $C_{32}H_{39}F_2N_4O_5$ $[M+H]^+$ 597.3, found 597.5.

Isomer 2: $^1H$ NMR (400 MHz, $CD_3OD$) δ 8.41 (s, 1H), 8.12-8.03 (m, 1H), 7.30-7.18 (m, 2H), 7.14-7.06 (m, 2H), 6.87 (d, J=8.0 Hz, 1H), 6.83 (s, 1H), 6.69 (d, J=7.6 Hz, 1H), 4.52-4.34 (m, 3H), 3.65 (s, 3H), 3.12-3.09 (m, 3H), 1.90-1.30 (m, 15H), 1.20 (s, 3H). MS: (ES) m/z calculated for $C_{32}H_{39}F_2N_4O_5$ $[M+H]^+$ 597.3, found 597.5.

Example 9: 5-(2,4-difluorophenyl)-N-(3-(2-((2-(5-fluoro-2-methoxyphenyl)propan-2-yl)amino)-2-oxoethyl)-1-(4-hydroxy-4-methylcyclohexyl)azetidin-3-yl)isoxazole-3-carboxamide

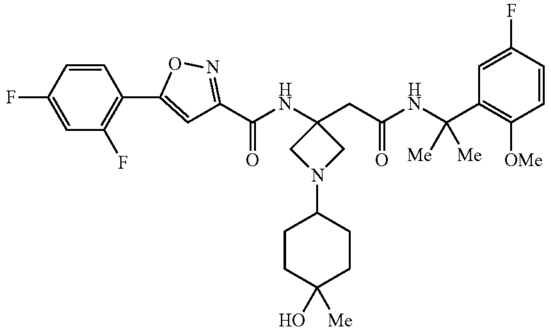 [SMILES: COc1ccc(F)cc1C(C)(C)NC(=O)CC1(NC(=O)c2cc(-c3ccc(F)cc3F)on2)CN(C2CCC(C)(O)CC2)C1]

Step a: To a solution of 5-fluoro-2-methoxybenzonitrile (1.00 g, 5.46 mmol) in ether (100 mL) was added dropwise a solution of 3.0 M methylmagnesium bromide (5.55 mL, 16.7 mmol) followed by titanium(IV) isopropoxide (1.65 mL, 5.46 mmol). The resulting mixture was refluxed overnight under $N_2$, then was cooled to 0° C. and quenched with water followed by 10% NaOH (aq). The contents were filtered through a plug of Celite and washed with DCM. The organic layer of the filtrate was collected, dried over $Na_2SO_4$, concentrated in vacuo and purified by silica gel column chromatography to give 2-(5-fluoro-2-methoxyphenyl)propan-2-amine. MS: (ES) m/z calculated for $C_{10}H_{15}FNO$ $[M+H]^+$ 184.1, found 184.0.

Step b: To a solution of 2-(3-(5-(2,4-difluorophenyl) isoxazole-3-carboxamido)-1-(4-hydroxy-4-methylcyclohexyl)azetidin-3-yl)acetic acid (50 mg, 0.10 mmol) in DMF (2 mL) was added 2-(5-fluoro-2-methoxyphenyl)propan-2-amine (37 mg, 0.20 mmol), HATU (77 mg, 0.20 mmol) and DIPEA (0.070 mL, 0.40 mmol). The reaction mixture was stirred at room temperature for 1 h and then quenched with 3 drops of $H_2O$. The mixture purified by preparative HPLC to give the two separated isomers of 5-(2,4-difluorophenyl)-N-(1-(4-hydroxy-4-methylcyclohexyl)-3-(2-((2-(5-fluoro-2-methoxyphenyl)propan-2-yl)amino)-2-oxoethyl)azetidin-3-yl)isoxazole-3-carboxamide.

Isomer 1: $^1H$ NMR (400 MHz, DMSO-$d_6$) δ 9.66-9.47 (m, 1H), 8.23-8.14 (m, 1H), 8.12-8.03 (m, 1H), 7.65-7.56 (m, 1H), 7.38-7.30 (m, 1H), 7.24-7.16 (m, 1H), 6.93-6.78 (m, 3H), 4.46-4.22 (m, 4H), 3.61 (s, 3H), 3.30-3.22 (m, 1H), 3.09-2.98 (m, 2H), 1.85-1.71 (m, 2H), 1.61-1.46 (m, 8H), 1.37-1.14 (m, 4H), 1.09-1.00 (m, 3H). MS: (ES) m/z calculated for $C_{32}H_{38}F_3N_4O_5$ $[M+H]^+$ 615.3, found 615.3.

Isomer 2: $^1H$ NMR (400 MHz, DMSO-$d_6$) δ 9.54 (s, 1H), 8.19-8.14 (m, 1H), 8.13-8.02 (m, 1H), 7.65-7.56 (m, 1H), 7.39-7.30 (m, 1H), 7.26-7.15 (m, 1H), 6.94-6.78 (m, 3H), 4.43-4.21 (m, 4H), 3.61 (s, 3H), 3.15-2.96 (m, 3H), 1.71-1.34 (m, 12H), 1.27-1.12 (m, 2H), 1.07 (s, 3H). MS: (ES) m/z calculated for $C_{32}H_{38}F_3N_4O_5$ $[M+H]^+$ 615.3, found 615.3.

Example 10: N-(1-cyclohexyl-3-(2-((2-(3-fluorophenyl)propan-2-yl)amino)-2-oxoethyl)azetidin-3-yl)-5-(2,4-difluorophenyl)isoxazole-3-carboxamide

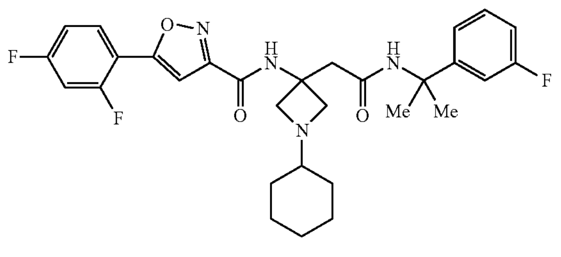 [SMILES: CC(C)(NC(=O)CC1(NC(=O)c2cc(-c3ccc(F)cc3F)on2)CN(C2CCCCC2)C1)c1cccc(F)c1]

Step a: To a solution of methyl 2-(3-(5-(2,4-difluorophenyl)isoxazole-3-carboxamido)azetidin-3-yl)acetate (1.4 g, 3.6 mmol) in 27 mL of DCM was added cyclohexanone (0.62 mL, 6.0 mmol) and DIPEA (2.1 mL, 12.0 mmol). After 30 min, $NaBH(OAc)_3$ (1.68 g, 8.0 mmol) was added and the mixture was stirred at room temperature. Upon completion, the reaction was quenched with $H_2O$ and aqueous layer was extracted with EtOAc. The organic layers were combined, dried with sodium sulfate, filtered and concentrated. The resultant residue was purified by silica gel column chromatography to provide methyl 2-(1-cyclohexyl-3-(5-(2,4-difluorophenyl)isoxazole-3-carboxamido)azetidin-3-yl)acetate. MS: (ES) m/z calculated for $C_{22}H_{26}F_2N_3O_4$ $[M+H]^+$ 434.2, found 434.2.

Step b: To a solution of methyl 2-(1-cyclohexyl-3-(5-(2,4-difluorophenyl)isoxazole-3-carboxamido)azetidin-3-yl) acetate (1.55 g, 3.9 mmol) in 10.7 mL of THF was added a solution of 1M LiOH (10.7 mL, 10.7 mmol). The reaction mixture was stirred at room temperature and then quenched with 1N HCl. The volatiles were removed in vacuo and the resultant solid was filtered, washed and collected to provide 2-(1-cyclohexyl-3-(5-(2,4-difluorophenyl)isoxazole-3-carboxamido)azetidin-3-yl)acetic acid. MS: (ES) m/z calculated for $C_{21}H_{24}F_2N_3O_4$ $[M+H]^+$ 420.2, found 420.1.

Step c: To a solution of 2-(1-cyclohexyl-3-(5-(2,4-difluorophenyl)isoxazole-3-carboxamido)azetidin-3-yl)acetic acid (75 mg, 0.18 mmol) in 1.2 mL of DMF was added 2-(3-fluorophenyl)propan-2-amine (41 mg, 0.30 mmol), DIPEA (0.16 mL, 0.92 mmol), and HATU (0.20 g, 0.53 mmol). The reaction mixture was stirred at room temperature for 2 h, then quenched with $H_2O$. The aqueous layer was extracted with EtOAc and the organic layers were combined, dried with sodium sulfate, filtered and concentrated. The crude residue was purified by silica gel column chromatography followed by preparative HPLC to yield N-(1-cyclohexyl-3-(2-((2-(3-fluorophenyl)propan-2-yl)amino)-2-oxoethyl)azetidin-3-yl)-5-(2,4-difluorophenyl)isoxazole-3-carboxamide. $^1H$ NMR (400 MHz, DMSO-$d_6$) δ: 9.53 (d, J=26.2 Hz, 1H), 8.38 (d, J=2.9 Hz, 1H), 8.08 (dddd, J=8.8, 8.8, 6.4, 2.5 Hz, 1H), 7.60 (ddd, J=10.2, 10.2, 2.0 Hz 1H), 7.34 (ddd, J=8.4, 8.4, 2.4 Hz, 1H), 7.23 (dd, J=20.4, 3.1 Hz, 1H), 7.16-7.06 (m, 1H), 7.03 (d, J=8.0 Hz, 1H), 6.95 (dddd, J=11.0, 2.2, 2.2, 2.2 Hz, 1H), 6.86 (dddd, J=8.3, 8.3, 5.8, 2.4 Hz, 1H), 4.53-4.03 (m, 4H), 3.32 (s, 1H), 3.18-3.08 (m, 1H), 3.06 (s, 1H), 1.94-1.65 (m, 4H), 1.65-1.52 (m, 1H), 1.47 (s, 6H), 1.36-0.90 (m, 5H). MS: (ES) m/z calculated for $C_{30}H_{34}F_3N_4O_3$ $[M+14]^+$ 555.3, found 555.3.

Example 11: N-(1-(cyclopropylmethyl)-3-(2-oxo-2-((1-(pyrimidin-2-yl)cyclopropyl)amino)ethyl)azetidin-3-yl)-5-(2,4-difluorophenyl)isoxazole-3-carboxamide

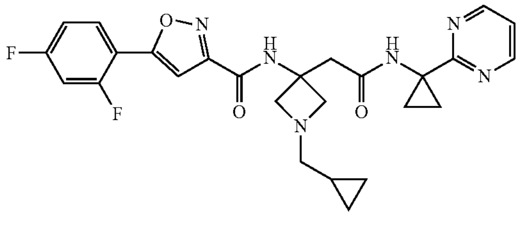 [SMILES: O=C(CC1(NC(=O)c2cc(-c3ccc(F)cc3F)on2)CN(CC2CC2)C1)NC1(c2ncccn2)CC1]

Step a: To a solution of tert-butyl 3-(5-(2,4-difluorophenyl)isoxazole-3-carboxamido)-3-(2-ethoxy-2-oxoethyl)azetidine-1-carboxylate (600 mg, 1.2 mmol) in 4:1 THF/$H_2O$ (5 mL) was added LiOH (240 mg, 6.0 mmol). The reaction mixture was stirred at room temperature overnight. The solvents were removed in vacuo and the residue was treated with 1N HCl. The mixture was then diluted with EtOAc and washed with $H_2O$. The organic layer was concentrated and the crude material was purified by silica gel column chromatography to yield 2-(1-(tert-butoxycarbonyl)-3-(5-(2,4-difluorophenyl)isoxazole-3-carboxamido)azetidin-3-yl)acetic acid. MS: (ES) m/z calculated for $C_{20}H_{22}F_2N_3O_6$ $[M+H]^+$ 438.1, found 438.2.

Step b: To a solution of 2-(1-(tert-butoxycarbonyl)-3-(5-(2,4-difluorophenyl)isoxazole-3-carboxamido)azetidin-3-yl)acetic acid (230 mg, 0.52 mmol) in DCM (2 mL) was added 1-(pyrimidin-2-yl)cyclopropan-1-amine dihydrochloride (110 mg, 0.52 mmol), DIPEA (0.36 mL, 2.08 mmol), and HATU (220 mg, 0.58 mmol). The reaction mixture was stirred at room temperature for 1 h. The solvent was removed in vacuo and the residue was purified by silica gel column chromatography to yield tert-butyl 3-(5-(2,4-difluorophenyl)isoxazole-3-carboxamido)-3-(2-oxo-2-((1-(pyrimidin-2-yl)cyclopropyl)amino)ethyl)azetidine-1-carboxylate. MS: (ES) m/z calculated for $C_{27}H_{29}F_2N_6O_5$ $[M+H]^+$ 555.2, found 555.2.

Step c: A mixture of tert-butyl 3-(5-(2,4-difluorophenyl)isoxazole-3-carboxamido)-3-(2-oxo-2-((1-(pyrimidin-2-yl)cyclopropyl)amino)ethyl)azetidine-1-carboxylate (288 mg, 0.52 mmol) in 1:1 DCM/TFA (2 mL) was stirred at room temperature for 1 h. The solvent was removed in vacuo to give 5-(2,4-difluorophenyl)-N-(3-(2-oxo-2-((1-(pyrimidin-2-yl)cyclopropyl)amino)ethyl)azetidin-3-yl)isoxazole-3-carboxamide.

Step d: To a mixture of 5-(2,4-difluorophenyl)-N-(3-(2-oxo-2-((1-(pyrimidin-2-yl)cyclopropyl)amino)ethyl)azetidin-3-yl)isoxazole-3-carboxamide (57 mg, 0.1 mmol), triethylamine (0.05 mL, 0.4 mmol), and cyclopropanecarbaldehyde (15 mg, 0.2 mmol) in 4:1 DCM/MeOH (2 mL) was added $NaBH(OAc)_3$ (42 mg, 0.2 mmol). The contents were stirred at room temperature for 1 h, then filtered and purified by preparative HPLC to give N-(1-(cyclopropylmethyl)-3-(2-oxo-2-((1-(pyrimidin-2-yl)cyclopropyl)amino)ethyl)azetidin-3-yl)-5-(2,4-difluorophenyl)isoxazole-3-carboxamide. $^1H$ NMR (400 MHz, $CD_3OD$) δ 8.60 (dd, J=5.1, 5.1 Hz, 2H), 8.05 (dd, J=6.4, 6.4 Hz, 1H), 7.31-7.17 (m, 3H), 7.12 (dd, J=11.9, 3.5 Hz, 1H), 4.69 (d, J=10.6 Hz, 2H), 4.56 (d, J=12.4 Hz, 2H), 3.25 (d, J=7.3 Hz, 1H), 3.20-3.09 (m, 3H), 1.66 (q, J=4.4 Hz, 2H), 1.31 (dd, J=3.9, 3.9 Hz, 2H), 1.04 (s, 1H), 0.70 (s, 2H), 0.41 (s, 2H). MS: (ES) m/z calculated for $C_{26}H_{27}F_2N_6O_3$ $[M+14]^+$ 509.2, found 509.2.

Example 12: 5-(2,4-difluorophenyl)-N-(1-((3-methyloxetan-3-yl)methyl)-3-(2-oxo-2-((2-(pyridin-2-yl)propan-2-yl)amino)ethyl)azetidin-3-yl)isoxazole-3-carboxamide

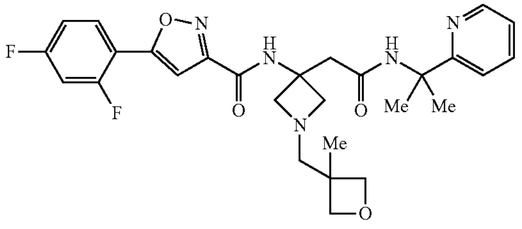 [SMILES: CC1(CN2CC(CC(=O)NC(C)(C)c3ccccn3)(NC(=O)c3cc(-c4ccc(F)cc4F)on3)C2)COC1]

Step a: To a mixture of ethyl 2-(3-(5-(2,4-difluorophenyl)isoxazole-3-carboxamido)azetidin-3-yl)acetate (600 mg, 1.29 mmol), triethylamine (0.55 mL, 4.0 mmol), and 3-methyloxetane-3-carbaldehyde (260 mg, 2.0 mmol) in 4:1 DCM/MeOH (10 mL) was added $NaBH(OAc)_3$ (551 mg, 2.0 mmol). After stirring at room temperature for 1 h, the reaction was quenched with saturated $NaHCO_3$ (aq) and the aqueous layer was extracted with DCM. The organic layers were combined, dried over $MgSO_4$, filtered and concentrated in vacuo. The crude residue was purified by silica gel column chromatography to give ethyl 2-(3-(5-(2,4-difluorophenyl)isoxazole-3-carboxamido)-1-((3-methyloxetan-3-yl)methyl)azetidin-3-yl)acetate. MS: (ES) m/z calculated for $C_{22}H_{26}F_2N_3O_5$ $[M+14]^+$ 450.2, found 450.2.

Step b: To a mixture of ethyl 2-(3-(5-(2,4-difluorophenyl)isoxazole-3-carboxamido)-1-((3-methyloxetan-3-yl)methyl)azetidin-3-yl)acetate (400 mg, 0.89 mmol) in 4:1 THF/$H_2O$ (5 mL) was added LiOH (224 mg, 5.34 mmol). The reaction mixture was stirred overnight at room temperature. The volatiles were removed in vacuo and the residue was treated with 1N HCl. The solid was filtered, washed with $H_2O$ and collected to yield 2-(3-(5-(2,4-difluorophenyl)isoxazole-3-carboxamido)-1-((3-methyloxetan-3-yl)methyl)azetidin-3-yl)acetic acid. MS: (ES) m/z calculated for $C_{20}H_{22}F_2N_3O_5$ $[M+H]^+$ 422.1, found 422.1.

Step c: To a solution of 2-(3-(5-(2,4-difluorophenyl)isoxazole-3-carboxamido)-1-((3-methyloxetan-3-yl)methyl)azetidin-3-yl)acetic acid (45 mg, 0.10 mmol) in DCM (2 mL) was added 2-(pyridin-2-yl)propan-2-amine dihydrochloride (23 mg, 0.10 mmol), DIPEA (0.07 mL, 0.40 mmol), and HATU (46 mg, 0.12 mmol). The reaction mixture was stirred for 1 h then concentrated in vacuo. The crude residue was purified by preparative HPLC to give 5-(2,4-difluorophenyl)-N-(1-((3-methyloxetan-3-yl)methyl)-3-(2-oxo-2-((2-(pyridin-2-yl)propan-2-yl)amino)ethyl)azetidin-3-yl)isoxazole-3-carboxamide. $^1H$ NMR (400 MHz, $CD_3OD$) δ 8.59 (s, 1H), 8.27 (s, 1H), 8.06 (ddd, J=8.5, 8.5, 6.2 Hz, 1H), 7.89 (s, 1H), 7.70 (s, 1H), 7.32-7.17 (m, 2H), 7.12 (s, 1H), 4.76-4.47 (m, 6H), 4.36 (d, J=6.3 Hz, 2H), 3.68 (d, J=20.0 Hz, 2H), 3.22 (d, J=20.0 Hz, 2H), 1.70 (s, 6H), 1.39 (s, 3H). MS: (ES) m/z calculated for $C_{28}H_{32}F_2N_5O_4$ $[M+H]^+$ 540.2, found 540.3.

Example 13: 5-(2,4-difluorophenyl)-N-(3-(2-((2-(2,6-dimethylpyridin-4-yl)propan-2-yl)amino)-2-oxoethyl)-1-(4-hydroxy-4-methylcyclohexyl)azetidin-3-yl)isoxazole-3-carboxamide

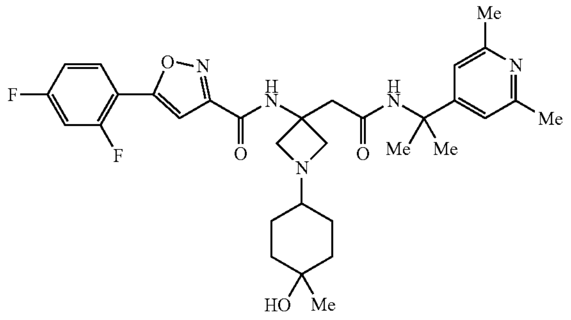 [SMILES: Cc1cc(C(C)(C)NC(=O)CC2(NC(=O)c3cc(-c4ccc(F)cc4F)on3)CN(C3CCC(C)(O)CC3)C2)cc(C)n1]

To a mixture of 2-(3-(5-(2,4-difluorophenyl)isoxazole-3-carboxamido)-1-(4-hydroxy-4-methylcyclohexyl)azetidin-3-yl)acetic acid (60 mg, 0.13 mmol) in DMF (2 mL) was added 2-(2,6-dimethylpyridin-4-yl)propan-2-amine (22 mg, 0.13 mmol), DIPEA (0.06 mL, 0.33 mmol), and HATU (61 mg, 0.16 mmol). The contents were stirred for 1 h then concentrated in vacuo. The crude material was purified by preparative HPLC to give the two separated isomers of 5-(2,4-difluorophenyl)-N-(3-(2-((2-(2,6-dimethylpyridin-4-yl)propan-2-yl)amino)-2-oxoethyl)-1-(4-hydroxy-4-methylcyclohexyl)azetidin-3-yl)isoxazole-3-carboxamide.

Isomer 1: $^1$H NMR (400 MHz, $CD_3OD$) δ 8.05-8.00 (m, 1H), 7.63 (s, 2H), 7.30-7.11 (m, 3H), 4.61-4.38 (m, 4H), 3.24-3.18 (m, 2H), 2.68 (s, 6H), 2.01-1.96 (m, 2H), 1.75-1.48 (m, 13H), 1.22 (s, 3H). MS: (ES) m/z calculated for $C_{32}H_{40}F_2N_5O_4$ $[M+H]^+$ 596.3, found 596.5.

Isomer 2: $^1$H NMR (400 MHz, $CD_3OD$) δ 8.08-8.00 (m, 1H), 7.63-7.61 (m, 2H), 7.30-7.12 (m, 3H), 4.58-4.37 (m, 4H), 3.30-3.19 (m, 2H), 2.67 (s, 6H), 1.82-1.73 (m, 13H), 1.48-1.38 (m, 2H), 1.21 (s, 3H). MS: (ES) m/z calculated for $C_{32}H_{40}F_2N_5O_4$ $[M+H]^+$ 596.3, found 596.5.

Example 14: 5-(2,4-difluorophenyl)-N-(1-isobutyl-3-(2-((2-(2-methylpyridin-4-yl)propan-2-yl)amino)-2-oxoethyl)azetidin-3-yl)isoxazole-3-carboxamide

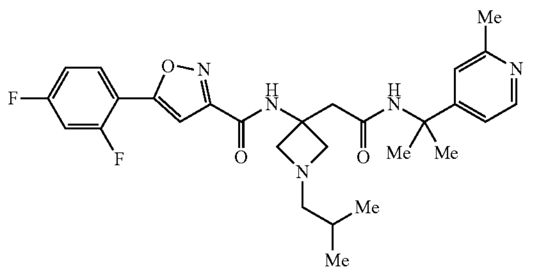 [SMILES: Cc1cc(C(C)(C)NC(=O)CC2(NC(=O)c3cc(-c4ccc(F)cc4F)on3)CN(CC(C)C)C2)ccn1]

Step a: To a mixture of ethyl 2-(3-(5-(2,4-difluorophenyl)isoxazole-3-carboxamido)azetidin-3-yl)acetate (300 mg, 0.8 mmol), DIPEA (0.29 mL, 1.6 mmol), acetic acid (0.19 mL, 3.2 mmol), and isobutyraldehyde (118 mg, 1.6 mmol) in 2:1 DCM/MeOH (9 mL) was added $NaBH_3CN$ (52 mg, 0.8 mmol). The contents were stirred at room temperature for 1 h and the reaction was quenched with saturated $NaHCO_3$ (aq) and extracted with DCM. The combined organic layers were dried over $MgSO_4$, filtered, and concentrated in vacuo. The crude residue was purified by silica gel column chromatography to give ethyl 2-(3-(5-(2,4-difluorophenyl)isoxazole-3-carboxamido)-1-isobutylazetidin-3-yl)acetate. MS: (ES) m/z calculated for $C_{21}H_{26}F_2N_3O_4$ $[M+H]^+$ 422.2, found 422.2.

Step b: To a mixture of ethyl 2-(3-(5-(2,4-difluorophenyl)isoxazole-3-carboxamido)-1-isobutylazetidin-3-yl)acetate (164 mg, 0.4 mmol) in 1:1:1 THF/$H_2O$/MeOH (9 mL) was added LiOH (49 mg, 1.2 mmol). The mixture was stirred at room temperature for 2 h, concentrated in vacuo, then treated with 1N HCl (10 mL) and concentrated in vacuo to yield 2-(3-(5-(2,4-difluorophenyl)isoxazole-3-carboxamido)-1-isobutylazetidin-3-yl)acetic acid. MS: (ES) m/z calculated for $C_{19}H_{22}F_2N_3O_4$ $[M+H]^+$ 394.2, found 394.2.

Step c: To a mixture of 2-(3-(5-(2,4-difluorophenyl)isoxazole-3-carboxamido)-1-isobutylazetidin-3-yl)acetic acid (55 mg, 0.14 mmol) in DMF (2 mL) was added 2-(2-methylpyridin-4-yl)propan-2-amine (21 mg, 0.14 mmol), DIPEA (0.06 mL, 0.35 mmol), and HATU (64 mg, 0.17 mmol). The contents were stirred for 1 h, filtered, then purified by preparative HPLC to give 5-(2,4-difluorophenyl)-N-(1-isobutyl-3-(2-((2-(2-methylpyridin-4-yl)propan-2-yl)amino)-2-oxoethyl)azetidin-3-yl)isoxazole-3-carboxamide. $^1$H NMR (400 MHz, DMSO-$d_6$) δ 9.56 (d, J=4.6 Hz, 1H), 8.72-8.69 (m, 1H), 8.48-8.44 (m, 1H), 8.15-8.07 (m, 1H), 7.65-7.53 (m, 2H), 7.47-7.37 (m, 1H), 7.35-7.28 (m, 1H), 7.27-7.23 (m, 1H), 4.56-4.39 (m, 2H), 4.35-4.22 (m, 2H), 3.15-2.99 (m, 4H), 2.51 (s, 3H), 1.89-1.78 (m, 1H), 1.51 (s, 6H), 0.89-0.86 (m, 6H). MS: (ES) m/z calculated for $C_{28}H_{34}F_2N_5O_3$ $[M+H]^+$ 526.3, found 526.3.

Example 15: N-(3-(2-((2-(3-chlorophenyl)propan-2-yl)amino)-2-oxoethyl)-1-isobutylazetidin-3-yl)-5-(2,4-difluorophenyl)isoxazole-3-carboxamide

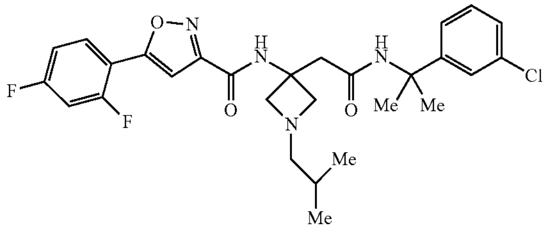 [SMILES: CC(C)CN1CC(CC(=O)NC(C)(C)c2cccc(Cl)c2)(NC(=O)c2cc(-c3ccc(F)cc3F)on2)C1]

To a solution of 2-(3-(5-(2,4-difluorophenyl)isoxazole-3-carboxamido)-1-isobutylazetidin-3-yl)acetic acid (40 mg, 0.10 mmol) in DMF (2 mL) was added 2-(3-chlorophenyl)propan-2-amine (17 mg, 0.10 mmol), DIPEA (0.04 mL, 0.25 mmol), and HATU (46 mg, 0.12 mmol). The mixture was stirred for 1 h, filtered, then purified by preparative HPLC to give N-(3-(2-((2-(3-chlorophenyl)propan-2-yl)amino)-2-oxoethyl)-1-isobutylazetidin-3-yl)-5-(2,4-difluorophenyl)isoxazole-3-carboxamide. MS: (ES) m/z calculated for $C_{28}H_{32}ClF_2N_4O_3$ $[M+H]^+$ 545.2, found 545.2.

Example 16: 5-(2,4-difluorophenyl)-N-(3-(2-oxo-2-((2-(pyridin-2-yl)propan-2-yl)amino)ethyl)-1-(2-oxaspiro[3.5]nonan-7-yl)azetidin-3-yl)isoxazole-3-carboxamide

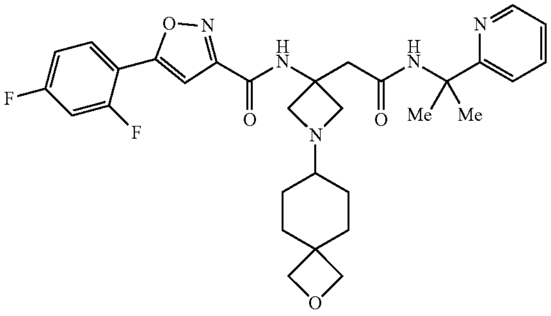 [SMILES: CC(C)(NC(=O)CC1(NC(=O)c2cc(-c3ccc(F)cc3F)on2)CN(C2CCC3(CC2)COC3)C1)c1ccccn1]

Step a: To a mixture of 5-(2,4-difluorophenyl)-N-(3-(2-oxo-2-((2-(pyridin-2-yl)propan-2-yl)amino)ethyl)azetidin-3-yl)isoxazole-3-carboxamide (70 mg, 0.1 mmol), DIPEA (0.04 mL, 0.2 mmol), acetic acid (0.03 mL, 0.4 mmol), and 2-oxaspiro[3.5]nonan-7-one (30 mg, 0.2 mmol) in 2:1 DCM/MeOH (3 mL) was added $NaBH_3CN$ (7 mg, 0.1 mmol). The contents were stirred at room temperature for 1 h, then the reaction was quenched with saturated $NaHCO_3$ (aq) and extracted with DCM. The combined organic layers were dried over $MgSO_4$, filtered, and concentrated in vacuo. The crude material was purified by silica gel column chromatography to give 5-(2,4-difluorophenyl)-N-(3-(2-oxo-2-((2-(pyridin-2-yl)propan-2-yl)amino)ethyl)-1-(2-oxaspiro[3.5]nonan-7-yl)azetidin-3-yl)isoxazole-3-carboxamide. $^1H$ NMR (400 MHz, $CD_3OD$) δ 8.39 (dd, J=4.9, 1.8 Hz, 1H), 8.07-8.01 (m, 1H), 7.69-7.64 (m, 1H), 7.41 (d, J=8.1 Hz, 1H), 7.30-7.14 (m, 3H), 7.07 (d, J=3.5 Hz, 1H), 4.42 (s, 2H), 4.34 (s, 2H), 3.77-3.66 (m, 4H), 3.05 (s, 2H), 2.39-2.30 (m, 1H), 2.15 (d, J=13.5 Hz, 2H), 1.79-1.75 (m, 2H), 1.60 (s, 6H), 1.50-1.43 (m, 2H), 1.05-0.95 (m, 2H). MS: (ES) m/z calculated for $C_{31}H_{36}F_2N_5O_4$ $[M+H]^+$ 580.3, found 580.2.

Example 17: 5-(2,4-difluorophenyl)-N-(1-(4-hydroxy-4-methylcyclohexyl)-3-(2-((2-(2-methylpyridin-4-yl)propan-2-yl)amino)-2-oxoethyl)azetidin-3-yl)isoxazole-3-carboxamide

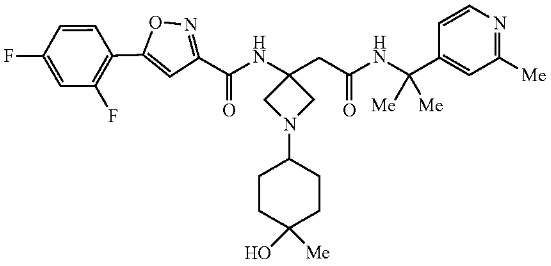 [SMILES: Cc1cc(C(C)(C)NC(=O)CC2(NC(=O)c3cc(-c4ccc(F)cc4F)on3)CN(C3CCC(C)(O)CC3)C2)ccn1]

To a mixture of 5-(2,4-difluorophenyl)-N-(3-(2-((2-(2-methylpyridin-4-yl)propan-2-yl)amino)-2-oxoethyl)azetidin-3-yl)isoxazole-3-carboxamide (65 mg, 0.10 mmol), $Et_3N$ (0.05 mL, 0.4 mmol) and 4-hydroxy-4-methylcyclohexan-1-one (26 mg, 0.20 mmol) in 4:1 DCM/MeOH (2 mL) was added $NaBH(OAc)_3$ (43 mg, 0.20 mmol). The contents were stirred at room temperature for 1 h, then concentrated in vacuo. The crude material was purified by preparative HPLC to give the two separated isomers of 5-(2,4-difluorophenyl)-N-(1-(4-hydroxy-4-methylcyclohexyl)-3-(2-((2-(2-methylpyridin-4-yl)propan-2-yl)amino)-2-oxoethyl)azetidin-3-yl)isoxazole-3-carboxamide.

Isomer 1: $^1H$ NMR (400 MHz, $CD_3OD$) δ 8.50 (d, J=6.3 Hz, 1H), 8.05 (ddd, J=8.5, 8.5, 6.0 Hz, 1H), 7.84 (s, 1H), 7.77 (d, J=5.6 Hz, 1H), 7.24 (dddd, J=22.5, 8.7, 8.7, 2.6 Hz, 2H), 7.11 (d, J=4.0 Hz, 1H), 4.60-4.35 (m, 4H), 3.30-3.10 (m, 3H), 2.75 (s, 3H), 1.98 (s, 2H), 1.74-1.61 (m, 8H), 1.56-1.36 (m, 4H), 1.21 (s, 3H). MS: (ES) m/z calculated for $C_{31}H_{38}F_2N_5O_4$ $[M+H]^+$ 582.3, found 582.3.

Isomer 2: $^1H$ NMR (400 MHz, $CD_3OD$) δ 8.50 (d, J=6.2 Hz, 1H), 8.06 (ddd, J=8.6, 8.6, 6.2 Hz, 1H), 7.83 (d, J=8.0 Hz, 1H), 7.77 (s, 1H), 7.32-7.17 (m, 2H), 7.13 (s, 1H), 4.57-4.35 (m, 4H), 3.38-3.10 (m, 3H), 2.72 (d, J=4.5 Hz, 3H), 1.85-1.70 (m, 4H), 1.68-1.50 (m, 8H), 1.48-1.36 (m, 2H), 1.20 (s, 3H). MS: (ES) m/z calculated for $C_{31}H_{37}F_2N_5O_4$ $[M+H]^+$ 582.3, found 582.3.

Example 18: 5-(2,4-difluorophenyl)-N-(1-(4-hydroxy-4-methylcyclohexyl)-3-(2-((2-(4-methylpyrimidin-2-yl)propan-2-yl)amino)-2-oxoethyl)azetidin-3-yl)isoxazole-3-carboxamide

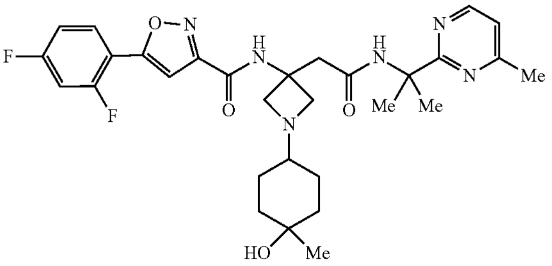 [SMILES: Cc1ccnc(C(C)(C)NC(=O)CC2(NC(=O)c3cc(-c4ccc(F)cc4F)on3)CN(C3CCC(C)(O)CC3)C2)n1]

To a mixture of 5-(2,4-difluorophenyl)-N-(3-(2-((2-(4-methylpyrimidin-2-yl)propan-2-yl)amino)-2-oxoethyl)azetidin-3-yl)isoxazole-3-carboxamide (70 mg, 0.14 mmol), $Et_3N$ (0.05 mL, 0.4 mmol) and 4-hydroxy-4-methylcyclohexan-1-one (36 mg, 0.28 mmol) in 4:1 DCM/MeOH (2 mL) was added $NaBH(OAc)_3$ (60 mg, 0.28 mmol). The contents were stirred at room temperature for 1 h, then concentrated in vacuo. The residue was purified by preparative HPLC to give 5-(2,4-difluorophenyl)-N-(1-(4-hydroxy-4-methylcyclohexyl)-3-(2-((2-(4-methylpyrimidin-2-yl)propan-2-yl)amino)-2-oxoethyl)azetidin-3-yl)isoxazole-3-carboxamide. $^1H$ NMR (400 MHz, $CD_3OD$) δ 8.49 (dd, J=11.3, 5.2 Hz, 1H), 8.05 (s, 1H), 7.30-7.06 (m, 4H), 4.59-4.38 (m, 4H), 3.14-3.06 (m, 3H), 2.55-2.42 (m, 3H), 1.98 (s, 2H), 1.75-1.56 (m, 2H), 1.63 (s, 3H), 1.62 (s, 3H), 1.56-1.30 (m, 4H), 1.20 (d, J=8.0 Hz, 3H). MS: (ES) m/z calculated for $C_{30}H_{37}F_2N_6O_4$ $[M+H]^+$ 583.3, found 583.3.

Example 19: 5-(2,4-difluorophenyl)-N-(1-(4-hydroxy-4-methylcyclohexyl)-3-(2-((2-(2-methoxypyridin-4-yl)propan-2-yl)amino)-2-oxoethyl)azetidin-3-yl)isoxazole-3-carboxamide

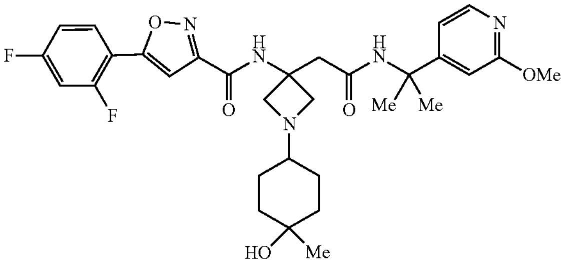 [SMILES: COc1cc(C(C)(C)NC(=O)CC2(NC(=O)c3cc(-c4ccc(F)cc4F)on3)CN(C3CCC(C)(O)CC3)C2)ccn1]

To a mixture of 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DCM (1 mL) was added 2-(2-methoxypyridin-4-yl)propan-2-amine (17 mg, 0.10 mmol), DIPEA (0.052 mL, 0.3 mmol), and HATU (40 mg, 0.11 mmol). The contents were stirred for 1 h, then concentrated in vacuo. The crude material was purified by preparative HPLC to give the two separated isomers of 5-(2,4-difluorophenyl)-N-(1-(4-hydroxy-4-methylcyclohexyl)-3-(2-((2-(2-methoxypyridin-4-yl)propan-2-yl)amino)-2-oxoethyl)azetidin-3-yl)isoxazole-3-carboxamide.

Isomer 1: $^1$H NMR (400 MHz, $CD_3OD$) δ 8.08 (d, J=8.4 Hz, 1H), 7.95 (dd, J=17.0, 6.0 Hz, 1H), 7.25 (dt, J=17.1, 9.1 Hz, 2H), 7.16-7.09 (m, 1H), 6.96 (dd, J=19.8, 5.9 Hz, 1H), 6.80 (d, J=18.6 Hz, 1H), 4.58-4.44 (m, 3H), 4.39 (d, J=11.3 Hz, 1H), 3.86 (s, 3H), 3.31-3.20 (m, 1H), 3.16 (d, J=10.7 Hz, 2H), 1.97 (s, 2H), 1.57 (s, 6H), 1.70-1.24 (m, 6H), 1.20 (d, J=1.6 Hz, 3H). MS: (ES) m/z calculated for $C_{31}H_{38}F_2N_5O_5$ $[M+H]^+$ 598.3, found 598.3.

Isomer 2: $^1$H NMR (400 MHz, $CD_3OD$) δ 8.12-7.97 (m, 2H), 7.31-7.07 (m, 4H), 7.00 (d, J=19.9 Hz, 1H), 4.57-4.42 (m, 3H), 4.37 (d, J=11.7 Hz, 1H), 3.97 (s, 3H), 3.30-3.10 (m, 3H), 1.80-1.68 (m, 4H), 1.65-1.50 (m, 2H), 1.59 (s, 6H), 1.50-1.36 (m, 2H), 1.20 (d, J=3.6 Hz, 3H). MS: (ES) m/z calculated for $C_{31}H_{38}F_2N_5O_5$ $[M+H]^+$ 598.3, found 598.3.

Example 20: 5-(2,4-difluorophenyl)-N-(3-(2-((2-(4,6-dimethylpyrimidin-2-yl)propan-2-yl)amino)-2-oxoethyl)-1-(4-hydroxy-4-methylcyclohexyl)azetidin-3-yl)isoxazole-3-carboxamide

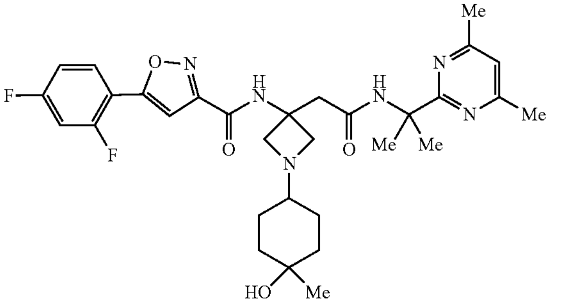 [SMILES: Cc1cc(C)nc(C(C)(C)NC(=O)CC2(NC(=O)c3cc(-c4ccc(F)cc4F)on3)CN(C3CCC(C)(O)CC3)C2)n1]

Step a: To the solution of 4,6-dimethylpyrimidine-2-carbonitrile (1.34 g, 10 mmol) in ether (35 mL) at room temperature was added a solution of 3.0 M methyl magnesium bromide (10 mL, 30 mmol) followed by titanium(IV) isopropoxide (3.04 mL, 10 mmol). The reaction mixture was stirred overnight at 40° C., then quenched with $H_2O$, followed by a 10% solution of NaOH (aq). The contents were diluted with DCM and passed through a plug of Celite. The filtrate was concentrated and the crude material was purified by silica gel column chromatography to yield 2-(4,6-dimethylpyrimidin-2-yl)propan-2-amine.

Step b: To a mixture of 2-(3-(5-(2,4-difluorophenyl)isoxazole-3-carboxamido)-1-(4-hydroxy-4-methylcyclohexyl)azetidin-3-yl)acetic acid (60 mg, 0.12 mmol) in DCM (2 mL) was added 2-(4,6-dimethylpyrimidin-2-yl)propan-2-amine (21 mg, 0.12 mmol), DIPEA (0.04 mL, 0.24 mmol), and HATU (52 mg, 0.14 mmol). The contents were stirred for 1 h then concentrated in vacuo. The crude material was purified by preparative HPLC to give the two separated isomers of 5-(2,4-difluorophenyl)-N-(3-(2-((2-(4,6-dimethylpyrimidin-2-yl)propan-2-yl)amino)-2-oxoethyl)-1-(4-hydroxy-4-methylcyclohexyl)azetidin-3-yl)isoxazole-3-carboxamide.

Isomer 1: $^1$H NMR (400 MHz, $CD_3OD$) δ 8.07-7.98 (m, 1H), 7.23 (ddd, J=18.7, 9.3, 9.3 Hz, 2H), 7.13-7.06 (m, 1H), 7.04 (s, 1H), 5.49 (s, 1H), 4.58-4.32 (m, 4H), 3.50-3.20 (m, 1H), 3.11 (d, J=9.8 Hz, 2H), 2.40 (s, 6H), 1.99 (s, 2H), 1.75-1.32 (m, 6H), 1.62 (s, 6H), 1.20 (s, 3H). MS: (ES) m/z calculated for $C_{31}H_{39}F_2N_6O_4$ $[M+H]^+$ 597.3, found 597.3.

Isomer 2: $^1$H NMR (400 MHz, $CD_3OD$) δ 8.07-7.98 (m, 1H), 7.23 (ddd, J=18.7, 9.3, 9.3 Hz, 2H), 7.14-7.06 (m, 1H), 7.04 (s, 1H), 4.58-4.38 (m, 4H), 3.30-3.10 (m, 3H), 2.40 (s, 6H), 1.82-1.70 (m, 4H), 1.62 (s, 6H), 1.62-1.50 (m, 2H), 1.48-1.36 (m, 2H), 1.21 (s, 3H). MS: (ES) m/z calculated for $C_{31}H_{39}F_2N_6O_4$ $[M+H]^+$ 597.3, found 597.3.

Example 21: 5-(2,4-difluorophenyl)-N-(1-(4-hydroxy-4-methylcyclohexyl)-3-(2-oxo-2-((2-(6-(trifluoromethyl)pyridin-2-yl)propan-2-yl)amino)ethyl)azetidin-3-yl)isoxazole-3-carboxamide

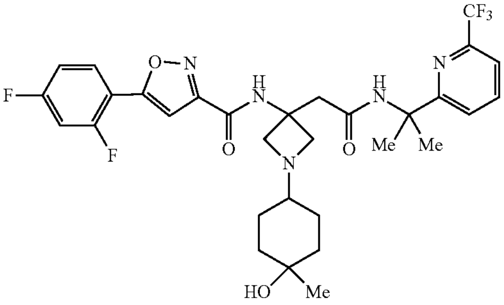 [SMILES: CC1(O)CCC(N2CC(CC(=O)NC(C)(C)c3cccc(C(F)(F)F)n3)(NC(=O)c3cc(-c4ccc(F)cc4F)on3)C2)CC1]

To a mixture of 2-(3-(5-(2,4-difluorophenyl)isoxazole-3-carboxamido)-1-(4-hydroxy-4-methylcyclohexyl)azetidin-3-yl)acetic acid (60 mg, 0.12 mmol) in DMF (1 mL) was added 2-(6-(trifluoromethyl)pyridin-2-yl)propan-2-amine (25 mg, 0.12 mmol), DIPEA (0.052 mL, 0.3 mmol), and HATU (52 mg, 0.14 mmol). The contents were stirred for 1 h then concentrated in vacuo. The crude material was purified by preparative HPLC to give the two separated isomers of 5-(2,4-difluorophenyl)-N-(1-(4-hydroxy-4-methylcyclohexyl)-3-(2-oxo-2-((2-(6-(trifluoromethyl)pyridin-2-yl)propan-2-yl)amino)ethyl)azetidin-3-yl)isoxazole-3-carboxamide.

Isomer 1: $^1$H NMR (400 MHz, $CD_3OD$) δ 8.06 (d, J=8.1 Hz, 1H), 7.87 (ddd, J=15.4, 7.9, 7.9 Hz, 1H), 7.68-7.54 (m, 2H), 7.31-7.17 (m, 2H), 7.14-7.06 (m, 1H), 4.56-4.30 (m, 4H), 3.40-3.20 (m, 1H), 3.15 (d, J=13.0 Hz, 2H), 1.96 (s, 2H), 1.63 (s, 6H), 1.74-1.30 (m, 6H), 1.19 (s, 3H). MS: (ES) m/z calculated for $C_{31}H_{35}F_5N_5O_4$ $[M+H]^+$ 636.3, found 636.3.

Isomer 2: $^1$H NMR (400 MHz, $CD_3OD$) δ 8.06 (d, J=8.5 Hz, 1H), 7.87 (ddd, J=8.4, 8.4, 8.4 Hz, 1H), 7.69-7.52 (m, 2H), 7.24 (ddd, J=17.8, 9.3, 9.3 Hz, 2H), 7.10 (dd, J=10.7, 3.5 Hz, 1H), 4.56-4.30 (m, 4H), 3.40-3.10 (m, 3H), 1.85-1.70 (m, 4H), 1.62 (s, 6H), 1.62-1.35 (s, 4H), 1.19 (s, 3H). MS: (ES) m/z calculated for $C_{31}H_{35}F_5N_5O_4$ $[M+H]^+$ 636.3, found 636.3.

Example 22: 5-(2,4-difluorophenyl)-N-(1-(4-hydroxy-4-methylcyclohexyl)-3-(2-oxo-2-((2-(3-(trifluoromethoxy)phenyl)propan-2-yl)amino)ethyl)azetidin-3-yl)isoxazole-3-carboxamide

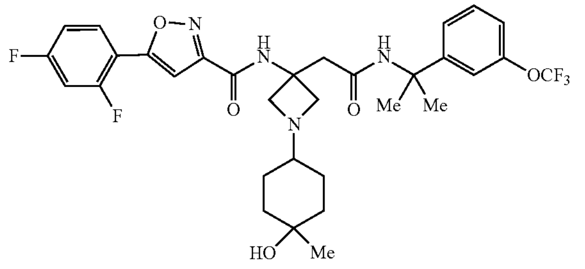 [SMILES: CC1(O)CCC(N2CC(CC(=O)NC(C)(C)c3cccc(OC(F)(F)F)c3)(NC(=O)c3cc(-c4ccc(F)cc4F)on3)C2)CC1]

To a mixture of 2-(3-(5-(2,4-difluorophenyl)isoxazole-3-carboxamido)-1-(4-hydroxy-4-methylcyclohexyl)azetidin-3-yl)acetic acid (45 mg, 0.093 mmol) in DMF (1.5 mL) was added 2-(3-(trifluoromethoxy)phenyl)propan-2-amine (65 mg, 0.30 mmol), HATU (57 mg, 0.15 mmol) and DIPEA (0.061 mL, 0.35 mmol). The contents were stirred for 1 h, quenched with water and purified by preparative HPLC to give two isomers of 5-(2,4-difluorophenyl)-N-(1-(4-hydroxy-4-methylcyclohexyl)-3-(2-oxo-2-((2-(3-(trifluoromethoxy)phenyl)propan-2-yl)amino)ethyl)azetidin-3-yl)isoxazole-3-carboxamide.

Isomer 1: $^1$H NMR (400 MHz, $CD_3OD$) δ 8.58 (s, 1H), 8.49 (s, 1H), 8.02-8.10 (m, 1H), 7.15-7.34 (m, 5H), 7.03-7.14 (m, 2H), 4.54 (d, J=11.6 Hz, 1H), 4.66 (s, 2H), 4.37 (d, J=11.6 Hz, 1H), 3.22-3.40 (m, 1H), 3.15 (d, J=12.4 Hz, 2H), 1.96 (bs, 2H), 1.30-1.56 (m, 12H), 1.20 (s, 3H). MS: (ES) m/z calculated for $C_{32}H_{36}F_5N_4O_5$ $[M+H]^+$ 651.3, found 651.5.

Isomer 2: $^1$H NMR (400 MHz, $CD_3OD$) δ 8.52 (s, 1H), 8.49 (s, 1H), 8.02-8.11 (m, 1H), 7.15-7.40 (m, 5H), 7.03-7.14 (m, 2H), 4.42-4.54 (m, 3H), 4.36 (d, J=12.4 Hz, 1H), 3.10-3.35 (m, 3H), 1.70-1.90 (m, 4H), 1.50-1.62 (m, 8H), 1.34-1.48 (m, 2H), 1.20 (s, 3H). MS: (ES) m/z calculated for $C_{32}H_{36}F_5N_4O_5$ $[M+H]^+$ 651.3, found 651.5.

Example 23: N-(3-(2-((2-(3,5-dichlorophenyl)propan-2-yl)amino)-2-oxoethyl)-1-(4-hydroxy-4-methylcyclohexyl)azetidin-3-yl)-5-(2,4-difluorophenyl)isoxazole-3-carboxamide

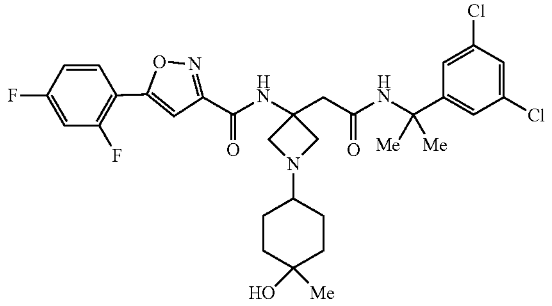 [SMILES: CC1(O)CCC(N2CC(CC(=O)NC(C)(C)c3cc(Cl)cc(Cl)c3)(NC(=O)c3cc(-c4ccc(F)cc4F)on3)C2)CC1]

To a mixture of 2-(3-(5-(2,4-difluorophenyl)isoxazole-3-carboxamido)-1-(4-hydroxy-4-methylcyclohexyl)azetidin-3-yl)acetic acid (30 mg, 0.062 mmol) in DMF (1.5 mL) was added 2-(3,5-dichlorophenyl)propan-2-amine (25 mg, 0.12 mmol), HATU (30 mg, 0.079 mmol) and $Et_3N$ (0.040 mL, 0.28 mmol). The mixture was stirred for 0.5 h, quenched with water and purified by preparative HPLC to give N-(3-(2-((2-(3,5-dichlorophenyl)propan-2-yl)amino)-2-oxoethyl)-1-(4-hydroxy-4-methylcyclohexyl)azetidin-3-yl)-5-(2,4-difluorophenyl)isoxazole-3-carboxamide. $^1$H NMR (400 MHz, $CD_3OD$) δ 8.61 (s, 1H), 8.51 (s, 1H), 8.00-8.10 (m, 1H), 7.15-7.32 (m, 5H), 7.06-7.13 (m, 1H), 4.54 (d, J=12.4 Hz, 1H), 4.47 (s, 2H), 4.39 (d, J=12.0 Hz, 1H), 3.22-3.40 (m, 1H), 3.15 (d, J=12.4 Hz, 2H), 1.97 (bs, 2H), 1.30-1.75 (m, 12H), 1.20 (s, 3H). MS: (ES) m/z calculated for $C_{31}H_{35}Cl_2F_2N_4O_4$ $[M+H]^+$ 635.2, found 635.5.

Example 24: 5-(2,4-difluorophenyl)-N-(3-(2-((2-(2-ethylpyridin-4-yl)propan-2-yl)amino)-2-oxoethyl)-1-(4-hydroxy-4-methylcyclohexyl)azetidin-3-yl)isoxazole-3-carboxamide

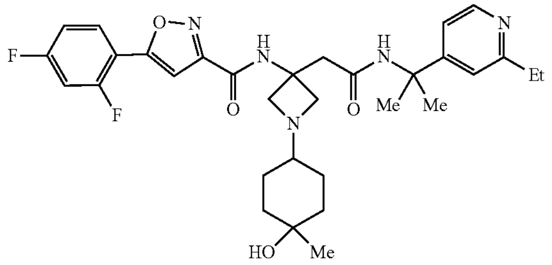 [SMILES: CCc1cc(C(C)(C)NC(=O)CC2(NC(=O)c3cc(-c4ccc(F)cc4F)on3)CN(C3CCC(C)(O)CC3)C2)ccn1]

Step a: To a flask containing 2-ethylisonicotinonitrile (1.00 g, 7.56 mmol) in ether (50 mL) under $N_2$ was added a solution of 3.0 M methylmagnesium bromide (7.56 mL, 22.7 mmol) and titanium(IV) isopropoxide (8.82 mL, 29.8 mmol). The mixture was stirred at 40° C. overnight, cooled to 0° C., quenched with water and diluted with a solution of 10% NaOH (aq). The contents were filtered through Celite and rinsed with DCM. The organic layer of the filtrate was dried over $NaSO_4$, filtered, concentrated in vacuo and purified by silica gel column chromatography to yield 2-(2-ethylpyridin-4-yl)propan-2-amine. MS: (ES) m/z calculated for $C_{10}H_{17}N_2$ $[M+H]^+$ 165.1, found 165.0.

Step b: To a mixture of 2-(3-(5-(2,4-difluorophenyl)isoxazole-3-carboxamido)-1-(4-hydroxy-4-methylcyclohexyl) azetidin-3-yl)acetic acid (45 mg, 0.093 mmol) in DMF (1.5 mL) was added 2-(2-ethylpyridin-4-yl)propan-2-amine (25 mg, 0.15 mmol), HATU (45 mg, 0.12 mmol) and $Et_3N$ (0.052 mL, 0.37 mmol). The contents were stirred for 1 h, quenched with water and purified by preparative HPLC to give two isomers of 5-(2,4-difluorophenyl)-N-(3-(2-((2-(2-ethylpyridin-4-yl)propan-2-yl)amino)-2-oxoethyl)-1-(4-hydroxy-4-methylcyclohexyl)azetidin-3-yl)isoxazole-3-carboxamide.

Isomer 1: $^1$H NMR (400 MHz, $CD_3OD$) δ 8.85 (s, 1H), 8.83 (s, 1H), 8.52 (d, J=6.0 Hz, 1H), 8.02-8.10 (m, 1H), 7.86 (s, 1H), 7.80 (s, 1H), 7.18-7.31 (m, 2H), 7.12 (s, 1H), 4.36-4.63 (m, 4H), 3.26-3.40 (m, 1H), 3.16-3.26 (m, 2H), 2.97-3.08 (m, 2H), 1.93-2.02 (m, 2H), 1.66-1.74 (m, 2H), 1.64 (s, 6H), 1.40-1.56 (m, 4H), 1.35 (t, J=7.6 Hz, 3H), 1.21 (s, 3H). MS: (ES) m/z calculated for $C_{32}H_{40}F_2N_5O_4$ $[M+H]^+$ 596.3, found 596.4.

Isomer 2: $^1$H NMR (400 MHz, $CD_3OD$) δ 8.85 (s, 1H), 8.81 (s, 1H), 8.52 (d, J=6.0 Hz, 1H), 8.02-8.10 (m, 1H), 7.74-7.87 (m, 2H), 7.18-7.31 (m, 2H), 7.12 (s, 1H), 4.34-4.60 (m, 4H), 3.16-3.26 (m, 1H), 3.18 (s, 2H), 2.98-3.04 (m, 2H), 1.72-1.84 (m, 4H), 1.64 (s, 6H), 1.37-1.63 (m, 4H), 1.34 (t, J=7.4 Hz, 3H), 1.20 (s, 3H). MS: (ES) m/z calculated for $C_{32}H_{40}F_2N_5O_4$ $[M+H]^+$ 596.3, found 596.4.

Example 25: 5-(2,4-difluorophenyl)-N-(1-isobutyl-3-(2-oxo-2-((2-(pyridin-2-yl)propan-2-yl)amino)ethyl)azetidin-3-yl)isoxazole-3-carboxamide

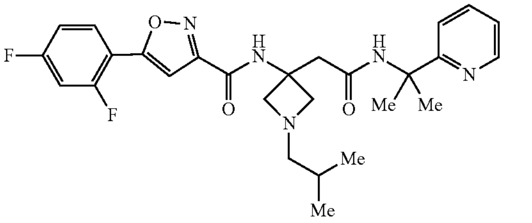 [SMILES: CC(C)CN1CC(CC(=O)NC(C)(C)c2ccccn2)(NC(=O)c2cc(-c3ccc(F)cc3F)on2)C1]

To a mixture of 5-(2,4-difluorophenyl)-N-(3-(2-oxo-2-((2-(pyridin-2-yl)propan-2-yl)amino)ethyl)azetidin-3-yl) isoxazole-3-carboxamide (35 mg, 0.071 mmol), isobutylaldehyde (30 mg, 0.042 mmol), $Et_3N$ (0.050 mL, 0.35 mmol) in DCM (2 mL) was added $NaBH(OAc)_3$ (50 mg, 0.23 mmol). The contents were stirred for 1 h, quenched with water, concentrated and purified by preparative HPLC to give 5-(2,4-difluorophenyl)-N-(1-isobutyl-3-(2-oxo-2-((2-(pyridin-2-yl)propan-2-yl)amino)ethyl)azetidin-3-yl)isoxazole-3-carboxamide. $^1$H NMR (400 MHz, $CD_3OD$) δ 8.64 (ddd, J=7.6, 2.0, 1.2 Hz, 1H), 8.43 (dd, J=10.4, 10.4 Hz, 1H), 7.97-8.10 (m, 2H), 7.83 (ddd, J=8.8, 8.8, 1.6 Hz, 1H), 7.16-7.29 (m, 2H), 7.09 (d, J=4.8 Hz, 1H), 4.25-4.75 (m, 4H), 3.00-3.40 (m, 4H), 1.85-2.00 (m, 1H), 1.72 (s, 6H), 0.97 (d, J=9.2 Hz, 6H). MS: (ES) m/z calculated for $C_{27}H_{32}F_2N_5O_3$ $[M+H]^+$ 512.2, found 512.4.

Example 26: N-(3-(2-((2-(1H-pyrrolo[2,3-b]pyridin-4-yl)propan-2-yl)amino)-2-oxoethyl)-1-(4-hydroxy-4-methylcyclohexyl)azetidin-3-yl)-5-(2,4-difluorophenyl)isoxazole-3-carboxamide

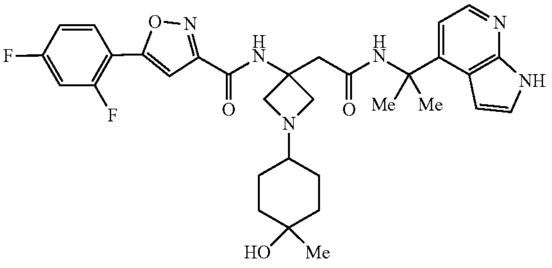 [SMILES: CC1(O)CCC(N2CC(CC(=O)NC(C)(C)c3ccnc4[nH]ccc34)(NC(=O)c3cc(-c4ccc(F)cc4F)on3)C2)CC1]

Step a: To a flask containing 1H-pyrrolo[2,3-b]pyridine-4-carbonitrile (1.00 g, 7.0 mmol) in ether (50 mL) and THF (50 mL) under $N_2$ was added a solution of 3.0 M methylmagnesium bromide (7.0 mL, 21 mmol) followed by titanium(IV) isopropoxide (2.07 mL, 7.0 mmol). The mixture was stirred at 40° C. overnight, cooled to 0° C., quenched with water and diluted with a solution of 10% NaOH (aq). The contents were filtered through Celite and rinsed with DCM. The organic layer of the filtrate was dried over $NaSO_4$, concentrated in vacuo and purified by silica gel column chromatography to yield 2-(1H-pyrrolo[2,3-b]pyridin-4-yl)propan-2-amine. MS: (ES) m/z calculated for $C_{10}H_{14}N_3$ $[M+H]^+$ 176.1, found 176.1.

Step b: To a mixture of 2-(3-(5-(2,4-difluorophenyl)isoxazole-3-carboxamido)-1-(4-hydroxy-4-methylcyclohexyl) azetidin-3-yl)acetic acid (35 mg, 0.072 mmol) in DMF (1.5 mL) was added 2-(1H-pyrrolo[2,3-b]pyridin-4-yl)propan-2-amine (25 mg, 0.14 mmol), HATU (30 mg, 0.079 mmol) and $Et_3N$ (0.040 mL, 0.28 mmol). The contents were stirred for 0.5 h, quenched with water and purified by preparative HPLC to give N-(3-(2-((2-(1H-pyrrolo[2,3-b]pyridin-4-yl) propan-2-yl)amino)-2-oxoethyl)-1-(4-hydroxy-4-methylcyclohexyl)azetidin-3-yl)-5-(2,4-difluorophenyl)isoxazole-3-carboxamide. $^1$H NMR (400 MHz, $CD_3OD$) δ 9.03 (s, 1H), 8.94 (s, 1H), 8.27 (d, J=5.2 Hz, 1H), 8.08 (d, J=6.8 Hz, 1H), 7.41 (d, J=6.0 Hz, 1H), 7.15-7.32 (m, 4H), 7.07 (s, 1H), 6.81 (d, J=14.8 Hz, 1H), 4.22-4.49 (m, 4H), 3.12-3.30 (m, 3H), 1.89 (s, 2H), 1.76 (s, 6H), 1.25-1.71 (m, 6H), 1.17 (s, 3H). MS: (ES) m/z calculated for $C_{32}H_{37}F_2N_6O_4$ $[M+H]^+$ 607.3, found 607.5.

Example 27: 5-(2,4-difluorophenyl)-N-(1-(4-hydroxy-4-methylcyclohexyl)-3-(2-((2-(4-methylpyridin-2-yl)propan-2-yl)amino)-2-oxoethyl)azetidin-3-yl)isoxazole-3-carboxamide

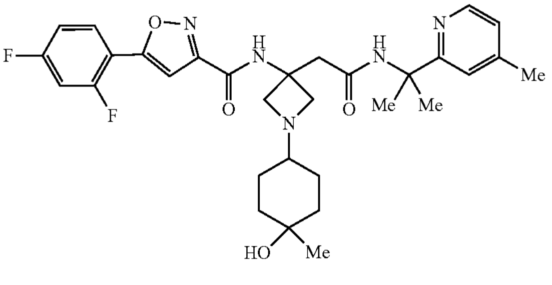 [SMILES: Cc1ccnc(C(C)(C)NC(=O)CC2(NC(=O)c3cc(-c4ccc(F)cc4F)on3)CN(C3CCC(C)(O)CC3)C2)c1]

To a mixture of 2-(3-(5-(2,4-difluorophenyl)isoxazole-3-carboxamido)-1-(4-hydroxy-4-methylcyclohexyl)azetidin-3-yl)acetic acid (0.075 g, 0.17 mmol) in DCM (1 mL) was added 2-(4-methylpyridin-2-yl)propan-2-amine (0.082 g, 0.55 mmol), DIPEA (0.09 mL, 0.50 mmol), and HATU (0.130 g, 0.33 mmol). The mixture was stirred at room temperature overnight then concentrated in vacuo. The residue was purified by preparative HPLC to give the two separated isomers of 5-(2,4-difluorophenyl)-N-(1-(4-hydroxy-4-methylcyclohexyl)-3-(2-((2-(4-methylpyridin-2-yl)propan-2-yl)amino)-2-oxoethyl)azetidin-3-yl)isoxazole-3-carboxamide.

Isomer 1: $^1$H NMR (400 MHz, $CD_3OD$) δ 8.40 (s, 1H), 8.05 (m, 1H), 7.75 (s, 1H), 7.59 (d, J=6.0 Hz, 1H), 7.34-7.16 (m, 2H), 7.11 (s, 1H), 4.58-4.34 (m, 3H), 3.21-3.11 (m, 3H), 2.55 (s, 3H), 2.02-1.92 (m, 2H), 1.82-1.72 (m, 1H), 1.68 (s, 6H), 1.58-1.45 (m, 5H), 1.44-1.32 (m, 1H), 1.21 (s, 3H). MS: (ES) m/z calculated for $C_{31}H_{38}F_2N_5O_4$ $[M+H]^+$ 582.3, found 582.5.

Isomer 2: $^1$H NMR (400 MHz, $CD_3OD$) δ 8.40 (s, 1H), 8.05 (m, 1H), 7.76 (s, 1H), 7.61 (d, J=6.0 Hz, 1H), 7.30-7.18 (m, 2H), 7.13-7.08 (m, 1H), 4.58-4.31 (m, 4H), 3.22-3.07 (m, 3H), 2.55 (s, 3H), 1.85-1.70 (m, 3H), 1.68 (s, 6H), 1.63-1.49 (m, 2H), 1.47-1.36 (m, 3H), 1.20 (s, 3H). MS: (ES) m/z calculated for $C_{31}H_{38}F_2N_5O_4$ $[M+H]^+$ 582.3, found 582.5.

Example 28: 5-(2,4-difluorophenyl)-N-(3-(2-((2-(4,6-dimethylpyridin-2-yl)propan-2-yl)amino)-2-oxoethyl)-1-(4-hydroxy-4-methylcyclohexyl)azetidin-3-yl)isoxazole-3-carboxamide

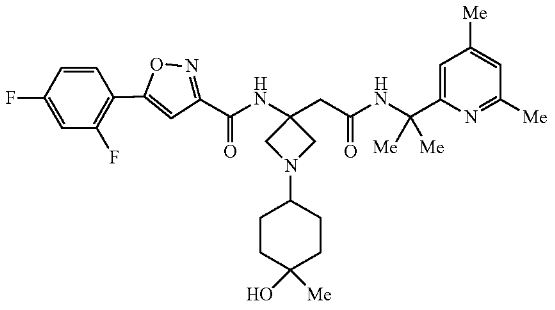 [SMILES: Cc1cc(C)nc(C(C)(C)NC(=O)CC2(NC(=O)c3cc(-c4ccc(F)cc4F)on3)CN(C3CCC(C)(O)CC3)C2)c1]

To a solution of 2-(3-(5-(2,4-difluorophenyl)isoxazole-3-carboxamido)-1-(4-hydroxy-4-methylcyclohexyl)azetidin-3-yl)acetic acid (0.075 g, 0.15 mmol) in DMF (1 mL) was added 2-(4,6-dimethylpyridin-2-yl)propan-2-amine (0.033 g, 0.20 mmol), HATU (0.129 g, 0.34 mmol) and DIPEA (0.09 mL, 0.50 mmol). The reaction mixture was stirred at room temperature for 5 h then concentrated in vacuo. The crude material was purified by preparative HPLC to give 5-(2,4-difluorophenyl)-N-(3-(2-((2-(4,6-dimethylpyridin-2-yl)propan-2-yl)amino)-2-oxoethyl)-1-(4-hydroxy-4-methylcyclohexyl)azetidin-3-yl)isoxazole-3-carboxamide. $^1$H NMR (400 MHz, $CD_3OD$) δ 8.08-8.00 (m, 1H), 7.69 (s, 1H), 7.57 (s, 1H), 7.34-7.16 (m, 2H), 7.10 (s, 1H), 4.65-4.35 (m, 4H), 3.40-3.15 (m, 2H), 2.70-2.60 (m, 1H), 2.57 (s, 6H), 2.05-1.90 (m, 2H), 1.75-1.70 (m, 1H), 1.70 (s, 6H), 1.57-1.33 (m, 5H), 1.21 (s, 3H). MS: (ES) m/z calculated for $C_{32}H_{40}F_2N_5O_4$ $[M+H]^+$ 596.3, found 596.5.

Example 29: 5-(2,4-difluorophenyl)-N-(1-(4-hydroxy-4-methylcyclohexyl)-3-(2-oxo-2-((2-(pyrimidin-2-yl)propan-2-yl)amino)ethyl)azetidin-3-yl)isoxazole-3-carboxamide

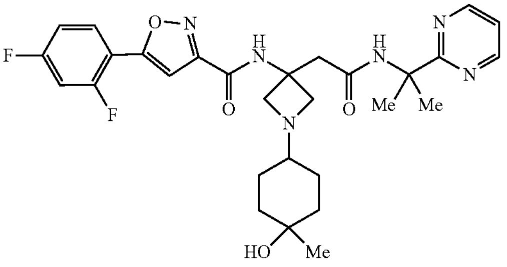 [SMILES: CC1(O)CCC(N2CC(CC(=O)NC(C)(C)c3ncccn3)(NC(=O)c3cc(-c4ccc(F)cc4F)on3)C2)CC1]

To a solution of 2-(3-(5-(2,4-difluorophenyl)isoxazole-3-carboxamido)-1-(4-hydroxy-4-methylcyclohexyl)azetidin-3-yl)acetic acid (0.06 g, 0.13 mmol) in DMF (1 mL) was added 2 2-(pyrimidin-2-yl)propan-2-amine dihydrochloride (0.06 g, 0.29 mmol), DIPEA (0.07 mL, 0.40 mmol), and HATU (0.10 g, 0.26 mmol). The reaction mixture was stirred at room temperature overnight then concentrated in vacuo. The aqueous layer was extracted with EtOAc and the organic layers were combined, dried with sodium sulfate, filtered and concentrated. The crude material was purified by preparative HPLC to yield the two separated isomers of 5-(2,4-difluorophenyl)-N-(1-(4-hydroxy-4-methylcyclohexyl)-3-(2-oxo-2-((2-(pyrimidin-2-yl)propan-2-yl)amino)ethyl)azetidin-3-yl)isoxazole-3-carboxamide.

Isomer 1: $^1$H NMR (400 MHz, $CD_3OD$) δ 8.68 (dd, J=9.2, 4.9 Hz, 2H), 8.15-7.96 (m, 1H), 7.32-7.27 (m, 2H), 7.27-7.16 (m, 1H), 7.11 (dd, J=8.1, 3.5 Hz, 1H), 4.58-4.37 (m, 4H), 3.27-3.20 (m, 1H), 3.09 (d, J=16.3 Hz, 2H), 1.97 (bs, 2H), 1.75-1.67 (m, 2H), 1.64 (s, 3H), 1.63 (s, 3H), 1.55-1.45 (m, 2H), 1.43-1.32 (m, 2H), 1.21 (s, 3H). MS: (ES) m/z calculated for $C_{29}H_{35}F_2N_6O_4$ $[M+H]^+$ 569.3, found 569.4.

Isomer 2: $^1$H NMR (400 MHz, $CD_3OD$) δ 8.67 (dd, J=7.5, 4.9 Hz, 2H), 8.05 (m, 1H), 7.33-7.26 (m, 2H), 7.26-7.16 (m, 1H), 7.11 (dd, J=10.7, 3.4 Hz, 1H), 4.56-4.36 (m, 4H), 3.19-3.05 (m, 3H), 1.87-1.70 (m, 4H), 1.63 (s, 3H), 1.62 (s, 3H), 1.61-1.51 (m, 2H), 1.48-1.35 (m, 2H), 1.21 (s, 3H). MS: (ES) m/z calculated for $C_{29}H_{35}F_2N_6O_4$ $[M+H]^+$ 569.3, found 569.4.

Example 30: 5-(2,4-difluorophenyl)-N-(1-(2,2-dimethylcyclohexyl)-3-(2-oxo-2-((2-(pyridin-2-yl)propan-2-yl)amino)ethyl)azetidin-3-yl)isoxazole-3-carboxamide

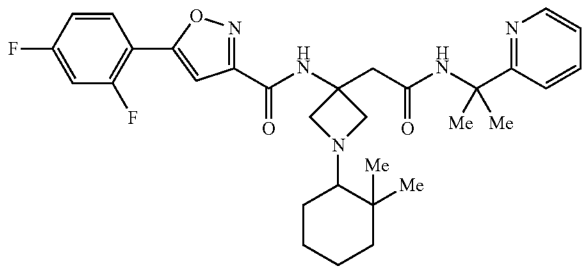 [SMILES: CC(C)(NC(=O)CC1(NC(=O)c2cc(-c3ccc(F)cc3F)on2)CN(C2CCCCC2(C)C)C1)c1ccccn1]

Step a: To a mixture of ethyl 2-(3-(5-(2,4-difluorophenyl)isoxazole-3-carboxamido)azetidin-3-yl)acetate (800 mg, 2.0 mmol), $Et_3N$ (0.55 mL, 4.0 mmol), and 2,2-dimethylcyclohexanone (505 mg, 4.0 mmol) in 4:1 DCM/MeOH (20 mL) was added $NaBH(OAc)_3$ (840 mg, 4.0 mmol). The reaction mixture was stirred at room temperature for 1 h, then quenched with saturated $NaHCO_3$ (aq) and extracted with DCM. The combined organic layers were dried over $MgSO_4$, filtered, and concentrated in vacuo. The crude residue was purified by silica gel column chromatography to give ethyl 2-(3-(5-(2,4-difluorophenyl)isoxazole-3-carboxamido)-1-(2,2-dimethylcyclohexyl)azetidin-3-yl)acetate. MS: (ES) m/z calculated for $C_{25}H_{32}F_2N_3O_4$ $[M+H]^+$ 476.2, found 476.5.

Step b: To a mixture of ethyl 2-(3-(5-(2,4-difluorophenyl)isoxazole-3-carboxamido)-1-(2,2-dimethylcyclohexyl)azetidin-3-yl)acetate (600 mg, 1.2 mmol) in 1:1 THF/$H_2O$ (20 mL) was added NaOH (300 mg, 7.5 mmol). The mixture was stirred at room temperature overnight then treated with 1N HCl and MeCN. The contents were concentrated in vacuo and the crude residue was triturated with acetone and filtered through Celite. The filtrate was concentrated to yield 2-(3-(5-(2,4-difluorophenyl)isoxazole-3-carboxamido)-1-(2,2-dimethylcyclohexyl)azetidin-3-yl)acetic acid. MS: (ES) m/z calculated for $C_{23}H_{28}F_2N_3O_4$ $[M+H]^+$ 448.2, found 448.4.

Step c: To a mixture of 2-(3-(5-(2,4-difluorophenyl)isoxazole-3-carboxamido)-1-(2,2-dimethylcyclohexyl)azetidin-3-yl)acetic acid (100 mg, 0.21 mmol) in DCM (2 mL) was added 2-(pyridin-2-yl)propan-2-amine dihydrochloride (43 mg, 0.21 mmol), DIPEA (0.14 mL, 0.82 mmol), and HATU (82 mg, 0.22 mmol). The contents were stirred for 1 h then concentrated in vacuo. The crude material was purified by preparative HPLC to give the two separated isomers of 5-(2,4-difluorophenyl)-N-(1-(2,2-methylcyclohexyl)-3-(2-oxo-2-((2-(pyridin-2-yl)propan-2-yl)amino)ethyl)azetidin-3-yl)isoxazole-3-carboxamide.

Isomer 1: $^1H$ NMR (400 MHz, DMSO-$d_6$) δ 9.81-9.50 (m, 2H), 8.51-8.37 (m, 2H), 8.17-8.06 (m, 1H), 7.69-7.48 (m, 1H), 7.41-7.10 (m, 4H), 4.57-4.22 (m, 3H), 3.36-3.25 (m, 1H), 3.17-3.01 (m, 2H), 2.26-2.14 (m, 1H), 1.76-1.10 (m, 14H), 0.90-0.79 (m, 6H). MS: (ES) m/z calculated for $C_{31}H_{38}F_2N_5O_3$ $[M+H]^+$ 566.3, found 566.3.

Isomer 2: $^1H$ NMR (400 MHz, DMSO-$d_6$) δ 9.55 (s, 1H), 9.40 (s, 1H), 8.50-8.37 (m, 2H), 8.18-8.03 (m, 1H), 7.63-7.44 (m, 2H), 7.42-7.10 (m, 3H), 4.44-4.25 (m, 1H), 3.18 (s, 2H), 1.79-1.63 (m, 2H), 1.79-1.63 (m, 3H), 1.59-1.46 (m, 6H), 1.24 (s, 7H), 1.06-1.00 (m, 3H), 0.94-0.88 (m, 3H). MS: (ES) m/z calculated for $C_{31}H_{38}F_2N_5O_4$ $[M+H]^+$ 566.3, found 566.3.

Example 31: 5-(2,4-difluorophenyl)-N-(1-(4-hydroxy-4-methylcyclohexyl)-3-(2-oxo-2-((1-(pyrimidin-2-yl)cyclopropyl)amino)ethyl)azetidin-3-yl)isoxazole-3-carboxamide

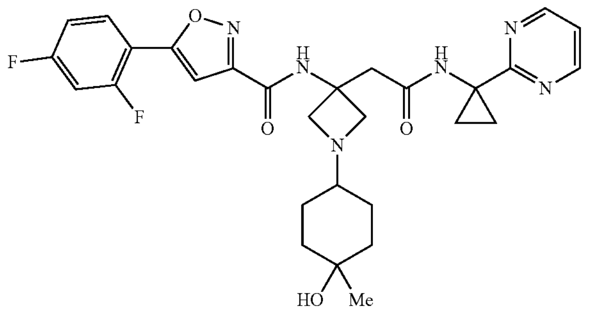 [SMILES: CC1(O)CCC(N2CC(CC(=O)NC3(c4ncccn4)CC3)(NC(=O)c3cc(-c4ccc(F)cc4F)on3)C2)CC1]

To a mixture of 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DMF (2 mL) was added 1-(pyrimidin-2-yl)cyclopropylamine dihydrochloride (42 mg, 0.20 mmol), HATU (77 mg, 0.20 mmol) and DIPEA (0.105 mL, 0.60 mmol). The contents were stirred at room temperature for 1 h and then quenched with 3 drops of $H_2O$. The crude material was purified by preparative HPLC to give 5-(2,4-difluorophenyl)-N-(1-(4-hydroxy-4-methylcyclohexyl)-3-(2-oxo-2-((1-(pyrimidin-2-yl)cyclopropyl)amino)ethyl)azetidin-3-yl)isoxazole-3-carboxamide. $^1H$ NMR (400 MHz, DMSO-$d_6$) δ 9.57 (s, 1H), 8.89 (s, 1H), 8.57-8.50 (m, 2H), 8.13-8.00 (m, 1H), 7.65-7.54 (m, 1H), 7.39-7.28 (m, 1H), 7.25-7.16 (m, 2H), 4.48-4.35 (m, 4H), 3.01-2.94 (m, 2H), 1.79-1.38 (m, 9H), 1.33-1.12 (m, 4H), 1.08 (s, 3H). MS: (ES) m/z calculated for $C_{29}H_{33}F_2N_6O_4$ $[M+H]^+$ 567.3, found 567.5.

Example 32: 5-(2,4-difluorophenyl)-N-(1-(4-hydroxy-4-methylcyclohexyl)-3-(2-((2-(2-methylphenyl)propan-2-yl)amino)-2-oxoethyl)azetidin-3-yl)isoxazole-3-carboxamide

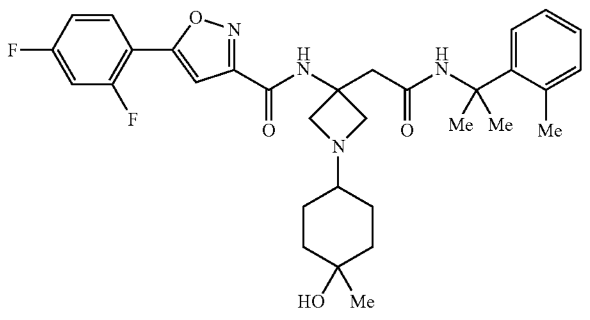 [SMILES: Cc1ccccc1C(C)(C)NC(=O)CC1(NC(=O)c2cc(-c3ccc(F)cc3F)on2)CN(C2CCC(C)(O)CC2)C1]

To a mixture of 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DMF (2 mL) was added 2-(o-tolyl)propan-2-amine (34 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The crude material was purified by preparative HPLC to give 5-(2,4-difluorophenyl)-N-(1-(4-hydroxy-4-methylcyclohexyl)-3-(2-oxo-2-((2-(o-tolyl)propan-2-yl)amino)ethyl)azetidin-3-yl)isoxazole-3-carboxamide. $^1H$ NMR (400 MHz, $CD_3OD$) δ 8.14-7.99 (m, 1H), 7.34-6.88 (m, 7H), 4.58-4.30 (m, 4H), 3.25-3.03 (m, 3H), 2.26-2.14 (m, 3H), 1.90-1.68 (m, 4H), 1.68-1.48 (m, 8H), 1.48-1.31 (m, 2H), 1.20 (s, 3H). MS: (ES) m/z calculated for $C_{32}H_{39}F_2N_4O_4$ $[M+H]^+$ 581.3, found 581.3.

Example 33: N-(3-(2-((2-(2-chlorophenyl)propan-2-yl)amino)-2-oxoethyl)-1-(4-hydroxy-4-methylcyclohexyl)azetidin-3-yl)-5-(2,4-difluorophenyl)isoxazole-3-carboxamide

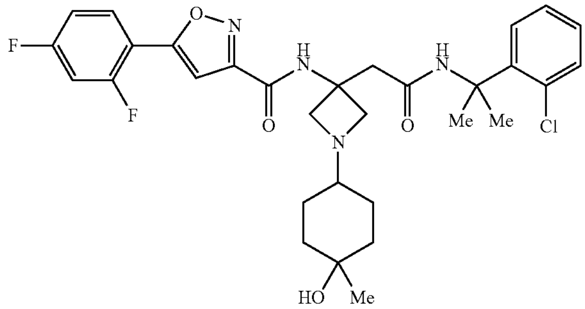 [SMILES: CC1(O)CCC(N2CC(CC(=O)NC(C)(C)c3ccccc3Cl)(NC(=O)c3cc(-c4ccc(F)cc4F)on3)C2)CC1]

To a mixture of 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DMF (2 mL) was added 2-(2-chlorophenyl)propan-2-amine (36 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The crude material was purified by preparative HPLC to give the two separated isomers of N-(3-(2-((2-(2-chlorophenyl)propan-2-yl)amino)-2-oxoethyl)-1-(4-hydroxy-4-methylcyclohexyl)azetidin-3-yl)-5-(2,4-difluorophenyl)isoxazole-3-carboxamide.

Isomer 1: $^1H$ NMR (400 MHz, $CD_3OD$) δ 8.14-8.02 (m, 1H), 7.56-7.48 (m, 1H), 7.33-7.18 (m, 3H), 7.18-7.04 (m, 3H), 4.56-4.29 (m, 4H), 3.27-3.08 (m, 3H), 2.00-1.88 (m, 2H), 1.77-1.64 (m, 7H), 1.59-1.26 (m, 5H), 1.22-1.16 (m, 3H). MS: (ES) m/z calculated for $C_{31}H_{36}ClF_2N_4O_4$ $[M+H]^+$ 601.2, found 601.3.

Isomer 2: $^1H$ NMR (400 MHz, $CD_3OD$) δ 8.13-8.02 (m, 1H), 7.54-7.48 (m, 1H), 7.32-7.18 (m, 3H), 7.17-7.04 (m, 3H), 4.58-4.25 (m, 4H), 3.24-3.04 (m, 3H), 1.83-1.66 (m, 10H), 1.63-1.33 (m, 4H), 1.23-1.16 (m, 3H). MS: (ES) m/z calculated for $C_{31}H_{36}ClF_2N_4O_4$ $[M+H]^+$ 601.2, found 601.3.

Example 34: 5-(2,4-difluorophenyl)-N-(3-(2-((2-(2-fluorophenyl)propan-2-yl)amino)-2-oxoethyl)-1-(4-hydroxy-4-methylcyclohexyl)azetidin-3-yl)isoxazole-3-carboxamide

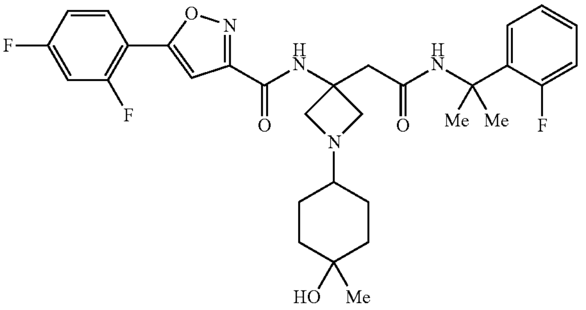 [SMILES: CC1(O)CCC(N2CC(CC(=O)NC(C)(C)c3ccccc3F)(NC(=O)c3cc(-c4ccc(F)cc4F)on3)C2)CC1]

To a mixture of 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DMF (2 mL) was added 2-(2-fluorophenyl)propan-2-amine (34 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The crude material was purified by preparative HPLC to give the two separated isomers of 5-(2,4-difluorophenyl)-N-(3-(2-((2-(2-fluorophenyl)propan-2-yl)amino)-2-oxoethyl)-1-(4-hydroxy-4-methylcyclohexyl)azetidin-3-yl)isoxazole-3-carboxamide.

Isomer 1: $^1H$ NMR (400 MHz, $CD_3OD$) δ 8.13-8.03 (m, 1H), 7.40-7.01 (m, 6H), 6.89-6.73 (m, 1H), 4.59-4.29 (m, 4H), 3.27-3.07 (m, 3H), 2.02-1.89 (m, 2H), 1.74-1.55 (m, 8H), 1.55-1.27 (m, 4H), 1.20 (s, 3H). MS: (ES) m/z calculated for $C_{31}H_{36}F_3N_4O_4$ $[M+H]^+$ 585.3, found 585.3.

Isomer 2: $^1H$ NMR (400 MHz, $CD_3OD$) δ 8.13-8.04 (m, 1H), 7.38-7.01 (m, 6H), 6.85-6.75 (m, 1H), 4.54-4.30 (m, 4H), 3.15-3.05 (m, 3H), 1.88-1.32 (m, 14H), 1.20 (s, 3H). MS: (ES) m/z calculated for $C_{31}H_{36}F_3N_4O_4$ $[M+H]^+$ 585.3, found 585.3.

Example 35: 5-(2,4-difluorophenyl)-N-(1-(4-hydroxy-4-methylcyclohexyl)-3-(2-oxo-2-((2-(m-tolyl)propan-2-yl)amino)ethyl)azetidin-3-yl)isoxazole-3-carboxamide

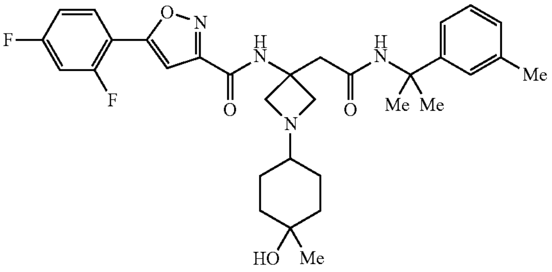 [SMILES: Cc1cccc(C(C)(C)NC(=O)CC2(NC(=O)c3cc(-c4ccc(F)cc4F)on3)CN(C3CCC(C)(O)CC3)C2)c1]

To a mixture of 2-(3-(5-(2,4-difluorophenyl)isoxazole-3-carboxamido)-1-(4-hydroxy-4-methylcyclohexyl)azetidin-3-yl)acetic acid (50 mg, 0.10 mmol) in DMF (2 mL) was added 2-(m-tolyl)propan-2-amine (34 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The crude material was purified by preparative HPLC to give the two separated isomers of 5-(2,4-difluorophenyl)-N-(1-(4-hydroxy-4-methylcyclohexyl)-3-(2-oxo-2-((2-(m-tolyl)propan-2-yl)amino)ethyl)azetidin-3-yl)isoxazole-3-carboxamide.

Isomer 1: $^1H$ NMR (400 MHz, $CD_3OD$) δ 8.11-8.01 (m, 1H), 7.32-7.18 (m, 2H), 7.16-7.01 (m, 4H), 6.98-6.90 (m, 1H), 4.61-4.27 (m, 4H), 3.39-3.18 (m, 1H), 3.16-3.07 (m, 2H), 2.25-2.16 (m, 3H), 2.02-1.88 (m, 2H), 1.74-1.27 (m, 12H), 1.24-1.16 (m, 3H). MS: (ES) m/z calculated for $C_{32}H_{39}F_2N_4O_4$ $[M+H]^+$ 581.3, found 581.3.

Isomer 2: $^1H$ NMR (400 MHz, $CD_3OD$) δ 8.14-7.99 (m, 1H), 7.34-6.88 (m, 7H), 4.58-4.30 (m, 4H), 3.25-3.03 (m, 3H), 2.26-2.14 (m, 3H), 1.90-1.68 (m, 4H), 1.68-1.48 (m, 8H), 1.48-1.31 (m, 2H), 1.20 (s, 3H). MS: (ES) m/z calculated for $C_{32}H_{39}F_2N_4O_4$ $[M+H]^+$ 581.3, found 581.3.

Example 36: N-(3-(2-((2-(3-chloro-5-fluorophenyl) propan-2-yl)amino)-2-oxoethyl)-1-(4-hydroxy-4-methylcyclohexyl)azetidin-3-yl)-5-(2,4-difluorophenyl)isoxazole-3-carboxamide

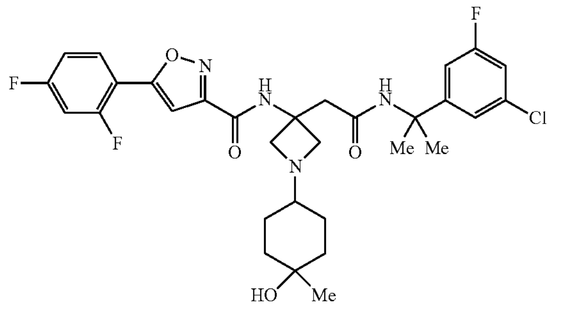 [SMILES: CC1(O)CCC(N2CC(CC(=O)NC(C)(C)c3cc(F)cc(Cl)c3)(NC(=O)c3cc(-c4ccc(F)cc4F)on3)C2)CC1]

Step a: To a solution of 3-chloro-5-fluorobenzonitrile (1.00 g, 6.37 mmol) in ether (100 mL) was added dropwise a solution of 3.0 M methylmagnesium bromide (7.30 mL, 21.9 mmol) followed by titanium(IV) isopropoxide (2.16 mL, 7.30 mmol). The resulting mixture was refluxed overnight under $N_2$, then cooled to 0° C. and quenched with water followed by a solution of 10% NaOH (aq). The contents were filtered through a plug of Celite and washed with DCM. The organic layer of the filtrate was collected, dried over $Na_2SO_4$, concentrated in vacuo and purified by silica gel column chromatography to give 2-(3-chloro-5-fluorophenyl)propan-2-amine. MS: (ES) m/z calculated for $C_9H_{12}ClFN$ $[M+H]^+$ 188.1, found 188.1.

Step b: To a mixture of 2-(3-(5-(2,4-difluorophenyl)isoxazole-3-carboxamido)-1-(4-hydroxy-4-methylcyclohexyl) azetidin-3-yl)acetic acid (50 mg, 0.10 mmol) in DMF (2 mL) was added 2-(3-chloro-5-fluorophenyl)propan-2-amine (38 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The crude residue was purified by preparative HPLC to give the two separated isomers of N-(3-(2-((2-(3-chloro-5-fluorophenyl)propan-2-yl)amino)-2-oxoethyl)-1-(4-hydroxy-4-methylcyclohexyl)azetidin-3-yl)-5-(2,4-difluorophenyl) isoxazole-3-carboxamide.

Isomer 1: $^1H$ NMR (400 MHz, $CD_3OD$) δ 8.11-7.98 (m, 1H), 7.30-7.07 (m, 4H), 7.04-6.93 (m, 2H), 4.58-4.33 (m, 4H), 3.40-3.22 (m, 1H), 3.14 (s, 2H), 2.04-1.91 (m, 2H), 1.78-1.46 (m, 10H), 1.46-1.29 (m, 2H), 1.21 (s, 3H). MS: (ES) m/z calculated for $C_{31}H_{35}ClF_3N_4O_4$ $[M+H]^+$ 619.2, found 619.2.

Isomer 2: $^1H$ NMR (400 MHz, $CD_3OD$) δ 8.10-7.99 (m, 1H), 7.30-7.18 (m, 2H), 7.15-7.07 (m, 2H), 7.02-6.94 (m, 2H), 4.57-4.32 (m, 4H), 3.15-3.10 (m, 3H), 1.86-1.69 (m, 4H), 1.59-1.55 (m, 8H), 1.47-1.35 (m, 2H), 1.20 (s, 3H). MS: (ES) m/z calculated for $C_{31}H_{35}ClF_3N_4O_4$ $[M+H]^+$ 619.2, found 619.2.

Example 37: 5-(2,4-difluorophenyl)-N-(3-(2-((2-(3-fluoro-5-methoxyphenyl)propan-2-yl)amino)-2-oxoethyl)-1-(4-hydroxy-4-methylcyclohexyl) azetidin-3-yl)isoxazole-3-carboxamide

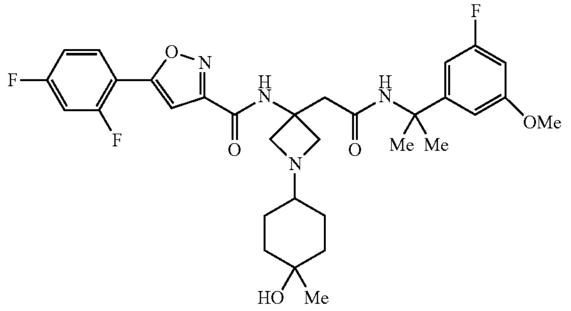 [SMILES: COc1cc(F)cc(C(C)(C)NC(=O)CC2(NC(=O)c3cc(-c4ccc(F)cc4F)on3)CN(C3CCC(C)(O)CC3)C2)c1]

Step a: To a solution of 3-fluoro-5-methoxybenzonitrile (1.00 g, 6.99 mmol) in ether (100 mL) was added dropwise a solution of 3.0 M methylmagnesium bromide (7.30 mL, 21.9 mmol) followed by titanium(IV) isopropoxide (2.16 mL, 7.30 mmol). The resulting mixture was refluxed overnight under $N_2$, then cooled to 0° C., quenched with water followed by a solution of 10% NaOH (aq). The contents were filtered through a plug of Celite and washed with DCM. The organic layer of the filtrate was collected, dried over $Na_2SO_4$, concentrated in vacuo and purified by silica gel column chromatography to give 2-(3-fluoro-5-methoxyphenyl)propan-2-amine. MS: (ES) m/z calculated for $C_{10}H_{15}FNO$ $[M+H]^+$ 184.1, found 184.1.

Step b: To a mixture of 2-(3-(5-(2,4-difluorophenyl)isoxazole-3-carboxamido)-1-(4-hydroxy-4-methylcyclohexyl) azetidin-3-yl)acetic acid (50 mg, 0.10 mmol) in DMF (2 mL) was added 2-(3-fluoro-5-methoxyphenyl)propan-2-amine (38 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The crude material was purified by preparative HPLC to give the two separated isomers of 5-(2,4-difluorophenyl)-N-(3-(2-((2-(3-fluoro-5-methoxyphenyl)propan-2-yl) amino)-2-oxoethyl)-1-(4-hydroxy-4-methylcyclohexyl)azetidin-3-yl)isoxazole-3-carboxamide.

Isomer 1: $^1H$ NMR (400 MHz, $CD_3OD$) δ 8.12-8.00 (m, 1H), 7.31-7.17 (m, 2H), 7.13-7.06 (m, 1H), 6.65 (s, 1H), 6.62-6.57 (m, 1H), 6.49-6.44 (m, 1H), 4.55-4.33 (m, 4H), 3.72-3.64 (m, 3H), 3.26-3.05 (m, 3H), 1.88-1.69 (m, 4H), 1.66-1.48 (m, 8H), 1.48-1.34 (m, 2H), 1.20 (s, 3H). MS: (ES) m/z calculated for $C_{32}H_{38}F_3N_4O_5$ $[M+H]^+$ 615.3, found 615.3.

Isomer 2: $^1H$ NMR (400 MHz, $CD_3OD$) δ 8.12-8.00 (m, 1H), 7.33-7.17 (m, 2H), 7.14-7.06 (m, 1H), 6.71-6.56 (m, 2H), 6.52-6.43 (m, 1H), 4.58-4.33 (m, 4H), 3.72-3.64 (m, 3H), 3.39-3.20 (m, 1H), 3.17-3.08 (m, 2H), 2.04-1.89 (m, 2H), 1.74-1.28 (m, 12H), 1.20 (s, 3H). MS: (ES) m/z calculated for $C_{32}H_{38}F_3N_4O_5$ $[M+H]^+$ 615.3, found 615.3.

Example 38: 5-(2,4-difluorophenyl)-N-(3-(2-((2-(2-fluoro-5-methoxyphenyl)propan-2-yl)amino)-2-oxoethyl)-1-(4-hydroxy-4-methylcyclohexyl)azetidin-3-yl)isoxazole-3-carboxamide

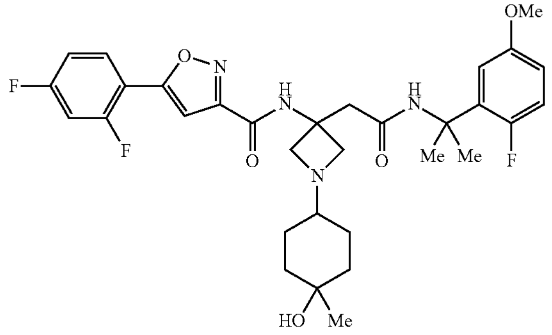 [SMILES: COc1ccc(F)c(C(C)(C)NC(=O)CC2(NC(=O)c3cc(-c4ccc(F)cc4F)on3)CN(C3CCC(C)(O)CC3)C2)c1]

Step a: To a solution of 2-fluoro-5-methoxybenzonitrile (1.00 g, 6.99 mmol) in ether (100 mL) was added dropwise a solution of 3.0 M methylmagnesium bromide (7.30 mL, 21.9 mmol) followed by titanium(IV) isopropoxide (2.16 mL, 7.30 mmol). The resulting mixture was refluxed overnight under $N_2$, then cooled to 0° C., quenched with water followed by a solution of 10% NaOH (aq). The mixture was filtered through a plug of Celite and washed with DCM. The organic layer of the filtrate was collected, dried over $Na_2SO_4$, concentrated in vacuo and purified by silica gel column chromatography to give 2-(2-fluoro-5-methoxyphenyl)propan-2-amine. MS: (ES) m/z calculated for $C_{10}H_{15}FNO$ $[M+H]^+$ 184.1, found 184.1.

Step b: To a mixture of 2-(3-(5-(2,4-difluorophenyl)isoxazole-3-carboxamido)-1-(4-hydroxy-4-methylcyclohexyl) azetidin-3-yl)acetic acid (50 mg, 0.10 mmol) in DMF (2 mL) was added 2-(2-fluoro-5-methoxyphenyl)propan-2-amine (38 mg, 0.20 mmol), HATU (77 mg, 0.20 mmol) and DIPEA (0.070 mL, 0.40 mmol). The reaction mixture was stirred at room temperature for 1 h and then quenched with 3 drops of $H_2O$. The crude material was purified by preparative HPLC to give the two separated isomers of 5-(2,4-difluorophenyl)-N-(3-(2-((2-(2-fluoro-5-methoxyphenyl) propan-2-yl)amino)-2-oxoethyl)-1-(4-hydroxy-4-methylcyclohexyl)azetidin-3-yl)isoxazole-3-carboxamide.

Isomer 1: $^1H$ NMR (400 MHz, $CD_3OD$) δ 8.12-8.02 (m, 1H), 7.32-7.18 (m, 2H), 7.14-7.07 (m, 1H), 6.88-6.81 (m, 1H), 6.80-6.67 (m, 2H), 4.57-4.32 (m, 4H), 3.71 (s, 3H), 3.28-3.02 (m, 3H), 2.03-1.90 (m, 2H), 1.75-1.27 (m, 12H), 1.20 (s, 3H). MS: (ES) m/z calculated for $C_{32}H_{38}F_3N_4O_5$ $[M+H]^+$ 615.3, found 615.3.

Isomer 2: $^1H$ NMR (400 MHz, $CD_3OD$) δ 8.12-8.03 (m, 1H), 7.32-7.18 (m, 2H), 7.14-7.07 (m, 1H), 6.87-6.81 (m, 1H), 6.74-6.67 (m, 2H), 4.58-4.29 (m, 4H), 3.70 (s, 3H), 3.15-3.05 (m, 3H), 1.85-1.70 (m, 4H), 1.67-1.33 (m, 10H), 1.20 (s, 3H). MS: (ES) m/z calculated for $C_{32}H_{38}F_3N_4O_5$ $[M+H]^+$ 615.3, found 615.3.

Example 39: 5-(2,4-difluorophenyl)-N-(3-(2-((2-(2-fluoro-5-methylphenyl)propan-2-yl)amino)-2-oxoethyl)-1-(4-hydroxy-4-methylcyclohexyl)azetidin-3-yl)isoxazole-3-carboxamide

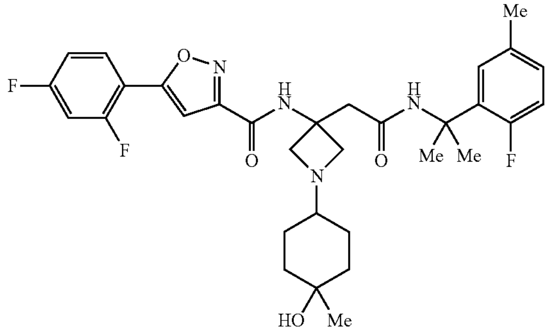 [SMILES: Cc1ccc(F)c(C(C)(C)NC(=O)CC2(NC(=O)c3cc(-c4ccc(F)cc4F)on3)CN(C3CCC(C)(O)CC3)C2)c1]

Step a: To a solution of 2-fluoro-5-methylbenzonitrile (1.00 g, 7.87 mmol) in ether (100 mL) was added dropwise a solution of 3.0 M methylmagnesium bromide (7.30 mL, 21.9 mmol) followed by titanium(IV) isopropoxide (2.16 mL, 7.30 mmol). The resulting mixture was refluxed overnight under $N_2$, then cooled to 0° C., quenched with water followed by a solution of 10% NaOH (aq). The mixture was filtered through a plug of Celite and washed with DCM. The organic layer of the filtrate was collected, dried over $Na_2SO_4$, concentrated in vacuo and purified by silica gel column chromatography to give 2-(2-fluoro-5-methylphenyl)propan-2-amine. MS: (ES) m/z calculated for $C_{10}H_{15}FN$ $[M+H]^+$ 168.1, found 168.1.

Step b: To a mixture of 2-(3-(5-(2,4-difluorophenyl)isoxazole-3-carboxamido)-1-(4-hydroxy-4-methylcyclohexyl) azetidin-3-yl)acetic acid (50 mg, 0.10 mmol) in DMF (2 mL) was added 2-(2-fluoro-5-methylphenyl)propan-2-amine (38 mg, 0.20 mmol), HATU (77 mg, 0.20 mmol) and DIPEA (0.070 mL, 0.40 mmol). The contents were stirred at room temperature for 1 h and then quenched with 3 drops of $H_2O$. The crude material was purified by preparative HPLC to give the two separated isomers of 5-(2,4-difluorophenyl)-N-(3-(2-((2-(2-fluoro-5-methylphenyl)propan-2-yl)amino)-2-oxoethyl)-1-(4-hydroxy-4-methylcyclohexyl)azetidin-3-yl)isoxazole-3-carboxamide.

Isomer 1: $^1H$ NMR (400 MHz, $CD_3OD$) δ 8.13-8.01 (m, 1H), 7.35-7.17 (m, 2H), 7.17-7.06 (m, 2H), 7.05-6.91 (m, 1H), 6.78-6.58 (m, 1H), 4.57-4.30 (m, 4H), 3.39-3.15 (m, 1H), 3.15-2.96 (m, 2H), 2.28-2.18 (m, 3H), 2.02-1.88 (m, 2H), 1.75-1.26 (m, 12H), 1.20 (s, 3H). MS: (ES) m/z calculated for $C_{32}H_{38}F_3N_4O_4$ $[M+H]^+$ 599.3, found 599.3.

Isomer 2: $^1H$ NMR (400 MHz, $CD_3OD$) δ 8.14-8.00 (m, 1H), 7.32-7.18 (m, 2H), 7.16-7.08 (m, 2H), 7.01-6.92 (m, 1H), 6.70-6.60 (m, 1H), 4.53-4.31 (m, 4H), 3.15-3.05 (m, 3H), 2.23 (s, 3H), 1.85-1.69 (m, 4H), 1.67-1.33 (m, 10H), 1.20 (s, 3H). MS: (ES) m/z calculated for $C_{32}H_{38}F_3N_4O_4$ $[M+H]^+$ 599.3, found 599.3.

Example 40: 5-(2,4-difluorophenyl)-N-(3-(2-((2-(4,6-dimethylpyrimidin-2-yl)propan-2-yl)amino)-2-oxoethyl)-1-(4-hydroxy-4-methylcyclohexyl)azetidin-3-yl)-1,3,4-thiadiazole-2-carboxamide

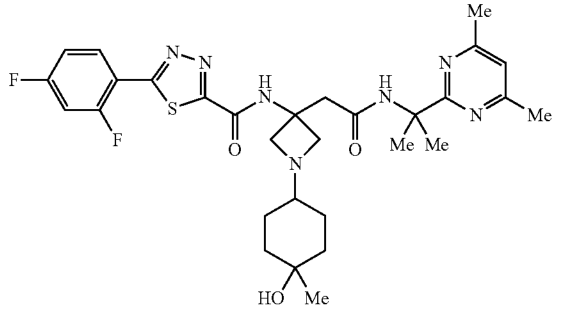 [SMILES: Cc1cc(C)nc(C(C)(C)NC(=O)CC2(NC(=O)c3nnc(-c4ccc(F)cc4F)s3)CN(C3CCC(C)(O)CC3)C2)n1]

Step a: To a solution of tert-butyl 3-amino-3-(2-ethoxy-2-oxoethyl)azetidine-1-carboxylate (2.31 g, 8.96 mmol) and lithium 5-(2,4-difluorophenyl)-1,3,4-thiadiazole-2-carboxylate (2.22 g, 8.96 mmol) in 20 mL DMF was added HATU (3.75 g, 9.86 mmol). The mixture was stirred at room temperature for 1 h and then quenched with $H_2O$. The solid crashed out was filtered, rinsed with water and dried in vacuo oven to give tert-butyl 3-(5-(2,4-difluorophenyl)-1,3,4-thiadiazole-2-carboxamido)-3-(2-ethoxy-2-oxoethyl)azetidine-1-carboxylate. MS: (ES) m/z calculated for $C_{21}H_{25}F_2N_4O_5S$ $[M+H]^+$ 483.1, found 483.2.

Step b: A mixture of tert-butyl 3-(5-(2,4-difluorophenyl)-1,3,4-thiadiazole-2-carboxamido)-3-(2-ethoxy-2-oxoethyl) azetidine-1-carboxylate (2.36 g, 4.89 mmol) in 4M HCl in dioxane (20 mL) was stirred for 1 h. The contents were concentrated in vacuo to give ethyl 2-(3-(5-(2,4-difluorophenyl)-1,3,4-thiadiazole-2-carboxamido)azetidin-3-yl)acetate. MS: (ES) m/z calculated for $C_{16}H_{17}F_2N_4O_3S$ $[M+H]^+$ 383.1, found 383.1.

Step c: A mixture of ethyl 2-(3-(5-(2,4-difluorophenyl)-1,3,4-thiadiazole-2-carboxamido)azetidin-3-yl)acetate (2.0 g, 5.23 mmol), pyridine (0.85 mL, 10.46 mmol), and 4-hydroxy-4-methylcyclohexan-1-one (1.0 g, 7.85 mmol) in 4:1 DCM/MeOH (50 mL) was stirred at room temperature for 1 h. To the contents was added $NaBH(OAc)_3$ (2.22 g, 10.46 mmol). The reaction mixture was stirred for an additional 1 h at room temperature, then quenched with saturated $NaHCO_3$ (aq) and extracted with DCM. The combined organic layers were dried over $MgSO_4$, filtered, and concentrated in vacuo. The crude residue was purified by silica gel column chromatography to give the two separated isomers of ethyl 2-(3-(5-(2,4-difluorophenyl)-1,3,4-thiadiazole-2-carboxamido)-1-(4-hydroxy-4-methylcyclohexyl)azetidin-3-yl)acetate. MS: (ES) m/z calculated for $C_{23}H_{29}F_2N_4O_4S$ $[M+H]^+$ 495.2, found 495.2.

Step d: To a solution of ethyl 2-(3-(5-(2,4-difluorophenyl)-1,3,4-thiadiazole-2-carboxamido)-1-(4-hydroxy-4-methylcyclohexyl)azetidin-3-yl)acetate (472 mg, 0.95 mmol) in 4:1 THF/$H_2O$ (2 mL) was added LiOH (48 mg, 1.2 mmol). The mixture was stirred at room temperature overnight, then concentrated to dryness, acidified to pH 3-4, and extracted with a solution of $CHCl_3$/IPA (2:1). The organic layers were combined, dried, filtered and concentrated to yield 2-(3-(5-(2,4-difluorophenyl)-1,3,4-thiadiazole-2-carboxamido)-1-(4-hydroxy-4-methylcyclohexyl)azetidin-3-yl)acetic acid. MS: (ES) m/z calculated for $C_{21}H_{25}F_2N_4O_4S$ $[M+H]^+$ 466.2, found 466.2.

Step e: To a mixture of 2-(3-(5-(2,4-difluorophenyl)-1,3,4-thiadiazole-2-carboxamido)-1-(4-hydroxy-4-methylcyclohexyl)azetidin-3-yl)acetic acid (47 mg, 0.10 mmol) in DMF (2 mL) was added 2-(4,6-dimethylpyrimidin-2-yl) propan-2-amine (17 mg, 0.10 mmol), DIPEA (0.04 mL, 0.24 mmol), and HATU (42 mg, 0.11 mmol). The contents were stirred for 1 h and then purified by preparative HPLC to give the desired product 5-(2,4-difluorophenyl)-N-(3-(2-((2-(4,6-dimethylpyrimidin-2-yl)propan-2-yl)amino)-2-oxoethyl)-1-(4-hydroxy-4-methylcyclohexyl)azetidin-3-yl)-1,3,4-thiadiazole-2-carboxamide.

Isomer 1: $^1H$ NMR (400 MHz, $CD_3OD$) δ 8.44 (ddd, J=8.0, 8.0, 8.0 Hz, 1H), 7.37-7.20 (m, 2H), 7.05 (s, 1H), 4.64-4.40 (m, 4H), 3.43-3.22 (m, 1H), 3.13 (d, J=9.3 Hz, 2H), 2.40 (s, 6H), 1.99 (s, 2H), 1.75-1.35 (m, 6H), 1.62 (s, 6H), 1.21 (s, 3H). MS: (ES) m/z calculated for $C_{30}H_{38}F_2N_7O_3S$ $[M+H]^+$ 614.3, found 614.0.

Isomer 2: $^1H$ NMR (400 MHz, $CD_3OD$) δ 8.50-8.40 (m, 1H), 7.35-7.22 (m, 2H), 7.05 (s, 1H), 4.62-4.40 (m, 4H), 3.39-3.22 (m, 3H), 2.39 (s, 6H), 1.84-1.71 (m, 4H), 1.61 (s, 6H), 1.62-1.35 (m, 4H), 1.21 (s, 3H). MS: (ES) m/z calculated for $C_{30}H_{37}F_2N_7O_3S$ $[M+H]^+$ 614.3, found 614.0.

Example 41: N-(3-(2-((2-(3-chlorophenyl)propan-2-yl)amino)-2-oxoethyl)-1-(4-hydroxy-4-methylcyclohexyl)azetidin-3-yl)-5-(2,4-difluorophenyl)thiazole-2-carboxamide

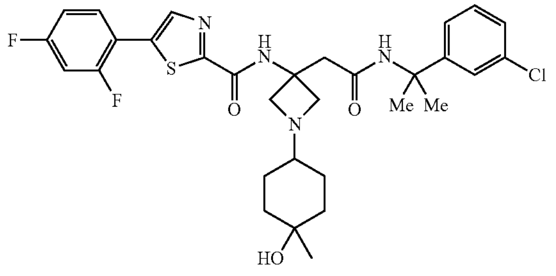 [SMILES: CC1(O)CCC(N2CC(CC(=O)NC(C)(C)c3cccc(Cl)c3)(NC(=O)c3ncc(-c4ccc(F)cc4F)s3)C2)CC1]

Step a: To a solution containing (2,4-difluorophenyl) boronic acid (370 mg, 2.3 mmol) and ethyl 5-bromothiazole-2-carboxylate (500 mg, 2.1 mmol) in a 2:1 mixture of toluene/$H_2O$ (4.2 mL/2.1 mL) was added $Pd(OAc)_2$ (48 mg, 0.21 mmol), Xantphos (98 mg, 0.21 mmol) and NMM (0.52 mL, 4.7 mmol). After two hours, the mixture was extracted with EtOAc. The organic layers were combined, dried with sodium sulfate, filtered and concentrated. The crude material was purified by silica gel column chromatography to give ethyl 5-(2,4-difluorophenyl)thiazole-2-carboxylate. MS: (ES) m/z calculated for $C_{12}H_{10}F_2NO_2S$ $[M+H]^+$ 270.0, found 270.1.

Step b: To a solution of ethyl 5-(2,4-difluorophenyl) thiazole-2-carboxylate (488 mg, 1.8 mmol) in 5.4 mL of THF was added a solution of 1M LiOH (5.4 mL). The reaction mixture was stirred at room temperature for 16 h, then quenched with 1N HCl. The contents were filtered and the solid was collected and dried to provide 5-(2,4-difluorophenyl)thiazole-2-carboxylic acid. MS: (ES) m/z calculated for $C_{10}H_6F_2NO_2S$ $[M+H]^+$ 242.0, 241.9.

Step c: To a solution containing 5-(2,4-difluorophenyl) thiazole-2-carboxylic acid (450 mg, 1.9 mmol) and tert-butyl 3-amino-3-(2-ethoxy-2-oxoethyl)azetidine-1-carboxylate (440 mg, 1.7 mmol) in 6.8 mL of DMF was added DIPEA (0.59 mL, 3.4 mmol) followed by HATU (780 mg, 2.1 mmol). The contents were stirred at room temperature for 16 h then concentrated in vacuo and purified by silica gel column chromatography to yield tert-butyl 3-(5-(2,4-difluorophenyl)thiazole-2-carboxamido)-3-(2-ethoxy-2-oxoethyl) azetidine-1-carboxylate. MS: (ES) m/z calculated for $C_{22}H_{26}F_2N_3O_5S$ $[M+H]^+$ 482.2, found 482.2.

Step d: To a solution of tert-butyl 3-(5-(2,4-difluorophenyl)thiazole-2-carboxamido)-3-(2-ethoxy-2-oxoethyl)azetidine-1-carboxylate (820 mg, 1.7 mmol) in 3.6 mL of dioxane was added a solution of 4.0 M HCl in dioxane (3.6 mL, 14.2 mmol). The contents were stirred at room temperature for 16 h then concentrated to give ethyl 2-(3-(5-(2,4-difluorophenyl)thiazole-2-carboxamido)azetidin-3-yl)acetate. MS: (ES) m/z calculated for $C_{17}H_{18}F_2N_3O_3S$ $[M+H]^+$ 382.1, found 382.2.

Step e: To a solution of ethyl 2-(3-(5-(2,4-difluorophenyl) thiazole-2-carboxamido)azetidin-3-yl)acetate (360 mg, 0.94 mmol) and 4-hydroxy-4-methylcyclohexan-1-one (165 mg, 1.3 mmol) in 3.4 mL of DCM was added pyridine (0.15 mL, 1.4 mmol). After stirring at room temperature for 10 min, $NaBH(OAc)_3$ (360 mg, 1.7 mmol) was added and the contents were stirred for an additional 16 h. The reaction was quenched with $H_2O$ and extracted with EtOAc. The combined organic layers were dried with sodium sulfate, filtered and concentrated. The crude material was purified by silica gel column chromatography to provide ethyl 2-(3-(5-(2,4-difluorophenyl)thiazole-2-carboxamido)-1-(4-hydroxy-4-methylcyclohexyl)azetidin-3-yl)acetate. MS: (ES) m/z calculated for $C_{24}H_{30}F_2N_3O_4S$ $[M+H]^+$ 494.2, found 494.4.

Step f: To a solution of ethyl 2-(3-(5-(2,4-difluorophenyl) thiazole-2-carboxamido)-1-(4-hydroxy-4-methylcyclohexyl)azetidin-3-yl)acetate (339 mg, 0.69 mmol) in 2 mL of THF was added a solution of 1M LiOH (2 mL, 2.0 mmol). The contents were stirred at room temperature for 16 h, then quenched with 1N HCl and concentrated to dryness to give 2-(3-(5-(2,4-difluorophenyl)thiazole-2-carboxamido)-1-(4-hydroxy-4-methylcyclohexyl)azetidin-3-yl)acetic acid. MS: (ES) m/z calculated for $C_{22}H_{26}F_2N_3O_4S$ $[M+H]^+$ 466.2, found 466.3.

Step g: To a solution of 2-(3-(5-(2,4-difluorophenyl) thiazole-2-carboxamido)-1-(4-hydroxy-4-methylcyclohexyl)azetidin-3-yl)acetic acid (160 mg, 0.35 mmol) and 2-(3-chlorophenyl)propan-2-amine (70 mg, 0.41 mmol) in 2 mL of DMF was added DIPEA (0.19 mL, 1.1 mmol) followed by HATU (245 mg, 0.65 mmol). The contents were stirred at room temperature for 4 h then concentrated in vacuo. The crude material was purified by preparative HPLC to yield the two separated isomers of N-(3-(2-((2-(3-chlorophenyl)propan-2-yl)amino)-2-oxoethyl)-1-(4-hydroxy-4-methylcyclohexyl)azetidin-3-yl)-5-(2,4-difluorophenyl)thiazole-2-carboxamide.

Isomer 1: $^1H$ NMR (400 MHz, $CD_3OD$) δ 8.31 (m, 1H), 7.88 (ddd, J=8.1, 8.1, 8.1 Hz, 1H), 7.38-7.05 (m, 6H), 4.68-4.29 (m, 4H), 3.13 (m, 2H), 2.05-1.90 (m, 2H), 1.78-1.62 (m, 2H), 1.59 (s, 3H), 1.57 (s, 3H), 1.55-1.44 (m, 3H), 1.44-1.28 (m, 2H), 1.20 (s, 3H). MS: (ES) m/z calculated for $C_{31}H_{36}ClF_2N_4O_3S$ $[M+H]^+$ 617.2, found 617.4.

Isomer 2: $^1H$ NMR (400 MHz, $CD_3OD$) δ 8.49 (d, J=10.6 Hz, 1H), 8.32 (d, J=3.4 Hz, 1H), 7.92-7.84 (m, 1H), 7.30-7.27 (m, 1H), 7.25-7.17 (m, 2H), 7.17-7.10 (m, 4H), 4.59-4.43 (m, 4H), 4.37 (d, J=11.8 Hz, 1H), 3.17-2.94 (m, 3H), 1.85-1.70 (m, 3H), 1.64-1.58 (m, 1H), 1.57 (s, 3H), 1.56 (s, 3H), 1.55-1.49 (m, 1H), 1.47-1.35 (m, 2H), 1.20 (s, 3H). MS: (ES) m/z calculated for $C_{31}H_{36}ClF_2N_4O_3S$ $[M+H]^+$ 617.2, found 617.4.

Biological Example 1

CXCR7 is fused in frame with a small enzyme donor fragment ProLink and co-expressed in CHO cells stably expressing a fusion protein of β-arrestin and the larger, N-terminal deletion mutant of β-galactosidase (called enzyme acceptor or EA). Activation of the CXCR7 stimulates binding of β-arrestin to the ProLink-tagged CXCR7 and forces complementation of the two enzyme fragments, resulting in the formation of an active β-galactosidase enzyme. The β-galactosidase enzyme activity is measured with a substrate that generates fluorescence.

CHO-CXCR7 cells ($0.22\times10^6$/mL) were cultured in growth medium (Ham's F-12 medium with 10% fetal bovine serum (FBS)), Hygromycin B (200 ug/mL) and G418 (250 ug/mL) were used to maintain the transgenes. The day before the assay, the cells were detached from culture dishes with 0.25% trypsin-EDTA (Corning, Catalog No. 25-053-CI), plated into 96 well plate ($2.2\times10^5$ cells/mL, 100 μL/well) and incubated overnight at 37° C. with 5% $CO_2$. On the day of the assay, cell culture medium was removed and 100 uL of assay buffer (PBS or FBS) was added to each well. 1 μL of compound that were serially diluted in DMSO was added to each well. 5 μL of human SDF-la (Pepro Tech, Catalog No. 300-28A, at EC50 concentration pre-determined on the same day) was then added and mixed to induce CXCR7-mediated β-arrestin recruitment. The plates were incubated for 1.5 hours at 37° C. The assay buffer was removed, 100 μL substrate solution was added and the reaction was carried out at 37° C. for 30 minutes. The substrate solution was prepared by mixing 100 mL Phosphate Buffer (1M, Sigma, Catalog No. P3619-1GA), 100 mL 10% Triton X 100 (Sigma, Catalog No. T8787.), 5 mL MgCl2 (1M, Sigma, Catalog No. M1028), 1.5 mL, β-mercaptoethanol (Gibco, Catalog No. 21985-023.). 3-carboxyumbelliferyl β-D-galactopyranoside (ThermoFisher Scientific, Catalo No. F2905) was added at 0.4 mM right before use. The reaction was then stopped by adding 50 μL of Stop Solution (2.1% w/v $Na_2CO_3$) to each well. Fluorescence intensity was measured with a FlexStation 3 microplate reader (Molecular Devices) with the following setting—excitation: 360 nm, emission: 465 nm, manual Gain: 55. $IC_{50}$ values were calculated with GraphPad Prism using 3 parameter nonlinear regression.

Validation

Compounds that are initially identified as being of interest by any of the foregoing screening methods can be further tested to validate the apparent activity in vivo. Preferably such studies are conducted with suitable animal models. The basic format of such methods involves administering a lead compound identified during an initial screen to an animal that serves as a disease model for humans and then determining if the disease (e.g., cancer, myocardial infarction, wound healing, inflammatory diseases or other diseases associated with CXCR7) is in fact modulated and/or the disease or condition is ameliorated. The animal models utilized in validation studies generally are mammals of any kind. Specific examples of suitable animals include, but are not limited to, primates, mice, rats and zebrafish.

The compounds in the Table below were prepared as described above. Where specific synthetic details are not provided, the compounds were prepared with minor variations on the methods above, with substitutions of selected reagents. Activity is provided for each, as follows: IC50<5 nM (++++); from 5 nM up to 100 nM (+++); from 100 nM up to 1000 nM (++); and from 1000 nM to 20,000 nM (+).

| Specific Examples (Table 1) | | |
|---|---|---|
| Compound ID | Structure | IC50 (buffer) |
| 1.001 | 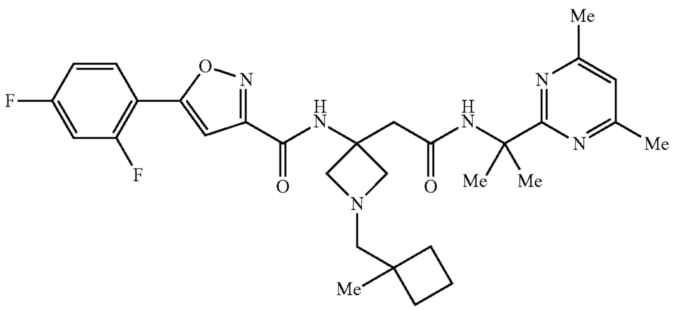 [SMILES: Cc1cc(C)nc(C(C)(C)NC(=O)CC2(NC(=O)c3cc(-c4ccc(F)cc4F)on3)CN(CC3(C)CCC3)C2)n1] | ++++ |
| 1.002 | 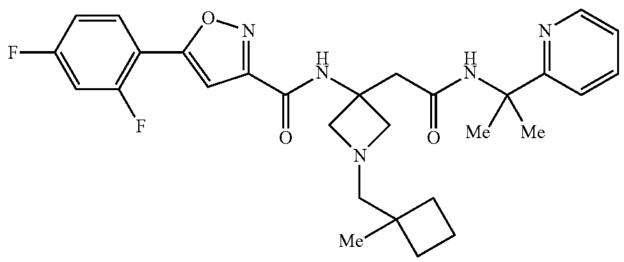 | ++++ |
| 1.003 | 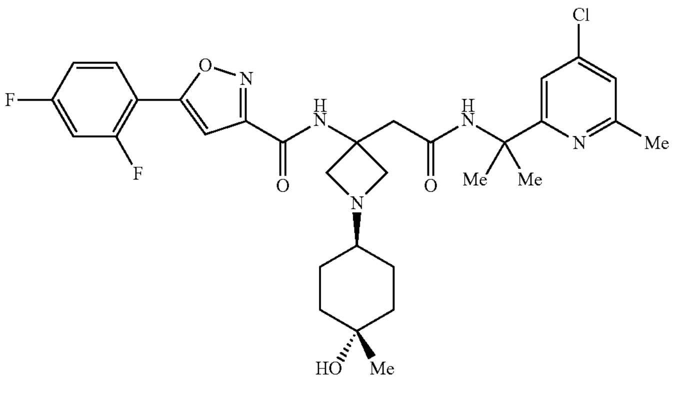 | ++++ |
| 1.004 | 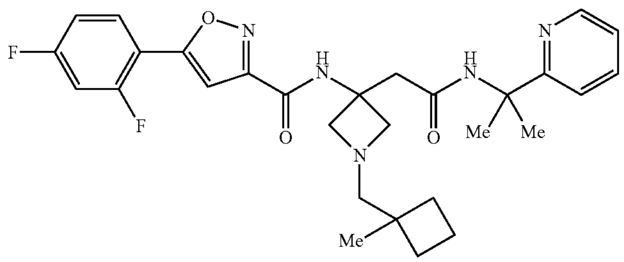 | ++++ |

-continued
| Specific Examples (Table 1) | | |
|---|---|---|
| Compound ID | Structure | IC50 (buffer) |
| 1.005 | 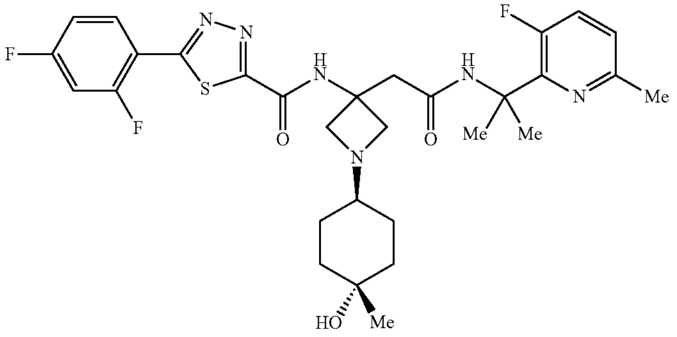 [SMILES: Cc1ccc(F)c(C(C)(C)NC(=O)CC2(NC(=O)c3nnc(-c4ccc(F)cc4F)s3)CN([C@H]3CC[C@](C)(O)CC3)C2)n1] | ++++ |
| 1.006 | 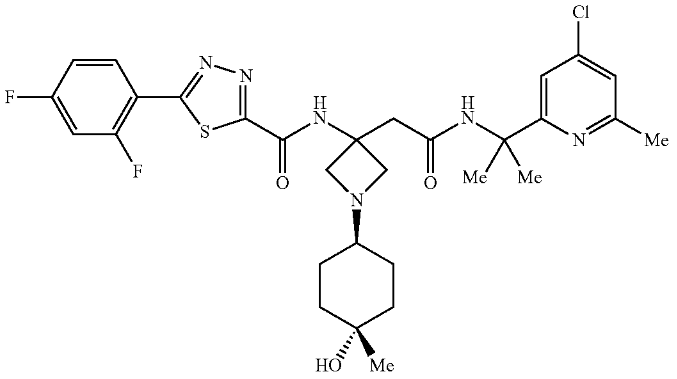 [SMILES: Cc1cc(Cl)cc(C(C)(C)NC(=O)CC2(NC(=O)c3nnc(-c4ccc(F)cc4F)s3)CN([C@H]3CC[C@](C)(O)CC3)C2)n1] | ++++ |
| 1.007 | 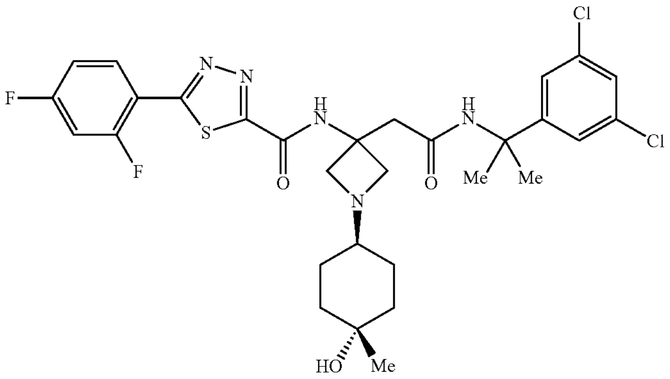 [SMILES: CC(C)(NC(=O)CC1(NC(=O)c2nnc(-c3ccc(F)cc3F)s2)CN([C@H]2CC[C@](C)(O)CC2)C1)c1cc(Cl)cc(Cl)c1] | ++++ |
| 1.008 | 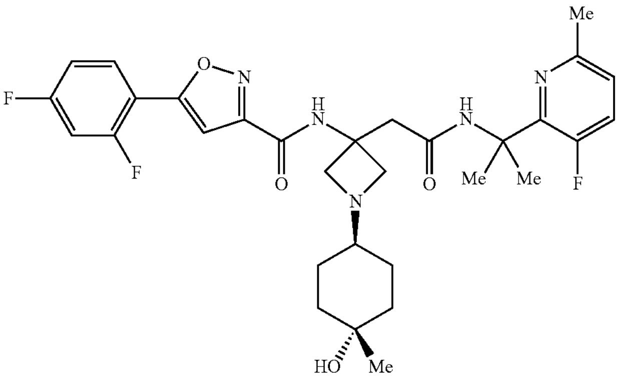 [SMILES: Cc1ccc(F)c(C(C)(C)NC(=O)CC2(NC(=O)c3cc(-c4ccc(F)cc4F)on3)CN([C@H]3CC[C@](C)(O)CC3)C2)n1] | ++++ |

-continued
Specific Examples (Table 1)
| Compound ID | Structure | IC50 (buffer) |
|---|---|---|
| 1.009 | 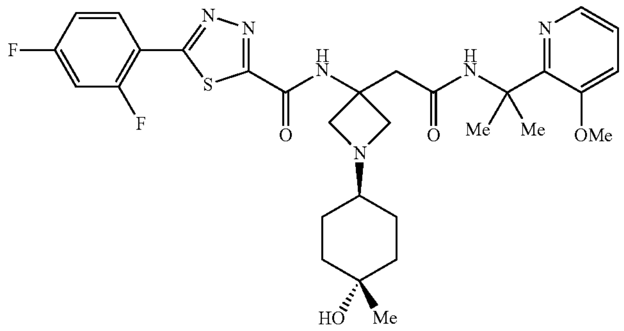 [SMILES: COc1cccnc1C(C)(C)NC(=O)CC1(NC(=O)c2nnc(-c3ccc(F)cc3F)s2)CN([C@H]2CC[C@](C)(O)CC2)C1] | +++ |
| 1.010 | 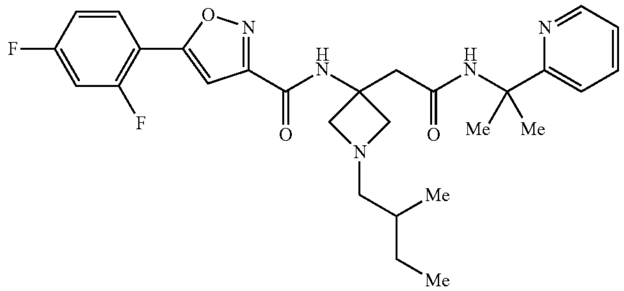 [SMILES: CCC(C)CN1CC(CC(=O)NC(C)(C)c2ccccn2)(NC(=O)c2cc(-c3ccc(F)cc3F)on2)C1] | ++++ |
| 1.011 | 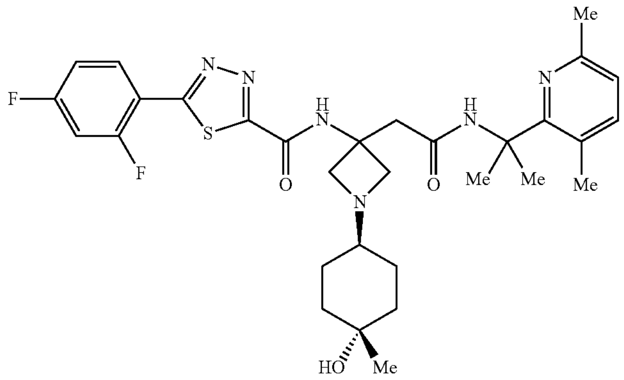 [SMILES: Cc1ccc(C)c(C(C)(C)NC(=O)CC2(NC(=O)c3nnc(-c4ccc(F)cc4F)s3)CN([C@H]3CC[C@](C)(O)CC3)C2)n1] | ++++ |
| 1.012 | 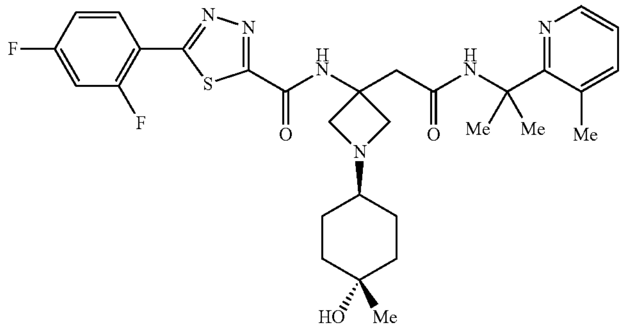 [SMILES: Cc1cccnc1C(C)(C)NC(=O)CC1(NC(=O)c2nnc(-c3ccc(F)cc3F)s2)CN([C@H]2CC[C@](C)(O)CC2)C1] | ++ |

-continued
| Specific Examples (Table 1) | | |
|---|---|---|
| Compound ID | Structure | IC50 (buffer) |
| 1.013 | 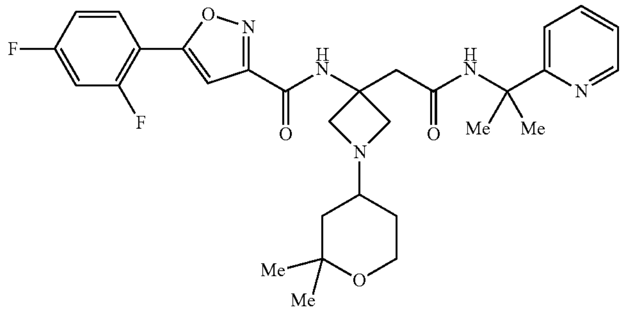 [SMILES: CC1(C)CC(N2CC(CC(=O)NC(C)(C)c3ccccn3)(NC(=O)c3cc(-c4ccc(F)cc4F)on3)C2)CCO1] | +++ |
| 1.014 | 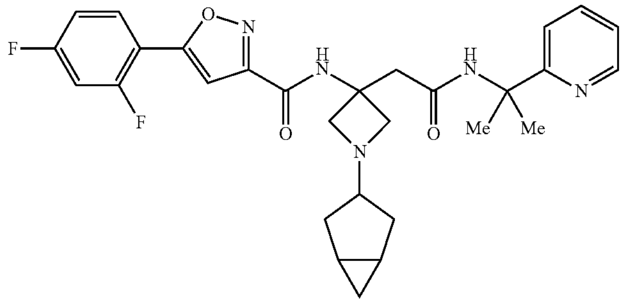 [SMILES: CC(C)(NC(=O)CC1(NC(=O)c2cc(-c3ccc(F)cc3F)on2)CN(C2CC3CC3C2)C1)c1ccccn1] | +++ |
| 1.015 | 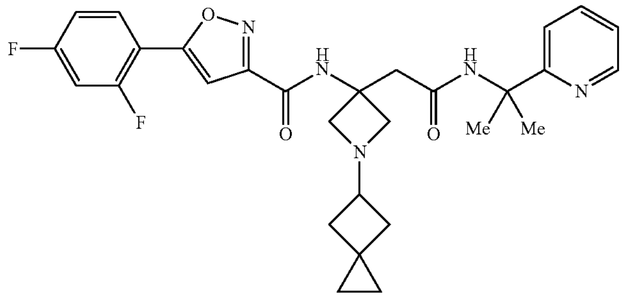 [SMILES: CC(C)(NC(=O)CC1(NC(=O)c2cc(-c3ccc(F)cc3F)on2)CN(C2CC3(CC3)C2)C1)c1ccccn1] | +++ |
| 1.016 | 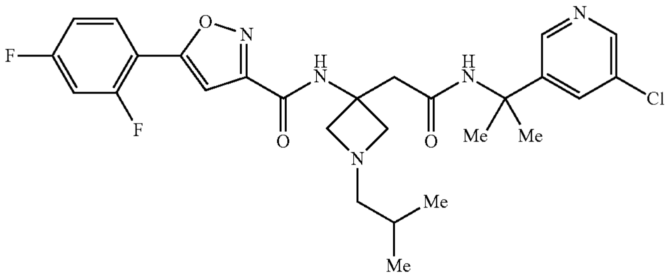 [SMILES: CC(C)CN1CC(CC(=O)NC(C)(C)c2cncc(Cl)c2)(NC(=O)c2cc(-c3ccc(F)cc3F)on2)C1] | +++ |

-continued
Specific Examples (Table 1)
| Compound ID | Structure | IC50 (buffer) |
| --- | --- | --- |
| 1.017 | 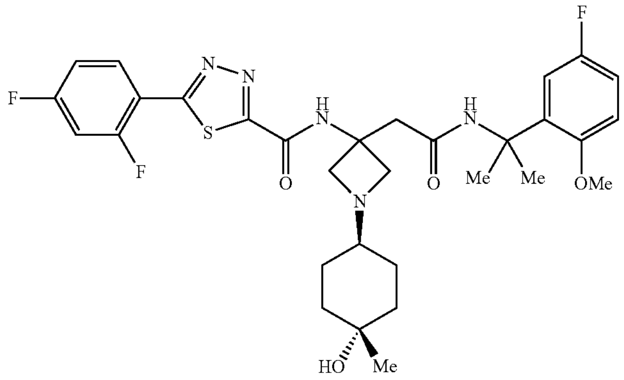 [SMILES: COc1ccc(F)cc1C(C)(C)NC(=O)CC1(NC(=O)c2nnc(-c3ccc(F)cc3F)s2)CN([C@H]2CC[C@](C)(O)CC2)C1] | +++ |
| 1.018 | 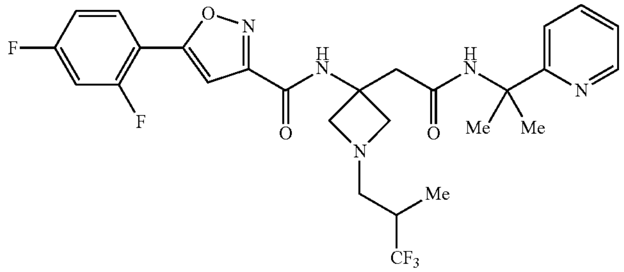 [SMILES: CC(CN1CC(CC(=O)NC(C)(C)c2ccccn2)(NC(=O)c2cc(-c3ccc(F)cc3F)on2)C1)C(F)(F)F] | ++ |
| 1.019 | 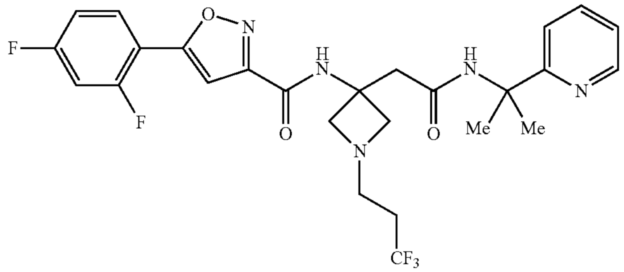 [SMILES: CC(C)(NC(=O)CC1(NC(=O)c2cc(-c3ccc(F)cc3F)on2)CN(CCC(F)(F)F)C1)c1ccccn1] | ++ |
| 1.020 | 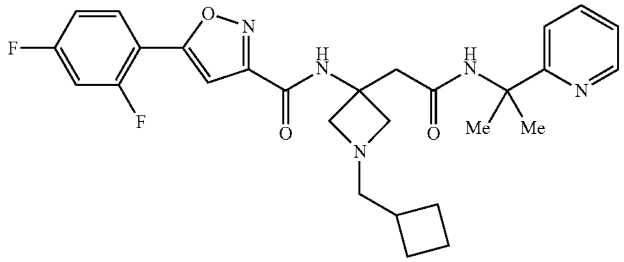 [SMILES: CC(C)(NC(=O)CC1(NC(=O)c2cc(-c3ccc(F)cc3F)on2)CN(CC2CCC2)C1)c1ccccn1] | +++ |

-continued
| Specific Examples (Table 1) | | |
|---|---|---|
| Compound ID | Structure | IC50 (buffer) |
| 1.021 | 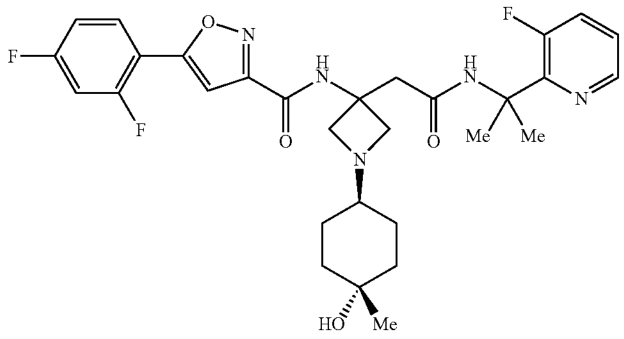 [SMILES: CC(C)(NC(=O)CC1(NC(=O)c2cc(-c3ccc(F)cc3F)on2)CN([C@H]2CC[C@](C)(O)CC2)C1)c1ncccc1F] | +++ |
| 1.022 | 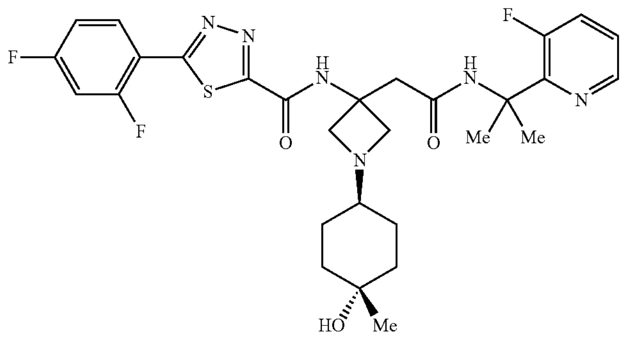 [SMILES: CC(C)(NC(=O)CC1(NC(=O)c2nnc(-c3ccc(F)cc3F)s2)CN([C@H]2CC[C@](C)(O)CC2)C1)c1ncccc1F] | +++ |
| 1.023 | 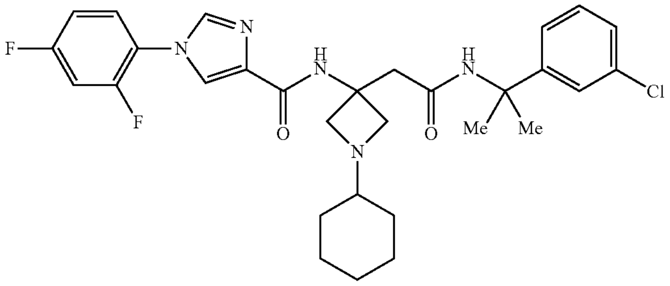 [SMILES: CC(C)(NC(=O)CC1(NC(=O)c2cn(-c3ccc(F)cc3F)cn2)CN(C2CCCCC2)C1)c1cccc(Cl)c1] | + |
| 1.024 | 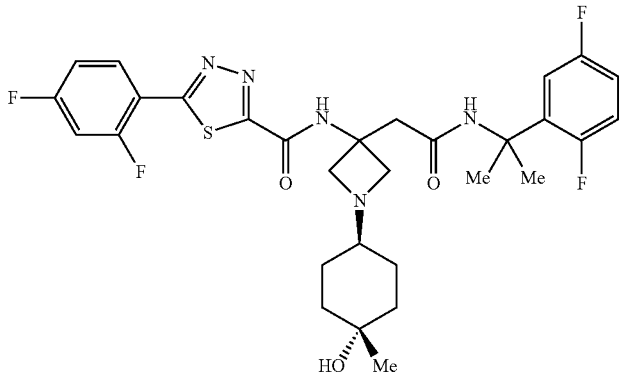 [SMILES: CC(C)(NC(=O)CC1(NC(=O)c2nnc(-c3ccc(F)cc3F)s2)CN([C@H]2CC[C@](C)(O)CC2)C1)c1cc(F)ccc1F] | +++ |

-continued
| Compound ID | Structure | IC50 (buffer) |
|---|---|---|
| 1.025 | 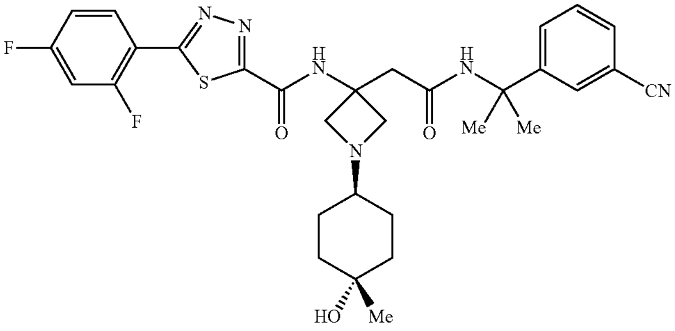 [SMILES: CC(C)(NC(=O)CC1(NC(=O)c2nnc(-c3ccc(F)cc3F)s2)CN([C@H]2CC[C@](C)(O)CC2)C1)c1cccc(C#N)c1] | +++ |
| 1.026 | 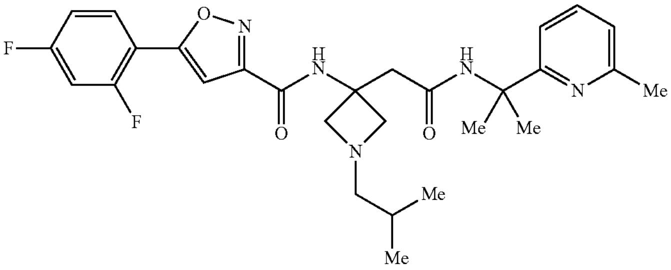 [SMILES: Cc1cccc(C(C)(C)NC(=O)CC2(NC(=O)c3cc(-c4ccc(F)cc4F)on3)CN(CC(C)C)C2)n1] | +++ |
| 1.027 | 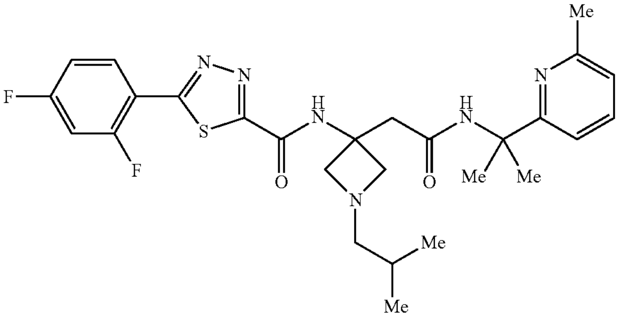 [SMILES: Cc1cccc(C(C)(C)NC(=O)CC2(NC(=O)c3nnc(-c4ccc(F)cc4F)s3)CN(CC(C)C)C2)n1] | +++ |
| 1.028 | 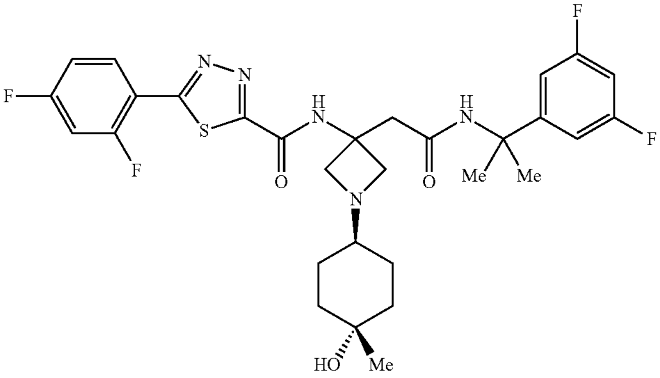 [SMILES: CC(C)(NC(=O)CC1(NC(=O)c2nnc(-c3ccc(F)cc3F)s2)CN([C@H]2CC[C@](C)(O)CC2)C1)c1cc(F)cc(F)c1] | +++ |
Specific Examples (Table 1)

-continued
| Specific Examples (Table 1) | | |
|---|---|---|
| Compound ID | Structure | IC50 (buffer) |
| 1.029 | 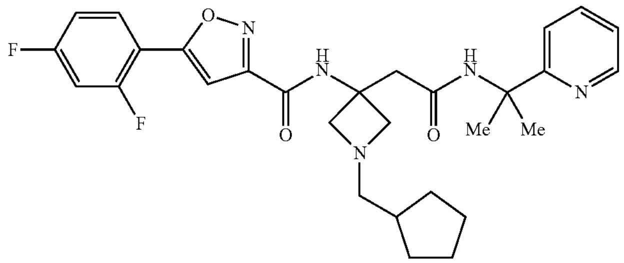 [SMILES: CC(C)(NC(=O)CC1(NC(=O)c2cc(-c3ccc(F)cc3F)on2)CN(CC2CCCC2)C1)c1ccccn1] | +++ |
| 1.030 | 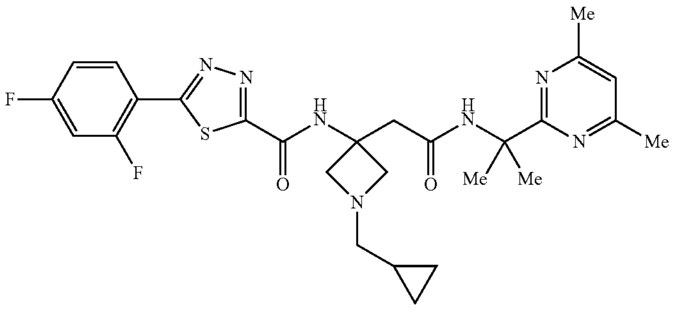 [SMILES: Cc1cc(C)nc(C(C)(C)NC(=O)CC2(NC(=O)c3nnc(-c4ccc(F)cc4F)s3)CN(CC3CC3)C2)n1] | +++ |
| 1.031 | 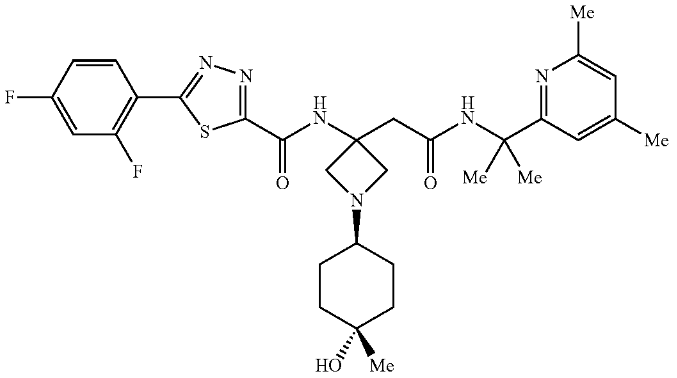 [SMILES: Cc1cc(C)nc(C(C)(C)NC(=O)CC2(NC(=O)c3nnc(-c4ccc(F)cc4F)s3)CN([C@H]3CC[C@](C)(O)CC3)C2)c1] | ++++ |
| 1.032 | 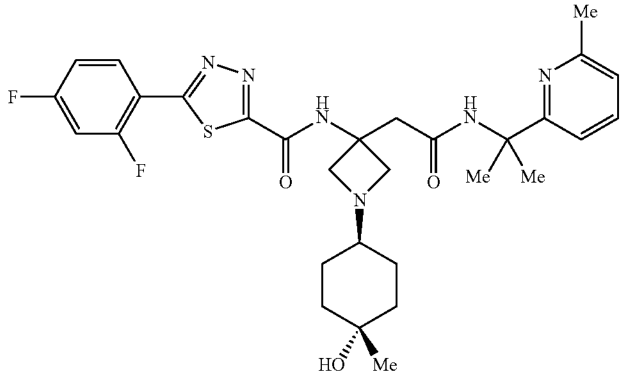 | ++++ |

-continued
Specific Examples (Table 1)
| Compound ID | Structure | IC50 (buffer) |
|---|---|---|
| 1.033 | 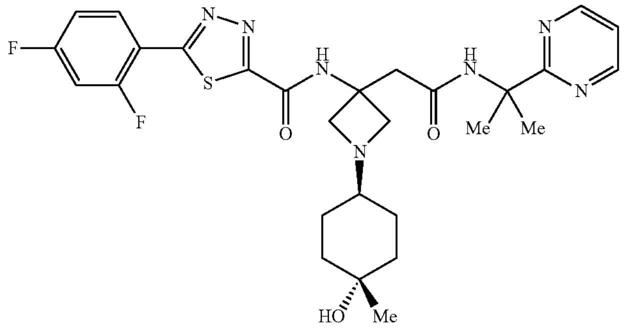 [SMILES: CC(C)(NC(=O)CC1(NC(=O)c2nnc(-c3ccc(F)cc3F)s2)CN([C@H]2CC[C@](C)(O)CC2)C1)c1ncccn1] | +++ |
| 1.034 | 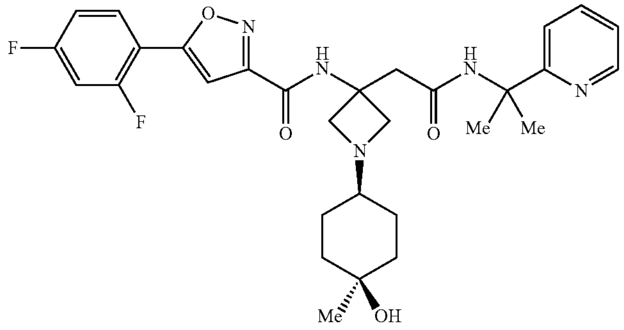 [SMILES: CC(C)(NC(=O)CC1(NC(=O)c2cc(-c3ccc(F)cc3F)on2)CN([C@H]2CC[C@@](C)(O)CC2)C1)c1ccccn1] | ++ |
| 1.035 | 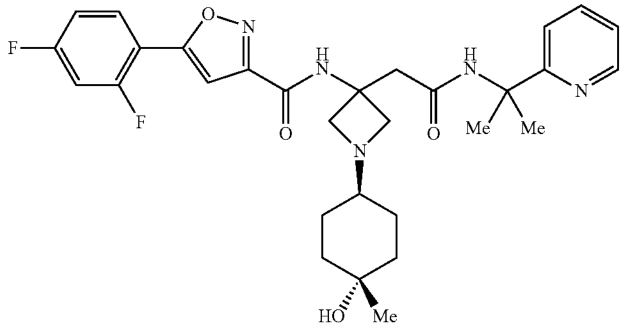 [SMILES: CC(C)(NC(=O)CC1(NC(=O)c2cc(-c3ccc(F)cc3F)on2)CN([C@H]2CC[C@](C)(O)CC2)C1)c1ccccn1] | +++ |
| 1.036 | 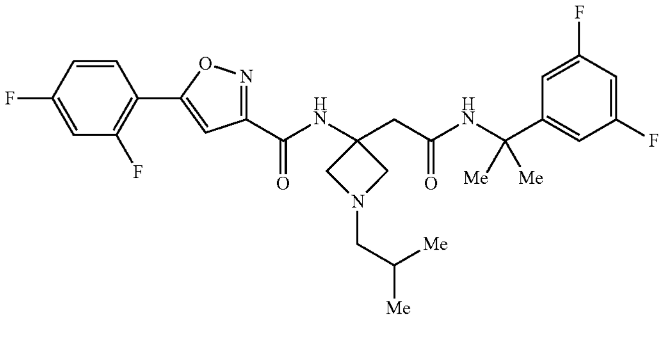 [SMILES: CC(C)CN1CC(CC(=O)NC(C)(C)c2cc(F)cc(F)c2)(NC(=O)c2cc(-c3ccc(F)cc3F)on2)C1] | +++ |

-continued
| Specific Examples (Table 1) | | |
|---|---|---|
| Compound ID | Structure | IC50 (buffer) |
| 1.037 | 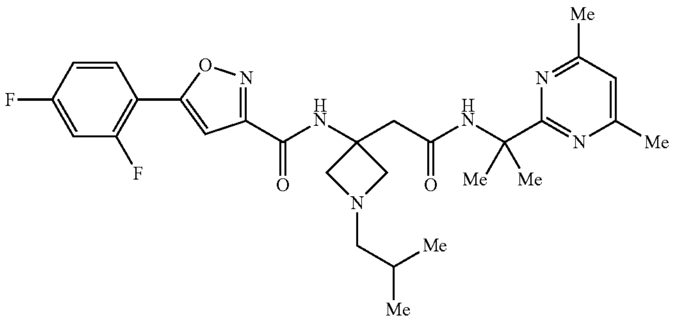 [SMILES: Cc1cc(C)nc(C(C)(C)NC(=O)CC2(NC(=O)c3cc(-c4ccc(F)cc4F)on3)CN(CC(C)C)C2)n1] | +++ |
| 1.038 | 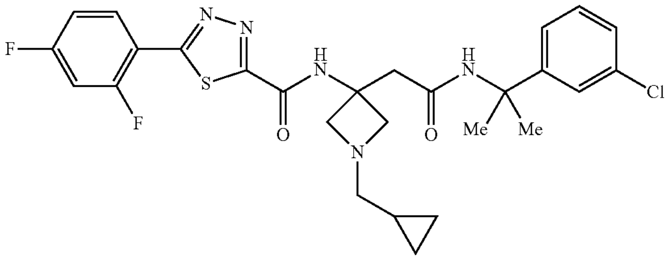 [SMILES: CC(C)(NC(=O)CC1(NC(=O)c2nnc(-c3ccc(F)cc3F)s2)CN(CC2CC2)C1)c1cccc(Cl)c1] | +++ |
| 1.039 | 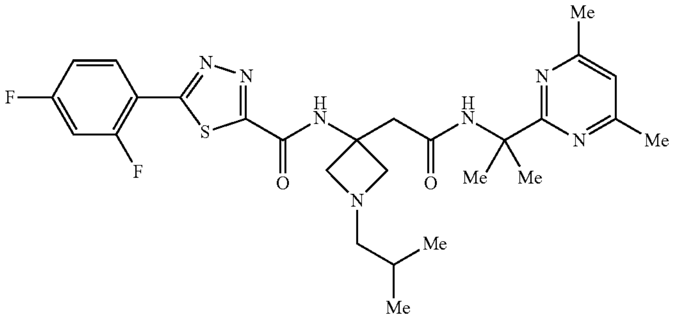 [SMILES: Cc1cc(C)nc(C(C)(C)NC(=O)CC2(NC(=O)c3nnc(-c4ccc(F)cc4F)s3)CN(CC(C)C)C2)n1] | +++ |
| 1.040 | 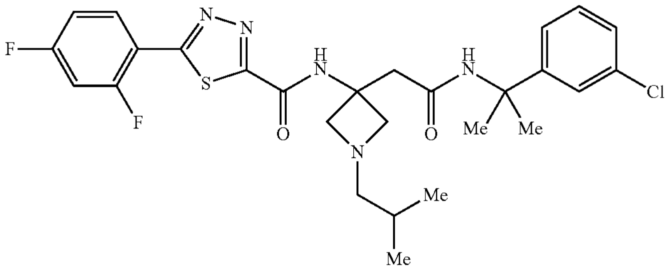 [SMILES: CC(C)CN1CC(CC(=O)NC(C)(C)c2cccc(Cl)c2)(NC(=O)c2nnc(-c3ccc(F)cc3F)s2)C1] | +++ |

-continued
Specific Examples (Table 1)
| Compound ID | Structure | IC50 (buffer) |
| --- | --- | --- |
| 1.041 | 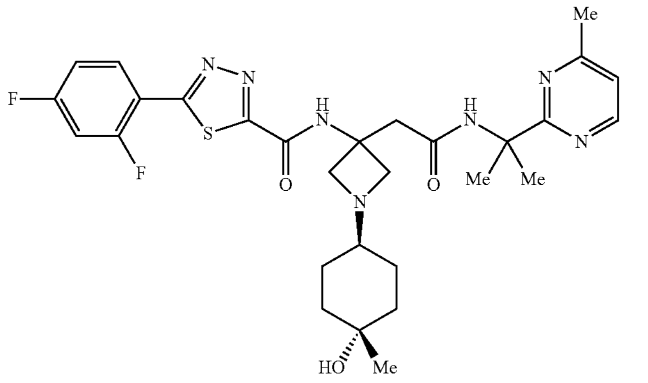 [SMILES: Cc1ccnc(C(C)(C)NC(=O)CC2(NC(=O)c3nnc(-c4ccc(F)cc4F)s3)CN([C@H]3CC[C@](C)(O)CC3)C2)n1] | +++ |
| 1.042 | 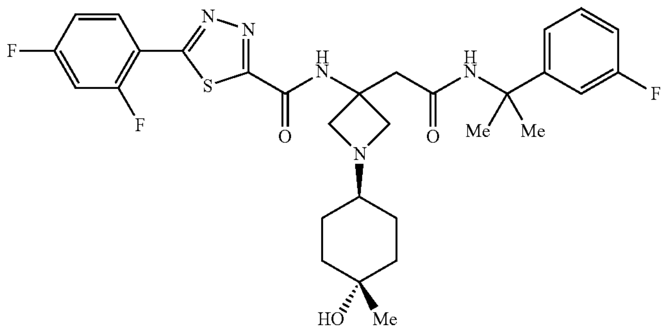 [SMILES: CC(C)(NC(=O)CC1(NC(=O)c2nnc(-c3ccc(F)cc3F)s2)CN([C@H]2CC[C@](C)(O)CC2)C1)c1cccc(F)c1] | ++++ |
| 1.043 | 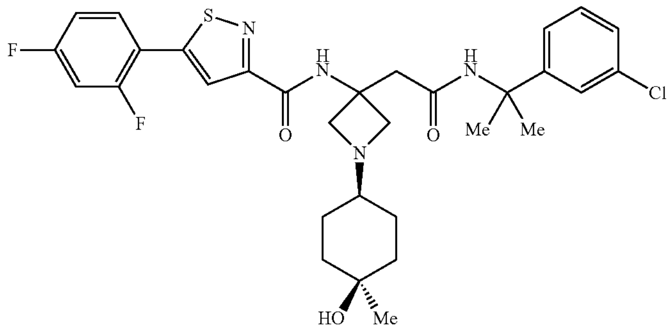 [SMILES: CC(C)(NC(=O)CC1(NC(=O)c2cc(-c3ccc(F)cc3F)sn2)CN([C@H]2CC[C@@](C)(O)CC2)C1)c1cccc(Cl)c1] | ++ |
| 1.044 | 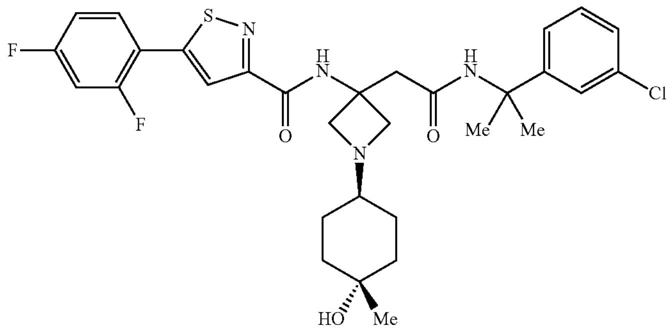 [SMILES: CC(C)(NC(=O)CC1(NC(=O)c2cc(-c3ccc(F)cc3F)sn2)CN([C@H]2CC[C@](C)(O)CC2)C1)c1cccc(Cl)c1] | ++ |

-continued
| Specific Examples (Table 1) | | |
|---|---|---|
| Compound ID | Structure | IC50 (buffer) |
| 1.045 | 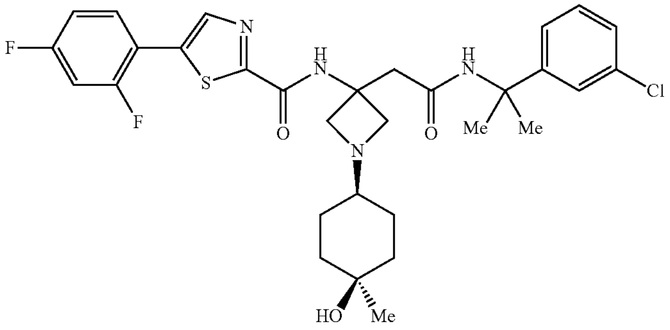 [SMILES: CC(C)(NC(=O)CC1(NC(=O)c2ncc(-c3ccc(F)cc3F)s2)CN([C@H]2CC[C@@](C)(O)CC2)C1)c1cccc(Cl)c1] | +++ |
| 1.046 | 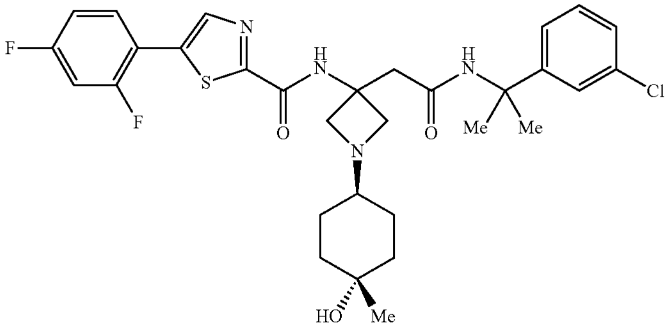 [SMILES: CC(C)(NC(=O)CC1(NC(=O)c2ncc(-c3ccc(F)cc3F)s2)CN([C@H]2CC[C@](C)(O)CC2)C1)c1cccc(Cl)c1] | +++ |
| 1.047 | 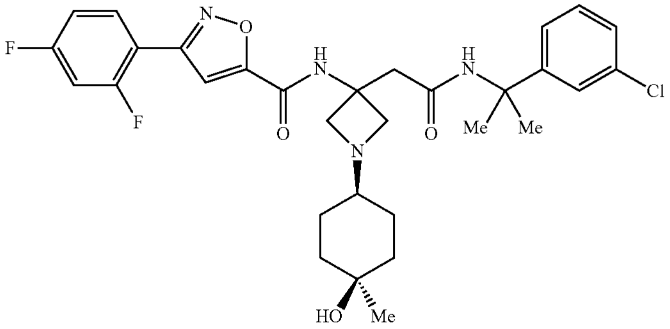 [SMILES: CC(C)(NC(=O)CC1(NC(=O)c2cc(-c3ccc(F)cc3F)no2)CN([C@H]2CC[C@@](C)(O)CC2)C1)c1cccc(Cl)c1] | +++ |
| 1.048 | 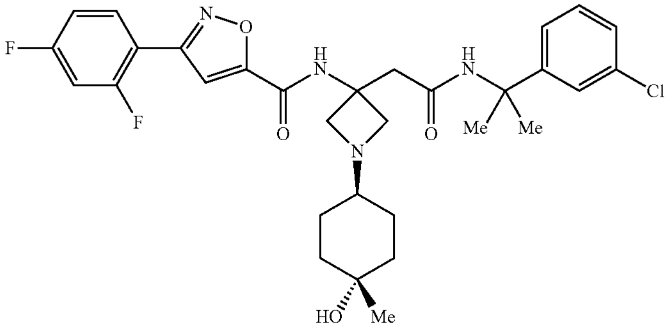 [SMILES: CC(C)(NC(=O)CC1(NC(=O)c2cc(-c3ccc(F)cc3F)no2)CN([C@H]2CC[C@](C)(O)CC2)C1)c1cccc(Cl)c1] | ++++ |

-continued
| Specific Examples (Table 1) | | |
|---|---|---|
| Compound ID | Structure | IC50 (buffer) |
| 1.049 | 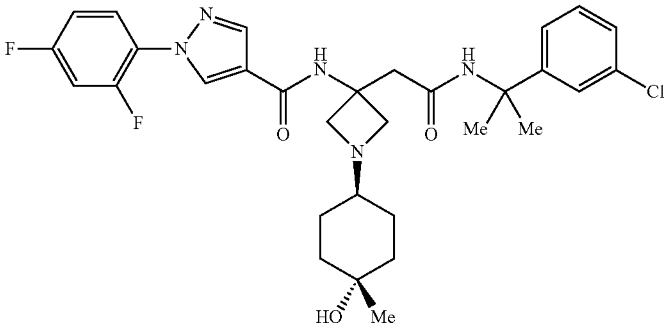 [SMILES: CC(C)(NC(=O)CC1(NC(=O)c2cnn(-c3ccc(F)cc3F)c2)CN([C@H]2CC[C@](C)(O)CC2)C1)c1cccc(Cl)c1] | + |
| 1.050 | 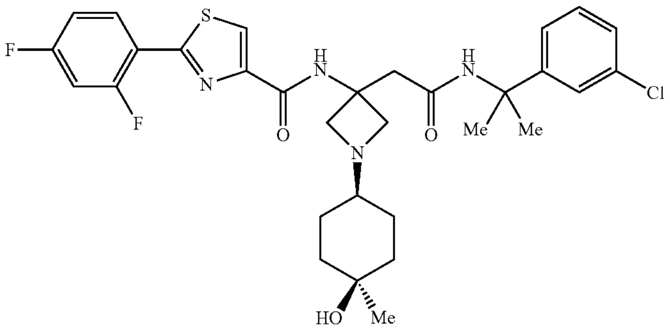 [SMILES: CC(C)(NC(=O)CC1(NC(=O)c2csc(-c3ccc(F)cc3F)n2)CN([C@H]2CC[C@@](C)(O)CC2)C1)c1cccc(Cl)c1] | + |
| 1.051 | 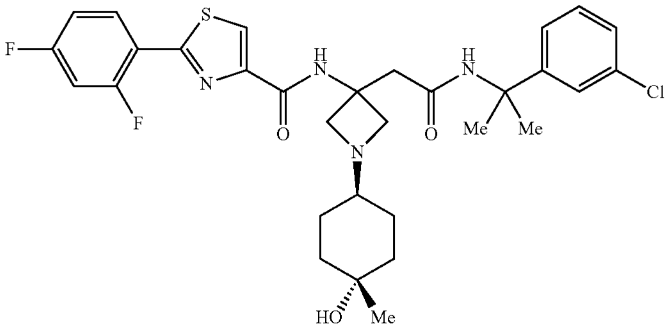 | + |
| 1.052 | 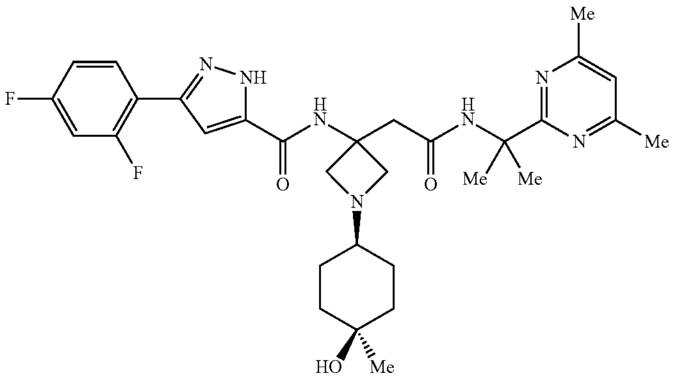 [SMILES: Cc1cc(C)nc(C(C)(C)NC(=O)CC2(NC(=O)c3cc(-c4ccc(F)cc4F)n[nH]3)CN([C@H]3CC[C@@](C)(O)CC3)C2)n1] | + |

-continued
Specific Examples (Table 1)
| Compound ID | Structure | IC50 (buffer) |
|---|---|---|
| 1.053 | 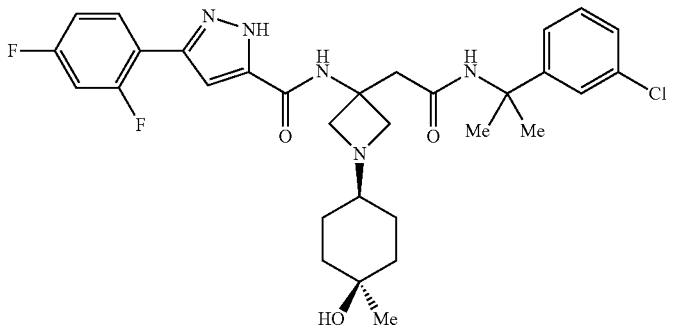 [SMILES: CC(C)(NC(=O)CC1(NC(=O)c2cc(-c3ccc(F)cc3F)n[nH]2)CN([C@H]2CC[C@@](C)(O)CC2)C1)c1cccc(Cl)c1] | + |
| 1.054 | 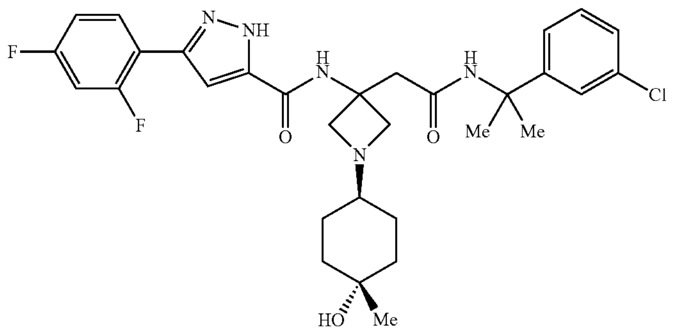 [SMILES: CC(C)(NC(=O)CC1(NC(=O)c2cc(-c3ccc(F)cc3F)n[nH]2)CN([C@H]2CC[C@](C)(O)CC2)C1)c1cccc(Cl)c1] | + |
| 1.055 | 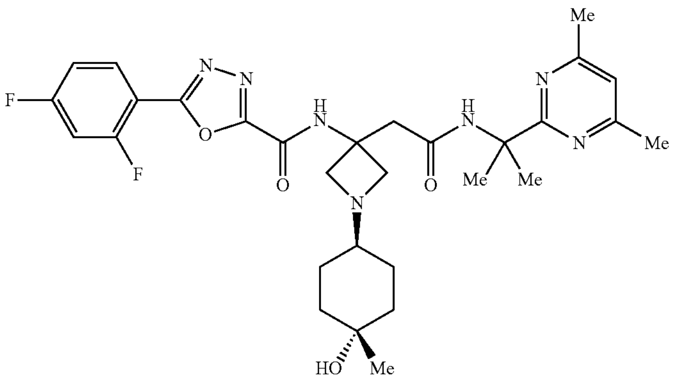 [SMILES: Cc1cc(C)nc(C(C)(C)NC(=O)CC2(NC(=O)c3nnc(-c4ccc(F)cc4F)o3)CN([C@H]3CC[C@](C)(O)CC3)C2)n1] | ++ |
| 1.056 | 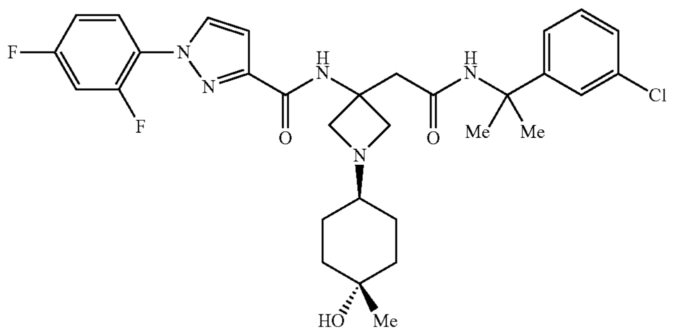 [SMILES: CC(C)(NC(=O)CC1(NC(=O)c2ccn(-c3ccc(F)cc3F)n2)CN([C@H]2CC[C@](C)(O)CC2)C1)c1cccc(Cl)c1] | + |

-continued
| Specific Examples (Table 1) | | |
|---|---|---|
| Compound ID | Structure | IC50 (buffer) |
| 1.057 | 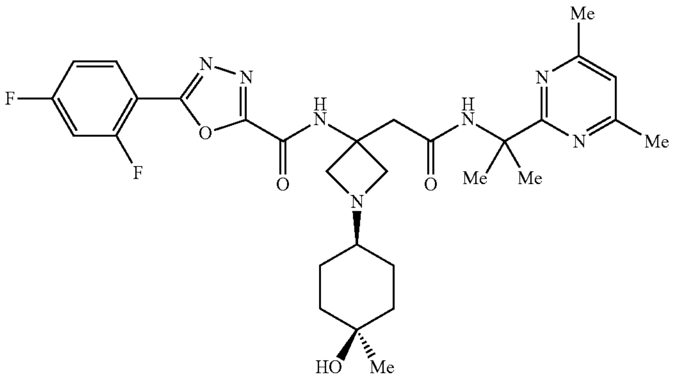 [SMILES: Cc1cc(C)nc(C(C)(C)NC(=O)CC2(NC(=O)c3nnc(-c4ccc(F)cc4F)o3)CN([C@H]3CC[C@@](C)(O)CC3)C2)n1] | ++ |
| 1.058 | 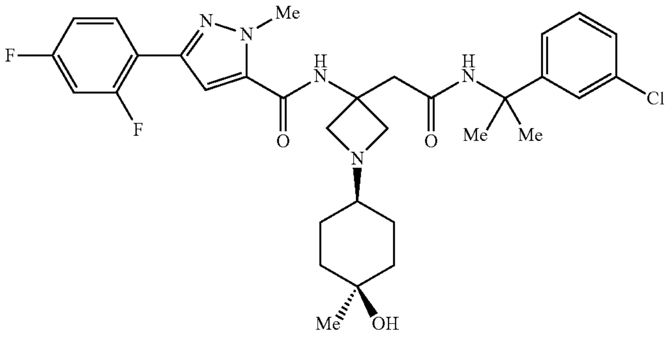 [SMILES: Cn1nc(-c2ccc(F)cc2F)cc1C(=O)NC1(CC(=O)NC(C)(C)c2cccc(Cl)c2)CN([C@H]2CC[C@@](C)(O)CC2)C1] | + |
| 1.059 | 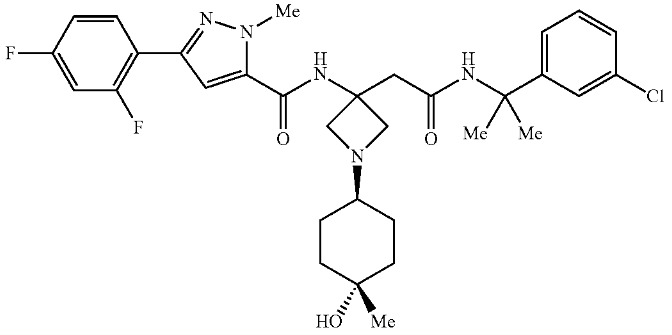 [SMILES: Cn1nc(-c2ccc(F)cc2F)cc1C(=O)NC1(CC(=O)NC(C)(C)c2cccc(Cl)c2)CN([C@H]2CC[C@](C)(O)CC2)C1] | + |
| 1.060 | 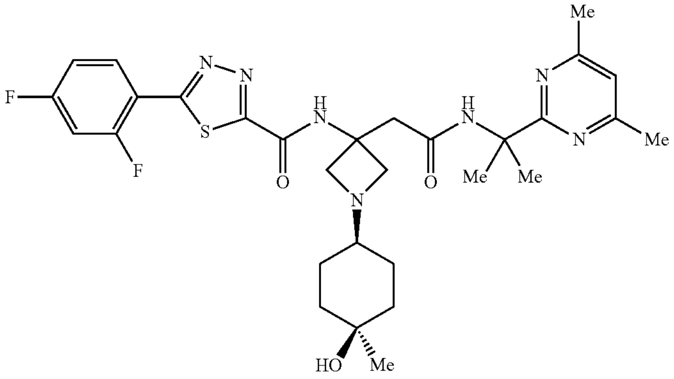 | +++ |

-continued
| Specific Examples (Table 1) | | |
|---|---|---|
| Compound ID | Structure | IC50 (buffer) |
| 1.061 | 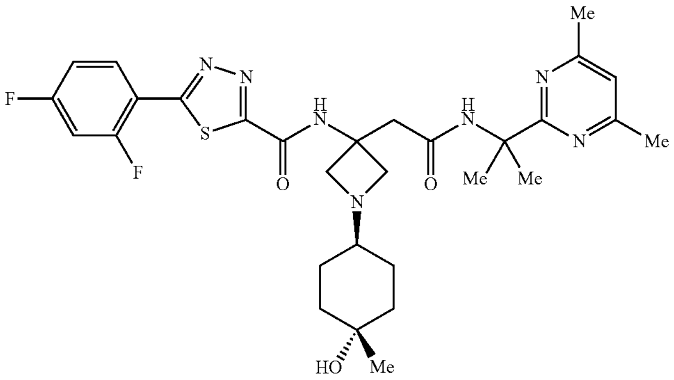 | ++++ |
| 1.062 | 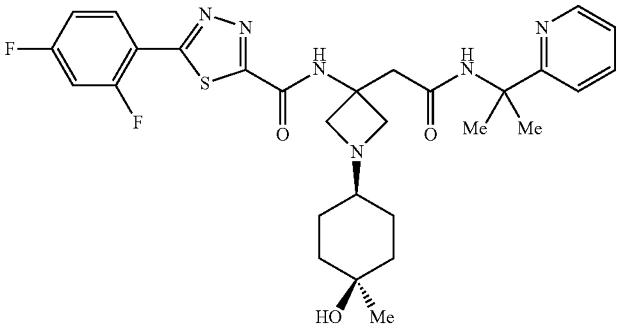 [SMILES: CC(C)(NC(=O)CC1(NC(=O)c2nnc(-c3ccc(F)cc3F)s2)CN([C@H]2CC[C@@](C)(O)CC2)C1)c1ccccn1] | +++ |
| 1.063 | 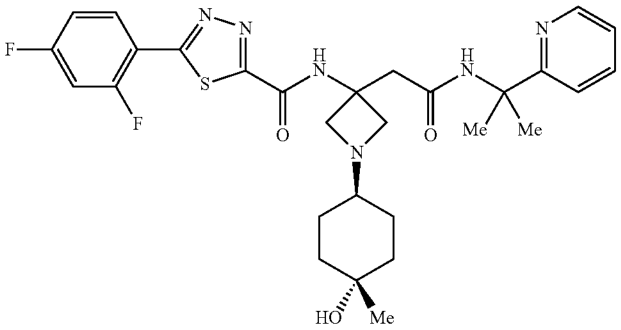 [SMILES: CC(C)(NC(=O)CC1(NC(=O)c2nnc(-c3ccc(F)cc3F)s2)CN([C@H]2CC[C@](C)(O)CC2)C1)c1ccccn1] | +++ |
| 1.064 | 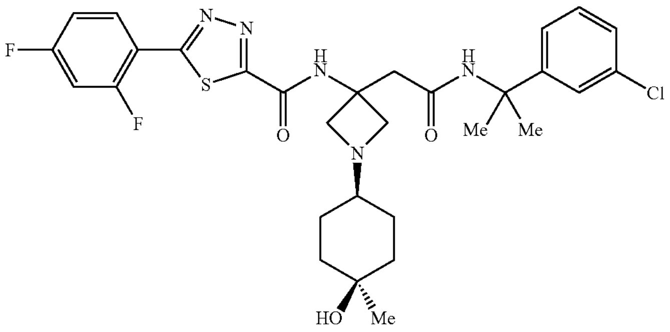 | ++++ |

-continued
| Specific Examples (Table 1) | | |
|---|---|---|
| Compound ID | Structure | IC50 (buffer) |
| 1.065 | 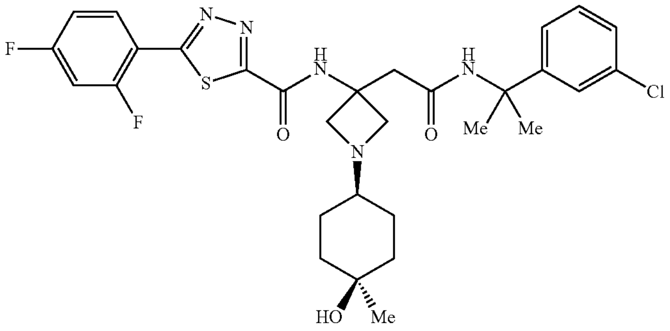 [SMILES: CC(C)(NC(=O)CC1(NC(=O)c2nnc(-c3ccc(F)cc3F)s2)CN([C@H]2CC[C@@](C)(O)CC2)C1)c1cccc(Cl)c1] | ++++ |
| 1.066 | 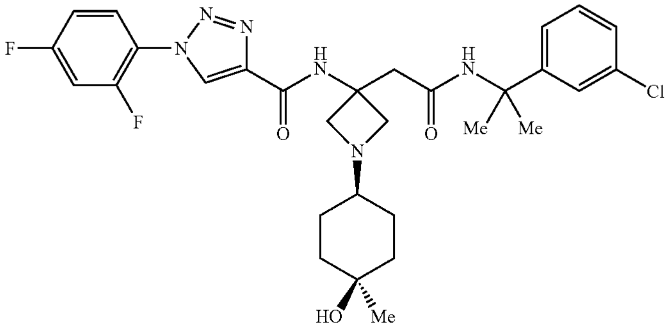 [SMILES: CC(C)(NC(=O)CC1(NC(=O)c2cn(-c3ccc(F)cc3F)nn2)CN([C@H]2CC[C@@](C)(O)CC2)C1)c1cccc(Cl)c1] | +++ |
| 1.067 | 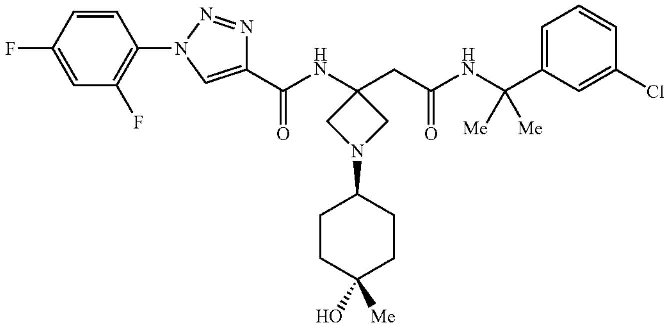 [SMILES: CC(C)(NC(=O)CC1(NC(=O)c2cn(-c3ccc(F)cc3F)nn2)CN([C@H]2CC[C@](C)(O)CC2)C1)c1cccc(Cl)c1] | +++ |
| 1.068 | 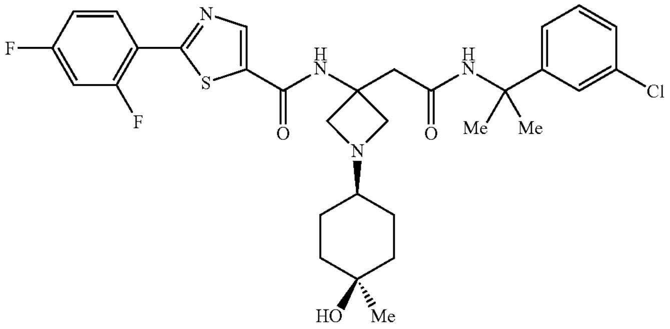 [SMILES: CC(C)(NC(=O)CC1(NC(=O)c2cnc(-c3ccc(F)cc3F)s2)CN([C@H]2CC[C@@](C)(O)CC2)C1)c1cccc(Cl)c1] | +++ |

-continued
| Specific Examples (Table 1) | | |
|---|---|---|
| Compound ID | Structure | IC50 (buffer) |
| 1.069 | 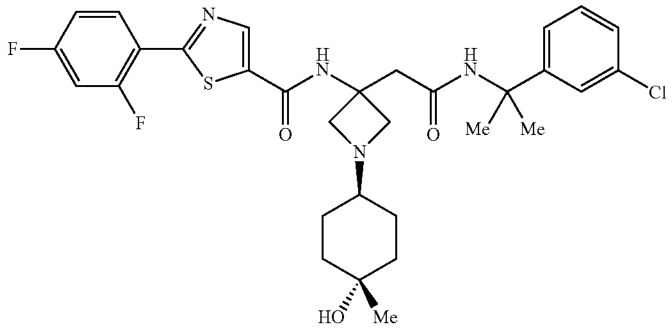 [SMILES: CC(C)(NC(=O)CC1(NC(=O)c2cnc(-c3ccc(F)cc3F)s2)CN([C@H]2CC[C@](C)(O)CC2)C1)c1cccc(Cl)c1] | +++ |
| 1.070 | 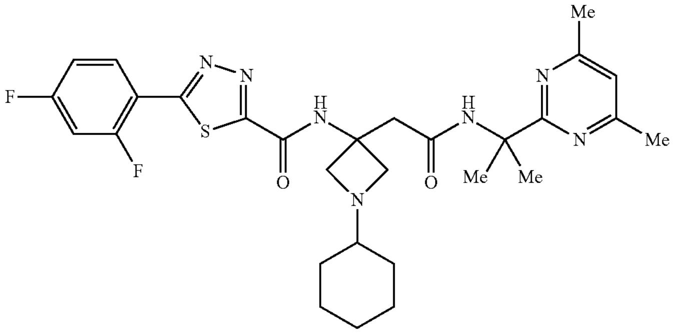 [SMILES: Cc1cc(C)nc(C(C)(C)NC(=O)CC2(NC(=O)c3nnc(-c4ccc(F)cc4F)s3)CN(C3CCCCC3)C2)n1] | ++++ |
| 1.071 | 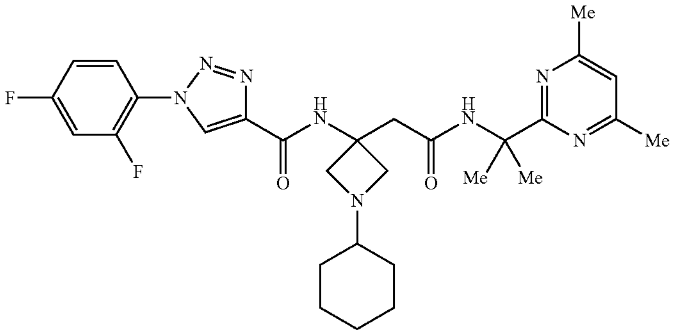 [SMILES: Cc1cc(C)nc(C(C)(C)NC(=O)CC2(NC(=O)c3cn(-c4ccc(F)cc4F)nn3)CN(C3CCCCC3)C2)n1] | +++ |
| 1.072 | 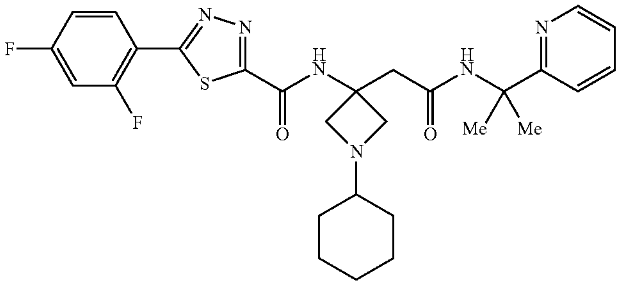 [SMILES: CC(C)(NC(=O)CC1(NC(=O)c2nnc(-c3ccc(F)cc3F)s2)CN(C2CCCCC2)C1)c1ccccn1] | ++++ |

-continued
| Specific Examples (Table 1) | | |
|---|---|---|
| Compound ID | Structure | IC50 (buffer) |
| 1.073 | 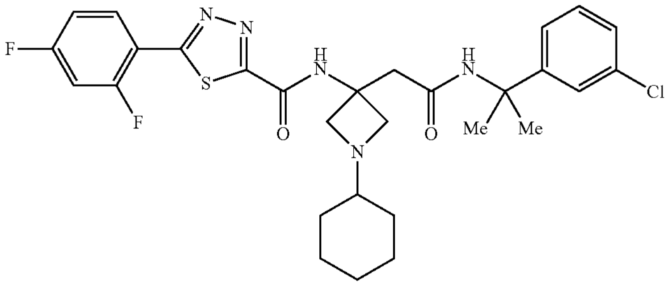 [SMILES: CC(C)(NC(=O)CC1(NC(=O)c2nnc(-c3ccc(F)cc3F)s2)CN(C2CCCCC2)C1)c1cccc(Cl)c1] | ++++ |
| 1.074 | 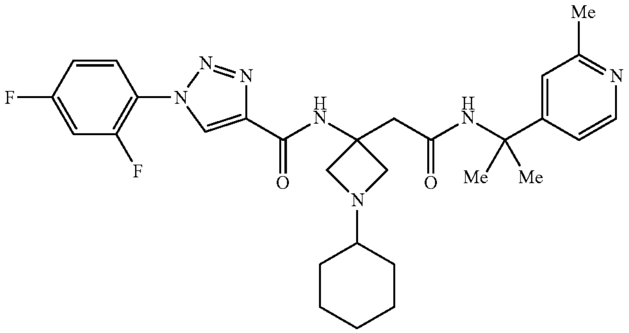 [SMILES: Cc1cc(C(C)(C)NC(=O)CC2(NC(=O)c3cn(-c4ccc(F)cc4F)nn3)CN(C3CCCCC3)C2)ccn1] | +++ |
| 1.075 | 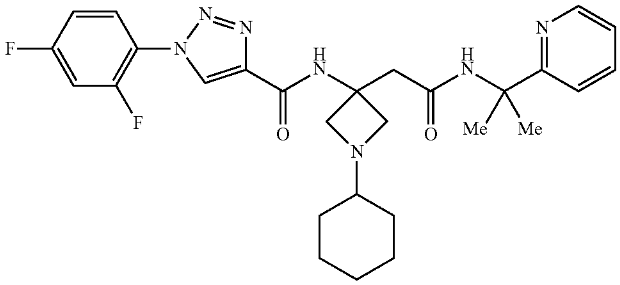 [SMILES: CC(C)(NC(=O)CC1(NC(=O)c2cn(-c3ccc(F)cc3F)nn2)CN(C2CCCCC2)C1)c1ccccn1] | +++ |
| 1.076 | 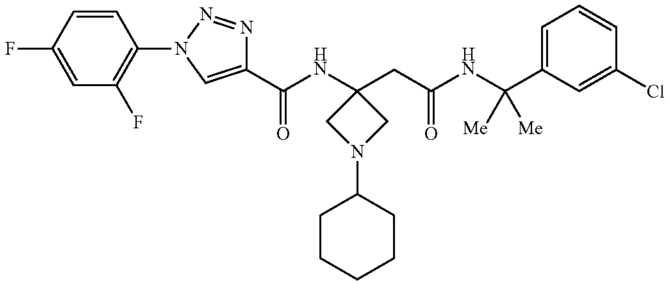 [SMILES: CC(C)(NC(=O)CC1(NC(=O)c2cn(-c3ccc(F)cc3F)nn2)CN(C2CCCCC2)C1)c1cccc(Cl)c1] | +++ |
| 1.077 | 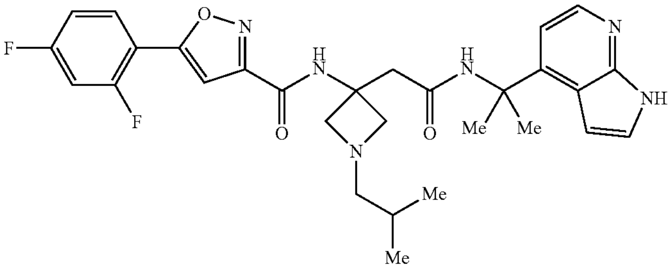 [SMILES: CC(C)CN1CC(CC(=O)NC(C)(C)c2ccnc3[nH]ccc23)(NC(=O)c2cc(-c3ccc(F)cc3F)on2)C1] | ++++ |

-continued
| Specific Examples (Table 1) | | |
|---|---|---|
| Compound ID | Structure | IC50 (buffer) |
| 1.078 | 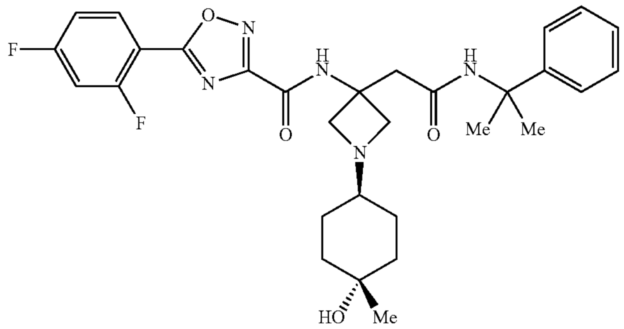 [SMILES: CC(C)(NC(=O)CC1(NC(=O)c2noc(-c3ccc(F)cc3F)n2)CN([C@H]2CC[C@](C)(O)CC2)C1)c1ccccc1] | ++ |
| 1.079 | 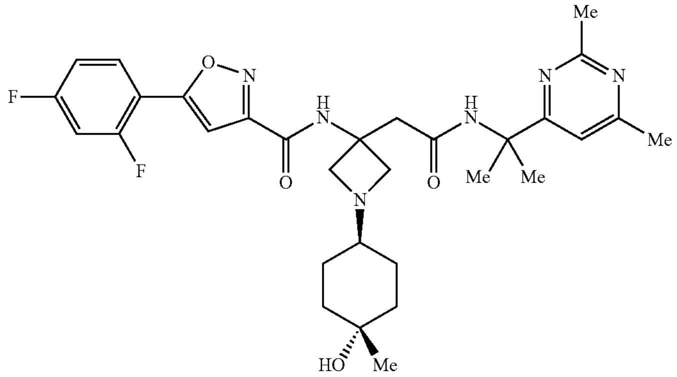 | +++ |
| 1.081 | 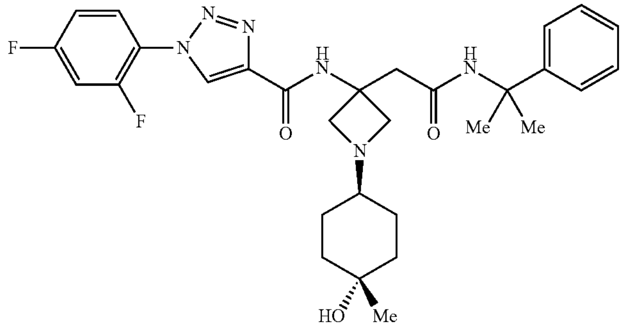 [SMILES: CC(C)(NC(=O)CC1(NC(=O)c2cn(-c3ccc(F)cc3F)nn2)CN([C@H]2CC[C@](C)(O)CC2)C1)c1ccccc1] | +++ |
| 1.082 | 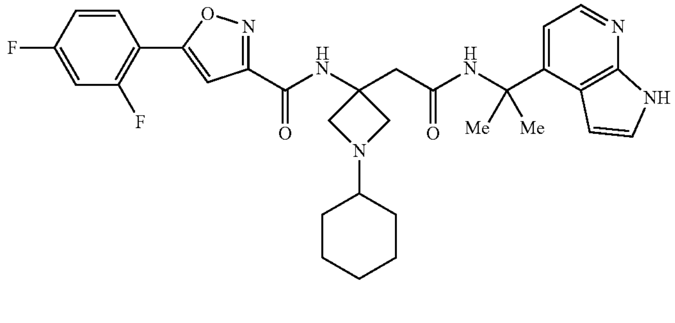 [SMILES: CC(C)(NC(=O)CC1(NC(=O)c2cc(-c3ccc(F)cc3F)on2)CN(C2CCCCC2)C1)c1ccnc2[nH]ccc12] | ++++ |

-continued
| Specific Examples (Table 1) | | |
|---|---|---|
| Compound ID | Structure | IC50 (buffer) |
| 1.083 | 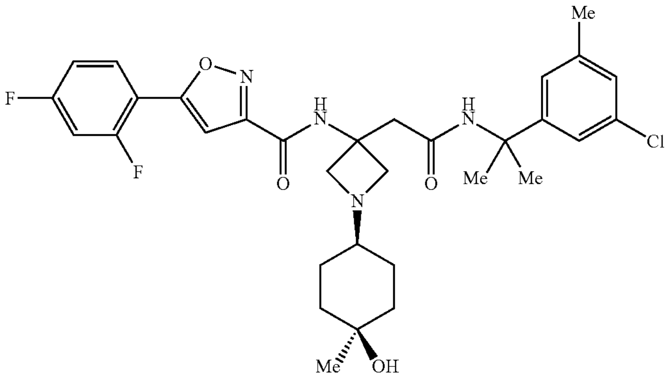 | ++++ |
| 1.084 | 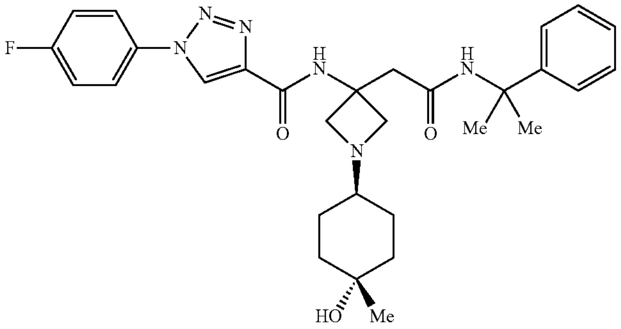 [SMILES: CC(C)(NC(=O)CC1(NC(=O)c2cn(-c3ccc(F)cc3)nn2)CN([C@H]2CC[C@](C)(O)CC2)C1)c1ccccc1] | ++ |
| 1.085 | 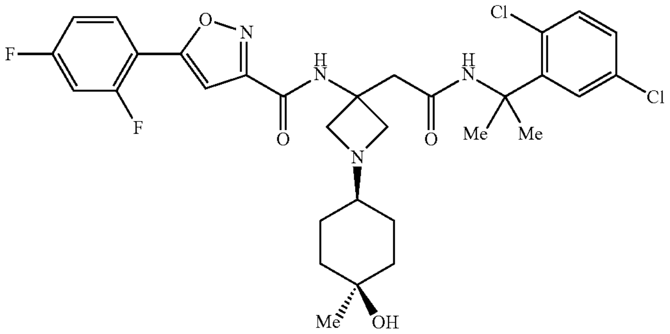 [SMILES: CC(C)(NC(=O)CC1(NC(=O)c2cc(-c3ccc(F)cc3F)on2)CN([C@H]2CC[C@@](C)(O)CC2)C1)c1cc(Cl)ccc1Cl] | ++++ |
| 1.086 | 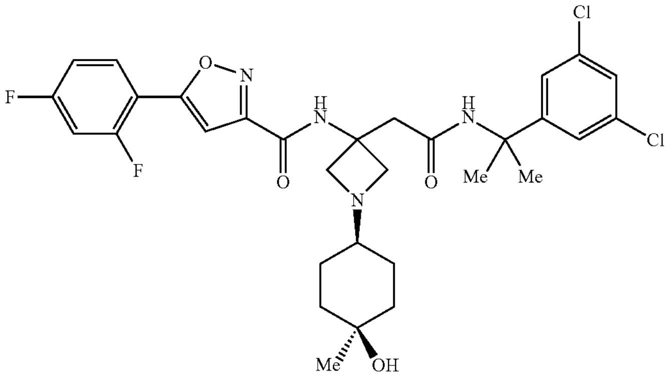 | ++++ |

-continued
| Specific Examples (Table 1) | | |
|---|---|---|
| Compound ID | Structure | IC50 (buffer) |
| 1.087 | 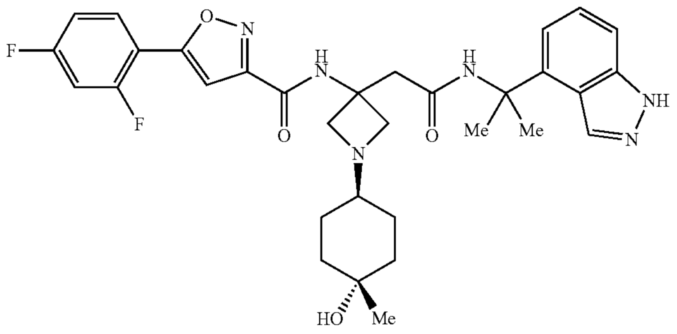 [SMILES: CC(C)(NC(=O)CC1(NC(=O)c2cc(-c3ccc(F)cc3F)on2)CN([C@H]2CC[C@](C)(O)CC2)C1)c1cccc2[nH]ncc12] | + |
| 1.088 | 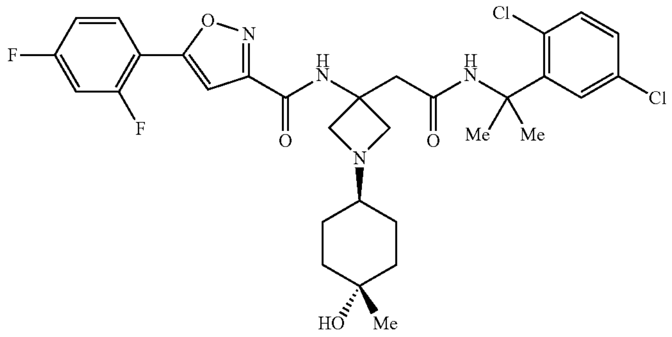 [SMILES: CC(C)(NC(=O)CC1(NC(=O)c2cc(-c3ccc(F)cc3F)on2)CN([C@H]2CC[C@](C)(O)CC2)C1)c1cc(Cl)ccc1Cl] | ++++ |
| 1.089 | 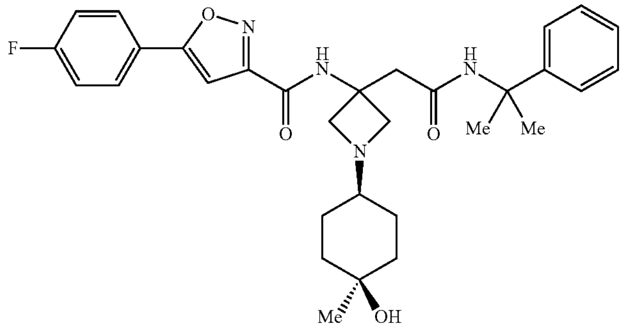 | +++ |
| 1.090 | 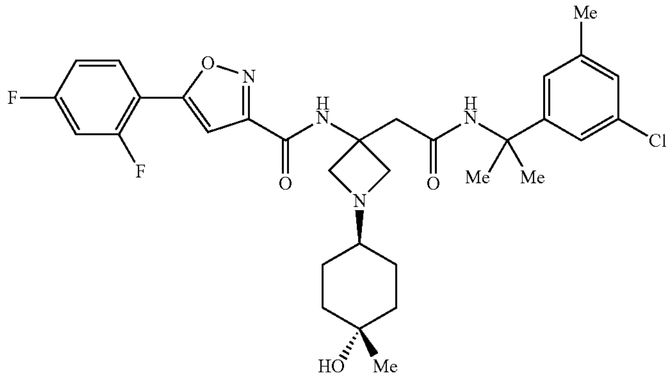 [SMILES: Cc1cc(Cl)cc(C(C)(C)NC(=O)CC2(NC(=O)c3cc(-c4ccc(F)cc4F)on3)CN([C@H]3CC[C@](C)(O)CC3)C2)c1] | ++++ |

-continued
| Specific Examples (Table 1) | | |
|---|---|---|
| Compound ID | Structure | IC50 (buffer) |
| 1.091 | 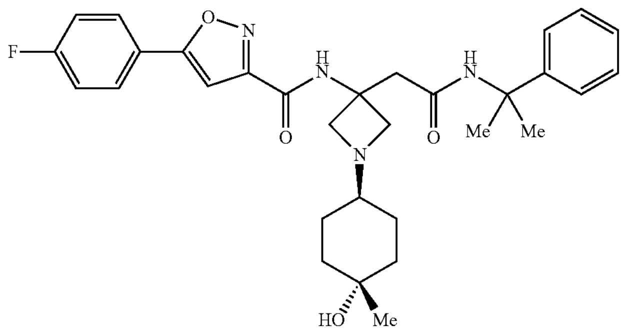 [SMILES: CC(C)(NC(=O)CC1(NC(=O)c2cc(-c3ccc(F)cc3)on2)CN([C@H]2CC[C@](C)(O)CC2)C1)c1ccccc1] | +++ |
| 1.092 | 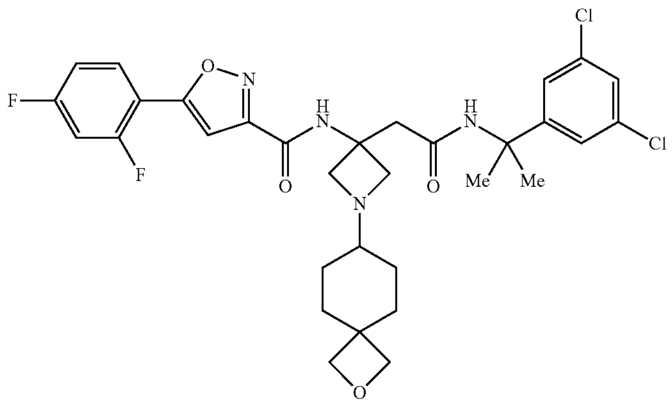 [SMILES: CC(C)(NC(=O)CC1(NC(=O)c2cc(-c3ccc(F)cc3F)on2)CN(C2CCC3(CC2)COC3)C1)c1cc(Cl)cc(Cl)c1] | +++ |
| 1.093 | 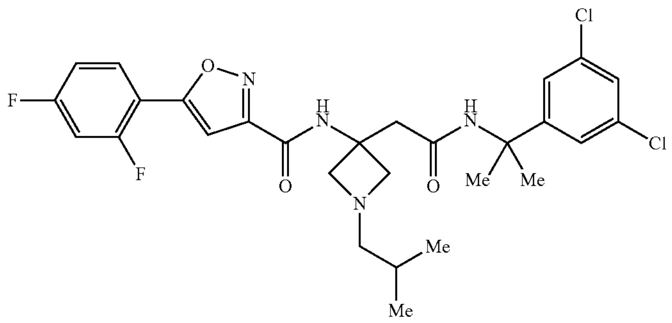 [SMILES: CC(C)CN1CC(CC(=O)NC(C)(C)c2cc(Cl)cc(Cl)c2)(NC(=O)c2cc(-c3ccc(F)cc3F)on2)C1] | +++ |
| 1.094 | 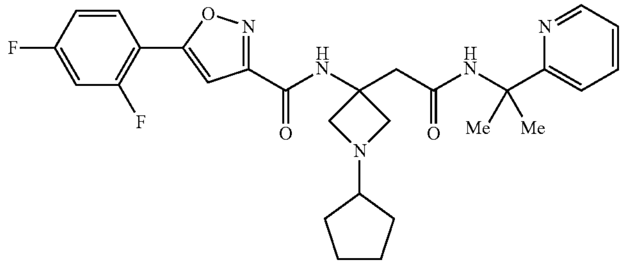 [SMILES: CC(C)(NC(=O)CC1(NC(=O)c2cc(-c3ccc(F)cc3F)on2)CN(C2CCCC2)C1)c1ccccn1] | +++ |

-continued
| Specific Examples (Table 1) | | |
|---|---|---|
| Compound ID | Structure | IC50 (buffer) |
| 1.095 | 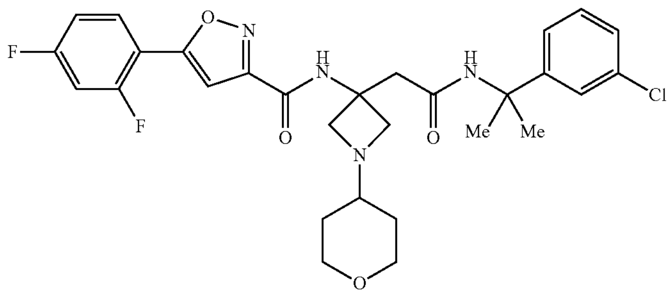 [SMILES: CC(C)(NC(=O)CC1(NC(=O)c2cc(-c3ccc(F)cc3F)on2)CN(C2CCOCC2)C1)c1cccc(Cl)c1] | +++ |
| 1.096 | 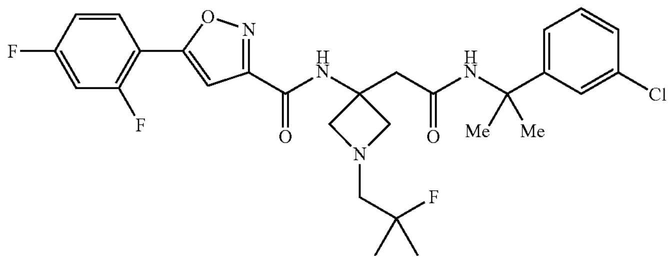 [SMILES: CC(C)(F)CN1CC(CC(=O)NC(C)(C)c2cccc(Cl)c2)(NC(=O)c2cc(-c3ccc(F)cc3F)on2)C1] | ++ |
| 1.097 | 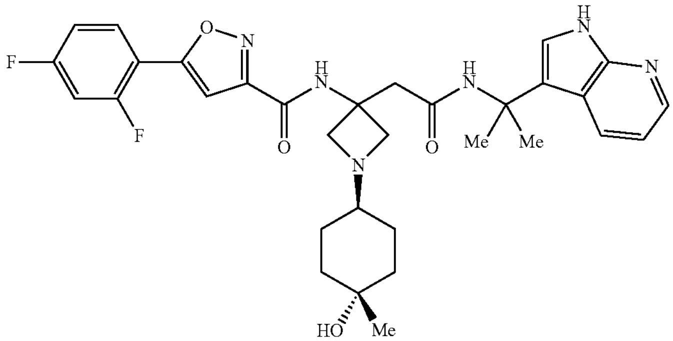 [SMILES: CC(C)(NC(=O)CC1(NC(=O)c2cc(-c3ccc(F)cc3F)on2)CN([C@H]2CC[C@](C)(O)CC2)C1)c1c[nH]c2ncccc12] | +++ |
| 1.098 | 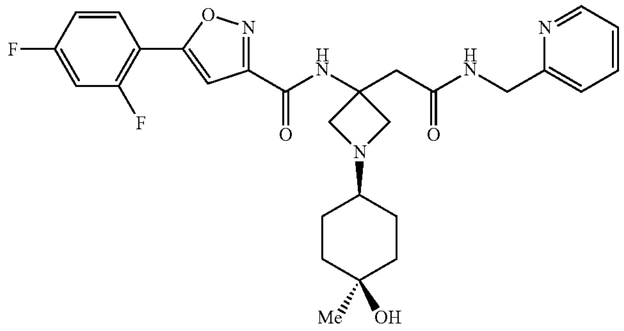 [SMILES: C[C@]1(O)CC[C@@H](N2CC(CC(=O)NCc3ccccn3)(NC(=O)c3cc(-c4ccc(F)cc4F)on3)C2)CC1] | + |

-continued
| Specific Examples (Table 1) | | |
|---|---|---|
| Compound ID | Structure | IC50 (buffer) |
| 1.099 | 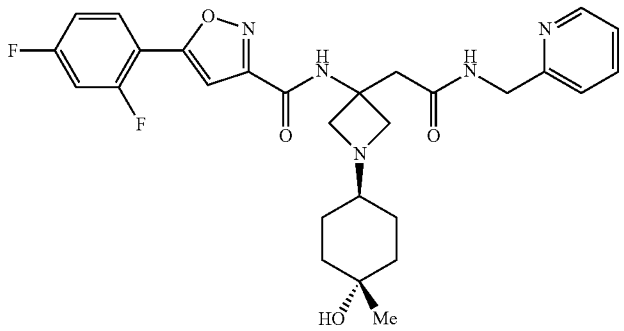 [SMILES: C[C@]1(O)CC[C@H](N2CC(CC(=O)NCc3ccccn3)(NC(=O)c3cc(-c4ccc(F)cc4F)on3)C2)CC1] | + |
| 1.100 | 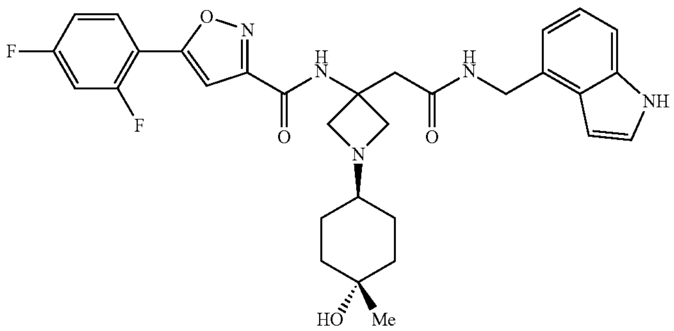 [SMILES: C[C@]1(O)CC[C@H](N2CC(CC(=O)NCc3cccc4[nH]ccc34)(NC(=O)c3cc(-c4ccc(F)cc4F)on3)C2)CC1] | ++++ |
| 1.101 | 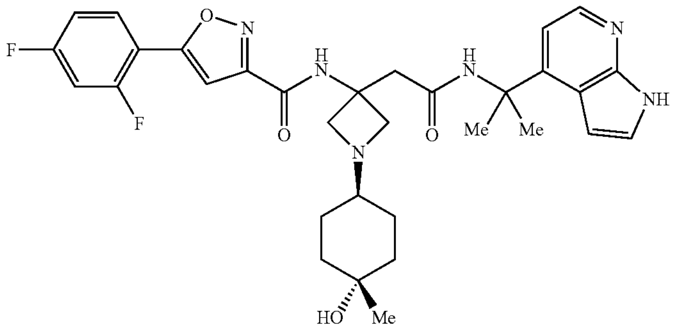 [SMILES: CC(C)(NC(=O)CC1(NC(=O)c2cc(-c3ccc(F)cc3F)on2)CN([C@H]2CC[C@](C)(O)CC2)C1)c1ccnc2[nH]ccc12] | +++ |
| 1.102 | 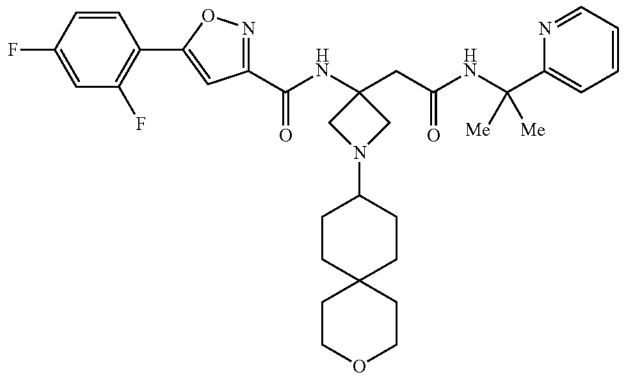 [SMILES: CC(C)(NC(=O)CC1(NC(=O)c2cc(-c3ccc(F)cc3F)on2)CN(C2CCC3(CCOCC3)CC2)C1)c1ccccn1] | ++ |

-continued
| Specific Examples (Table 1) | | |
|---|---|---|
| Compound ID | Structure | IC50 (buffer) |
| 1.103 | 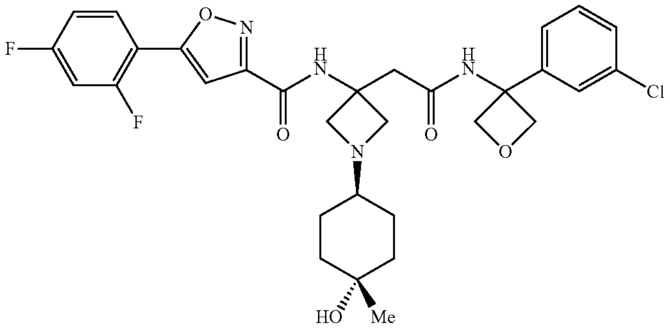 [SMILES: C[C@]1(O)CC[C@H](N2CC(CC(=O)NC3(c4cccc(Cl)c4)COC3)(NC(=O)c3cc(-c4ccc(F)cc4F)on3)C2)CC1] | +++ |
| 1.104 | 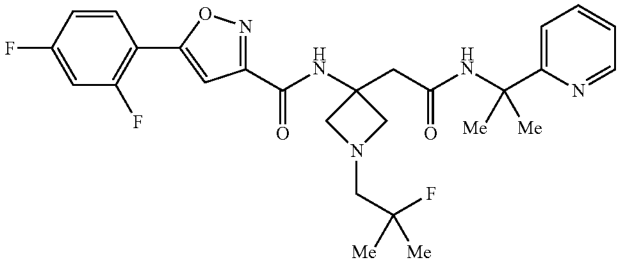 [SMILES: CC(C)(F)CN1CC(CC(=O)NC(C)(C)c2ccccn2)(NC(=O)c2cc(-c3ccc(F)cc3F)on2)C1] | + |
| 1.105 | 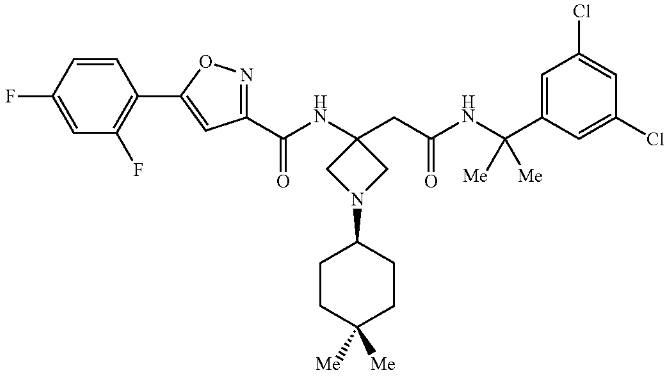 | ++++ |
| 1.106 | 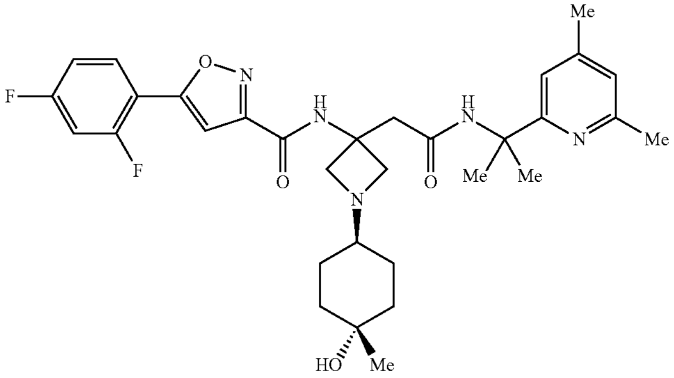 | ++++ |

-continued
Specific Examples (Table 1)
| Compound ID | Structure | IC50 (buffer) |
| --- | --- | --- |
| 1.107 | 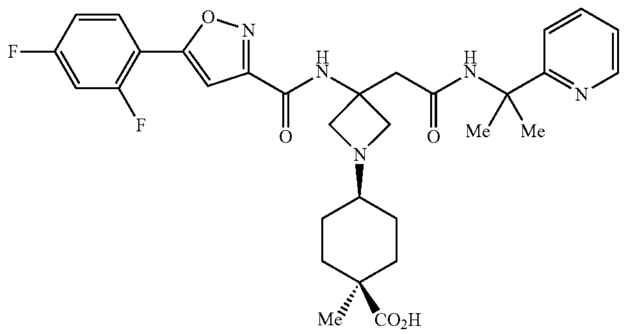 [SMILES: CC(C)(NC(=O)CC1(NC(=O)c2cc(-c3ccc(F)cc3F)on2)CN([C@H]2CC[C@@](C)(C(=O)O)CC2)C1)c1ccccn1] | + |
| 1.108 | 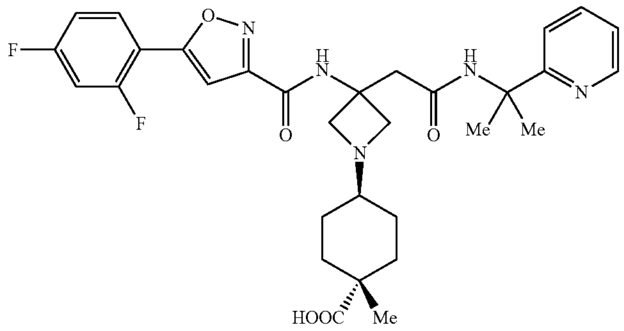 [SMILES: CC(C)(NC(=O)CC1(NC(=O)c2cc(-c3ccc(F)cc3F)on2)CN([C@H]2CC[C@](C)(C(=O)O)CC2)C1)c1ccccn1] | ++ |
| 1.109 | 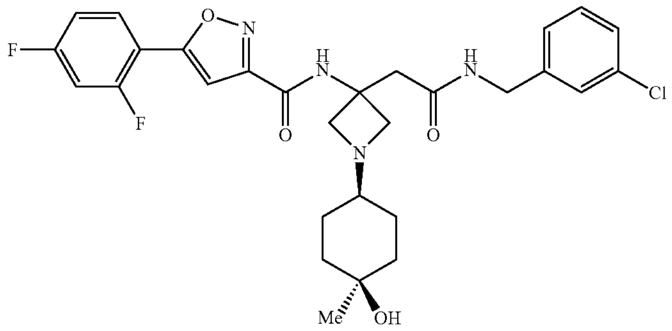 [SMILES: C[C@]1(O)CC[C@@H](N2CC(CC(=O)NCc3cccc(Cl)c3)(NC(=O)c3cc(-c4ccc(F)cc4F)on3)C2)CC1] | ++ |
| 1.110 | 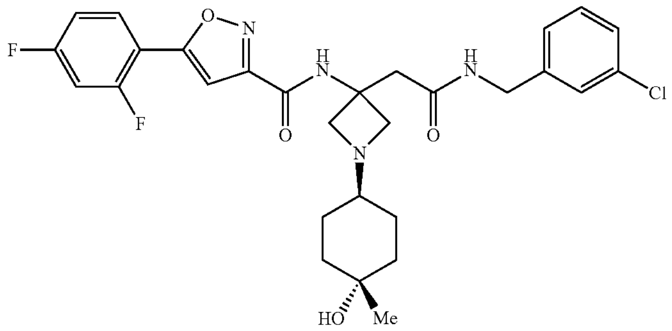 [SMILES: C[C@]1(O)CC[C@H](N2CC(CC(=O)NCc3cccc(Cl)c3)(NC(=O)c3cc(-c4ccc(F)cc4F)on3)C2)CC1] | + |

-continued
Specific Examples (Table 1)
| Compound ID | Structure | IC50 (buffer) |
|---|---|---|
| 1.111 | 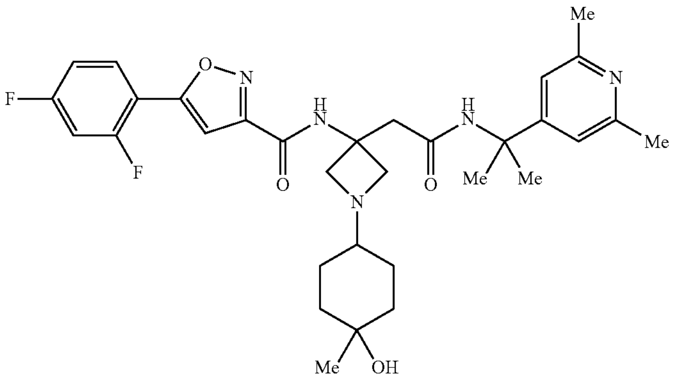 [SMILES: Cc1cc(C(C)(C)NC(=O)CC2(NC(=O)c3cc(-c4ccc(F)cc4F)on3)CN(C3CCC(C)(O)CC3)C2)cc(C)n1] | +++ |
| 1.112 | 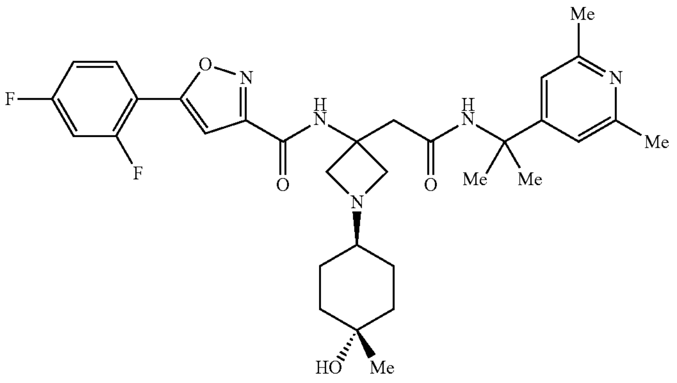 [SMILES: Cc1cc(C(C)(C)NC(=O)CC2(NC(=O)c3cc(-c4ccc(F)cc4F)on3)CN([C@H]3CC[C@](C)(O)CC3)C2)cc(C)n1] | +++ |
| 1.113 | 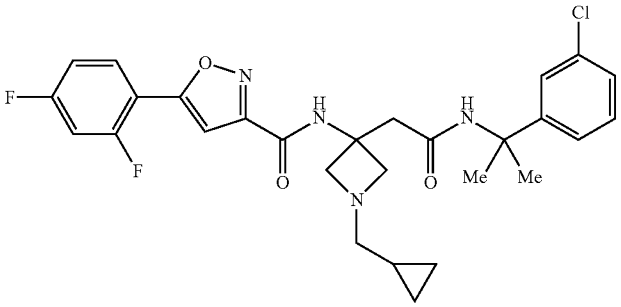 [SMILES: CC(C)(NC(=O)CC1(NC(=O)c2cc(-c3ccc(F)cc3F)on2)CN(CC2CC2)C1)c1cccc(Cl)c1] | +++ |
| 1.114 | 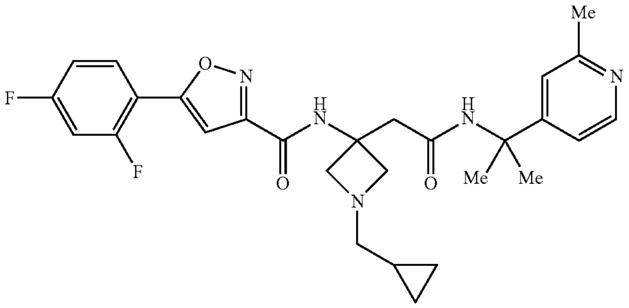 [SMILES: Cc1cc(C(C)(C)NC(=O)CC2(NC(=O)c3cc(-c4ccc(F)cc4F)on3)CN(CC3CC3)C2)ccn1] | +++ |

-continued
| Specific Examples (Table 1) | | |
|---|---|---|
| Compound ID | Structure | IC50 (buffer) |
| 1.115 | 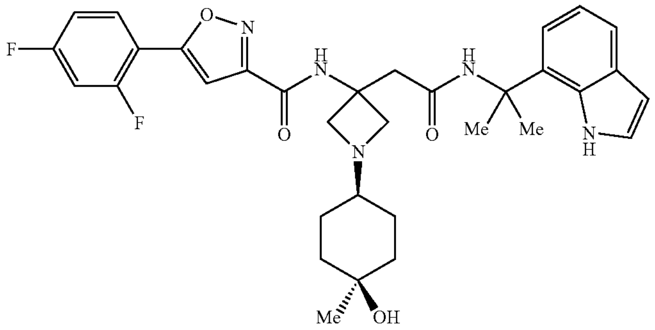 [SMILES: CC(C)(NC(=O)CC1(NC(=O)c2cc(-c3ccc(F)cc3F)on2)CN([C@H]2CC[C@@](C)(O)CC2)C1)c1cccc2cc[nH]c12] | ++++ |
| 1.116 | 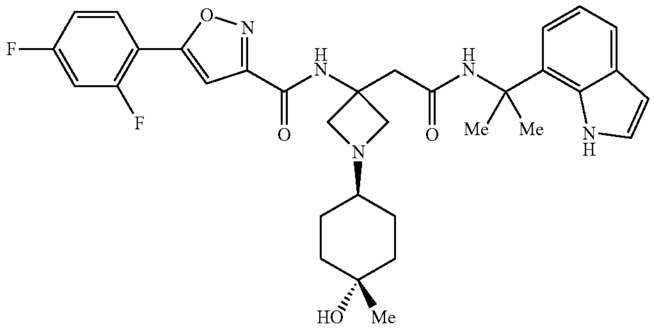 [SMILES: CC(C)(NC(=O)CC1(NC(=O)c2cc(-c3ccc(F)cc3F)on2)CN([C@H]2CC[C@](C)(O)CC2)C1)c1cccc2cc[nH]c12] | ++++ |
| 1.117 | 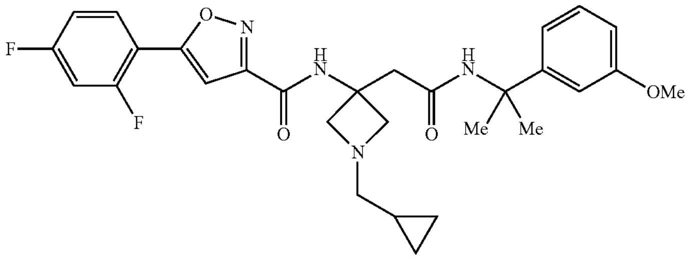 [SMILES: COc1cccc(C(C)(C)NC(=O)CC2(NC(=O)c3cc(-c4ccc(F)cc4F)on3)CN(CC3CC3)C2)c1] | ++ |
| 1.118 | 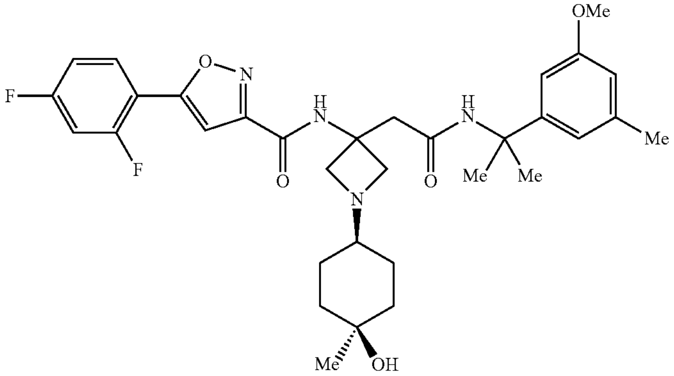 [SMILES: COc1cc(C)cc(C(C)(C)NC(=O)CC2(NC(=O)c3cc(-c4ccc(F)cc4F)on3)CN([C@H]3CC[C@@](C)(O)CC3)C2)c1] | +++ |

-continued
| Specific Examples (Table 1) | | |
|---|---|---|
| Compound ID | Structure | IC50 (buffer) |
| 1.119 | 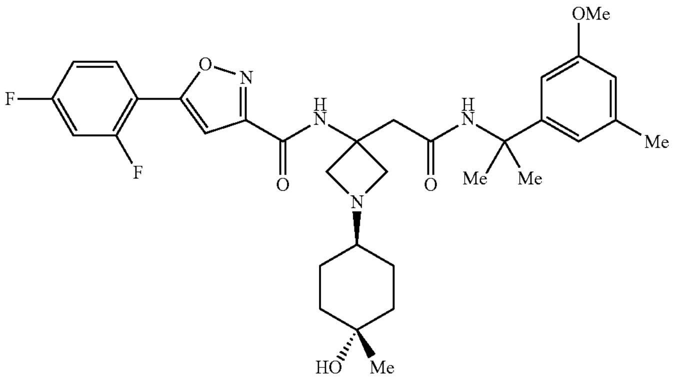 [SMILES: COc1cc(C)cc(C(C)(C)NC(=O)CC2(NC(=O)c3cc(-c4ccc(F)cc4F)on3)CN([C@H]3CC[C@](C)(O)CC3)C2)c1] | +++ |
| 1.120 | 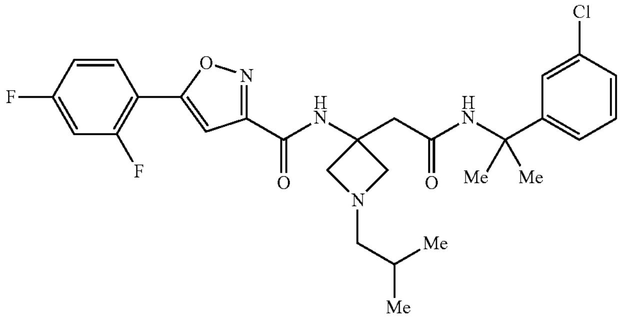 [SMILES: CC(C)CN1CC(CC(=O)NC(C)(C)c2cccc(Cl)c2)(NC(=O)c2cc(-c3ccc(F)cc3F)on2)C1] | +++ |
| 1.121 | 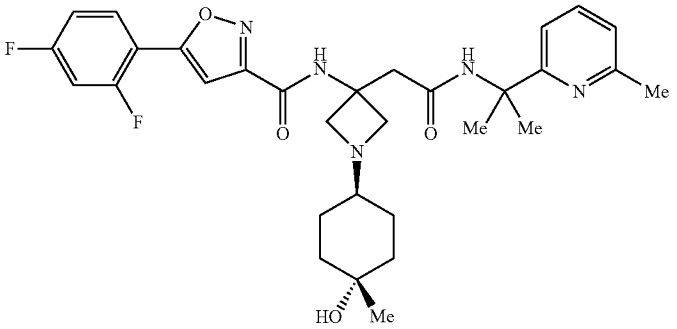 | ++++ |
| 1.122 | 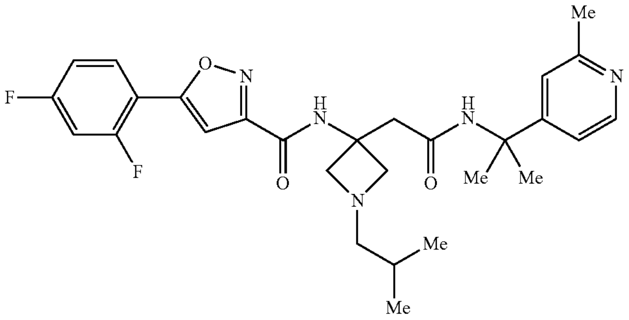 [SMILES: Cc1cc(C(C)(C)NC(=O)CC2(NC(=O)c3cc(-c4ccc(F)cc4F)on3)CN(CC(C)C)C2)ccn1] | +++ |

-continued
| Compound ID | Structure | IC50 (buffer) |
|---|---|---|
| 1.123 | 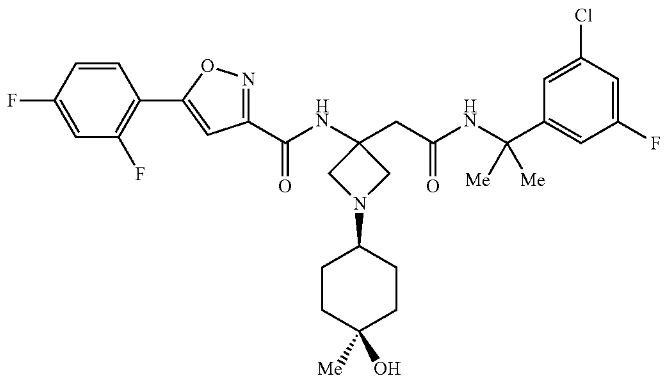 [SMILES: CC(C)(NC(=O)CC1(NC(=O)c2cc(-c3ccc(F)cc3F)on2)CN([C@H]2CC[C@@](C)(O)CC2)C1)c1cc(F)cc(Cl)c1] | ++++ |
| 1.124 | 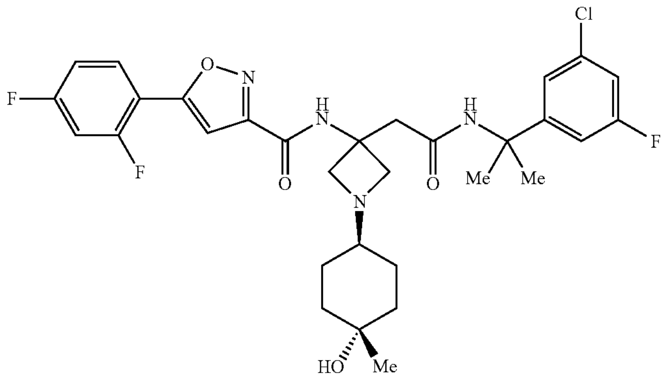 [SMILES: CC(C)(NC(=O)CC1(NC(=O)c2cc(-c3ccc(F)cc3F)on2)CN([C@H]2CC[C@](C)(O)CC2)C1)c1cc(F)cc(Cl)c1] | ++++ |
| 1.125 | 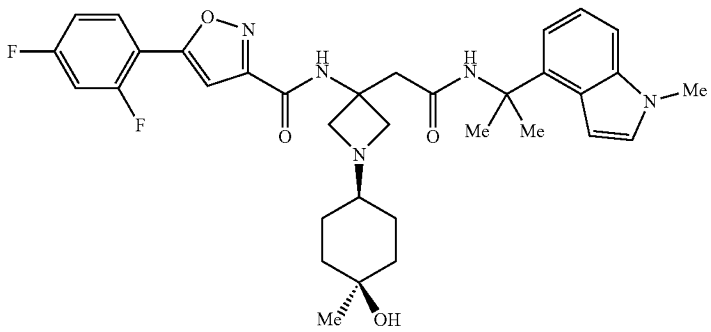 [SMILES: Cn1ccc2c(C(C)(C)NC(=O)CC3(NC(=O)c4cc(-c5ccc(F)cc5F)on4)CN([C@H]4CC[C@@](C)(O)CC4)C3)cccc21] | +++ |
| 1.126 | 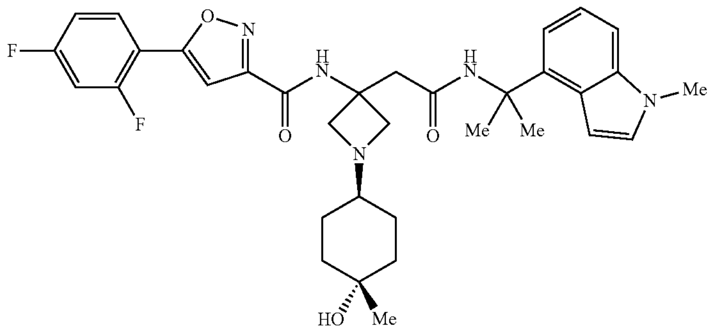 [SMILES: Cn1ccc2c(C(C)(C)NC(=O)CC3(NC(=O)c4cc(-c5ccc(F)cc5F)on4)CN([C@H]4CC[C@](C)(O)CC4)C3)cccc21] | +++ |

-continued
| Specific Examples (Table 1) | | |
|---|---|---|
| Compound ID | Structure | IC50 (buffer) |
| 1.127 | 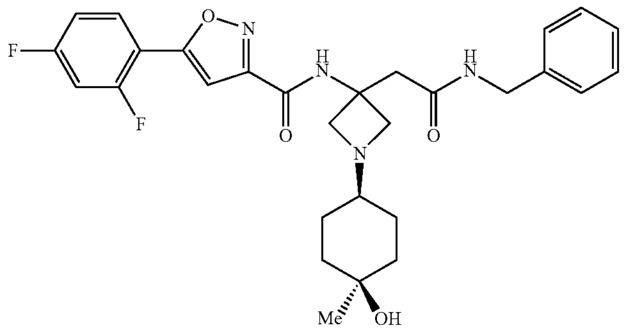 | + |
| 1.128 | 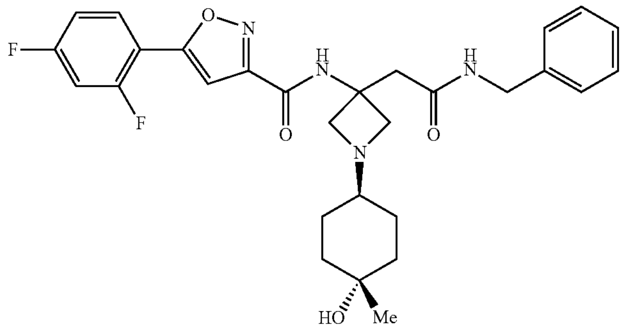 | + |
| 1.129 | 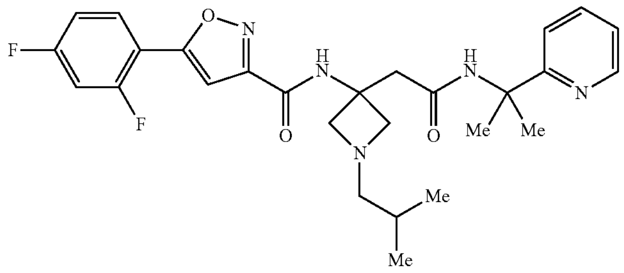 [SMILES: CC(C)CN1CC(CC(=O)NC(C)(C)c2ccccn2)(NC(=O)c2cc(-c3ccc(F)cc3F)on2)C1] | +++ |
| 1.130 | 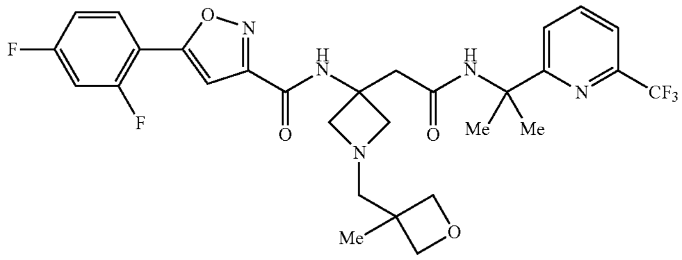 [SMILES: CC1(CN2CC(CC(=O)NC(C)(C)c3cccc(C(F)(F)F)n3)(NC(=O)c3cc(-c4ccc(F)cc4F)on3)C2)COC1] | + |
| 1.131 | 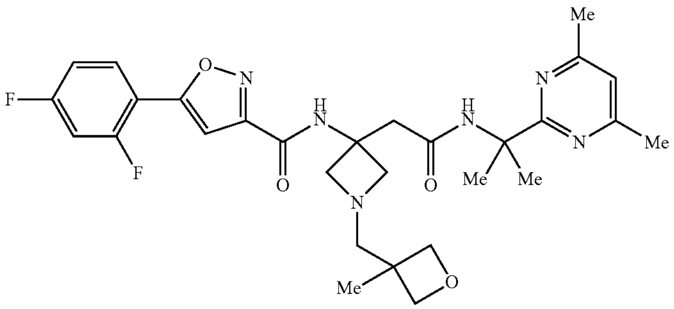 [SMILES: Cc1cc(C)nc(C(C)(C)NC(=O)CC2(NC(=O)c3cc(-c4ccc(F)cc4F)on3)CN(CC3(C)COC3)C2)n1] | + |

-continued
| Specific Examples (Table 1) | | |
|---|---|---|
| Compound ID | Structure | IC50 (buffer) |
| 1.132 | 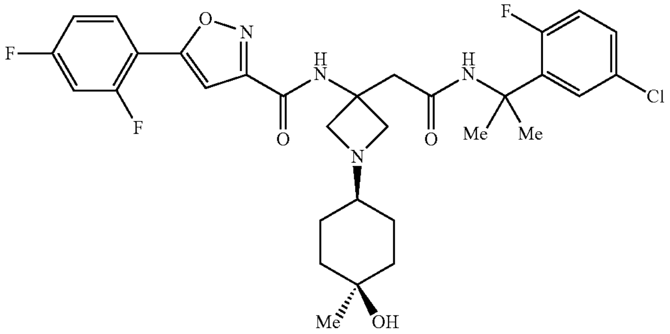 [SMILES: CC(C)(NC(=O)CC1(NC(=O)c2cc(-c3ccc(F)cc3F)on2)CN([C@H]2CC[C@@](C)(O)CC2)C1)c1cc(Cl)ccc1F] | ++++ |
| 1.133 | 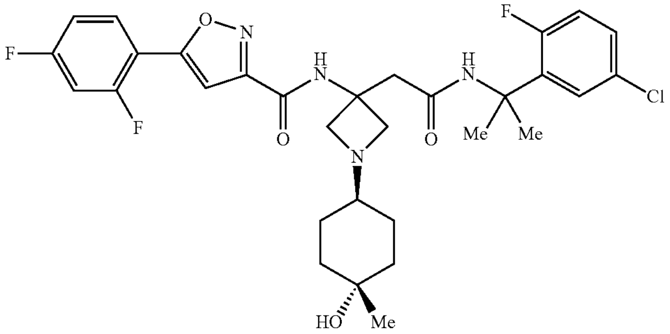 [SMILES: CC(C)(NC(=O)CC1(NC(=O)c2cc(-c3ccc(F)cc3F)on2)CN([C@H]2CC[C@](C)(O)CC2)C1)c1cc(Cl)ccc1F] | ++++ |
| 1.134 | 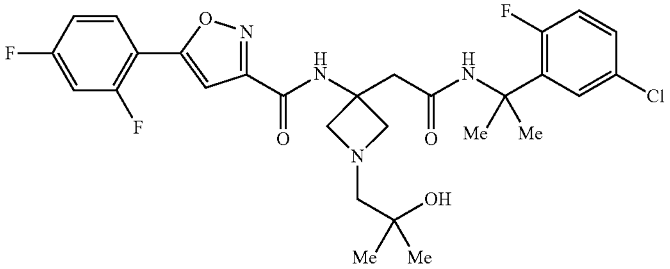 [SMILES: CC(C)(O)CN1CC(CC(=O)NC(C)(C)c2cc(Cl)ccc2F)(NC(=O)c2cc(-c3ccc(F)cc3F)on2)C1] | +++ |
| 1.135 | 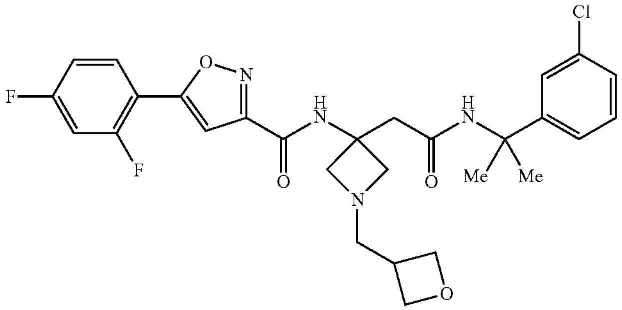 [SMILES: CC(C)(NC(=O)CC1(NC(=O)c2cc(-c3ccc(F)cc3F)on2)CN(CC2COC2)C1)c1cccc(Cl)c1] | ++ |

-continued
| Specific Examples (Table 1) | | |
|---|---|---|
| Compound ID | Structure | IC50 (buffer) |
| 1.136 | 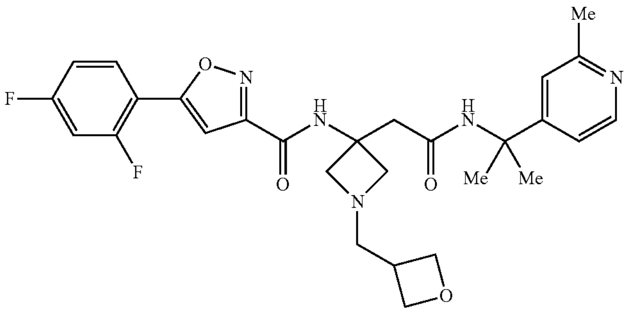 [SMILES: Cc1cc(C(C)(C)NC(=O)CC2(NC(=O)c3cc(-c4ccc(F)cc4F)on3)CN(CC3COC3)C2)ccn1] | ++ |
| 1.137 | 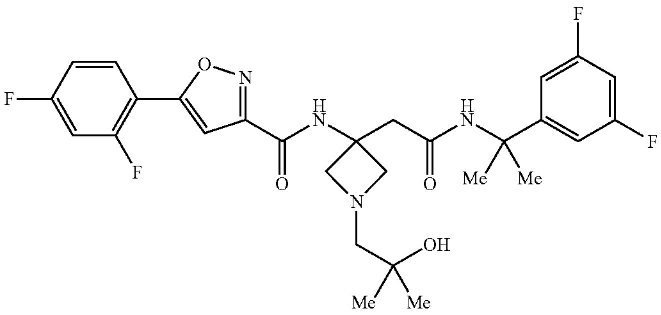 [SMILES: CC(C)(O)CN1CC(CC(=O)NC(C)(C)c2cc(F)cc(F)c2)(NC(=O)c2cc(-c3ccc(F)cc3F)on2)C1] | +++ |
| 1.138 | 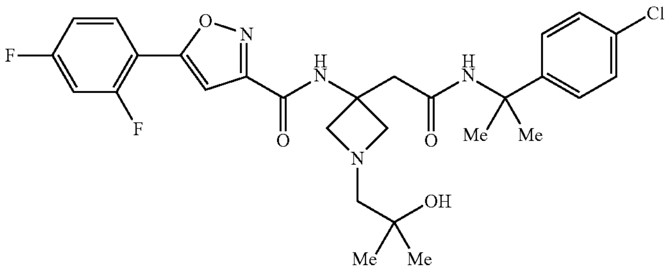 [SMILES: CC(C)(O)CN1CC(CC(=O)NC(C)(C)c2ccc(Cl)cc2)(NC(=O)c2cc(-c3ccc(F)cc3F)on2)C1] | ++ |
| 1.139 | 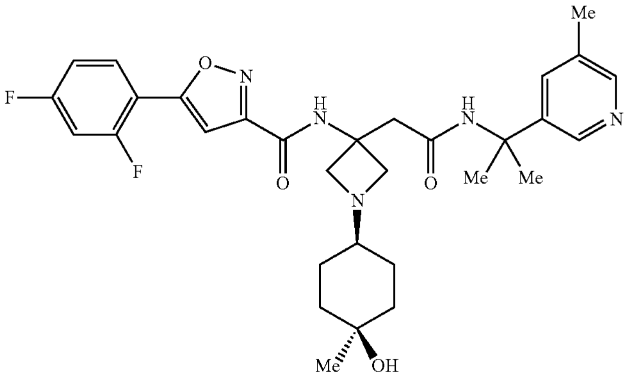 [SMILES: Cc1cncc(C(C)(C)NC(=O)CC2(NC(=O)c3cc(-c4ccc(F)cc4F)on3)CN([C@H]3CC[C@@](C)(O)CC3)C2)c1] | +++ |

-continued
| Specific Examples (Table 1) | | |
|---|---|---|
| Compound ID | Structure | IC50 (buffer) |
| 1.140 | 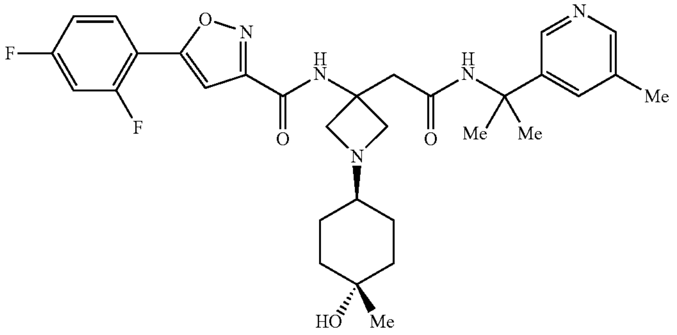 [SMILES: Cc1cncc(C(C)(C)NC(=O)CC2(NC(=O)c3cc(-c4ccc(F)cc4F)on3)CN([C@H]3CC[C@](C)(O)CC3)C2)c1] | +++ |
| 1.141 | 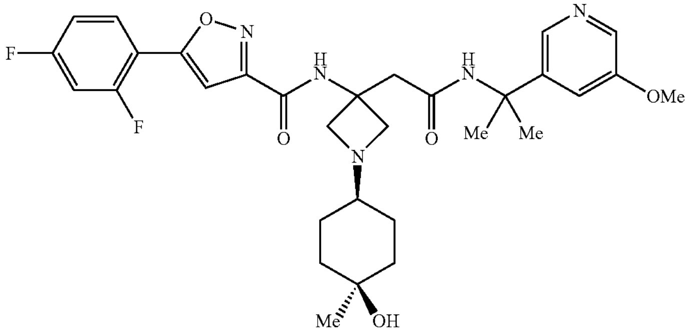 [SMILES: COc1cncc(C(C)(C)NC(=O)CC2(NC(=O)c3cc(-c4ccc(F)cc4F)on3)CN([C@H]3CC[C@@](C)(O)CC3)C2)c1] | +++ |
| 1.142 | 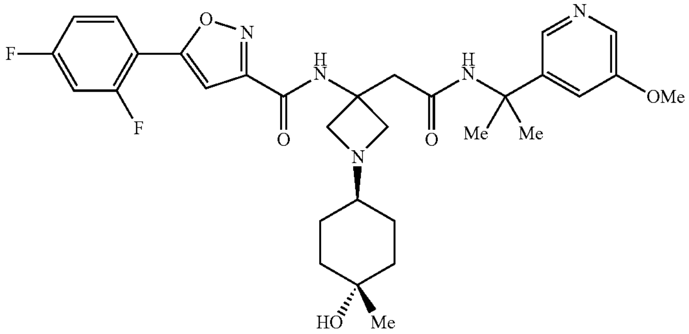 [SMILES: COc1cncc(C(C)(C)NC(=O)CC2(NC(=O)c3cc(-c4ccc(F)cc4F)on3)CN([C@H]3CC[C@](C)(O)CC3)C2)c1] | +++ |
| 1.143 | 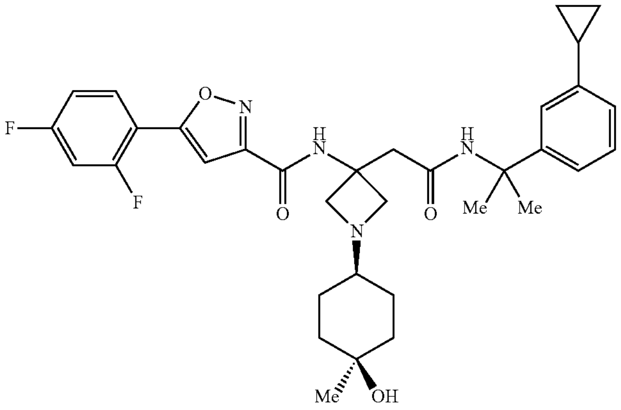 [SMILES: CC(C)(NC(=O)CC1(NC(=O)c2cc(-c3ccc(F)cc3F)on2)CN([C@H]2CC[C@@](C)(O)CC2)C1)c1cccc(C2CC2)c1] | +++ |

-continued
| Specific Examples (Table 1) | | |
|---|---|---|
| Compound ID | Structure | IC50 (buffer) |
| 1.144 | 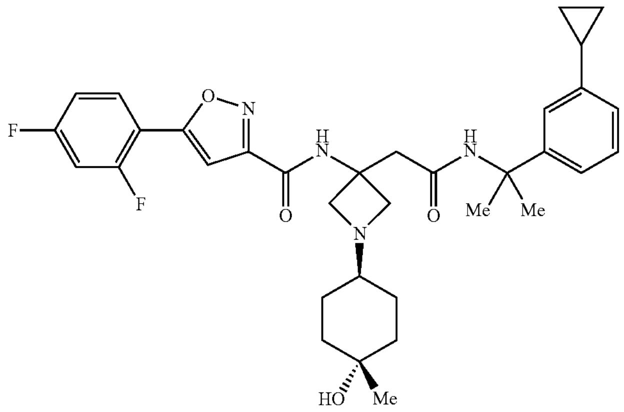 [SMILES: CC(C)(NC(=O)CC1(NC(=O)c2cc(-c3ccc(F)cc3F)on2)CN([C@H]2CC[C@](C)(O)CC2)C1)c1cccc(C2CC2)c1] | +++ |
| 1.145 | 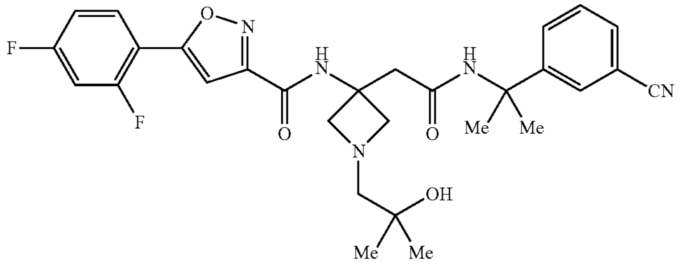 [SMILES: CC(C)(O)CN1CC(CC(=O)NC(C)(C)c2cccc(C#N)c2)(NC(=O)c2cc(-c3ccc(F)cc3F)on2)C1] | +++ |
| 1.146 | 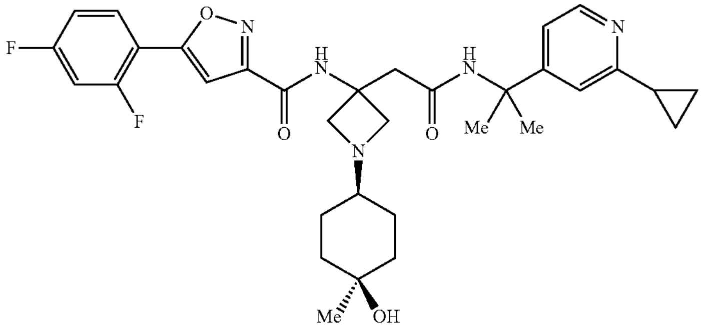 [SMILES: CC(C)(NC(=O)CC1(NC(=O)c2cc(-c3ccc(F)cc3F)on2)CN([C@H]2CC[C@@](C)(O)CC2)C1)c1ccnc(C2CC2)c1] | +++ |
| 1.147 | 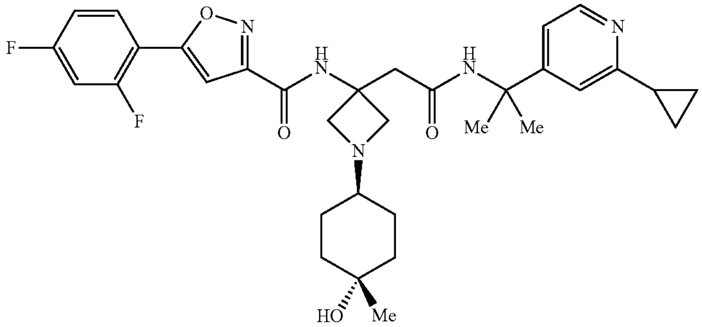 [SMILES: CC(C)(NC(=O)CC1(NC(=O)c2cc(-c3ccc(F)cc3F)on2)CN([C@H]2CC[C@](C)(O)CC2)C1)c1ccnc(C2CC2)c1] | +++ |

-continued
| Specific Examples (Table 1) | | |
|---|---|---|
| Compound ID | Structure | IC50 (buffer) |
| 1.148 | 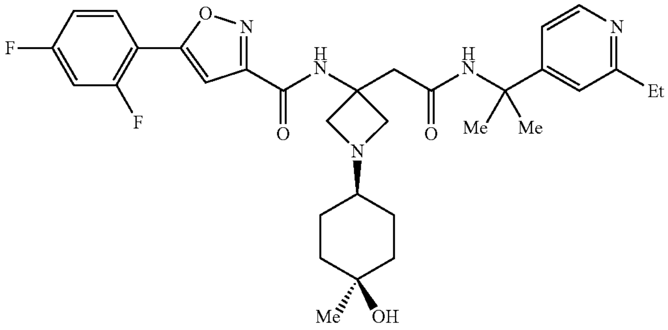 [SMILES: CCc1cc(C(C)(C)NC(=O)CC2(NC(=O)c3cc(-c4ccc(F)cc4F)on3)CN([C@H]3CC[C@@](C)(O)CC3)C2)ccn1] | +++ |
| 1.149 | 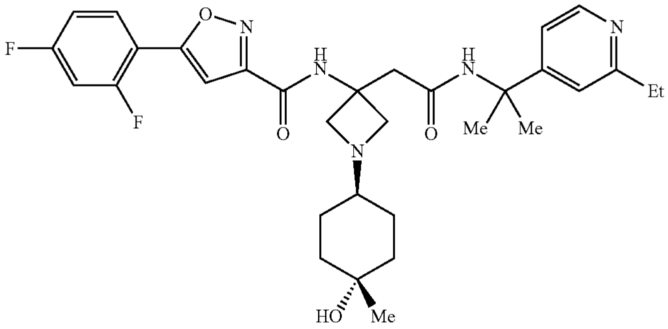 [SMILES: CCc1cc(C(C)(C)NC(=O)CC2(NC(=O)c3cc(-c4ccc(F)cc4F)on3)CN([C@H]3CC[C@](C)(O)CC3)C2)ccn1] | +++ |
| 1.150 | 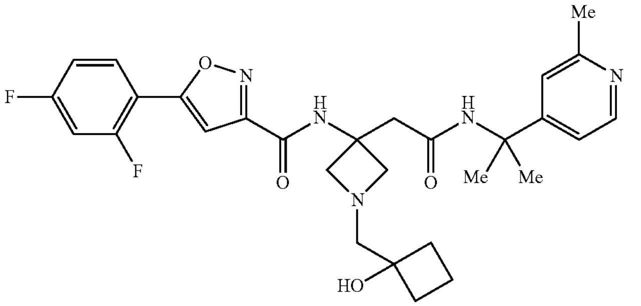 [SMILES: Cc1cc(C(C)(C)NC(=O)CC2(NC(=O)c3cc(-c4ccc(F)cc4F)on3)CN(CC3(O)CCC3)C2)ccn1] | ++ |
| 1.151 | 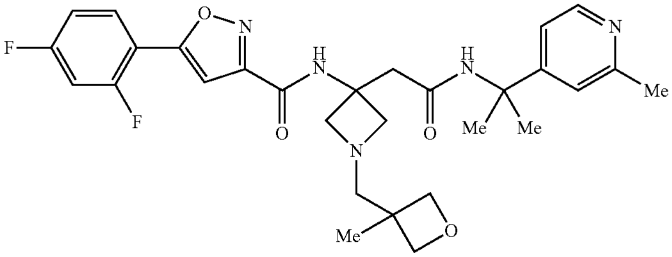 [SMILES: Cc1cc(C(C)(C)NC(=O)CC2(NC(=O)c3cc(-c4ccc(F)cc4F)on3)CN(CC3(C)COC3)C2)ccn1] | +++ |

-continued
Specific Examples (Table 1)
| Compound ID | Structure | IC50 (buffer) |
|---|---|---|
| 1.152 | 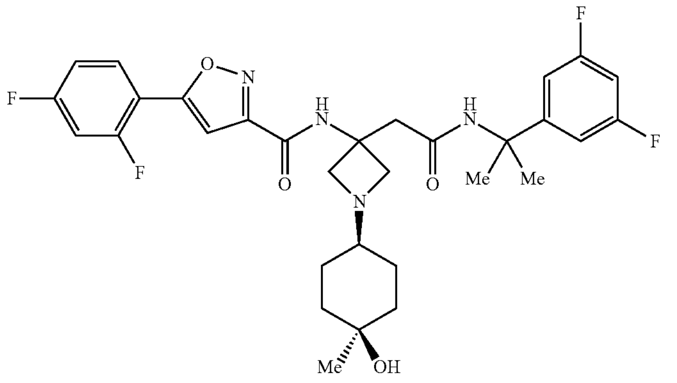 [SMILES: CC(C)(NC(=O)CC1(NC(=O)c2cc(-c3ccc(F)cc3F)on2)CN([C@H]2CC[C@@](C)(O)CC2)C1)c1cc(F)cc(F)c1] | ++++ |
| 1.153 | 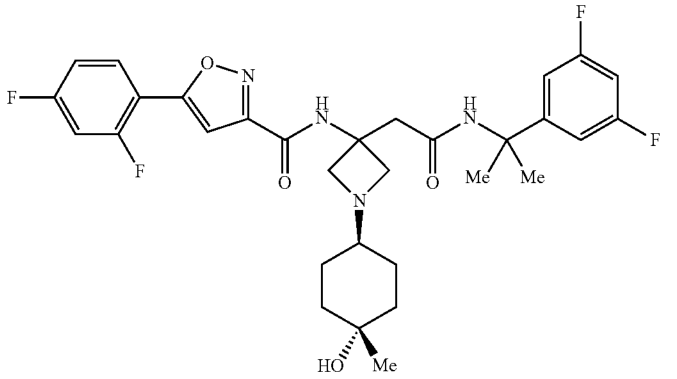 [SMILES: CC(C)(NC(=O)CC1(NC(=O)c2cc(-c3ccc(F)cc3F)on2)CN([C@H]2CC[C@](C)(O)CC2)C1)c1cc(F)cc(F)c1] | ++++ |
| 1.154 | 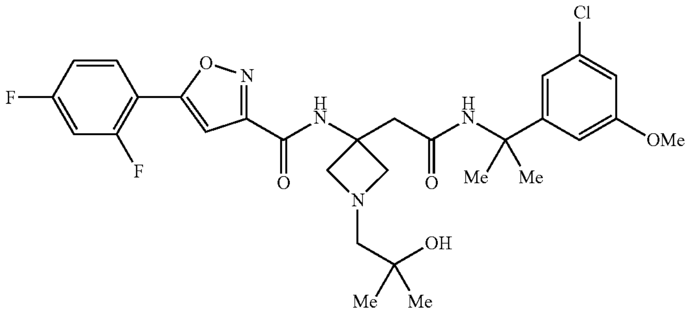 [SMILES: COc1cc(Cl)cc(C(C)(C)NC(=O)CC2(NC(=O)c3cc(-c4ccc(F)cc4F)on3)CN(CC(C)(C)O)C2)c1] | ++++ |
| 1.155 | 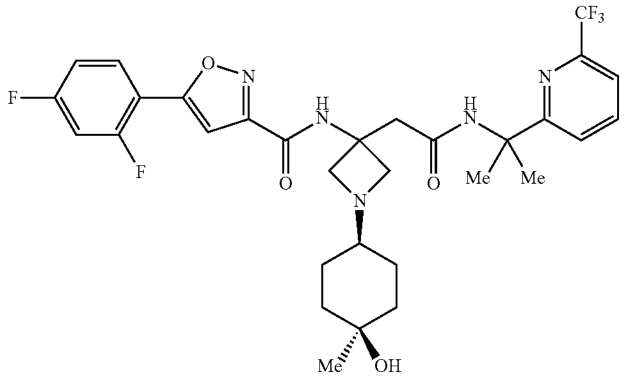 [SMILES: CC(C)(NC(=O)CC1(NC(=O)c2cc(-c3ccc(F)cc3F)on2)CN([C@H]2CC[C@@](C)(O)CC2)C1)c1cccc(C(F)(F)F)n1] | ++++ |

-continued
| Specific Examples (Table 1) | | |
|---|---|---|
| Compound ID | Structure | IC50 (buffer) |
| 1.156 | 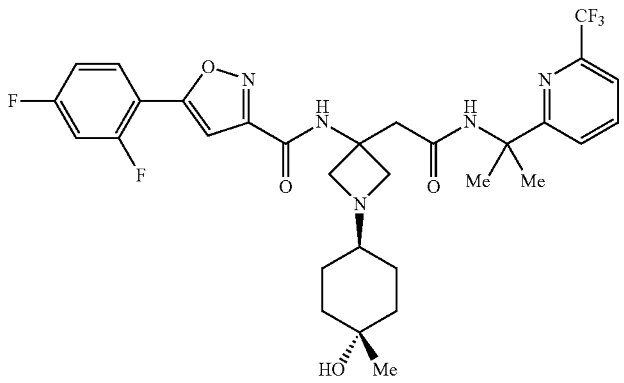 | ++++ |
| 1.157 | 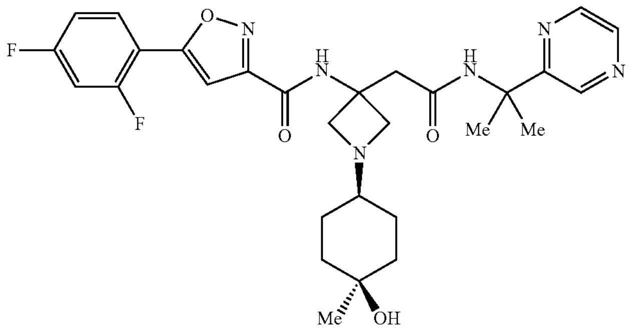 [SMILES: CC(C)(NC(=O)CC1(NC(=O)c2cc(-c3ccc(F)cc3F)on2)CN([C@H]2CC[C@@](C)(O)CC2)C1)c1cnccn1] | +++ |
| 1.158 | 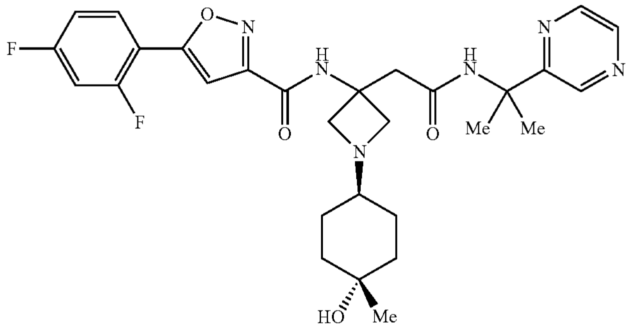 [SMILES: CC(C)(NC(=O)CC1(NC(=O)c2cc(-c3ccc(F)cc3F)on2)CN([C@H]2CC[C@](C)(O)CC2)C1)c1cnccn1] | +++ |
| 1.159 | 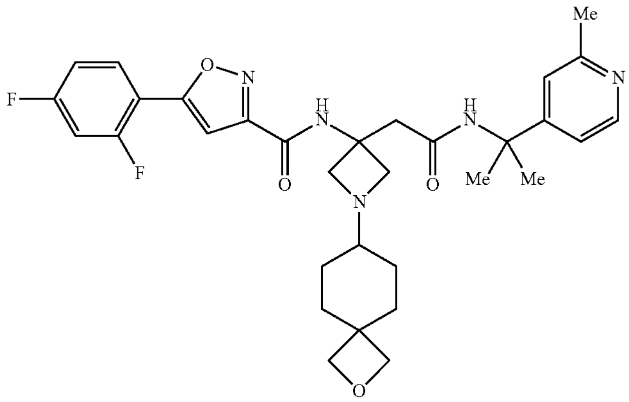 [SMILES: Cc1cc(C(C)(C)NC(=O)CC2(NC(=O)c3cc(-c4ccc(F)cc4F)on3)CN(C3CCC4(CC3)COC4)C2)ccn1] | +++ |

-continued
| Specific Examples (Table 1) | | |
|---|---|---|
| Compound ID | Structure | IC50 (buffer) |
| 1.160 | 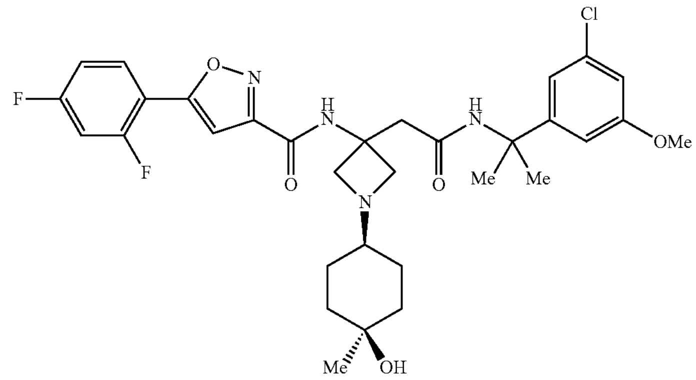 [SMILES: COc1cc(Cl)cc(C(C)(C)NC(=O)CC2(NC(=O)c3cc(-c4ccc(F)cc4F)on3)CN([C@H]3CC[C@@](C)(O)CC3)C2)c1] | ++++ |
| 1.161 | 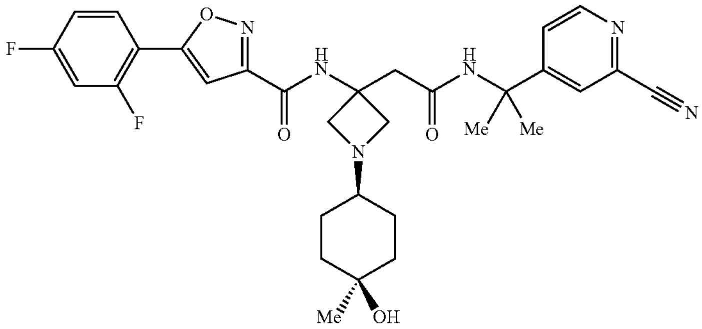 [SMILES: CC(C)(NC(=O)CC1(NC(=O)c2cc(-c3ccc(F)cc3F)on2)CN([C@H]2CC[C@@](C)(O)CC2)C1)c1ccnc(C#N)c1] | +++ |
| 1.162 | 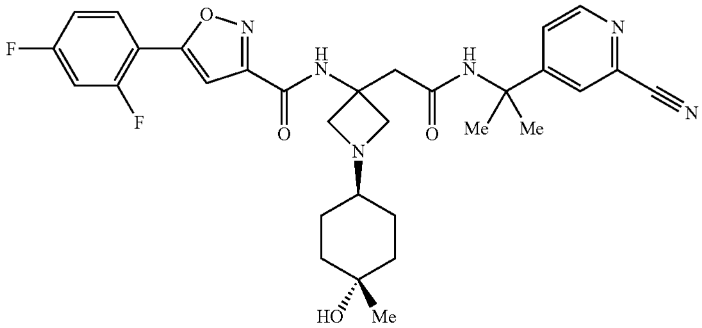 [SMILES: CC(C)(NC(=O)CC1(NC(=O)c2cc(-c3ccc(F)cc3F)on2)CN([C@H]2CC[C@](C)(O)CC2)C1)c1ccnc(C#N)c1] | +++ |
| 1.163 | 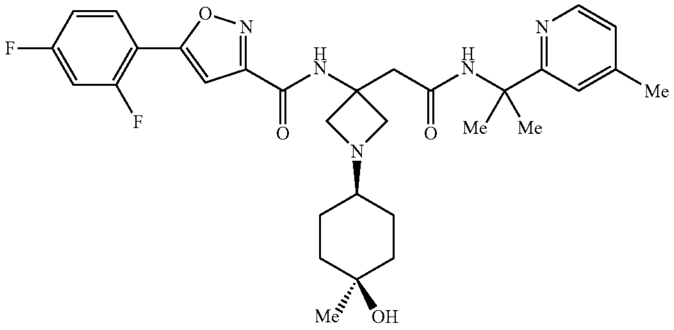 | ++++ |

-continued
| Specific Examples (Table 1) | | |
|---|---|---|
| Compound ID | Structure | IC50 (buffer) |
| 1.164 | 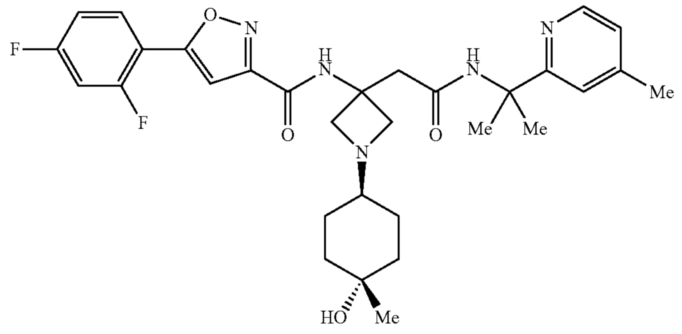 | ++++ |
| 1.165 | 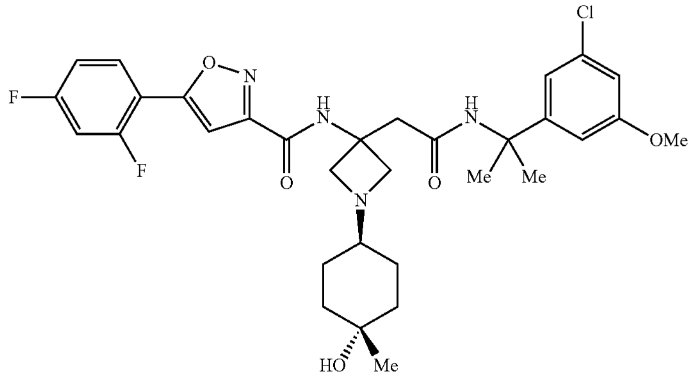 [SMILES: COc1cc(Cl)cc(C(C)(C)NC(=O)CC2(NC(=O)c3cc(-c4ccc(F)cc4F)on3)CN([C@H]3CC[C@](C)(O)CC3)C2)c1] | ++++ |
| 1.166 | 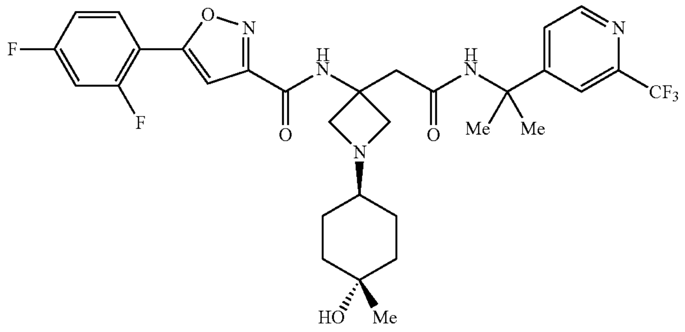 | +++ |
| 1.167 | 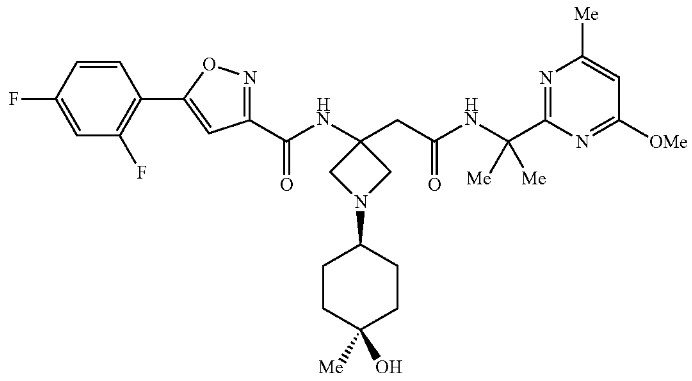 [SMILES: COc1cc(C)nc(C(C)(C)NC(=O)CC2(NC(=O)c3cc(-c4ccc(F)cc4F)on3)CN([C@H]3CC[C@@](C)(O)CC3)C2)n1] | ++++ |

-continued
| Specific Examples (Table 1) | | |
|---|---|---|
| Compound ID | Structure | IC50 (buffer) |
| 1.168 | 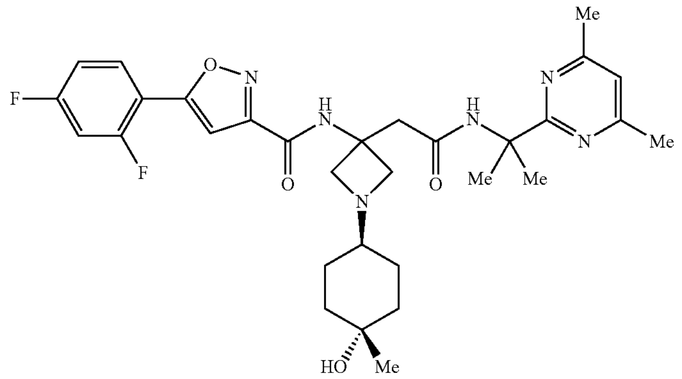 [SMILES: Cc1cc(C)nc(C(C)(C)NC(=O)CC2(NC(=O)c3cc(-c4ccc(F)cc4F)on3)CN([C@H]3CC[C@](C)(O)CC3)C2)n1] | ++++ |
| 1.169 | 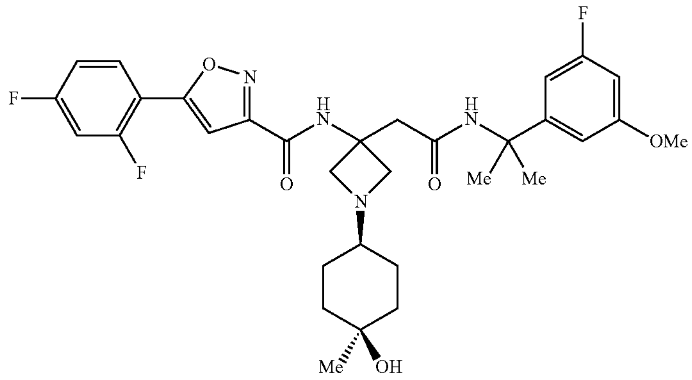 [SMILES: COc1cc(F)cc(C(C)(C)NC(=O)CC2(NC(=O)c3cc(-c4ccc(F)cc4F)on3)CN([C@H]3CC[C@@](C)(O)CC3)C2)c1] | ++++ |
| 1.170 | 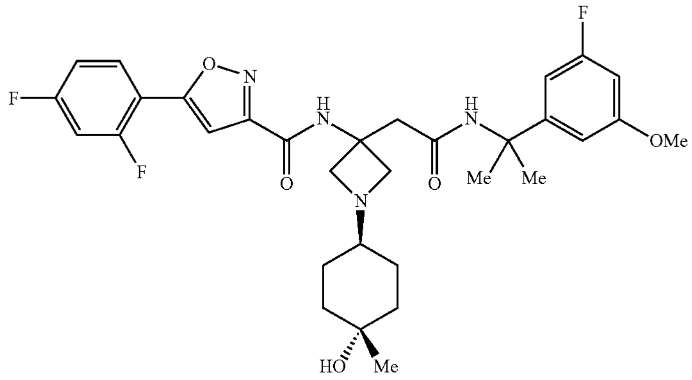 [SMILES: COc1cc(F)cc(C(C)(C)NC(=O)CC2(NC(=O)c3cc(-c4ccc(F)cc4F)on3)CN([C@H]3CC[C@](C)(O)CC3)C2)c1] | +++ |
| 1.171 | 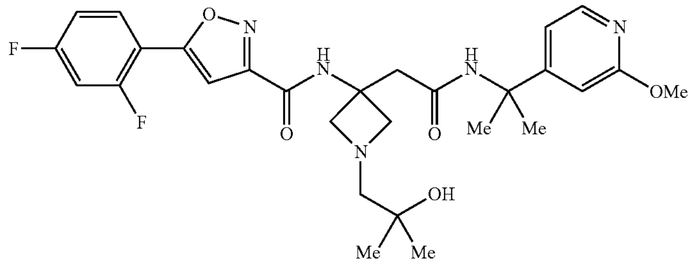 [SMILES: COc1cc(C(C)(C)NC(=O)CC2(NC(=O)c3cc(-c4ccc(F)cc4F)on3)CN(CC(C)(C)O)C2)ccn1] | ++ |

-continued
| Specific Examples (Table 1) | | |
|---|---|---|
| Compound ID | Structure | IC50 (buffer) |
| 1.172 | 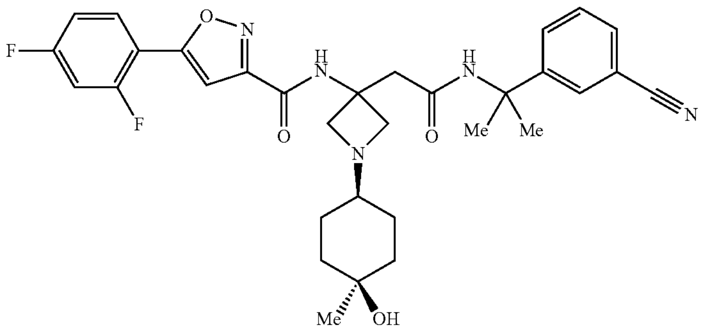 [SMILES: CC(C)(NC(=O)CC1(NC(=O)c2cc(-c3ccc(F)cc3F)on2)CN([C@H]2CC[C@@](C)(O)CC2)C1)c1cccc(C#N)c1] | ++++ |
| 1.173 | 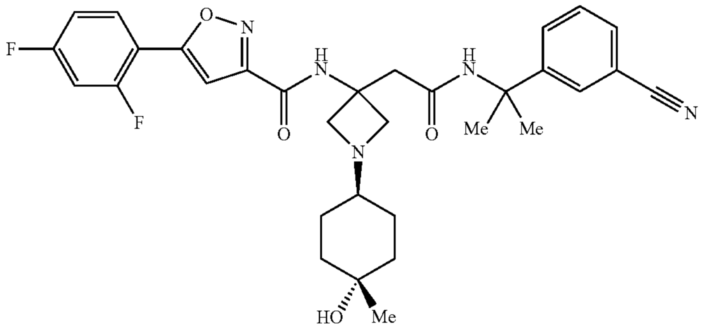 [SMILES: CC(C)(NC(=O)CC1(NC(=O)c2cc(-c3ccc(F)cc3F)on2)CN([C@H]2CC[C@](C)(O)CC2)C1)c1cccc(C#N)c1] | ++++ |
| 1.174 | 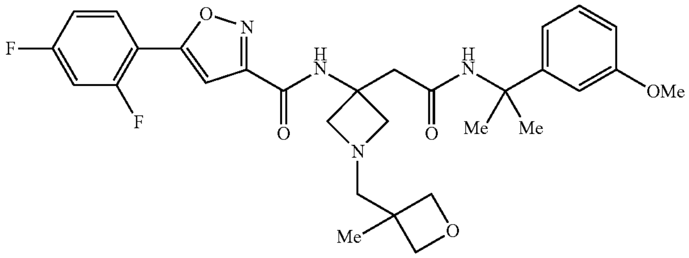 [SMILES: COc1cccc(C(C)(C)NC(=O)CC2(NC(=O)c3cc(-c4ccc(F)cc4F)on3)CN(CC3(C)COC3)C2)c1] | ++ |
| 1.175 | 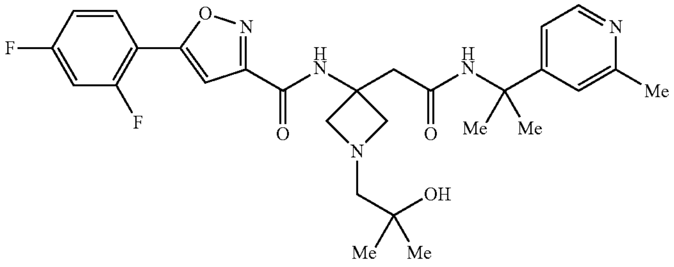 [SMILES: Cc1cc(C(C)(C)NC(=O)CC2(NC(=O)c3cc(-c4ccc(F)cc4F)on3)CN(CC(C)(C)O)C2)ccn1] | +++ |

-continued
| Specific Examples (Table 1) | | |
|---|---|---|
| Compound ID | Structure | IC50 (buffer) |
| 1.176 | 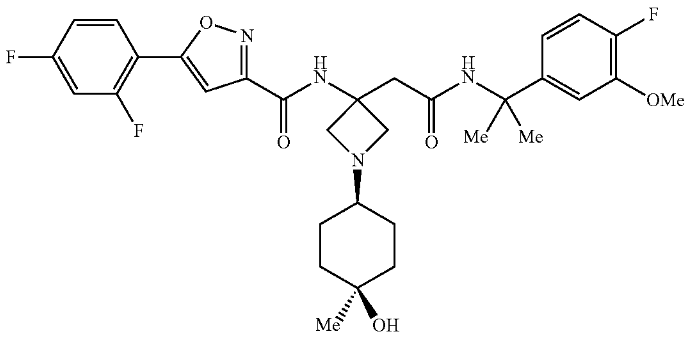 [SMILES: COc1cc(C(C)(C)NC(=O)CC2(NC(=O)c3cc(-c4ccc(F)cc4F)on3)CN([C@H]3CC[C@@](C)(O)CC3)C2)ccc1F] | +++ |
| 1.177 | 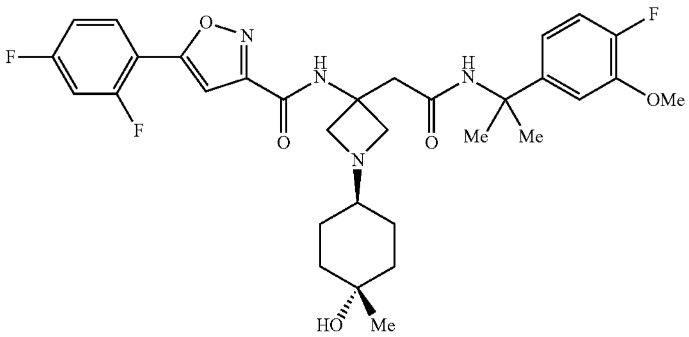 [SMILES: COc1cc(C(C)(C)NC(=O)CC2(NC(=O)c3cc(-c4ccc(F)cc4F)on3)CN([C@H]3CC[C@](C)(O)CC3)C2)ccc1F] | +++ |
| 1.178 | 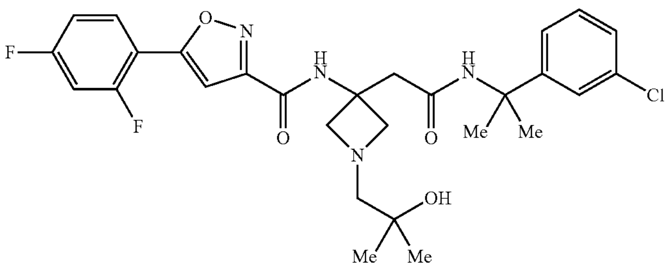 [SMILES: CC(C)(O)CN1CC(CC(=O)NC(C)(C)c2cccc(Cl)c2)(NC(=O)c2cc(-c3ccc(F)cc3F)on2)C1] | ++++ |
| 1.179 | 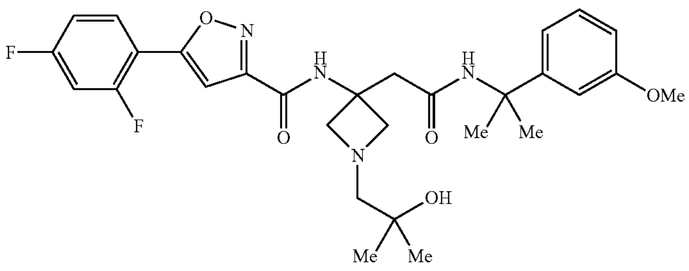 [SMILES: COc1cccc(C(C)(C)NC(=O)CC2(NC(=O)c3cc(-c4ccc(F)cc4F)on3)CN(CC(C)(C)O)C2)c1] | +++ |

-continued
| Specific Examples (Table 1) | | |
|---|---|---|
| Compound ID | Structure | IC50 (buffer) |
| 1.180 | 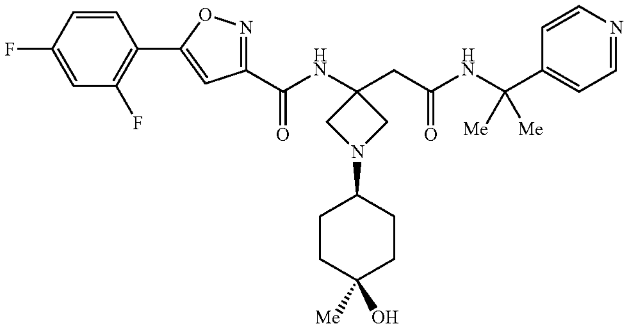 [SMILES: CC(C)(NC(=O)CC1(NC(=O)c2cc(-c3ccc(F)cc3F)on2)CN([C@H]2CC[C@@](C)(O)CC2)C1)c1ccncc1] | ++++ |
| 1.181 | 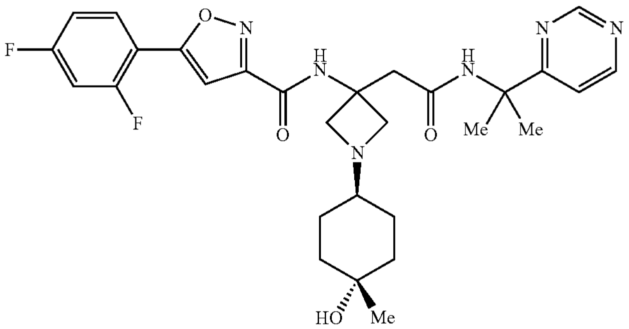 [SMILES: CC(C)(NC(=O)CC1(NC(=O)c2cc(-c3ccc(F)cc3F)on2)CN([C@H]2CC[C@](C)(O)CC2)C1)c1ccncn1] | +++ |
| 1.182 | 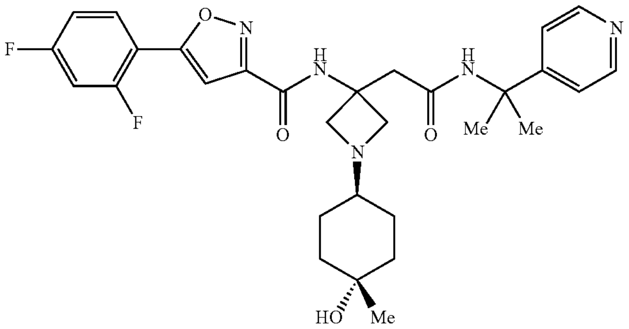 [SMILES: CC(C)(NC(=O)CC1(NC(=O)c2cc(-c3ccc(F)cc3F)on2)CN([C@H]2CC[C@](C)(O)CC2)C1)c1ccncc1] | ++++ |
| 1.183 | 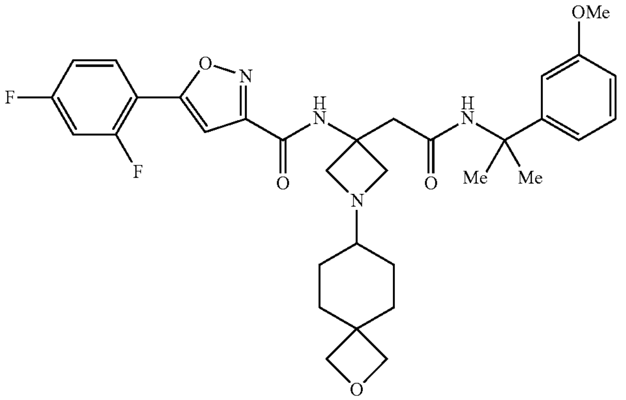 [SMILES: COc1cccc(C(C)(C)NC(=O)CC2(NC(=O)c3cc(-c4ccc(F)cc4F)on3)CN(C3CCC4(CC3)COC4)C2)c1] | +++ |

-continued
| Specific Examples (Table 1) | | |
|---|---|---|
| Compound ID | Structure | IC50 (buffer) |
| 1.184 | 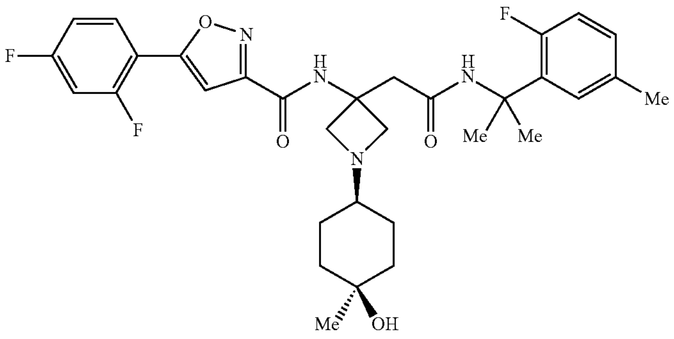 [SMILES: Cc1ccc(F)c(C(C)(C)NC(=O)CC2(NC(=O)c3cc(-c4ccc(F)cc4F)on3)CN([C@H]3CC[C@@](C)(O)CC3)C2)c1] | ++++ |
| 1.185 | 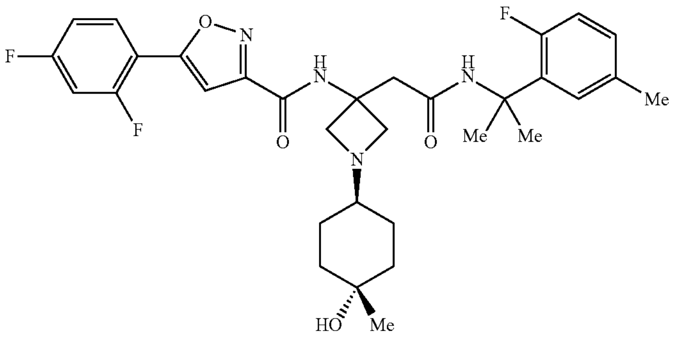 [SMILES: Cc1ccc(F)c(C(C)(C)NC(=O)CC2(NC(=O)c3cc(-c4ccc(F)cc4F)on3)CN([C@H]3CC[C@](C)(O)CC3)C2)c1] | ++++ |
| 1.186 | 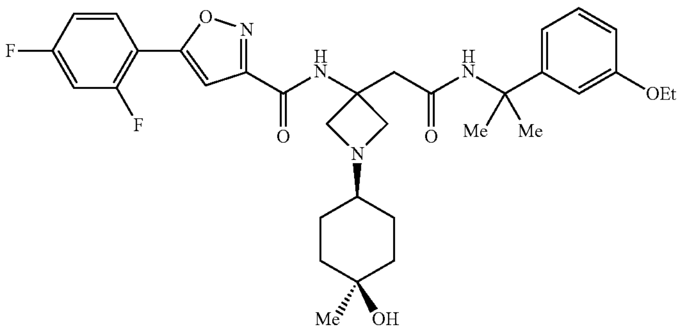 | +++ |
| 1.187 | 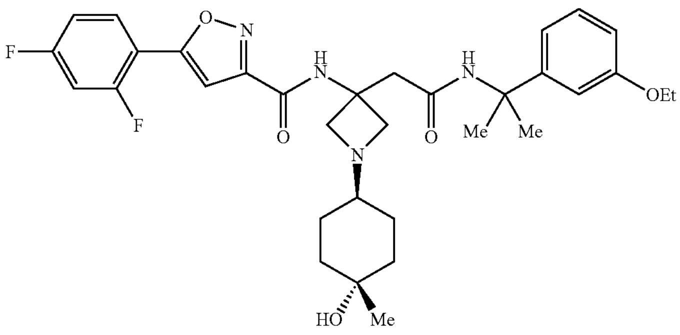 | +++ |

-continued
| Specific Examples (Table 1) | | |
|---|---|---|
| Compound ID | Structure | IC50 (buffer) |
| 1.188 | 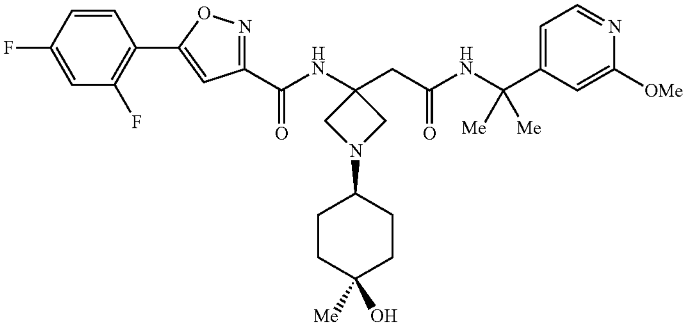 | ++++ |
| 1.189 | 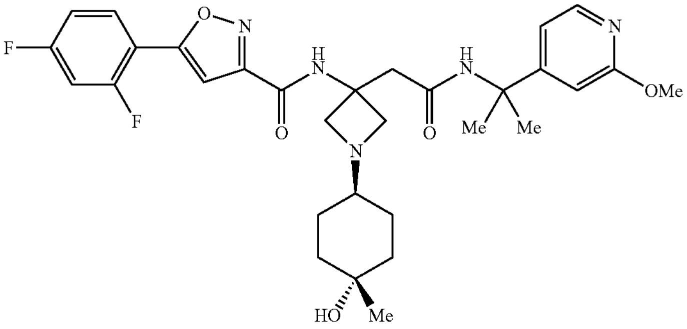 | ++++ |
| 1.190 | 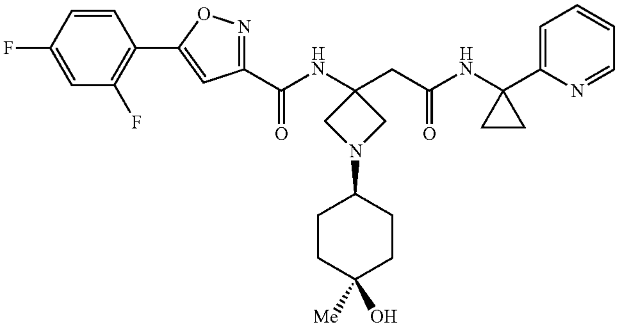 [SMILES: C[C@]1(O)CC[C@@H](N2CC(CC(=O)NC3(c4ccccn4)CC3)(NC(=O)c3cc(-c4ccc(F)cc4F)on3)C2)CC1] | +++ |
| 1.191 | 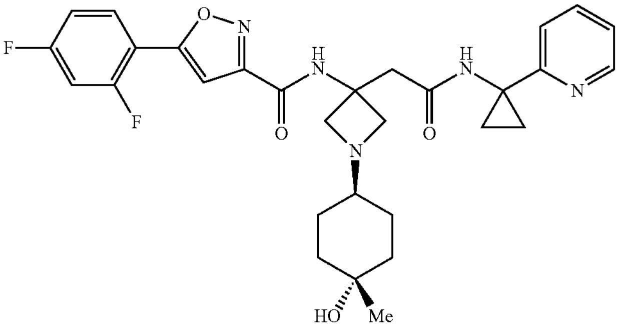 [SMILES: C[C@]1(O)CC[C@H](N2CC(CC(=O)NC3(c4ccccn4)CC3)(NC(=O)c3cc(-c4ccc(F)cc4F)on3)C2)CC1] | +++ |

-continued
| Specific Examples (Table 1) | | |
|---|---|---|
| Compound ID | Structure | IC50 (buffer) |
| 1.192 | 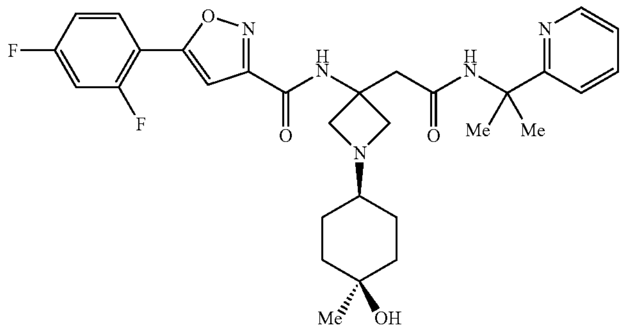 [SMILES: CC(C)(NC(=O)CC1(NC(=O)c2cc(-c3ccc(F)cc3F)on2)CN([C@H]2CC[C@@](C)(O)CC2)C1)c1ccccn1] | ++++ |
| 1.193 | 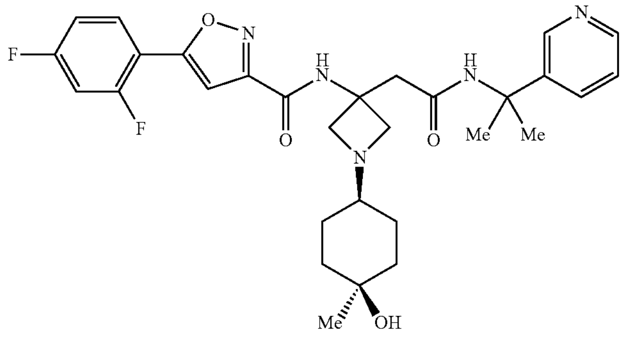 [SMILES: CC(C)(NC(=O)CC1(NC(=O)c2cc(-c3ccc(F)cc3F)on2)CN([C@H]2CC[C@@](C)(O)CC2)C1)c1cccnc1] | +++ |
| 1.194 | 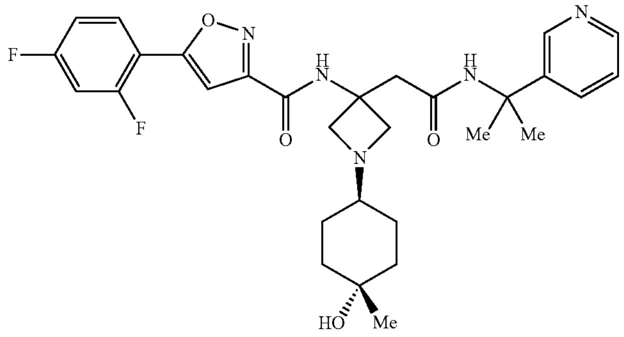 [SMILES: CC(C)(NC(=O)CC1(NC(=O)c2cc(-c3ccc(F)cc3F)on2)CN([C@H]2CC[C@](C)(O)CC2)C1)c1cccnc1] | +++ |
| 1.195 | 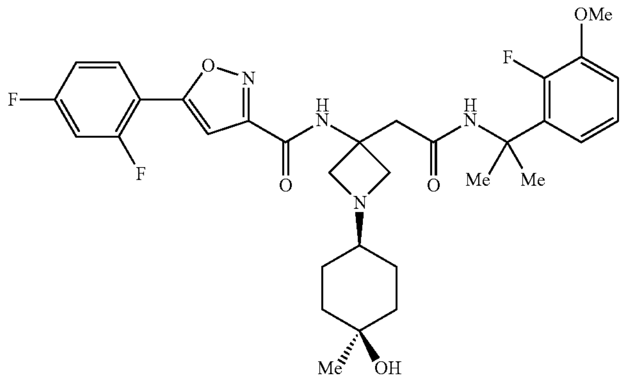 [SMILES: COc1cccc(C(C)(C)NC(=O)CC2(NC(=O)c3cc(-c4ccc(F)cc4F)on3)CN([C@H]3CC[C@@](C)(O)CC3)C2)c1F] | +++ |

-continued
Specific Examples (Table 1)
| Compound ID | Structure | IC50 (buffer) |
|---|---|---|
| 1.196 | 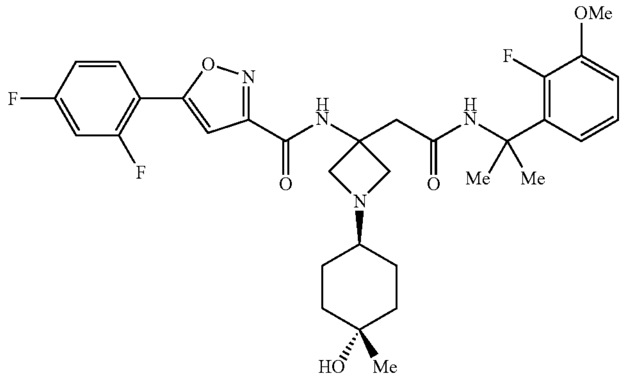 [SMILES: COc1cccc(C(C)(C)NC(=O)CC2(NC(=O)c3cc(-c4ccc(F)cc4F)on3)CN([C@H]3CC[C@](C)(O)CC3)C2)c1F] | ++ |
| 1.197 | 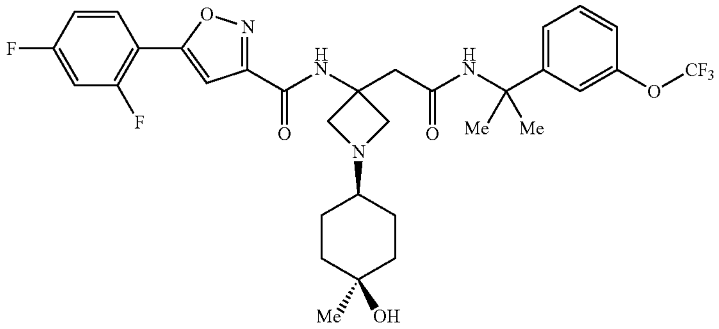 [SMILES: CC(C)(NC(=O)CC1(NC(=O)c2cc(-c3ccc(F)cc3F)on2)CN([C@H]2CC[C@@](C)(O)CC2)C1)c1cccc(OC(F)(F)F)c1] | ++++ |
| 1.198 | 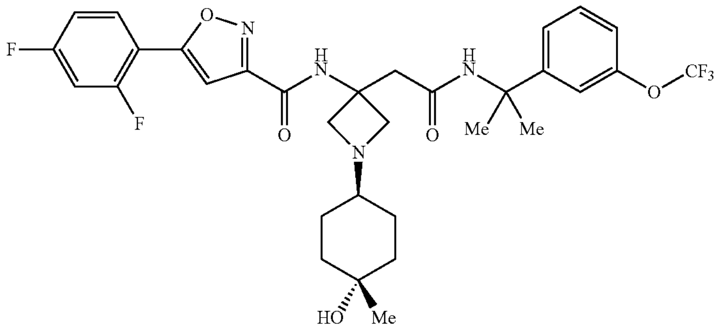 [SMILES: CC(C)(NC(=O)CC1(NC(=O)c2cc(-c3ccc(F)cc3F)on2)CN([C@H]2CC[C@](C)(O)CC2)C1)c1cccc(OC(F)(F)F)c1] | +++ |
| 1.199 | 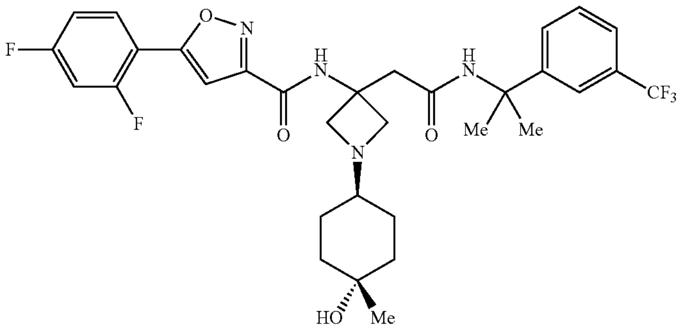 [SMILES: CC(C)(NC(=O)CC1(NC(=O)c2cc(-c3ccc(F)cc3F)on2)CN([C@H]2CC[C@](C)(O)CC2)C1)c1cccc(C(F)(F)F)c1] | +++ |

-continued
Specific Examples (Table 1)
| Compound ID | Structure | IC50 (buffer) |
| --- | --- | --- |
| 1.200 | 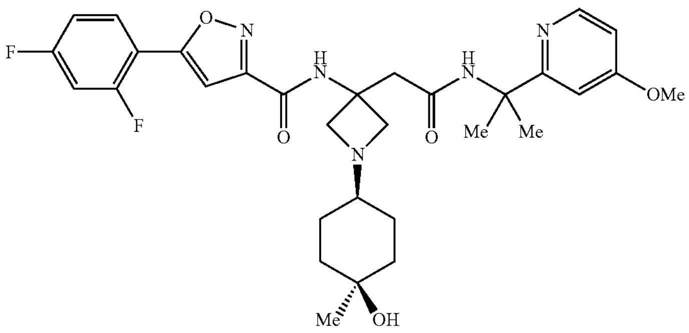 [SMILES: COc1ccnc(C(C)(C)NC(=O)CC2(NC(=O)c3cc(-c4ccc(F)cc4F)on3)CN([C@H]3CC[C@@](C)(O)CC3)C2)c1] | +++ |
| 1.201 | 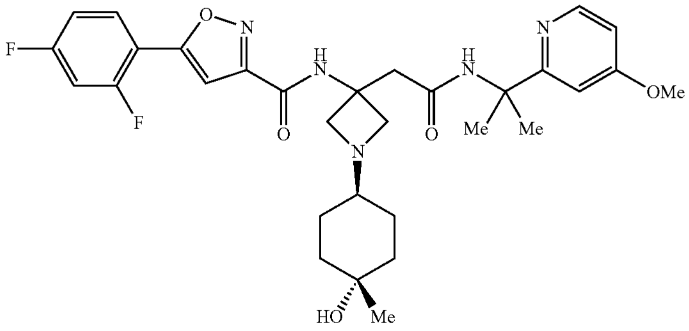 [SMILES: COc1ccnc(C(C)(C)NC(=O)CC2(NC(=O)c3cc(-c4ccc(F)cc4F)on3)CN([C@H]3CC[C@](C)(O)CC3)C2)c1] | ++++ |
| 1.202 | 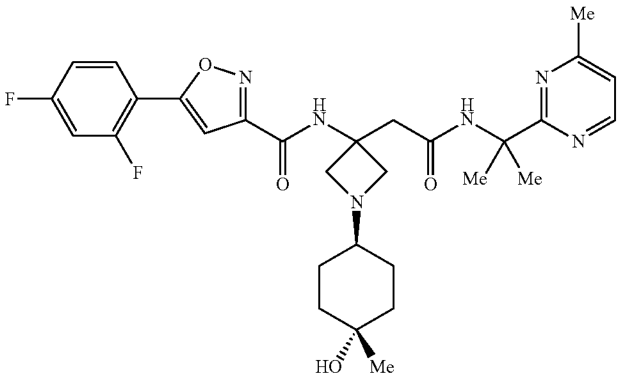 [SMILES: Cc1ccnc(C(C)(C)NC(=O)CC2(NC(=O)c3cc(-c4ccc(F)cc4F)on3)CN([C@H]3CC[C@](C)(O)CC3)C2)n1] | ++++ |
| 1.203 | 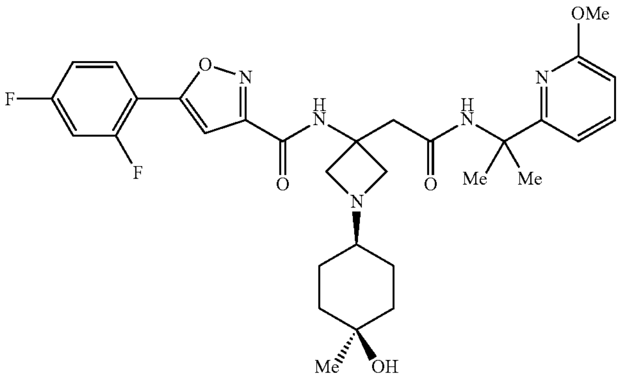 [SMILES: COc1cccc(C(C)(C)NC(=O)CC2(NC(=O)c3cc(-c4ccc(F)cc4F)on3)CN([C@H]3CC[C@@](C)(O)CC3)C2)n1] | ++++ |

-continued
| Specific Examples (Table 1) | | |
|---|---|---|
| Compound ID | Structure | IC50 (buffer) |
| 1.204 | 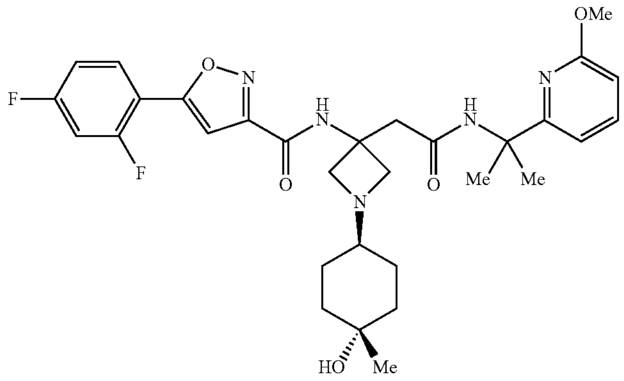 [SMILES: COc1cccc(C(C)(C)NC(=O)CC2(NC(=O)c3cc(-c4ccc(F)cc4F)on3)CN([C@H]3CC[C@](C)(O)CC3)C2)n1] | ++++ |
| 1.205 | 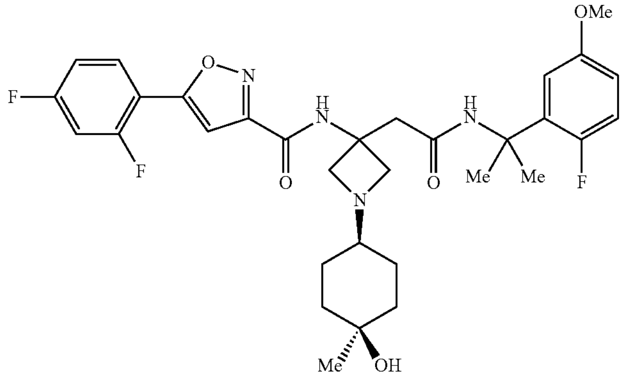 [SMILES: COc1ccc(F)c(C(C)(C)NC(=O)CC2(NC(=O)c3cc(-c4ccc(F)cc4F)on3)CN([C@H]3CC[C@@](C)(O)CC3)C2)c1] | +++ |
| 1.206 | 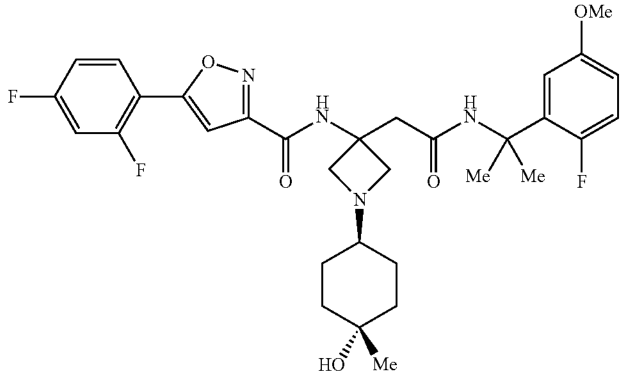 [SMILES: COc1ccc(F)c(C(C)(C)NC(=O)CC2(NC(=O)c3cc(-c4ccc(F)cc4F)on3)CN([C@H]3CC[C@](C)(O)CC3)C2)c1] | +++ |
| 1.207 | 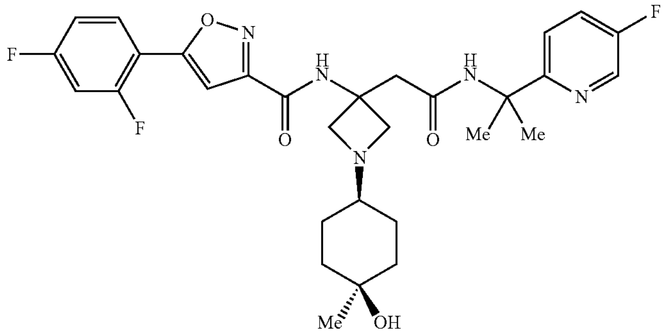 [SMILES: CC(C)(NC(=O)CC1(NC(=O)c2cc(-c3ccc(F)cc3F)on2)CN([C@H]2CC[C@@](C)(O)CC2)C1)c1ccc(F)cn1] | ++ |

-continued
| Specific Examples (Table 1) | | |
|---|---|---|
| Compound ID | Structure | IC50 (buffer) |
| 1.208 | 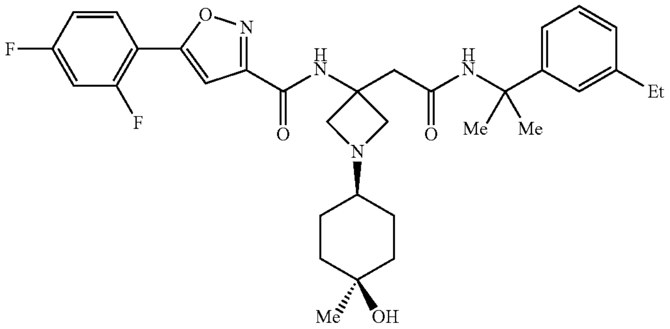 [SMILES: CCc1cccc(C(C)(C)NC(=O)CC2(NC(=O)c3cc(-c4ccc(F)cc4F)on3)CN([C@H]3CC[C@@](C)(O)CC3)C2)c1] | ++++ |
| 1.209 | 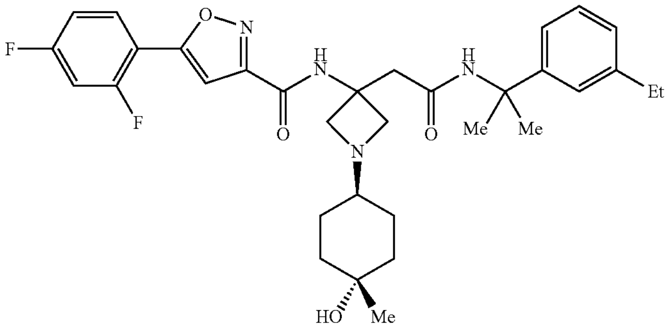 [SMILES: CCc1cccc(C(C)(C)NC(=O)CC2(NC(=O)c3cc(-c4ccc(F)cc4F)on3)CN([C@H]3CC[C@](C)(O)CC3)C2)c1] | +++ |
| 1.210 | 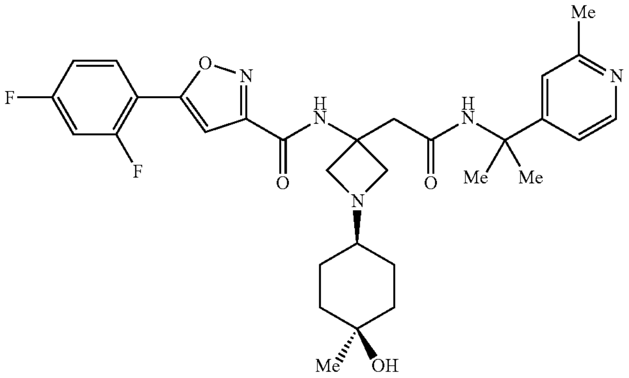 | ++++ |
| 1.211 | 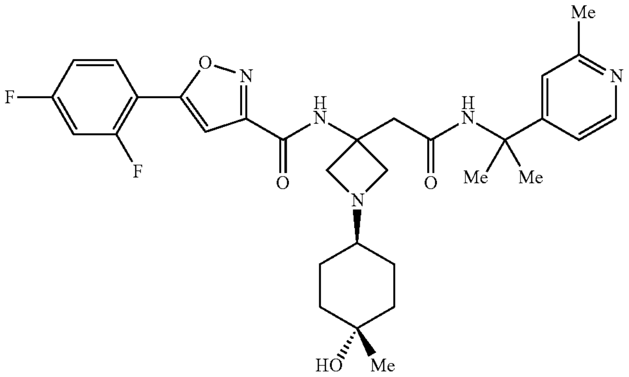 [SMILES: Cc1cc(C(C)(C)NC(=O)CC2(NC(=O)c3cc(-c4ccc(F)cc4F)on3)CN([C@H]3CC[C@](C)(O)CC3)C2)ccn1] | ++++ |

-continued
| Specific Examples (Table 1) | | |
|---|---|---|
| Compound ID | Structure | IC50 (buffer) |
| 1.212 | 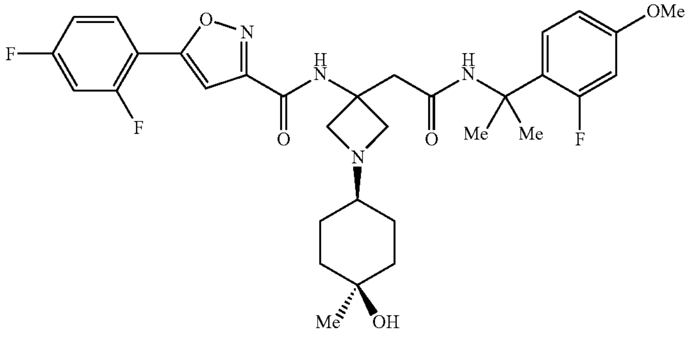 [SMILES: COc1ccc(C(C)(C)NC(=O)CC2(NC(=O)c3cc(-c4ccc(F)cc4F)on3)CN([C@H]3CC[C@@](C)(O)CC3)C2)c(F)c1] | +++ |
| 1.213 | 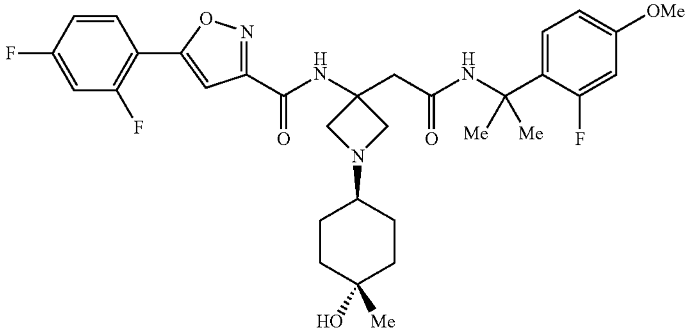 [SMILES: COc1ccc(C(C)(C)NC(=O)CC2(NC(=O)c3cc(-c4ccc(F)cc4F)on3)CN([C@H]3CC[C@](C)(O)CC3)C2)c(F)c1] | ++ |
| 1.214 | 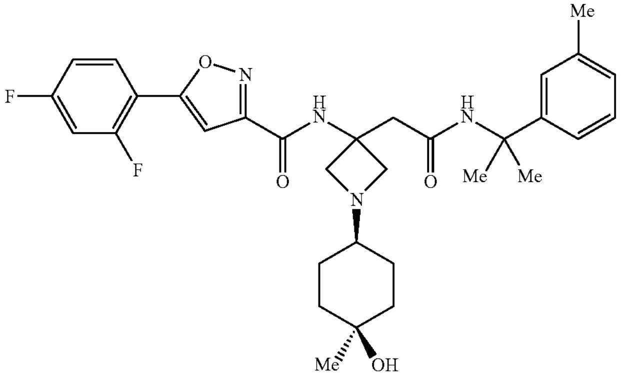 [SMILES: Cc1cccc(C(C)(C)NC(=O)CC2(NC(=O)c3cc(-c4ccc(F)cc4F)on3)CN([C@H]3CC[C@@](C)(O)CC3)C2)c1] | ++++ |
| 1.215 | 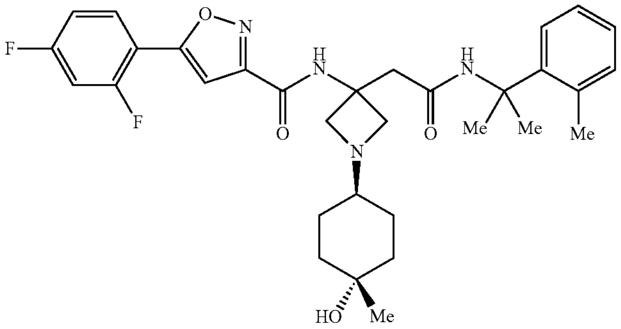 [SMILES: Cc1ccccc1C(C)(C)NC(=O)CC1(NC(=O)c2cc(-c3ccc(F)cc3F)on2)CN([C@H]2CC[C@](C)(O)CC2)C1] | ++++ |

-continued
| Specific Examples (Table 1) | | |
|---|---|---|
| Compound ID | Structure | IC50 (buffer) |
| 1.216 | 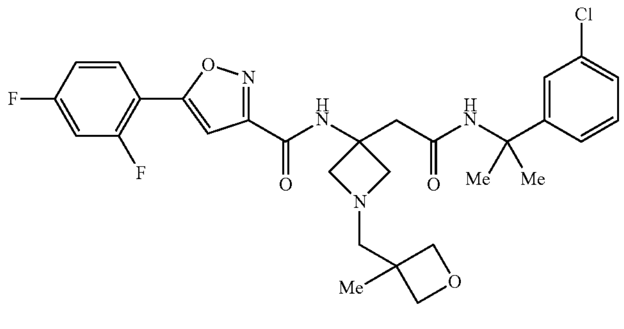 [SMILES: CC1(CN2CC(CC(=O)NC(C)(C)c3cccc(Cl)c3)(NC(=O)c3cc(-c4ccc(F)cc4F)on3)C2)COC1] | ++++ |
| 1.217 | 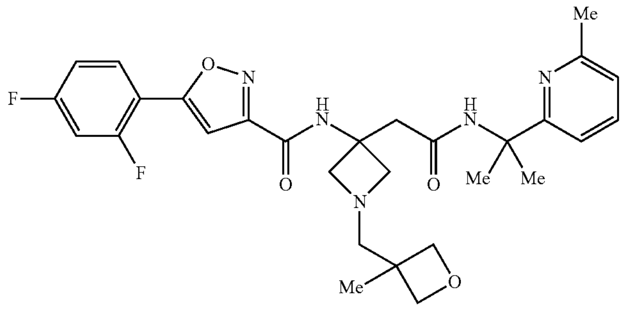 [SMILES: Cc1cccc(C(C)(C)NC(=O)CC2(NC(=O)c3cc(-c4ccc(F)cc4F)on3)CN(CC3(C)COC3)C2)n1] | +++ |
| 1.218 | 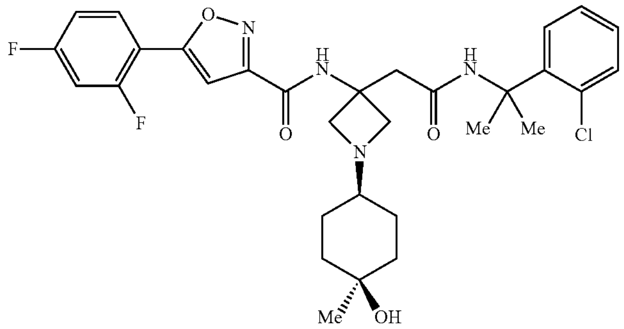 [SMILES: CC(C)(NC(=O)CC1(NC(=O)c2cc(-c3ccc(F)cc3F)on2)CN([C@H]2CC[C@@](C)(O)CC2)C1)c1ccccc1Cl] | ++++ |
| 1.219 | 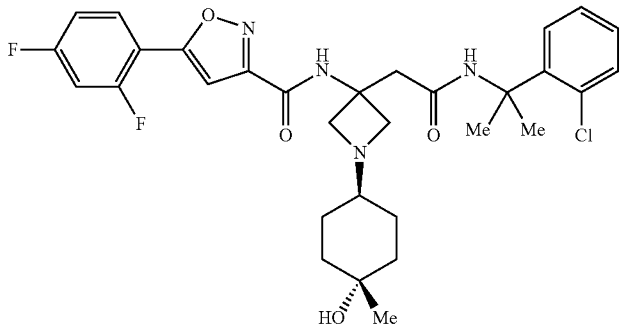 [SMILES: CC(C)(NC(=O)CC1(NC(=O)c2cc(-c3ccc(F)cc3F)on2)CN([C@H]2CC[C@](C)(O)CC2)C1)c1ccccc1Cl] | ++++ |

-continued
| Specific Examples (Table 1) | | |
|---|---|---|
| Compound ID | Structure | IC50 (buffer) |
| 1.220 | 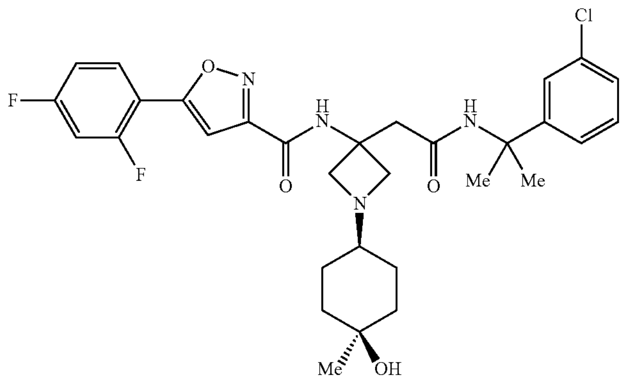 [SMILES: CC(C)(NC(=O)CC1(NC(=O)c2cc(-c3ccc(F)cc3F)on2)CN([C@H]2CC[C@@](C)(O)CC2)C1)c1cccc(Cl)c1] | ++++ |
| 1.221 | 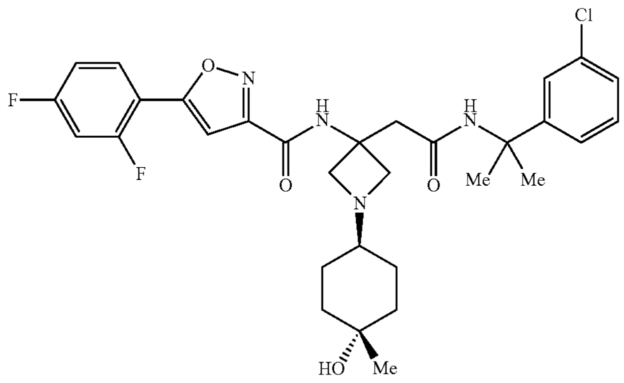 [SMILES: CC(C)(NC(=O)CC1(NC(=O)c2cc(-c3ccc(F)cc3F)on2)CN([C@H]2CC[C@](C)(O)CC2)C1)c1cccc(Cl)c1] | ++++ |
| 1.222 | 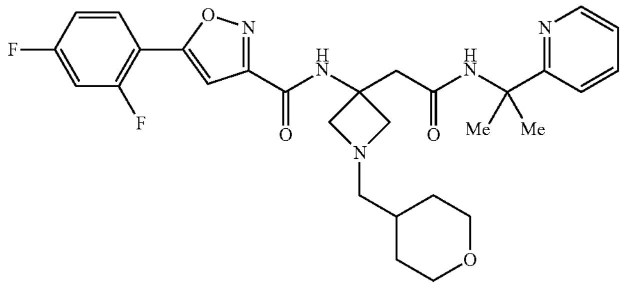 [SMILES: CC(C)(NC(=O)CC1(NC(=O)c2cc(-c3ccc(F)cc3F)on2)CN(CC2CCOCC2)C1)c1ccccn1] | ++ |
| 1.223 | 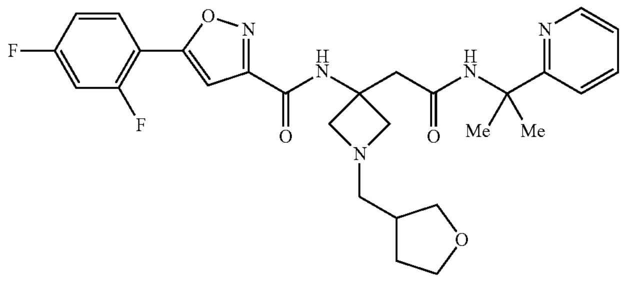 [SMILES: CC(C)(NC(=O)CC1(NC(=O)c2cc(-c3ccc(F)cc3F)on2)CN(CC2CCOC2)C1)c1ccccn1] | ++ |

-continued
| Specific Examples (Table 1) | | |
|---|---|---|
| Compound ID | Structure | IC50 (buffer) |
| 1.224 | 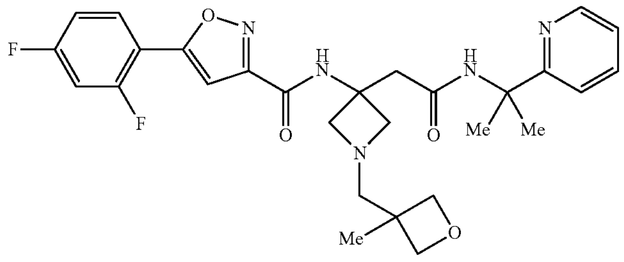 [SMILES: CC1(CN2CC(CC(=O)NC(C)(C)c3ccccn3)(NC(=O)c3cc(-c4ccc(F)cc4F)on3)C2)COC1] | +++ |
| 1.225 | 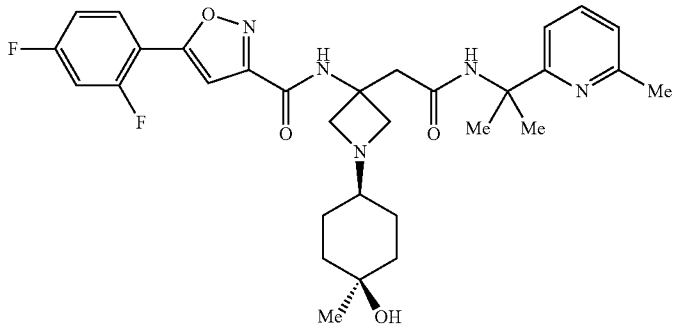 [SMILES: Cc1cccc(C(C)(C)NC(=O)CC2(NC(=O)c3cc(-c4ccc(F)cc4F)on3)CN([C@H]3CC[C@@](C)(O)CC3)C2)n1] | ++++ |
| 1.226 | 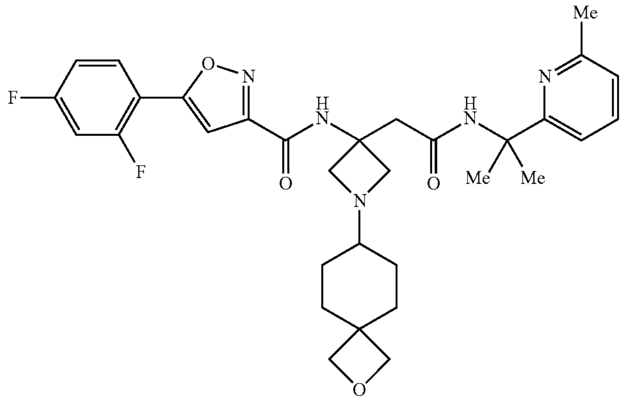 [SMILES: Cc1cccc(C(C)(C)NC(=O)CC2(NC(=O)c3cc(-c4ccc(F)cc4F)on3)CN(C3CCC4(CC3)COC4)C2)n1] | +++ |
| 1.227 | 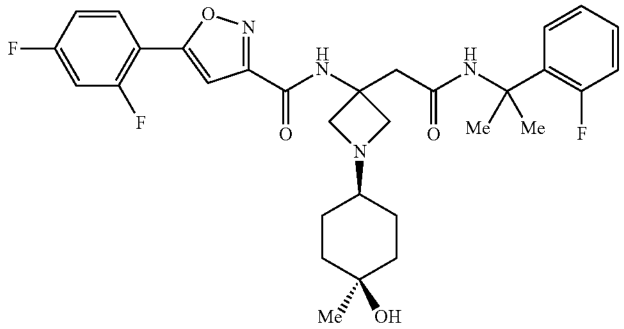 [SMILES: CC(C)(NC(=O)CC1(NC(=O)c2cc(-c3ccc(F)cc3F)on2)CN([C@H]2CC[C@@](C)(O)CC2)C1)c1ccccc1F] | ++++ |

-continued
| Specific Examples (Table 1) | | |
|---|---|---|
| Compound ID | Structure | IC50 (buffer) |
| 1.228 | 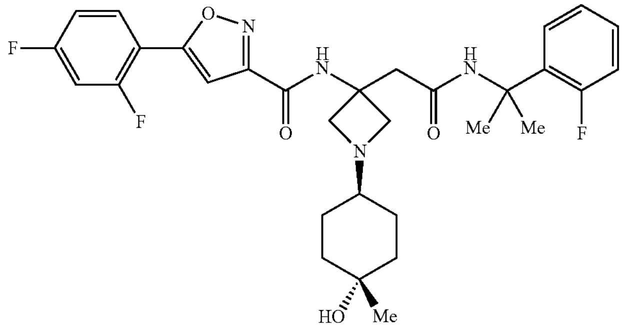 [SMILES: CC(C)(NC(=O)CC1(NC(=O)c2cc(-c3ccc(F)cc3F)on2)CN([C@H]2CC[C@](C)(O)CC2)C1)c1ccccc1F] | ++++ |
| 1.229 | 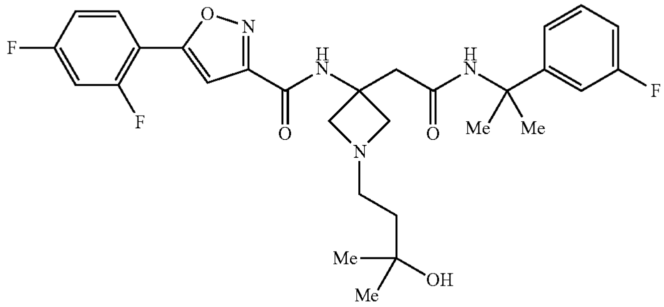 [SMILES: CC(C)(O)CCN1CC(CC(=O)NC(C)(C)c2cccc(F)c2)(NC(=O)c2cc(-c3ccc(F)cc3F)on2)C1] | +++ |
| 1.230 | 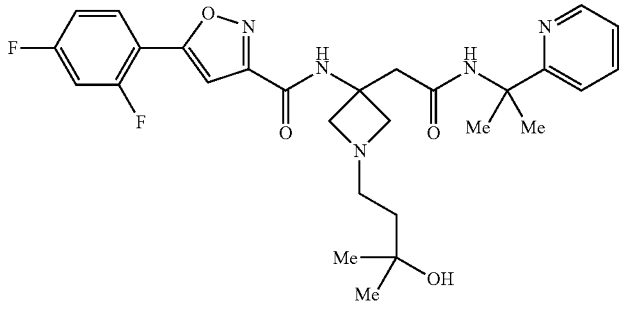 [SMILES: CC(C)(O)CCN1CC(CC(=O)NC(C)(C)c2ccccn2)(NC(=O)c2cc(-c3ccc(F)cc3F)on2)C1] | + |
| 1.231 | 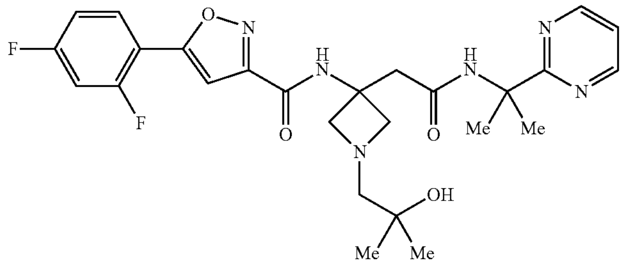 [SMILES: CC(C)(O)CN1CC(CC(=O)NC(C)(C)c2ncccn2)(NC(=O)c2cc(-c3ccc(F)cc3F)on2)C1] | ++ |

-continued
| Specific Examples (Table 1) | | |
|---|---|---|
| Compound ID | Structure | IC50 (buffer) |
| 1.232 | 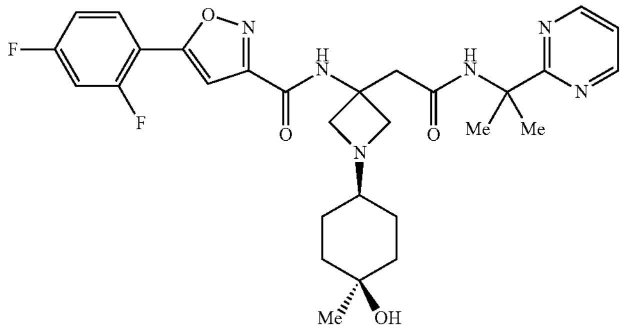 | ++++ |
| 1.233 | 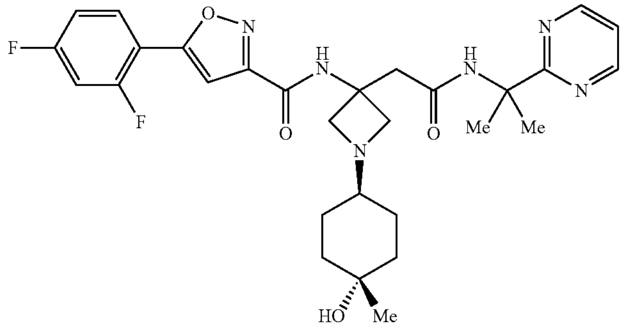 | ++++ |
| 1.234 | 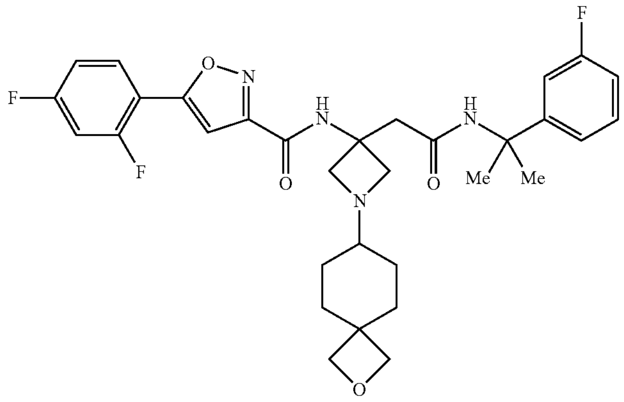 [SMILES: CC(C)(NC(=O)CC1(NC(=O)c2cc(-c3ccc(F)cc3F)on2)CN(C2CCC3(CC2)COC3)C1)c1cccc(F)c1] | +++ |
| 1.235 | 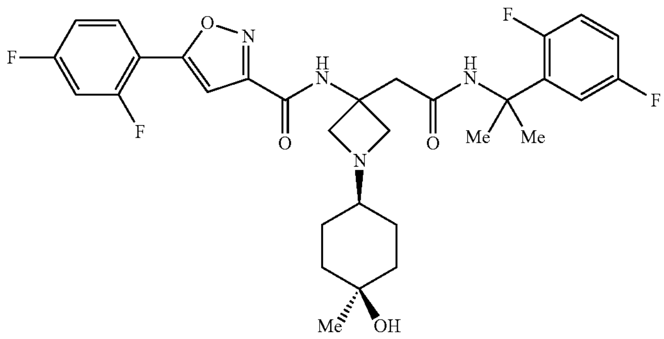 [SMILES: CC(C)(NC(=O)CC1(NC(=O)c2cc(-c3ccc(F)cc3F)on2)CN([C@H]2CC[C@@](C)(O)CC2)C1)c1cc(F)ccc1F] | ++++ |

-continued
| Specific Examples (Table 1) | | |
|---|---|---|
| Compound ID | Structure | IC50 (buffer) |
| 1.236 | 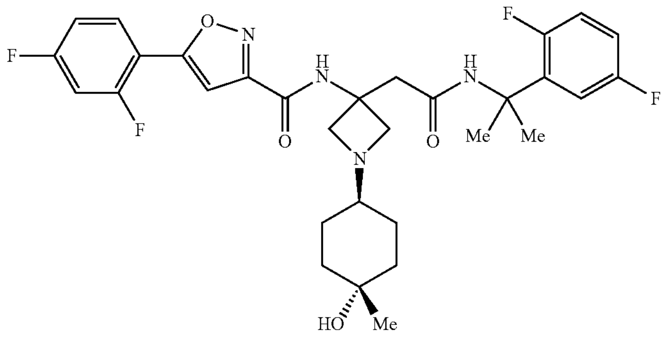 [SMILES: CC(C)(NC(=O)CC1(NC(=O)c2cc(-c3ccc(F)cc3F)on2)CN([C@H]2CC[C@](C)(O)CC2)C1)c1cc(F)ccc1F] | ++++ |
| 1.237 | 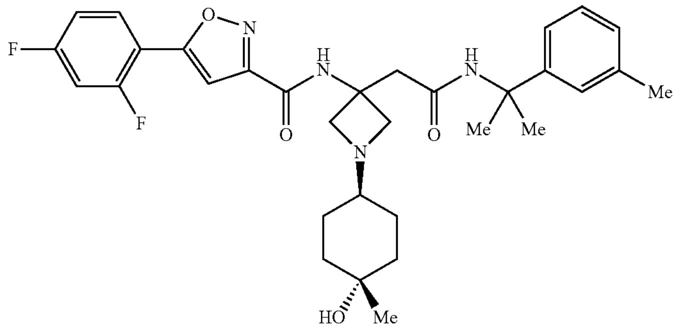 [SMILES: Cc1cccc(C(C)(C)NC(=O)CC2(NC(=O)c3cc(-c4ccc(F)cc4F)on3)CN([C@H]3CC[C@](C)(O)CC3)C2)c1] | ++++ |
| 1.238 | 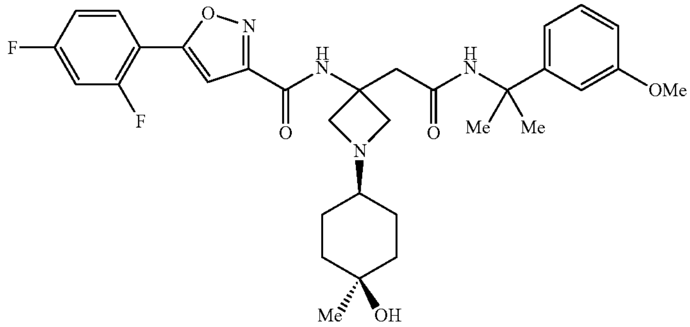 [SMILES: COc1cccc(C(C)(C)NC(=O)CC2(NC(=O)c3cc(-c4ccc(F)cc4F)on3)CN([C@H]3CC[C@@](C)(O)CC3)C2)c1] | +++ |
| 1.239 | 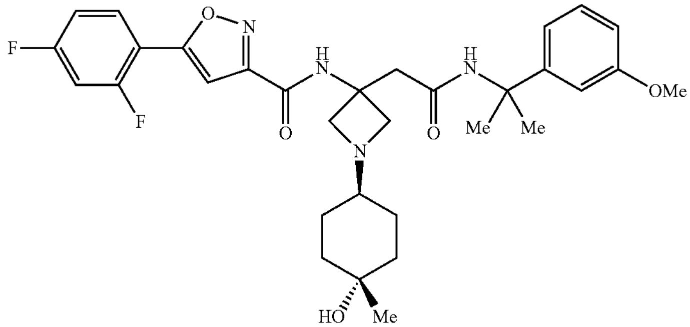 | +++ |

-continued
| Specific Examples (Table 1) | | |
|---|---|---|
| Compound ID | Structure | IC50 (buffer) |
| 1.240 | 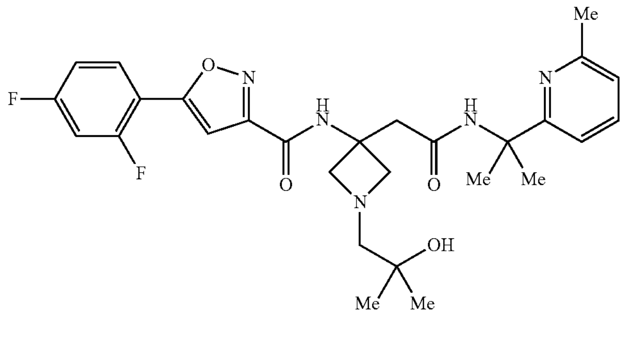 [SMILES: Cc1cccc(C(C)(C)NC(=O)CC2(NC(=O)c3cc(-c4ccc(F)cc4F)on3)CN(CC(C)(C)O)C2)n1] | +++ |
| 1.241 | 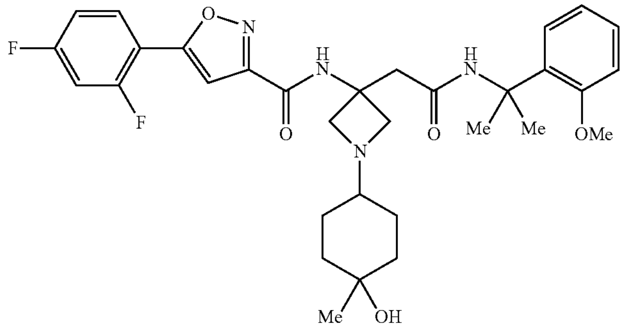 [SMILES: COc1ccccc1C(C)(C)NC(=O)CC1(NC(=O)c2cc(-c3ccc(F)cc3F)on2)CN(C2CCC(C)(O)CC2)C1] | ++++ |
| 1.242 | 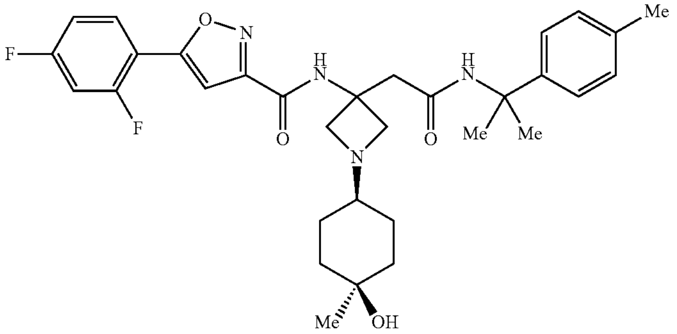 [SMILES: Cc1ccc(C(C)(C)NC(=O)CC2(NC(=O)c3cc(-c4ccc(F)cc4F)on3)CN([C@H]3CC[C@@](C)(O)CC3)C2)cc1] | ++ |
| 1.243 | 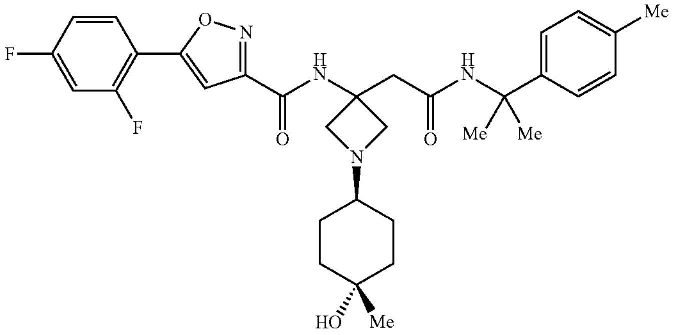 [SMILES: Cc1ccc(C(C)(C)NC(=O)CC2(NC(=O)c3cc(-c4ccc(F)cc4F)on3)CN([C@H]3CC[C@](C)(O)CC3)C2)cc1] | ++ |

-continued
| Specific Examples (Table 1) | | |
|---|---|---|
| Compound ID | Structure | IC50 (buffer) |
| 1.244 | 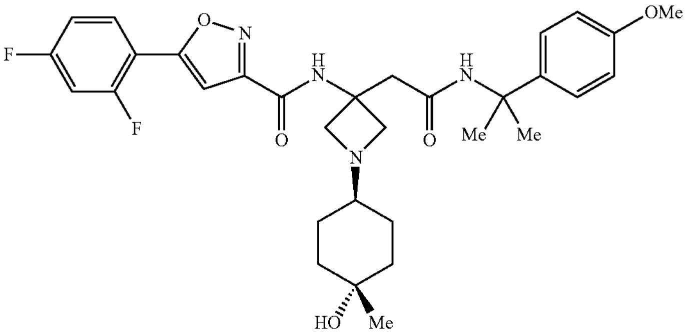 [SMILES: COc1ccc(C(C)(C)NC(=O)CC2(NC(=O)c3cc(-c4ccc(F)cc4F)on3)CN([C@H]3CC[C@](C)(O)CC3)C2)cc1] | + |
| 1.245 | 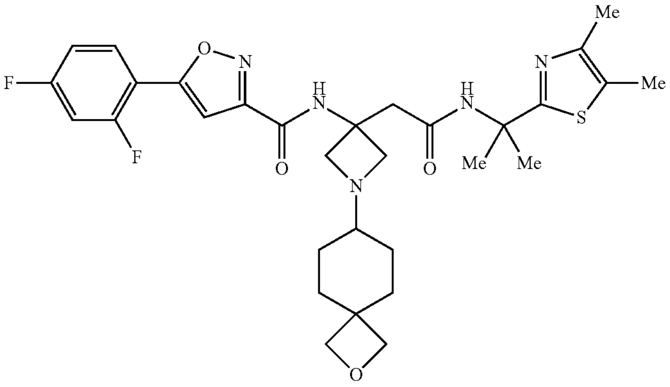 [SMILES: Cc1nc(C(C)(C)NC(=O)CC2(NC(=O)c3cc(-c4ccc(F)cc4F)on3)CN(C3CCC4(CC3)COC4)C2)sc1C] | ++ |
| 1.246 | 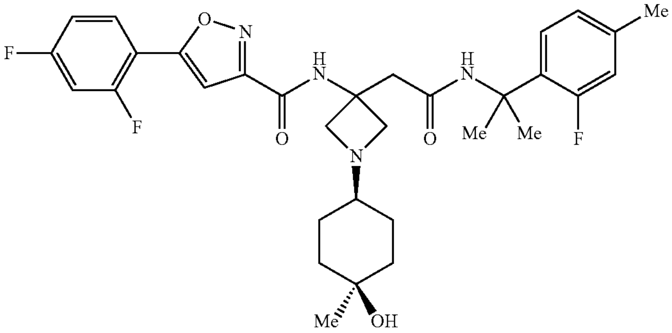 [SMILES: Cc1ccc(C(C)(C)NC(=O)CC2(NC(=O)c3cc(-c4ccc(F)cc4F)on3)CN([C@H]3CC[C@@](C)(O)CC3)C2)c(F)c1] | +++ |
| 1.247 | 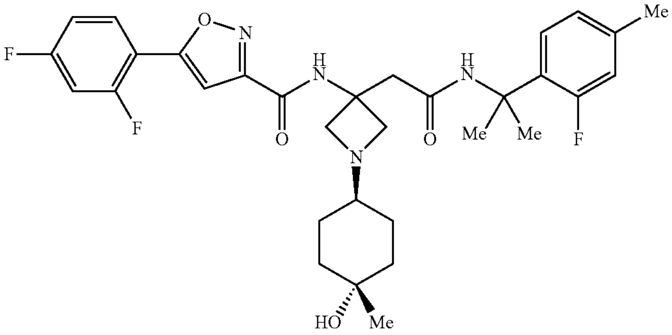 [SMILES: Cc1ccc(C(C)(C)NC(=O)CC2(NC(=O)c3cc(-c4ccc(F)cc4F)on3)CN([C@H]3CC[C@](C)(O)CC3)C2)c(F)c1] | ++ |

-continued
| Specific Examples (Table 1) | | |
|---|---|---|
| Compound ID | Structure | IC50 (buffer) |
| 1.248 | 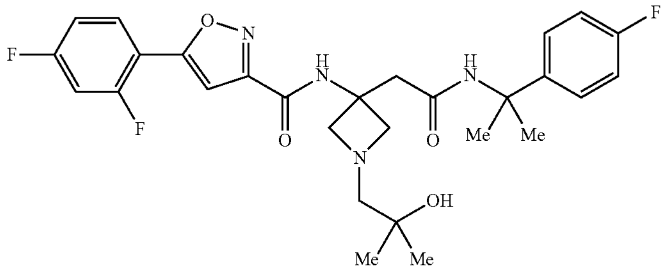 [SMILES: CC(C)(O)CN1CC(CC(=O)NC(C)(C)c2ccc(F)cc2)(NC(=O)c2cc(-c3ccc(F)cc3F)on2)C1] | ++ |
| 1.249 | 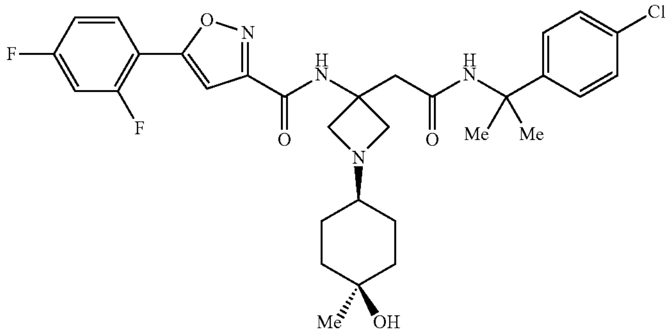 [SMILES: CC(C)(NC(=O)CC1(NC(=O)c2cc(-c3ccc(F)cc3F)on2)CN([C@H]2CC[C@@](C)(O)CC2)C1)c1ccc(Cl)cc1] | +++ |
| 1.250 | 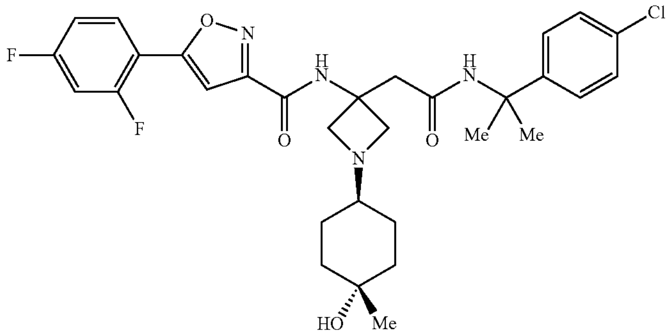 [SMILES: CC(C)(NC(=O)CC1(NC(=O)c2cc(-c3ccc(F)cc3F)on2)CN([C@H]2CC[C@](C)(O)CC2)C1)c1ccc(Cl)cc1] | ++ |
| 1.251 | 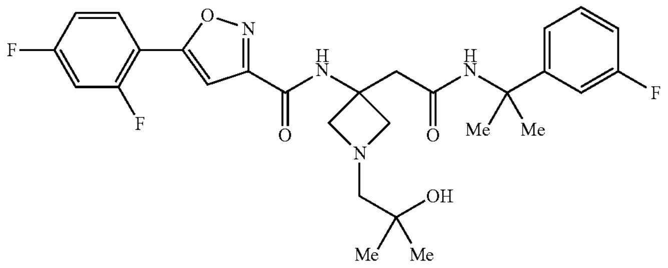 [SMILES: CC(C)(O)CN1CC(CC(=O)NC(C)(C)c2cccc(F)c2)(NC(=O)c2cc(-c3ccc(F)cc3F)on2)C1] | +++ |

-continued
| Specific Examples (Table 1) | | |
|---|---|---|
| Compound ID | Structure | IC50 (buffer) |
| 1.252 | 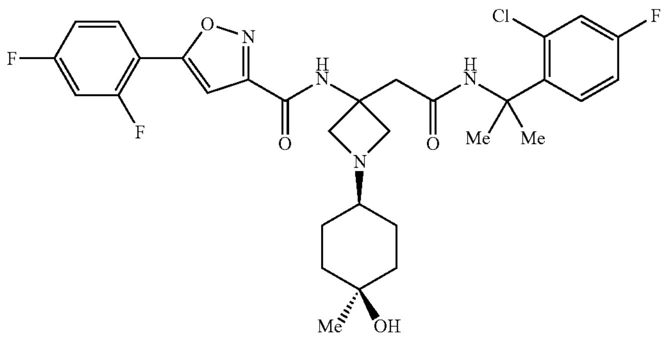 [SMILES: CC(C)(NC(=O)CC1(NC(=O)c2cc(-c3ccc(F)cc3F)on2)CN([C@H]2CC[C@@](C)(O)CC2)C1)c1ccc(F)cc1Cl] | +++ |
| 1.253 | 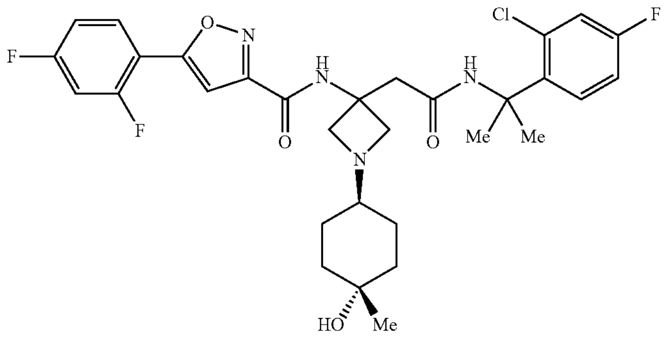 [SMILES: CC(C)(NC(=O)CC1(NC(=O)c2cc(-c3ccc(F)cc3F)on2)CN([C@H]2CC[C@](C)(O)CC2)C1)c1ccc(F)cc1Cl] | +++ |
| 1.254 | 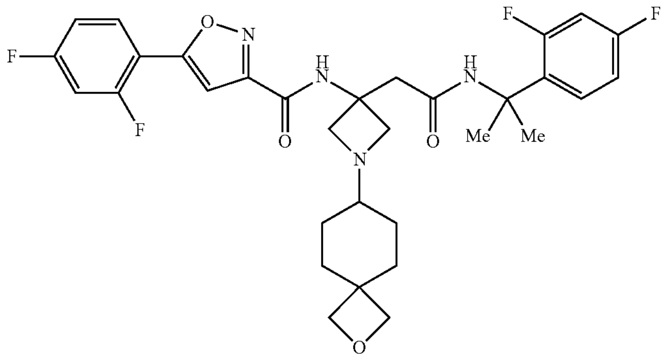 [SMILES: CC(C)(NC(=O)CC1(NC(=O)c2cc(-c3ccc(F)cc3F)on2)CN(C2CCC3(CC2)COC3)C1)c1ccc(F)cc1F] | ++ |
| 1.255 | 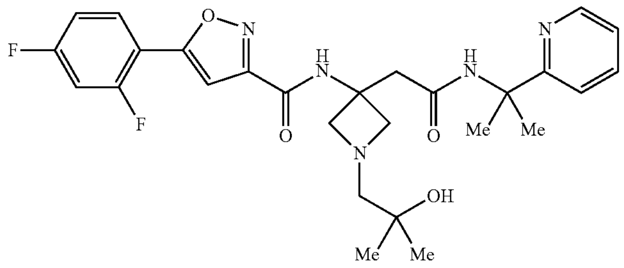 [SMILES: CC(C)(O)CN1CC(CC(=O)NC(C)(C)c2ccccn2)(NC(=O)c2cc(-c3ccc(F)cc3F)on2)C1] | +++ |

-continued
| Specific Examples (Table 1) | | |
|---|---|---|
| Compound ID | Structure | IC50 (buffer) |
| 1.256 | 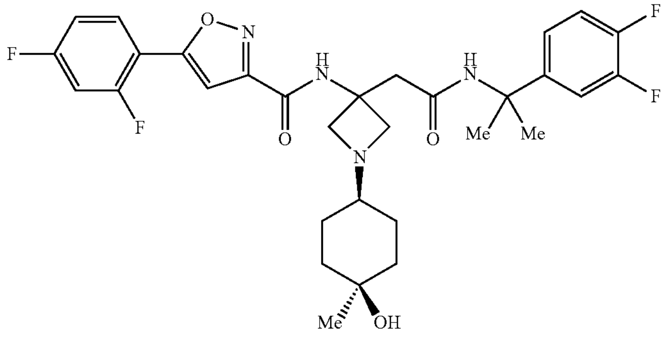 [SMILES: CC(C)(NC(=O)CC1(NC(=O)c2cc(-c3ccc(F)cc3F)on2)CN([C@H]2CC[C@@](C)(O)CC2)C1)c1ccc(F)c(F)c1] | +++ |
| 1.257 | 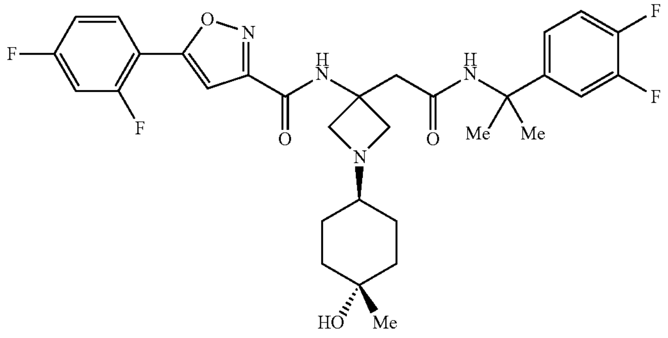 [SMILES: CC(C)(NC(=O)CC1(NC(=O)c2cc(-c3ccc(F)cc3F)on2)CN([C@H]2CC[C@](C)(O)CC2)C1)c1ccc(F)c(F)c1] | +++ |
| 1.258 | 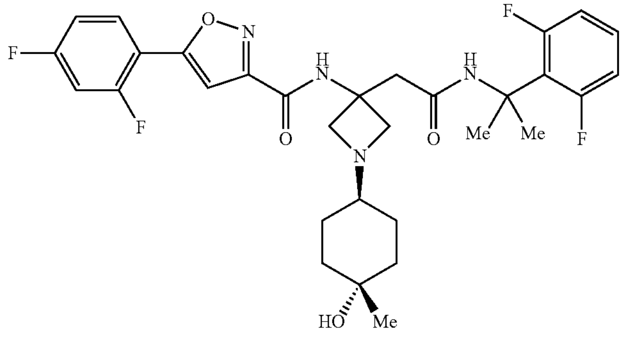 [SMILES: CC(C)(NC(=O)CC1(NC(=O)c2cc(-c3ccc(F)cc3F)on2)CN([C@H]2CC[C@](C)(O)CC2)C1)c1c(F)cccc1F] | ++ |
| 1.259 | 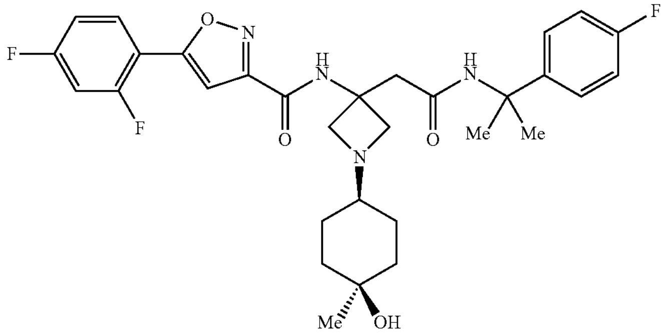 [SMILES: CC(C)(NC(=O)CC1(NC(=O)c2cc(-c3ccc(F)cc3F)on2)CN([C@H]2CC[C@@](C)(O)CC2)C1)c1ccc(F)cc1] | +++ |

-continued
Specific Examples (Table 1)
| Compound ID | Structure | IC50 (buffer) |
|---|---|---|
| 1.260 | 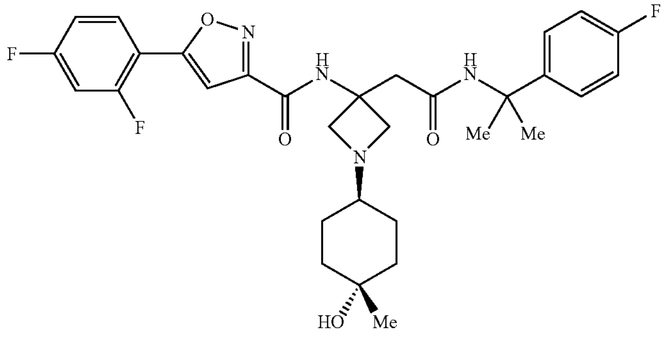 [SMILES: CC(C)(NC(=O)CC1(NC(=O)c2cc(-c3ccc(F)cc3F)on2)CN([C@H]2CC[C@](C)(O)CC2)C1)c1ccc(F)cc1] | +++ |
| 1.261 | 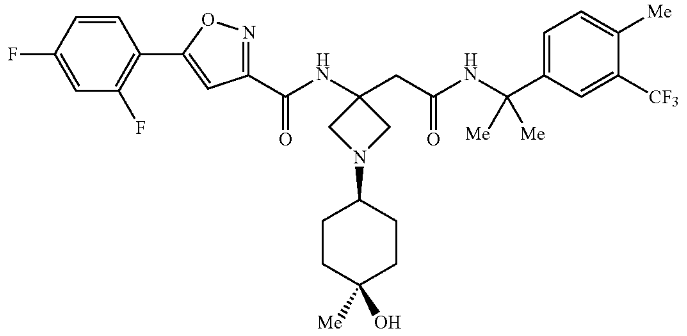 [SMILES: Cc1ccc(C(C)(C)NC(=O)CC2(NC(=O)c3cc(-c4ccc(F)cc4F)on3)CN([C@H]3CC[C@@](C)(O)CC3)C2)cc1C(F)(F)F] | ++ |
| 1.262 | 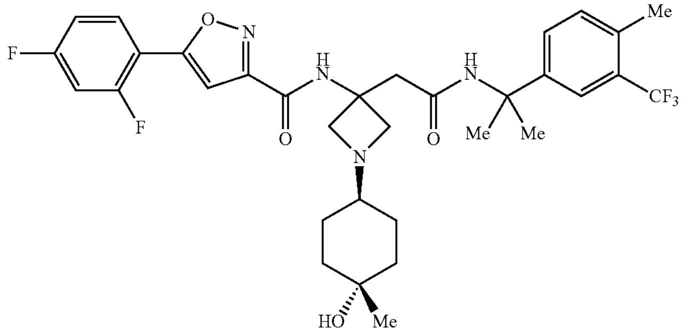 [SMILES: Cc1ccc(C(C)(C)NC(=O)CC2(NC(=O)c3cc(-c4ccc(F)cc4F)on3)CN([C@H]3CC[C@](C)(O)CC3)C2)cc1C(F)(F)F] | ++ |
| 1.263 | 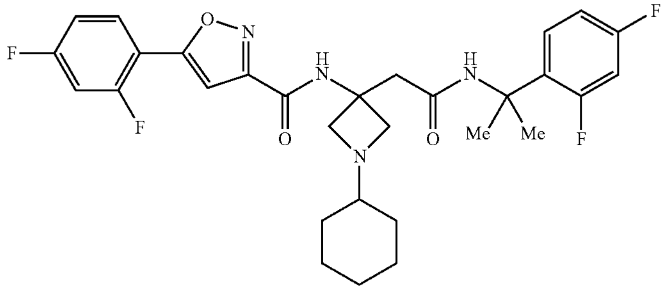 [SMILES: CC(C)(NC(=O)CC1(NC(=O)c2cc(-c3ccc(F)cc3F)on2)CN(C2CCCCC2)C1)c1ccc(F)cc1F] | + |

-continued
| Specific Examples (Table 1) | | |
|---|---|---|
| Compound ID | Structure | IC50 (buffer) |
| 1.264 | 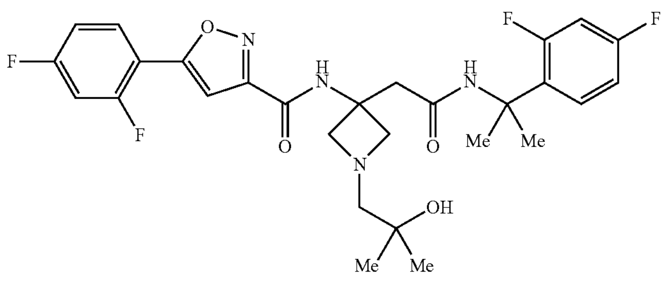 [SMILES: CC(C)(O)CN1CC(CC(=O)NC(C)(C)c2ccc(F)cc2F)(NC(=O)c2cc(-c3ccc(F)cc3F)on2)C1] | + |
| 1.265 | 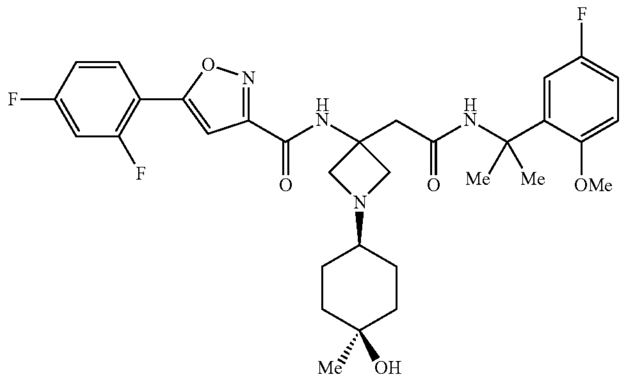 [SMILES: COc1ccc(F)cc1C(C)(C)NC(=O)CC1(NC(=O)c2cc(-c3ccc(F)cc3F)on2)CN([C@H]2CC[C@@](C)(O)CC2)C1] | 0.16 |
| 1.266 | 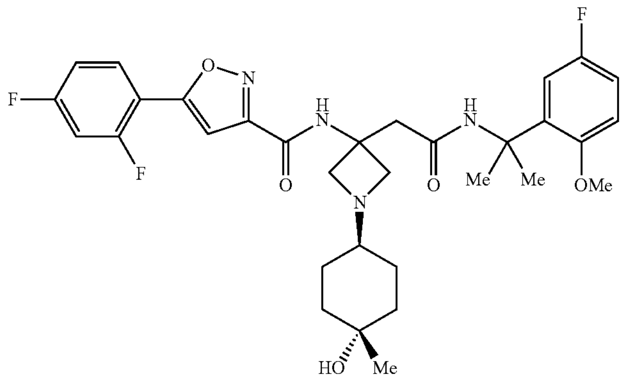 [SMILES: COc1ccc(F)cc1C(C)(C)NC(=O)CC1(NC(=O)c2cc(-c3ccc(F)cc3F)on2)CN([C@H]2CC[C@](C)(O)CC2)C1] | ++++ |
| 1.267 | 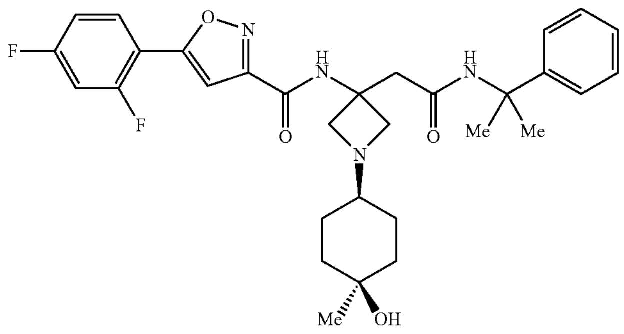 [SMILES: CC(C)(NC(=O)CC1(NC(=O)c2cc(-c3ccc(F)cc3F)on2)CN([C@H]2CC[C@@](C)(O)CC2)C1)c1ccccc1] | ++++ |

-continued
| Specific Examples (Table 1) | | |
|---|---|---|
| Compound ID | Structure | IC50 (buffer) |
| 1.268 | 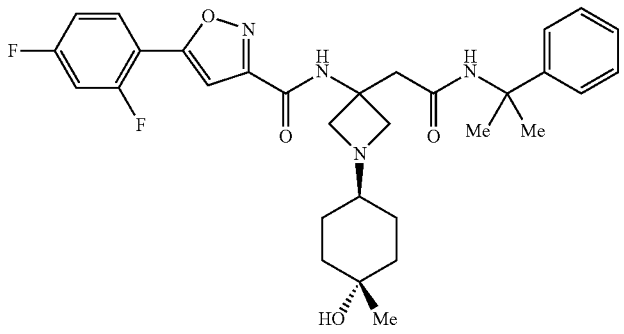 | ++++ |
| 1.269 | 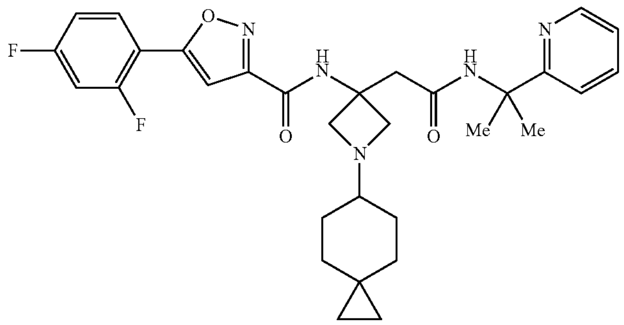 [SMILES: CC(C)(NC(=O)CC1(NC(=O)c2cc(-c3ccc(F)cc3F)on2)CN(C2CCC3(CC2)CC3)C1)c1ccccn1] | +++ |
| 1.270 | 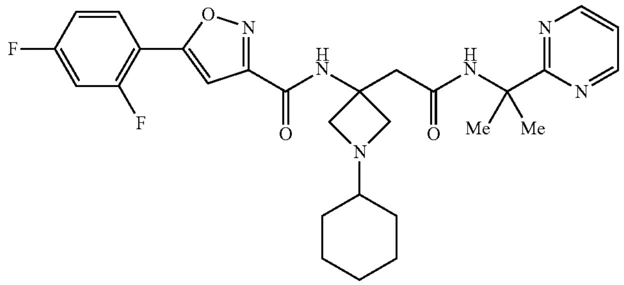 | +++ |
| 1.271 | 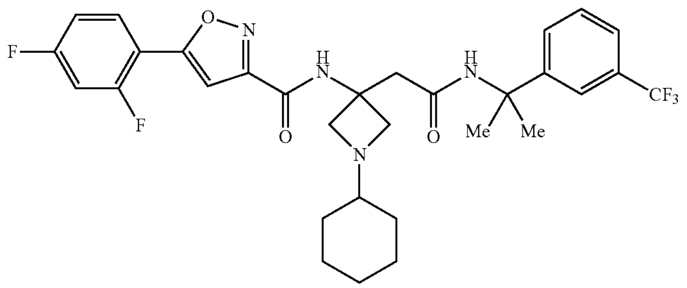 [SMILES: CC(C)(NC(=O)CC1(NC(=O)c2cc(-c3ccc(F)cc3F)on2)CN(C2CCCCC2)C1)c1cccc(C(F)(F)F)c1] | ++ |

-continued
| Specific Examples (Table 1) | | |
|---|---|---|
| Compound ID | Structure | IC50 (buffer) |
| 1.272 | 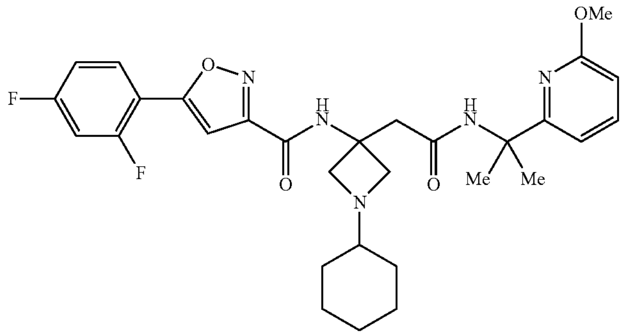 [SMILES: COc1cccc(C(C)(C)NC(=O)CC2(NC(=O)c3cc(-c4ccc(F)cc4F)on3)CN(C3CCCCC3)C2)n1] | +++ |
| 1.273 | 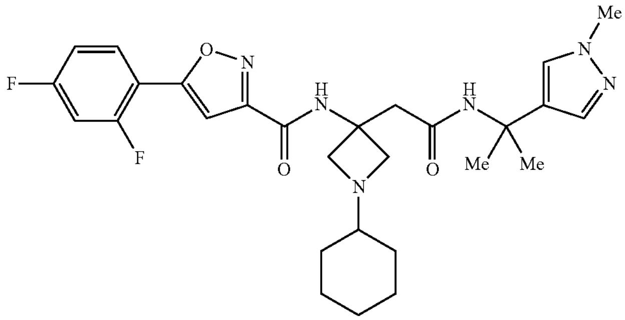 [SMILES: Cn1cc(C(C)(C)NC(=O)CC2(NC(=O)c3cc(-c4ccc(F)cc4F)on3)CN(C3CCCCC3)C2)cn1] | +++ |
| 1.274 | 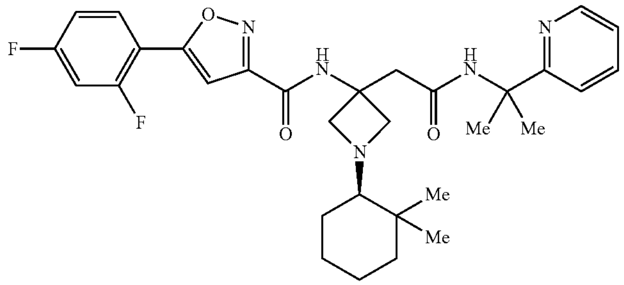 [SMILES: CC(C)(NC(=O)CC1(NC(=O)c2cc(-c3ccc(F)cc3F)on2)CN([C@@H]2CCCCC2(C)C)C1)c1ccccn1] | ++++ |
| 1.275 | 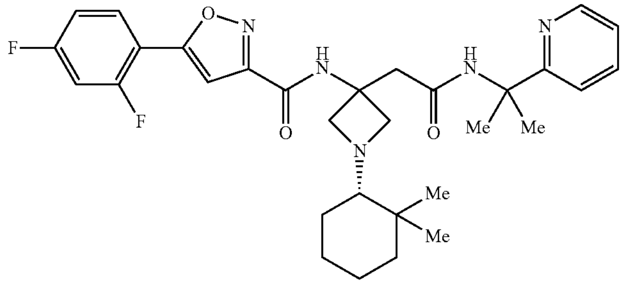 [SMILES: CC(C)(NC(=O)CC1(NC(=O)c2cc(-c3ccc(F)cc3F)on2)CN([C@H]2CCCCC2(C)C)C1)c1ccccn1] | ++++ |

-continued
Specific Examples (Table 1)
| Compound ID | Structure | IC50 (buffer) |
| --- | --- | --- |
| 1.276 | 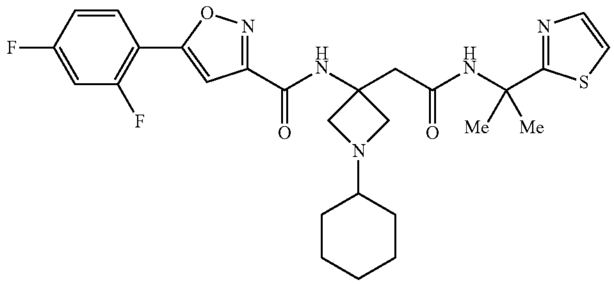 [SMILES: CC(C)(NC(=O)CC1(NC(=O)c2cc(-c3ccc(F)cc3F)on2)CN(C2CCCCC2)C1)c1nccs1] | +++ |
| 1.277 | 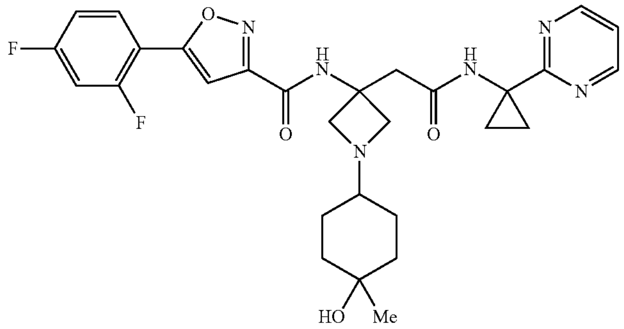 [SMILES: CC1(O)CCC(N2CC(CC(=O)NC3(c4ncccn4)CC3)(NC(=O)c3cc(-c4ccc(F)cc4F)on3)C2)CC1] | ++++ |
| 1.278 | 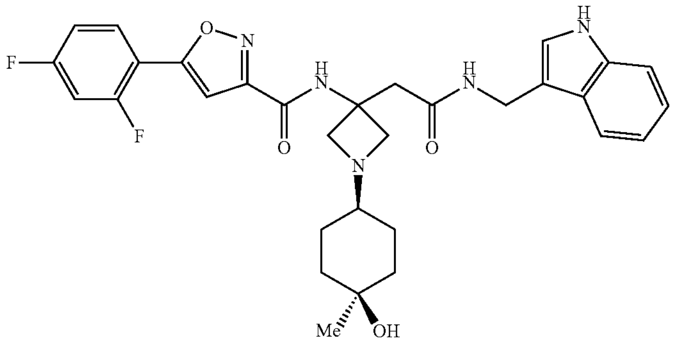 [SMILES: C[C@]1(O)CC[C@@H](N2CC(CC(=O)NCc3c[nH]c4ccccc34)(NC(=O)c3cc(-c4ccc(F)cc4F)on3)C2)CC1] | + |
| 1.279 | 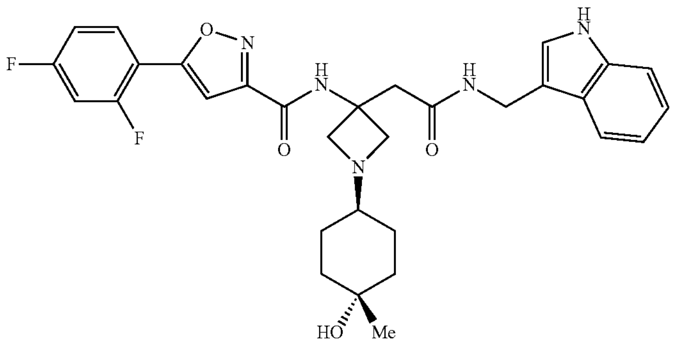 [SMILES: C[C@]1(O)CC[C@H](N2CC(CC(=O)NCc3c[nH]c4ccccc34)(NC(=O)c3cc(-c4ccc(F)cc4F)on3)C2)CC1] | +++ |

-continued
| Specific Examples (Table 1) | | |
|---|---|---|
| Compound ID | Structure | IC50 (buffer) |
| 1.280 | 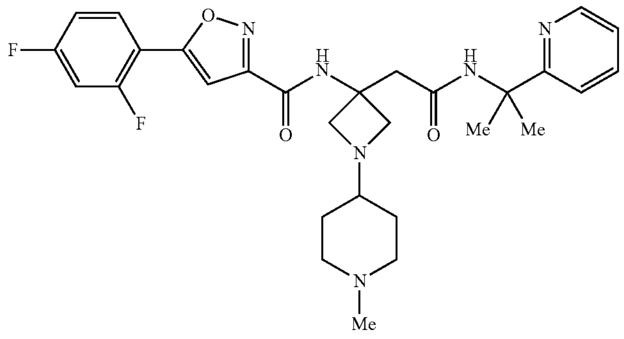 [SMILES: CN1CCC(N2CC(CC(=O)NC(C)(C)c3ccccn3)(NC(=O)c3cc(-c4ccc(F)cc4F)on3)C2)CC1] | ++ |
| 1.281 | 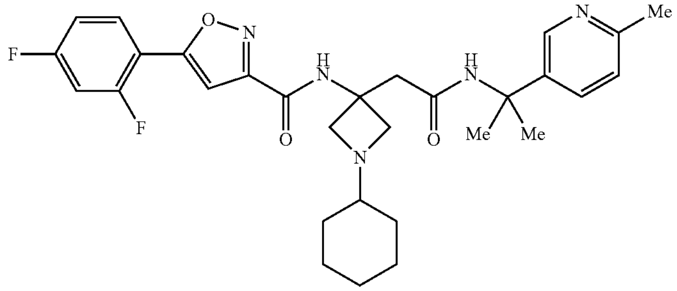 [SMILES: Cc1ccc(C(C)(C)NC(=O)CC2(NC(=O)c3cc(-c4ccc(F)cc4F)on3)CN(C3CCCCC3)C2)cn1] | +++ |
| 1.282 | 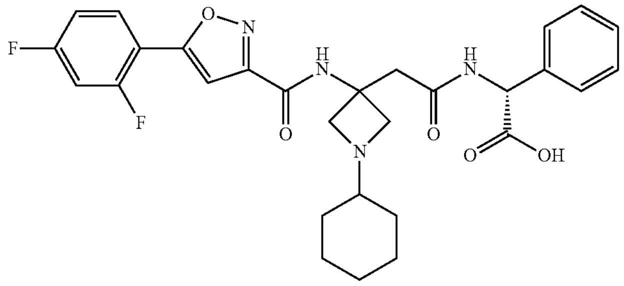 [SMILES: O=C(CC1(NC(=O)c2cc(-c3ccc(F)cc3F)on2)CN(C2CCCCC2)C1)N[C@@H](C(=O)O)c1ccccc1] | + |
| 1.283 | 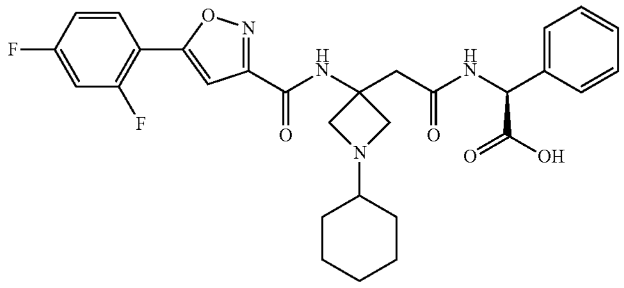 [SMILES: O=C(CC1(NC(=O)c2cc(-c3ccc(F)cc3F)on2)CN(C2CCCCC2)C1)N[C@H](C(=O)O)c1ccccc1] | + |

-continued
Specific Examples (Table 1)
| Compound ID | Structure | IC50 (buffer) |
|---|---|---|
| 1.284 | 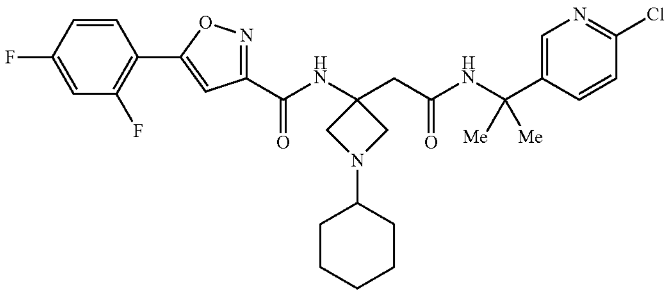 [SMILES: CC(C)(NC(=O)CC1(NC(=O)c2cc(-c3ccc(F)cc3F)on2)CN(C2CCCCC2)C1)c1ccc(Cl)nc1] | +++ |
| 1.285 | 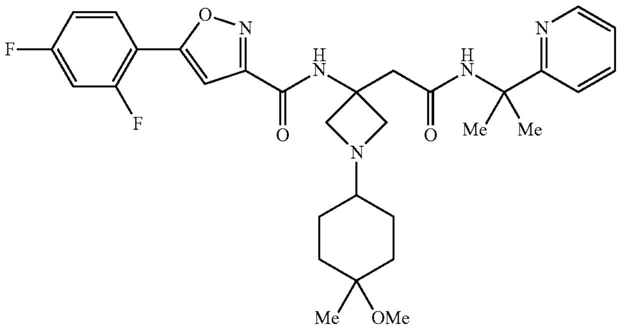 [SMILES: COC1(C)CCC(N2CC(CC(=O)NC(C)(C)c3ccccn3)(NC(=O)c3cc(-c4ccc(F)cc4F)on3)C2)CC1] | +++ |
| 1.286 | 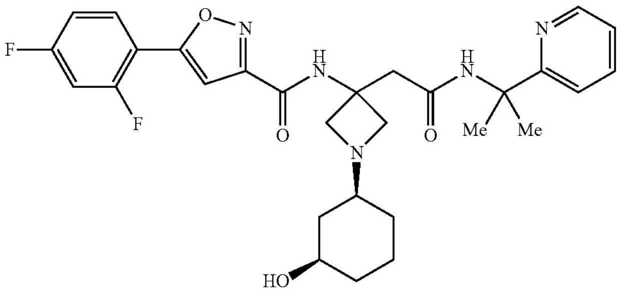 [SMILES: CC(C)(NC(=O)CC1(NC(=O)c2cc(-c3ccc(F)cc3F)on2)CN([C@H]2CCC[C@@H](O)C2)C1)c1ccccn1] | +++ |
| 1.287 | 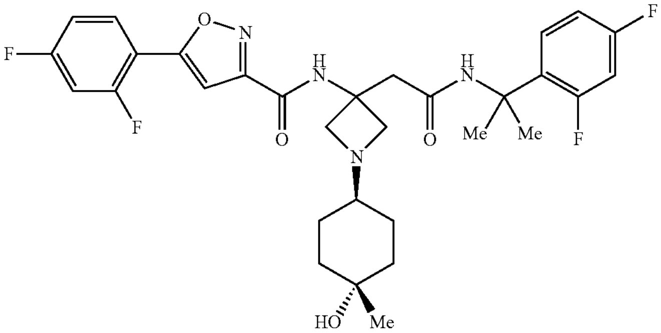 [SMILES: CC(C)(NC(=O)CC1(NC(=O)c2cc(-c3ccc(F)cc3F)on2)CN([C@H]2CC[C@](C)(O)CC2)C1)c1ccc(F)cc1F] | +++ |

-continued
Specific Examples (Table 1)
| Compound ID | Structure | IC50 (buffer) |
|---|---|---|
| 1.288 | 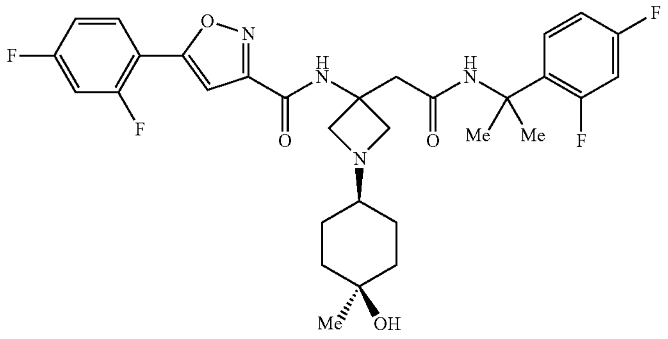 [SMILES: CC(C)(NC(=O)CC1(NC(=O)c2cc(-c3ccc(F)cc3F)on2)CN([C@H]2CC[C@@](C)(O)CC2)C1)c1ccc(F)cc1F] | +++ |
| 1.289 | 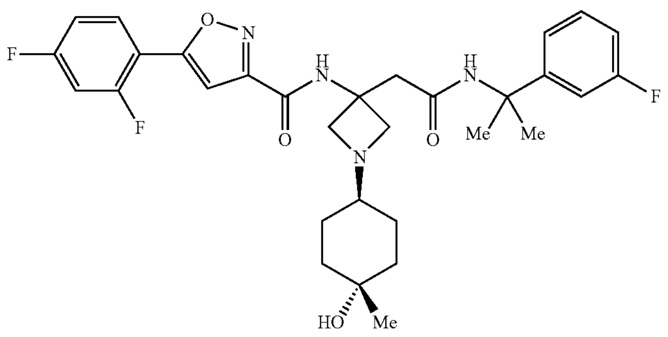 [SMILES: CC(C)(NC(=O)CC1(NC(=O)c2cc(-c3ccc(F)cc3F)on2)CN([C@H]2CC[C@](C)(O)CC2)C1)c1cccc(F)c1] | ++++ |
| 1.290 | 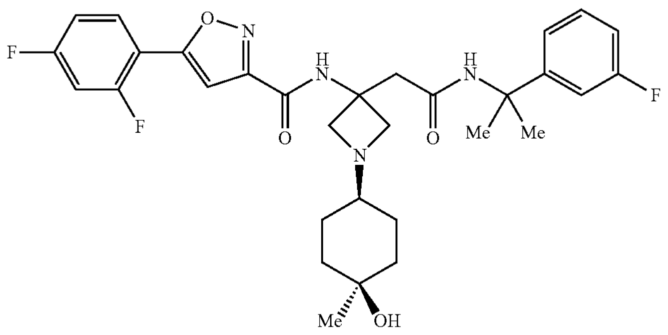 [SMILES: CC(C)(NC(=O)CC1(NC(=O)c2cc(-c3ccc(F)cc3F)on2)CN([C@H]2CC[C@@](C)(O)CC2)C1)c1cccc(F)c1] | ++++ |
| 1.291 | 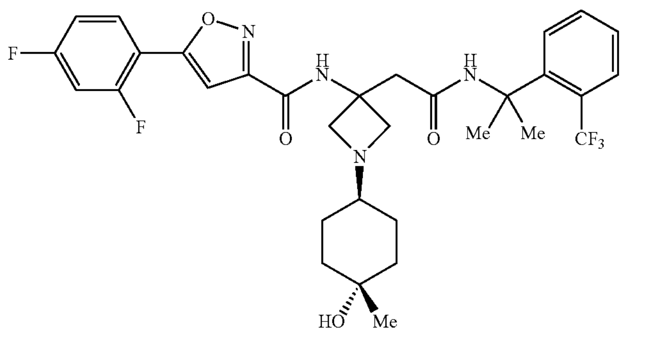 [SMILES: CC(C)(NC(=O)CC1(NC(=O)c2cc(-c3ccc(F)cc3F)on2)CN([C@H]2CC[C@](C)(O)CC2)C1)c1ccccc1C(F)(F)F] | ++++ |

-continued
| Specific Examples (Table 1) | | |
|---|---|---|
| Compound ID | Structure | IC50 (buffer) |
| 1.292 | 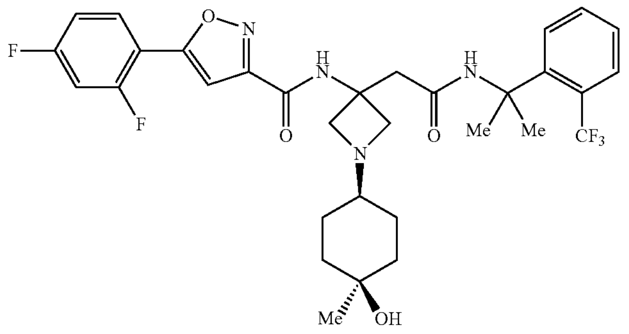 [SMILES: CC(C)(NC(=O)CC1(NC(=O)c2cc(-c3ccc(F)cc3F)on2)CN([C@H]2CC[C@@](C)(O)CC2)C1)c1ccccc1C(F)(F)F] | ++++ |
| 1.293 | 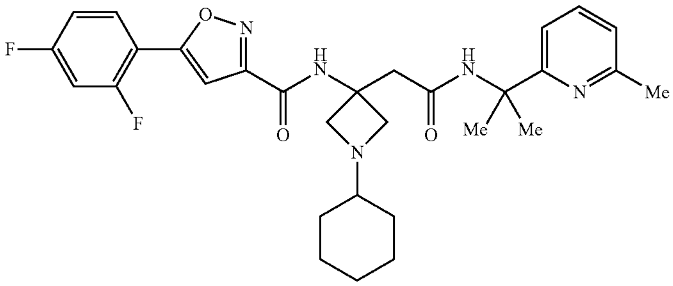 [SMILES: Cc1cccc(C(C)(C)NC(=O)CC2(NC(=O)c3cc(-c4ccc(F)cc4F)on3)CN(C3CCCCC3)C2)n1] | ++++ |
| 1.294 | 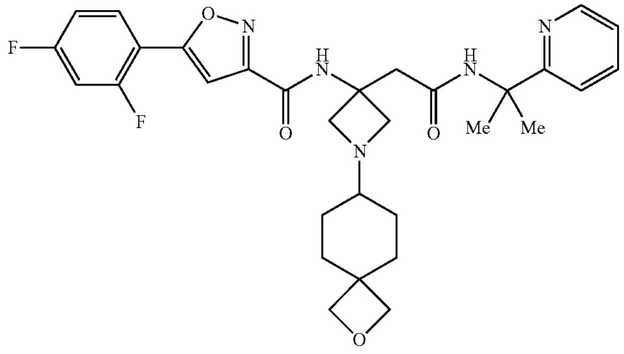 [SMILES: CC(C)(NC(=O)CC1(NC(=O)c2cc(-c3ccc(F)cc3F)on2)CN(C2CCC3(CC2)COC3)C1)c1ccccn1] | ++++ |
| 1.295 | 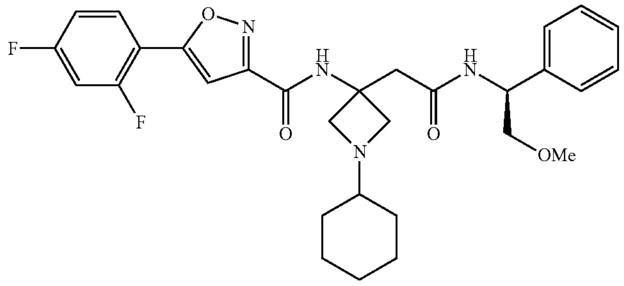 | ++ |

-continued
| Specific Examples (Table 1) | | |
|---|---|---|
| Compound ID | Structure | IC50 (buffer) |
| 1.296 | 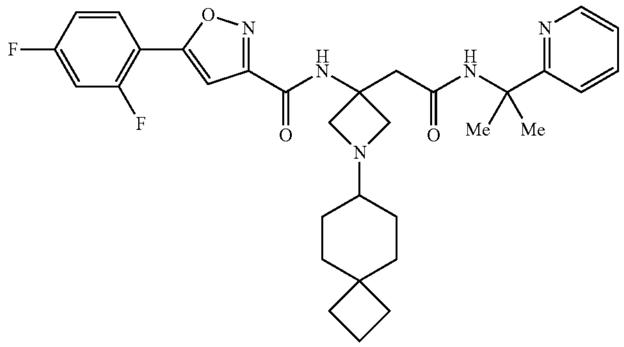 [SMILES: CC(C)(NC(=O)CC1(NC(=O)c2cc(-c3ccc(F)cc3F)on2)CN(C2CCC3(CCC3)CC2)C1)c1ccccn1] | ++ |
| 1.297 | 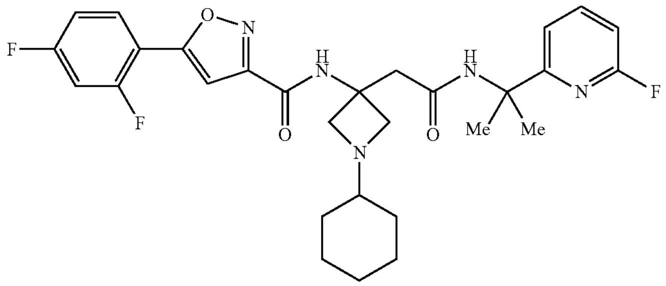 [SMILES: CC(C)(NC(=O)CC1(NC(=O)c2cc(-c3ccc(F)cc3F)on2)CN(C2CCCCC2)C1)c1cccc(F)n1] | ++++ |
| 1.298 | 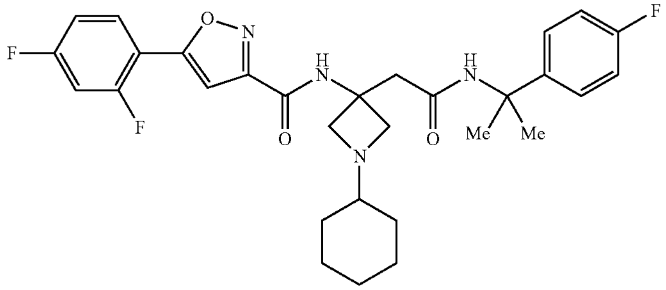 [SMILES: CC(C)(NC(=O)CC1(NC(=O)c2cc(-c3ccc(F)cc3F)on2)CN(C2CCCCC2)C1)c1ccc(F)cc1] | +++ |
| 1.299 | 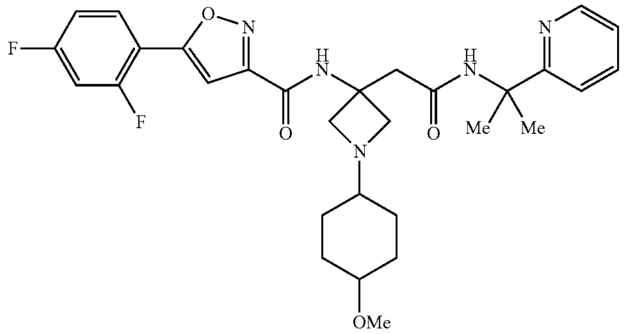 [SMILES: COC1CCC(N2CC(CC(=O)NC(C)(C)c3ccccn3)(NC(=O)c3cc(-c4ccc(F)cc4F)on3)C2)CC1] | +++ |

-continued
| Specific Examples (Table 1) | | |
|---|---|---|
| Compound ID | Structure | IC50 (buffer) |
| 1.300 | 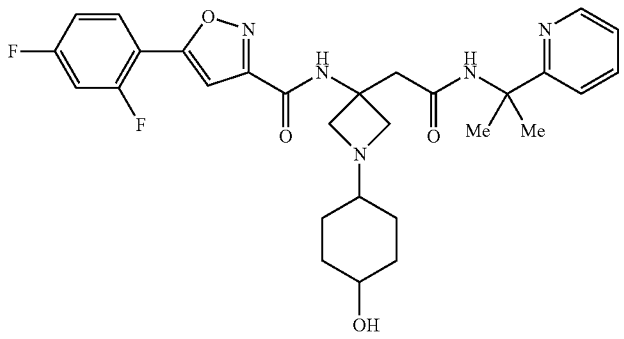 [SMILES: CC(C)(NC(=O)CC1(NC(=O)c2cc(-c3ccc(F)cc3F)on2)CN(C2CCC(O)CC2)C1)c1ccccn1] | +++ |
| 1.301 | 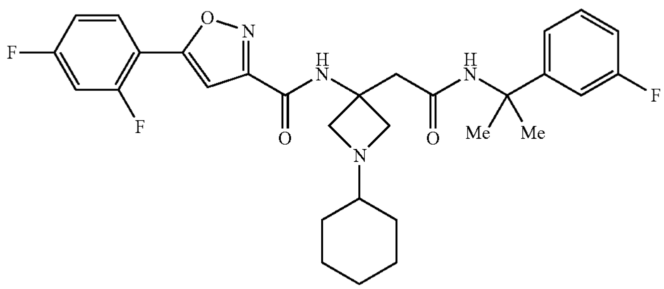 [SMILES: CC(C)(NC(=O)CC1(NC(=O)c2cc(-c3ccc(F)cc3F)on2)CN(C2CCCCC2)C1)c1cccc(F)c1] | ++++ |
| 1.302 | 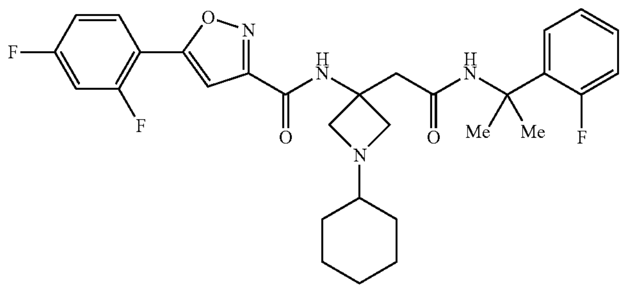 [SMILES: CC(C)(NC(=O)CC1(NC(=O)c2cc(-c3ccc(F)cc3F)on2)CN(C2CCCCC2)C1)c1ccccc1F] | ++++ |
| 1.303 | 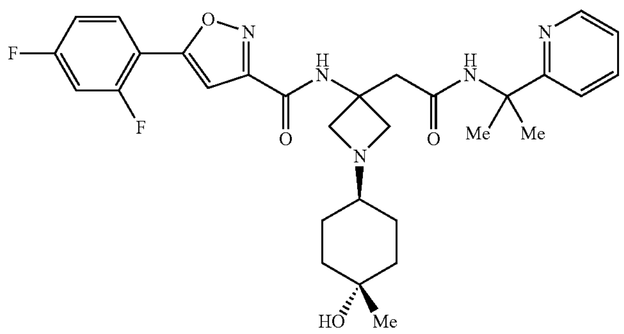 [SMILES: CC(C)(NC(=O)CC1(NC(=O)c2cc(-c3ccc(F)cc3F)on2)CN([C@H]2CC[C@](C)(O)CC2)C1)c1ccccn1] | ++++ |

-continued
| Specific Examples (Table 1) | | |
|---|---|---|
| Compound ID | Structure | IC50 (buffer) |
| 1.304 | 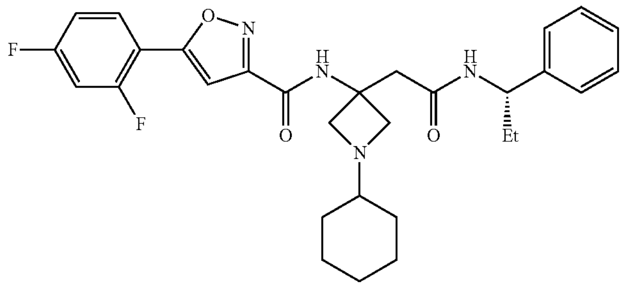 [SMILES: CC[C@H](NC(=O)CC1(NC(=O)c2cc(-c3ccc(F)cc3F)on2)CN(C2CCCCC2)C1)c1ccccc1] | +++ |
| 1.305 | 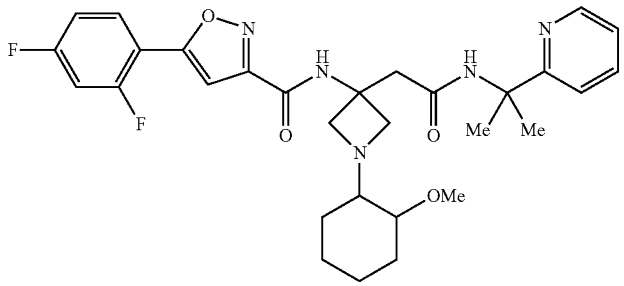 [SMILES: COC1CCCCC1N1CC(CC(=O)NC(C)(C)c2ccccn2)(NC(=O)c2cc(-c3ccc(F)cc3F)on2)C1] | ++++ |
| 1.306 | 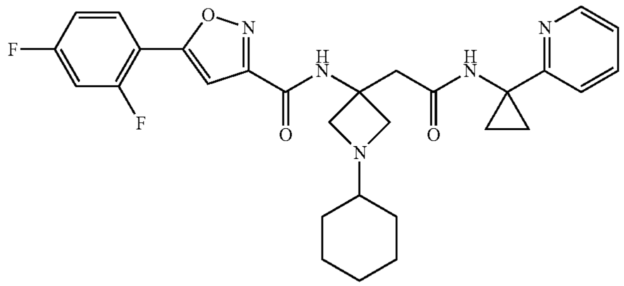 [SMILES: O=C(CC1(NC(=O)c2cc(-c3ccc(F)cc3F)on2)CN(C2CCCCC2)C1)NC1(c2ccccn2)CC1] | +++ |
| 1.307 | 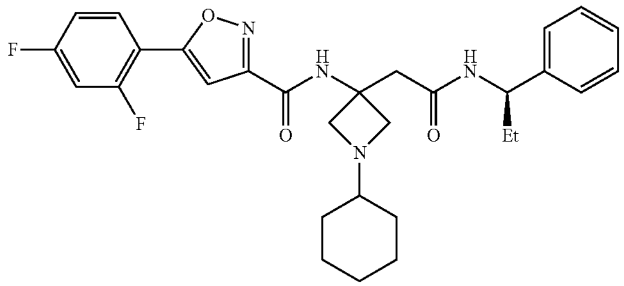 [SMILES: CC[C@@H](NC(=O)CC1(NC(=O)c2cc(-c3ccc(F)cc3F)on2)CN(C2CCCCC2)C1)c1ccccc1] | +++ |
| 1.308 | 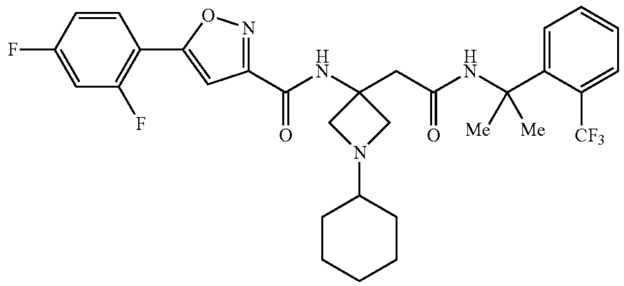 [SMILES: CC(C)(NC(=O)CC1(NC(=O)c2cc(-c3ccc(F)cc3F)on2)CN(C2CCCCC2)C1)c1ccccc1C(F)(F)F] | ++++ |

-continued
| Compound ID | Structure | IC50 (buffer) |
| --- | --- | --- |
| 1.309 | 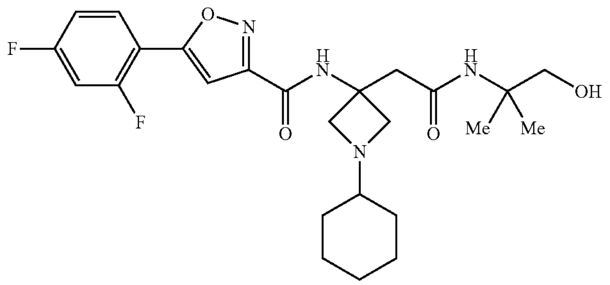 [SMILES: CC(C)(CO)NC(=O)CC1(NC(=O)c2cc(-c3ccc(F)cc3F)on2)CN(C2CCCCC2)C1] | ++ |
| 1.310 | 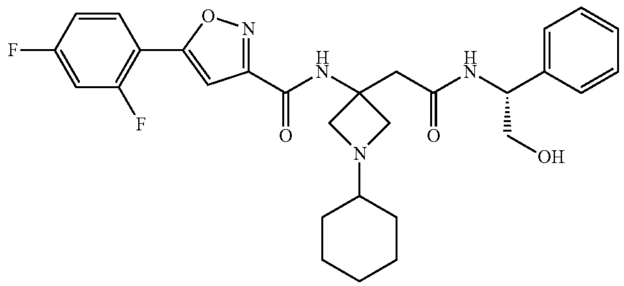 [SMILES: O=C(CC1(NC(=O)c2cc(-c3ccc(F)cc3F)on2)CN(C2CCCCC2)C1)N[C@@H](CO)c1ccccc1] | + |
| 1.311 | 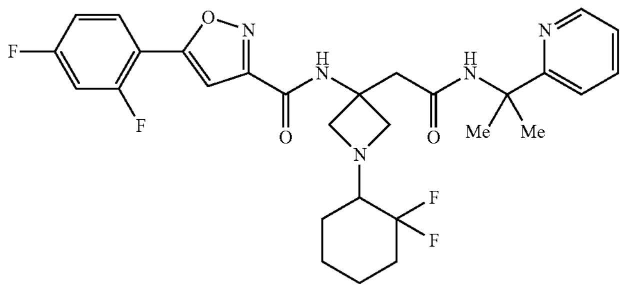 [SMILES: CC(C)(NC(=O)CC1(NC(=O)c2cc(-c3ccc(F)cc3F)on2)CN(C2CCCCC2(F)F)C1)c1ccccn1] | +++ |
| 1.312 | 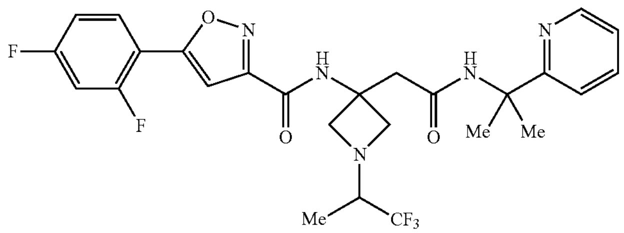 [SMILES: CC(N1CC(CC(=O)NC(C)(C)c2ccccn2)(NC(=O)c2cc(-c3ccc(F)cc3F)on2)C1)C(F)(F)F] | + |
| 1.313 | 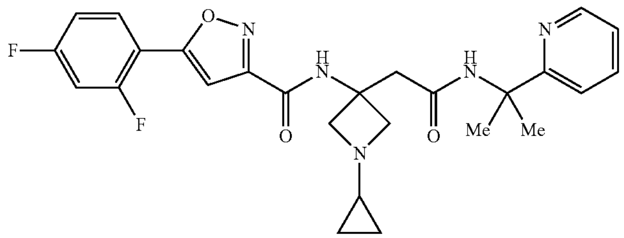 [SMILES: CC(C)(NC(=O)CC1(NC(=O)c2cc(-c3ccc(F)cc3F)on2)CN(C2CC2)C1)c1ccccn1] | +++ |
Specific Examples (Table 1)

-continued
| Specific Examples (Table 1) | | |
|---|---|---|
| Compound ID | Structure | IC50 (buffer) |
| 1.314 | 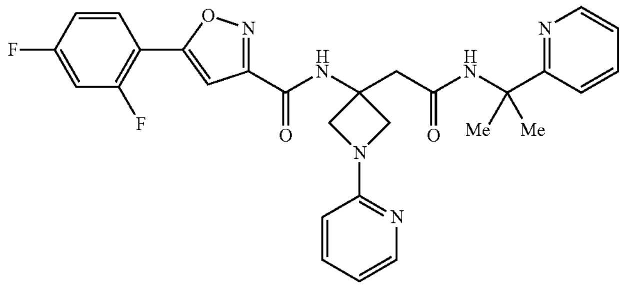 [SMILES: CC(C)(NC(=O)CC1(NC(=O)c2cc(-c3ccc(F)cc3F)on2)CN(c2ccccn2)C1)c1ccccn1] | + |
| 1.315 | 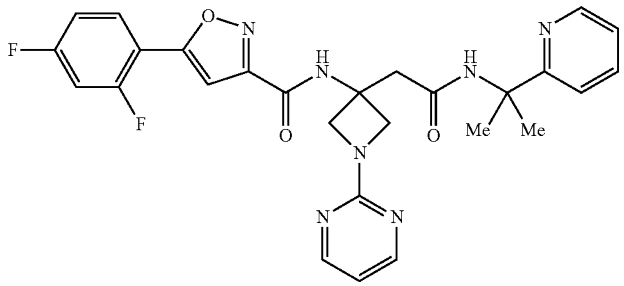 [SMILES: CC(C)(NC(=O)CC1(NC(=O)c2cc(-c3ccc(F)cc3F)on2)CN(c2ncccn2)C1)c1ccccn1] | + |
| 1.316 | 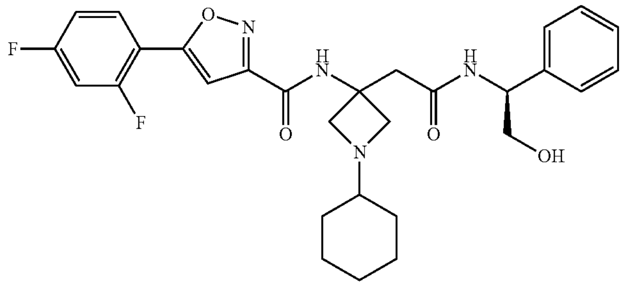 [SMILES: O=C(CC1(NC(=O)c2cc(-c3ccc(F)cc3F)on2)CN(C2CCCCC2)C1)N[C@H](CO)c1ccccc1] | +++ |
| 1.317 | 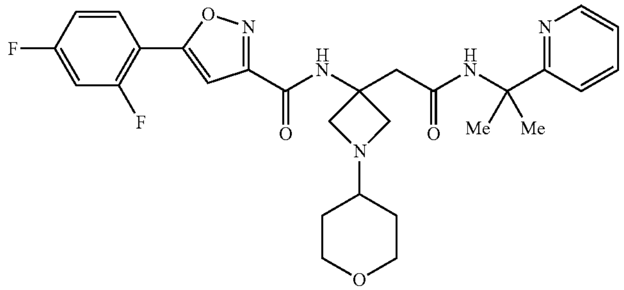 [SMILES: CC(C)(NC(=O)CC1(NC(=O)c2cc(-c3ccc(F)cc3F)on2)CN(C2CCOCC2)C1)c1ccccn1] | +++ |
| 1.318 | 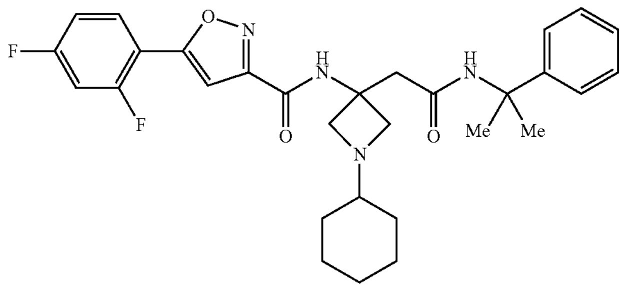 [SMILES: CC(C)(NC(=O)CC1(NC(=O)c2cc(-c3ccc(F)cc3F)on2)CN(C2CCCCC2)C1)c1ccccc1] | ++++ |

-continued
| Specific Examples (Table 1) | | |
|---|---|---|
| Compound ID | Structure | IC50 (buffer) |
| 1.319 | 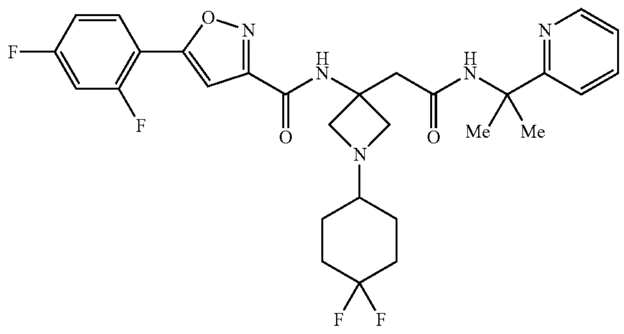 [SMILES: CC(C)(NC(=O)CC1(NC(=O)c2cc(-c3ccc(F)cc3F)on2)CN(C2CCC(F)(F)CC2)C1)c1ccccn1] | +++ |
| 1.320 | 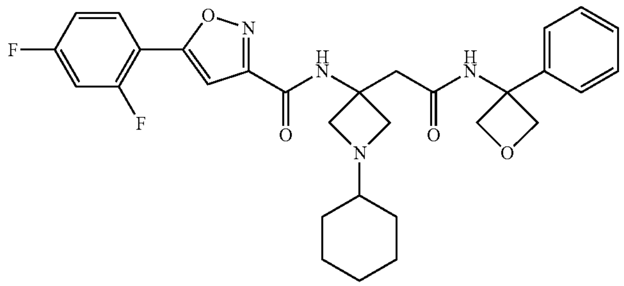 [SMILES: O=C(CC1(NC(=O)c2cc(-c3ccc(F)cc3F)on2)CN(C2CCCCC2)C1)NC1(c2ccccc2)COC1] | +++ |
| 1.321 | 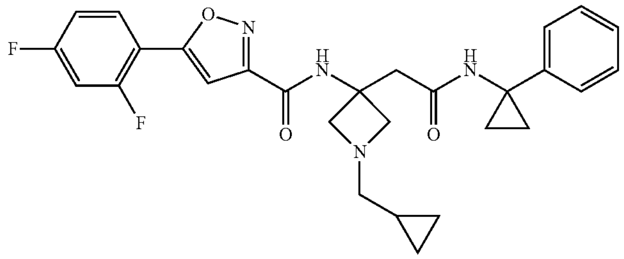 [SMILES: O=C(CC1(NC(=O)c2cc(-c3ccc(F)cc3F)on2)CN(CC2CC2)C1)NC1(c2ccccc2)CC1] | ++ |
| 1.322 | 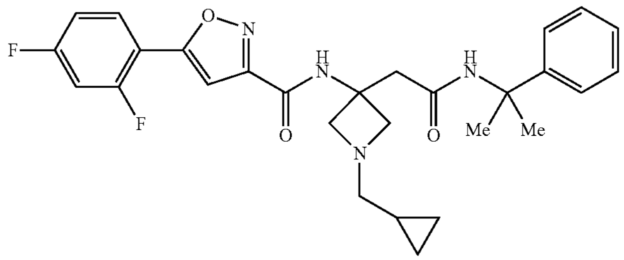 [SMILES: CC(C)(NC(=O)CC1(NC(=O)c2cc(-c3ccc(F)cc3F)on2)CN(CC2CC2)C1)c1ccccc1] | +++ |
| 1.323 | 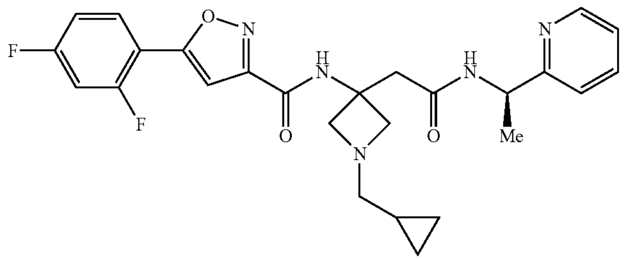 [SMILES: C[C@@H](NC(=O)CC1(NC(=O)c2cc(-c3ccc(F)cc3F)on2)CN(CC2CC2)C1)c1ccccn1] | ++ |

-continued
| Specific Examples (Table 1) | | |
|---|---|---|
| Compound ID | Structure | IC50 (buffer) |
| 1.324 | 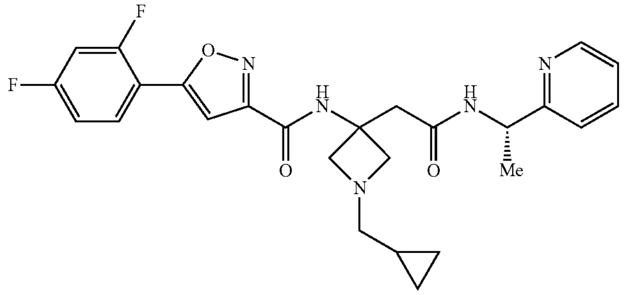 [SMILES: C[C@H](NC(=O)CC1(NC(=O)c2cc(-c3ccc(F)cc3F)on2)CN(CC2CC2)C1)c1ccccn1] | + |
| 1.325 | 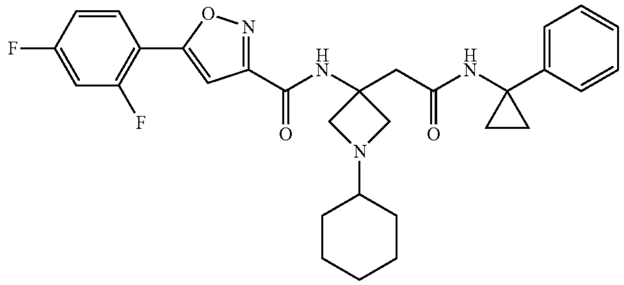 [SMILES: O=C(CC1(NC(=O)c2cc(-c3ccc(F)cc3F)on2)CN(C2CCCCC2)C1)NC1(c2ccccc2)CC1] | +++ |
| 1.326 | 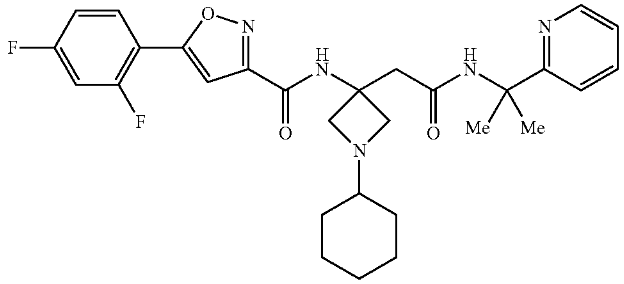 [SMILES: CC(C)(NC(=O)CC1(NC(=O)c2cc(-c3ccc(F)cc3F)on2)CN(C2CCCCC2)C1)c1ccccn1] | ++++ |
| 1.327 | 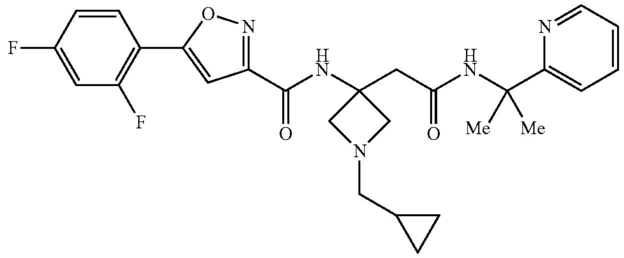 [SMILES: CC(C)(NC(=O)CC1(NC(=O)c2cc(-c3ccc(F)cc3F)on2)CN(CC2CC2)C1)c1ccccn1] | +++ |
| 1.328 | 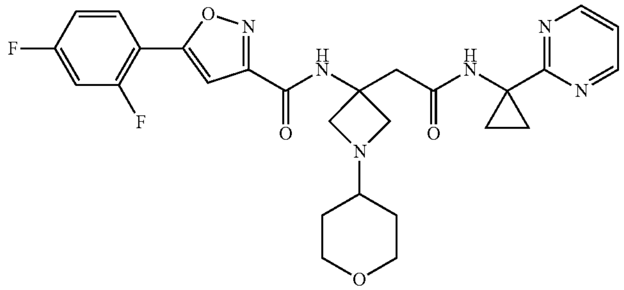 [SMILES: O=C(CC1(NC(=O)c2cc(-c3ccc(F)cc3F)on2)CN(C2CCOCC2)C1)NC1(c2ncccn2)CC1] | ++ |

-continued
| Specific Examples (Table 1) | | |
|---|---|---|
| Compound ID | Structure | IC50 (buffer) |
| 1.329 | 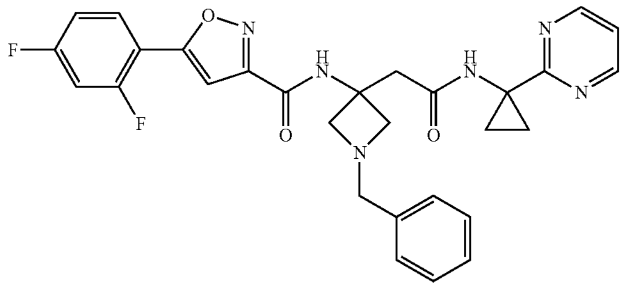 [SMILES: O=C(CC1(NC(=O)c2cc(-c3ccc(F)cc3F)on2)CN(Cc2ccccc2)C1)NC1(c2ncccn2)CC1] | ++ |
| 1.330 | 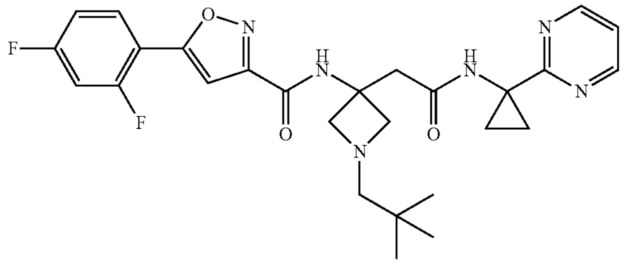 [SMILES: CC(C)(C)CN1CC(CC(=O)NC2(c3ncccn3)CC2)(NC(=O)c2cc(-c3ccc(F)cc3F)on2)C1] | +++ |
| 1.331 | 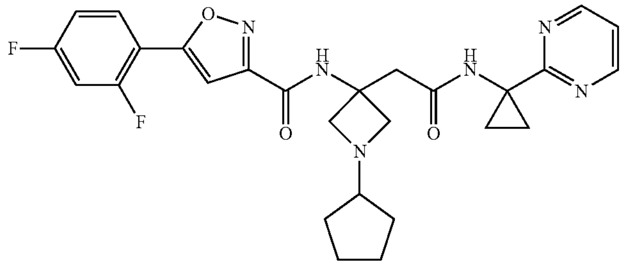 [SMILES: O=C(CC1(NC(=O)c2cc(-c3ccc(F)cc3F)on2)CN(C2CCCC2)C1)NC1(c2ncccn2)CC1] | +++ |
| 1.332 | 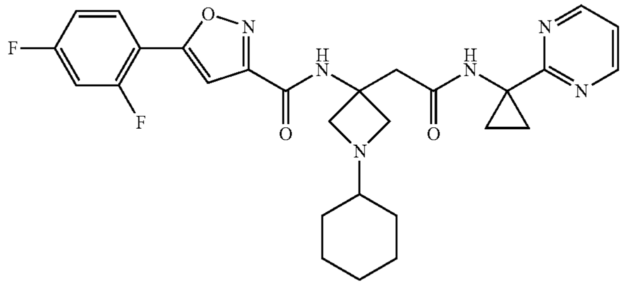 [SMILES: O=C(CC1(NC(=O)c2cc(-c3ccc(F)cc3F)on2)CN(C2CCCCC2)C1)NC1(c2ncccn2)CC1] | +++ |
| 1.333 | 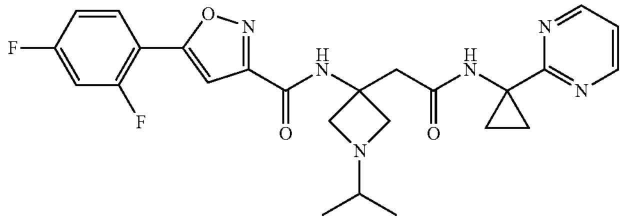 [SMILES: CC(C)N1CC(CC(=O)NC2(c3ncccn3)CC2)(NC(=O)c2cc(-c3ccc(F)cc3F)on2)C1] | ++ |

-continued
| Specific Examples (Table 1) | | |
|---|---|---|
| Compound ID | Structure | IC50 (buffer) |
| 1.334 | 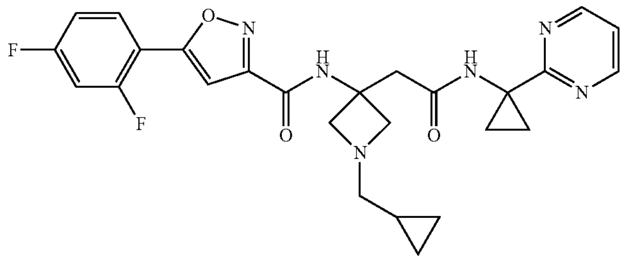 [SMILES: O=C(CC1(NC(=O)c2cc(-c3ccc(F)cc3F)on2)CN(CC2CC2)C1)NC1(c2ncccn2)CC1] | +++ |
| 1.335 | 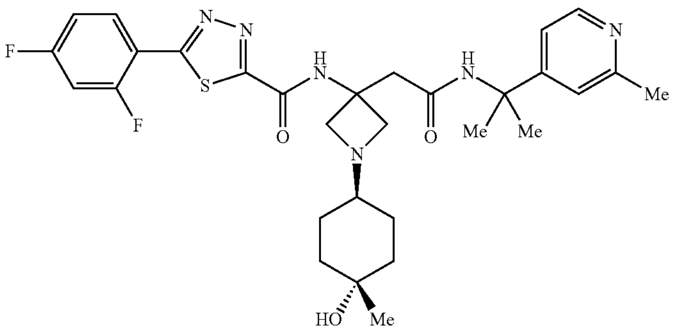 [SMILES: Cc1cc(C(C)(C)NC(=O)CC2(NC(=O)c3nnc(-c4ccc(F)cc4F)s3)CN([C@H]3CC[C@](C)(O)CC3)C2)ccn1] | +++ |
| 1.336 | 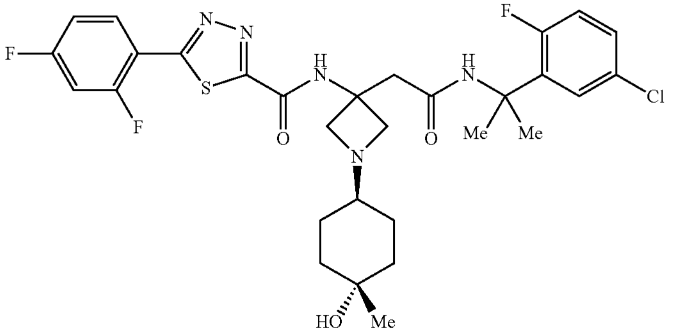 [SMILES: CC(C)(NC(=O)CC1(NC(=O)c2nnc(-c3ccc(F)cc3F)s2)CN([C@H]2CC[C@](C)(O)CC2)C1)c1cc(Cl)ccc1F] | +++ |
| 1.337 | 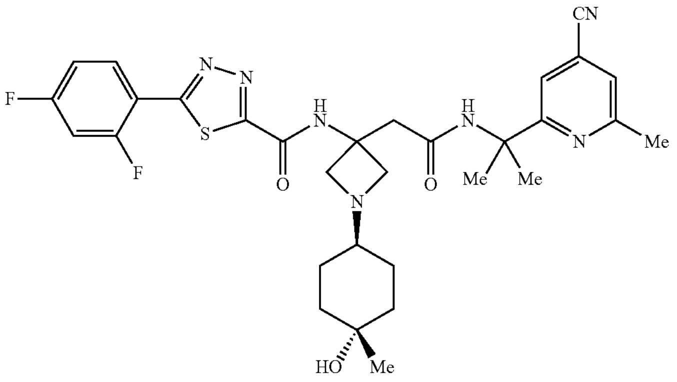 [SMILES: Cc1cc(C#N)cc(C(C)(C)NC(=O)CC2(NC(=O)c3nnc(-c4ccc(F)cc4F)s3)CN([C@H]3CC[C@](C)(O)CC3)C2)n1] | ++++ |

-continued
| Specific Examples (Table 1) | | |
|---|---|---|
| Compound ID | Structure | IC50 (buffer) |
| 1.338 | 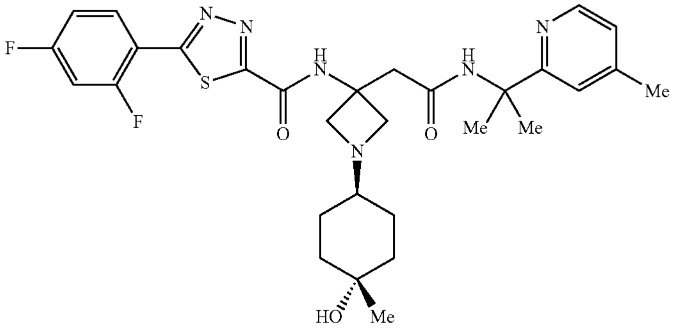 [SMILES: Cc1ccnc(C(C)(C)NC(=O)CC2(NC(=O)c3nnc(-c4ccc(F)cc4F)s3)CN([C@H]3CC[C@](C)(O)CC3)C2)c1] | +++ |
| 1.339 | 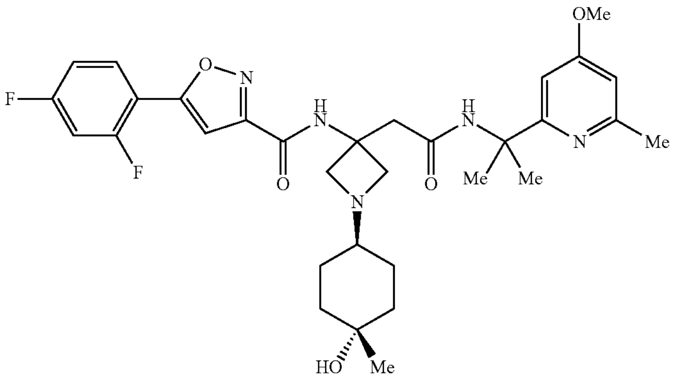 [SMILES: COc1cc(C)nc(C(C)(C)NC(=O)CC2(NC(=O)c3cc(-c4ccc(F)cc4F)on3)CN([C@H]3CC[C@](C)(O)CC3)C2)c1] | +++ |
| 1.340 | 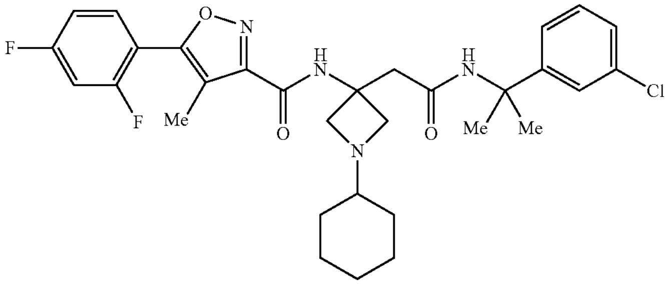 [SMILES: Cc1c(C(=O)NC2(CC(=O)NC(C)(C)c3cccc(Cl)c3)CN(C3CCCCC3)C2)noc1-c1ccc(F)cc1F] | + |
| 1.341 | 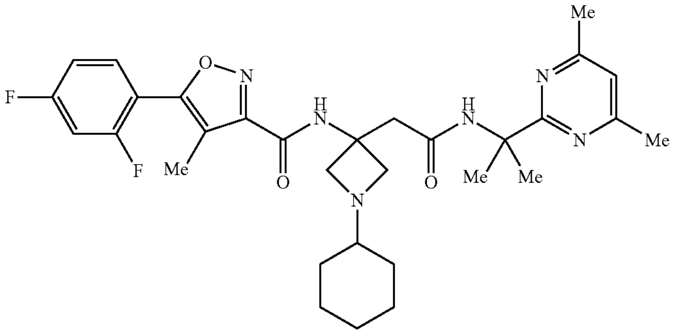 [SMILES: Cc1cc(C)nc(C(C)(C)NC(=O)CC2(NC(=O)c3noc(-c4ccc(F)cc4F)c3C)CN(C3CCCCC3)C2)n1] | + |

-continued
| Specific Examples (Table 1) | | |
|---|---|---|
| Compound ID | Structure | IC50 (buffer) |
| 1.342 | 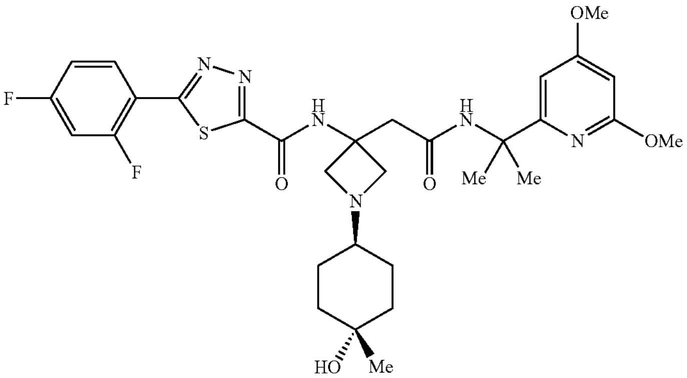 [SMILES: COc1cc(OC)nc(C(C)(C)NC(=O)CC2(NC(=O)c3nnc(-c4ccc(F)cc4F)s3)CN([C@H]3CC[C@](C)(O)CC3)C2)c1] | +++ |
| 1.343 | 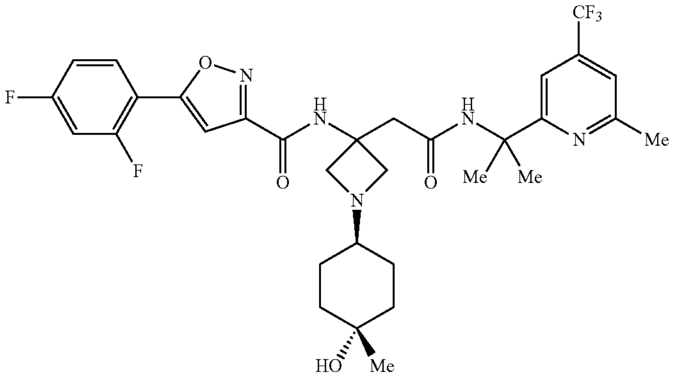 [SMILES: Cc1cc(C(F)(F)F)cc(C(C)(C)NC(=O)CC2(NC(=O)c3cc(-c4ccc(F)cc4F)on3)CN([C@H]3CC[C@](C)(O)CC3)C2)n1] | +++ |
| 1.344 | 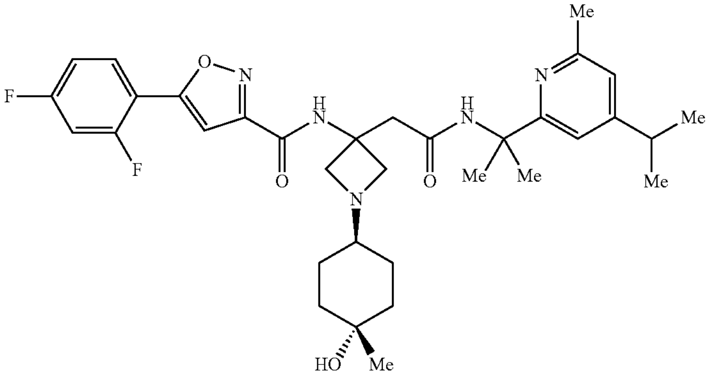 [SMILES: Cc1cc(C(C)C)cc(C(C)(C)NC(=O)CC2(NC(=O)c3cc(-c4ccc(F)cc4F)on3)CN([C@H]3CC[C@](C)(O)CC3)C2)n1] | ++ |
| 1.345 | 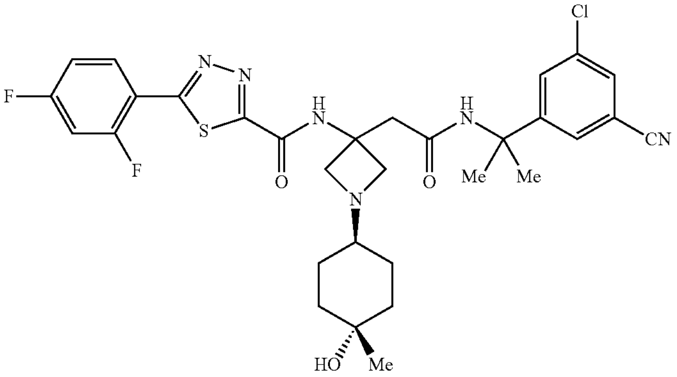 [SMILES: CC(C)(NC(=O)CC1(NC(=O)c2nnc(-c3ccc(F)cc3F)s2)CN([C@H]2CC[C@](C)(O)CC2)C1)c1cc(Cl)cc(C#N)c1] | +++ |

-continued
| Specific Examples (Table 1) | | |
|---|---|---|
| Compound ID | Structure | IC50 (buffer) |
| 1.346 | 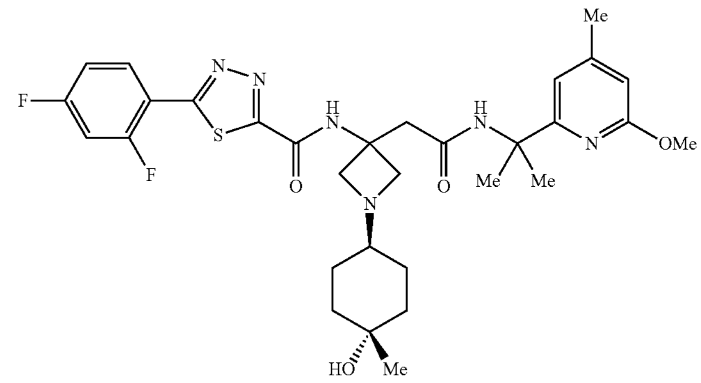 [SMILES: COc1cc(C)cc(C(C)(C)NC(=O)CC2(NC(=O)c3nnc(-c4ccc(F)cc4F)s3)CN([C@H]3CC[C@](C)(O)CC3)C2)n1] | +++ |
| 1.347 | 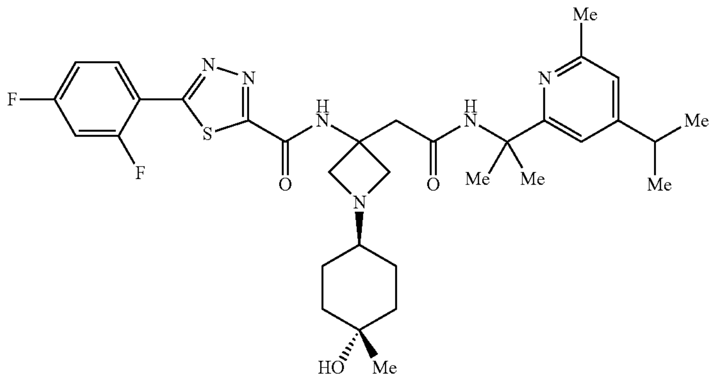 [SMILES: Cc1cc(C(C)C)cc(C(C)(C)NC(=O)CC2(NC(=O)c3nnc(-c4ccc(F)cc4F)s3)CN([C@H]3CC[C@](C)(O)CC3)C2)n1] | ++ |
| 1.348 | 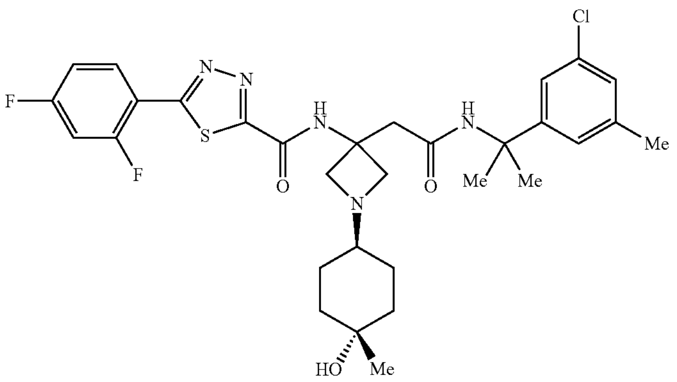 | +++ |

-continued
| Specific Examples (Table 1) | | |
|---|---|---|
| Compound ID | Structure | IC50 (buffer) |
| 1.349 | 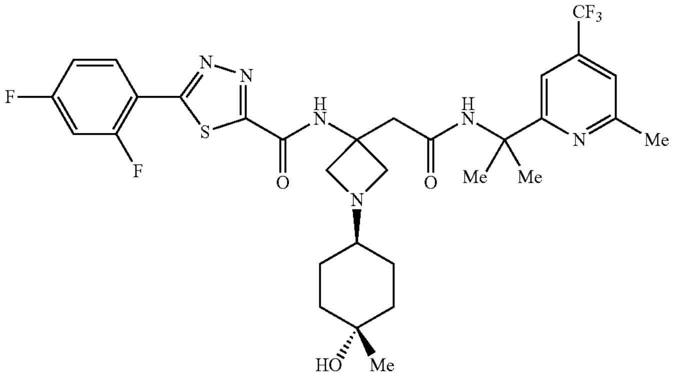 [SMILES: Cc1cc(C(F)(F)F)cc(C(C)(C)NC(=O)CC2(NC(=O)c3nnc(-c4ccc(F)cc4F)s3)CN([C@H]3CC[C@](C)(O)CC3)C2)n1] | +++ |
| 1.350 | 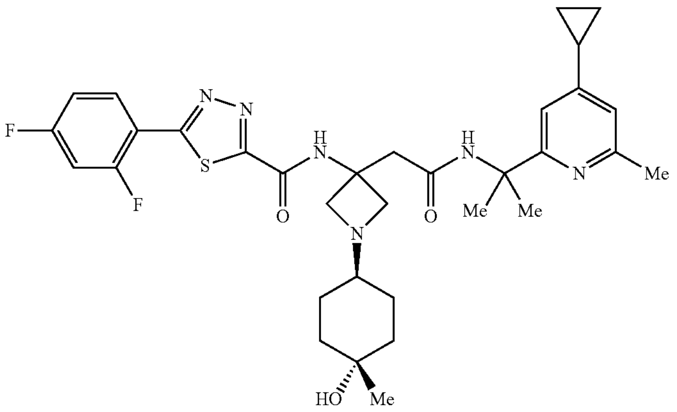 [SMILES: Cc1cc(C2CC2)cc(C(C)(C)NC(=O)CC2(NC(=O)c3nnc(-c4ccc(F)cc4F)s3)CN([C@H]3CC[C@](C)(O)CC3)C2)n1] | +++ |
| 1.351 | 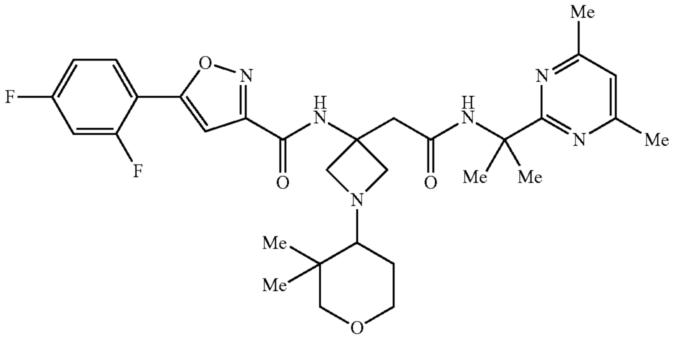 [SMILES: Cc1cc(C)nc(C(C)(C)NC(=O)CC2(NC(=O)c3cc(-c4ccc(F)cc4F)on3)CN(C3CCOCC3(C)C)C2)n1] | ++ |
| 1.352 | 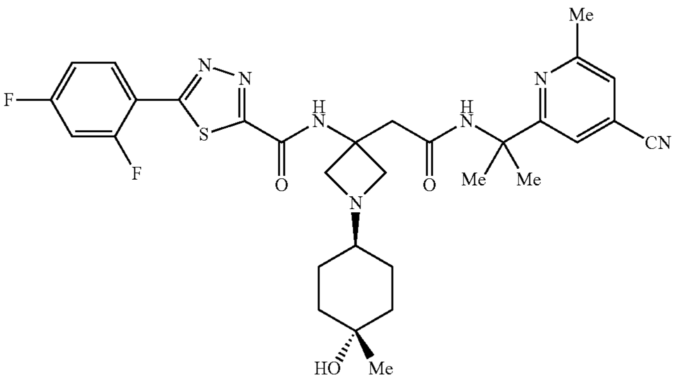 [SMILES: Cc1cc(C#N)cc(C(C)(C)NC(=O)CC2(NC(=O)c3nnc(-c4ccc(F)cc4F)s3)CN([C@H]3CC[C@](C)(O)CC3)C2)n1] | +++ |

-continued
| Specific Examples (Table 1) | | |
|---|---|---|
| Compound ID | Structure | IC50 (buffer) |
| 1.353 | 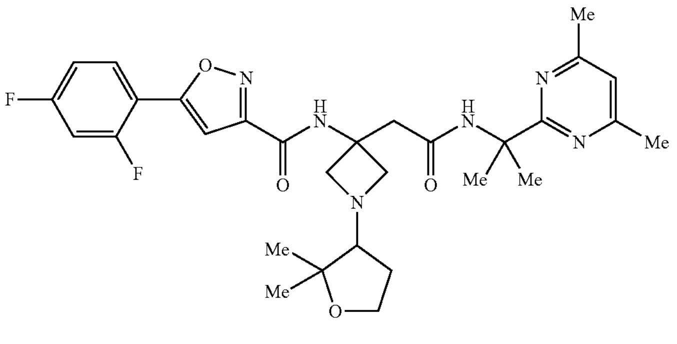 [SMILES: Cc1cc(C)nc(C(C)(C)NC(=O)CC2(NC(=O)c3cc(-c4ccc(F)cc4F)on3)CN(C3CCOC3(C)C)C2)n1] | ++ |
| 1.354 | 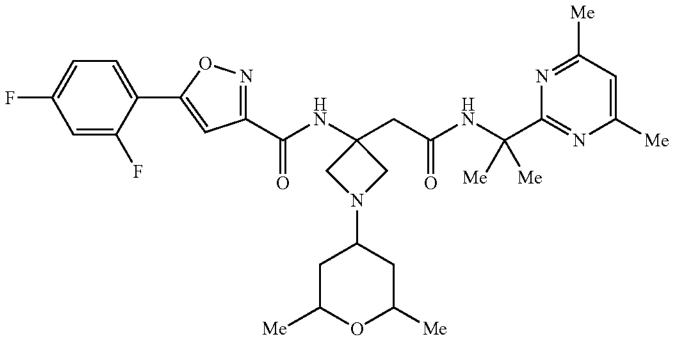 [SMILES: Cc1cc(C)nc(C(C)(C)NC(=O)CC2(NC(=O)c3cc(-c4ccc(F)cc4F)on3)CN(C3CC(C)OC(C)C3)C2)n1] | ++ |
| 1.355 | 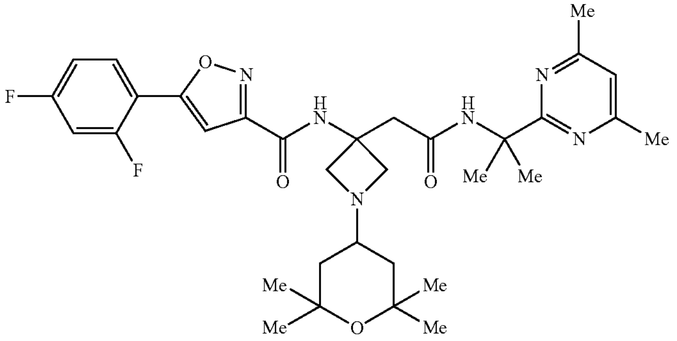 [SMILES: Cc1cc(C)nc(C(C)(C)NC(=O)CC2(NC(=O)c3cc(-c4ccc(F)cc4F)on3)CN(C3CC(C)(C)OC(C)(C)C3)C2)n1] | ++++ |
| 1.356 | 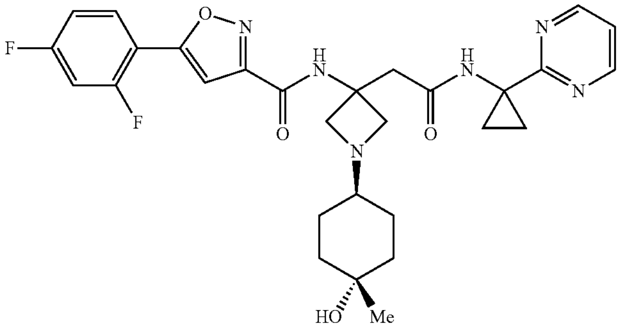 [SMILES: C[C@]1(O)CC[C@H](N2CC(CC(=O)NC3(c4ncccn4)CC3)(NC(=O)c3cc(-c4ccc(F)cc4F)on3)C2)CC1] | +++ |

-continued
| Specific Examples (Table 1) | | |
|---|---|---|
| Compound ID | Structure | IC50 (buffer) |
| 1.357 | 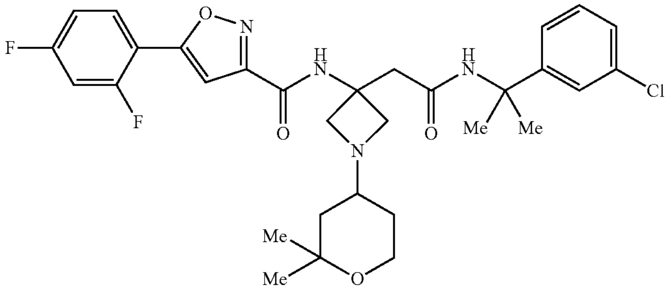 [SMILES: CC1(C)CC(N2CC(CC(=O)NC(C)(C)c3cccc(Cl)c3)(NC(=O)c3cc(-c4ccc(F)cc4F)on3)C2)CCO1] | +++ |
| 1.358 | 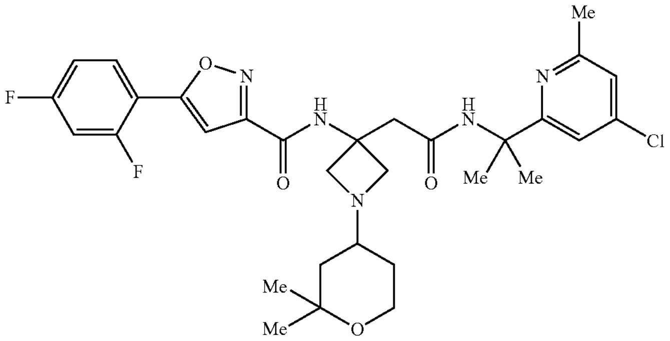 [SMILES: Cc1cc(Cl)cc(C(C)(C)NC(=O)CC2(NC(=O)c3cc(-c4ccc(F)cc4F)on3)CN(C3CCOC(C)(C)C3)C2)n1] | ++++ |
| 1.359 | 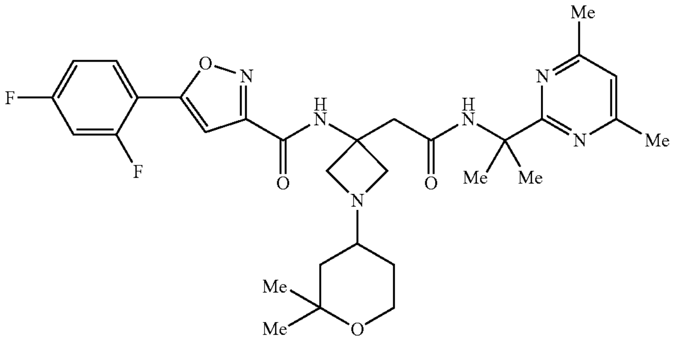 [SMILES: Cc1cc(C)nc(C(C)(C)NC(=O)CC2(NC(=O)c3cc(-c4ccc(F)cc4F)on3)CN(C3CCOC(C)(C)C3)C2)n1] | +++ |
| 1.360 | 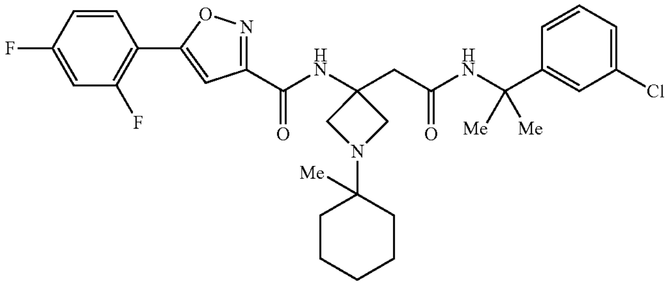 [SMILES: CC(C)(NC(=O)CC1(NC(=O)c2cc(-c3ccc(F)cc3F)on2)CN(C2(C)CCCCC2)C1)c1cccc(Cl)c1] | ++++ |

One of ordinary skill in the art will recognize from the provided description, figures, and examples, that modifications and changes can be made to the various embodiments of the invention without departing from the scope of the invention defined by the following claims and their equivalents.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A compound having formula (I):

(I)

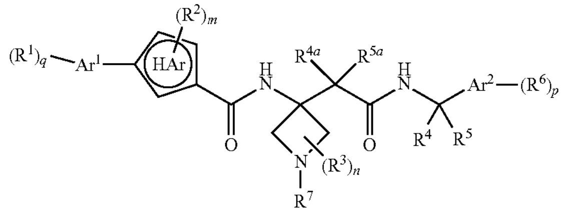

or a pharmaceutically acceptable salt, hydrate, N-oxide, isotopically enriched or enantiomerically enriched version or a rotamer thereof, wherein HAr is a five-membered heteroaryl ring;

$Ar^1$ is selected from the group consisting of phenyl, pyridyl, pyrimidinyl, and pyrazinyl;

$Ar^2$ is aryl or heteroaryl, each of which is independently monocyclic or fused-bicyclic;

the subscript m is 0, 1 or 2;

the subscript n is 0, 1, 2 or 3;

the subscript p is 0, 1, 2 or 3;

the subscript q is 0, 1, 2, 3 or 4;

each $R^1$ is a member independently selected from the group consisting of halogen, CN, $C_{1-4}$ alkyl, $C_{1-4}$ haloalkyl, —$NR^aR^b$, —$OR^a$, —$CO_2R^a$, and —C(O)$NR^aR^b$;

each $R^2$ is a member independently selected from the group consisting of halogen, CN, $C_{1-4}$ alkyl, $C_{1-4}$ haloalkyl, —$NR^aR^b$, —$OR^a$, —$CO_2R^a$, and —C(O)$NR^aR^b$;

each $R^3$ is a member selected from the group consisting of $C_{1-4}$ alkyl, $C_{1-4}$ haloalkyl, $C_{1-4}$ hydroxyalkyl, —$CO_2R^a$, —X—$CO_2R^a$, —C(O)$NR^aR^b$ and —X—C(O)$NR^aR^b$;

each of $R^{4a}$ and $R^{5a}$, is a member independently selected from the group consisting of H, $C_{1-6}$ alkyl, $C_{1-6}$ haloalkyl, $C_{1-6}$ hydroxyalkyl, —X—$OR^a$, —$CO_2R^a$, —X—$CO_2R^a$, —X—$NR^aR^b$, —C(O)$NR^aR^b$ and —X—C(O)$NR^aR^b$, each of $R^4$ and $R^5$, is a member independently selected from the group consisting of H, $C_{1-6}$ alkyl, $C_{1-6}$ haloalkyl, $C_{1-6}$ hydroxyalkyl, —X—$OR^a$, —$CO_2R^a$, —X—$CO_2R^a$, —X—$NR^aR^b$, —C(O)$NR^aR^b$ and —X—C(O)$NR^aR^b$; or $R^4$ and $R^5$ are combined to form a three- to five-membered ring having 0 or 1 heteroatom ring vertex selected from O, S or N, wherein said three- to five-membered ring is unsubstituted or substituted with 1-4 substituents independently selected from the group consisting of halogen, CN, $C_{1-4}$ alkyl, $C_{1-4}$ haloalkyl, $C_{1-4}$ alkoxy, and $C_{1-4}$ haloalkoxy;

each $R^6$ is a member independently selected from the group consisting of halogen, CN, —X—CN, $C_{1-4}$ alkyl, $C_{1-4}$ haloalkyl, $C_{3-6}$ cycloalkyl, $C_{1-4}$ hydroxyalkyl, —$OR^a$, —$CO_2R^a$, —X—$CO_2R^a$, —$NR^aR^b$, —X—$NR^aR^b$, —C(O)$NR^aR^b$, and —X—C(O)$NR^aR^b$, $R^7$ is a member selected from the group consisting of $C_{1-8}$ alkyl, $C_{3-8}$ hydroxyalkyl, $C_{1-4}$ alkoxy-$C_{2-4}$ alkyl, —C(O)NH—$C_{1-8}$ alkyl, —C(O)—$C_{1-8}$ alkyl, —$S(O)_2$—$C_{1-8}$ alkyl, $C_{3-8}$ cycloalkyl, —X—$C_{3-8}$ cycloalkyl, $C_{6-9}$ spirocycloalkyl, —X—$C_{6-9}$ spirocycloalkyl, 4- to 7-membered heterocycloalkyl, —X-4- to 7-membered heterocycloalkyl, 7- to 11-membered spiroheterocycloalkyl, and —X-7- to 11-membered spiroheterocycloalkyl, wherein each $R^7$ is substituted with zero to four substituents independently selected from the group consisting of hydroxy, methyl, ethyl, hydroxymethyl, fluoro, chloro, methoxy, ethoxy and cyclopropyl;

each $R^a$ and $R^b$ is independently selected from the group consisting of H, $C_{1-4}$ alkyl, $C_{1-4}$ haloalkyl, $C_{3-6}$ cycloalkyl, and $C_{3-6}$ cycloalkyl-$C_{1-4}$ alkyl;

each X is a $C_{1-4}$ alkylene linking group wherein any of the methylene portions of X are unsubstituted or substituted with one or two methyl groups.

2. The compound of claim 1, or a pharmaceutically acceptable salt thereof, wherein HAr is selected from the group consisting of isoxazole, isothiazole, imidazole, pyrazole, thiazole, 1,2,4-oxadiazole, 1,3,4-oxadiazole, 1,2,4-thiadiazole, 1,3,4-thiadiazole, 1,2,3-triazole, and 1,2,4-triazole.

3. The compound of claim 1, or a pharmaceutically acceptable salt thereof, wherein HAr is selected from the group consisting of isoxazole and thiadiazole.

4. The compound of claim 1, or a pharmaceutically acceptable salt thereof, wherein $Ar^1$ is phenyl.

5. The compound of claim 4, or a pharmaceutically acceptable salt thereof, wherein the subscript q is 1, 2, or 3; and each $R^1$ is a member independently selected from the group consisting of halogen, CN, $C_{1-4}$ alkyl and $C_{1-4}$ haloalkyl.

6. The compound of claim 1, or a pharmaceutically acceptable salt thereof, wherein $Ar^2$ is selected from the group consisting of pyridyl, pyrimidinyl, pyrazinyl, phenyl, indolyl, thiazolyl, pyrazolyl, indazolyl and pyrrolopyridinyl.

7. The compound of claim 6, or a pharmaceutically acceptable salt thereof, wherein $Ar^2$ is selected from the group consisting of pyrimidinyl, pyridyl and phenyl.

8. The compound of claim 1, wherein $Ar^2$ is selected from the group consisting of 2-pyridyl, 4-pyridyl, 2-pyrimidinyl, 4-pyrimidinyl, 2-thiazolyl, 4-pyrazolyl, phenyl and indolyl; and each $R^6$ is independently selected from the group consisting of halogen, CN, $C_{1-4}$ alkyl, $C_{1-4}$ haloalkyl, $C_{3-6}$ cycloalkyl and $C_{1-4}$ alkoxy.

9. The compound of claim 1, or a pharmaceutically acceptable salt thereof, wherein —$Ar^2$—$(R^6)_p$ is selected from the group consisting of:

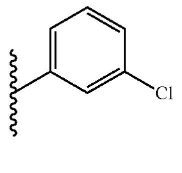
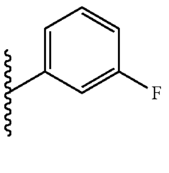
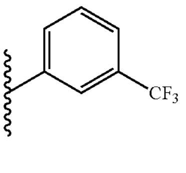

-continued

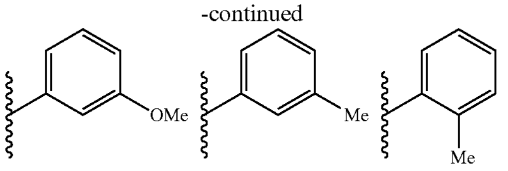
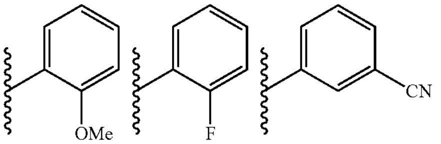
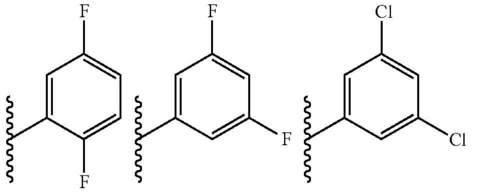
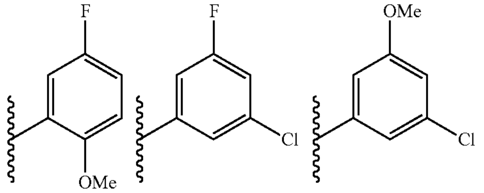
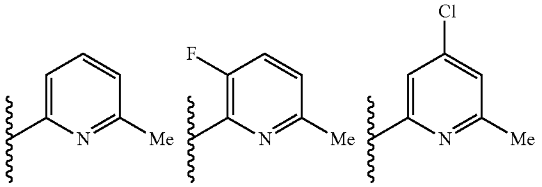
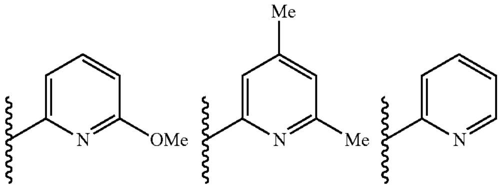
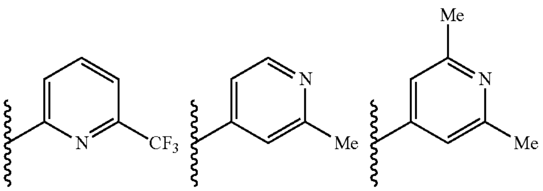
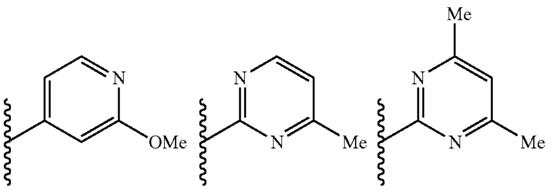
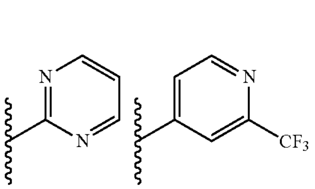
and
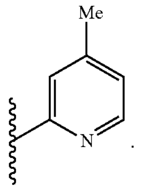

10. The compound of claim 1, or a pharmaceutically acceptable salt thereof, wherein $R^7$ is selected from the group consisting of

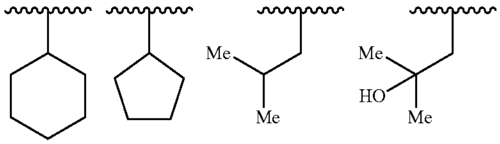
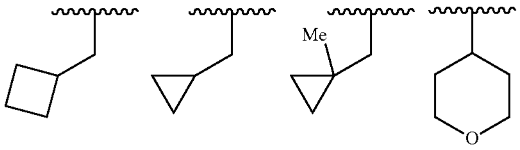
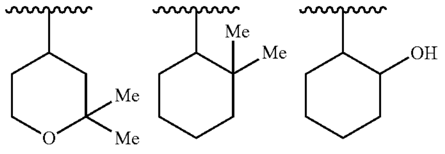
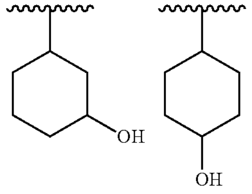
and
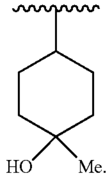

11. The compound of claim 1, or a pharmaceutically acceptable salt thereof, wherein the subscript m is 0.

12. The compound of claim 1, or a pharmaceutically acceptable salt thereof, wherein the subscript n is 0.

13. The compound of claim 1, or a pharmaceutically acceptable salt thereof, wherein the subscript p is 0, 1 or 2.

14. The compound of claim 1, or a pharmaceutically acceptable salt thereof, wherein the subscript q is 1 or 2.

15. The compound of claim 1, having formula (Ia):

(Ia)

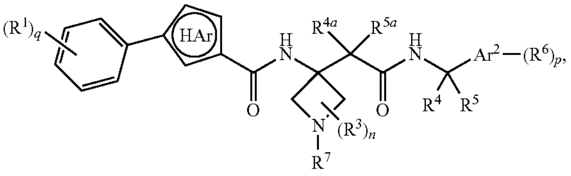

or a pharmaceutically acceptable salt thereof.

16. The compound of claim 15, wherein HAr is selected from the group consisting of isoxazole and thiadiazole.

17. The compound of claim 15, having formula (Ia1) or (Ia2):

(Ia1)

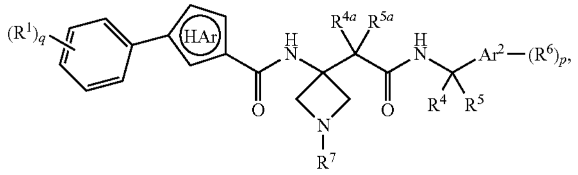

-continued (Ia2)

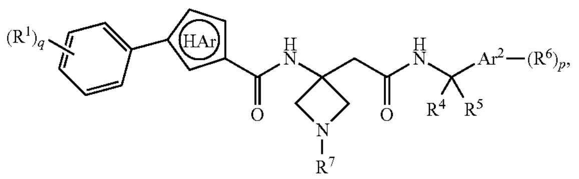

or a pharmaceutically acceptable salt thereof.

18. The compound of claim 1, or a pharmaceutically acceptable salt thereof, wherein HAr is selected from the group consisting of isoxazole and thiadiazole.

19. The compound of claim 1, having formula (Ib), (Ic) or (Id):

(Ib)

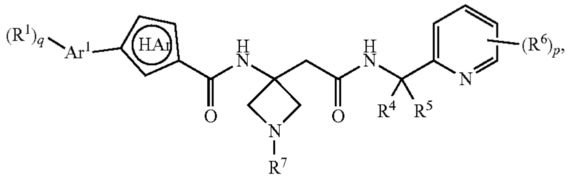

(Ic)

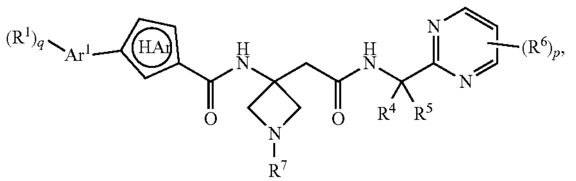

(Id)

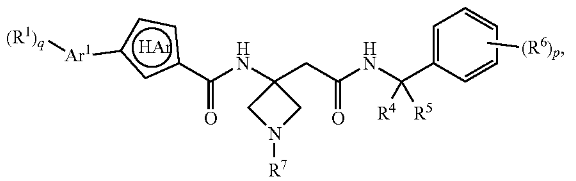

or a pharmaceutically acceptable salt thereof.

20. The compound of claim 19, having formula (Ib1), (Ic1) or (Id1):

(Ib1)

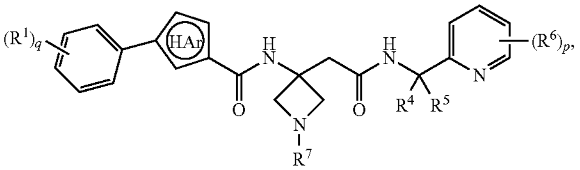

(Ic1)

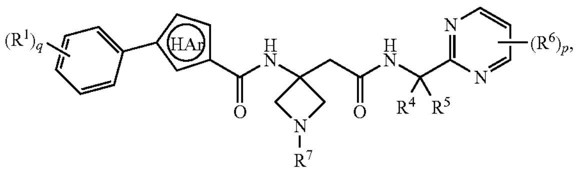

(Id1)

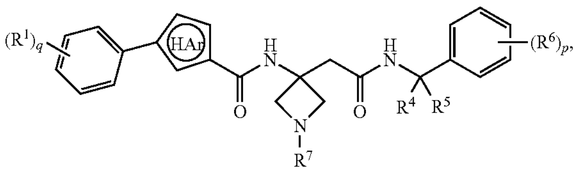

or a pharmaceutically acceptable salt thereof.

21. The compound of claim 20, or a pharmaceutically acceptable salt thereof, wherein HAr is selected from the group consisting of isoxazole and thiadiazole.

22. The compound of claim 1, or a pharmaceutically acceptable salt thereof, wherein $R^7$ is a member selected from the group consisting of $C_{1-8}$ alkyl, $C_{3-8}$ hydroxyalkyl, $C_{1-4}$ alkoxy-$C_{2-4}$ alkyl, $C_{3-8}$ cycloalkyl, $C_{6-9}$ spirocycloalkyl, 4- to 7-membered heterocycloalkyl, and 7- to 11-membered spiroheterocycloalkyl, wherein each $R^7$ is substituted with zero to four substituents independently selected from the group consisting of hydroxy, methyl, ethyl, hydroxymethyl, fluoro, chloro, methoxy, ethoxy and cyclopropyl.

23. The compound of claim 1, or a pharmaceutically acceptable salt thereof, wherein $R^7$ a member selected from the group consisting of —X—$C_{3-8}$ cycloalkyl, —X—$C_{6-9}$ spirocycloalkyl, —X—4- to 7-membered heterocycloalkyl, and —X-7- to 11-membered spiroheterocycloalkyl, wherein each $R^7$ is substituted with zero to four substituents independently selected from the group consisting of hydroxy, methyl, ethyl, hydroxymethyl, fluoro, chloro, methoxy, ethoxy and cyclopropyl.

24. The compound of claim 1, or a pharmaceutically acceptable salt thereof, wherein $R^7$ is selected from the group consisting of cyclohexyl, cyclopentyl, piperidinyl, tetrahydropyranyl, and tetrahydrofuranyl, each of which is substituted with zero to two substituents independently selected from the group consisting of hydroxy, methyl, ethyl, hydroxymethyl, fluoro, chloro, methoxy, and ethoxy.

25. A compound, or a pharmaceutically acceptable salt thereof, selected from one of the following:

| Compound ID | Structure |
|---|---|
| 1.001 | 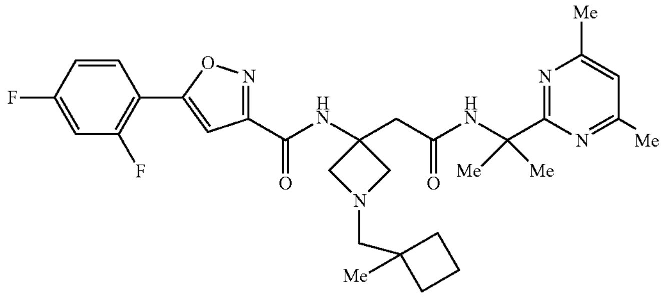 [SMILES: Cc1cc(C)nc(C(C)(C)NC(=O)CC2(NC(=O)c3cc(-c4ccc(F)cc4F)on3)CN(CC3(C)CCC3)C2)n1] |
| 1.002 | 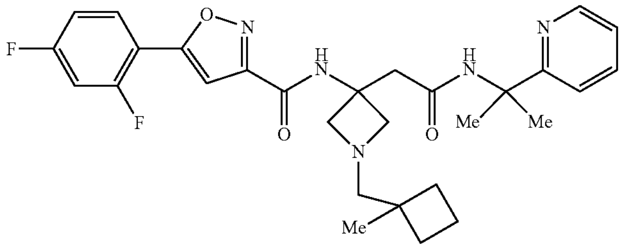 [SMILES: CC1(CN2CC(CC(=O)NC(C)(C)c3ccccn3)(NC(=O)c3cc(-c4ccc(F)cc4F)on3)C2)CCC1] |
| 1.003 | 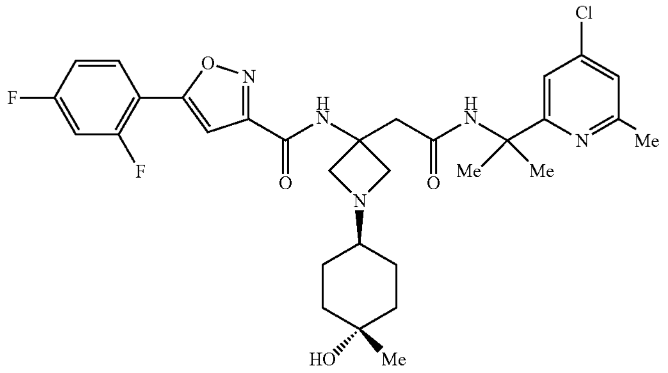 [SMILES: Cc1cc(Cl)cc(C(C)(C)NC(=O)CC2(NC(=O)c3cc(-c4ccc(F)cc4F)on3)CN([C@H]3CC[C@](C)(O)CC3)C2)n1] |
| 1.004 | 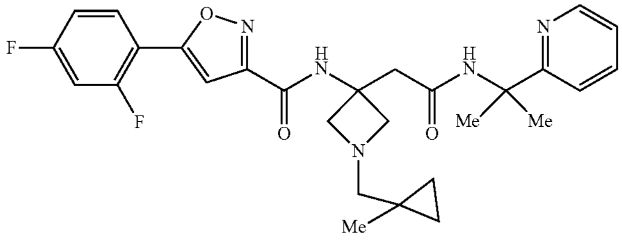 [SMILES: CC1(CN2CC(CC(=O)NC(C)(C)c3ccccn3)(NC(=O)c3cc(-c4ccc(F)cc4F)on3)C2)CC1] |
| 1.005 | 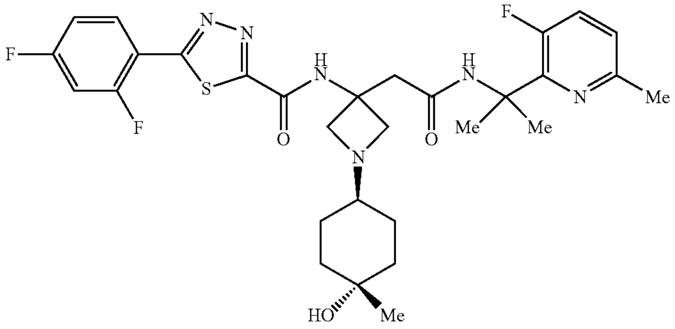 [SMILES: Cc1ccc(F)c(C(C)(C)NC(=O)CC2(NC(=O)c3nnc(-c4ccc(F)cc4F)s3)CN([C@H]3CC[C@](C)(O)CC3)C2)n1] |

-continued
| Compound ID | Structure |
|---|---|
| 1.006 | 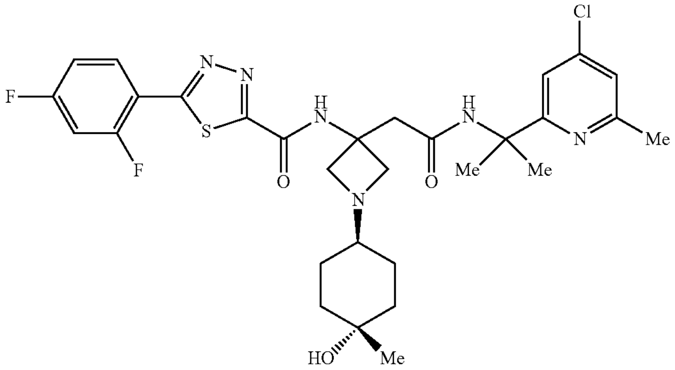 [SMILES: Cc1cc(Cl)cc(C(C)(C)NC(=O)CC2(NC(=O)c3nnc(-c4ccc(F)cc4F)s3)CN([C@H]3CC[C@](C)(O)CC3)C2)n1] |
| 1.007 | 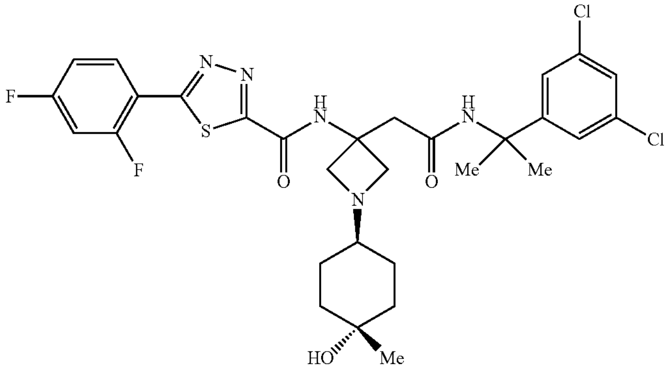 [SMILES: CC(C)(NC(=O)CC1(NC(=O)c2nnc(-c3ccc(F)cc3F)s2)CN([C@H]2CC[C@](C)(O)CC2)C1)c1cc(Cl)cc(Cl)c1] |
| 1.008 | 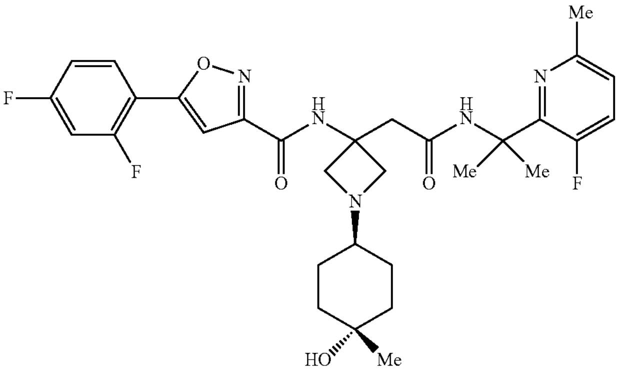 [SMILES: Cc1ccc(F)c(C(C)(C)NC(=O)CC2(NC(=O)c3cc(-c4ccc(F)cc4F)on3)CN([C@H]3CC[C@](C)(O)CC3)C2)n1] |
| 1.009 | 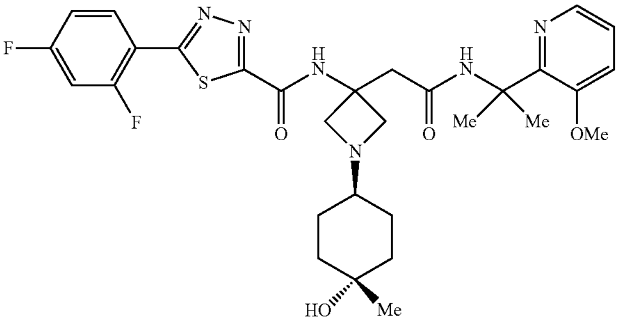 [SMILES: COc1cccnc1C(C)(C)NC(=O)CC1(NC(=O)c2nnc(-c3ccc(F)cc3F)s2)CN([C@H]2CC[C@](C)(O)CC2)C1] |

-continued
| Compound ID | Structure |
| --- | --- |
| 1.010 | 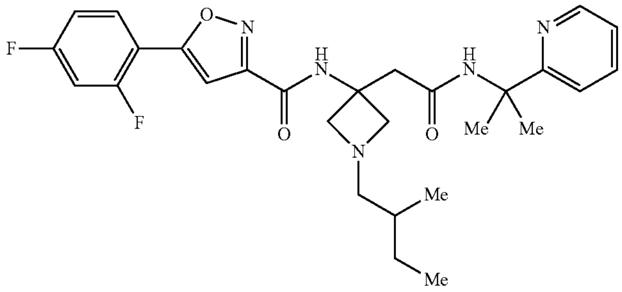 [SMILES: CCC(C)CN1CC(CC(=O)NC(C)(C)c2ccccn2)(NC(=O)c2cc(-c3ccc(F)cc3F)on2)C1] |
| 1.011 | 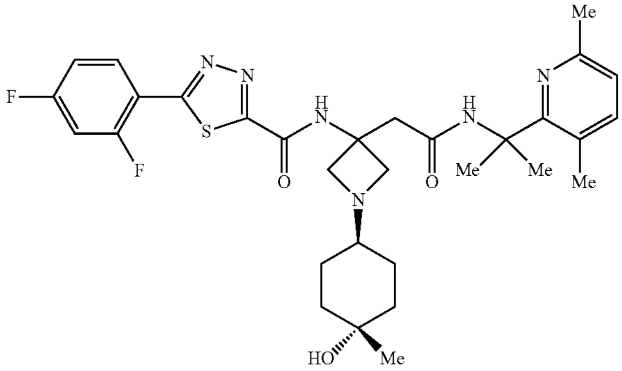 [SMILES: Cc1ccc(C)c(C(C)(C)NC(=O)CC2(NC(=O)c3nnc(-c4ccc(F)cc4F)s3)CN([C@H]3CC[C@](C)(O)CC3)C2)n1] |
| 1.012 | 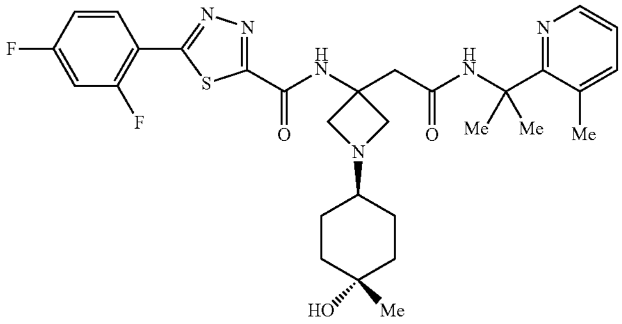 [SMILES: Cc1cccnc1C(C)(C)NC(=O)CC1(NC(=O)c2nnc(-c3ccc(F)cc3F)s2)CN([C@H]2CC[C@](C)(O)CC2)C1] |
| 1.013 | 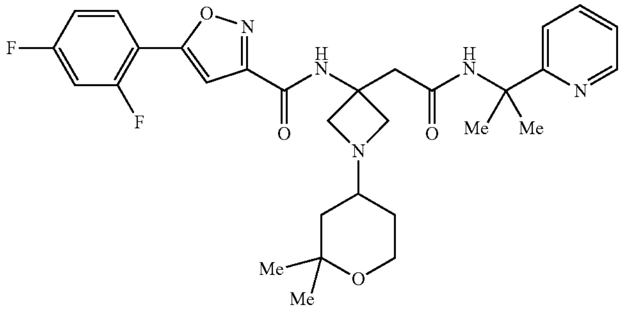 [SMILES: CC1(C)CC(N2CC(CC(=O)NC(C)(C)c3ccccn3)(NC(=O)c3cc(-c4ccc(F)cc4F)on3)C2)CCO1] |

-continued
| Compound ID | Structure |
| --- | --- |
| 1.014 | 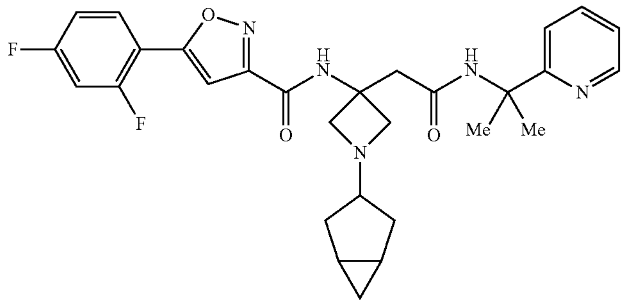 [SMILES: CC(C)(NC(=O)CC1(NC(=O)c2cc(-c3ccc(F)cc3F)on2)CN(C2CC3CC3C2)C1)c1ccccn1] |
| 1.015 | 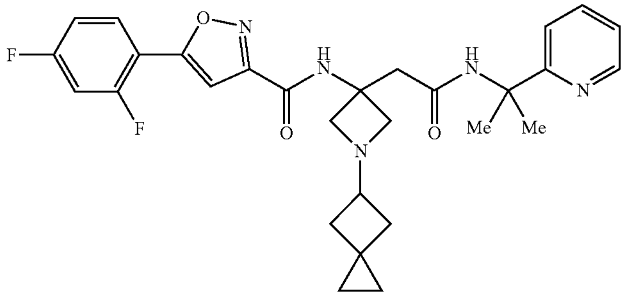 [SMILES: CC(C)(NC(=O)CC1(NC(=O)c2cc(-c3ccc(F)cc3F)on2)CN(C2CC3(CC3)C2)C1)c1ccccn1] |
| 1.016 | 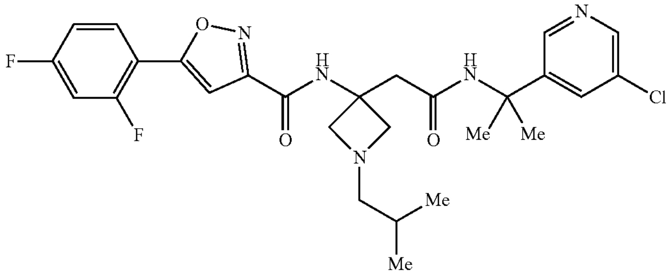 [SMILES: CC(C)CN1CC(CC(=O)NC(C)(C)c2cncc(Cl)c2)(NC(=O)c2cc(-c3ccc(F)cc3F)on2)C1] |
| 1.017 | 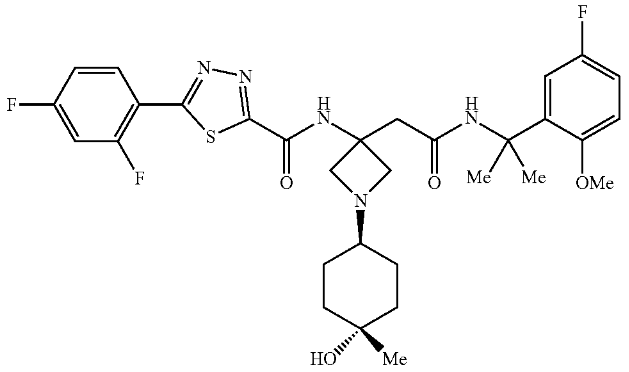 [SMILES: COc1ccc(F)cc1C(C)(C)NC(=O)CC1(NC(=O)c2nnc(-c3ccc(F)cc3F)s2)CN([C@H]2CC[C@](C)(O)CC2)C1] |
| 1.018 | 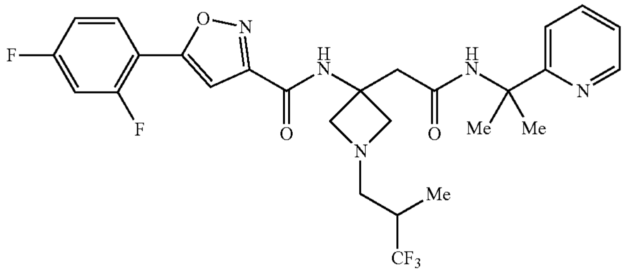 [SMILES: CC(CN1CC(CC(=O)NC(C)(C)c2ccccn2)(NC(=O)c2cc(-c3ccc(F)cc3F)on2)C1)C(F)(F)F] |

-continued
| Compound ID | Structure |
|---|---|
| 1.019 | 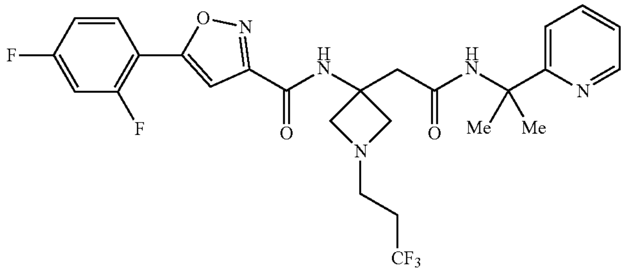 [SMILES: CC(C)(NC(=O)CC1(NC(=O)c2cc(-c3ccc(F)cc3F)on2)CN(CCC(F)(F)F)C1)c1ccccn1] |
| 1.020 | 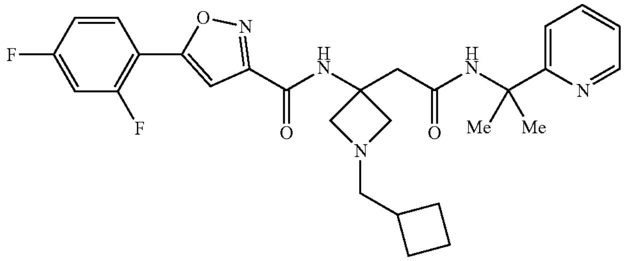 [SMILES: CC(C)(NC(=O)CC1(NC(=O)c2cc(-c3ccc(F)cc3F)on2)CN(CC2CCC2)C1)c1ccccn1] |
| 1.021 | 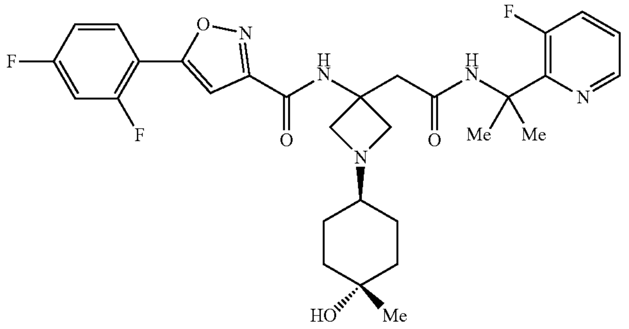 [SMILES: CC(C)(NC(=O)CC1(NC(=O)c2cc(-c3ccc(F)cc3F)on2)CN([C@H]2CC[C@](C)(O)CC2)C1)c1ncccc1F] |
| 1.022 | 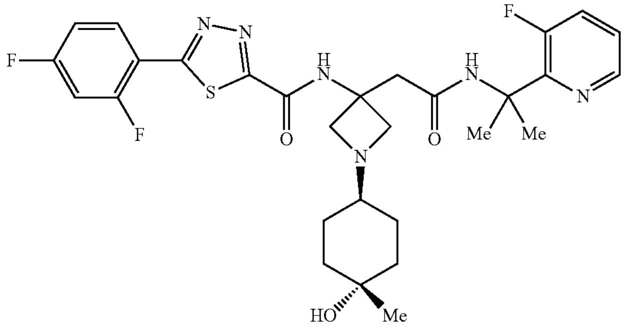 [SMILES: CC(C)(NC(=O)CC1(NC(=O)c2nnc(-c3ccc(F)cc3F)s2)CN([C@H]2CC[C@](C)(O)CC2)C1)c1ncccc1F] |
| 1.023 | 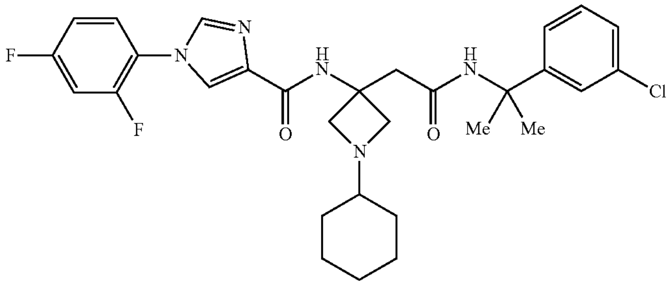 [SMILES: CC(C)(NC(=O)CC1(NC(=O)c2cn(-c3ccc(F)cc3F)cn2)CN(C2CCCCC2)C1)c1cccc(Cl)c1] |

-continued
| Compound ID | Structure |
| --- | --- |
| 1.024 | 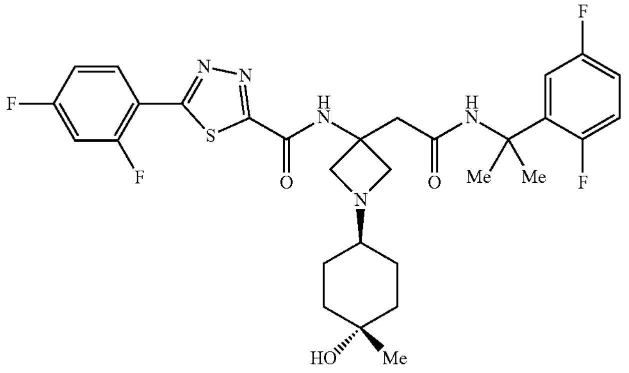 [SMILES: CC(C)(NC(=O)CC1(NC(=O)c2nnc(-c3ccc(F)cc3F)s2)CN([C@H]2CC[C@](C)(O)CC2)C1)c1cc(F)ccc1F] |
| 1.025 | 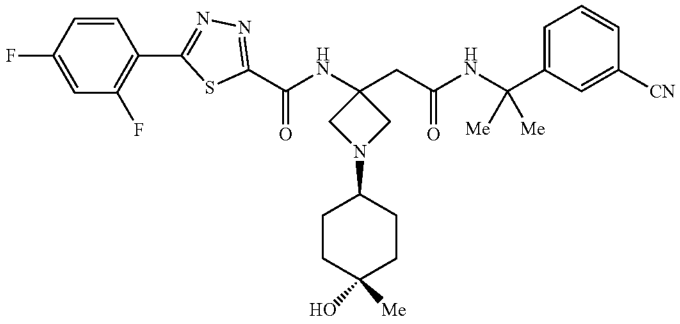 [SMILES: CC(C)(NC(=O)CC1(NC(=O)c2nnc(-c3ccc(F)cc3F)s2)CN([C@H]2CC[C@](C)(O)CC2)C1)c1cccc(C#N)c1] |
| 1.026 | 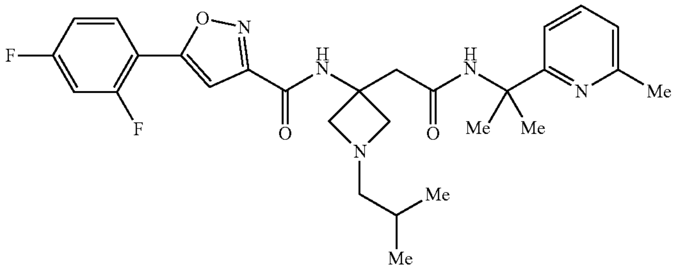 [SMILES: Cc1cccc(C(C)(C)NC(=O)CC2(NC(=O)c3cc(-c4ccc(F)cc4F)on3)CN(CC(C)C)C2)n1] |
| 1.027 | 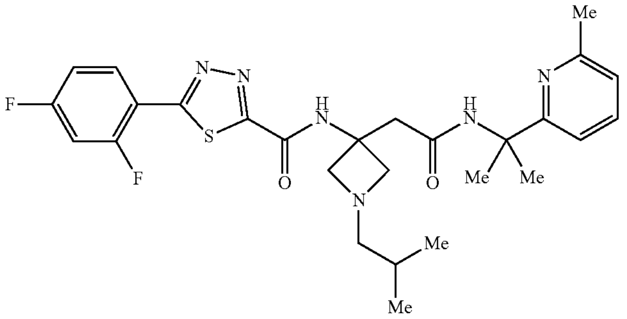 [SMILES: Cc1cccc(C(C)(C)NC(=O)CC2(NC(=O)c3nnc(-c4ccc(F)cc4F)s3)CN(CC(C)C)C2)n1] |

-continued
| Compound ID | Structure |
| --- | --- |
| 1.028 | 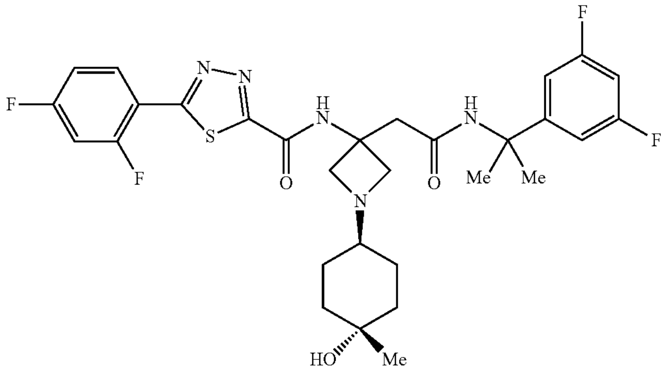 [SMILES: CC(C)(NC(=O)CC1(NC(=O)c2nnc(-c3ccc(F)cc3F)s2)CN([C@H]2CC[C@](C)(O)CC2)C1)c1cc(F)cc(F)c1] |
| 1.029 | 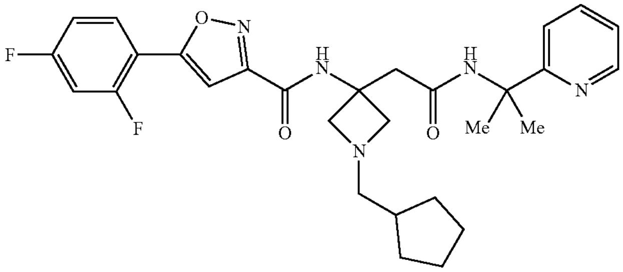 [SMILES: CC(C)(NC(=O)CC1(NC(=O)c2cc(-c3ccc(F)cc3F)on2)CN(CC2CCCC2)C1)c1ccccn1] |
| 1.030 | 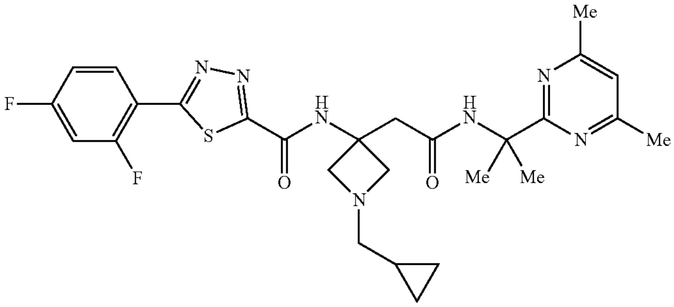 [SMILES: Cc1cc(C)nc(C(C)(C)NC(=O)CC2(NC(=O)c3nnc(-c4ccc(F)cc4F)s3)CN(CC3CC3)C2)n1] |
| 1.031 | 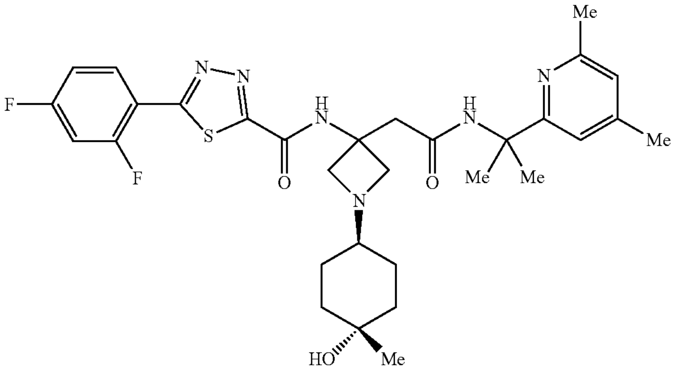 [SMILES: Cc1cc(C)nc(C(C)(C)NC(=O)CC2(NC(=O)c3nnc(-c4ccc(F)cc4F)s3)CN([C@H]3CC[C@](C)(O)CC3)C2)c1] |

-continued
| Compound ID | Structure |
| --- | --- |
| 1.032 | 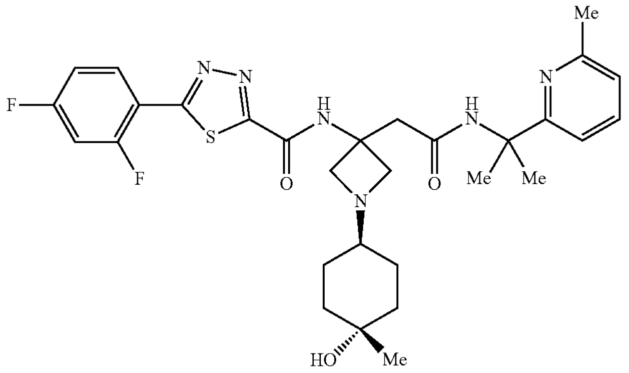 [SMILES: Cc1cccc(C(C)(C)NC(=O)CC2(NC(=O)c3nnc(-c4ccc(F)cc4F)s3)CN([C@H]3CC[C@](C)(O)CC3)C2)n1] |
| 1.033 | 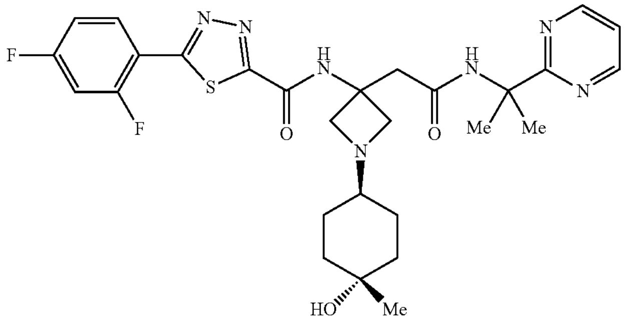 [SMILES: CC(C)(NC(=O)CC1(NC(=O)c2nnc(-c3ccc(F)cc3F)s2)CN([C@H]2CC[C@](C)(O)CC2)C1)c1ncccn1] |
| 1.034 | 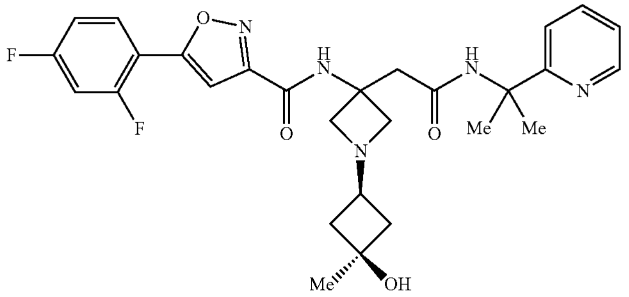 [SMILES: CC(C)(NC(=O)CC1(NC(=O)c2cc(-c3ccc(F)cc3F)on2)CN([C@H]2C[C@@](C)(O)C2)C1)c1ccccn1] |
| 1.035 | 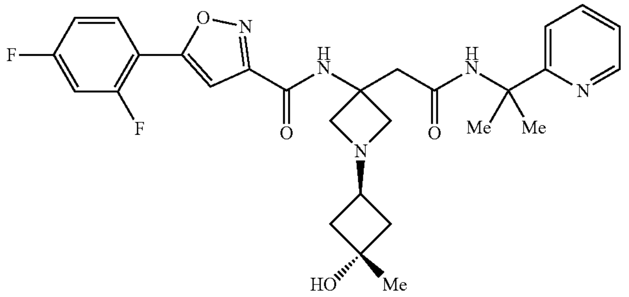 [SMILES: CC(C)(NC(=O)CC1(NC(=O)c2cc(-c3ccc(F)cc3F)on2)CN([C@H]2C[C@](C)(O)C2)C1)c1ccccn1] |

-continued
| Compound ID | Structure |
| --- | --- |
| 1.036 | 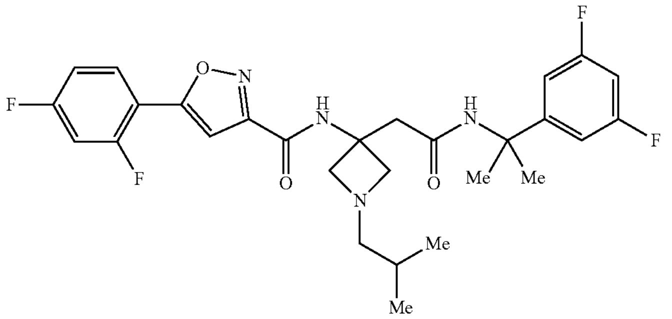 [SMILES: CC(C)CN1CC(CC(=O)NC(C)(C)c2cc(F)cc(F)c2)(NC(=O)c2cc(-c3ccc(F)cc3F)on2)C1] |
| 1.037 | 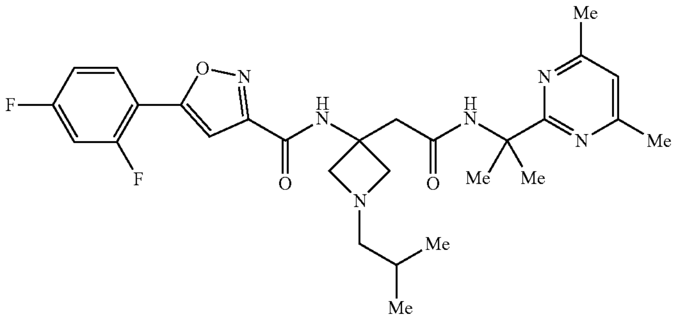 [SMILES: Cc1cc(C)nc(C(C)(C)NC(=O)CC2(NC(=O)c3cc(-c4ccc(F)cc4F)on3)CN(CC(C)C)C2)n1] |
| 1.038 | 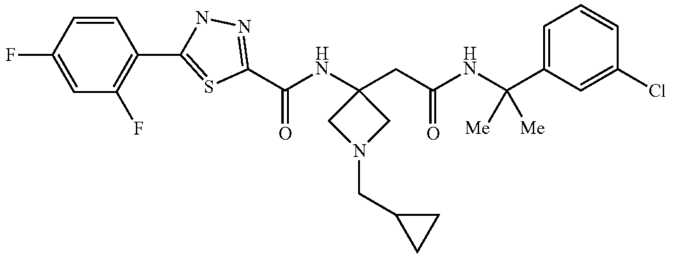 |
| 1.039 | 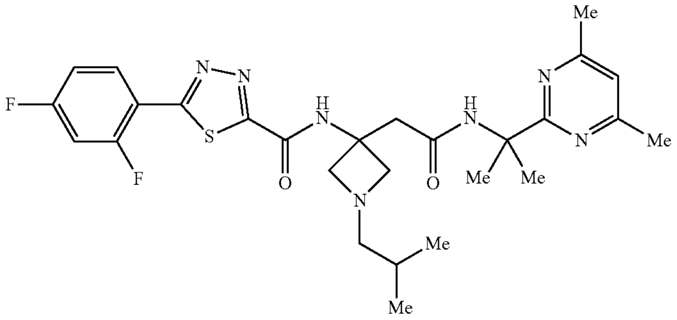 [SMILES: Cc1cc(C)nc(C(C)(C)NC(=O)CC2(NC(=O)c3nnc(-c4ccc(F)cc4F)s3)CN(CC(C)C)C2)n1] |
| 1.040 | 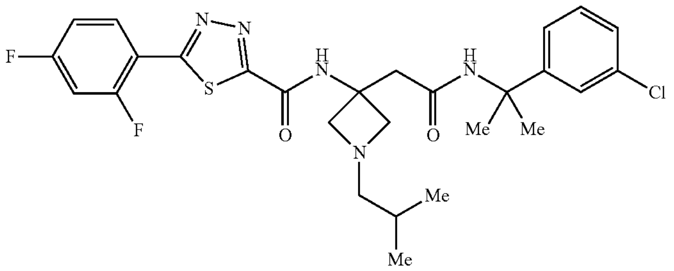 [SMILES: CC(C)CN1CC(CC(=O)NC(C)(C)c2cccc(Cl)c2)(NC(=O)c2nnc(-c3ccc(F)cc3F)s2)C1] |

-continued
| Compound ID | Structure |
|---|---|
| 1.041 | 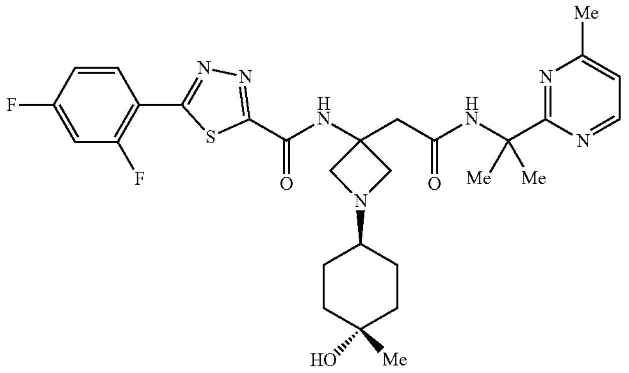 [SMILES: Cc1ccnc(C(C)(C)NC(=O)CC2(NC(=O)c3nnc(-c4ccc(F)cc4F)s3)CN([C@H]3CC[C@](C)(O)CC3)C2)n1] |
| 1.042 | 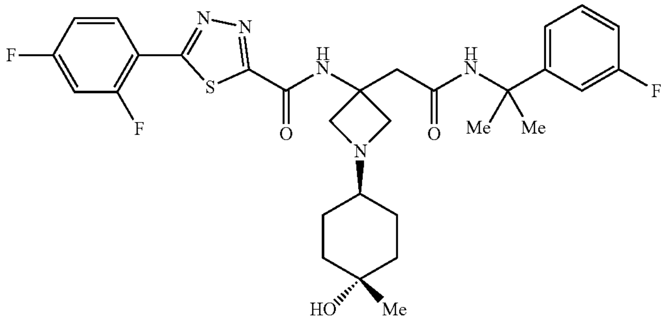 [SMILES: CC(C)(NC(=O)CC1(NC(=O)c2nnc(-c3ccc(F)cc3F)s2)CN([C@H]2CC[C@](C)(O)CC2)C1)c1cccc(F)c1] |
| 1.043 | 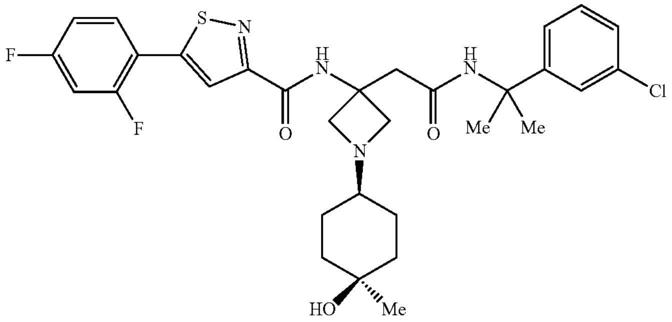 [SMILES: CC(C)(NC(=O)CC1(NC(=O)c2cc(-c3ccc(F)cc3F)sn2)CN([C@H]2CC[C@@](C)(O)CC2)C1)c1cccc(Cl)c1] |
| 1.044 | 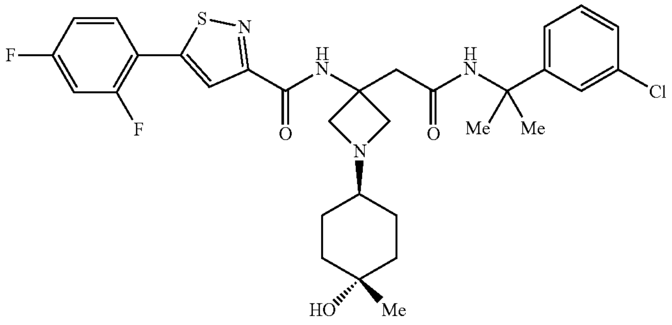 [SMILES: CC(C)(NC(=O)CC1(NC(=O)c2cc(-c3ccc(F)cc3F)sn2)CN([C@H]2CC[C@](C)(O)CC2)C1)c1cccc(Cl)c1] |

-continued
| Compound ID | Structure |
|---|---|
| 1.045 | 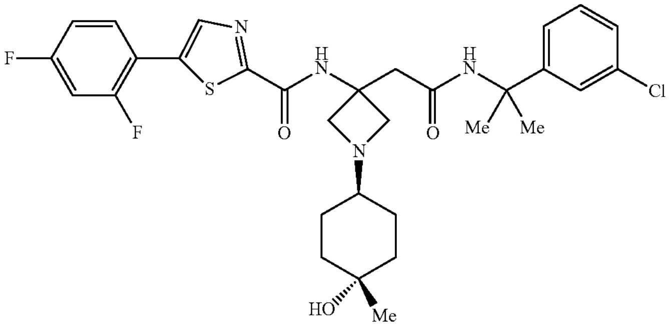 [SMILES: CC(C)(NC(=O)CC1(NC(=O)c2ncc(-c3ccc(F)cc3F)s2)CN([C@H]2CC[C@](C)(O)CC2)C1)c1cccc(Cl)c1] |
| 1.046 | 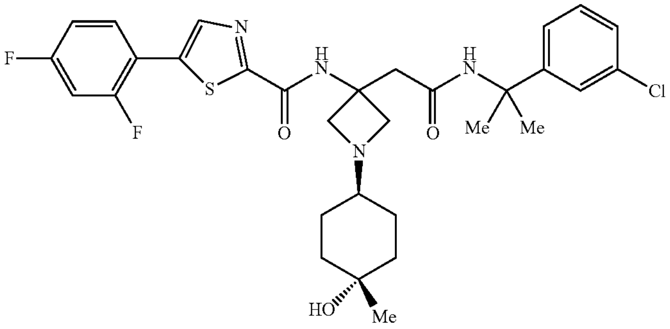 [SMILES: CC(C)(NC(=O)CC1(NC(=O)c2ncc(-c3ccc(F)cc3F)s2)CN([C@H]2CC[C@](C)(O)CC2)C1)c1cccc(Cl)c1] |
| 1.047 | 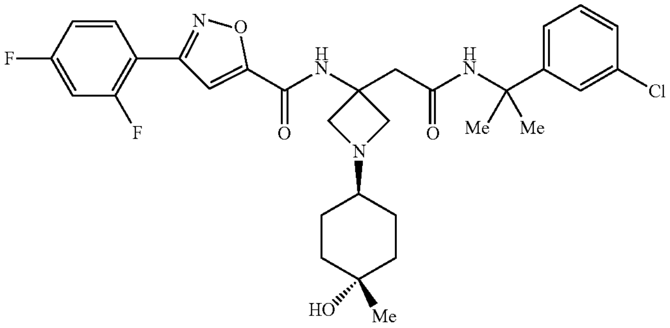 [SMILES: CC(C)(NC(=O)CC1(NC(=O)c2cc(-c3ccc(F)cc3F)no2)CN([C@H]2CC[C@](C)(O)CC2)C1)c1cccc(Cl)c1] |
| 1.048 | 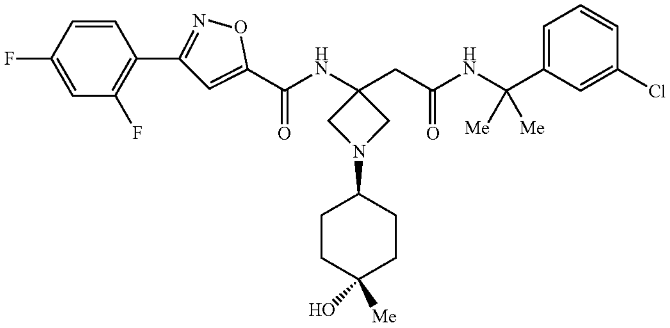 [SMILES: CC(C)(NC(=O)CC1(NC(=O)c2cc(-c3ccc(F)cc3F)no2)CN([C@H]2CC[C@](C)(O)CC2)C1)c1cccc(Cl)c1] |

-continued
| Compound ID | Structure |
| --- | --- |
| 1.049 | 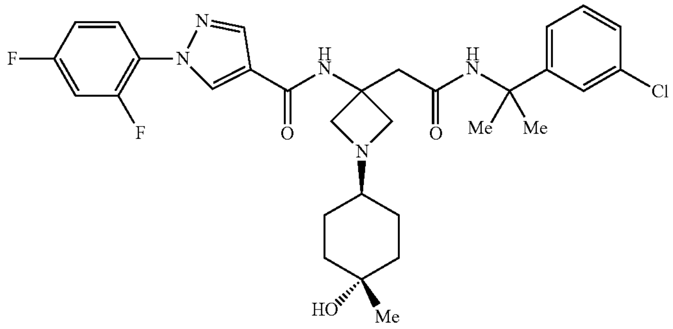 [SMILES: CC(C)(NC(=O)CC1(NC(=O)c2cnn(-c3ccc(F)cc3F)c2)CN([C@H]2CC[C@](C)(O)CC2)C1)c1cccc(Cl)c1] |
| 1.050 | 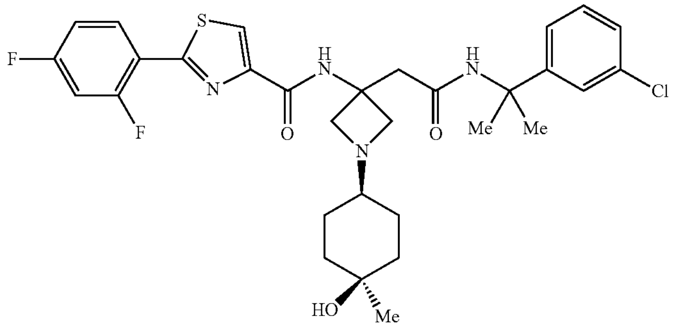 [SMILES: CC(C)(NC(=O)CC1(NC(=O)c2csc(-c3ccc(F)cc3F)n2)CN([C@H]2CC[C@@](C)(O)CC2)C1)c1cccc(Cl)c1] |
| 1.051 | 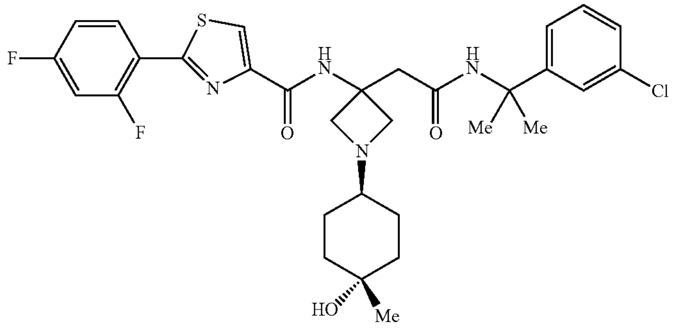 [SMILES: CC(C)(NC(=O)CC1(NC(=O)c2csc(-c3ccc(F)cc3F)n2)CN([C@H]2CC[C@](C)(O)CC2)C1)c1cccc(Cl)c1] |
| 1.052 | 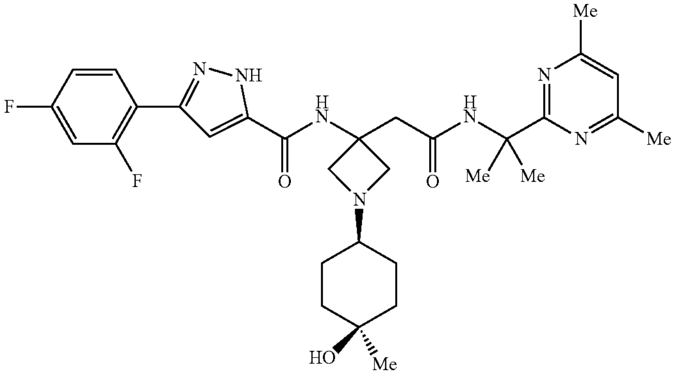 [SMILES: Cc1cc(C)nc(C(C)(C)NC(=O)CC2(NC(=O)c3cc(-c4ccc(F)cc4F)n[nH]3)CN([C@H]3CC[C@@](C)(O)CC3)C2)n1] |

-continued
| Compound ID | Structure |
| --- | --- |
| 1.053 | 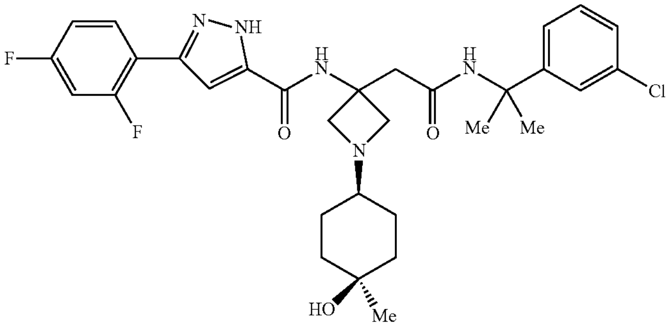 [SMILES: CC(C)(NC(=O)CC1(NC(=O)c2cc(-c3ccc(F)cc3F)n[nH]2)CN([C@H]2CC[C@@](C)(O)CC2)C1)c1cccc(Cl)c1] |
| 1.054 | 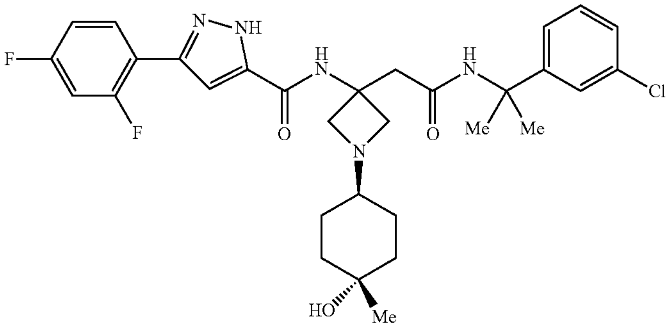 [SMILES: CC(C)(NC(=O)CC1(NC(=O)c2cc(-c3ccc(F)cc3F)n[nH]2)CN([C@H]2CC[C@](C)(O)CC2)C1)c1cccc(Cl)c1] |
| 1.055 | 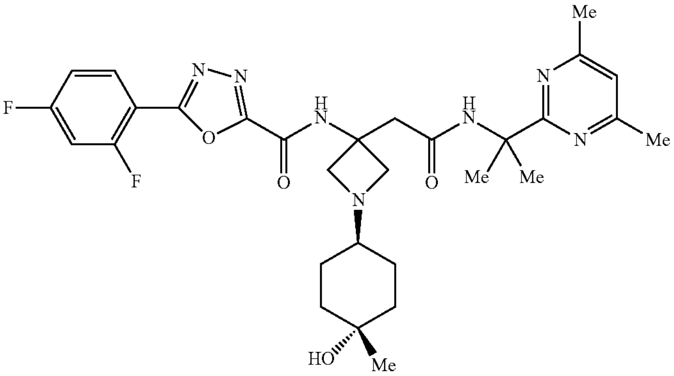 [SMILES: Cc1cc(C)nc(C(C)(C)NC(=O)CC2(NC(=O)c3nnc(-c4ccc(F)cc4F)o3)CN([C@H]3CC[C@](C)(O)CC3)C2)n1] |
| 1.056 | 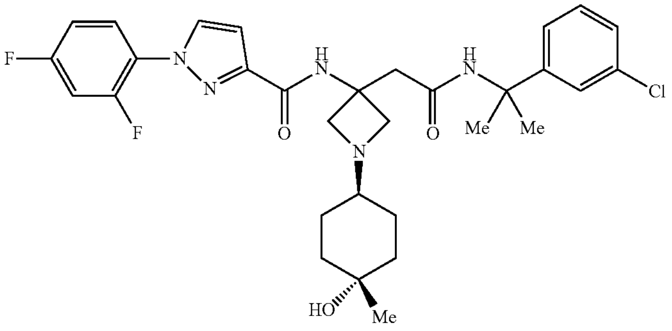 [SMILES: CC(C)(NC(=O)CC1(NC(=O)c2ccn(-c3ccc(F)cc3F)n2)CN([C@H]2CC[C@](C)(O)CC2)C1)c1cccc(Cl)c1] |

-continued
| Compound ID | Structure |
|---|---|
| 1.057 | 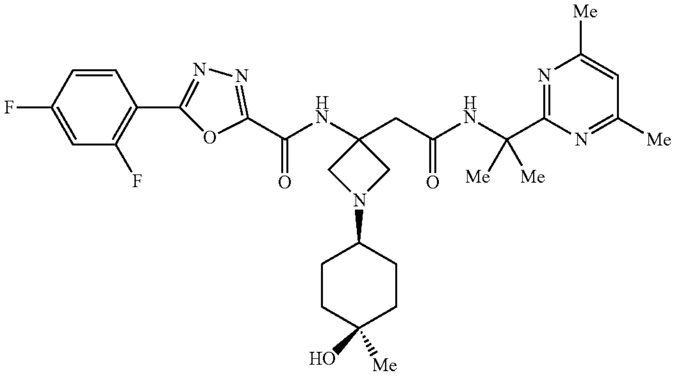 [SMILES: Cc1cc(C)nc(C(C)(C)NC(=O)CC2(NC(=O)c3nnc(-c4ccc(F)cc4F)o3)CN([C@H]3CC[C@@](C)(O)CC3)C2)n1] |
| 1.058 | 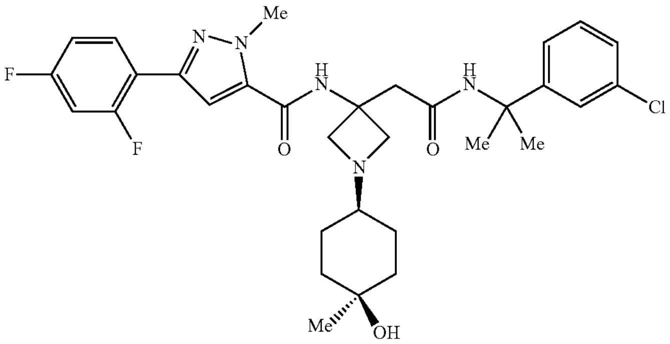 [SMILES: Cn1nc(-c2ccc(F)cc2F)cc1C(=O)NC1(CC(=O)NC(C)(C)c2cccc(Cl)c2)CN([C@H]2CC[C@@](C)(O)CC2)C1] |
| 1.059 | 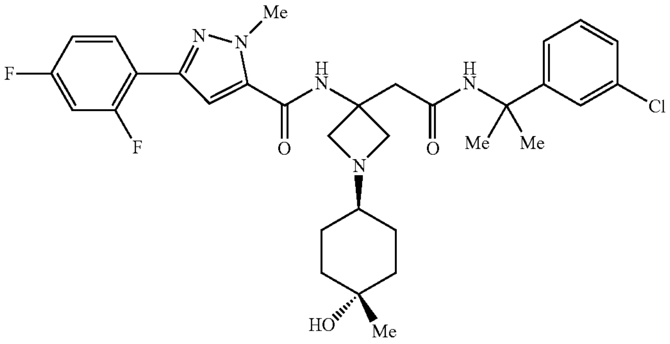 [SMILES: Cn1nc(-c2ccc(F)cc2F)cc1C(=O)NC1(CC(=O)NC(C)(C)c2cccc(Cl)c2)CN([C@H]2CC[C@](C)(O)CC2)C1] |
| 1.060 | 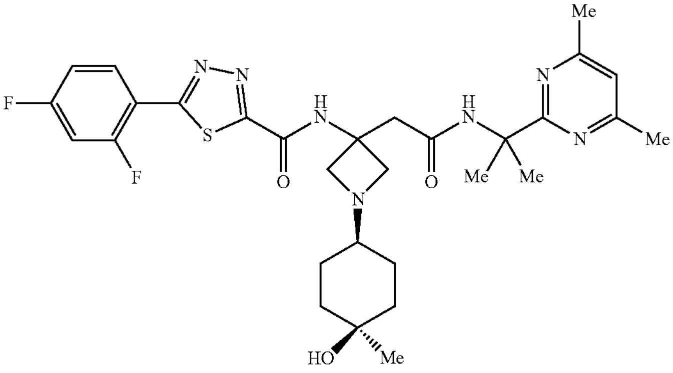 [SMILES: Cc1cc(C)nc(C(C)(C)NC(=O)CC2(NC(=O)c3nnc(-c4ccc(F)cc4F)s3)CN([C@H]3CC[C@@](C)(O)CC3)C2)n1] |

-continued
| Compound ID | Structure |
| --- | --- |
| 1.061 | 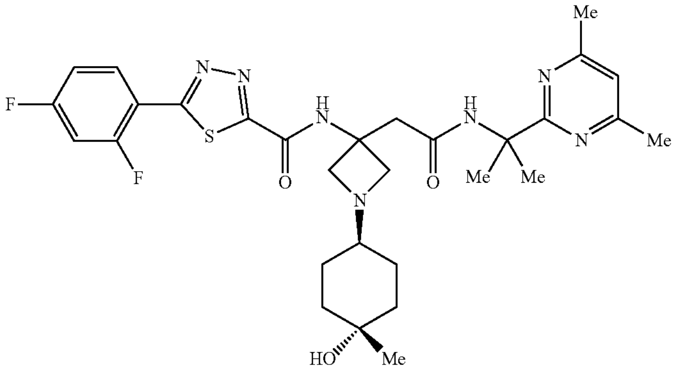 |
| 1.062 | 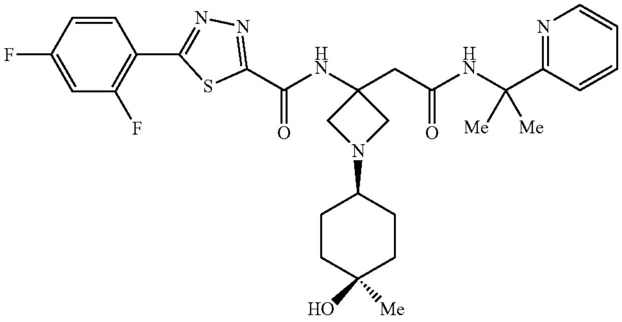 [SMILES: CC(C)(NC(=O)CC1(NC(=O)c2nnc(-c3ccc(F)cc3F)s2)CN([C@H]2CC[C@@](C)(O)CC2)C1)c1ccccn1] |
| 1.063 | 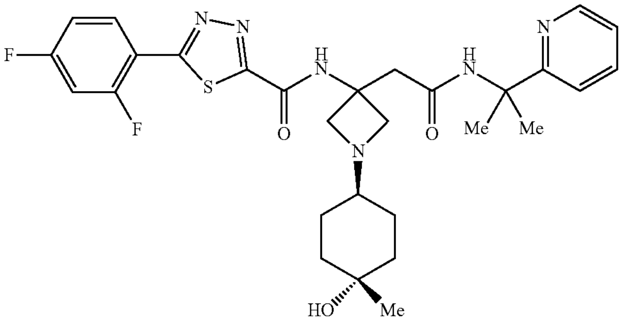 [SMILES: CC(C)(NC(=O)CC1(NC(=O)c2nnc(-c3ccc(F)cc3F)s2)CN([C@H]2CC[C@](C)(O)CC2)C1)c1ccccn1] |
| 1.064 | 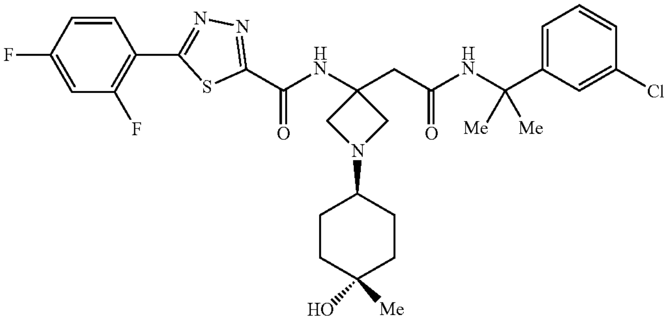 [SMILES: CC(C)(NC(=O)CC1(NC(=O)c2nnc(-c3ccc(F)cc3F)s2)CN([C@H]2CC[C@](C)(O)CC2)C1)c1cccc(Cl)c1] |

-continued
| Compound ID | Structure |
| --- | --- |
| 1.065 | 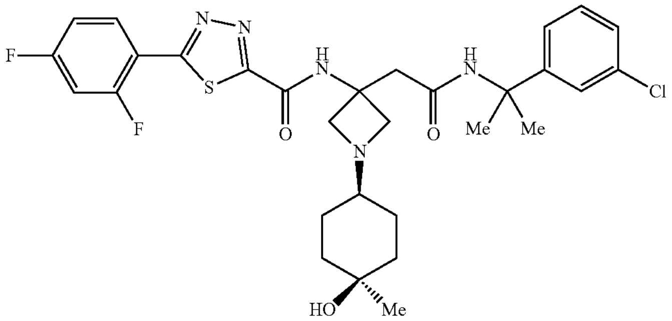 [SMILES: CC(C)(NC(=O)CC1(NC(=O)c2nnc(-c3ccc(F)cc3F)s2)CN([C@H]2CC[C@@](C)(O)CC2)C1)c1cccc(Cl)c1] |
| 1.066 | 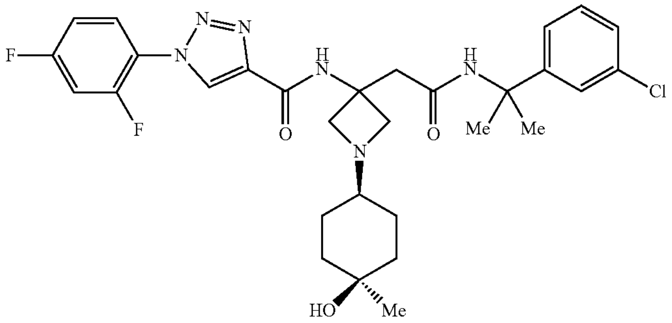 [SMILES: CC(C)(NC(=O)CC1(NC(=O)c2cn(-c3ccc(F)cc3F)nn2)CN([C@H]2CC[C@@](C)(O)CC2)C1)c1cccc(Cl)c1] |
| 1.067 | 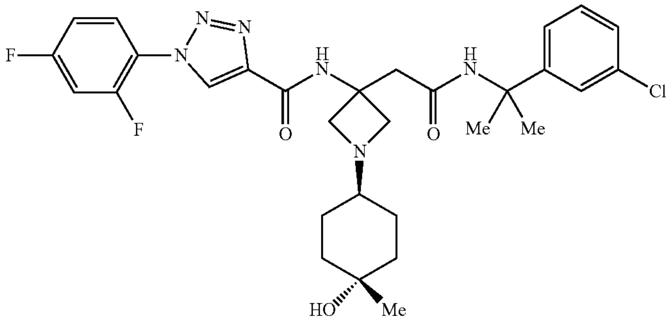 [SMILES: CC(C)(NC(=O)CC1(NC(=O)c2cn(-c3ccc(F)cc3F)nn2)CN([C@H]2CC[C@](C)(O)CC2)C1)c1cccc(Cl)c1] |
| 1.068 | 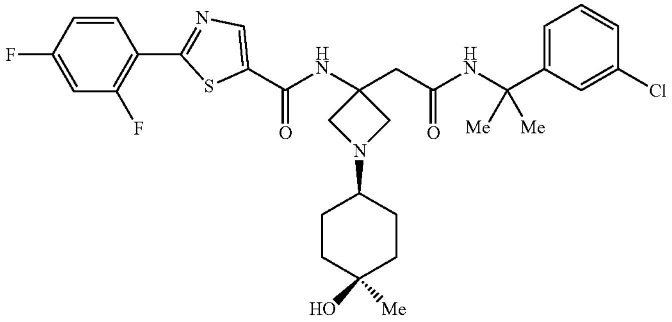 |

-continued
| Compound ID | Structure |
| --- | --- |
| 1.069 | 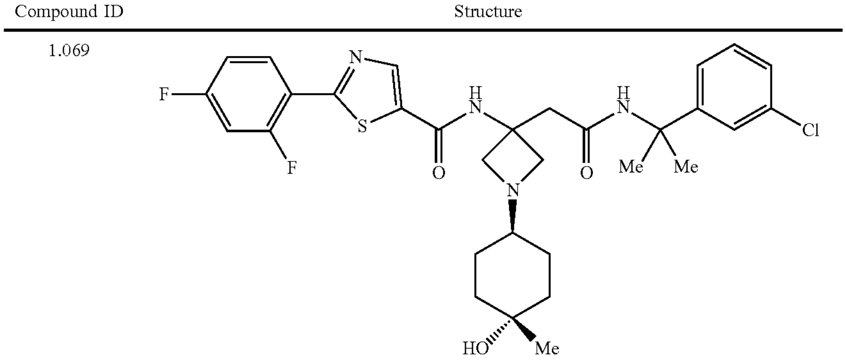 |
| 1.070 | 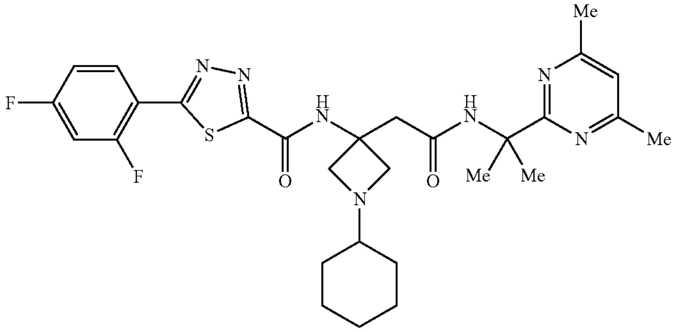 [SMILES: Cc1cc(C)nc(C(C)(C)NC(=O)CC2(NC(=O)c3nnc(-c4ccc(F)cc4F)s3)CN(C3CCCCC3)C2)n1] |
| 1.071 | 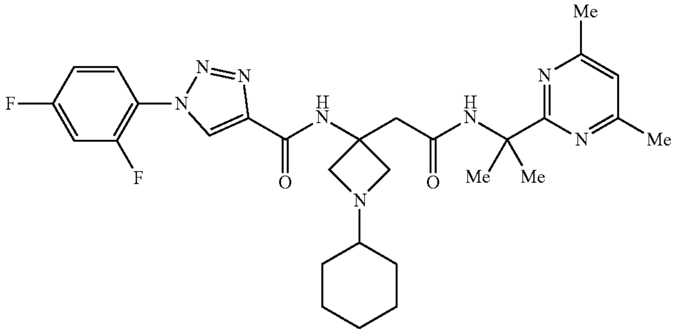 [SMILES: Cc1cc(C)nc(C(C)(C)NC(=O)CC2(NC(=O)c3cn(-c4ccc(F)cc4F)nn3)CN(C3CCCCC3)C2)n1] |
| 1.072 | 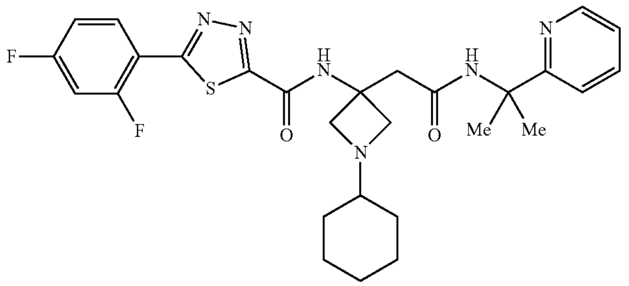 [SMILES: CC(C)(NC(=O)CC1(NC(=O)c2nnc(-c3ccc(F)cc3F)s2)CN(C2CCCCC2)C1)c1ccccn1] |
| 1.073 | 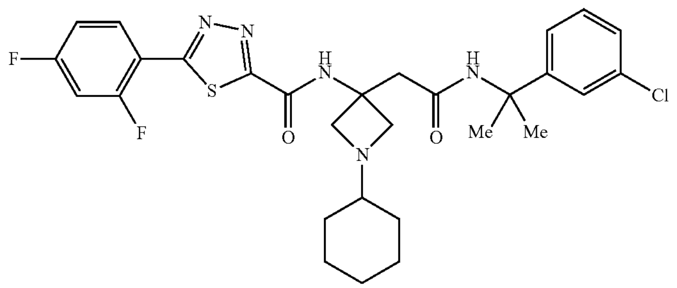 [SMILES: CC(C)(NC(=O)CC1(NC(=O)c2nnc(-c3ccc(F)cc3F)s2)CN(C2CCCCC2)C1)c1cccc(Cl)c1] |

-continued
| Compound ID | Structure |
|---|---|
| 1.074 | 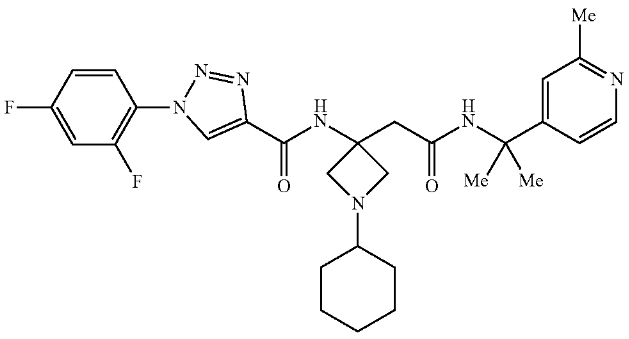 [SMILES: Cc1cc(C(C)(C)NC(=O)CC2(NC(=O)c3cn(-c4ccc(F)cc4F)nn3)CN(C3CCCCC3)C2)ccn1] |
| 1.075 | 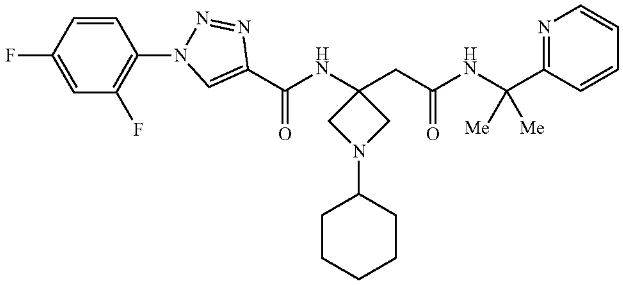 [SMILES: CC(C)(NC(=O)CC1(NC(=O)c2cn(-c3ccc(F)cc3F)nn2)CN(C2CCCCC2)C1)c1ccccn1] |
| 1.076 | 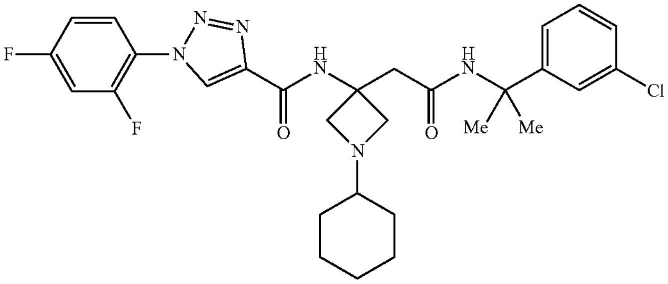 [SMILES: CC(C)(NC(=O)CC1(NC(=O)c2cn(-c3ccc(F)cc3F)nn2)CN(C2CCCCC2)C1)c1cccc(Cl)c1] |
| 1.077 | 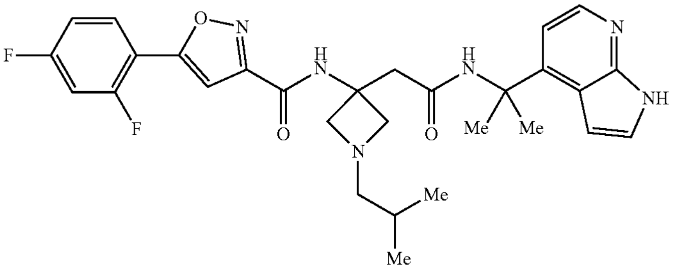 [SMILES: CC(C)CN1CC(CC(=O)NC(C)(C)c2ccnc3[nH]ccc23)(NC(=O)c2cc(-c3ccc(F)cc3F)on2)C1] |
| 1.078 | 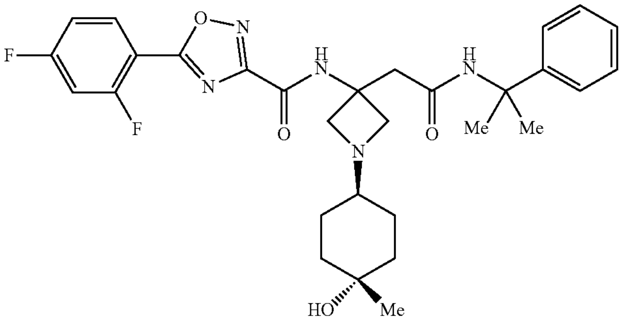 |

-continued
| Compound ID | Structure |
|---|---|
| 1.079 | 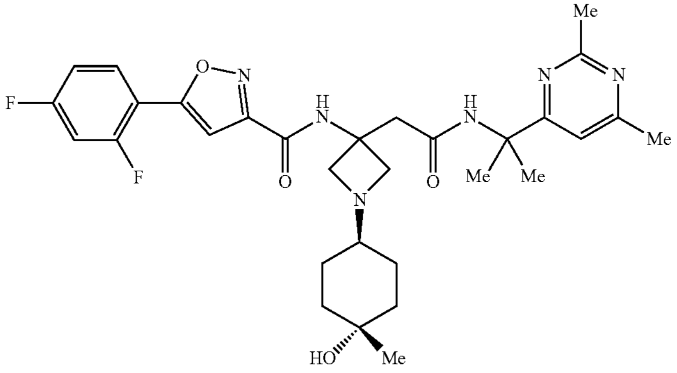 |
| 1.081 | 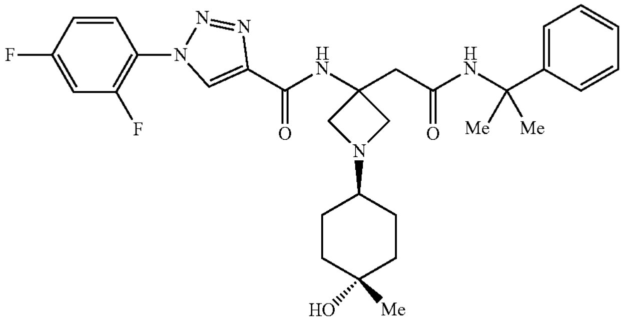 [SMILES: CC(C)(NC(=O)CC1(NC(=O)c2cn(-c3ccc(F)cc3F)nn2)CN([C@H]2CC[C@](C)(O)CC2)C1)c1ccccc1] |
| 1.082 | 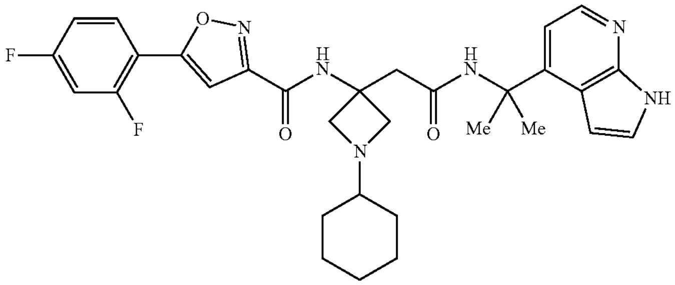 [SMILES: CC(C)(NC(=O)CC1(NC(=O)c2cc(-c3ccc(F)cc3F)on2)CN(C2CCCCC2)C1)c1ccnc2[nH]ccc12] |
| 1.083 | 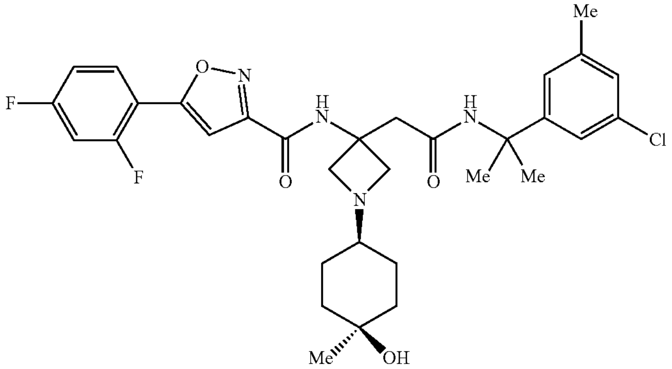 |

-continued
| Compound ID | Structure |
|---|---|
| 1.084 | 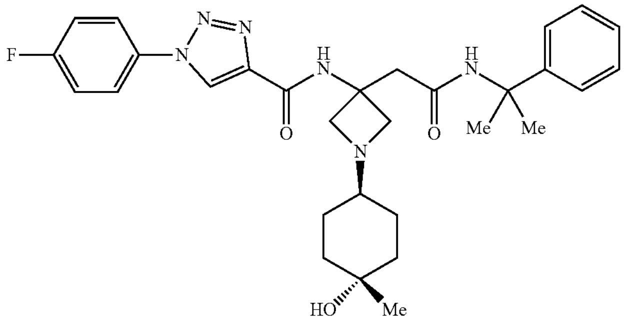 |
| 1.085 | 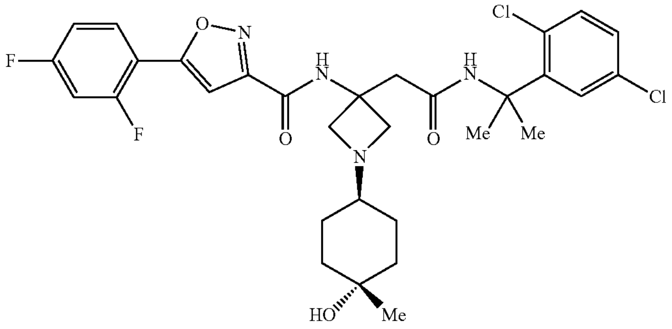 [SMILES: CC(C)(NC(=O)CC1(NC(=O)c2cc(-c3ccc(F)cc3F)on2)CN([C@H]2CC[C@](C)(O)CC2)C1)c1cc(Cl)ccc1Cl] |
| 1.086 | 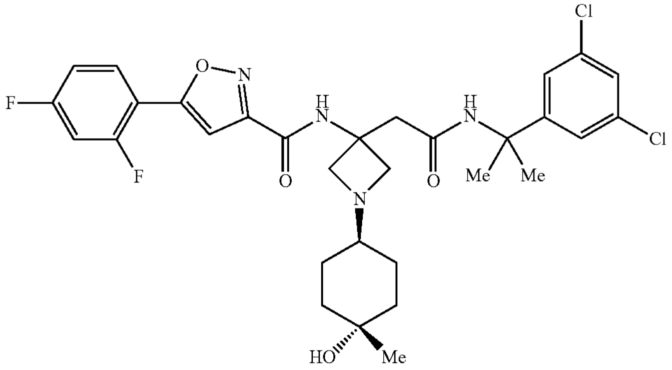 [SMILES: CC(C)(NC(=O)CC1(NC(=O)c2cc(-c3ccc(F)cc3F)on2)CN([C@H]2CC[C@](C)(O)CC2)C1)c1cc(Cl)cc(Cl)c1] |
| 1.087 | 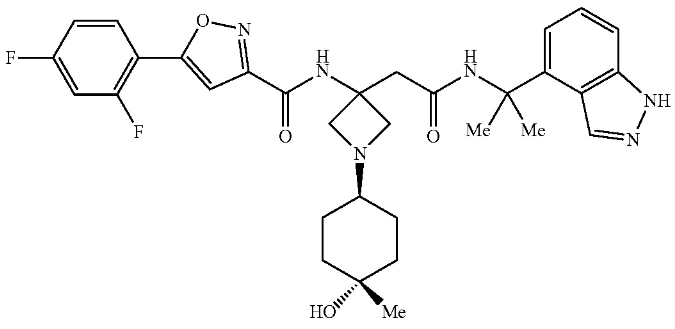 [SMILES: CC(C)(NC(=O)CC1(NC(=O)c2cc(-c3ccc(F)cc3F)on2)CN([C@H]2CC[C@](C)(O)CC2)C1)c1cccc2[nH]ncc12] |

-continued
| Compound ID | Structure |
|---|---|
| 1.088 | 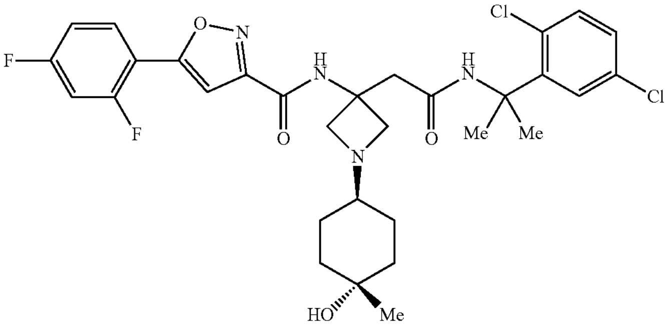 [SMILES: CC(C)(NC(=O)CC1(NC(=O)c2cc(-c3ccc(F)cc3F)on2)CN([C@H]2CC[C@](C)(O)CC2)C1)c1cc(Cl)ccc1Cl] |
| 1.089 | 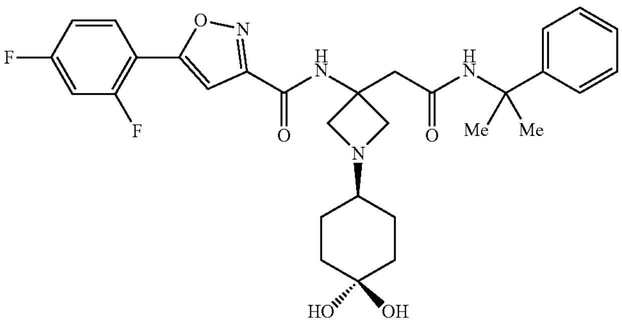 |
| 1.090 | 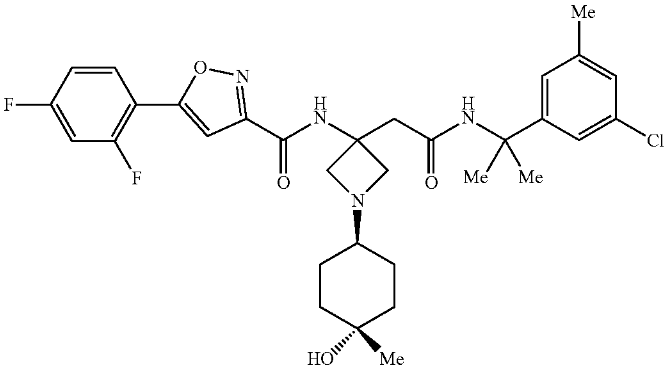 |
| 1.091 | 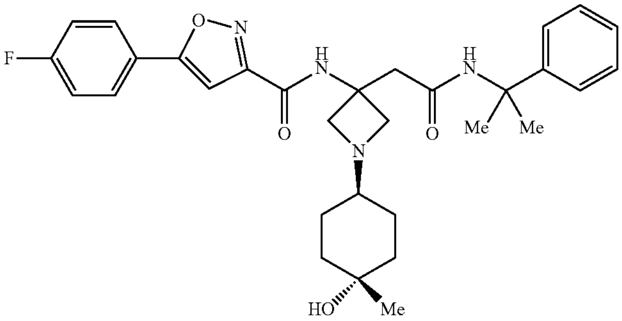 [SMILES: CC(C)(NC(=O)CC1(NC(=O)c2cc(-c3ccc(F)cc3)on2)CN([C@H]2CC[C@](C)(O)CC2)C1)c1ccccc1] |

-continued
| Compound ID | Structure |
| --- | --- |
| 1.092 | 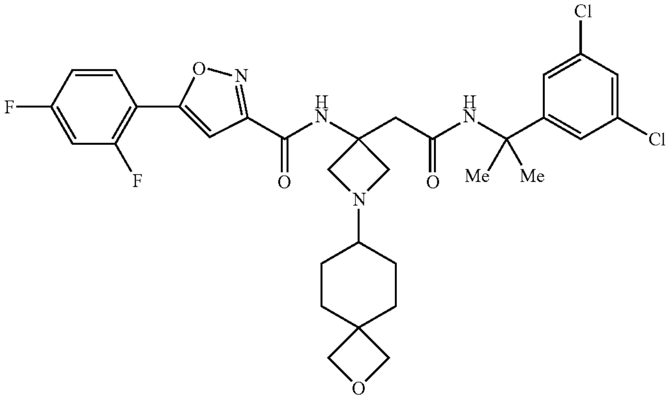 [SMILES: CC(C)(NC(=O)CC1(NC(=O)c2cc(-c3ccc(F)cc3F)on2)CN(C2CCC3(CC2)COC3)C1)c1cc(Cl)cc(Cl)c1] |
| 1.093 | 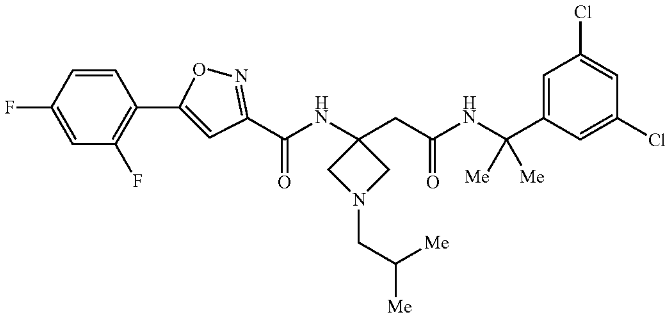 [SMILES: CC(C)CN1CC(CC(=O)NC(C)(C)c2cc(Cl)cc(Cl)c2)(NC(=O)c2cc(-c3ccc(F)cc3F)on2)C1] |
| 1.094 | 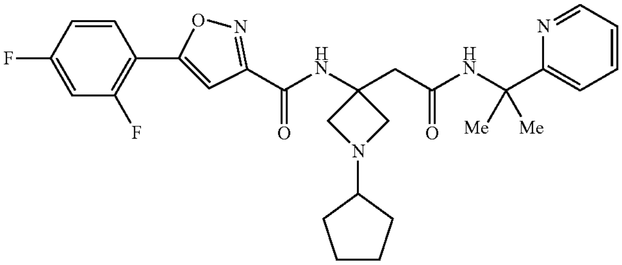 [SMILES: CC(C)(NC(=O)CC1(NC(=O)c2cc(-c3ccc(F)cc3F)on2)CN(C2CCCC2)C1)c1ccccn1] |
| 1.095 | 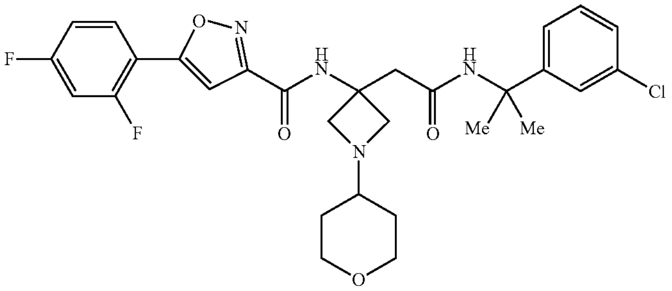 [SMILES: CC(C)(NC(=O)CC1(NC(=O)c2cc(-c3ccc(F)cc3F)on2)CN(C2CCOCC2)C1)c1cccc(Cl)c1] |
| 1.096 | 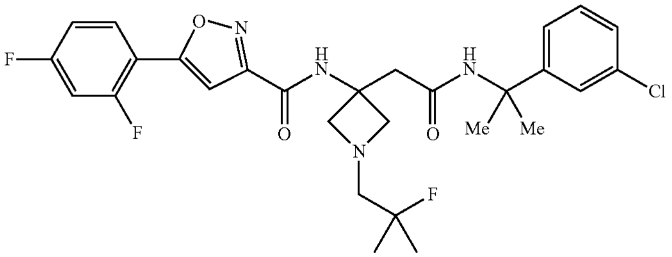 [SMILES: CC(C)(F)CN1CC(CC(=O)NC(C)(C)c2cccc(Cl)c2)(NC(=O)c2cc(-c3ccc(F)cc3F)on2)C1] |

-continued
| Compound ID | Structure |
| --- | --- |
| 1.097 | 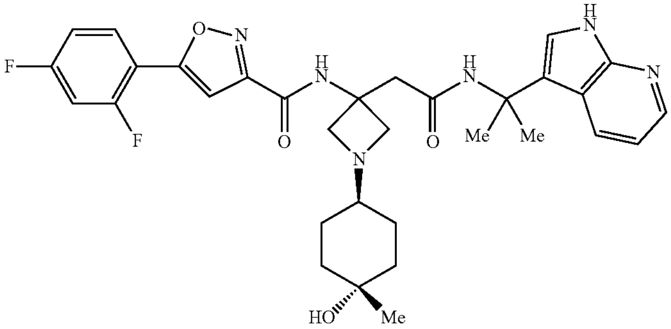 [SMILES: CC(C)(NC(=O)CC1(NC(=O)c2cc(-c3ccc(F)cc3F)on2)CN([C@H]2CC[C@](C)(O)CC2)C1)c1c[nH]c2ncccc12] |
| 1.098 | 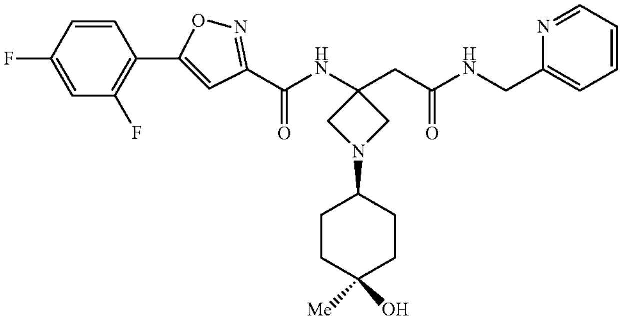 [SMILES: C[C@]1(O)CC[C@@H](N2CC(CC(=O)NCc3ccccn3)(NC(=O)c3cc(-c4ccc(F)cc4F)on3)C2)CC1] |
| 1.099 | 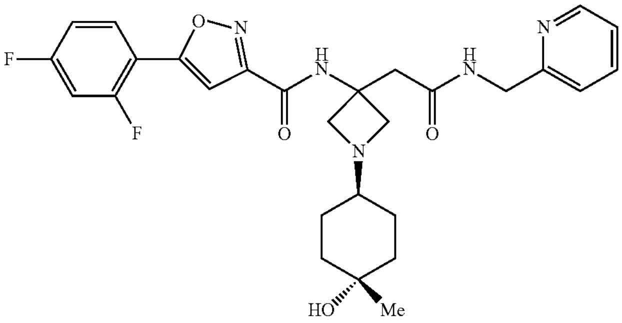 [SMILES: C[C@]1(O)CC[C@H](N2CC(CC(=O)NCc3ccccn3)(NC(=O)c3cc(-c4ccc(F)cc4F)on3)C2)CC1] |
| 1.100 | 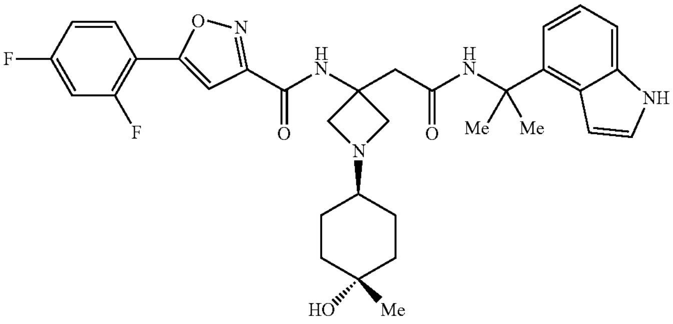 [SMILES: CC(C)(NC(=O)CC1(NC(=O)c2cc(-c3ccc(F)cc3F)on2)CN([C@H]2CC[C@](C)(O)CC2)C1)c1cccc2[nH]ccc12] |

-continued
| Compound ID | Structure |
| --- | --- |
| 1.101 | 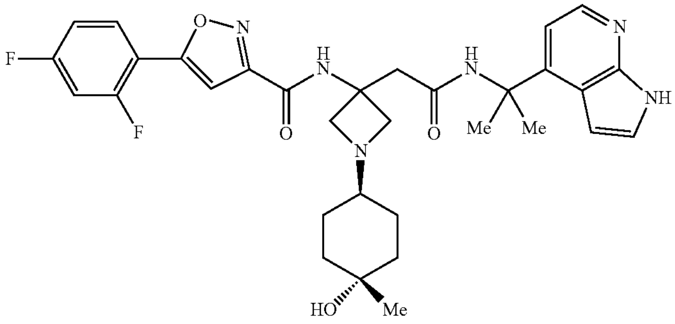 [SMILES: CC(C)(NC(=O)CC1(NC(=O)c2cc(-c3ccc(F)cc3F)on2)CN([C@H]2CC[C@](C)(O)CC2)C1)c1ccnc2[nH]ccc12] |
| 1.102 | 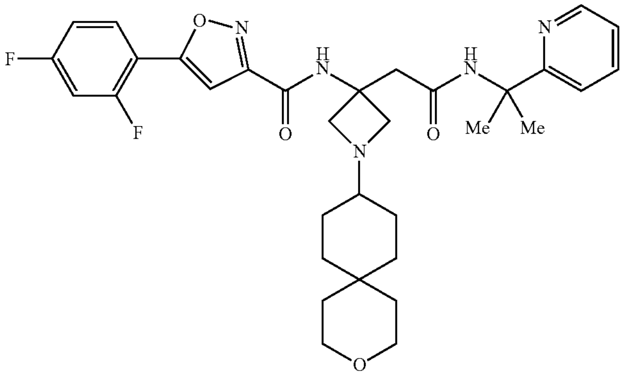 [SMILES: CC(C)(NC(=O)CC1(NC(=O)c2cc(-c3ccc(F)cc3F)on2)CN(C2CCC3(CCOCC3)CC2)C1)c1ccccn1] |
| 1.103 | 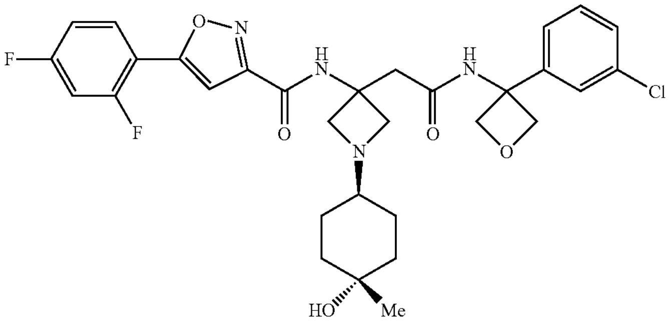 [SMILES: C[C@]1(O)CC[C@H](N2CC(CC(=O)NC3(c4cccc(Cl)c4)COC3)(NC(=O)c3cc(-c4ccc(F)cc4F)on3)C2)CC1] |
| 1.104 | 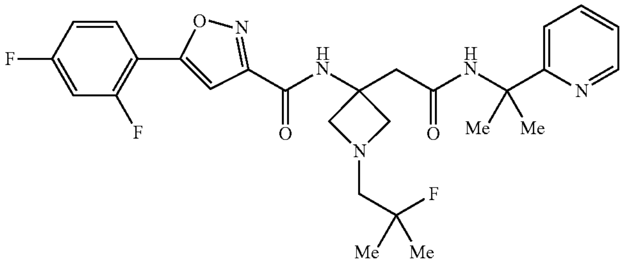 [SMILES: CC(C)(F)CN1CC(CC(=O)NC(C)(C)c2ccccn2)(NC(=O)c2cc(-c3ccc(F)cc3F)on2)C1] |

-continued
| Compound ID | Structure |
| --- | --- |
| 1.105 | 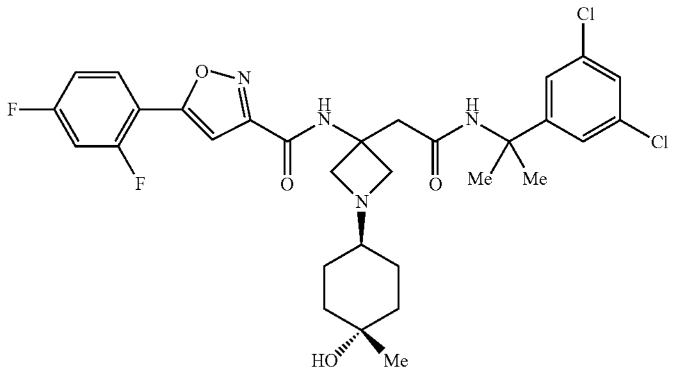 [SMILES: CC(C)(NC(=O)CC1(NC(=O)c2cc(-c3ccc(F)cc3F)on2)CN([C@H]2CC[C@](C)(O)CC2)C1)c1cc(Cl)cc(Cl)c1] |
| 1.106 | 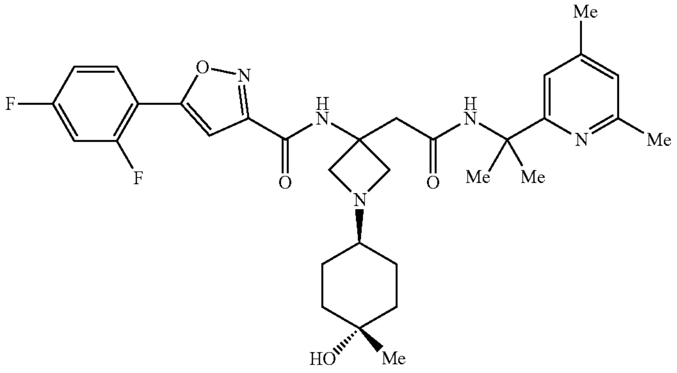 |
| 1.107 | 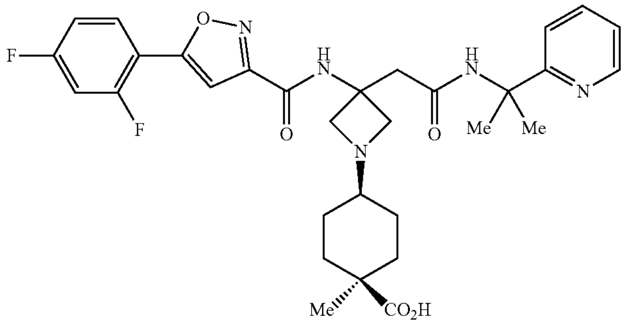 |
| 1.108 | 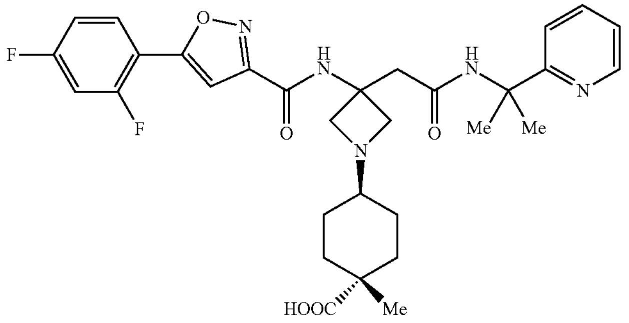 |

-continued
| Compound ID | Structure |
| --- | --- |
| 1.109 | 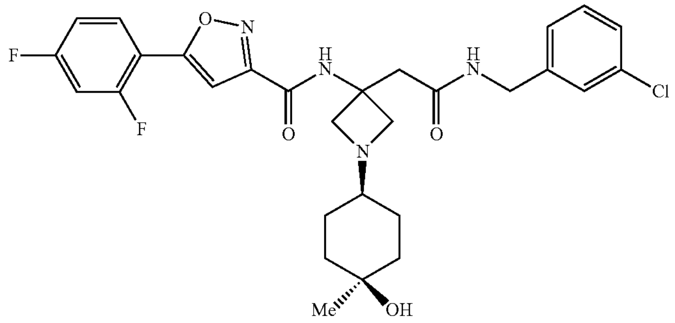 [SMILES: C[C@]1(O)CC[C@@H](N2CC(CC(=O)NCc3cccc(Cl)c3)(NC(=O)c3cc(-c4ccc(F)cc4F)on3)C2)CC1] |
| 1.110 | 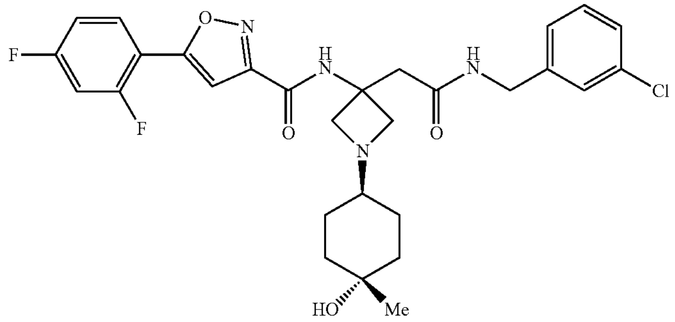 |
| 1.111 | 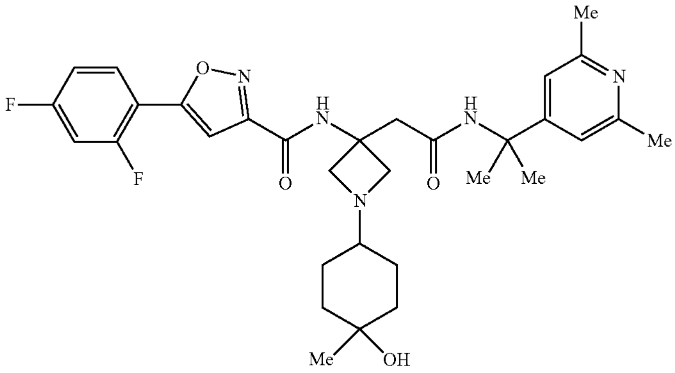 [SMILES: Cc1cc(C(C)(C)NC(=O)CC2(NC(=O)c3cc(-c4ccc(F)cc4F)on3)CN(C3CCC(C)(O)CC3)C2)cc(C)n1] |
| 1.112 | 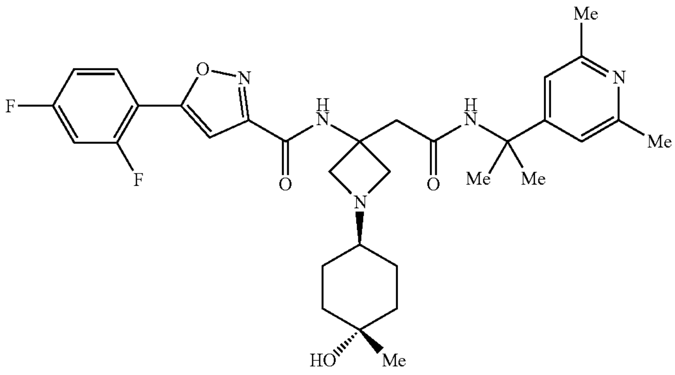 [SMILES: Cc1cc(C(C)(C)NC(=O)CC2(NC(=O)c3cc(-c4ccc(F)cc4F)on3)CN([C@H]3CC[C@](C)(O)CC3)C2)cc(C)n1] |

-continued
| Compound ID | Structure |
| --- | --- |
| 1.113 | 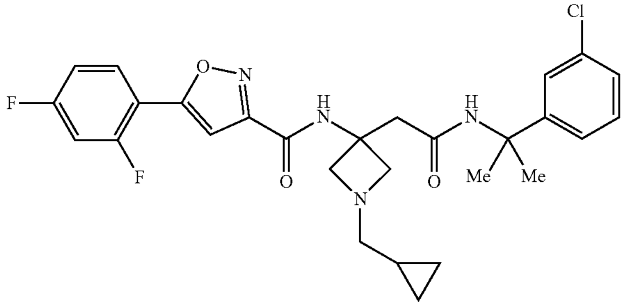 [SMILES: CC(C)(NC(=O)CC1(NC(=O)c2cc(-c3ccc(F)cc3F)on2)CN(CC2CC2)C1)c1cccc(Cl)c1] |
| 1.114 | 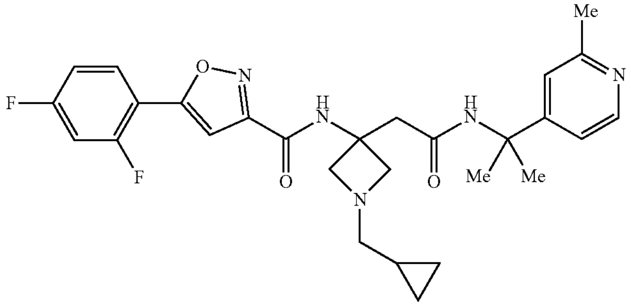 [SMILES: Cc1cc(C(C)(C)NC(=O)CC2(NC(=O)c3cc(-c4ccc(F)cc4F)on3)CN(CC3CC3)C2)ccn1] |
| 1.115 | 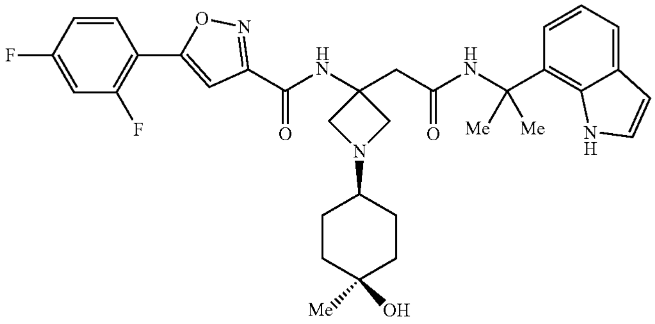 [SMILES: CC(C)(NC(=O)CC1(NC(=O)c2cc(-c3ccc(F)cc3F)on2)CN([C@H]2CC[C@](C)(O)CC2)C1)c1cccc2cc[nH]c12] |
| 1.116 | 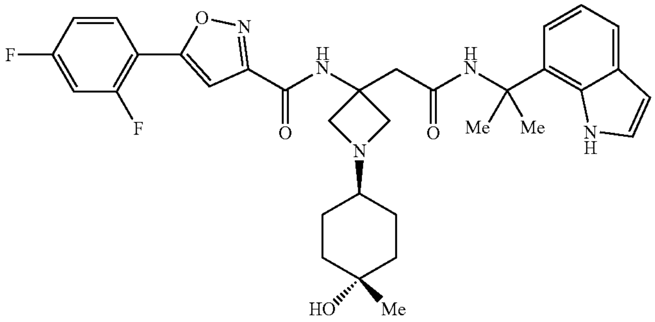 |
| 1.117 | 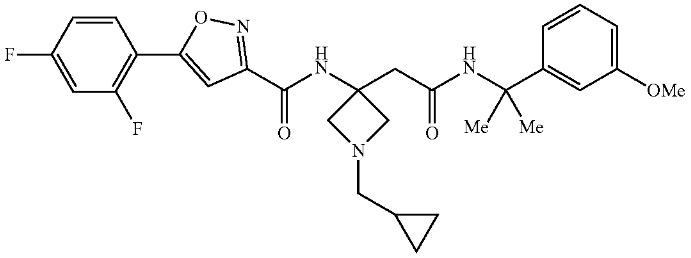 [SMILES: COc1cccc(C(C)(C)NC(=O)CC2(NC(=O)c3cc(-c4ccc(F)cc4F)on3)CN(CC3CC3)C2)c1] |

-continued
| Compound ID | Structure |
| --- | --- |
| 1.118 | 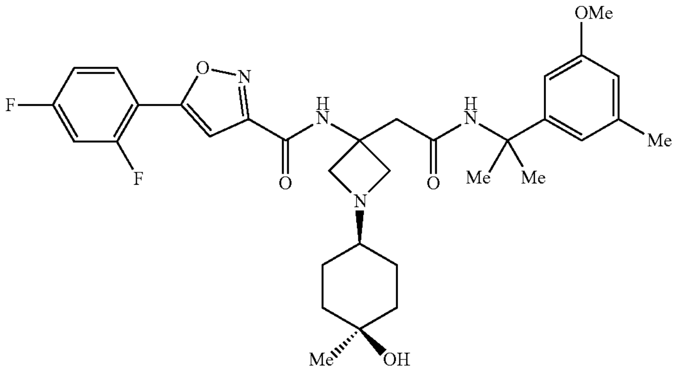 |
| 1.119 | 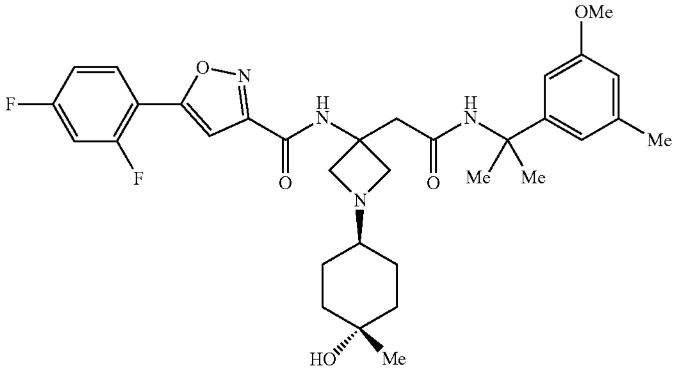 |
| 1.120 | 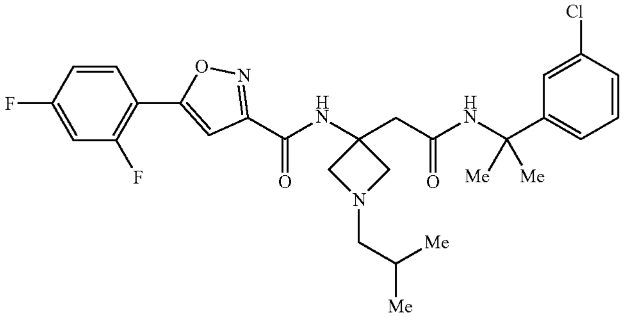 [SMILES: CC(C)CN1CC(CC(=O)NC(C)(C)c2cccc(Cl)c2)(NC(=O)c2cc(-c3ccc(F)cc3F)on2)C1] |
| 1.121 | 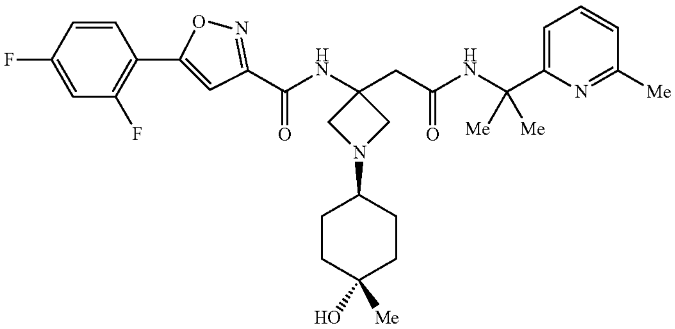 [SMILES: Cc1cccc(C(C)(C)NC(=O)CC2(NC(=O)c3cc(-c4ccc(F)cc4F)on3)CN([C@H]3CC[C@](C)(O)CC3)C2)n1] |

-continued
| Compound ID | Structure |
|---|---|
| 1.122 | 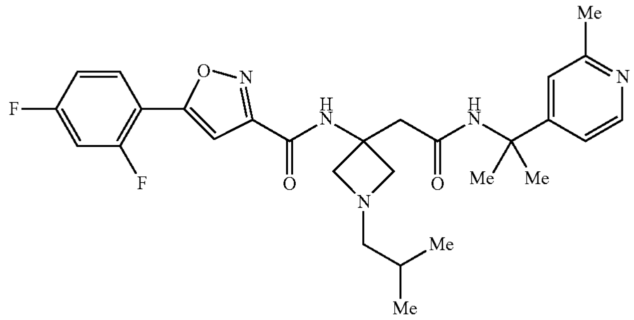 [SMILES: Cc1cc(C(C)(C)NC(=O)CC2(NC(=O)c3cc(-c4ccc(F)cc4F)on3)CN(CC(C)C)C2)ccn1] |
| 1.123 | 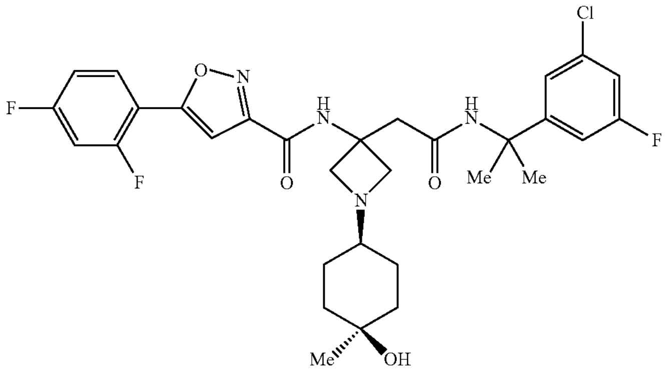 [SMILES: CC(C)(NC(=O)CC1(NC(=O)c2cc(-c3ccc(F)cc3F)on2)CN([C@H]2CC[C@@](C)(O)CC2)C1)c1cc(F)cc(Cl)c1] |
| 1.124 | 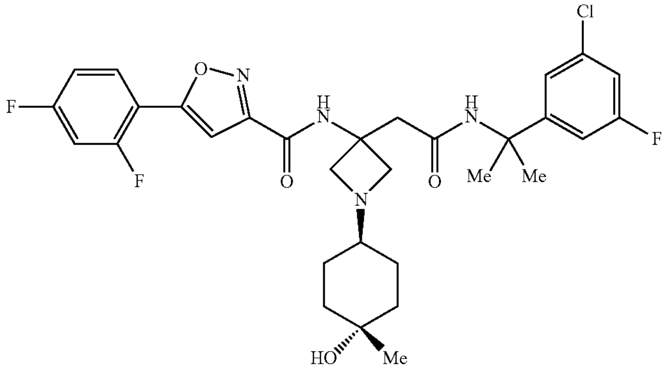 [SMILES: CC(C)(NC(=O)CC1(NC(=O)c2cc(-c3ccc(F)cc3F)on2)CN([C@H]2CC[C@](C)(O)CC2)C1)c1cc(F)cc(Cl)c1] |
| 1.125 | 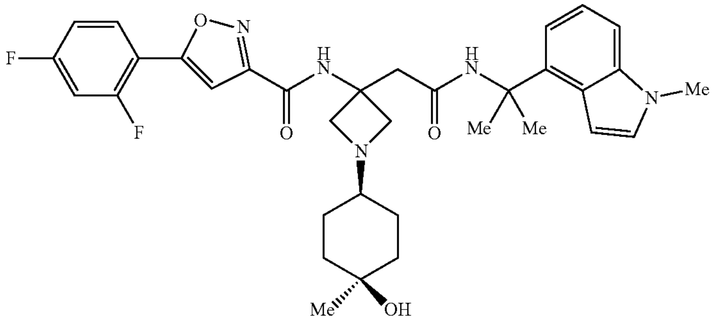 [SMILES: Cn1ccc2c(C(C)(C)NC(=O)CC3(NC(=O)c4cc(-c5ccc(F)cc5F)on4)CN([C@H]4CC[C@@](C)(O)CC4)C3)cccc21] |

-continued
| Compound ID | Structure |
|---|---|
| 1.126 | 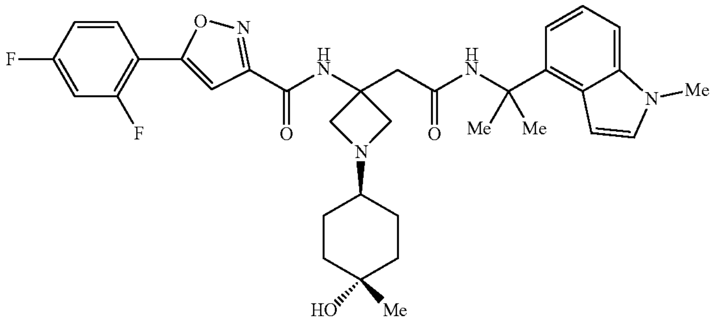 [SMILES: Cn1ccc2c(C(C)(C)NC(=O)CC3(NC(=O)c4cc(-c5ccc(F)cc5F)on4)CN([C@H]4CC[C@](C)(O)CC4)C3)cccc21] |
| 1.127 | 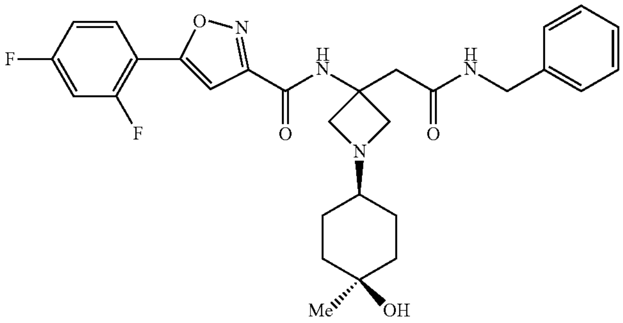 [SMILES: C[C@]1(O)CC[C@@H](N2CC(CC(=O)NCc3ccccc3)(NC(=O)c3cc(-c4ccc(F)cc4F)on3)C2)CC1] |
| 1.128 | 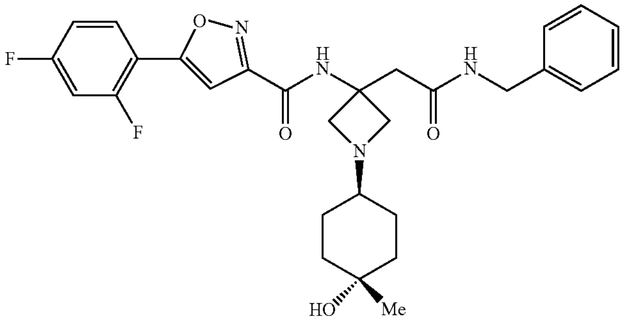 [SMILES: C[C@]1(O)CC[C@H](N2CC(CC(=O)NCc3ccccc3)(NC(=O)c3cc(-c4ccc(F)cc4F)on3)C2)CC1] |
| 1.129 | 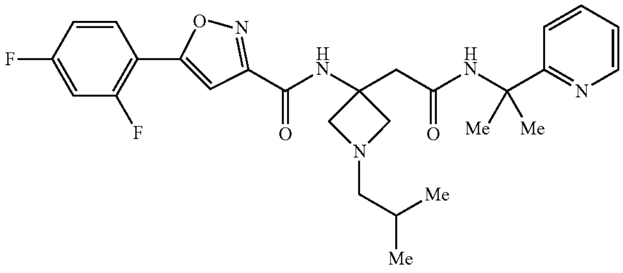 [SMILES: CC(C)CN1CC(CC(=O)NC(C)(C)c2ccccn2)(NC(=O)c2cc(-c3ccc(F)cc3F)on2)C1] |
| 1.130 | 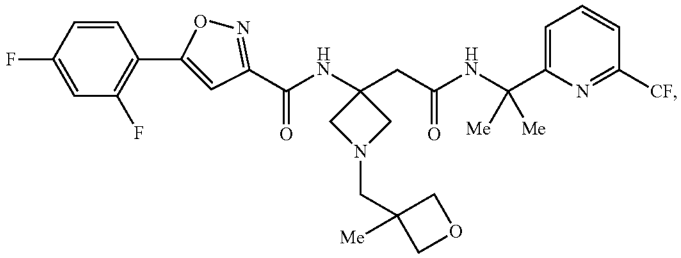 |

-continued
| Compound ID | Structure |
|---|---|
| 1.131 | 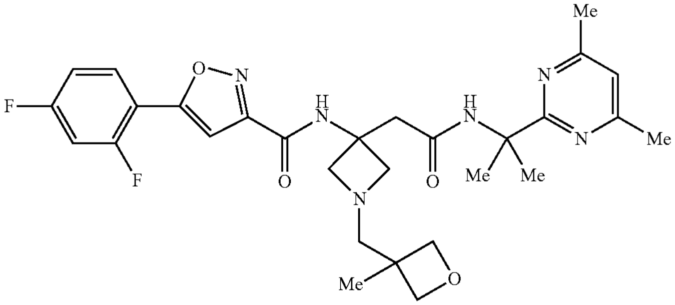 [SMILES: Cc1cc(C)nc(C(C)(C)NC(=O)CC2(NC(=O)c3cc(-c4ccc(F)cc4F)on3)CN(CC3(C)COC3)C2)n1] |
| 1.132 | 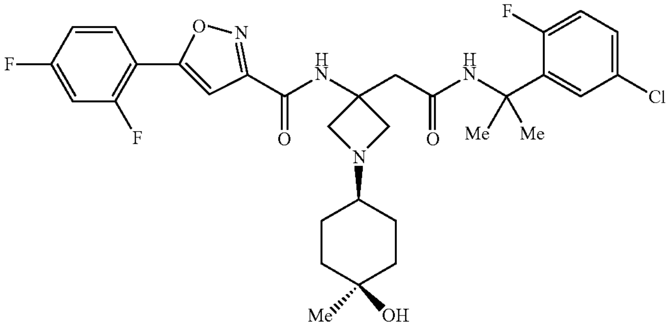 [SMILES: CC(C)(NC(=O)CC1(NC(=O)c2cc(-c3ccc(F)cc3F)on2)CN([C@H]2CC[C@@](C)(O)CC2)C1)c1cc(Cl)ccc1F] |
| 1.133 | 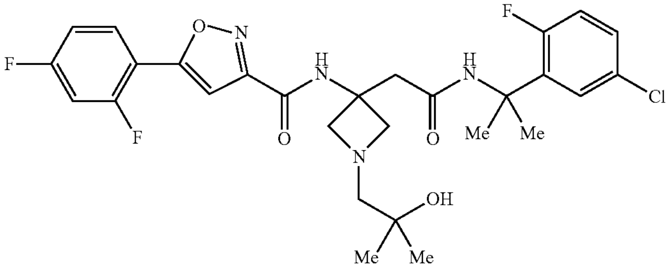 [SMILES: CC(C)(O)CN1CC(CC(=O)NC(C)(C)c2cc(Cl)ccc2F)(NC(=O)c2cc(-c3ccc(F)cc3F)on2)C1] |
| 1.134 | 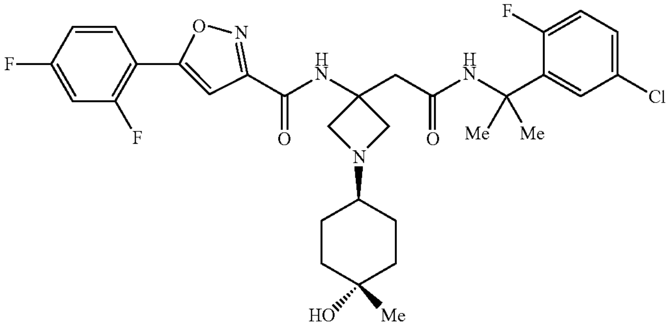 [SMILES: CC(C)(NC(=O)CC1(NC(=O)c2cc(-c3ccc(F)cc3F)on2)CN([C@H]2CC[C@](C)(O)CC2)C1)c1cc(Cl)ccc1F] |
| 1.135 | 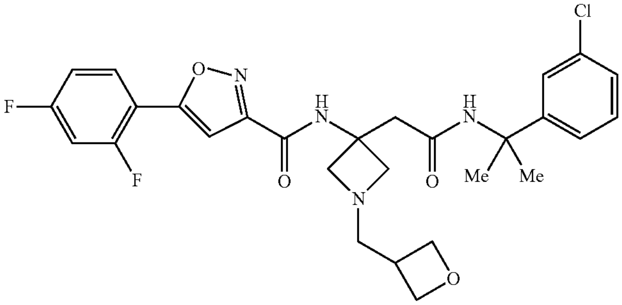 [SMILES: CC(C)(NC(=O)CC1(NC(=O)c2cc(-c3ccc(F)cc3F)on2)CN(CC2COC2)C1)c1cccc(Cl)c1] |

-continued
| Compound ID | Structure |
| --- | --- |
| 1.136 | 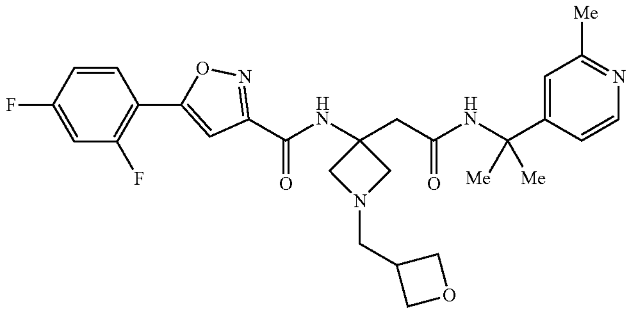 [SMILES: Cc1cc(C(C)(C)NC(=O)CC2(NC(=O)c3cc(-c4ccc(F)cc4F)on3)CN(CC3COC3)C2)ccn1] |
| 1.137 | 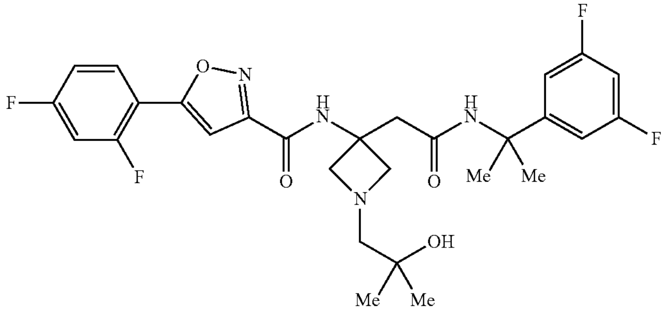 [SMILES: CC(C)(O)CN1CC(CC(=O)NC(C)(C)c2cc(F)cc(F)c2)(NC(=O)c2cc(-c3ccc(F)cc3F)on2)C1] |
| 1.138 | 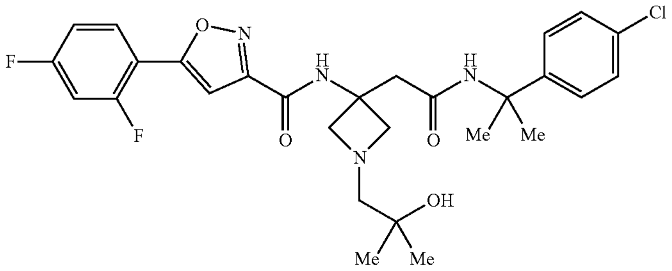 [SMILES: CC(C)(O)CN1CC(CC(=O)NC(C)(C)c2ccc(Cl)cc2)(NC(=O)c2cc(-c3ccc(F)cc3F)on2)C1] |
| 1.139 | 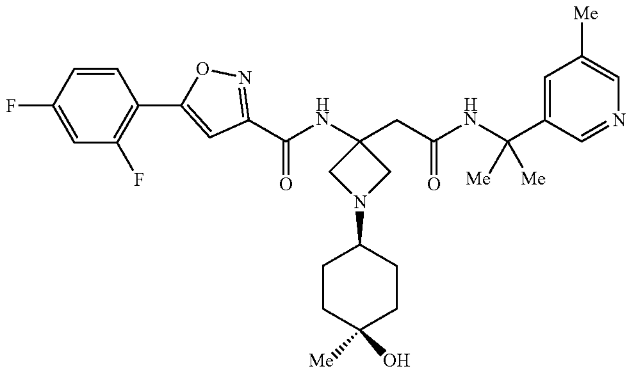 [SMILES: Cc1cncc(C(C)(C)NC(=O)CC2(NC(=O)c3cc(-c4ccc(F)cc4F)on3)CN([C@H]3CC[C@@](C)(O)CC3)C2)c1] |

-continued
| Compound ID | Structure |
| --- | --- |
| 1.140 | 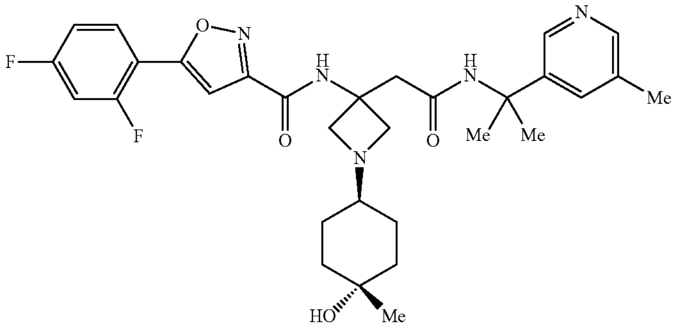 [SMILES: Cc1cncc(C(C)(C)NC(=O)CC2(NC(=O)c3cc(-c4ccc(F)cc4F)on3)CN([C@H]3CC[C@](C)(O)CC3)C2)c1] |
| 1.141 | 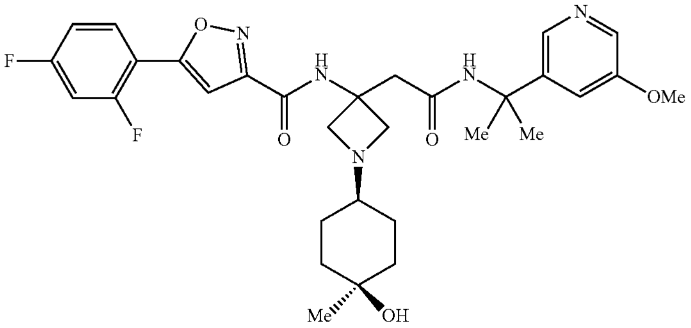 [SMILES: COc1cncc(C(C)(C)NC(=O)CC2(NC(=O)c3cc(-c4ccc(F)cc4F)on3)CN([C@H]3CC[C@@](C)(O)CC3)C2)c1] |
| 1.142 | 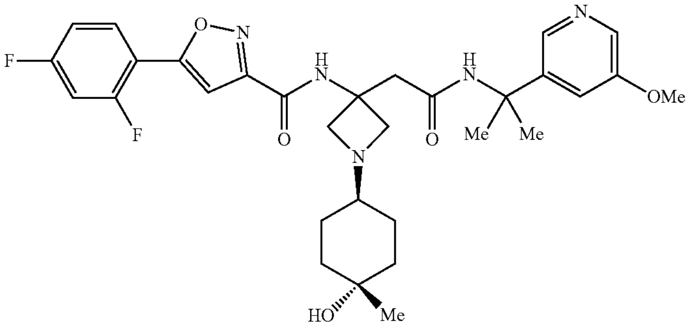 [SMILES: COc1cncc(C(C)(C)NC(=O)CC2(NC(=O)c3cc(-c4ccc(F)cc4F)on3)CN([C@H]3CC[C@](C)(O)CC3)C2)c1] |
| 1.143 | 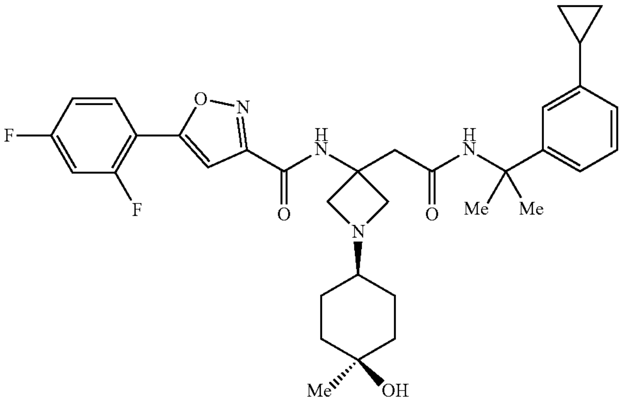 [SMILES: CC(C)(NC(=O)CC1(NC(=O)c2cc(-c3ccc(F)cc3F)on2)CN([C@H]2CC[C@@](C)(O)CC2)C1)c1cccc(C2CC2)c1] |

-continued
| Compound ID | Structure |
|---|---|
| 1.144 | 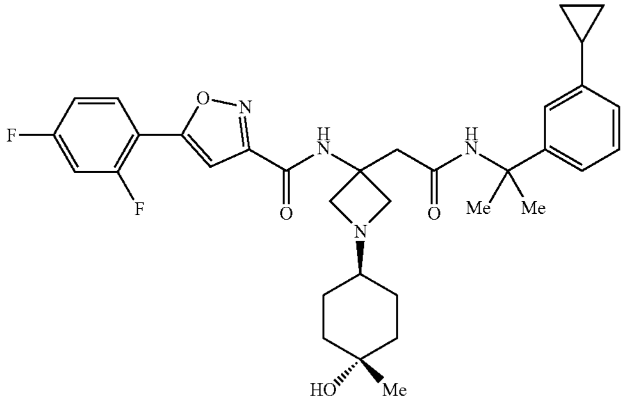 [SMILES: CC(C)(NC(=O)CC1(NC(=O)c2cc(-c3ccc(F)cc3F)on2)CN([C@H]2CC[C@](C)(O)CC2)C1)c1cccc(C2CC2)c1] |
| 1.145 | 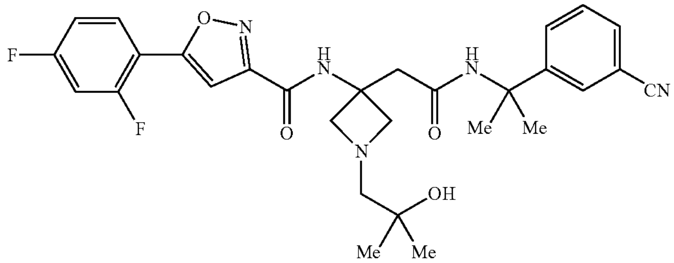 |
| 1.146 | 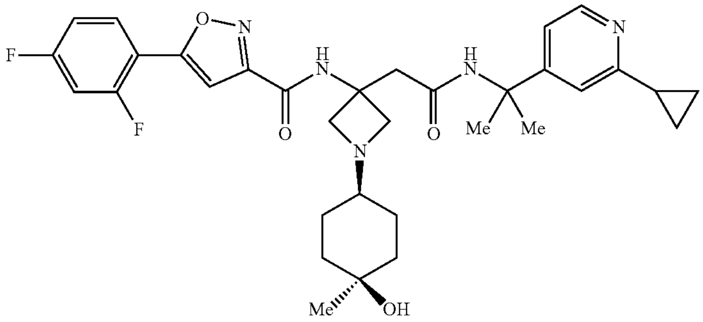 [SMILES: CC(C)(NC(=O)CC1(NC(=O)c2cc(-c3ccc(F)cc3F)on2)CN([C@H]2CC[C@@](C)(O)CC2)C1)c1ccnc(C2CC2)c1] |
| 1.147 | 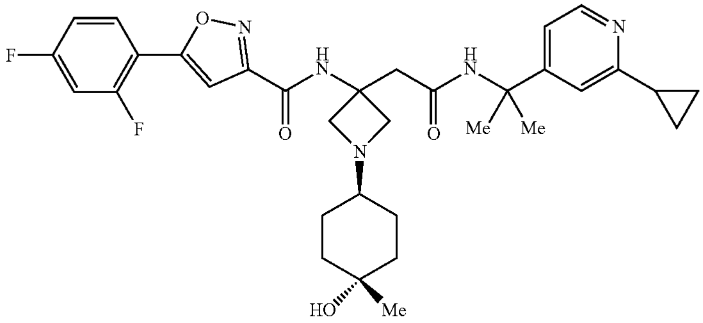 [SMILES: CC(C)(NC(=O)CC1(NC(=O)c2cc(-c3ccc(F)cc3F)on2)CN([C@H]2CC[C@](C)(O)CC2)C1)c1ccnc(C2CC2)c1] |

-continued
| Compound ID | Structure |
| --- | --- |
| 1.148 | 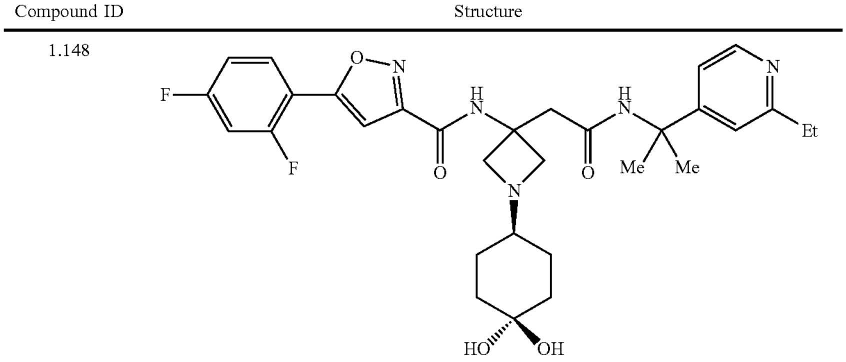 |
| 1.149 | 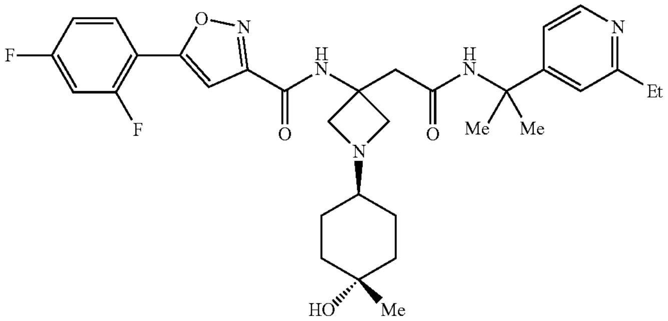 [SMILES: CCc1cc(C(C)(C)NC(=O)CC2(NC(=O)c3cc(-c4ccc(F)cc4F)on3)CN([C@H]3CC[C@](C)(O)CC3)C2)ccn1] |
| 1.150 | 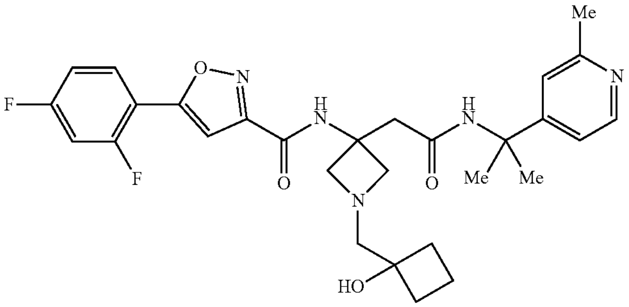 [SMILES: Cc1cc(C(C)(C)NC(=O)CC2(NC(=O)c3cc(-c4ccc(F)cc4F)on3)CN(CC3(O)CCC3)C2)ccn1] |
| 1.151 | 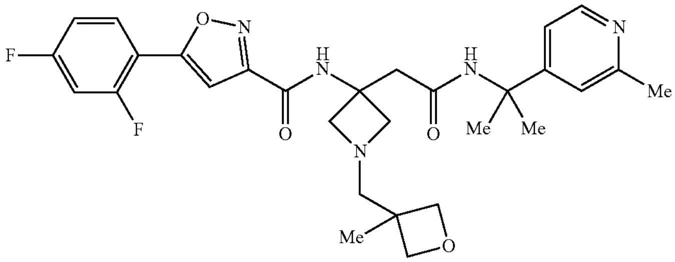 [SMILES: Cc1cc(C(C)(C)NC(=O)CC2(NC(=O)c3cc(-c4ccc(F)cc4F)on3)CN(CC3(C)COC3)C2)ccn1] |
| 1.152 | 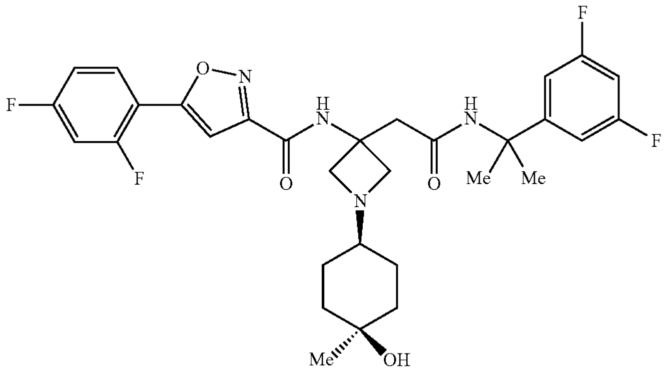 [SMILES: CC(C)(NC(=O)CC1(NC(=O)c2cc(-c3ccc(F)cc3F)on2)CN([C@H]2CC[C@@](C)(O)CC2)C1)c1cc(F)cc(F)c1] |

-continued
| Compound ID | Structure |
| --- | --- |
| 1.153 | 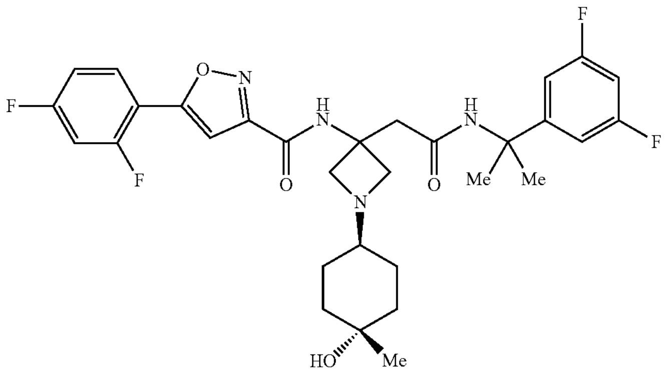 [SMILES: CC(C)(NC(=O)CC1(NC(=O)c2cc(-c3ccc(F)cc3F)on2)CN([C@H]2CC[C@](C)(O)CC2)C1)c1cc(F)cc(F)c1] |
| 1.154 | 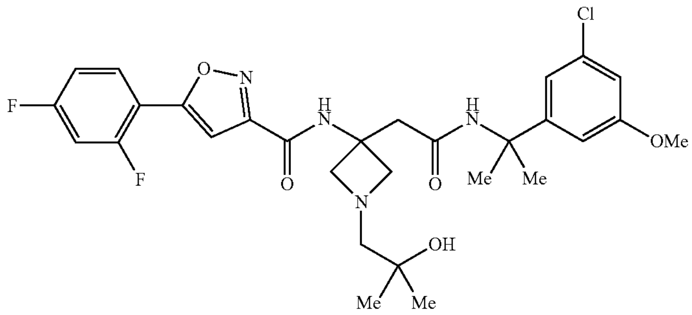 [SMILES: COc1cc(Cl)cc(C(C)(C)NC(=O)CC2(NC(=O)c3cc(-c4ccc(F)cc4F)on3)CN(CC(C)(C)O)C2)c1] |
| 1.155 | 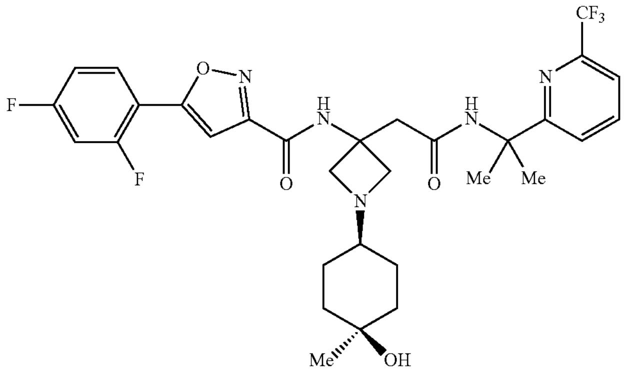 [SMILES: CC(C)(NC(=O)CC1(NC(=O)c2cc(-c3ccc(F)cc3F)on2)CN([C@H]2CC[C@@](C)(O)CC2)C1)c1cccc(C(F)(F)F)n1] |
| 1.156 | 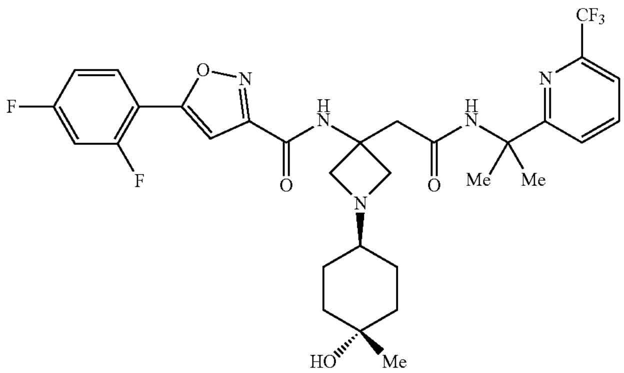 |

-continued
| Compound ID | Structure |
| --- | --- |
| 1.157 | 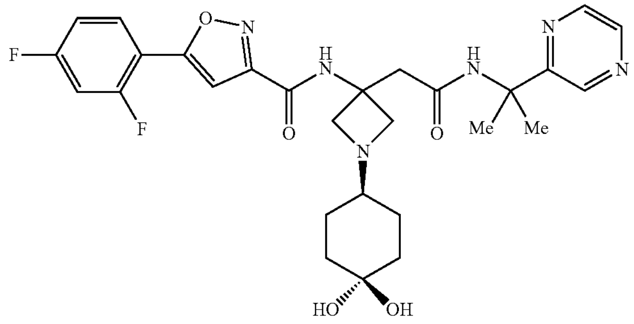 |
| 1.158 | 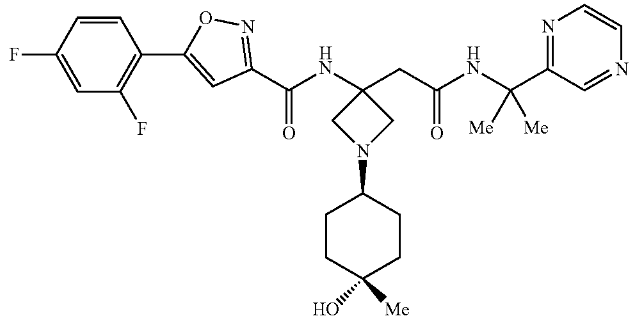 |
| 1.159 | 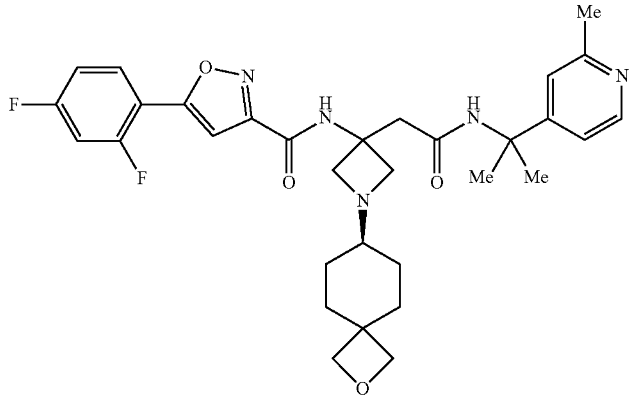 |
| 1.160 | 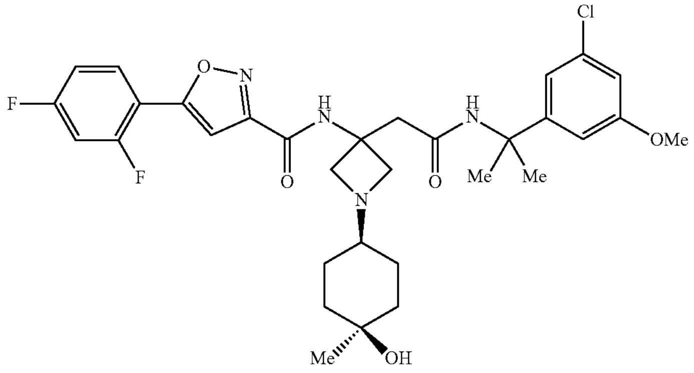 [SMILES: COc1cc(Cl)cc(C(C)(C)NC(=O)CC2(NC(=O)c3cc(-c4ccc(F)cc4F)on3)CN([C@H]3CC[C@@](C)(O)CC3)C2)c1] |

-continued
| Compound ID | Structure |
|---|---|
| 1.161 | 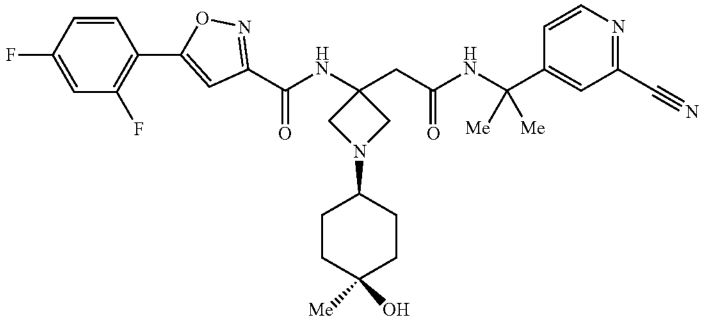 |
| 1.162 | 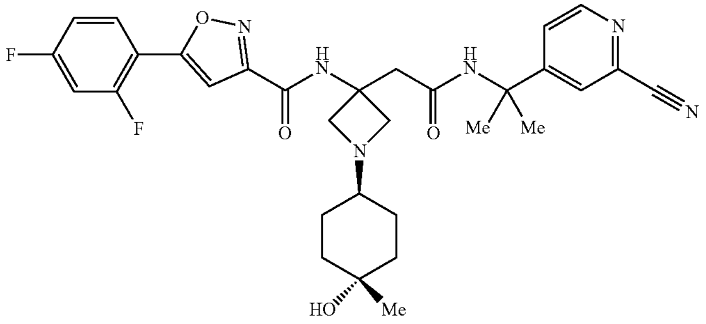 [SMILES: CC(C)(NC(=O)CC1(NC(=O)c2cc(-c3ccc(F)cc3F)on2)CN([C@H]2CC[C@](C)(O)CC2)C1)c1ccnc(C#N)c1] |
| 1.163 | 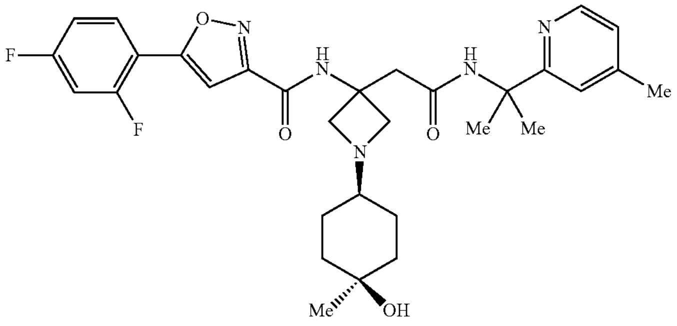 [SMILES: Cc1ccnc(C(C)(C)NC(=O)CC2(NC(=O)c3cc(-c4ccc(F)cc4F)on3)CN([C@H]3CC[C@@](C)(O)CC3)C2)c1] |
| 1.164 | 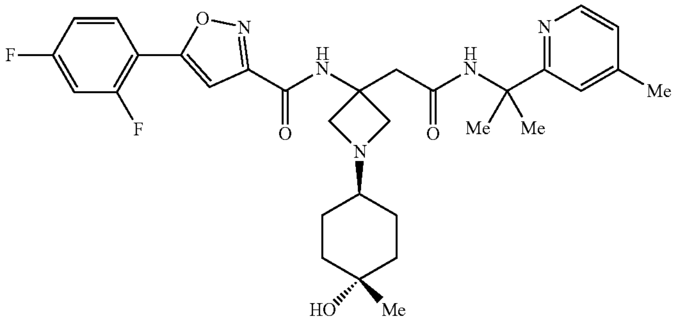 [SMILES: Cc1ccnc(C(C)(C)NC(=O)CC2(NC(=O)c3cc(-c4ccc(F)cc4F)on3)CN([C@H]3CC[C@](C)(O)CC3)C2)c1] |

-continued
| Compound ID | Structure |
|---|---|
| 1.165 | 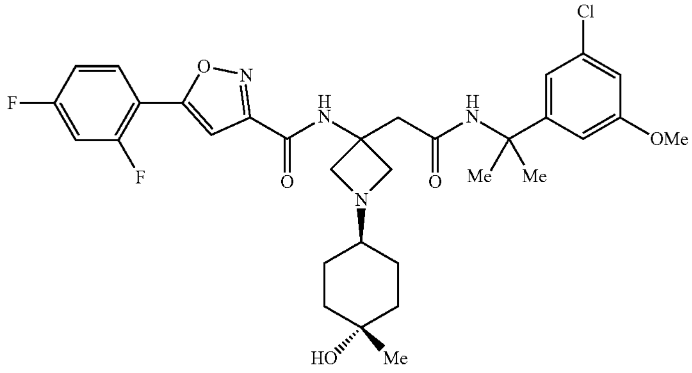 [SMILES: COc1cc(Cl)cc(C(C)(C)NC(=O)CC2(NC(=O)c3cc(-c4ccc(F)cc4F)on3)CN([C@H]3CC[C@](C)(O)CC3)C2)c1] |
| 1.166 | 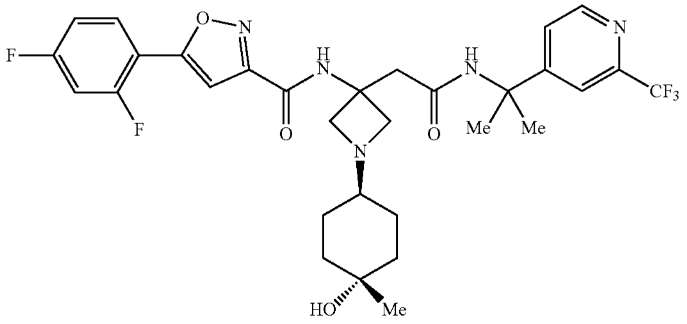 |
| 1.167 | 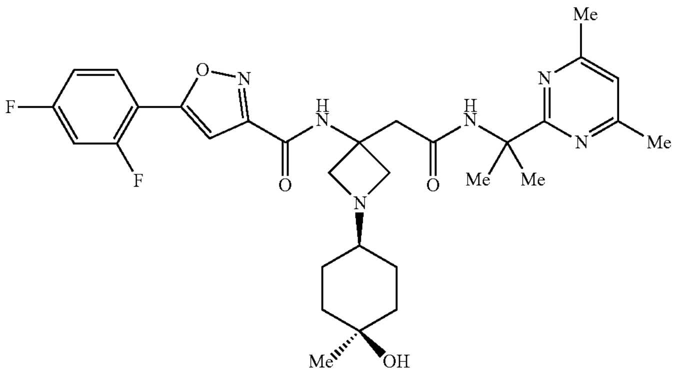 [SMILES: Cc1cc(C)nc(C(C)(C)NC(=O)CC2(NC(=O)c3cc(-c4ccc(F)cc4F)on3)CN([C@H]3CC[C@@](C)(O)CC3)C2)n1] |
| 1.168 | 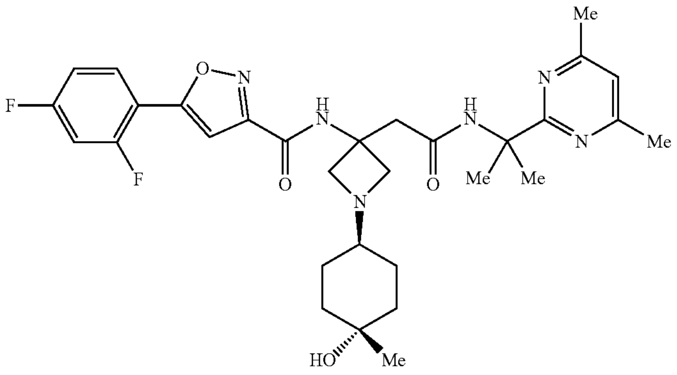 [SMILES: Cc1cc(C)nc(C(C)(C)NC(=O)CC2(NC(=O)c3cc(-c4ccc(F)cc4F)on3)CN([C@H]3CC[C@](C)(O)CC3)C2)n1] |

-continued
| Compound ID | Structure |
| --- | --- |
| 1.169 | 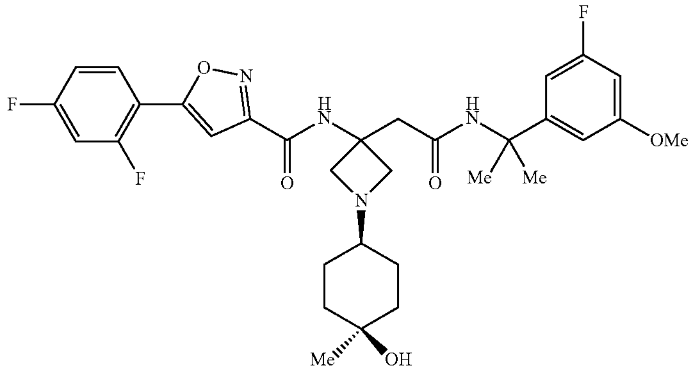 [SMILES: COc1cc(F)cc(C(C)(C)NC(=O)CC2(NC(=O)c3cc(-c4ccc(F)cc4F)on3)CN([C@H]3CC[C@@](C)(O)CC3)C2)c1] |
| 1.170 | 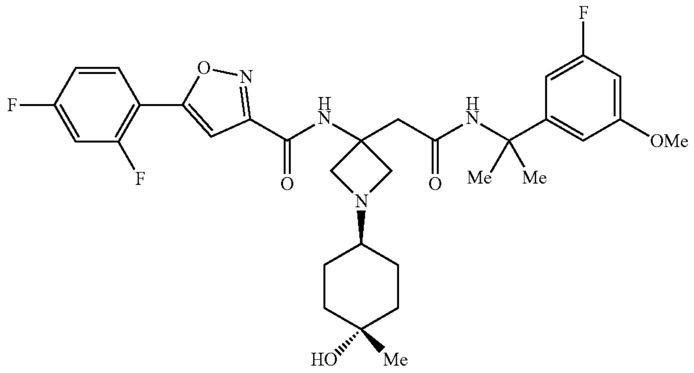 [SMILES: COc1cc(F)cc(C(C)(C)NC(=O)CC2(NC(=O)c3cc(-c4ccc(F)cc4F)on3)CN([C@H]3CC[C@](C)(O)CC3)C2)c1] |
| 1.171 | 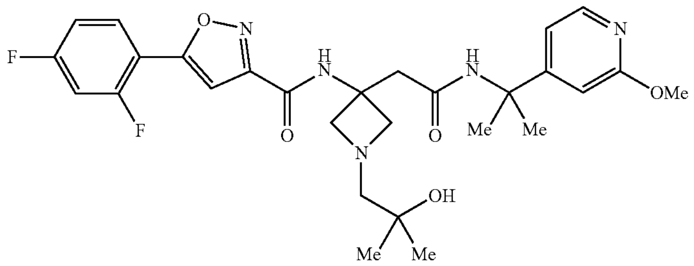 [SMILES: COc1cc(C(C)(C)NC(=O)CC2(NC(=O)c3cc(-c4ccc(F)cc4F)on3)CN(CC(C)(C)O)C2)ccn1] |
| 1.172 | 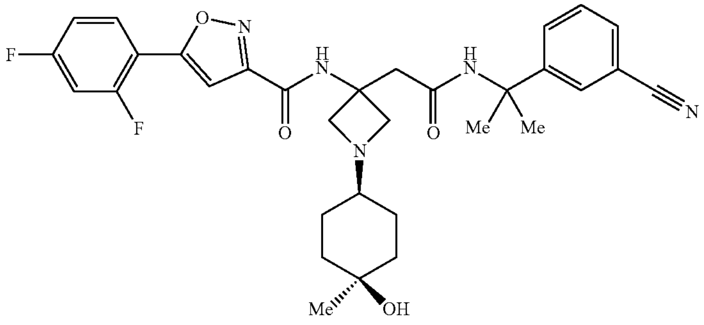 |

-continued
| Compound ID | Structure |
|---|---|
| 1.173 | 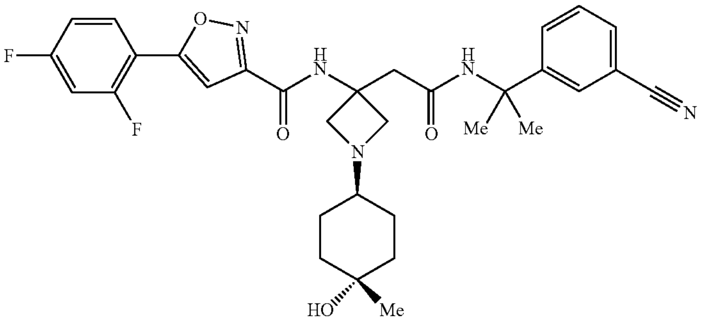 [SMILES: CC(C)(NC(=O)CC1(NC(=O)c2cc(-c3ccc(F)cc3F)on2)CN([C@H]2CC[C@](C)(O)CC2)C1)c1cccc(C#N)c1] |
| 1.174 | 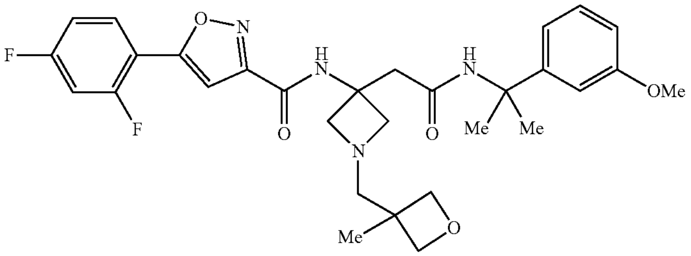 [SMILES: COc1cccc(C(C)(C)NC(=O)CC2(NC(=O)c3cc(-c4ccc(F)cc4F)on3)CN(CC3(C)COC3)C2)c1] |
| 1.175 | 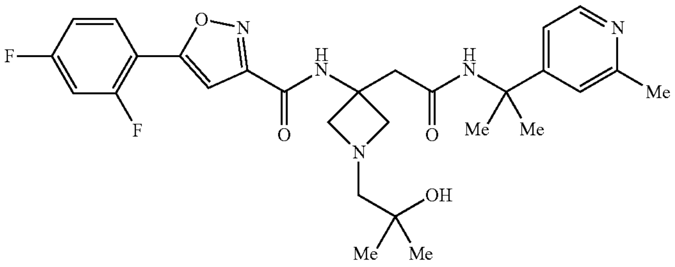 [SMILES: Cc1cc(C(C)(C)NC(=O)CC2(NC(=O)c3cc(-c4ccc(F)cc4F)on3)CN(CC(C)(C)O)C2)ccn1] |
| 1.176 | 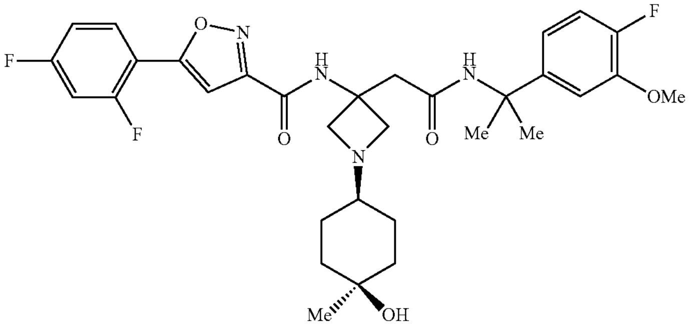 [SMILES: COc1cc(C(C)(C)NC(=O)CC2(NC(=O)c3cc(-c4ccc(F)cc4F)on3)CN([C@H]3CC[C@@](C)(O)CC3)C2)ccc1F] |
| 1.177 | 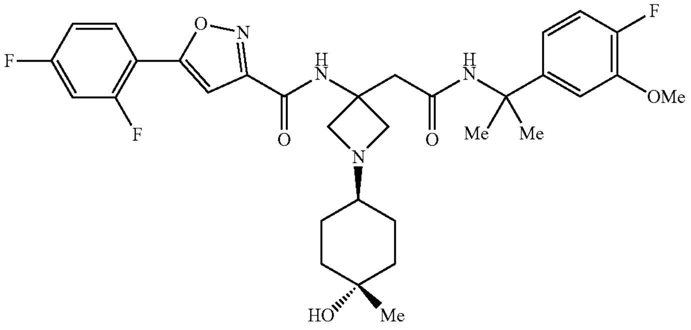 [SMILES: COc1cc(C(C)(C)NC(=O)CC2(NC(=O)c3cc(-c4ccc(F)cc4F)on3)CN([C@H]3CC[C@](C)(O)CC3)C2)ccc1F] |

-continued
| Compound ID | Structure |
|---|---|
| 1.178 | 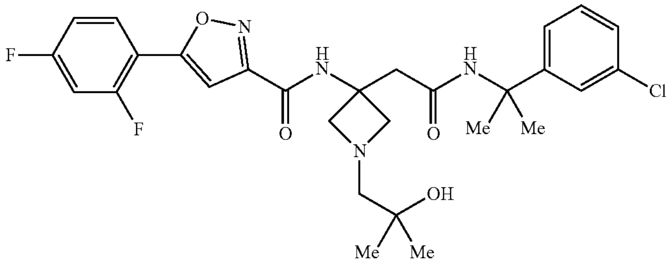 [SMILES: CC(C)(O)CN1CC(CC(=O)NC(C)(C)c2cccc(Cl)c2)(NC(=O)c2cc(-c3ccc(F)cc3F)on2)C1] |
| 1.179 | 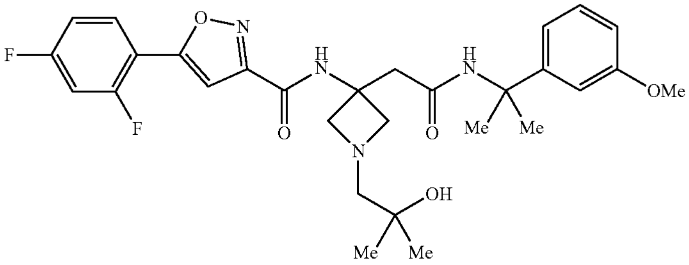 [SMILES: COc1cccc(C(C)(C)NC(=O)CC2(NC(=O)c3cc(-c4ccc(F)cc4F)on3)CN(CC(C)(C)O)C2)c1] |
| 1.180 | 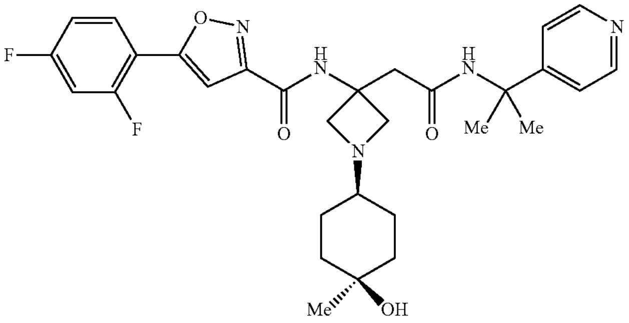 |
| 1.181 | 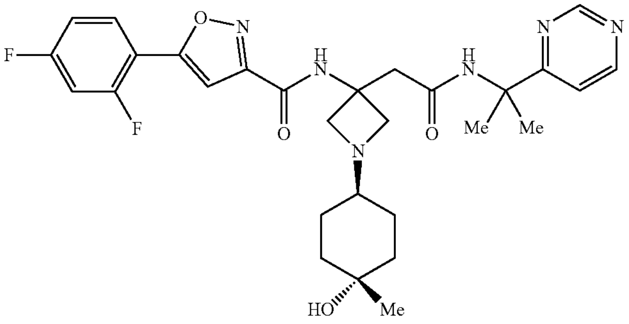 [SMILES: CC(C)(NC(=O)CC1(NC(=O)c2cc(-c3ccc(F)cc3F)on2)CN([C@H]2CC[C@](C)(O)CC2)C1)c1ccncn1] |
| 1.182 | 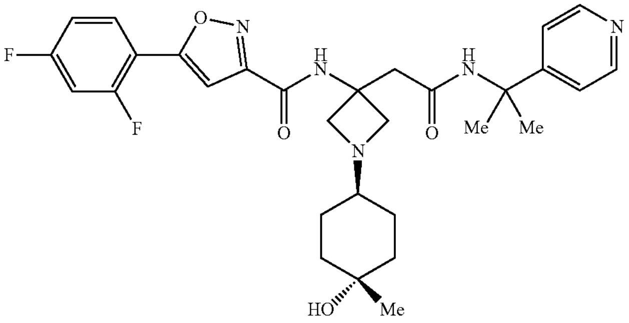 [SMILES: CC(C)(NC(=O)CC1(NC(=O)c2cc(-c3ccc(F)cc3F)on2)CN([C@H]2CC[C@](C)(O)CC2)C1)c1ccncc1] |

-continued
| Compound ID | Structure |
|---|---|
| 1.183 | 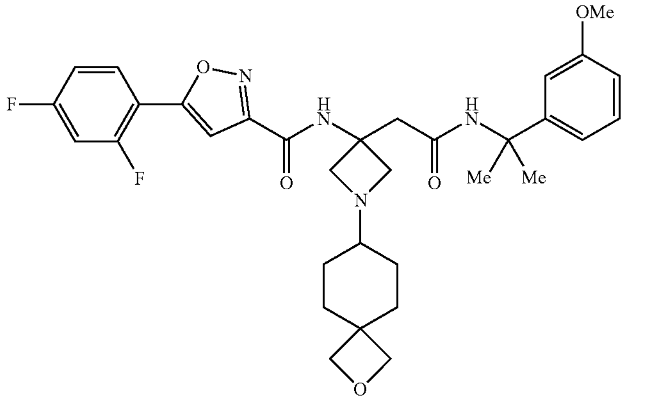 [SMILES: COc1cccc(C(C)(C)NC(=O)CC2(NC(=O)c3cc(-c4ccc(F)cc4F)on3)CN(C3CCC4(CC3)COC4)C2)c1] |
| 1.184 | 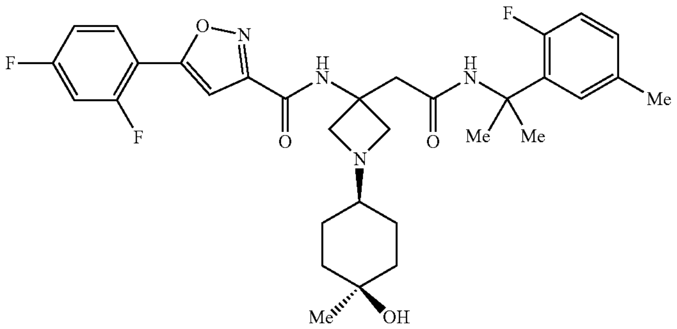 [SMILES: Cc1ccc(F)c(C(C)(C)NC(=O)CC2(NC(=O)c3cc(-c4ccc(F)cc4F)on3)CN([C@H]3CC[C@@](C)(O)CC3)C2)c1] |
| 1.185 | 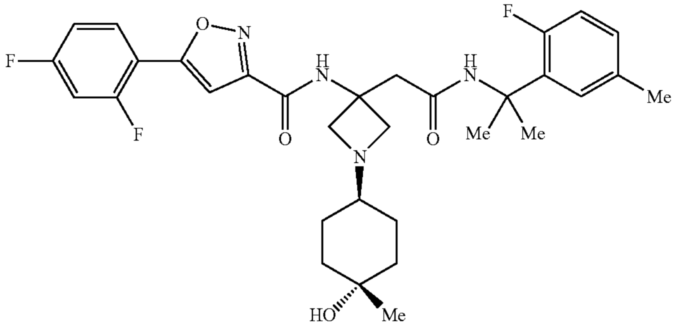 [SMILES: Cc1ccc(F)c(C(C)(C)NC(=O)CC2(NC(=O)c3cc(-c4ccc(F)cc4F)on3)CN([C@H]3CC[C@](C)(O)CC3)C2)c1] |
| 1.186 | 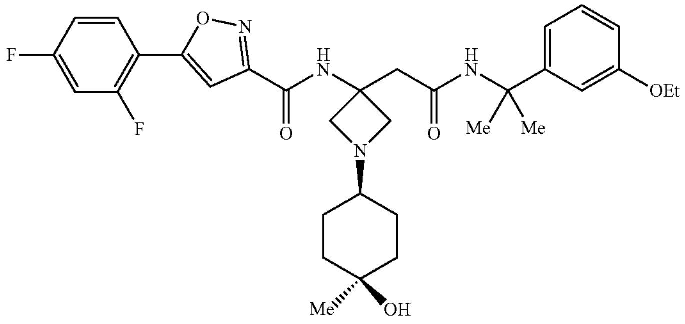 [SMILES: CCOc1cccc(C(C)(C)NC(=O)CC2(NC(=O)c3cc(-c4ccc(F)cc4F)on3)CN([C@H]3CC[C@@](C)(O)CC3)C2)c1] |

-continued
| Compound ID | Structure |
| --- | --- |
| 1.187 | 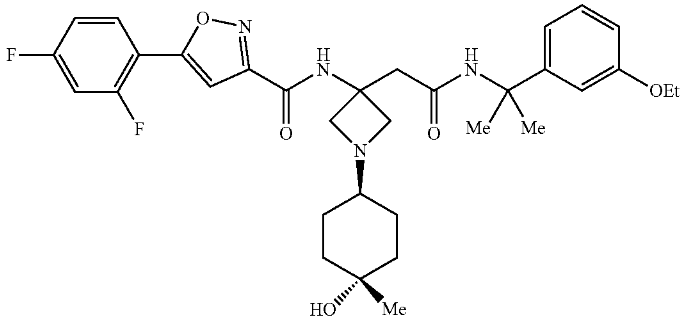 [SMILES: CCOc1cccc(C(C)(C)NC(=O)CC2(NC(=O)c3cc(-c4ccc(F)cc4F)on3)CN([C@H]3CC[C@](C)(O)CC3)C2)c1] |
| 1.188 | 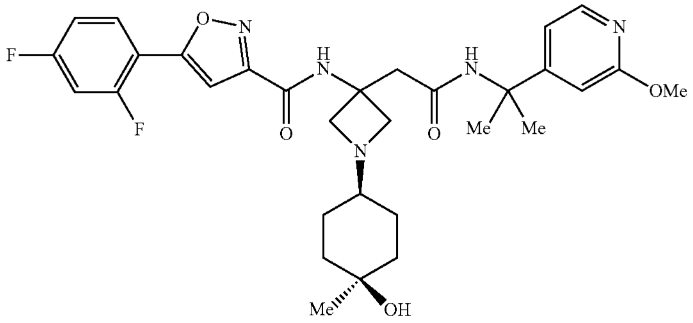 |
| 1.189 | 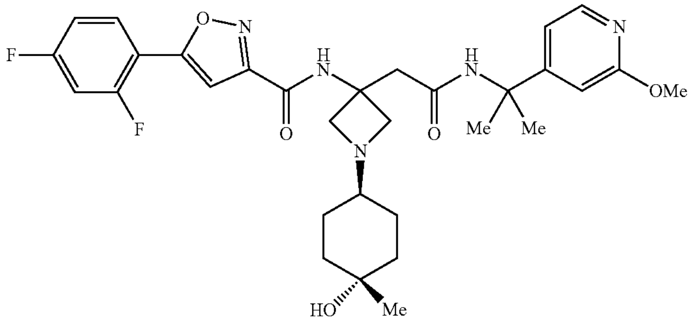 [SMILES: COc1cc(C(C)(C)NC(=O)CC2(NC(=O)c3cc(-c4ccc(F)cc4F)on3)CN([C@H]3CC[C@](C)(O)CC3)C2)ccn1] |
| 1.190 | 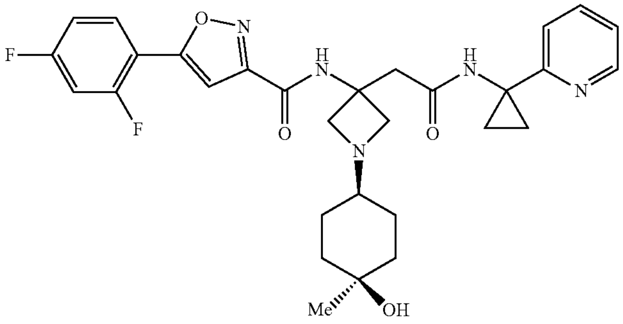 [SMILES: C[C@]1(O)CC[C@@H](N2CC(CC(=O)NC3(c4ccccn4)CC3)(NC(=O)c3cc(-c4ccc(F)cc4F)on3)C2)CC1] |

-continued
| Compound ID | Structure |
| --- | --- |
| 1.191 | 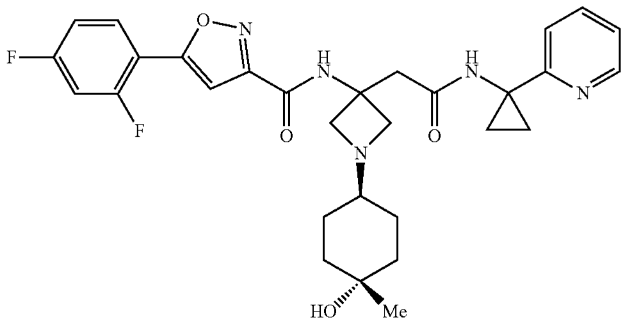 [SMILES: C[C@]1(O)CC[C@H](N2CC(CC(=O)NC3(c4ccccn4)CC3)(NC(=O)c3cc(-c4ccc(F)cc4F)on3)C2)CC1] |
| 1.192 | 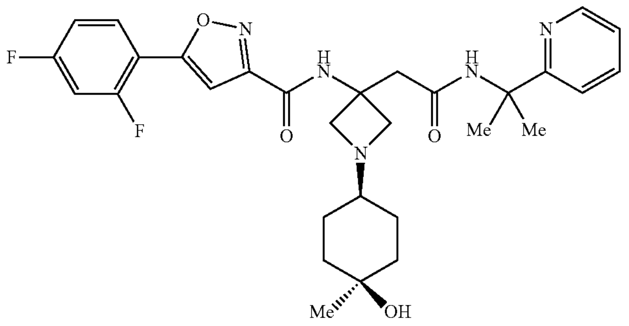 [SMILES: CC(C)(NC(=O)CC1(NC(=O)c2cc(-c3ccc(F)cc3F)on2)CN([C@H]2CC[C@@](C)(O)CC2)C1)c1ccccn1] |
| 1.193 | 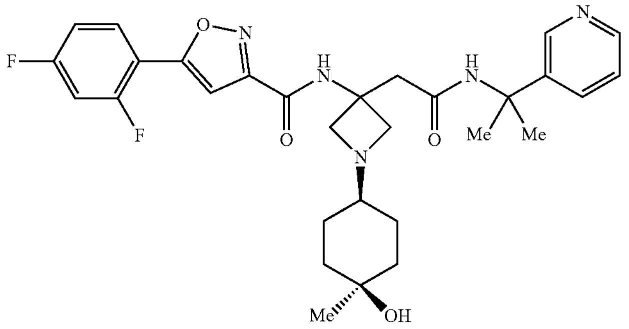 [SMILES: CC(C)(NC(=O)CC1(NC(=O)c2cc(-c3ccc(F)cc3F)on2)CN([C@H]2CC[C@@](C)(O)CC2)C1)c1cccnc1] |
| 1.194 | 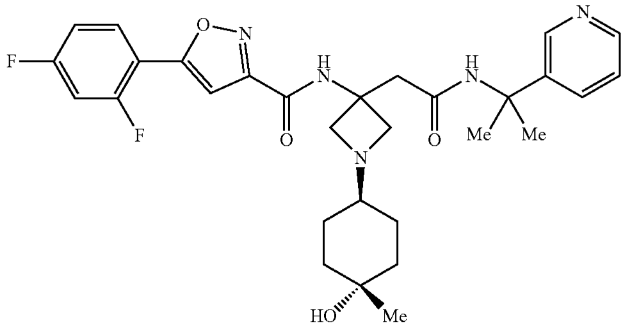 [SMILES: CC(C)(NC(=O)CC1(NC(=O)c2cc(-c3ccc(F)cc3F)on2)CN([C@H]2CC[C@](C)(O)CC2)C1)c1cccnc1] |

-continued
| Compound ID | Structure |
|---|---|
| 1.195 | 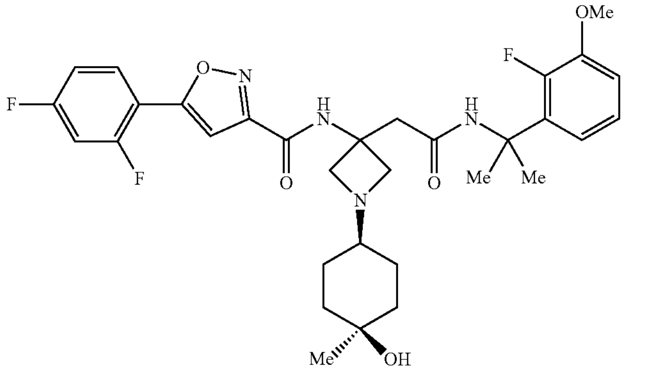 [SMILES: COc1cccc(C(C)(C)NC(=O)CC2(NC(=O)c3cc(-c4ccc(F)cc4F)on3)CN([C@H]3CC[C@@](C)(O)CC3)C2)c1F] |
| 1.196 | 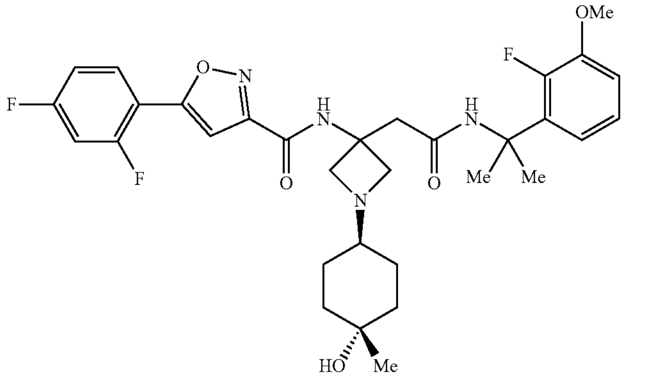 [SMILES: COc1cccc(C(C)(C)NC(=O)CC2(NC(=O)c3cc(-c4ccc(F)cc4F)on3)CN([C@H]3CC[C@](C)(O)CC3)C2)c1F] |
| 1.197 | 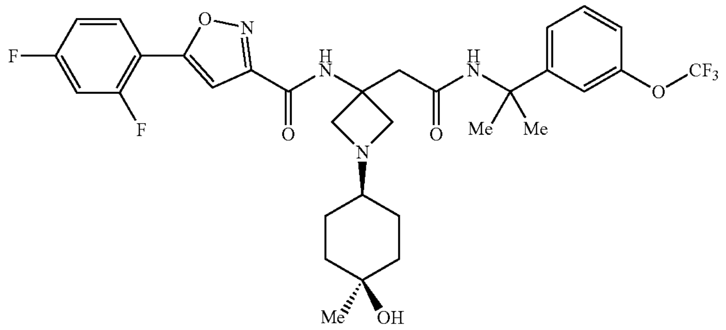 [SMILES: CC(C)(NC(=O)CC1(NC(=O)c2cc(-c3ccc(F)cc3F)on2)CN([C@H]2CC[C@@](C)(O)CC2)C1)c1cccc(OC(F)(F)F)c1] |
| 1.198 | 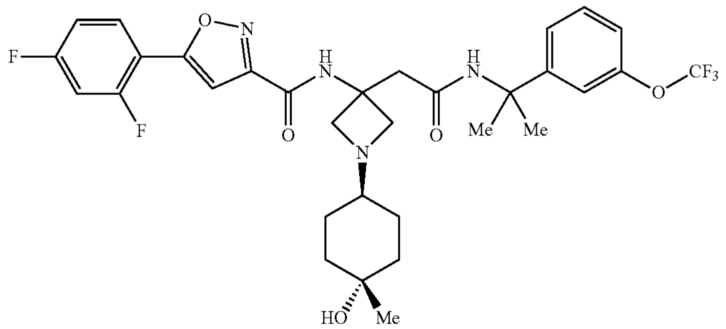 [SMILES: CC(C)(NC(=O)CC1(NC(=O)c2cc(-c3ccc(F)cc3F)on2)CN([C@H]2CC[C@](C)(O)CC2)C1)c1cccc(OC(F)(F)F)c1] |

-continued
| Compound ID | Structure |
|---|---|
| 1.199 | 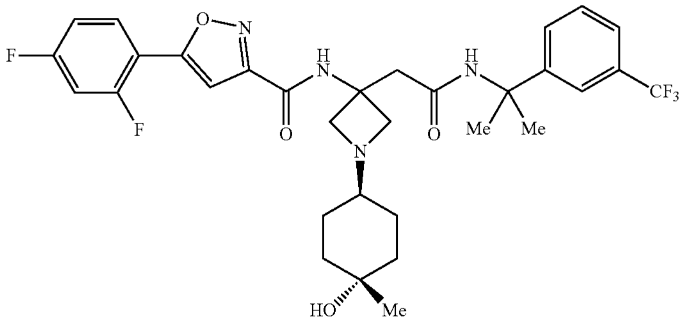 |
| 1.200 | 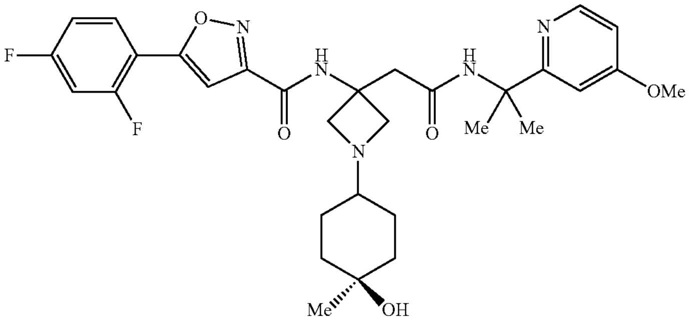 |
| 1.201 | 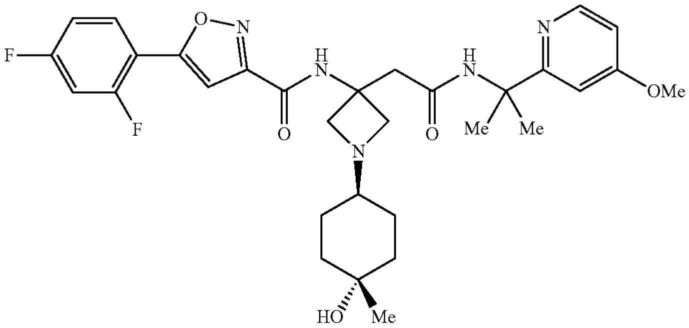 [SMILES: COc1ccnc(C(C)(C)NC(=O)CC2(NC(=O)c3cc(-c4ccc(F)cc4F)on3)CN([C@H]3CC[C@](C)(O)CC3)C2)c1] |
| 1.202 | 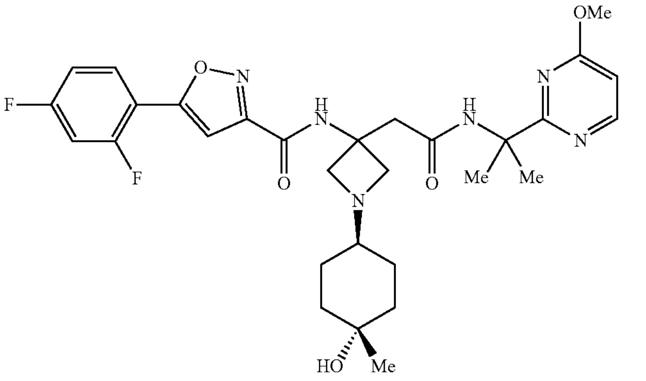 [SMILES: COc1ccnc(C(C)(C)NC(=O)CC2(NC(=O)c3cc(-c4ccc(F)cc4F)on3)CN([C@H]3CC[C@](C)(O)CC3)C2)n1] |

-continued
| Compound ID | Structure |
|---|---|
| 1.203 | 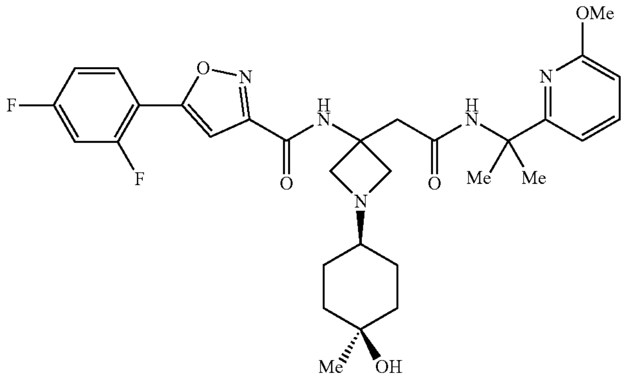 [SMILES: COc1cccc(C(C)(C)NC(=O)CC2(NC(=O)c3cc(-c4ccc(F)cc4F)on3)CN([C@H]3CC[C@@](C)(O)CC3)C2)n1] |
| 1.204 | 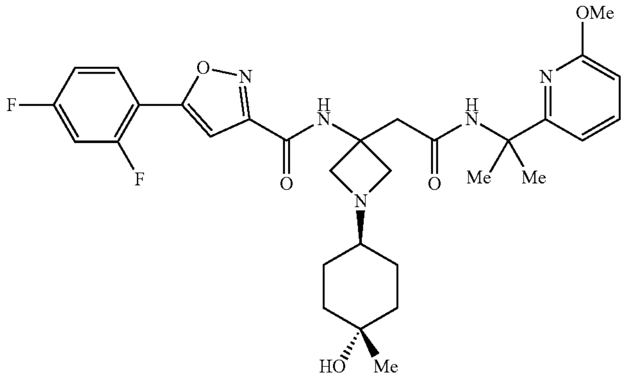 [SMILES: COc1cccc(C(C)(C)NC(=O)CC2(NC(=O)c3cc(-c4ccc(F)cc4F)on3)CN([C@H]3CC[C@](C)(O)CC3)C2)n1] |
| 1.205 | 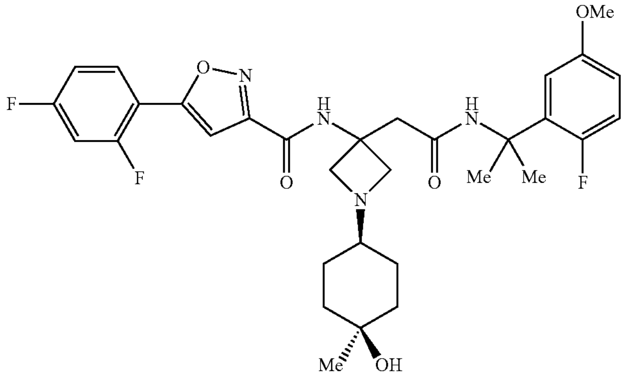 [SMILES: COc1ccc(F)c(C(C)(C)NC(=O)CC2(NC(=O)c3cc(-c4ccc(F)cc4F)on3)CN([C@H]3CC[C@@](C)(O)CC3)C2)c1] |
| 1.206 | 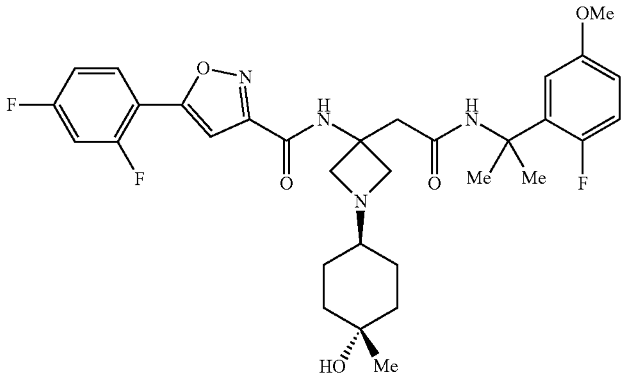 [SMILES: COc1ccc(F)c(C(C)(C)NC(=O)CC2(NC(=O)c3cc(-c4ccc(F)cc4F)on3)CN([C@H]3CC[C@](C)(O)CC3)C2)c1] |

-continued
| Compound ID | Structure |
|---|---|
| 1.207 | 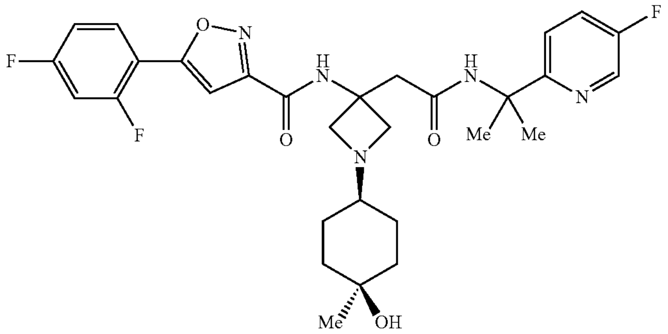 [SMILES: CC(C)(NC(=O)CC1(NC(=O)c2cc(-c3ccc(F)cc3F)on2)CN([C@H]2CC[C@@](C)(O)CC2)C1)c1ccc(F)cn1] |
| 1.208 | 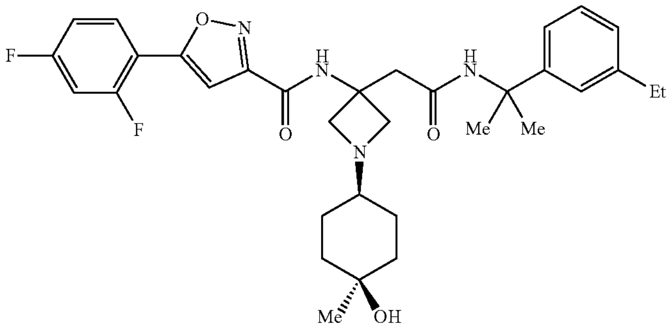 [SMILES: CCc1cccc(C(C)(C)NC(=O)CC2(NC(=O)c3cc(-c4ccc(F)cc4F)on3)CN([C@H]3CC[C@@](C)(O)CC3)C2)c1] |
| 1.209 | 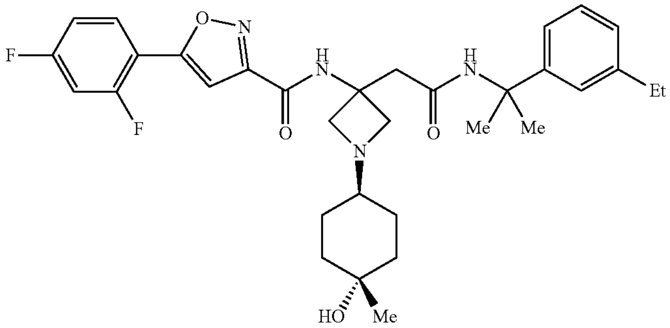 [SMILES: CCc1cccc(C(C)(C)NC(=O)CC2(NC(=O)c3cc(-c4ccc(F)cc4F)on3)CN([C@H]3CC[C@](C)(O)CC3)C2)c1] |
| 1.210 | 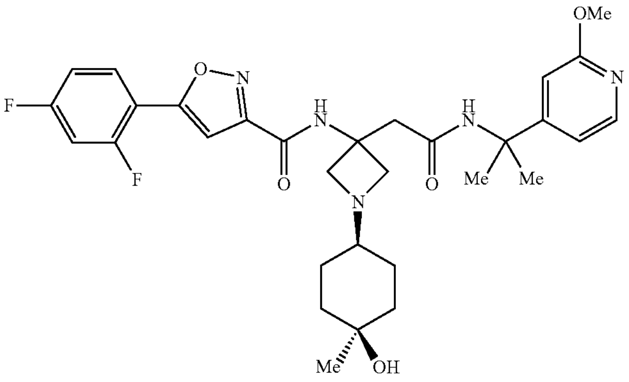 [SMILES: COc1cc(C(C)(C)NC(=O)CC2(NC(=O)c3cc(-c4ccc(F)cc4F)on3)CN([C@H]3CC[C@@](C)(O)CC3)C2)ccn1] |

-continued
| Compound ID | Structure |
|---|---|
| 1.211 | 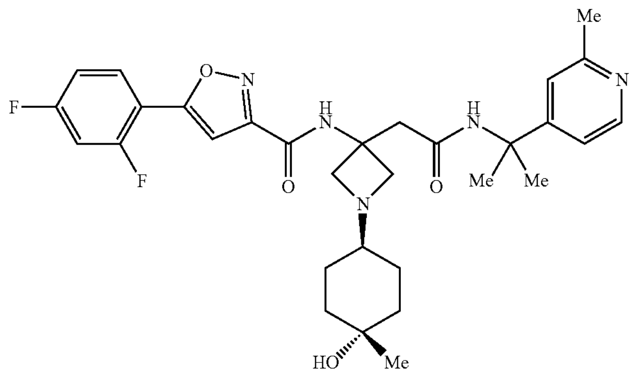 [SMILES: Cc1cc(C(C)(C)NC(=O)CC2(NC(=O)c3cc(-c4ccc(F)cc4F)on3)CN([C@H]3CC[C@](C)(O)CC3)C2)ccn1] |
| 1.212 | 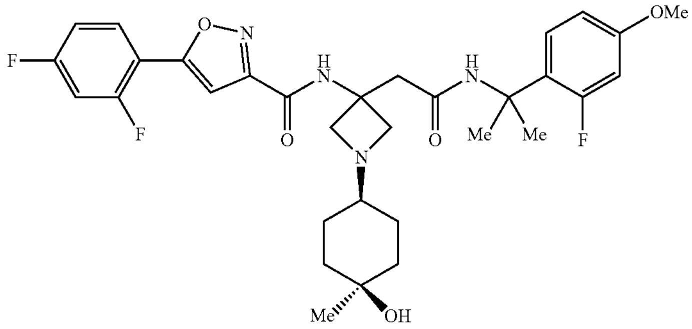 [SMILES: COc1ccc(C(C)(C)NC(=O)CC2(NC(=O)c3cc(-c4ccc(F)cc4F)on3)CN([C@H]3CC[C@@](C)(O)CC3)C2)c(F)c1] |
| 1.213 | 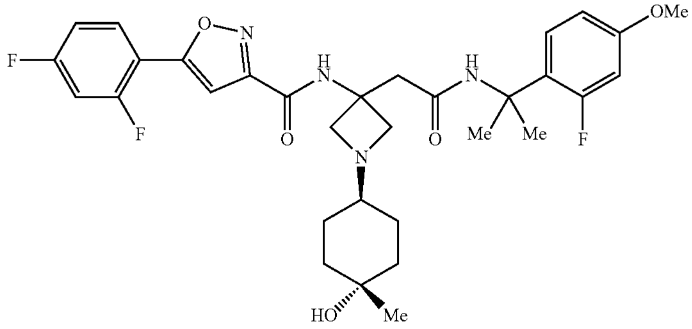 [SMILES: COc1ccc(C(C)(C)NC(=O)CC2(NC(=O)c3cc(-c4ccc(F)cc4F)on3)CN([C@H]3CC[C@](C)(O)CC3)C2)c(F)c1] |
| 1.214 | 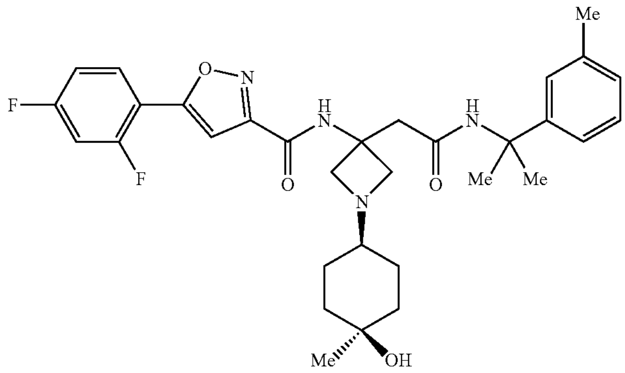 [SMILES: Cc1cccc(C(C)(C)NC(=O)CC2(NC(=O)c3cc(-c4ccc(F)cc4F)on3)CN([C@H]3CC[C@@](C)(O)CC3)C2)c1] |

-continued
| Compound ID | Structure |
| --- | --- |
| 1.215 | 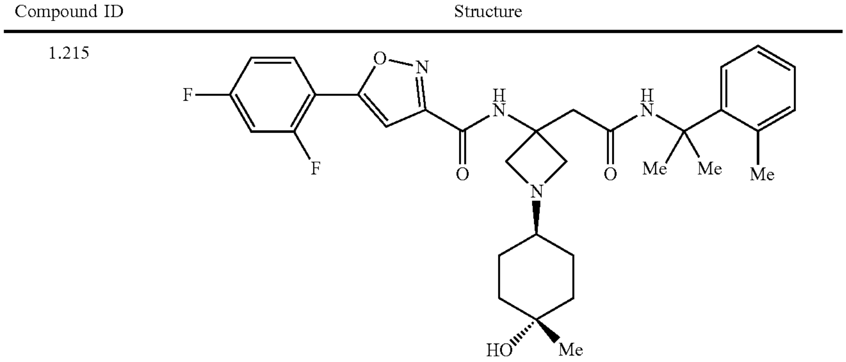 |
| 1.216 | 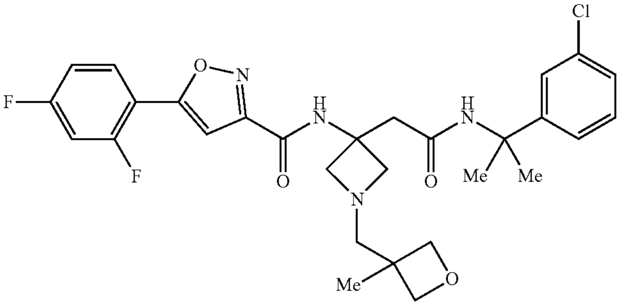 [SMILES: CC1(CN2CC(CC(=O)NC(C)(C)c3cccc(Cl)c3)(NC(=O)c3cc(-c4ccc(F)cc4F)on3)C2)COC1] |
| 1.217 | 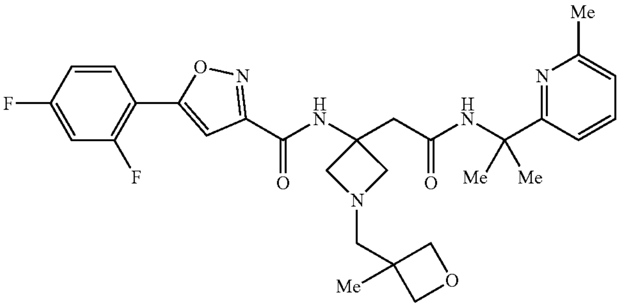 [SMILES: Cc1cccc(C(C)(C)NC(=O)CC2(NC(=O)c3cc(-c4ccc(F)cc4F)on3)CN(CC3(C)COC3)C2)n1] |
| 1.218 | 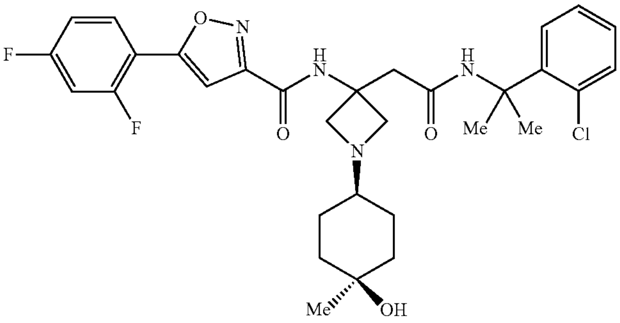 [SMILES: CC(C)(NC(=O)CC1(NC(=O)c2cc(-c3ccc(F)cc3F)on2)CN([C@H]2CC[C@@](C)(O)CC2)C1)c1ccccc1Cl] |
| 1.219 | 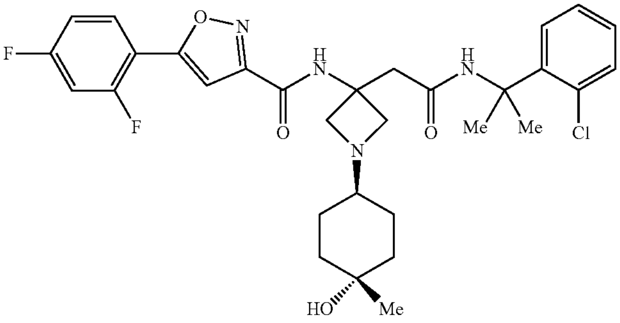 [SMILES: CC(C)(NC(=O)CC1(NC(=O)c2cc(-c3ccc(F)cc3F)on2)CN([C@H]2CC[C@](C)(O)CC2)C1)c1ccccc1Cl] |

-continued
| Compound ID | Structure |
|---|---|
| 1.220 | 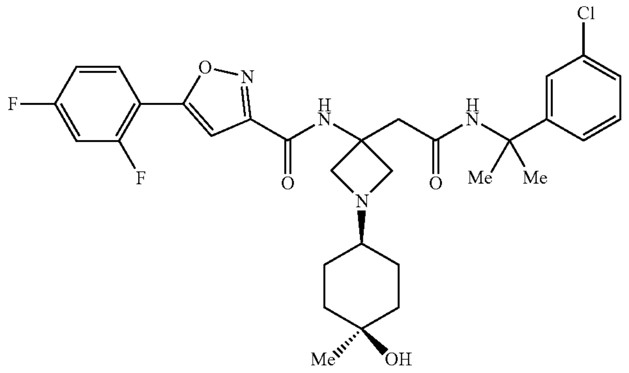 |
| 1.221 | 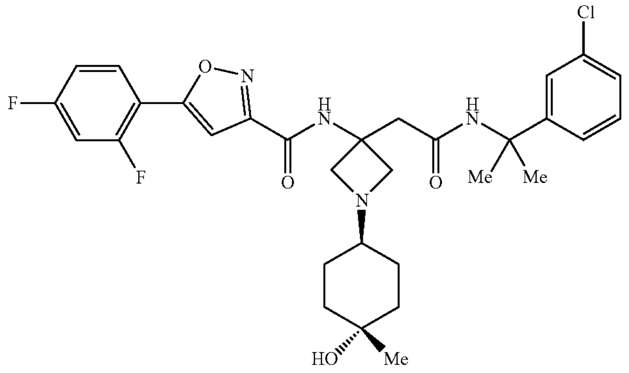 [SMILES: CC(C)(NC(=O)CC1(NC(=O)c2cc(-c3ccc(F)cc3F)on2)CN([C@H]2CC[C@](C)(O)CC2)C1)c1cccc(Cl)c1] |
| 1.222 | 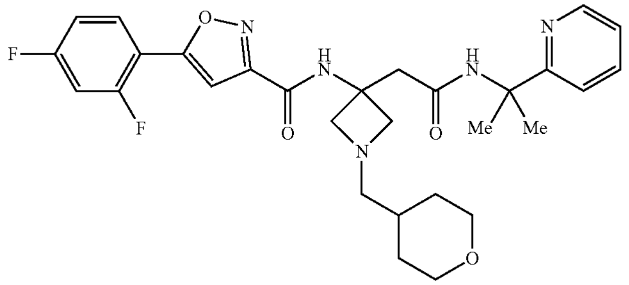 [SMILES: CC(C)(NC(=O)CC1(NC(=O)c2cc(-c3ccc(F)cc3F)on2)CN(CC2CCOCC2)C1)c1ccccn1] |
| 1.223 | 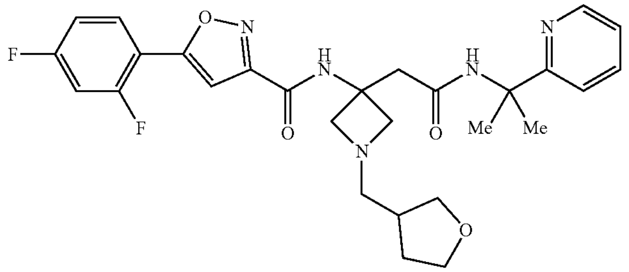 [SMILES: CC(C)(NC(=O)CC1(NC(=O)c2cc(-c3ccc(F)cc3F)on2)CN(CC2CCOC2)C1)c1ccccn1] |
| 1.224 | 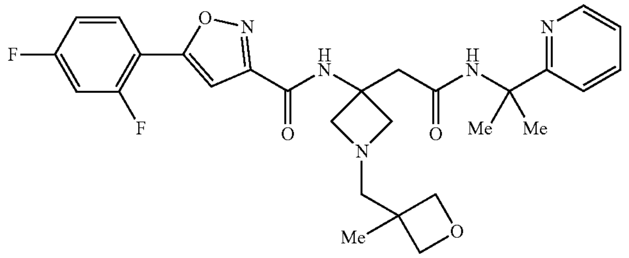 [SMILES: CC1(CN2CC(CC(=O)NC(C)(C)c3ccccn3)(NC(=O)c3cc(-c4ccc(F)cc4F)on3)C2)COC1] |

-continued
| Compound ID | Structure |
| --- | --- |
| 1.225 | 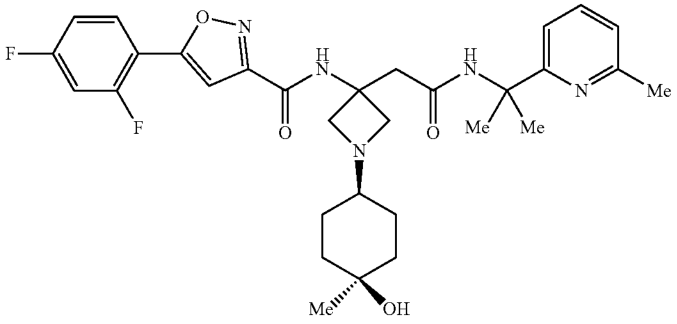 [SMILES: Cc1cccc(C(C)(C)NC(=O)CC2(NC(=O)c3cc(-c4ccc(F)cc4F)on3)CN([C@H]3CC[C@@](C)(O)CC3)C2)n1] |
| 1.226 | 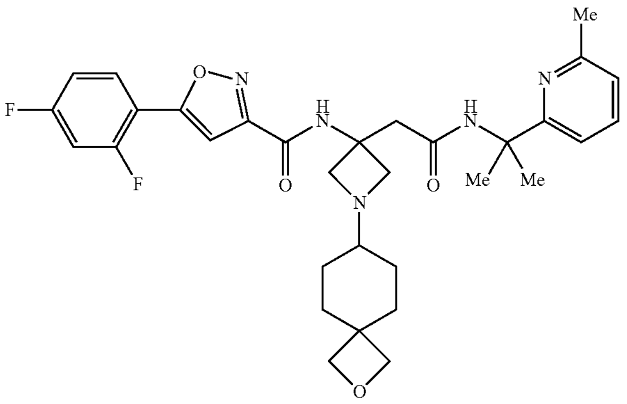 [SMILES: Cc1cccc(C(C)(C)NC(=O)CC2(NC(=O)c3cc(-c4ccc(F)cc4F)on3)CN(C3CCC4(CC3)COC4)C2)n1] |
| 1.227 | 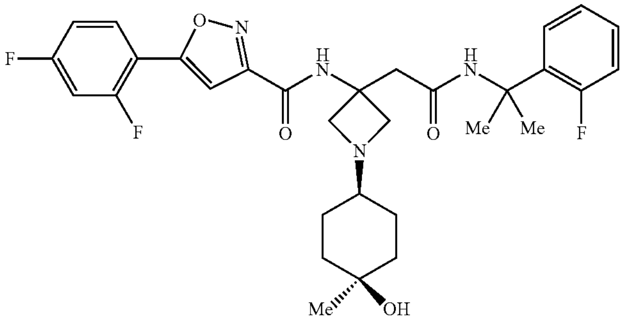 [SMILES: CC(C)(NC(=O)CC1(NC(=O)c2cc(-c3ccc(F)cc3F)on2)CN([C@H]2CC[C@@](C)(O)CC2)C1)c1ccccc1F] |
| 1.228 | 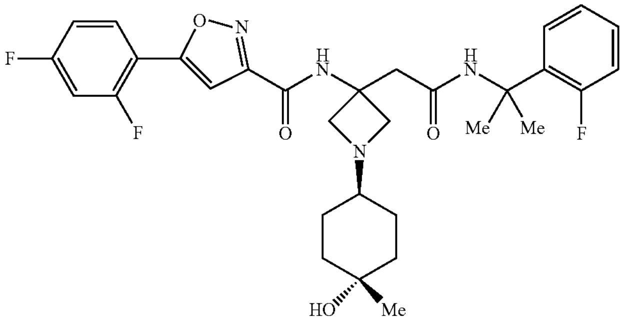 [SMILES: CC(C)(NC(=O)CC1(NC(=O)c2cc(-c3ccc(F)cc3F)on2)CN([C@H]2CC[C@](C)(O)CC2)C1)c1ccccc1F] |

-continued
| Compound ID | Structure |
| --- | --- |
| 1.229 | 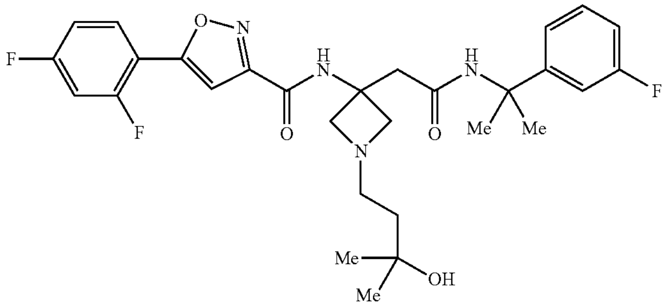 [SMILES: CC(C)(O)CCN1CC(CC(=O)NC(C)(C)c2cccc(F)c2)(NC(=O)c2cc(-c3ccc(F)cc3F)on2)C1] |
| 1.230 | 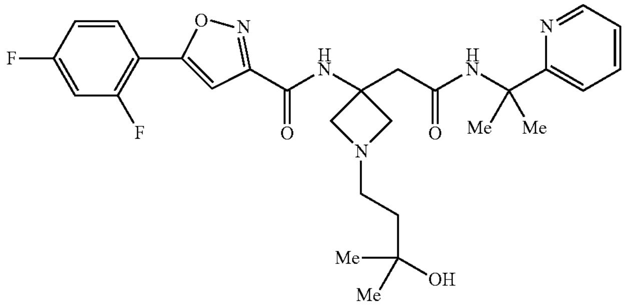 [SMILES: CC(C)(O)CCN1CC(CC(=O)NC(C)(C)c2ccccn2)(NC(=O)c2cc(-c3ccc(F)cc3F)on2)C1] |
| 1.231 | 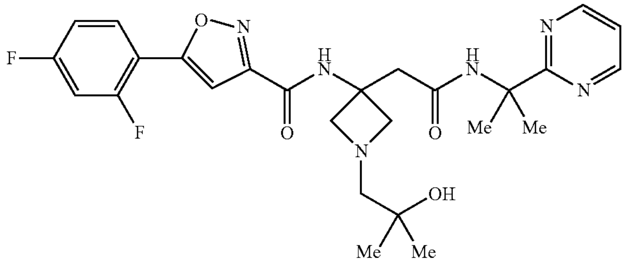 [SMILES: CC(C)(O)CN1CC(CC(=O)NC(C)(C)c2ncccn2)(NC(=O)c2cc(-c3ccc(F)cc3F)on2)C1] |
| 1.232 | 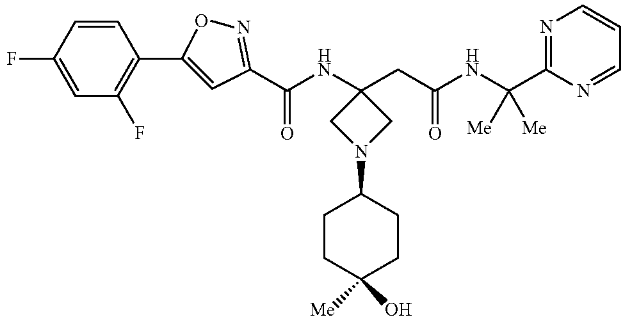 [SMILES: CC(C)(NC(=O)CC1(NC(=O)c2cc(-c3ccc(F)cc3F)on2)CN([C@H]2CC[C@@](C)(O)CC2)C1)c1ncccn1] |
| 1.233 | 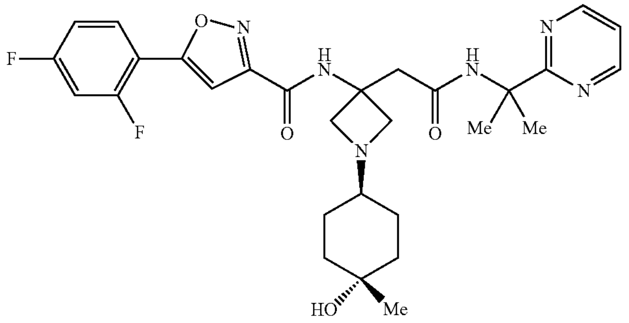 [SMILES: CC(C)(NC(=O)CC1(NC(=O)c2cc(-c3ccc(F)cc3F)on2)CN([C@H]2CC[C@](C)(O)CC2)C1)c1ncccn1] |

-continued
| Compound ID | Structure |
| --- | --- |
| 1.234 | 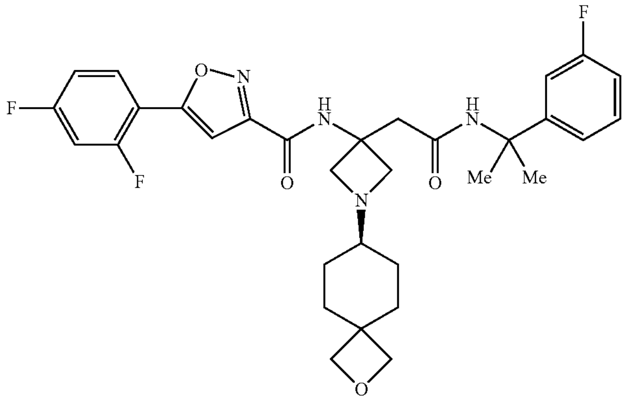 |
| 1.235 | 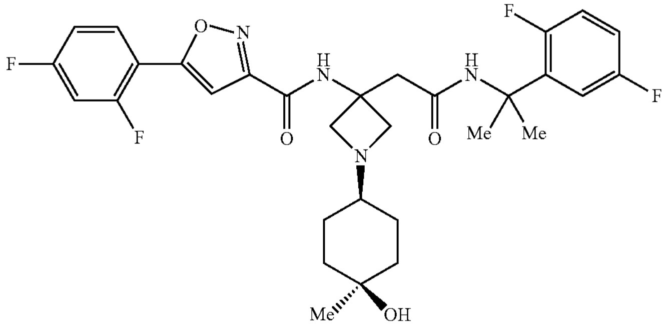 [SMILES: CC(C)(NC(=O)CC1(NC(=O)c2cc(-c3ccc(F)cc3F)on2)CN([C@H]2CC[C@@](C)(O)CC2)C1)c1cc(F)ccc1F] |
| 1.236 | 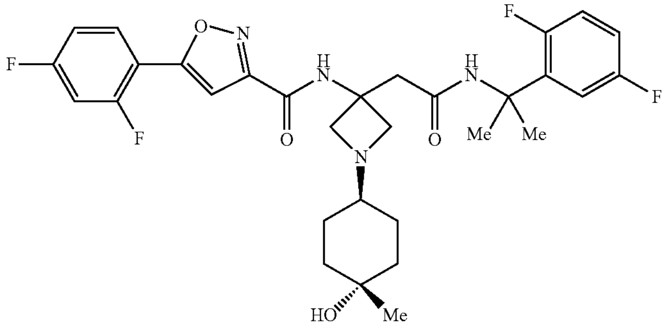 [SMILES: CC(C)(NC(=O)CC1(NC(=O)c2cc(-c3ccc(F)cc3F)on2)CN([C@H]2CC[C@](C)(O)CC2)C1)c1cc(F)ccc1F] |
| 1.237 | 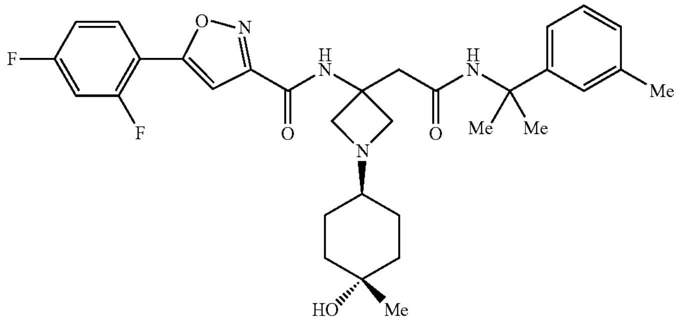 [SMILES: Cc1cccc(C(C)(C)NC(=O)CC2(NC(=O)c3cc(-c4ccc(F)cc4F)on3)CN([C@H]3CC[C@](C)(O)CC3)C2)c1] |

-continued
| Compound ID | Structure |
| --- | --- |
| 1.238 | 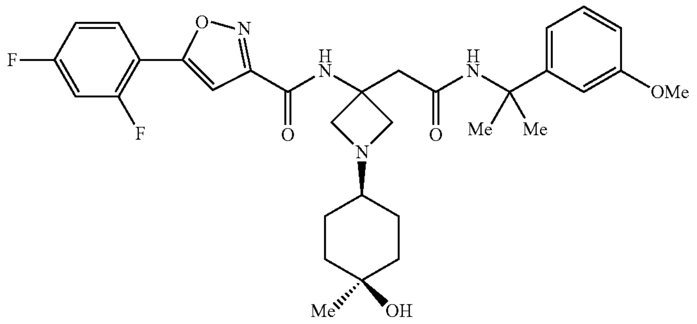 [SMILES: COc1cccc(C(C)(C)NC(=O)CC2(NC(=O)c3cc(-c4ccc(F)cc4F)on3)CN([C@H]3CC[C@@](C)(O)CC3)C2)c1] |
| 1.239 | 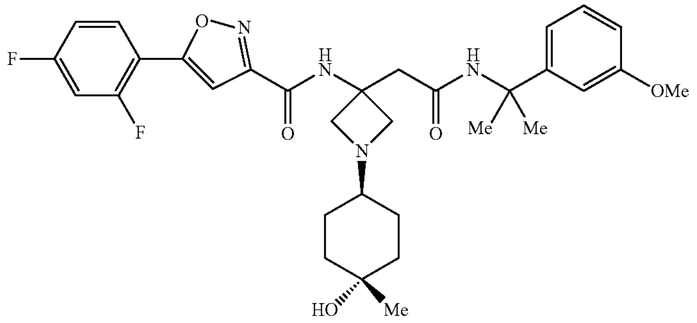 [SMILES: COc1cccc(C(C)(C)NC(=O)CC2(NC(=O)c3cc(-c4ccc(F)cc4F)on3)CN([C@H]3CC[C@](C)(O)CC3)C2)c1] |
| 1.240 | 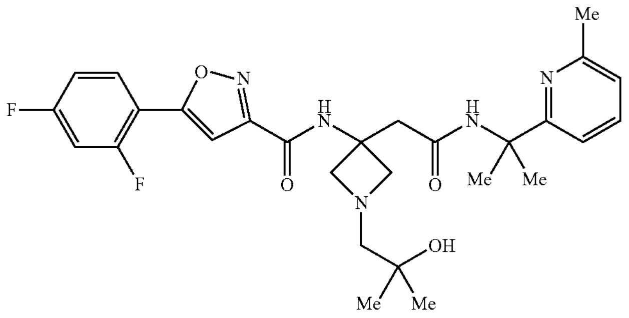 [SMILES: Cc1cccc(C(C)(C)NC(=O)CC2(NC(=O)c3cc(-c4ccc(F)cc4F)on3)CN(CC(C)(C)O)C2)n1] |
| 1.241 | 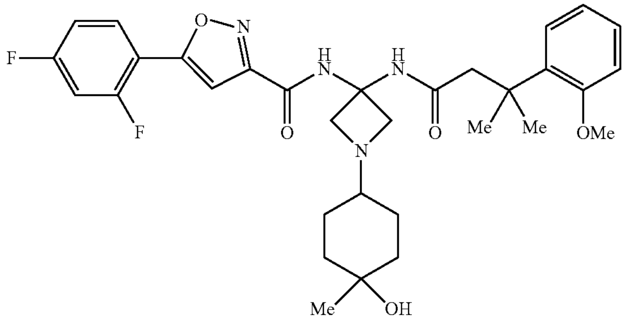 [SMILES: COc1ccccc1C(C)(C)CC(=O)NC1(NC(=O)c2cc(-c3ccc(F)cc3F)on2)CN(C2CCC(C)(O)CC2)C1] |

-continued
| Compound ID | Structure |
| --- | --- |
| 1.242 | 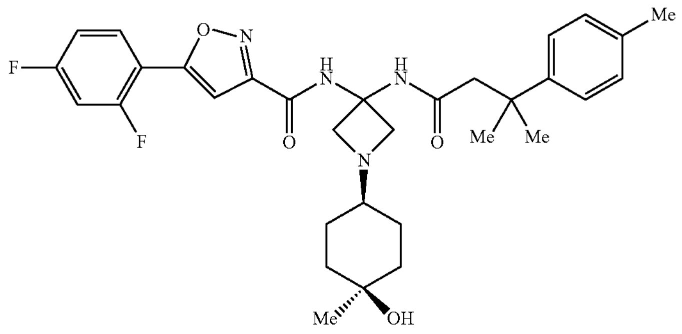 [SMILES: Cc1ccc(C(C)(C)CC(=O)NC2(NC(=O)c3cc(-c4ccc(F)cc4F)on3)CN([C@H]3CC[C@@](C)(O)CC3)C2)cc1] |
| 1.243 | 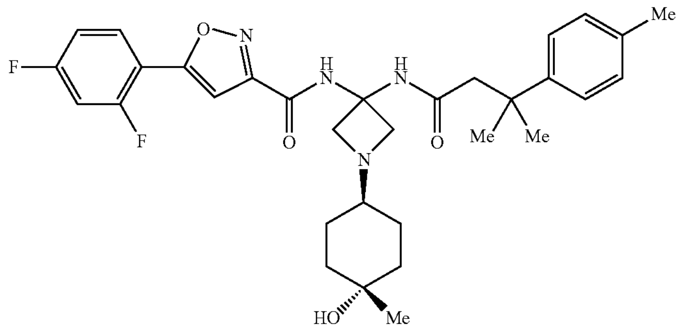 [SMILES: Cc1ccc(C(C)(C)CC(=O)NC2(NC(=O)c3cc(-c4ccc(F)cc4F)on3)CN([C@H]3CC[C@](C)(O)CC3)C2)cc1] |
| 1.244 | 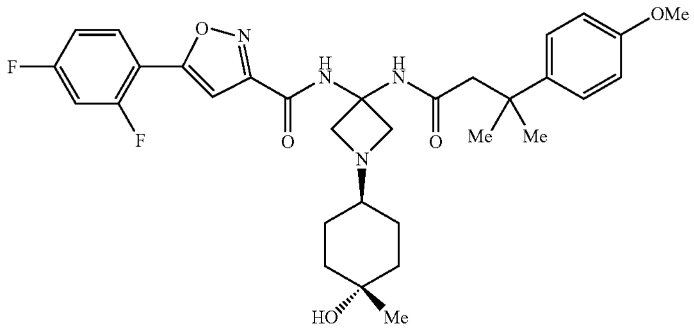 [SMILES: COc1ccc(C(C)(C)CC(=O)NC2(NC(=O)c3cc(-c4ccc(F)cc4F)on3)CN([C@H]3CC[C@](C)(O)CC3)C2)cc1] |
| 1.245 | 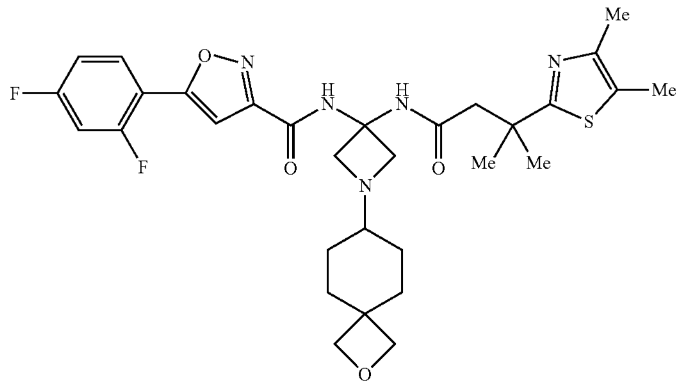 [SMILES: Cc1nc(C(C)(C)CC(=O)NC2(NC(=O)c3cc(-c4ccc(F)cc4F)on3)CN(C3CCC4(CC3)COC4)C2)sc1C] |

-continued
| Compound ID | Structure |
|---|---|
| 1.246 | 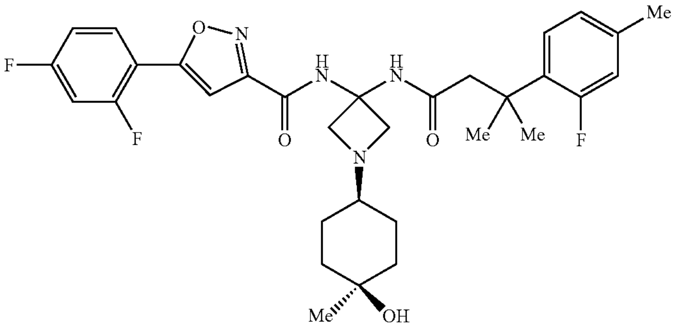 [SMILES: Cc1ccc(C(C)(C)CC(=O)NC2(NC(=O)c3cc(-c4ccc(F)cc4F)on3)CN([C@H]3CC[C@@](C)(O)CC3)C2)c(F)c1] |
| 1.247 | 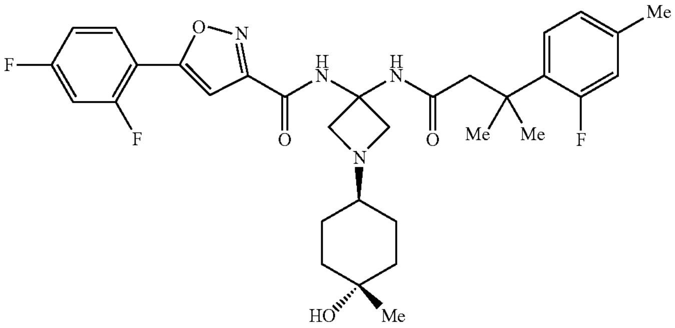 [SMILES: Cc1ccc(C(C)(C)CC(=O)NC2(NC(=O)c3cc(-c4ccc(F)cc4F)on3)CN([C@H]3CC[C@](C)(O)CC3)C2)c(F)c1] |
| 1.248 | 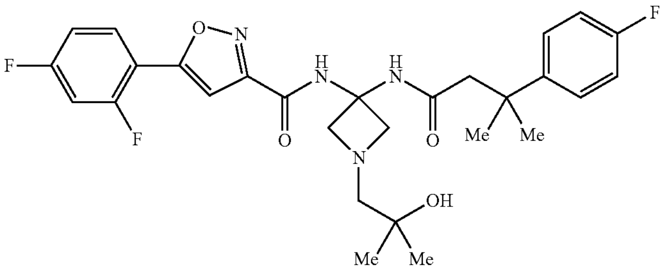 [SMILES: CC(C)(O)CN1CC(NC(=O)CC(C)(C)c2ccc(F)cc2)(NC(=O)c2cc(-c3ccc(F)cc3F)on2)C1] |
| 1.249 | 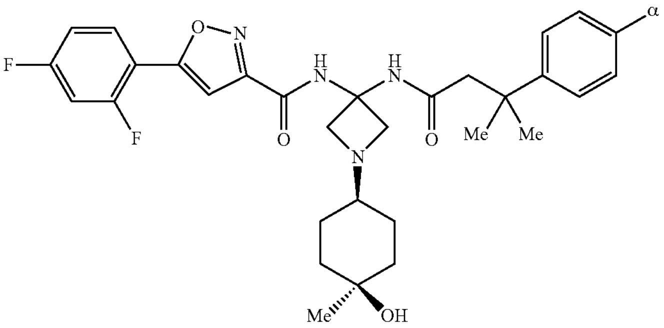 |
| 1.250 | 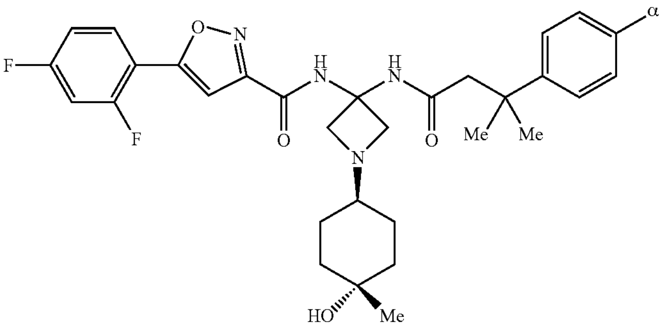 |

-continued
| Compound ID | Structure |
|---|---|
| 1.251 | 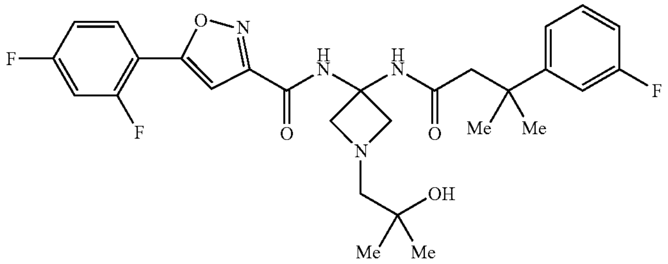 [SMILES: CC(C)(O)CN1CC(NC(=O)CC(C)(C)c2cccc(F)c2)(NC(=O)c2cc(-c3ccc(F)cc3F)on2)C1] |
| 1.252 | 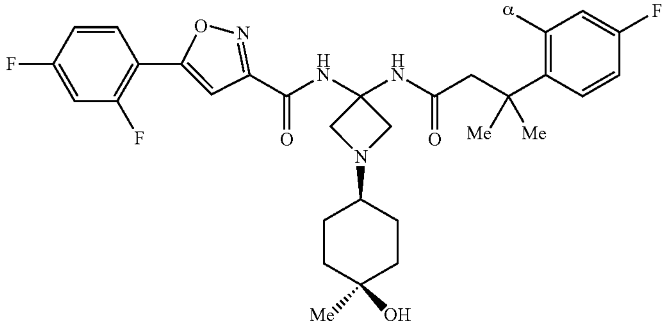 |
| 1.253 | 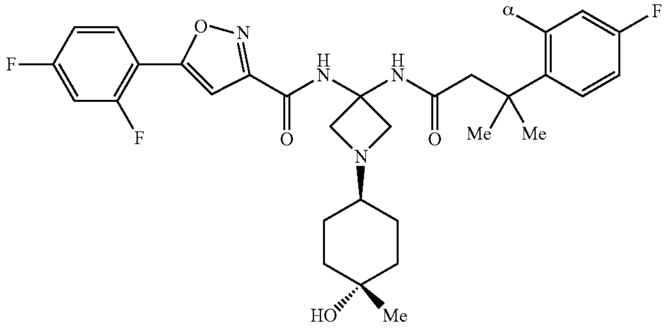 |
| 1.254 | 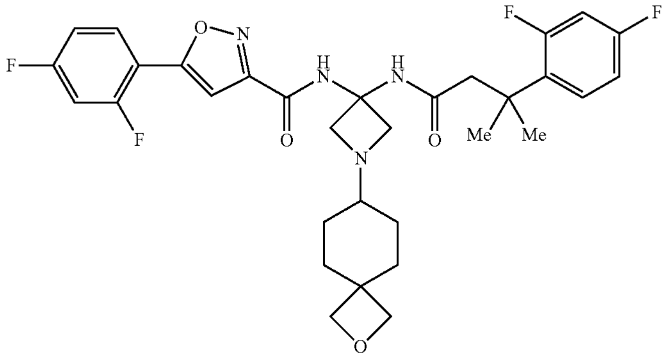 [SMILES: CC(C)(CC(=O)NC1(NC(=O)c2cc(-c3ccc(F)cc3F)on2)CN(C2CCC3(CC2)COC3)C1)c1ccc(F)cc1F] |
| 1.255 | 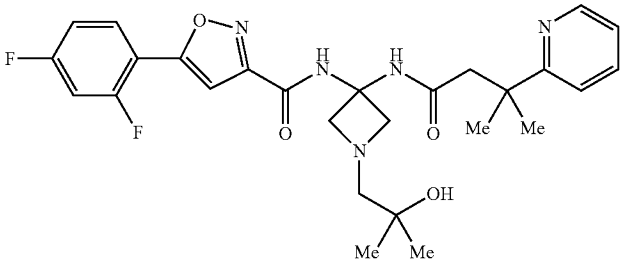 [SMILES: CC(C)(O)CN1CC(NC(=O)CC(C)(C)c2ccccn2)(NC(=O)c2cc(-c3ccc(F)cc3F)on2)C1] |

-continued
| Compound ID | Structure |
|---|---|
| 1.256 | 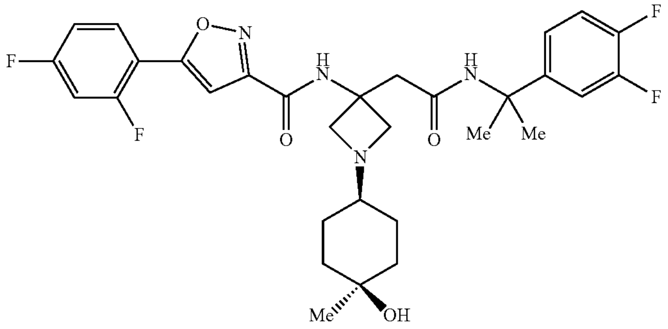 [SMILES: CC(C)(NC(=O)CC1(NC(=O)c2cc(-c3ccc(F)cc3F)on2)CN([C@H]2CC[C@@](C)(O)CC2)C1)c1ccc(F)c(F)c1] |
| 1.257 | 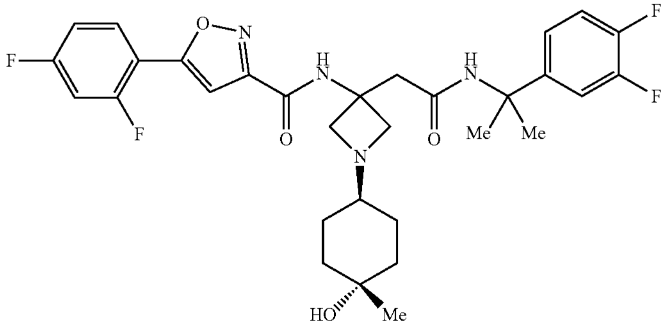 [SMILES: CC(C)(NC(=O)CC1(NC(=O)c2cc(-c3ccc(F)cc3F)on2)CN([C@H]2CC[C@](C)(O)CC2)C1)c1ccc(F)c(F)c1] |
| 1.258 | 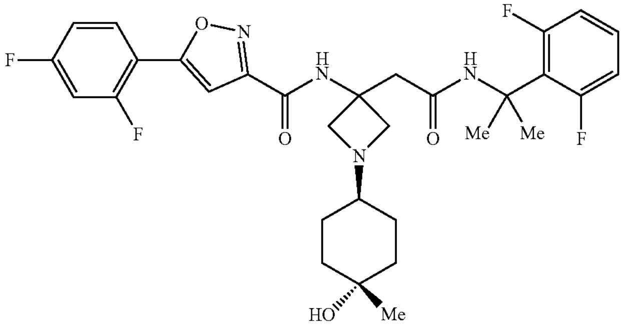 [SMILES: CC(C)(NC(=O)CC1(NC(=O)c2cc(-c3ccc(F)cc3F)on2)CN([C@H]2CC[C@](C)(O)CC2)C1)c1c(F)cccc1F] |
| 1.259 | 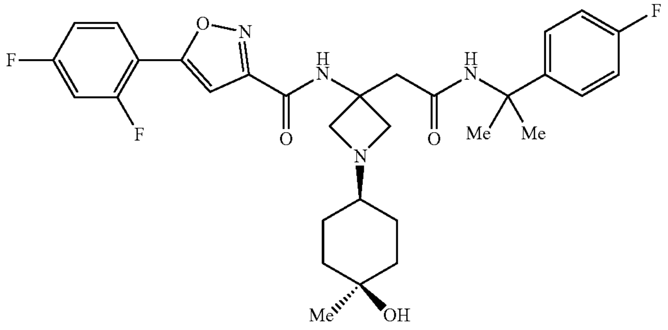 [SMILES: CC(C)(NC(=O)CC1(NC(=O)c2cc(-c3ccc(F)cc3F)on2)CN([C@H]2CC[C@@](C)(O)CC2)C1)c1ccc(F)cc1] |

-continued
| Compound ID | Structure |
|---|---|
| 1.260 | 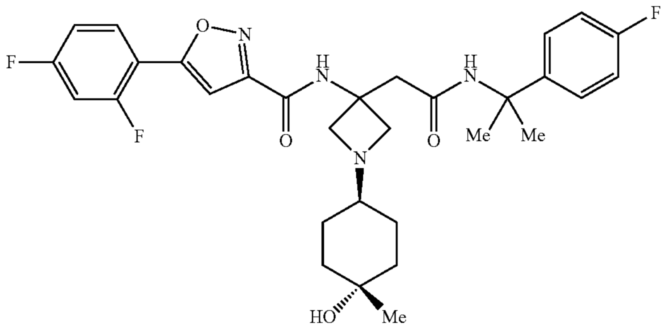 [SMILES: CC(C)(NC(=O)CC1(NC(=O)c2cc(-c3ccc(F)cc3F)on2)CN([C@H]2CC[C@](C)(O)CC2)C1)c1ccc(F)cc1] |
| 1.261 | 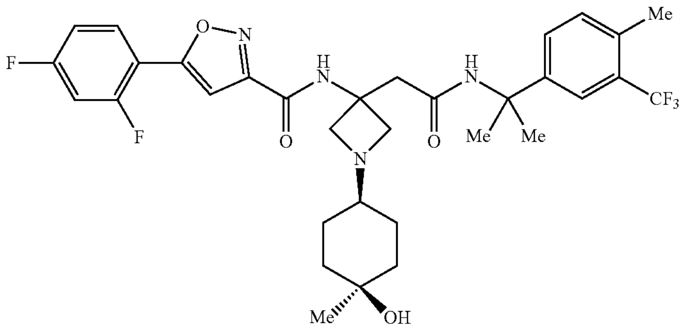 [SMILES: Cc1ccc(C(C)(C)NC(=O)CC2(NC(=O)c3cc(-c4ccc(F)cc4F)on3)CN([C@H]3CC[C@@](C)(O)CC3)C2)cc1C(F)(F)F] |
| 1.262 | 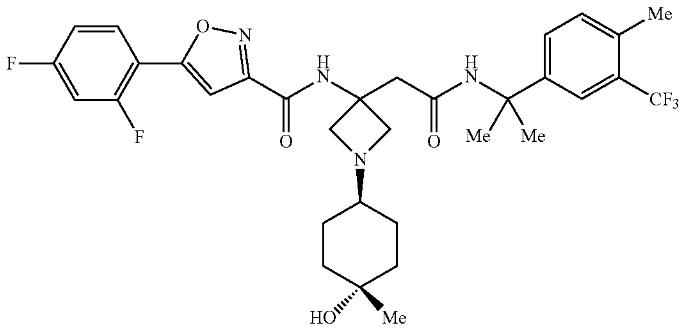 [SMILES: Cc1ccc(C(C)(C)NC(=O)CC2(NC(=O)c3cc(-c4ccc(F)cc4F)on3)CN([C@H]3CC[C@](C)(O)CC3)C2)cc1C(F)(F)F] |
| 1.263 | 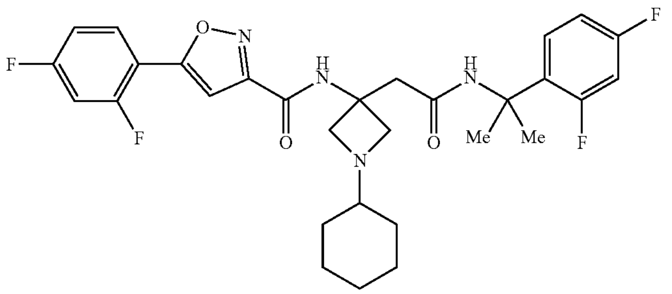 [SMILES: CC(C)(NC(=O)CC1(NC(=O)c2cc(-c3ccc(F)cc3F)on2)CN(C2CCCCC2)C1)c1ccc(F)cc1F] |
| 1.264 | 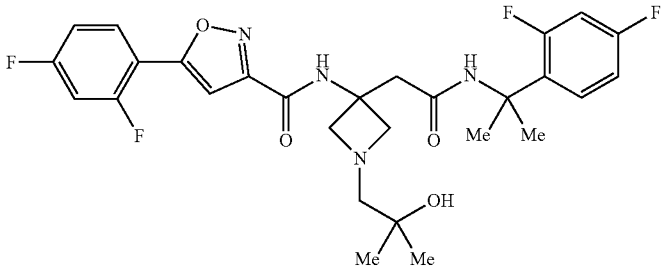 [SMILES: CC(C)(O)CN1CC(CC(=O)NC(C)(C)c2ccc(F)cc2F)(NC(=O)c2cc(-c3ccc(F)cc3F)on2)C1] |

-continued
| Compound ID | Structure |
|---|---|
| 1.265 | 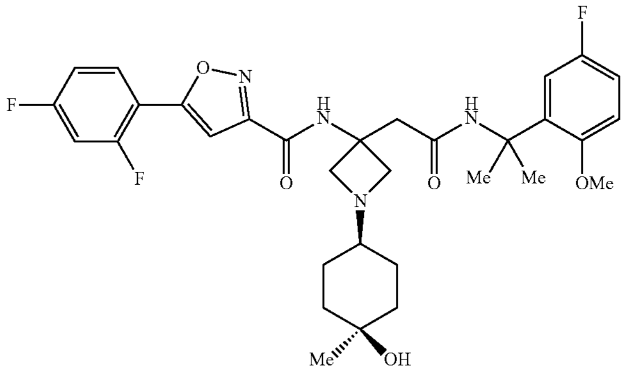 [SMILES: COc1ccc(F)cc1C(C)(C)NC(=O)CC1(NC(=O)c2cc(-c3ccc(F)cc3F)on2)CN([C@H]2CC[C@@](C)(O)CC2)C1] |
| 1.266 | 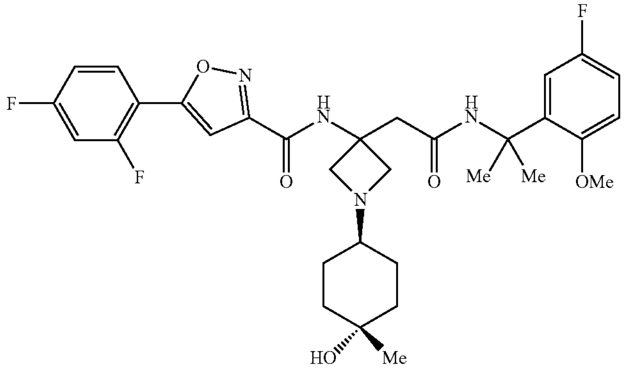 [SMILES: COc1ccc(F)cc1C(C)(C)NC(=O)CC1(NC(=O)c2cc(-c3ccc(F)cc3F)on2)CN([C@H]2CC[C@](C)(O)CC2)C1] |
| 1.267 | 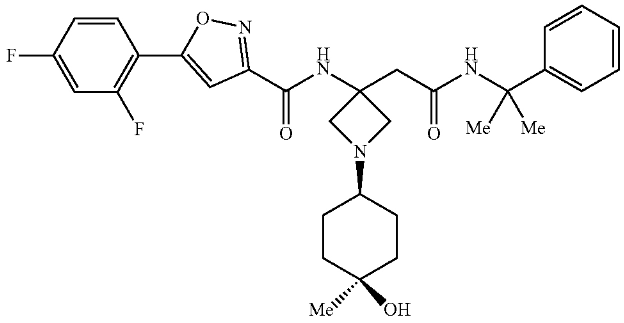 [SMILES: CC(C)(NC(=O)CC1(NC(=O)c2cc(-c3ccc(F)cc3F)on2)CN([C@H]2CC[C@@](C)(O)CC2)C1)c1ccccc1] |
| 1.268 | 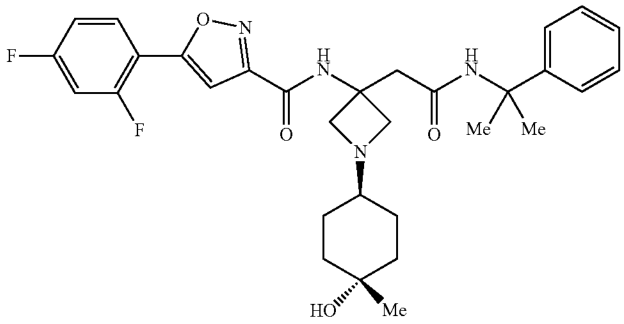 [SMILES: CC(C)(NC(=O)CC1(NC(=O)c2cc(-c3ccc(F)cc3F)on2)CN([C@H]2CC[C@](C)(O)CC2)C1)c1ccccc1] |

-continued
| Compound ID | Structure |
|---|---|
| 1.269 | 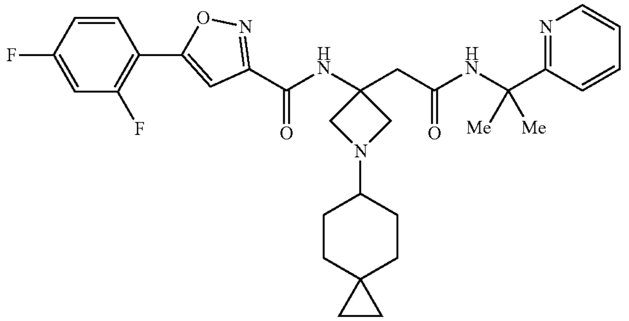 [SMILES: CC(C)(NC(=O)CC1(NC(=O)c2cc(-c3ccc(F)cc3F)on2)CN(C2CCC3(CC2)CC3)C1)c1ccccn1] |
| 1.270 | 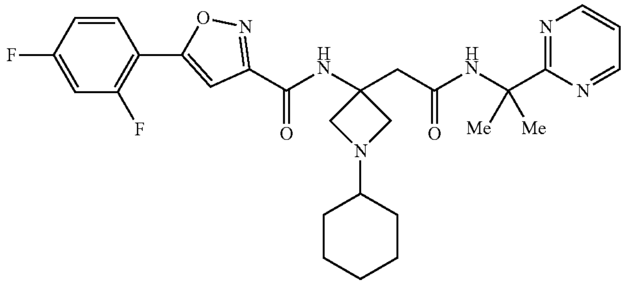 [SMILES: CC(C)(NC(=O)CC1(NC(=O)c2cc(-c3ccc(F)cc3F)on2)CN(C2CCCCC2)C1)c1ncccn1] |
| 1.271 | 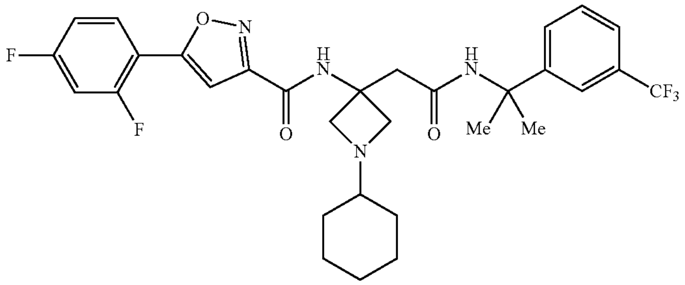 [SMILES: CC(C)(NC(=O)CC1(NC(=O)c2cc(-c3ccc(F)cc3F)on2)CN(C2CCCCC2)C1)c1cccc(C(F)(F)F)c1] |
| 1.272 | 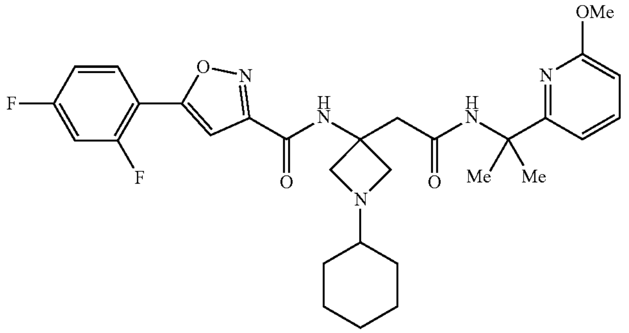 [SMILES: COc1cccc(C(C)(C)NC(=O)CC2(NC(=O)c3cc(-c4ccc(F)cc4F)on3)CN(C3CCCCC3)C2)n1] |
| 1.273 | 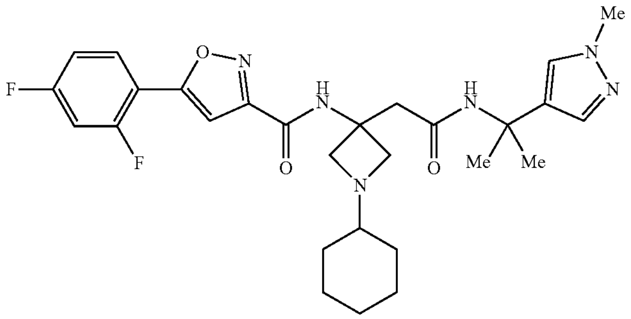 [SMILES: Cn1cc(C(C)(C)NC(=O)CC2(NC(=O)c3cc(-c4ccc(F)cc4F)on3)CN(C3CCCCC3)C2)cn1] |

-continued
| Compound ID | Structure |
| --- | --- |
| 1.274 | 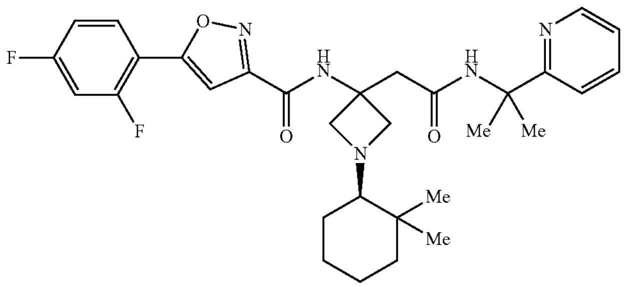 [SMILES: CC(C)(NC(=O)CC1(NC(=O)c2cc(-c3ccc(F)cc3F)on2)CN([C@@H]2CCCCC2(C)C)C1)c1ccccn1] |
| 1.275 | 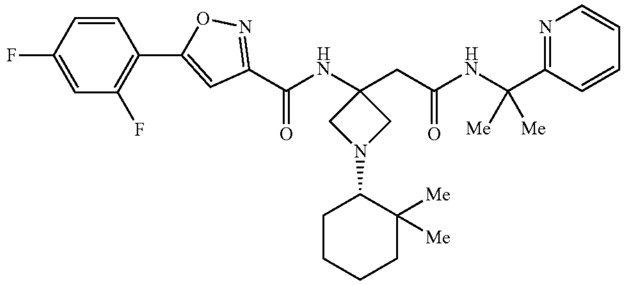 [SMILES: CC(C)(NC(=O)CC1(NC(=O)c2cc(-c3ccc(F)cc3F)on2)CN([C@H]2CCCCC2(C)C)C1)c1ccccn1] |
| 1.276 | 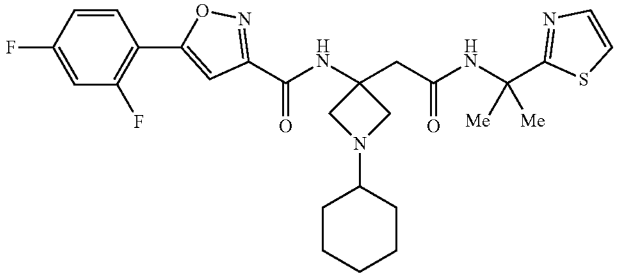 [SMILES: CC(C)(NC(=O)CC1(NC(=O)c2cc(-c3ccc(F)cc3F)on2)CN(C2CCCCC2)C1)c1nccs1] |
| 1.277 | 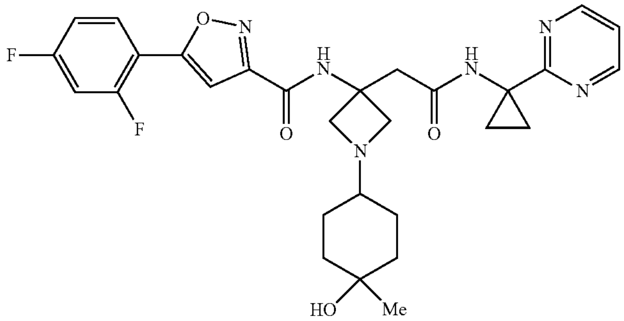 [SMILES: CC1(O)CCC(N2CC(CC(=O)NC3(c4ncccn4)CC3)(NC(=O)c3cc(-c4ccc(F)cc4F)on3)C2)CC1] |
| 1.278 | 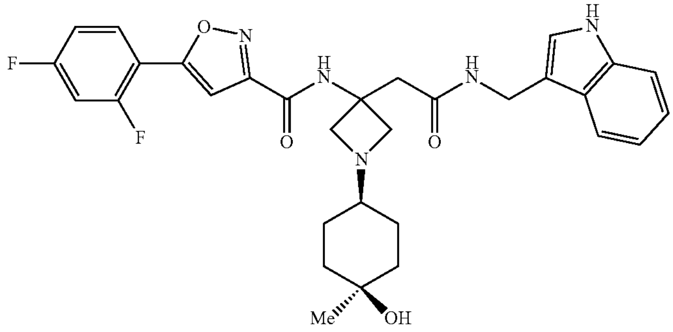 [SMILES: C[C@]1(O)CC[C@@H](N2CC(CC(=O)NCc3c[nH]c4ccccc34)(NC(=O)c3cc(-c4ccc(F)cc4F)on3)C2)CC1] |

-continued
| Compound ID | Structure |
|---|---|
| 1.279 | 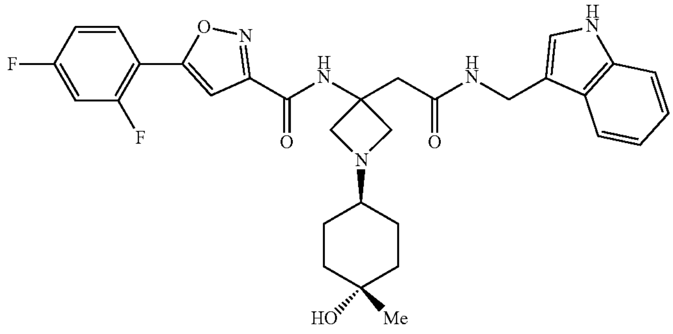 [SMILES: C[C@]1(O)CC[C@H](N2CC(CC(=O)NCc3c[nH]c4ccccc34)(NC(=O)c3cc(-c4ccc(F)cc4F)on3)C2)CC1] |
| 1.280 | 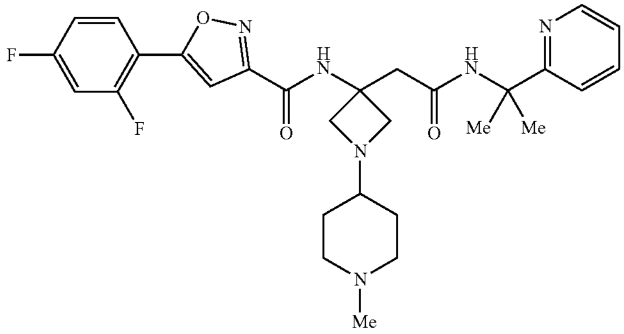 [SMILES: CN1CCC(N2CC(CC(=O)NC(C)(C)c3ccccn3)(NC(=O)c3cc(-c4ccc(F)cc4F)on3)C2)CC1] |
| 1.281 | 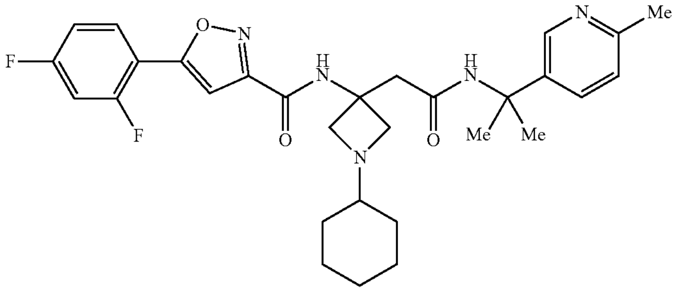 [SMILES: Cc1ccc(C(C)(C)NC(=O)CC2(NC(=O)c3cc(-c4ccc(F)cc4F)on3)CN(C3CCCCC3)C2)cn1] |
| 1.282 | 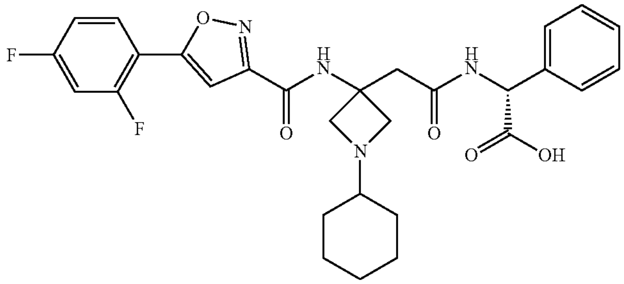 [SMILES: O=C(CC1(NC(=O)c2cc(-c3ccc(F)cc3F)on2)CN(C2CCCCC2)C1)N[C@@H](C(=O)O)c1ccccc1] |
| 1.283 | 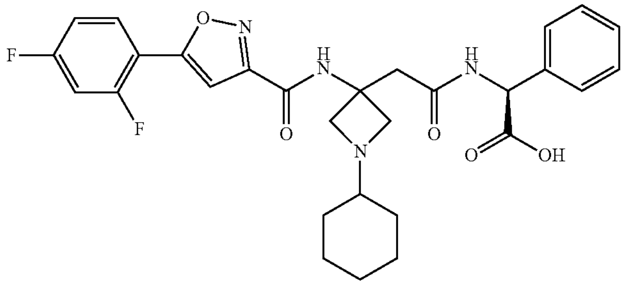 [SMILES: O=C(CC1(NC(=O)c2cc(-c3ccc(F)cc3F)on2)CN(C2CCCCC2)C1)N[C@H](C(=O)O)c1ccccc1] |

-continued
| Compound ID | Structure |
|---|---|
| 1.284 | 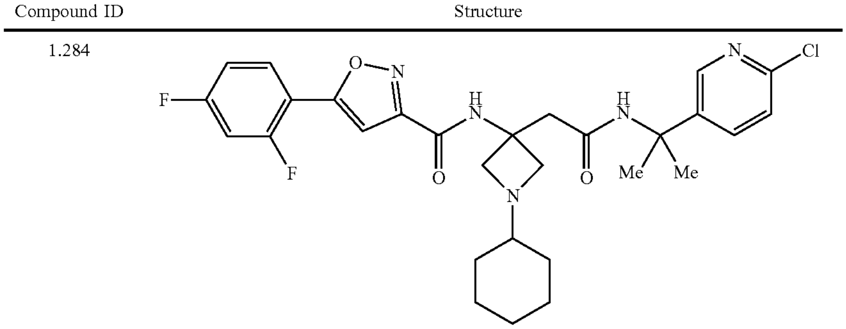 |
| 1.285 | 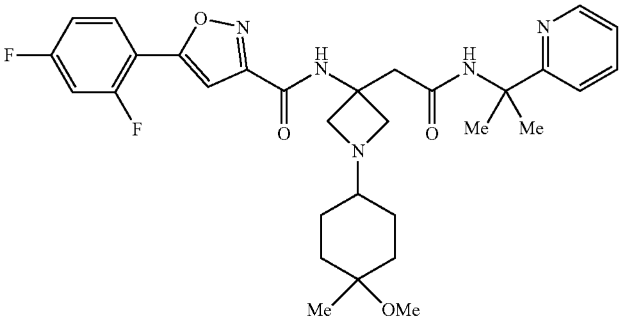 [SMILES: COC1(C)CCC(N2CC(CC(=O)NC(C)(C)c3ccccn3)(NC(=O)c3cc(-c4ccc(F)cc4F)on3)C2)CC1] |
| 1.286 | 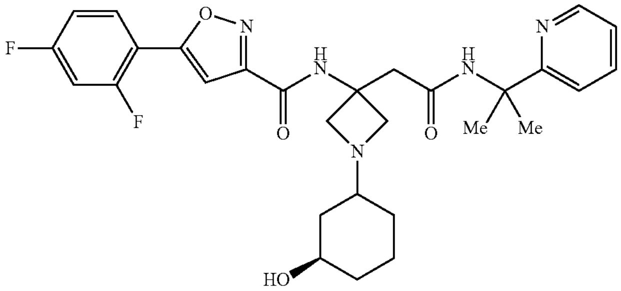 [SMILES: CC(C)(NC(=O)CC1(NC(=O)c2cc(-c3ccc(F)cc3F)on2)CN(C2CCC[C@@H](O)C2)C1)c1ccccn1] |
| 1.287 | 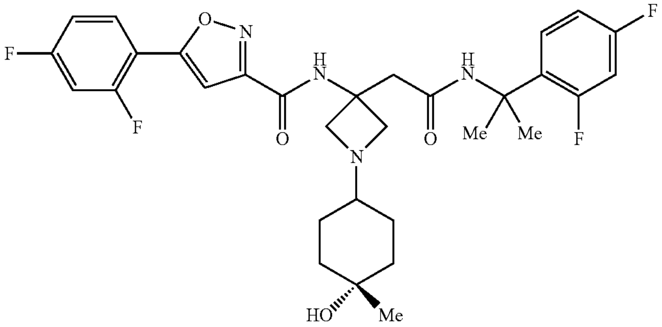 |
| 1.288 | 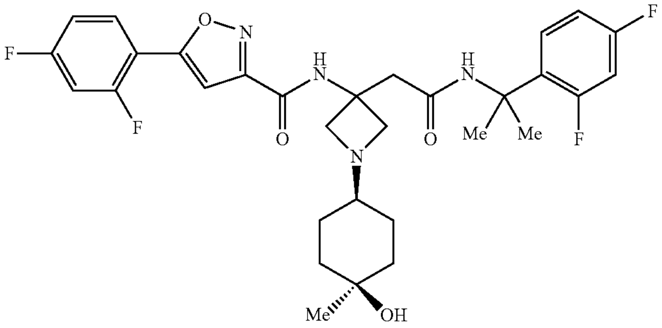 [SMILES: CC(C)(NC(=O)CC1(NC(=O)c2cc(-c3ccc(F)cc3F)on2)CN([C@H]2CC[C@@](C)(O)CC2)C1)c1ccc(F)cc1F] |

-continued
| Compound ID | Structure |
|---|---|
| 1.289 | 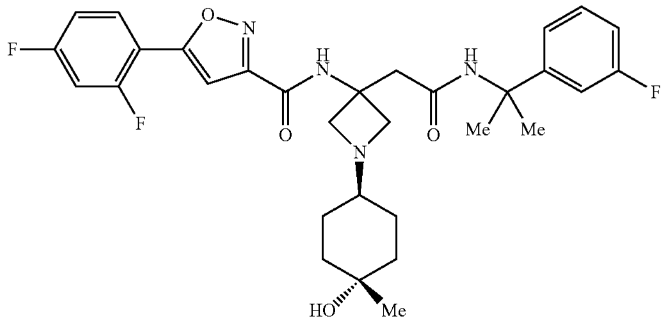 |
| 1.290 | 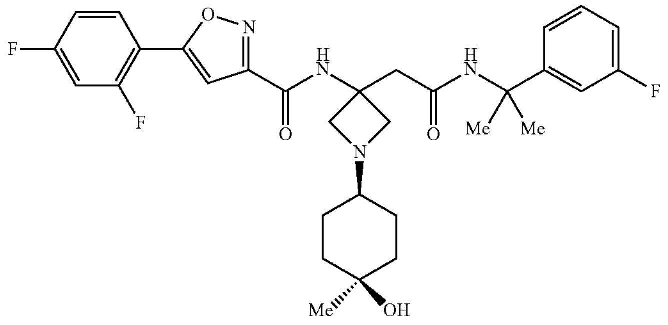 [SMILES: CC(C)(NC(=O)CC1(NC(=O)c2cc(-c3ccc(F)cc3F)on2)CN([C@H]2CC[C@@](C)(O)CC2)C1)c1cccc(F)c1] |
| 1.291 | 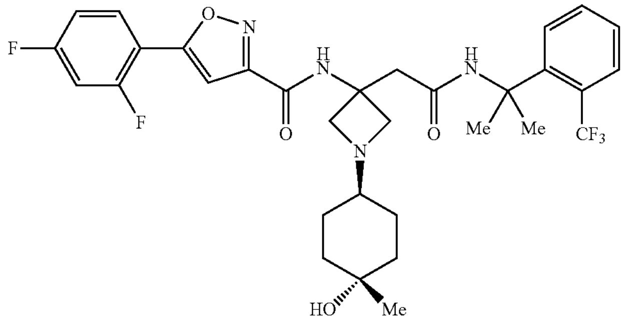 |
| 1.292 | 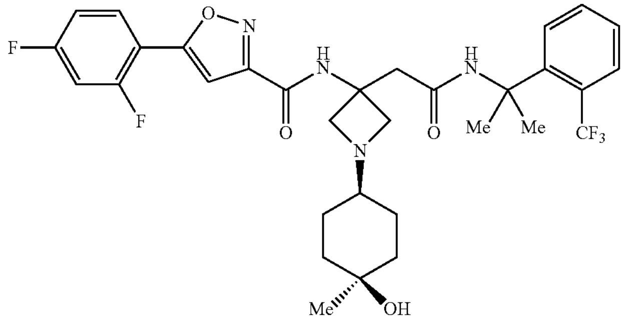 [SMILES: CC(C)(NC(=O)CC1(NC(=O)c2cc(-c3ccc(F)cc3F)on2)CN([C@H]2CC[C@@](C)(O)CC2)C1)c1ccccc1C(F)(F)F] |
| 1.293 | 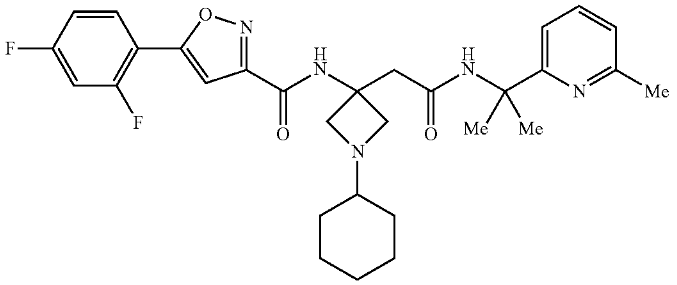 [SMILES: Cc1cccc(C(C)(C)NC(=O)CC2(NC(=O)c3cc(-c4ccc(F)cc4F)on3)CN(C3CCCCC3)C2)n1] |

-continued
| Compound ID | Structure |
| --- | --- |
| 1.294 | 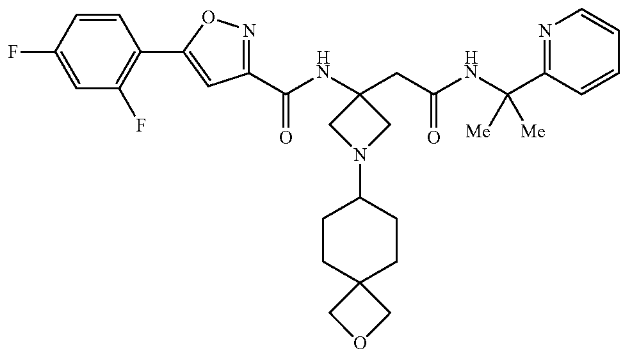 [SMILES: CC(C)(NC(=O)CC1(NC(=O)c2cc(-c3ccc(F)cc3F)on2)CN(C2CCC3(CC2)COC3)C1)c1ccccn1] |
| 1.295 | 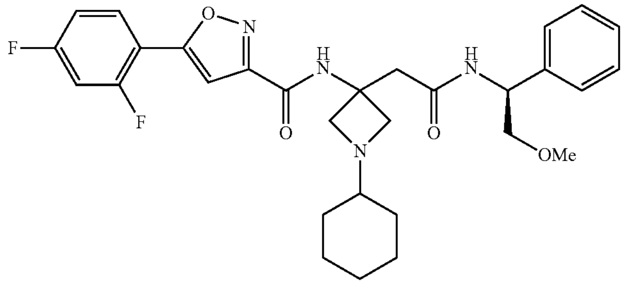 [SMILES: COC[C@@H](NC(=O)CC1(NC(=O)c2cc(-c3ccc(F)cc3F)on2)CN(C2CCCCC2)C1)c1ccccc1] |
| 1.296 | 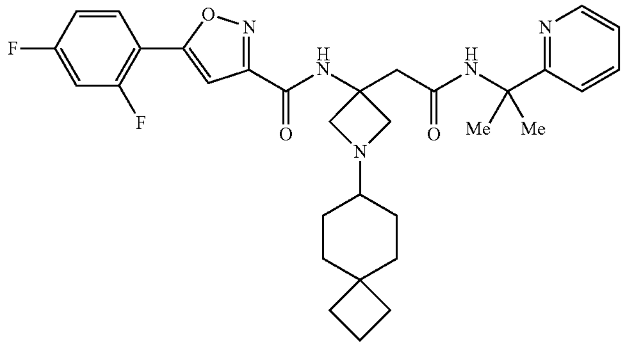 [SMILES: CC(C)(NC(=O)CC1(NC(=O)c2cc(-c3ccc(F)cc3F)on2)CN(C2CCC3(CCC3)CC2)C1)c1ccccn1] |
| 1.297 | 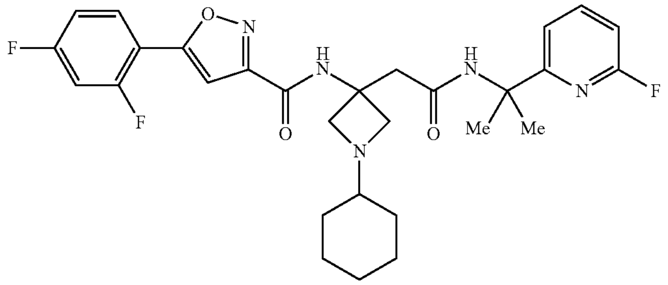 |
| 1.298 | 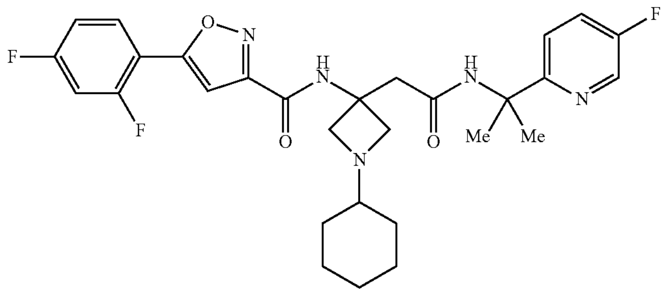 [SMILES: CC(C)(NC(=O)CC1(NC(=O)c2cc(-c3ccc(F)cc3F)on2)CN(C2CCCCC2)C1)c1ccc(F)cn1] |

-continued
| Compound ID | Structure |
| --- | --- |
| 1.299 | 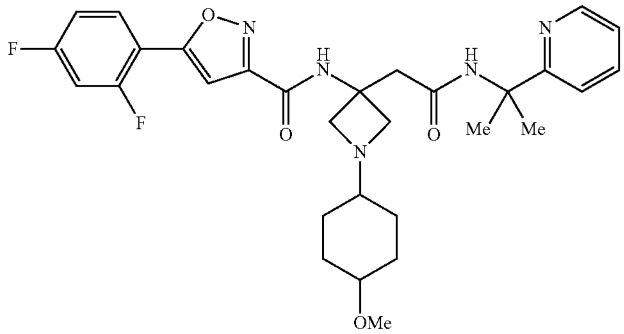 [SMILES: COC1CCC(N2CC(CC(=O)NC(C)(C)c3ccccn3)(NC(=O)c3cc(-c4ccc(F)cc4F)on3)C2)CC1] |
| 1.300 | 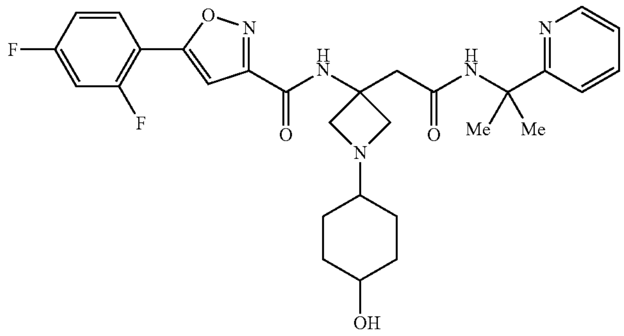 [SMILES: CC(C)(NC(=O)CC1(NC(=O)c2cc(-c3ccc(F)cc3F)on2)CN(C2CCC(O)CC2)C1)c1ccccn1] |
| 1.301 | 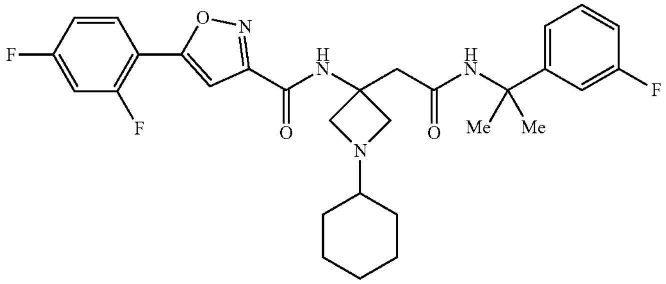 [SMILES: CC(C)(NC(=O)CC1(NC(=O)c2cc(-c3ccc(F)cc3F)on2)CN(C2CCCCC2)C1)c1cccc(F)c1] |
| 1.302 | 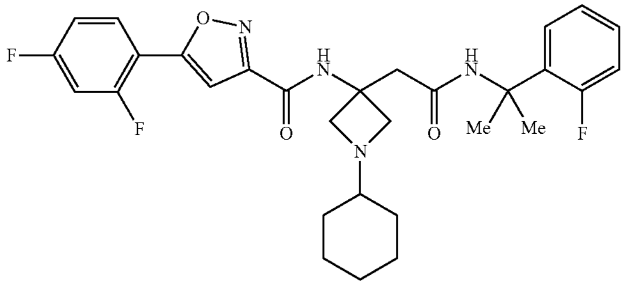 [SMILES: CC(C)(NC(=O)CC1(NC(=O)c2cc(-c3ccc(F)cc3F)on2)CN(C2CCCCC2)C1)c1ccccc1F] |
| 1.303 | 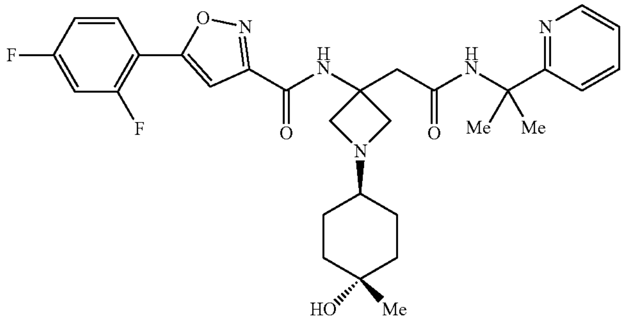 |

-continued
| Compound ID | Structure |
|---|---|
| 1.304 | 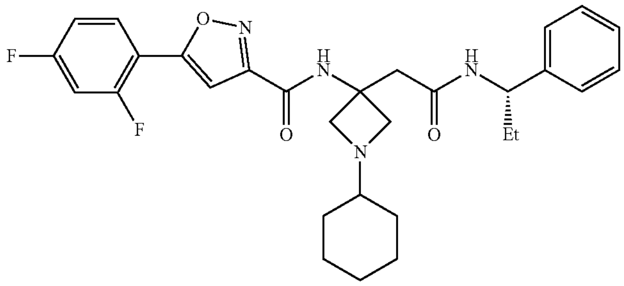 [SMILES: CC[C@H](NC(=O)CC1(NC(=O)c2cc(-c3ccc(F)cc3F)on2)CN(C2CCCCC2)C1)c1ccccc1] |
| 1.305 | 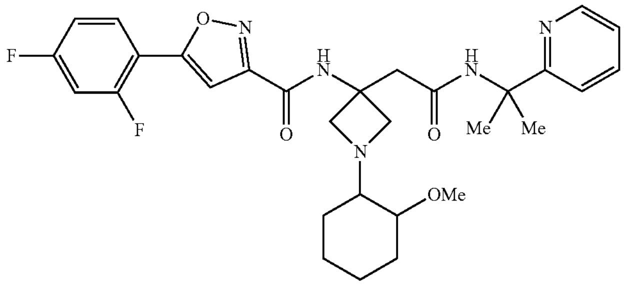 [SMILES: COC1CCCCC1N1CC(CC(=O)NC(C)(C)c2ccccn2)(NC(=O)c2cc(-c3ccc(F)cc3F)on2)C1] |
| 1.306 | 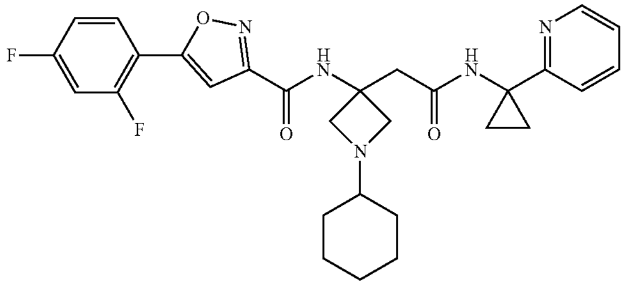 [SMILES: O=C(CC1(NC(=O)c2cc(-c3ccc(F)cc3F)on2)CN(C2CCCCC2)C1)NC1(c2ccccn2)CC1] |
| 1.307 | 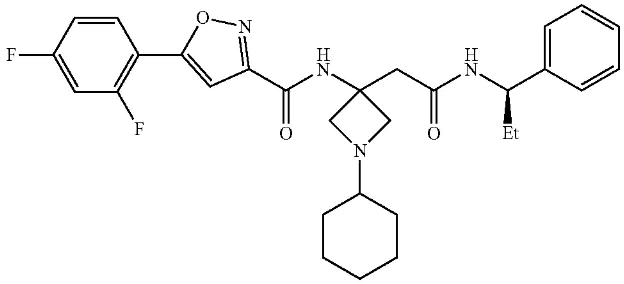 |
| 1.308 | 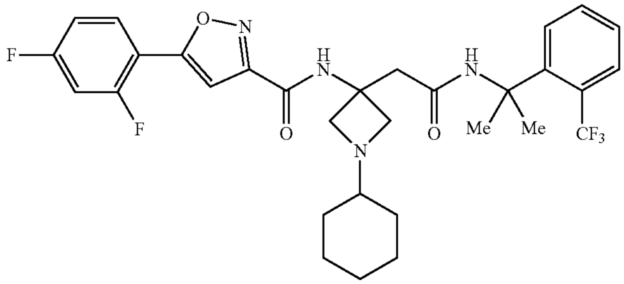 |

-continued
| Compound ID | Structure |
|---|---|
| 1.309 | 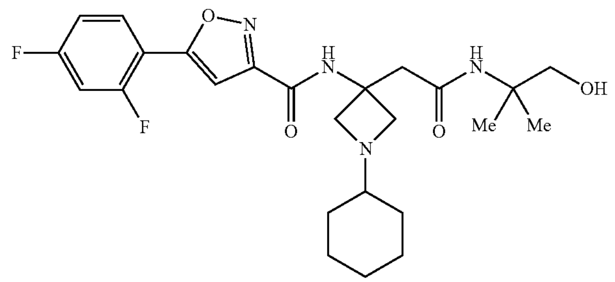 [SMILES: CC(C)(CO)NC(=O)CC1(NC(=O)c2cc(-c3ccc(F)cc3F)on2)CN(C2CCCCC2)C1] |
| 1.310 | 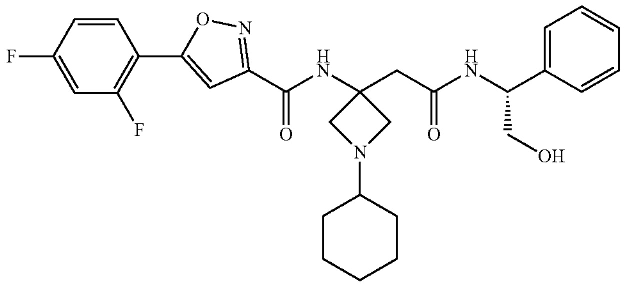 [SMILES: O=C(CC1(NC(=O)c2cc(-c3ccc(F)cc3F)on2)CN(C2CCCCC2)C1)N[C@@H](CO)c1ccccc1] |
| 1.311 | 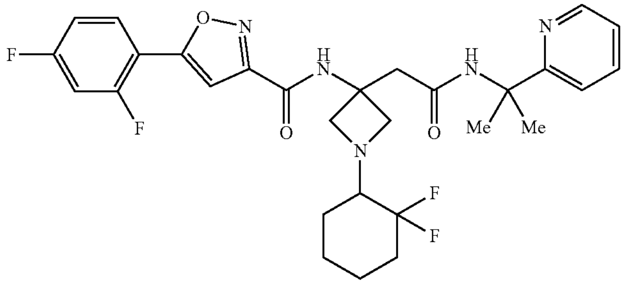 [SMILES: CC(C)(NC(=O)CC1(NC(=O)c2cc(-c3ccc(F)cc3F)on2)CN(C2CCCCC2(F)F)C1)c1ccccn1] |
| 1.312 | 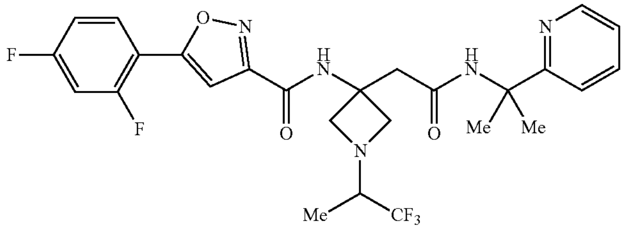 [SMILES: CC(N1CC(CC(=O)NC(C)(C)c2ccccn2)(NC(=O)c2cc(-c3ccc(F)cc3F)on2)C1)C(F)(F)F] |
| 1.313 | 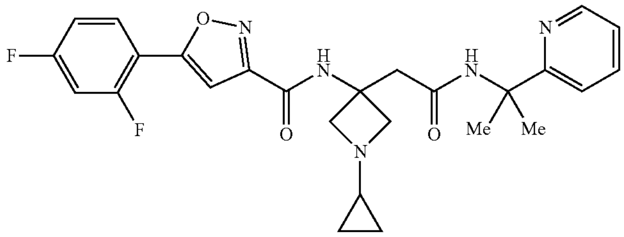 [SMILES: CC(C)(NC(=O)CC1(NC(=O)c2cc(-c3ccc(F)cc3F)on2)CN(C2CC2)C1)c1ccccn1] |

-continued
| Compound ID | Structure |
| --- | --- |
| 1.314 | 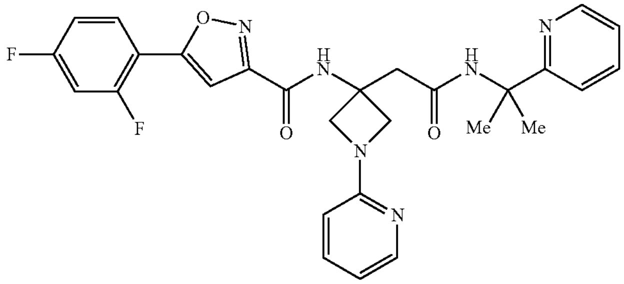 [SMILES: CC(C)(NC(=O)CC1(NC(=O)c2cc(-c3ccc(F)cc3F)on2)CN(c2ccccn2)C1)c1ccccn1] |
| 1.315 | 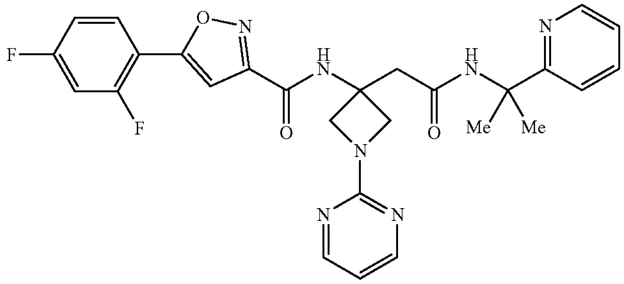 [SMILES: CC(C)(NC(=O)CC1(NC(=O)c2cc(-c3ccc(F)cc3F)on2)CN(c2ncccn2)C1)c1ccccn1] |
| 1.316 | 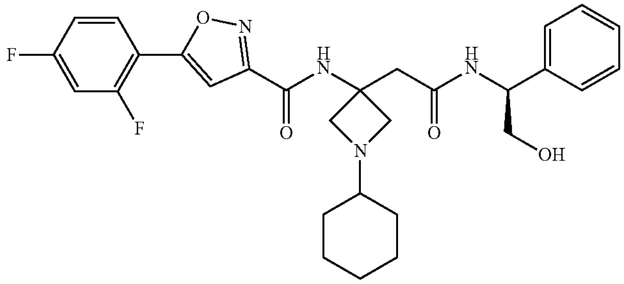 [SMILES: O=C(CC1(NC(=O)c2cc(-c3ccc(F)cc3F)on2)CN(C2CCCCC2)C1)N[C@H](CO)c1ccccc1] |
| 1.317 | 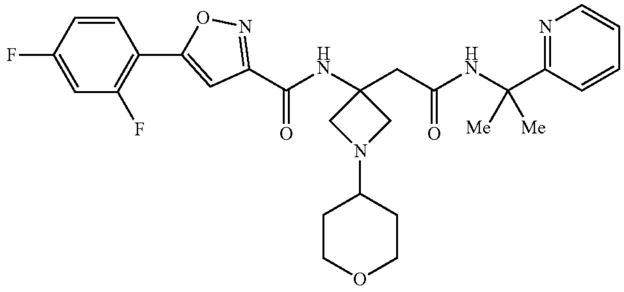 [SMILES: CC(C)(NC(=O)CC1(NC(=O)c2cc(-c3ccc(F)cc3F)on2)CN(C2CCOCC2)C1)c1ccccn1] |
| 1.318 | 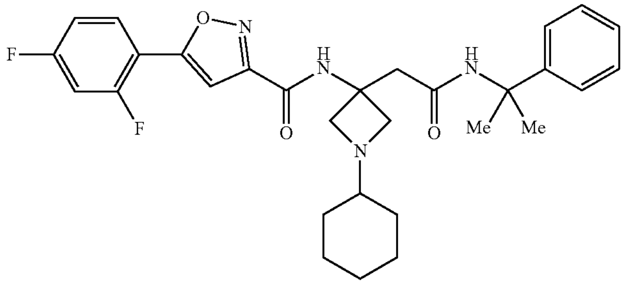 |

-continued
| Compound ID | Structure |
| --- | --- |
| 1.319 | 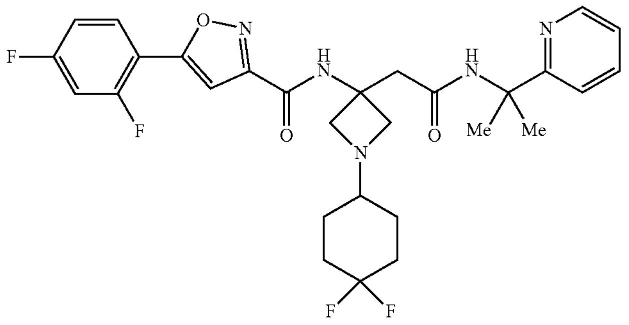 [SMILES: CC(C)(NC(=O)CC1(NC(=O)c2cc(-c3ccc(F)cc3F)on2)CN(C2CCC(F)(F)CC2)C1)c1ccccn1] |
| 1.320 | 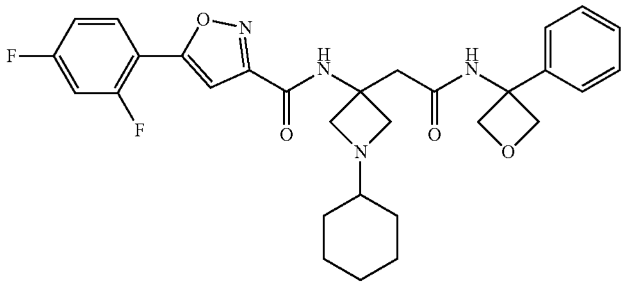 [SMILES: O=C(CC1(NC(=O)c2cc(-c3ccc(F)cc3F)on2)CN(C2CCCCC2)C1)NC1(c2ccccc2)COC1] |
| 1.321 | 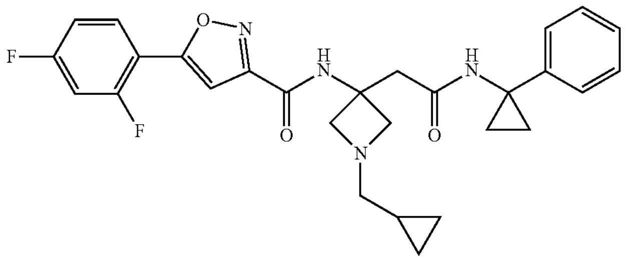 [SMILES: O=C(CC1(NC(=O)c2cc(-c3ccc(F)cc3F)on2)CN(CC2CC2)C1)NC1(c2ccccc2)CC1] |
| 1.322 | 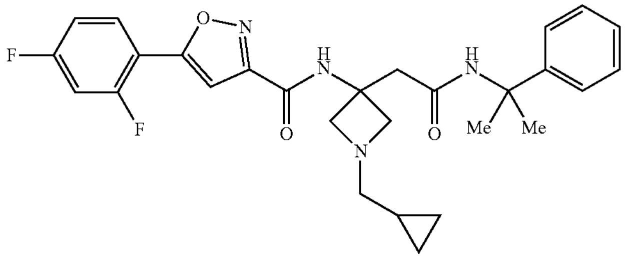 [SMILES: CC(C)(NC(=O)CC1(NC(=O)c2cc(-c3ccc(F)cc3F)on2)CN(CC2CC2)C1)c1ccccc1] |
| 1.323 | 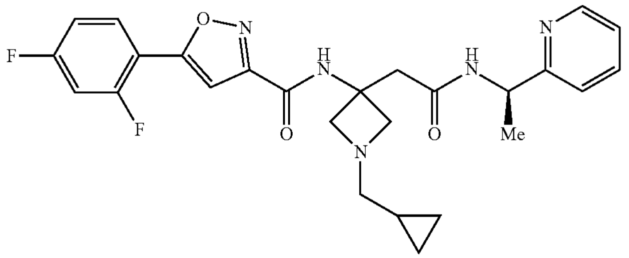 |

-continued
| Compound ID | Structure |
|---|---|
| 1.324 | 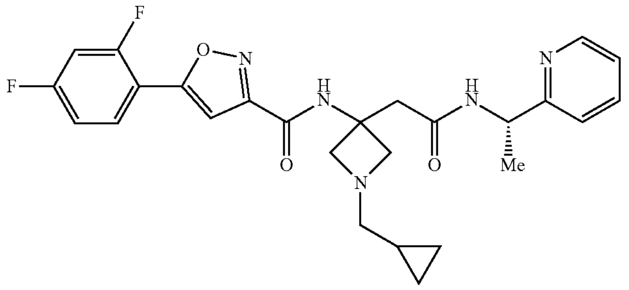 |
| 1.325 | 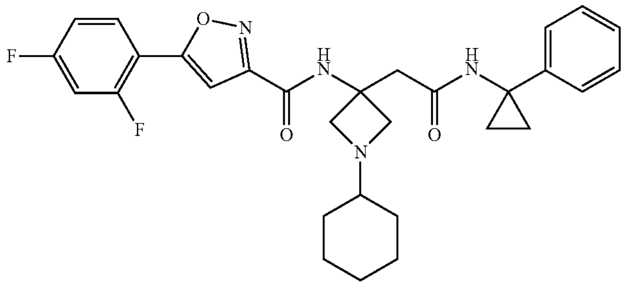 [SMILES: O=C(CC1(NC(=O)c2cc(-c3ccc(F)cc3F)on2)CN(C2CCCCC2)C1)NC1(c2ccccc2)CC1] |
| 1.326 | 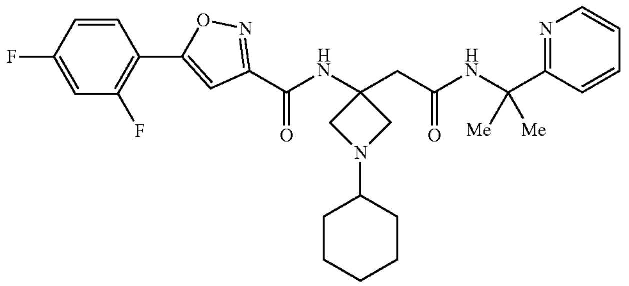 |
| 1.327 | 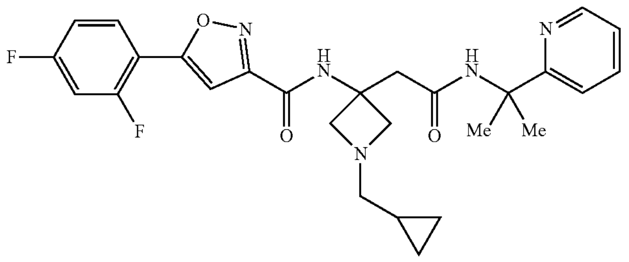 [SMILES: CC(C)(NC(=O)CC1(NC(=O)c2cc(-c3ccc(F)cc3F)on2)CN(CC2CC2)C1)c1ccccn1] |
| 1.328 | 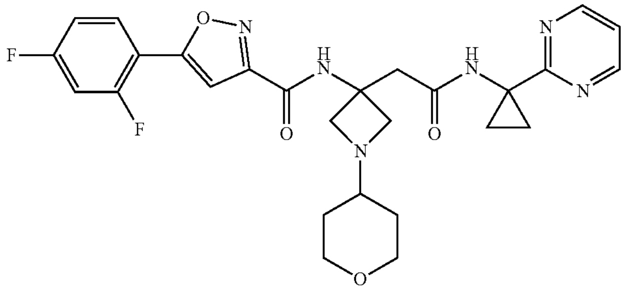 [SMILES: O=C(CC1(NC(=O)c2cc(-c3ccc(F)cc3F)on2)CN(C2CCOCC2)C1)NC1(c2ncccn2)CC1] |

-continued
| Compound ID | Structure |
| --- | --- |
| 1.329 | 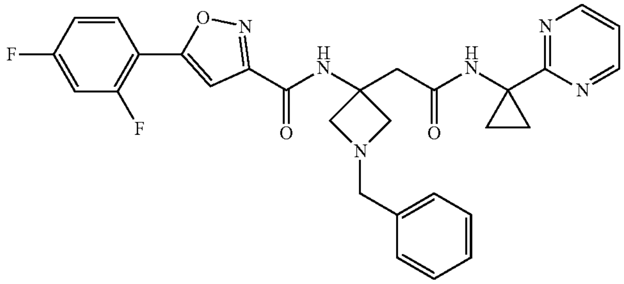 [SMILES: O=C(CC1(NC(=O)c2cc(-c3ccc(F)cc3F)on2)CN(Cc2ccccc2)C1)NC1(c2ncccn2)CC1] |
| 1.330 | 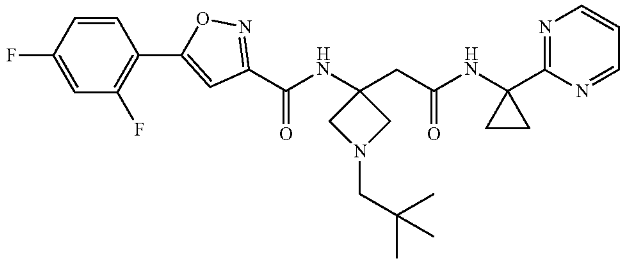 [SMILES: CC(C)(C)CN1CC(CC(=O)NC2(c3ncccn3)CC2)(NC(=O)c2cc(-c3ccc(F)cc3F)on2)C1] |
| 1.331 | 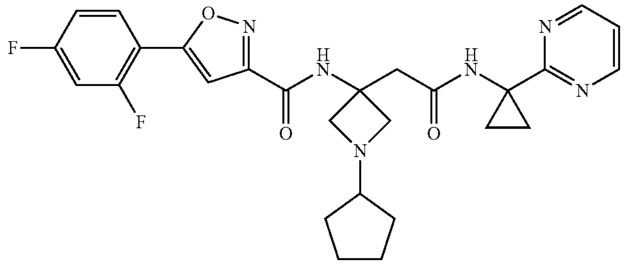 [SMILES: O=C(CC1(NC(=O)c2cc(-c3ccc(F)cc3F)on2)CN(C2CCCC2)C1)NC1(c2ncccn2)CC1] |
| 1.332 | 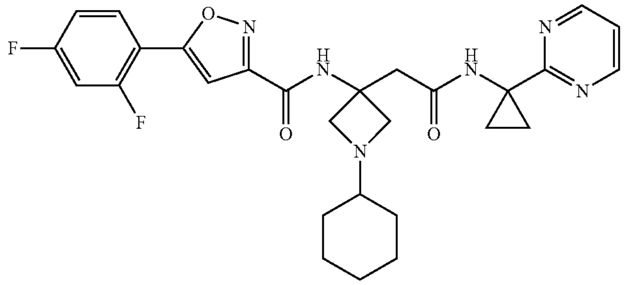 [SMILES: O=C(CC1(NC(=O)c2cc(-c3ccc(F)cc3F)on2)CN(C2CCCCC2)C1)NC1(c2ncccn2)CC1] |
| 1.333 | 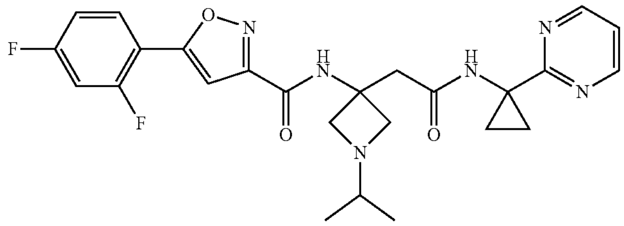 [SMILES: CC(C)N1CC(CC(=O)NC2(c3ncccn3)CC2)(NC(=O)c2cc(-c3ccc(F)cc3F)on2)C1] |

-continued
| Compound ID | Structure |
|---|---|
| 1.334 | 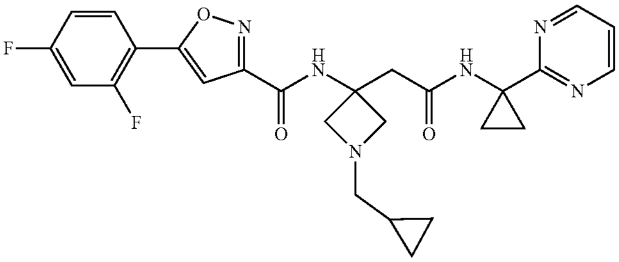 [SMILES: O=C(CC1(NC(=O)c2cc(-c3ccc(F)cc3F)on2)CN(CC2CC2)C1)NC1(c2ncccn2)CC1] |
| 1.335 | 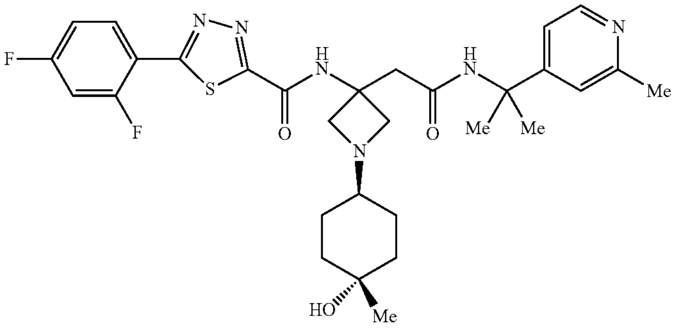 [SMILES: Cc1cc(C(C)(C)NC(=O)CC2(NC(=O)c3nnc(-c4ccc(F)cc4F)s3)CN([C@H]3CC[C@](C)(O)CC3)C2)ccn1] |
| 1.336 | 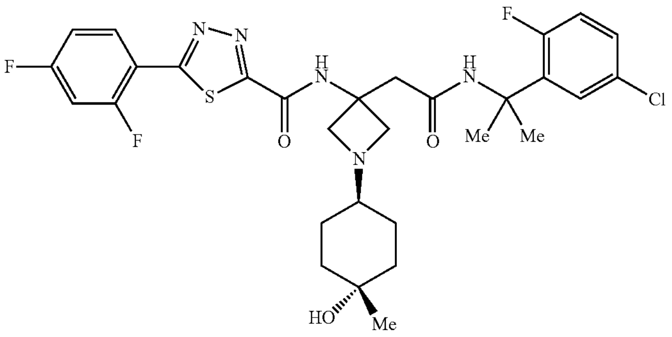 [SMILES: CC(C)(NC(=O)CC1(NC(=O)c2nnc(-c3ccc(F)cc3F)s2)CN([C@H]2CC[C@](C)(O)CC2)C1)c1cc(Cl)ccc1F] |
| 1.337 | 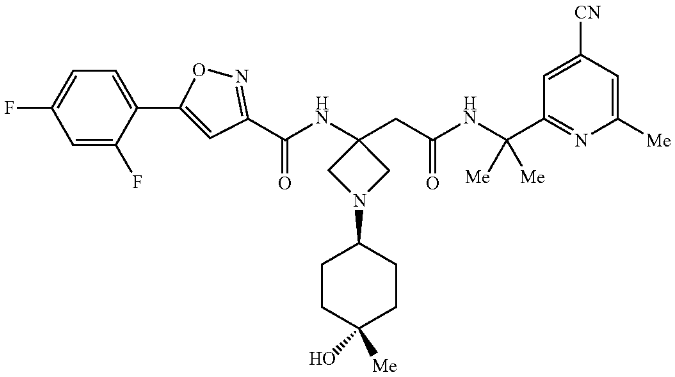 [SMILES: Cc1cc(C#N)cc(C(C)(C)NC(=O)CC2(NC(=O)c3cc(-c4ccc(F)cc4F)on3)CN([C@H]3CC[C@](C)(O)CC3)C2)n1] |

-continued
| Compound ID | Structure |
|---|---|
| 1.338 | 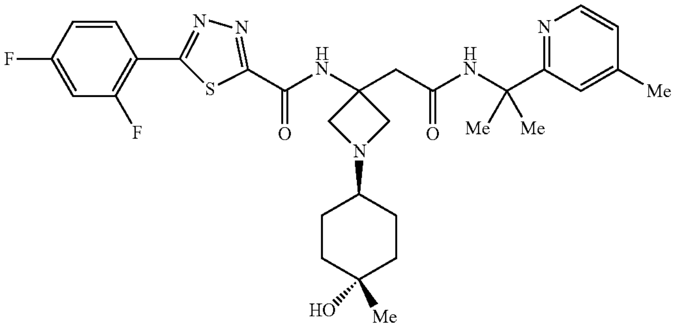 [SMILES: Cc1ccnc(C(C)(C)NC(=O)CC2(NC(=O)c3nnc(-c4ccc(F)cc4F)s3)CN([C@H]3CC[C@](C)(O)CC3)C2)c1] |
| 1.339 | 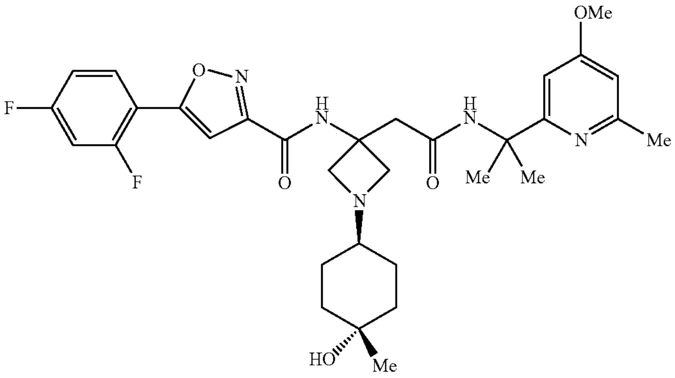 |
| 1.340 | 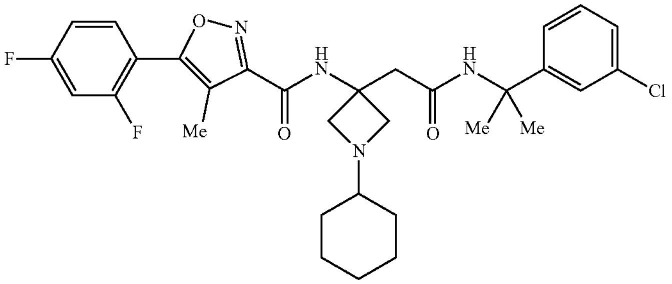 [SMILES: Cc1c(C(=O)NC2(CC(=O)NC(C)(C)c3cccc(Cl)c3)CN(C3CCCCC3)C2)noc1-c1ccc(F)cc1F] |
| 1.341 | 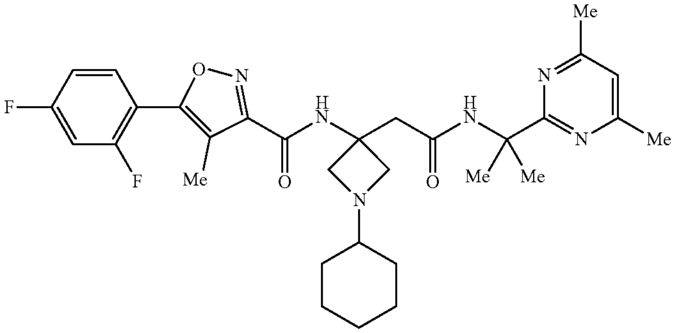 [SMILES: Cc1cc(C)nc(C(C)(C)NC(=O)CC2(NC(=O)c3noc(-c4ccc(F)cc4F)c3C)CN(C3CCCCC3)C2)n1] |

-continued
| Compound ID | Structure |
|---|---|
| 1.342 | 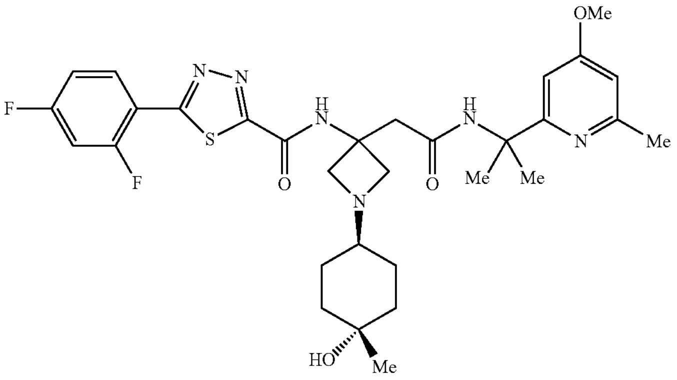 [SMILES: COc1cc(C)nc(C(C)(C)NC(=O)CC2(NC(=O)c3nnc(-c4ccc(F)cc4F)s3)CN([C@H]3CC[C@](C)(O)CC3)C2)c1] |
| 1.343 | 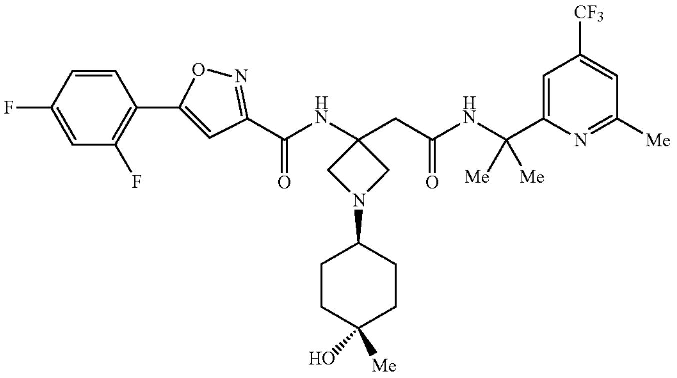 [SMILES: Cc1cc(C(F)(F)F)cc(C(C)(C)NC(=O)CC2(NC(=O)c3cc(-c4ccc(F)cc4F)on3)CN([C@H]3CC[C@](C)(O)CC3)C2)n1] |
| 1.344 | 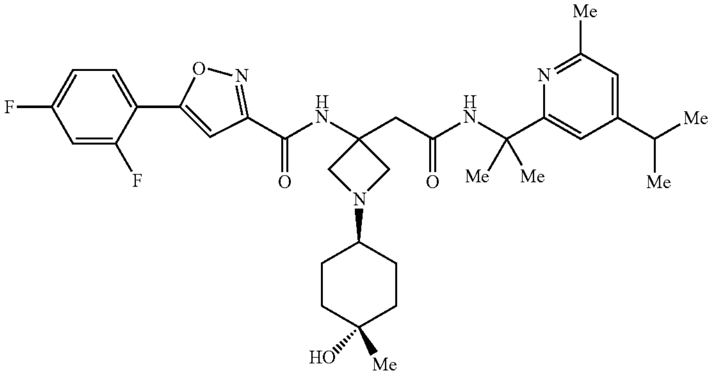 [SMILES: Cc1cc(C(C)C)cc(C(C)(C)NC(=O)CC2(NC(=O)c3cc(-c4ccc(F)cc4F)on3)CN([C@H]3CC[C@](C)(O)CC3)C2)n1] |
| 1.345 | 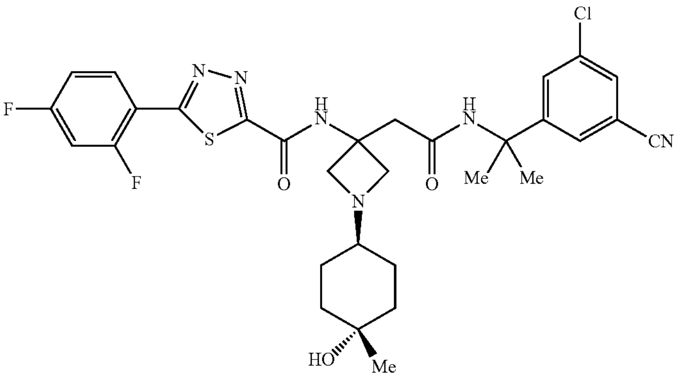 [SMILES: CC(C)(NC(=O)CC1(NC(=O)c2nnc(-c3ccc(F)cc3F)s2)CN([C@H]2CC[C@](C)(O)CC2)C1)c1cc(Cl)cc(C#N)c1] |

-continued
| Compound ID | Structure |
| --- | --- |
| 1.346 | 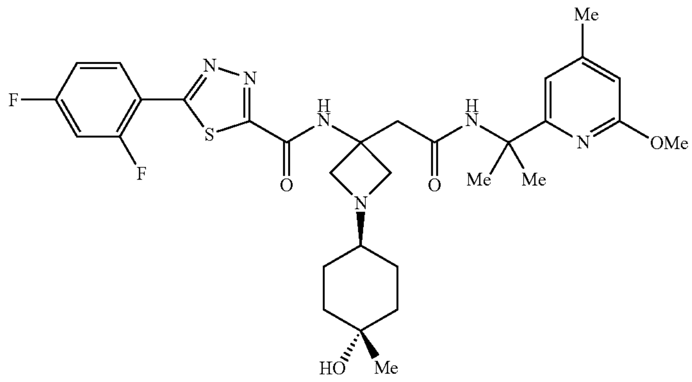 [SMILES: COc1cc(C)cc(C(C)(C)NC(=O)CC2(NC(=O)c3nnc(-c4ccc(F)cc4F)s3)CN([C@H]3CC[C@](C)(O)CC3)C2)n1] |
| 1.347 | 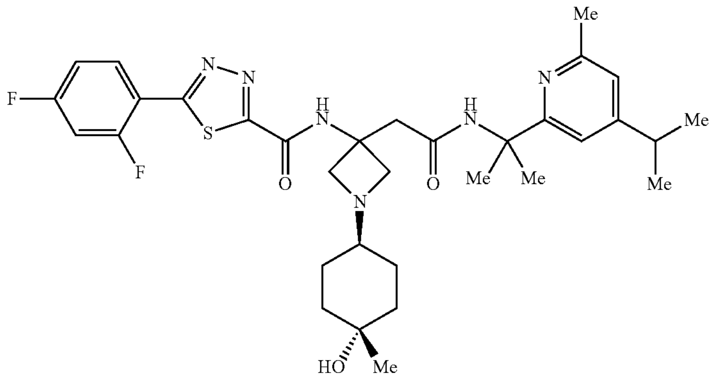 [SMILES: Cc1cc(C(C)C)cc(C(C)(C)NC(=O)CC2(NC(=O)c3nnc(-c4ccc(F)cc4F)s3)CN([C@H]3CC[C@](C)(O)CC3)C2)n1] |
| 1.348 | 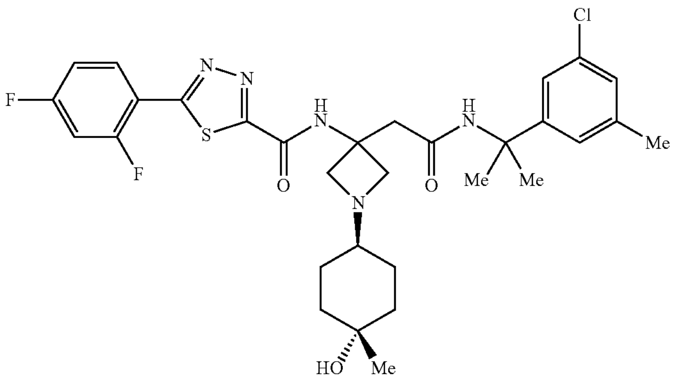 [SMILES: Cc1cc(Cl)cc(C(C)(C)NC(=O)CC2(NC(=O)c3nnc(-c4ccc(F)cc4F)s3)CN([C@H]3CC[C@](C)(O)CC3)C2)c1] |
| 1.349 | 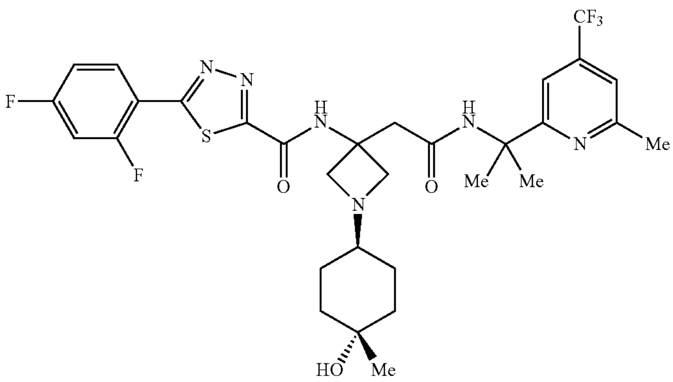 [SMILES: Cc1cc(C(F)(F)F)cc(C(C)(C)NC(=O)CC2(NC(=O)c3nnc(-c4ccc(F)cc4F)s3)CN([C@H]3CC[C@](C)(O)CC3)C2)n1] |

-continued
| Compound ID | Structure |
|---|---|
| 1.350 | 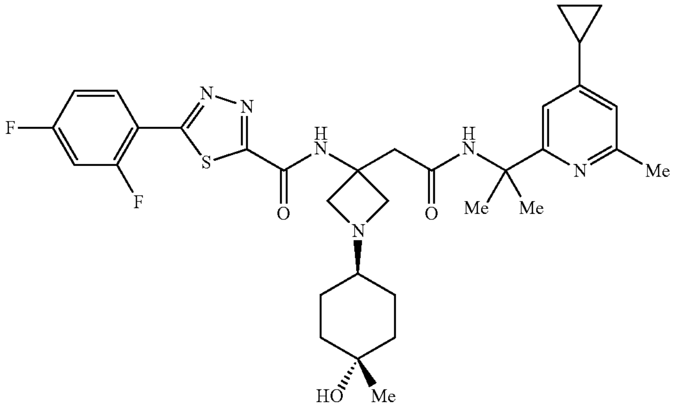 [SMILES: Cc1cc(C2CC2)cc(C(C)(C)NC(=O)CC2(NC(=O)c3nnc(-c4ccc(F)cc4F)s3)CN([C@H]3CC[C@](C)(O)CC3)C2)n1] |
| 1.351 | 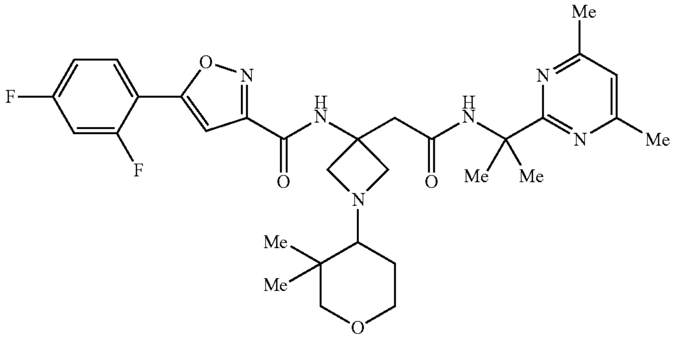 [SMILES: Cc1cc(C)nc(C(C)(C)NC(=O)CC2(NC(=O)c3cc(-c4ccc(F)cc4F)on3)CN(C3CCOCC3(C)C)C2)n1] |
| 1.352 | 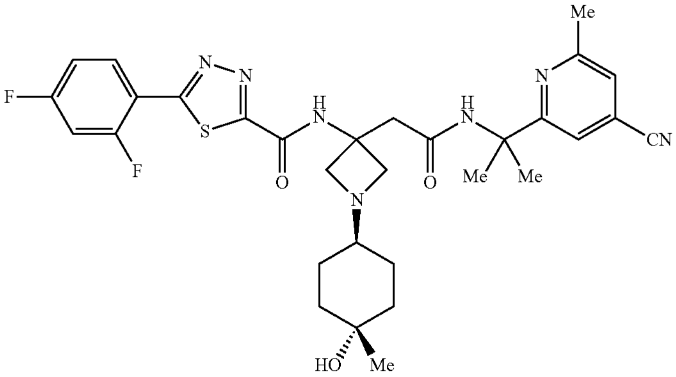 [SMILES: Cc1cc(C#N)cc(C(C)(C)NC(=O)CC2(NC(=O)c3nnc(-c4ccc(F)cc4F)s3)CN([C@H]3CC[C@](C)(O)CC3)C2)n1] |
| 1.353 | 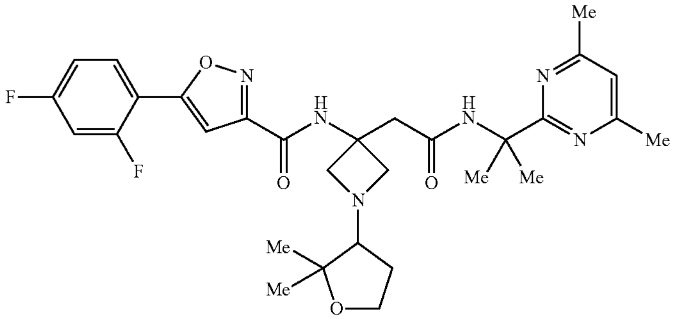 [SMILES: Cc1cc(C)nc(C(C)(C)NC(=O)CC2(NC(=O)c3cc(-c4ccc(F)cc4F)on3)CN(C3CCOC3(C)C)C2)n1] |

-continued
| Compound ID | Structure |
|---|---|
| 1.354 | 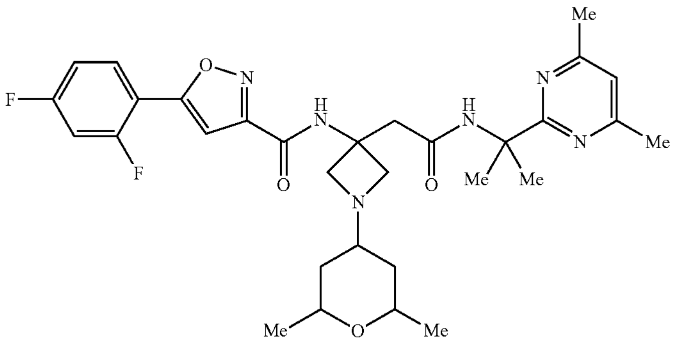 [SMILES: Cc1cc(C)nc(C(C)(C)NC(=O)CC2(NC(=O)c3cc(-c4ccc(F)cc4F)on3)CN(C3CC(C)OC(C)C3)C2)n1] |
| 1.355 | 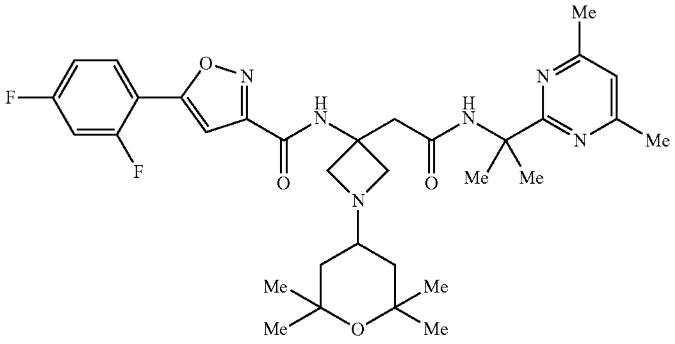 [SMILES: Cc1cc(C)nc(C(C)(C)NC(=O)CC2(NC(=O)c3cc(-c4ccc(F)cc4F)on3)CN(C3CC(C)(C)OC(C)(C)C3)C2)n1] |
| 1.356 | 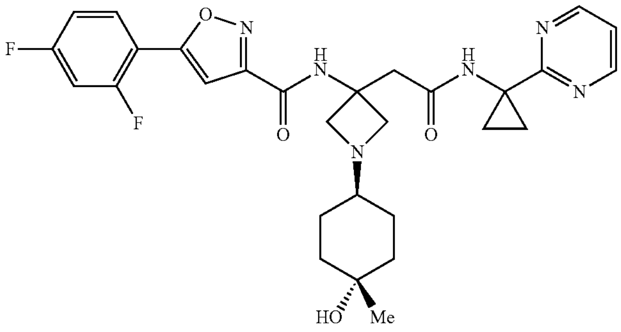 [SMILES: C[C@]1(O)CC[C@H](N2CC(CC(=O)NC3(c4ncccn4)CC3)(NC(=O)c3cc(-c4ccc(F)cc4F)on3)C2)CC1] |
| 1.357 | 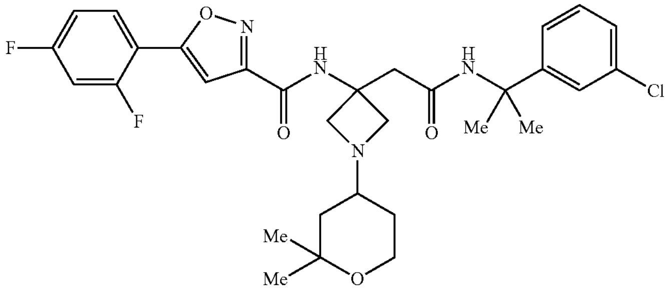 [SMILES: CC1(C)CC(N2CC(CC(=O)NC(C)(C)c3cccc(Cl)c3)(NC(=O)c3cc(-c4ccc(F)cc4F)on3)C2)CCO1] |

-continued

| Compound ID | Structure |
|---|---|
| 1.358 | 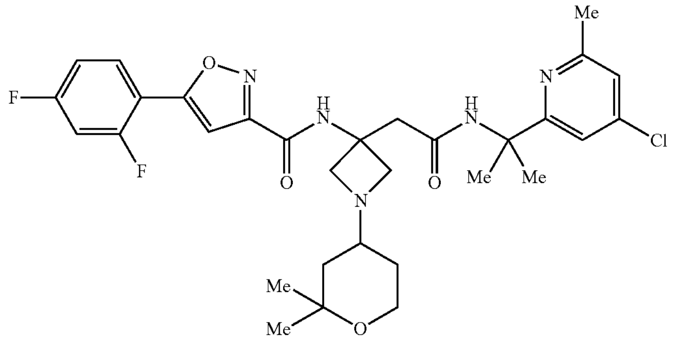 [SMILES: Cc1cc(Cl)cc(C(C)(C)NC(=O)CC2(NC(=O)c3cc(-c4ccc(F)cc4F)on3)CN(C3CCOC(C)(C)C3)C2)n1] |
| 1.359 | 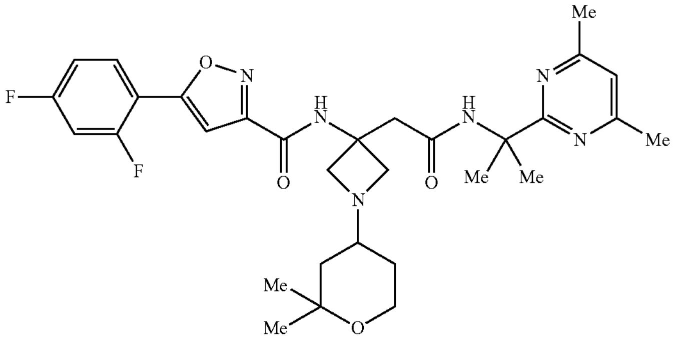 [SMILES: Cc1cc(C)nc(C(C)(C)NC(=O)CC2(NC(=O)c3cc(-c4ccc(F)cc4F)on3)CN(C3CCOC(C)(C)C3)C2)n1] |
| 1.360 | 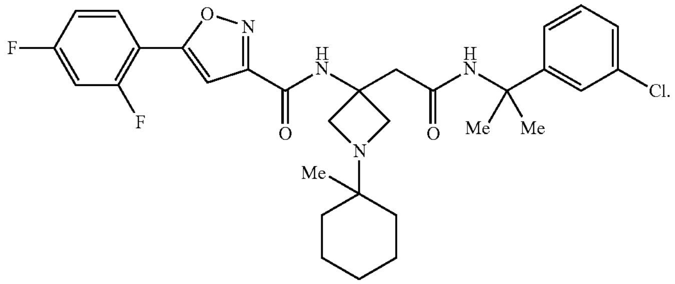 [SMILES: CC(C)(NC(=O)CC1(NC(=O)c2cc(-c3ccc(F)cc3F)on2)CN(C2(C)CCCCC2)C1)c1cccc(Cl)c1] |

26. A pharmaceutical composition comprising a compound of claim 1 and a pharmaceutically acceptable excipient.

27. A pharmaceutical composition comprising a compound from claim 25.

28. A method of treating a disease or disorder in a mammal, said method comprising administering to said subject a therapeutically effective amount of a compound of claim 1, for a period of time sufficient to treat said disease or disorder.

29. A method for imaging a tumor, organ, or tissue, said method comprising:

(a) administering to a subject in need of such imaging, a radiolabeled or detectable form of a compound of claim 1; and (b) detecting said compound to determine where said compound is concentrated in said subject.

30. A method for detecting elevated levels of CXCR7 in a sample, said method comprising:

(a) contacting a sample suspected of having elevated levels of CXCR7 with a radiolabeled or detectable form of a compound of claim 1;

(b) determining a level of compound that is bound to CXCR7 present in said sample to determine the level of CXCR7 present in said sample; and (c) comparing the level determined in step (b) with a control sample to determine if elevated levels of CXCR7 are present in said sample.

* * * * *